US008969557B2

(12) United States Patent
Harriman et al.

(10) Patent No.: US 8,969,557 B2
(45) Date of Patent: Mar. 3, 2015

(54) ACC INHIBITORS AND USES THEREOF

(71) Applicant: Nimbus Apollo, Inc., Cambridge, MA (US)

(72) Inventors: Geraldine C. Harriman, Charlestown, RI (US); Craig E. Masse, Cambridge, MA (US); James Harwood, Ledyard, CT (US); Sathesh Bhat, West New York, NY (US); Jeremy Robert Greenwood, Brooklyn, NY (US)

(73) Assignee: Nimbus Apollo, Inc., Cambridge, MA (US)

( * ) Notice: Subject to any disclaimer, the term of this patent is extended or adjusted under 35 U.S.C. 154(b) by 0 days.

(21) Appl. No.: 13/673,610

(22) Filed: Nov. 9, 2012

(65) Prior Publication Data
US 2013/0123231 A1    May 16, 2013

Related U.S. Application Data

(60) Provisional application No. 61/559,023, filed on Nov. 11, 2011, provisional application No. 61/615,092, filed on Mar. 23, 2012, provisional application No. 61/651,878, filed on May 25, 2012, provisional application No. 61/675,513, filed on Jul. 25, 2012.

(51) Int. Cl.
*C07D 495/04* (2006.01)
*A61K 31/519* (2006.01)

(52) U.S. Cl.
CPC ............ *C07D 495/04* (2013.01); *A61K 31/519* (2013.01)
USPC ....................... 544/278; 514/260.1

(58) Field of Classification Search
None
See application file for complete search history.

(56) References Cited

U.S. PATENT DOCUMENTS

| 6,180,635 | B1 | 1/2001 | Cheshire et al. |
| 2003/0187254 | A1 | 10/2003 | Perry et al. |
| 2003/0191142 | A1* | 10/2003 | Cheshire et al. ........... 514/260.1 |
| 2005/0124636 | A1 | 6/2005 | Sharma et al. |
| 2006/0039943 | A1 | 2/2006 | Applebaum et al. |
| 2007/0208040 | A1 | 9/2007 | Elzein et al. |
| 2008/0287465 | A1 | 11/2008 | Tumey et al. |

FOREIGN PATENT DOCUMENTS

| EP | 0640606 A1 | 3/1995 |
| EP | 2351743 A1 | 8/2011 |
| WO | WO-2004014916 A1 | 2/2004 |

OTHER PUBLICATIONS

CAPLUS record for US 2007/0208040 A1 by Elzein et al. (retrieved Nov. 2013).*
"Thieno[2,3-d]pyrimidine-3-acetic acids. A new class of nonpeptide endothelin receptor antagonists" by Cho et al., Chem. Pharm. Bull. 46, 1724-37 (1998).*
International Search Report for PCT/US12/64528, 3 pages (Feb. 4, 2013).
Written Opinion for PCT/US12/64528, 11 pages (Feb. 4, 2013).

* cited by examiner

*Primary Examiner* — Theodore R West
(74) *Attorney, Agent, or Firm* — Choate Hall & Stewart LLP; Andrea L. C. Reid; Thomas H. McLean

(57) ABSTRACT

The present invention provides compounds useful as inhibitors of Acetyl CoA Carboxylase (ACC), compositions thereof, and methods of using the same.

10 Claims, 16 Drawing Sheets

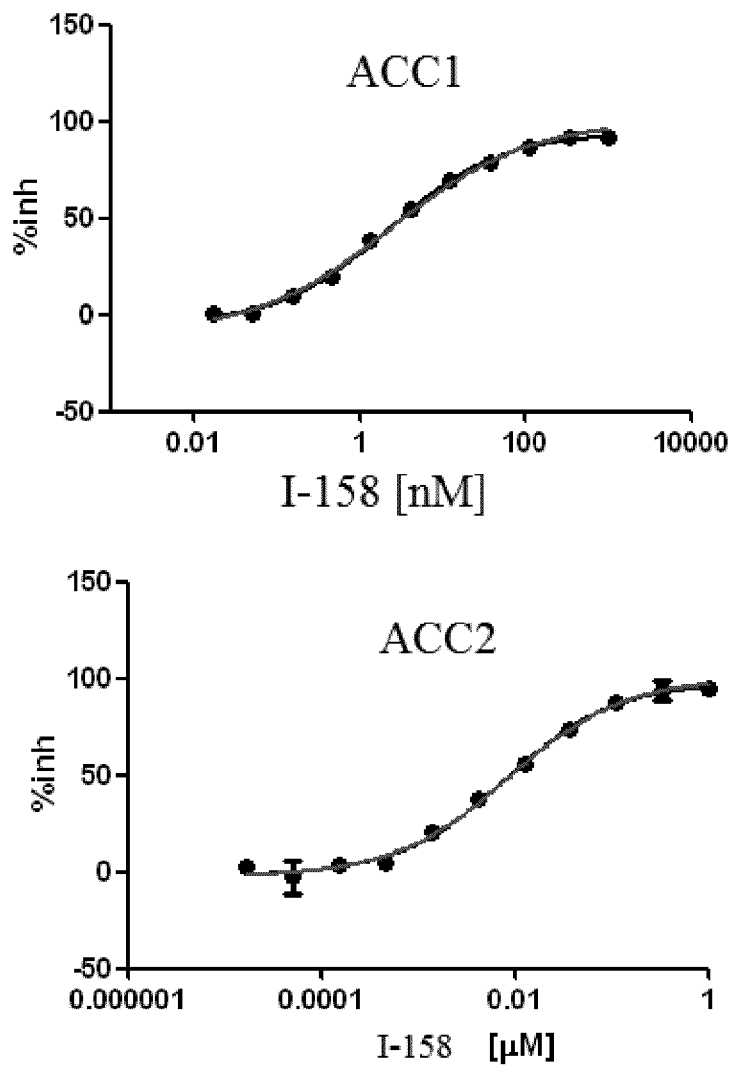
Figure 1. ACC1 and ACC2 enzyme inhibition curves for compound I-158.

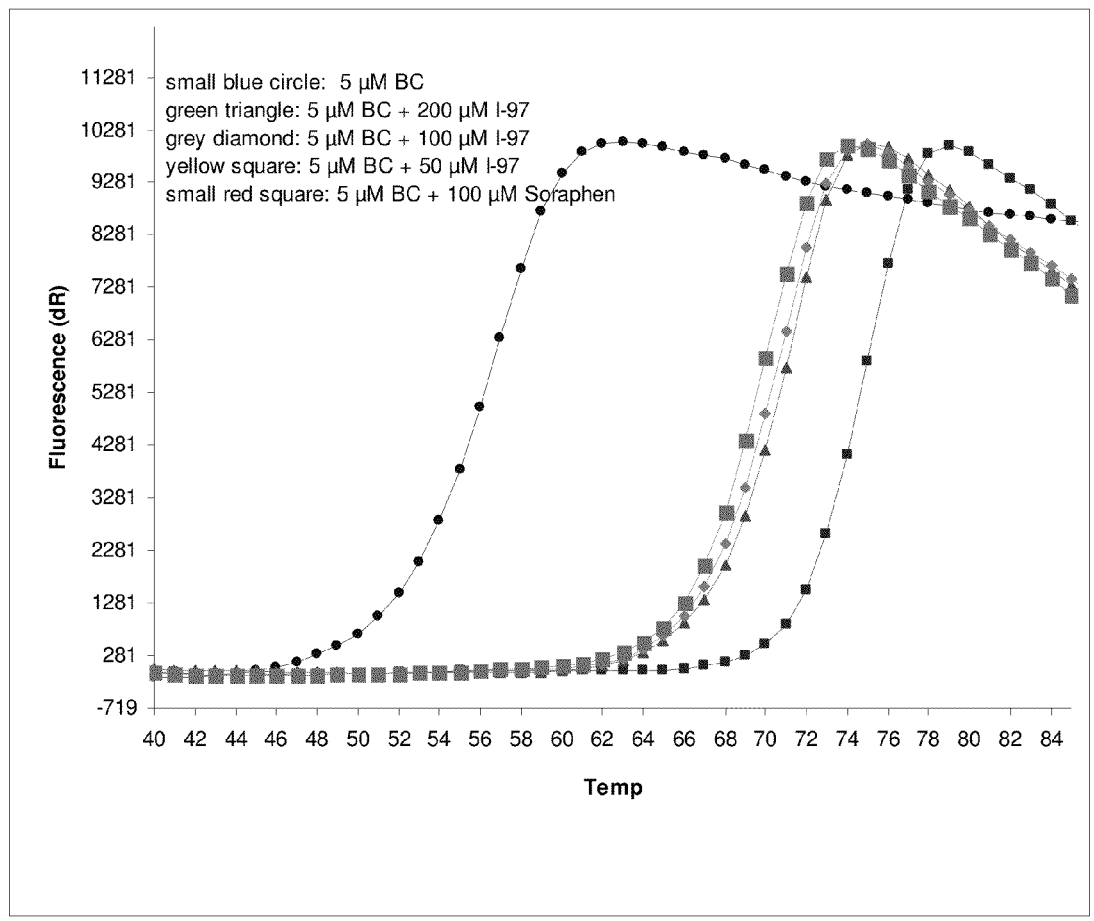
Figure 2. Results of the thermal shift assay of compound I-97 against the Biotin Carboxylase domain of ACC2.

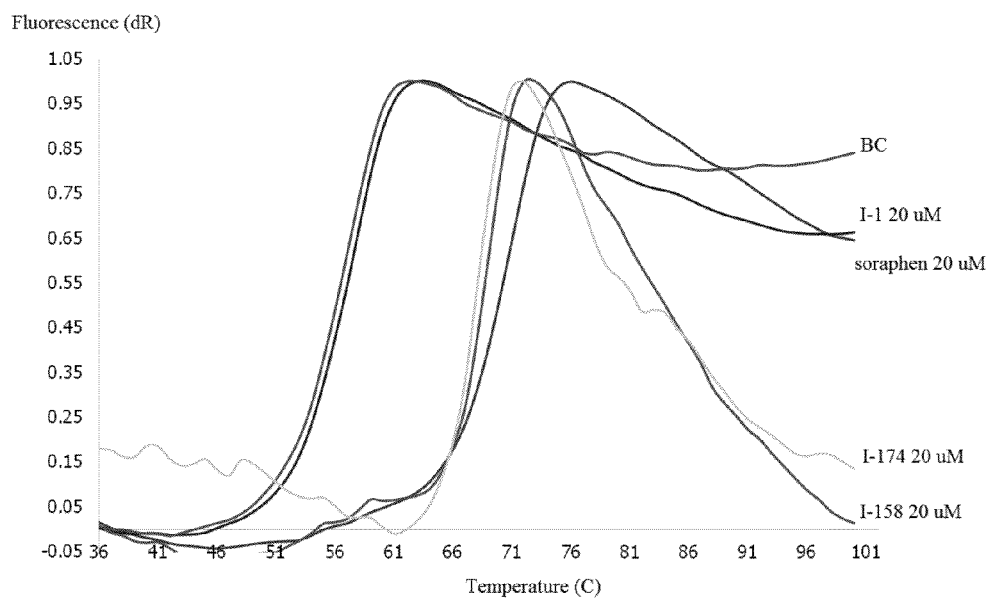
Figure 3. Results of the thermal shift assay of compounds I-1, I-158, I-174, and soraphen A against the Biotin Carboxylase domain of ACC2.

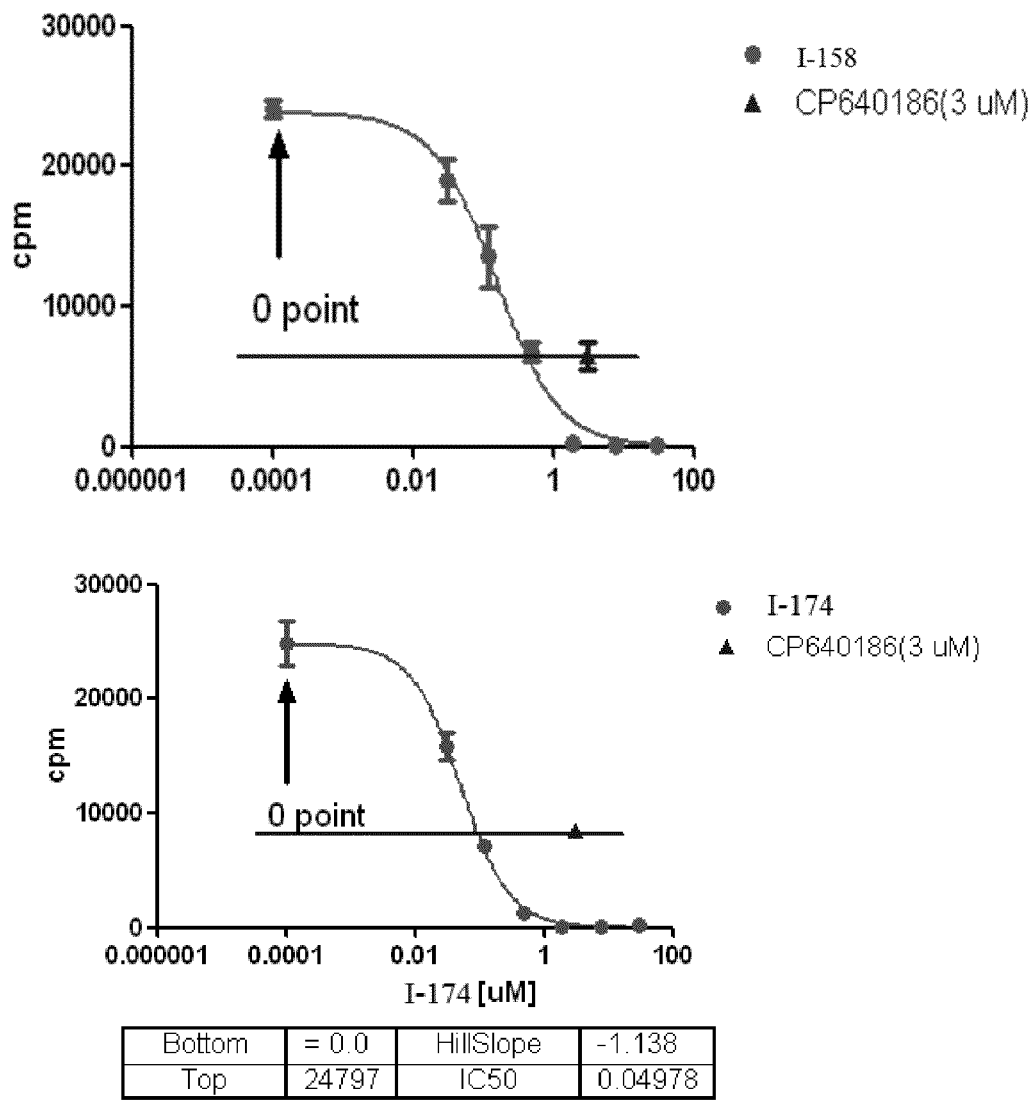
Figure 4. Results of the [$^{14}$C] Acetate Incorporation HepG2 Cellular Assay for compounds I-158, I-174, and CP640186.

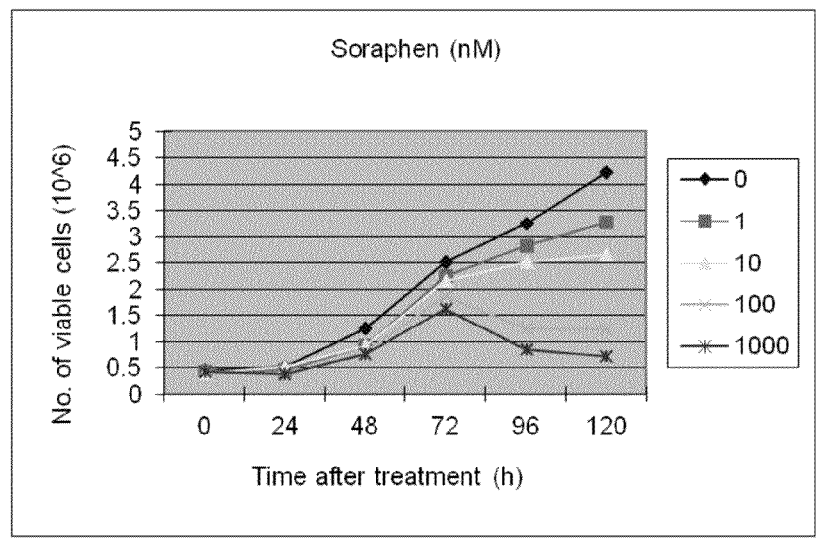
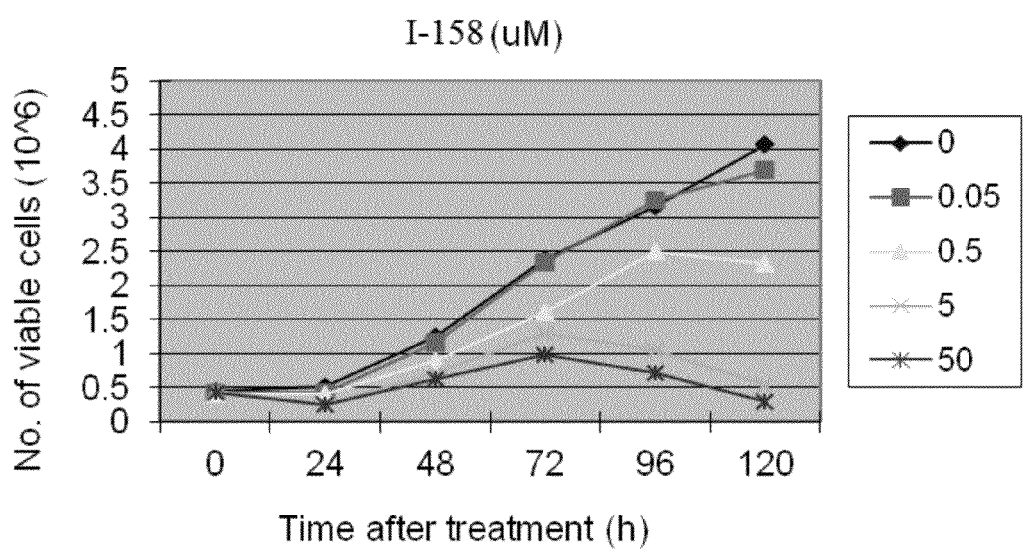
Figure 5. Results of LnCaP (Prostate) Cancer Cell Viability Assay for I-158 and Soraphen A.

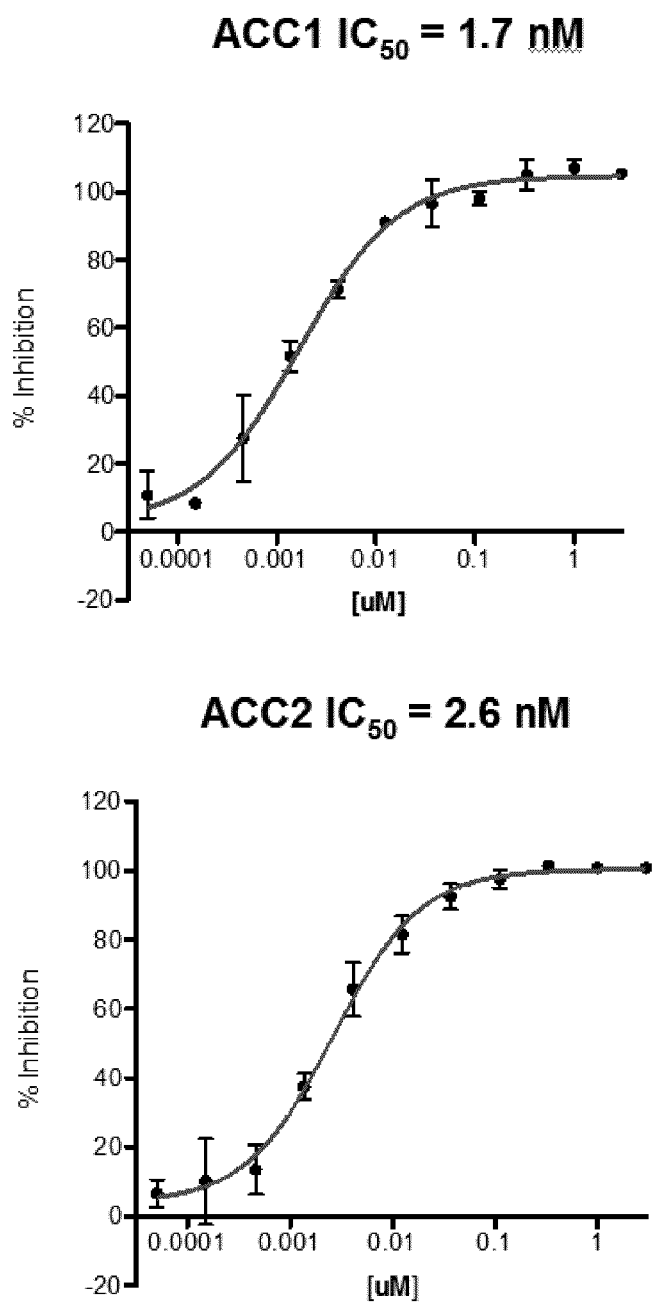
Figure 6. Enzyme inhibition curves for compound I-181 against ACC1 and ACC2 in vitro.

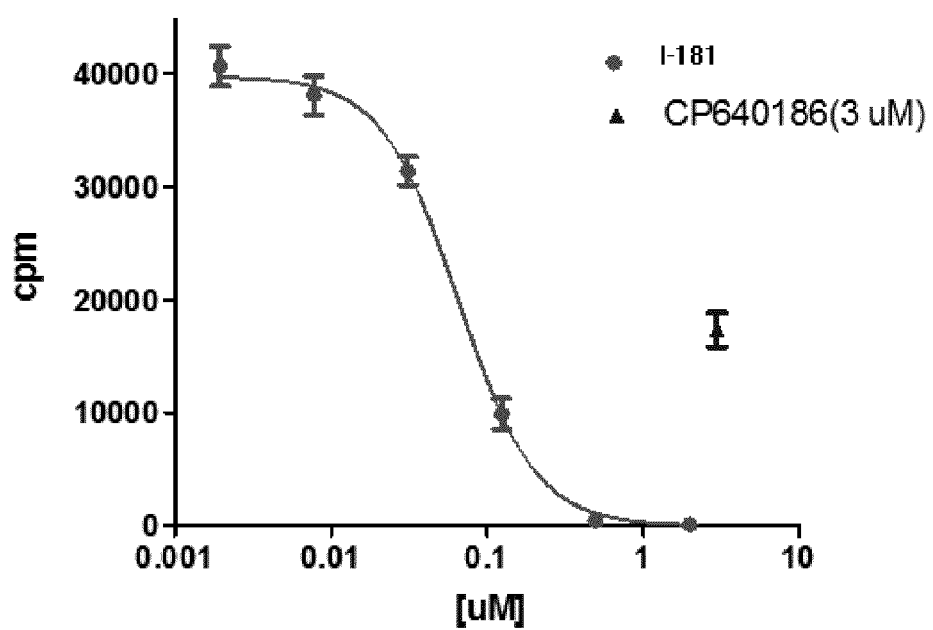
Figure 7. Inhibition of fatty acid synthesis in Hep-G2 cells by compound I-181, measured by [$^{14}$C]-acetate incorporation.

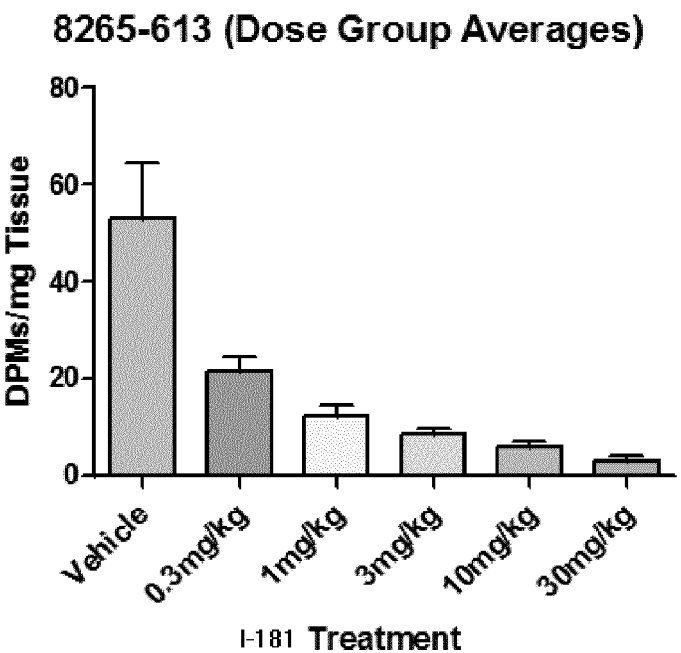
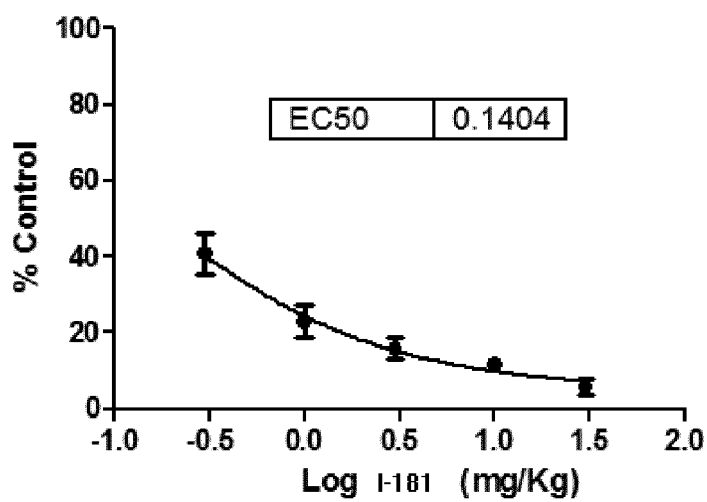
Figure 8 depicts inhibition of fatty acid synthesis in rats by compound I-181, showing an $ED_{50}$ of less than 0.3 mg/kg.

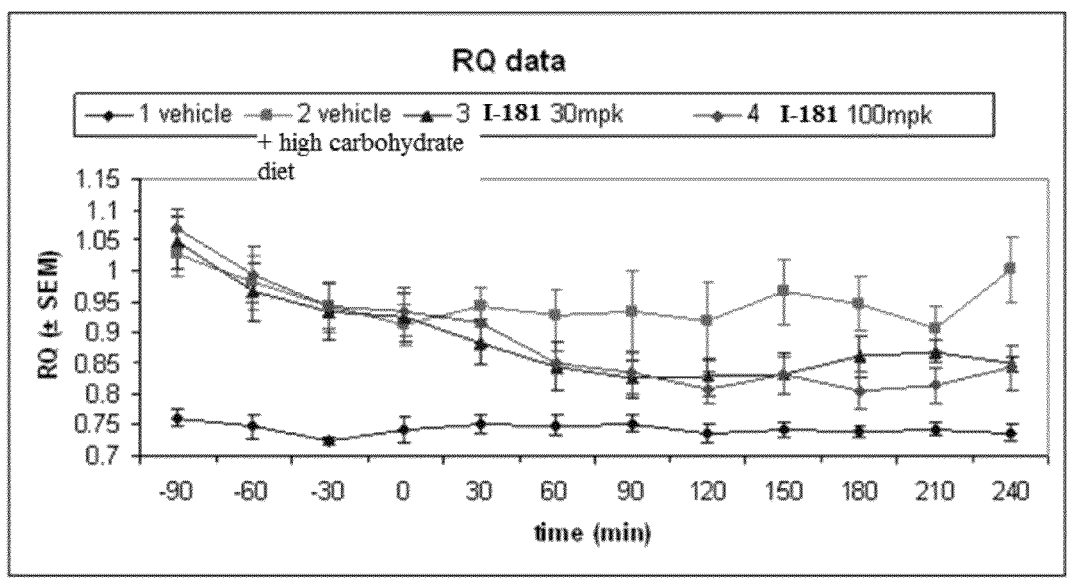
Figure 9 depicts results of a respiratory quotient (RQ) study measuring the ratio of $CO_2$ production to $O_2$ consumption in rats, using compound I-181 at doses of 30 and 100 mg/kg bodyweight.

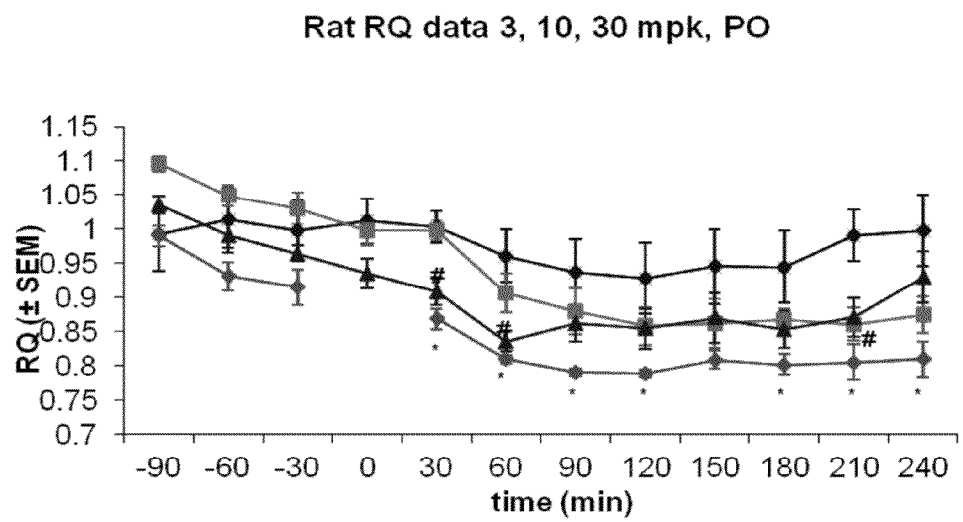
Figure 10 depicts results of a respiratory quotient (RQ) study measuring the ratio of $CO_2$ production to $O_2$ consumption in rats, using vehicle only (dark blue diamond), or compound I-181 at doses of 3 mg/kg (pink square), 10 mg/kg (blue triangle), and 30 mg/kg (red diamond) bodyweight administered PO.

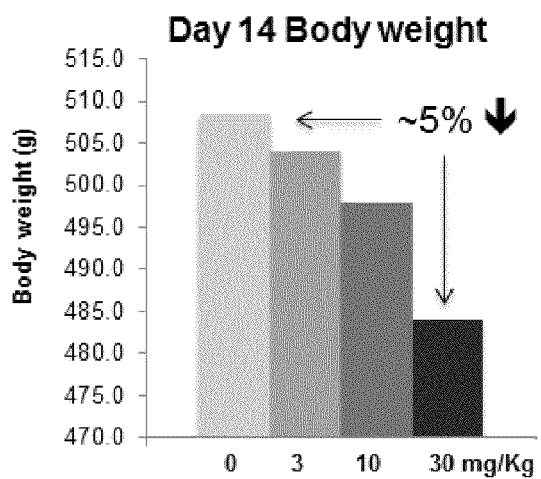
Figure 11 depicts results of a high fat diet-induced obesity (DIO) weight gain experiment, wherein rats were treated with 3, 10, or 30 mg/Kg of I-181. The results show that rats treated with a dose of 30 mg/Kg, p.o., q.i.d. gained approximately 5% less body weight after 14 days than control rats.

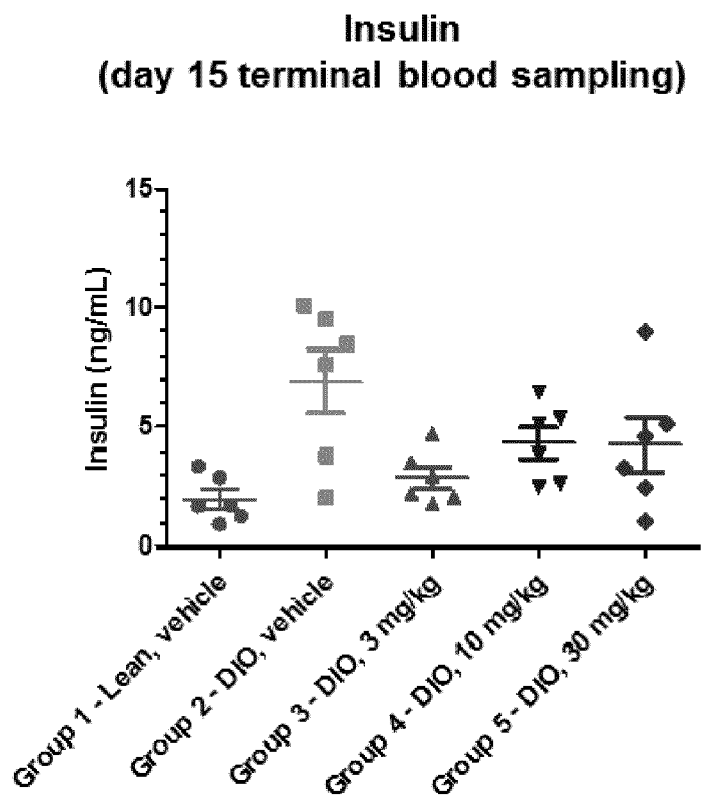
Figure 12 depicts results of an insulin level reduction experiment, wherein rats on a high fat diet-induced obesity (DIO) diet were treated with 3, 10, or 30 mg/Kg of I-181. The results show that rats treated with a dose of 30 mg/Kg of I-181, p.o., q.i.d showed lower insulin levels after 15 days than control rats.

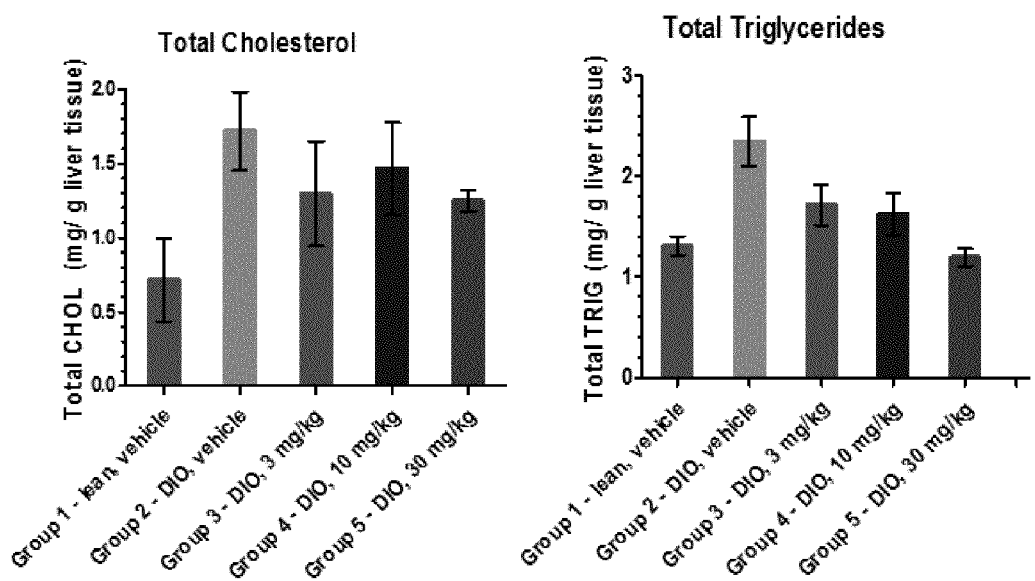
Figure 13 depicts results of a hepatic cholesterol and triglyceride measurement experiment, wherein rats on a high fat diet-induced obesity (DIO) diet were treated with 3, 10, or 30 mg/Kg of I-181. The results show that rats treated with a dose of 30 mg/Kg of I-181, p.o., q.i.d showed lower levels of liver cholesterol and triglycerides than control rats.

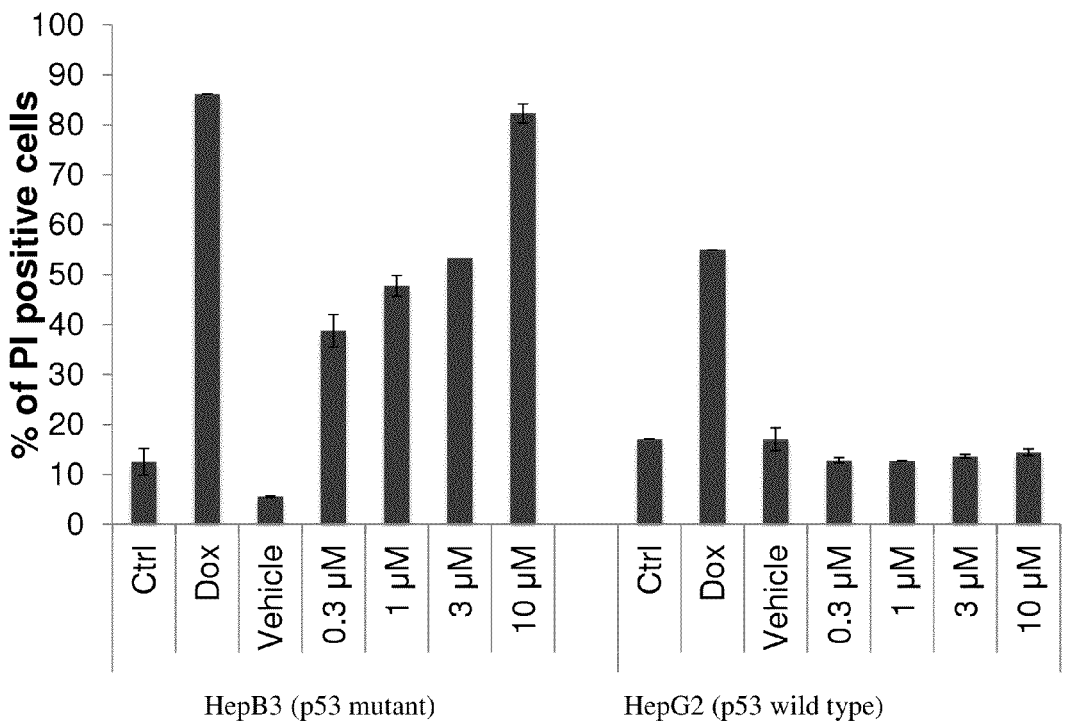
Figure 14 depicts results of an experiment measuring cell death induction in wild type and p53 mutant hepatocellular tumor lines (HepG2 and HepB3) following administration of compound I-246 and doxycycline as positive control. These results show differential sensitivity to ACC1 and ACC2 inhibition and that compound I-246 shows an $EC_{50}$ of 8 nM in wild type HepG2 cells.

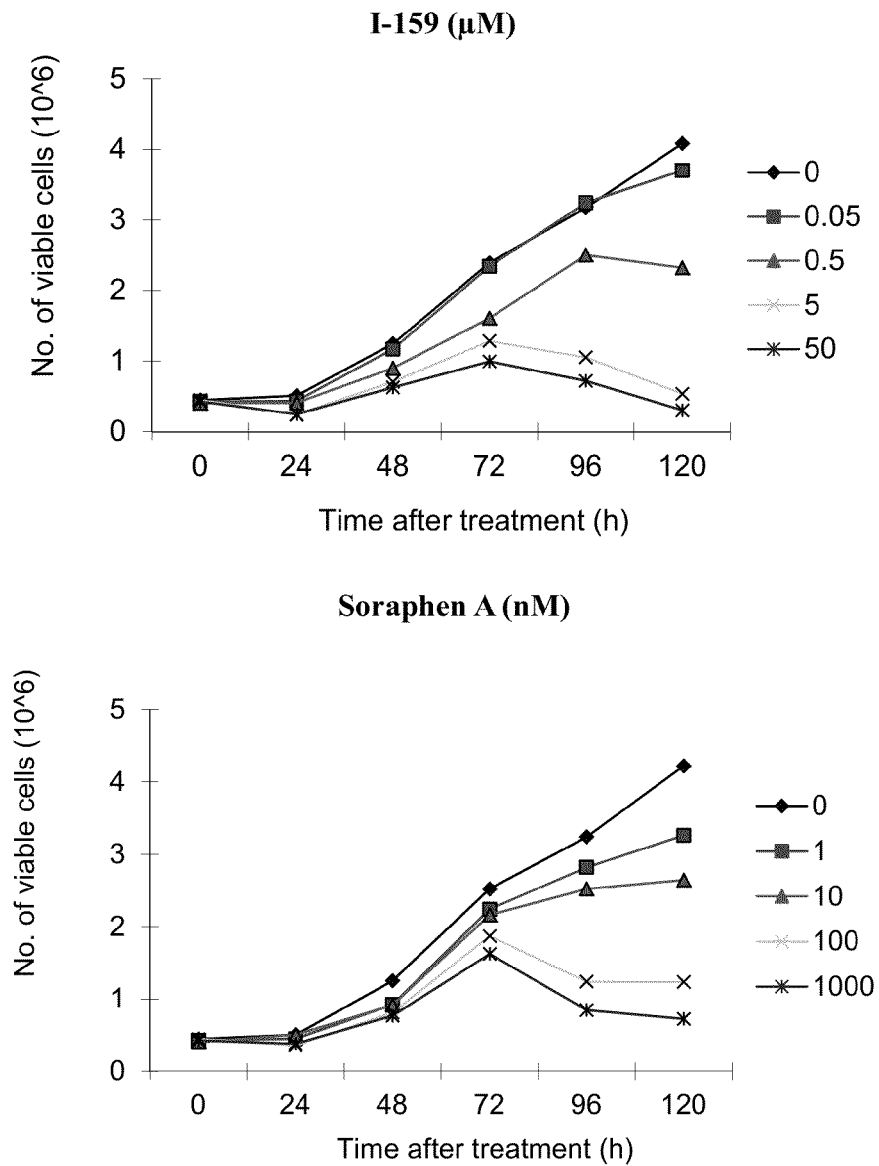
Figure 15 depicts results of an experiment measuring cell death in an androgen-sensitive human prostate adenocarcinoma (LNCaP) tumor line following administration of compound I-159 or Soraphen A. These results show dose-dependent cell death for both compounds.

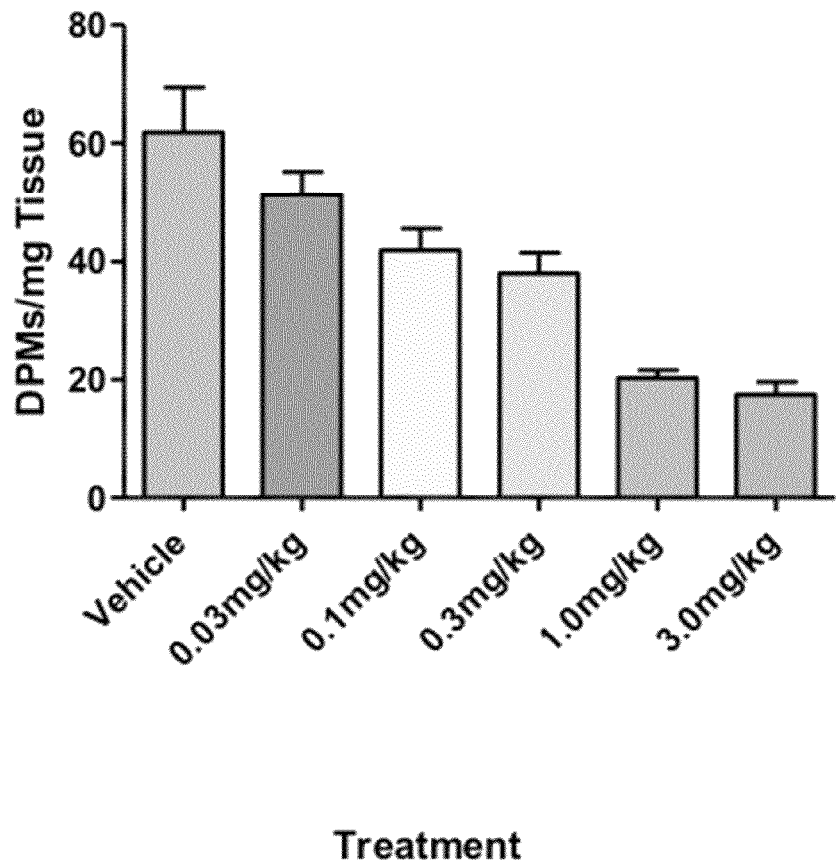
Figure 16 depicts results of an experiment measuring fatty acid (FA) synthesis in rats following administration of compound I-278. These results show a dose-dependent decrease in FA synthesis.

ACC INHIBITORS AND USES THEREOF

CROSS-REFERENCE TO RELATED APPLICATIONS

The present invention claims priority to U.S. provisional patent application Ser. No. 61/559,023, filed Nov. 11, 2011, U.S. provisional application Ser. No. 61/615,092, filed Mar. 23, 2012, U.S. provisional patent application Ser. No. 61/651,878, filed May 25, 2012, and U.S. provisional patent application Ser. No. 61/675,513, filed Jul. 25, 2012, the entirety of each of which is hereby incorporated herein by reference.

BACKGROUND OF THE INVENTION

Obesity is a health crisis of epic proportions. The health burden of obesity, measured by quality-adjusted life-years lost per adult, has surpassed that of smoking to become the most serious, preventable cause of death. In the US, about 34% of adults have obesity, up from 31% in 1999 and about 15% in the years 1960 through 1980. Obesity increases the rate of mortality from all causes for both men and women at all ages and in all racial and ethnic groups. Obesity also leads to social stigmatization and discrimination, which decreases quality of life dramatically. The chronic diseases that result from obesity cost the US economy more than $150 billion in weight-related medical bills each year. Furthermore, about half of the obese population, and 25% of the general population, have metabolic syndrome, a condition associated with abdominal obesity, hypertension, increased plasma triglycerides, decreased HDL cholesterol, and insulin resistance, which increases the risk for type-2 diabetes (T2DM), stroke and coronary heart disease. [Harwood, *Expert Opin. Ther. Targets* 9: 267, 2005].

Diet and exercise, even when used in conjunction with the current pharmacotherapy, do not provide sustainable weight loss needed for long-term health benefit. Currently, only a few anti-obesity drugs are approved in the US, the fat absorption inhibitor orlistat (Xenical®), the 5-HT$_{2C}$ antagonist lorcaserin (Belviq®), and the combination therapy phentermine/topiramate) (Qsymia®). Unfortunately, poor efficacy and unappealing gastrointestinal side effects limit the use of orlistat. Surgery can be effective but is limited to patients with extremely high body-bass indices (BMI) and the low throughput of surgery limits the impact of this modality to about 200 k patients per year. The majority of obesity drugs in clinical development are designed to reduce caloric intake through central action in the CNS (e.g., anorectics and satiety agents). However, the FDA has taken an unfavorable position against CNS-active agents, due to their modest efficacy and observed/potential side-effect profiles.

The continuing and increasing problem of obesity, and the current lack of safe and effective drugs for treating it, highlight the overwhelming need for new drugs to treat this condition and its underlying causes.

SUMMARY OF THE INVENTION

It has now been found that compounds of this invention, and pharmaceutically acceptable compositions thereof, are effective as inhibitors of Acetyl-CoA carboxylase (ACC). Such compounds have the general formula I:

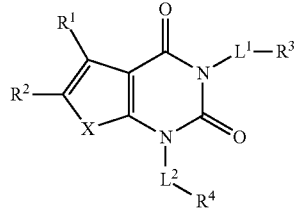

or a pharmaceutically acceptable salt thereof, wherein each variable is as defined and described herein.

Compounds of the present invention, and pharmaceutically acceptable compositions thereof, are useful for treating a variety of diseases, disorders or conditions, associated with regulation of the production or oxidation of fatty acids. Such diseases, disorders, or conditions include those described herein.

Compounds provided by this invention are also useful for the study of ACC enzymes in biological and pathological phenomena; the study of intracellular signal transduction pathways occurring in lipogenic tissues; and the comparative evaluation of new ACC inhibitors or other regulators of fatty acid levels in vitro or in vivo.

BRIEF DESCRIPTION OF THE DRAWINGS

FIG. 1 depicts enzyme inhibition curves for compound I-158 against ACC1 and ACC2.

FIG. 2 depicts the results of a thermal shift assay of compound I-97.

FIG. 3 depicts the results of a thermal shift assay of compounds I-1, I-158, I-174, and Soraphen A.

FIG. 4 depicts results of a [$^{14}$C] Acetate Incorporation HepG2 Cellular Assay for compounds I-158, I-174 and CP640186.

FIG. 5 depicts results of a LnCAP cancer cell viability assay for I-158 and Soraphen A.

FIG. 6 depicts enzyme inhibition curves for compound I-181 against ACC1 and ACC2 in vitro.

FIG. 7 depicts inhibition of fatty acid synthesis in Hep-G2 cells by compound I-181, measured by [$^{14}$C]-acetate incorporation.

FIG. 8 depicts inhibition of fatty acid synthesis in rats by compound I-181, showing an ED$_{50}$ of less than 0.3 mg/kg.

FIG. 9 depicts results of a respiratory quotient (RQ) study measuring the ratio of CO$_2$ production to O$_2$ consumption in rats, using compound I-181 at doses of 30 and 100 mg/kg bodyweight.

FIG. 10 depicts results of a respiratory quotient (RQ) study measuring the ratio of CO$_2$ production to O$_2$ consumption in rats, using compound I-181 at doses of 3, 10, and 30 mg/kg bodyweight.

FIG. 11 depicts results of a high fat diet-induced obesity (DIO) weight gain experiment, wherein rats were treated with 3, 10, or 30 mg/Kg of I-181.

FIG. 12 depicts results of an insulin level reduction experiment, wherein rats on high fat diet-induced obesity (DIO) diet were treated with 3, 10, or 30 mg/Kg of I-181.

FIG. 13 depicts results of a hepatic cholesterol and triglyceride measurement experiment, wherein rats on a high fat diet-induced obesity (DIO) diet were treated with 3, 10, or 30 mg/Kg of I-181.

FIG. 14 depicts results of an experiment measuring cell death induction in wild type and p53 mutant hepatocellular tumor lines (HepG2 and HepB3) following administration of compound I-246.

FIG. 15 depicts results of an experiment measuring cell death in an androgen-sensitive human prostate adenocarcinoma (LNCaP) tumor line following administration of compound I-159 or Soraphen A.

FIG. 16 depicts results of an experiment measuring fatty acid (FA) synthesis in rats following administration of compound I-278. These results show a dose-dependent decrease in FA synthesis.

DETAILED DESCRIPTION OF CERTAIN EMBODIMENTS

1. General Description of Compounds of the Invention

In certain embodiments, the present invention provides inhibitors of ACC. In some embodiments, such compounds include those of formula I:

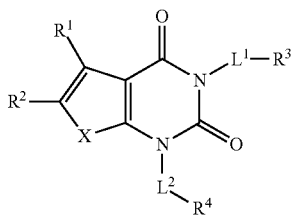

or a pharmaceutically acceptable salt thereof, wherein:
X is —O—, —S—, or —NR—;
$R^1$ is hydrogen or $C_{1-4}$ aliphatic, optionally substituted with one or more halogen, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$RN(R)$_2$, —C(O)R, —C(O)OR, —OC(O)R, —C(O)OR, —S(O)R, or —SO$_2$R;
$R^2$ is halogen, —R, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, or —SO$_2$R or Hy, where Hy is selected from 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; or
$R^1$ and $R^2$ are taken together to form an optionally substituted 4-7 membered partially unsaturated carbocyclo-, or heterocyclo-, benzo-, or 5-6 membered heteroarylo-fused ring;
each R is independently hydrogen, deuterium, or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring; a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;
each of $L^1$ and $L^2$ is independently a covalent bond or an optionally substituted 1-6 membered straight or branched bivalent hydrocarbon chain;
$R^3$ is hydrogen, halogen, —CN, —OR, —SR, —N(R)$_2$, —N(R)C(O)R, —C(O)RN(R)$_2$, —C(O)N(R)S(O)$_2$R, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, —SO$_2$R, or an optionally substituted ring selected from phenyl or 5-6 membered heteroaryl having 1-4 heteroatoms independently selected from nitrogen, oxygen, or sulfur;
$R^4$ is hydrogen or an optionally substituted ring selected from a 3-8 membered monocyclic saturated or partially unsaturated carbocyclic ring, a 4-8 membered monocyclic saturated or partially unsaturated heterocyclic ring having 1-2 heteroatoms independently selected from nitrogen, oxygen, or sulfur, phenyl, an 8-10 membered bicyclic aryl ring, a 5-6 membered monocyclic heteroaryl ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR⁺ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

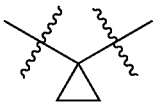

As used herein, the term "cyclobutylenyl" refers to a bivalent cyclobutyl group of the following structure:

As used herein, the term "oxetanyl" refers to a bivalent oxetanyl group of the following structure:

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring."

The term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or ⁺NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be monoor bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched)alkylene)O—N(R°)$_2$; or —(C$_{1-4}$ straight or branched)alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention. In certain embodiments, a warhead moiety, $R^1$, of a provided compound comprises one or more deuterium atoms.

3. Description of Exemplary Embodiments

In certain embodiments, the present invention provides inhibitors of ACC. In some embodiments, such compounds include those of formula I:

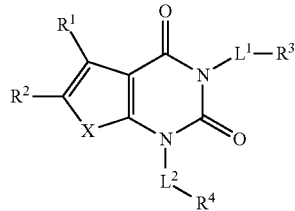

or a pharmaceutically acceptable salt thereof, wherein:

X is —O—, —S—, or —NR—;

$R^1$ is hydrogen or $C_{1-4}$ aliphatic, optionally substituted with one or more halogen, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, or —SO$_2$R;

$R^2$ is halogen, —R, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, or —SO$_2$R, or Hy, where Hy is selected from 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

or $R^1$ and $R^2$ are taken together to form an optionally substituted 4-7 membered partially unsaturated carbocyclo-, or heterocyclo-, benzo-, or 5-6 membered heteroarylo-fused ring;

each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring; a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each of $L^1$ and $L^2$ is independently a covalent bond or an optionally substituted 1-6 membered straight or branched bivalent hydrocarbon chain; or a cyclopropylenyl, cyclobutylenyl, or oxetanyl group;

$R^3$ is hydrogen, halogen, —CN, —OR, —SR, —N(R)$_2$, —N(R)C(O)R, —C(O)N(R)$_2$, —C(O)N(R)S(O)$_2$R, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, —SO$_2$R, —B(OH)$_2$, or an optionally substituted ring selected from phenyl or 5-6 membered heteroaryl having 1-4 heteroatoms independently selected from nitrogen, oxygen, or sulfur; and $R^4$ is hydrogen or an optionally substituted ring selected from a 3-8 membered monocyclic saturated or partially unsaturated carbocyclic ring, a 4-8 membered monocyclic saturated or partially unsaturated heterocyclic ring having 1-2 heteroatoms independently selected from nitrogen, oxygen, or sulfur, phenyl, an 8-10 membered bicyclic aryl ring, a 5-6 membered monocyclic heteroaryl ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur.

In certain embodiments, if $L^2$ is a covalent bond, then $R^4$ is not hydrogen. In certain embodiments, the group $-L^2-R^4$ is not alkyl when $R^2$ is unsubstituted alkyl. In certain embodiments, the group $-L^1-R^3$ taken together is not unsubstituted alkyl. In certain embodiments, $R^1$ is not the group $—CH_2C(O)N(R)V$, where V is an aryl or heteroaryl ring, when $-L^1-R^3$ taken together is unsubstituted alkyl.

As defined generally above, X is —O—, —S—, or —NR—. In certain embodiments, X is —O—. In certain embodiments, X is —S—. In some embodiments, X is —NR—. In certain embodiments, X is —NH—.

As defined generally above, $R^1$ is hydrogen or $C_{1-4}$ aliphatic, optionally substituted with one or more halogen, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, or —SO$_2$R. In certain embodiments, $R^1$ is hydrogen. In some embodiments, $R^1$ is $C_{1-4}$ aliphatic. In some embodiments, $R^1$ is methyl. In some embodiments, $R^1$ is trifluoromethyl.

As defined generally above, $R^2$ is halogen, —R, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, or —SO$_2$R, or Hy, where Hy is selected from 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur. In certain embodiments, $R^2$ is halogen. In certain embodiments, $R^2$ is methyl. In certain embodiments, $R^2$ is trifluoromethyl. In certain embodiments, $R^2$ is fluorine. In certain embodiments, $R^2$ is chlorine. In certain embodiments, $R^2$ is bromine. In certain embodiments, $R^2$ is iodine. In certain embodiments, $R^2$ is —C(O)OR or —C(O)N(R)$_2$. In some embodiments, $R^2$ is Hy.

As defined generally above, Hy is selected from 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur. In some embodiments, Hy is a 4-8 membered saturated or partially unsaturated monocyclic heterocyclic ring having 1-2 heteroatoms independently selected from nitrogen, oxygen, or sulfur. In some embodiments, Hy is a 5-6 membered monocyclic heteroaromatic ring having 1-4 heteroatoms independently selected from nitrogen, oxygen, or sulfur. In some embodiments, Hy is an 8-10 membered bicyclic heteroaromatic ring having 1-5 heteroatoms independently selected from nitrogen, oxygen, or sulfur. In some embodiments, Hy is oxazolyl.

In some embodiments, $R^1$ and $R^2$ are taken together to form an optionally substituted 4-7 membered partially unsaturated carbocyclic ring. In some embodiments, $R^1$ and $R^2$ are taken together to form an optionally substituted 4-7 membered partially unsaturated carbocyclo-, or heterocyclo-, benzo-, or 5-6 membered heteroarylo-fused ring;

As defined generally above, $R^3$ is hydrogen, halogen, —CN, —OR, —SR, —N(R)$_2$, —N(R)C(O)R, —C(O)N(R)$_2$, —C(O)N(R)S(O)$_2$R, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, —SO$_2$R, —B(OH)$_2$ or an optionally substituted ring selected from phenyl or 5-6 membered heteroaryl having 1-4 heteroatoms independently selected from nitrogen, oxygen, or sulfur. In certain embodiments, $R^3$ is —CN, —OR, —C(O)OR, —C(O)N(R)$_2$, —SO$_2$R, or an optionally substituted ring selected from phenyl or a 5-6 membered heteroaryl having 1-4 heteroatoms independently selected from nitrogen, oxygen, or sulfur. In some embodiments, $R^3$ is —OR. In some embodiments, $R^3$ is —C(O)OR. In some embodiments, $R^3$ is phenyl or tetrazolyl.

As defined generally above, each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring; a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur.

In certain embodiments, each R is independently hydrogen or an optionally substituted group selected from $C_{1-6}$ aliphatic, 3-8 membered unsaturated or partially unsaturated monocyclic carbocyclic ring. In some embodiments, each R is independently hydrogen or optionally substituted $C_{1-6}$ aliphatic.

As defined generally above, each of $L^1$ and $L^2$ is independently a covalent bond or an optionally substituted 1-6 membered straight or branched bivalent hydrocarbon chain, or a cyclopropylenyl, cyclobutylenyl, or oxetanyl group. In certain embodiments, $L^1$ is a $C_{1-3}$ straight or branched bivalent hydrocarbon chain. In some embodiments, $L^1$ is a straight or branched bivalent $C_2$ hydrocarbon chain. In some embodiments $L^1$ is a straight or branched bivalent $C_3$ hydrocarbon chain. In some embodiments, $L^1$ is a cyclopropylenyl, cyclobutylenyl, or oxetanyl group.

In some embodiments, $L^2$ is an optionally substituted $C_{1-3}$ straight or branched hydrocarbon chain. In some embodiments $L^2$ is an optionally substituted $C_2$ straight hydrocarbon chain. In some embodiments $L^2$ is an optionally substituted $C_3$ straight or branched hydrocarbon chain.

As defined generally above, $R^4$ is hydrogen or an optionally substituted ring selected from a 3-8 membered monocyclic saturated or partially unsaturated carbocyclic ring, a 4-8 membered monocyclic saturated or partially unsaturated heterocyclic ring having 1-2 heteroatoms independently selected from nitrogen, oxygen, or sulfur, phenyl, an 8-10 membered bicyclic aryl ring, a 5-6 membered monocyclic heteroaryl ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur.

In certain embodiments, $R^4$ is hydrogen. In some embodiments, $R^4$ is an optionally substituted 5-6 membered monocyclic saturated or partially unsaturated ring. In some embodiments $R^4$ is an optionally substituted 5-6 membered monocyclic saturated or partially unsaturated heterocyclic ring having 1-2 heteroatoms independently selected from nitrogen, oxygen, or sulfur. In some embodiments, $R^4$ is optionally substituted phenyl. In some embodiments $R^4$ is an optionally substituted 10 membered bicyclic aryl ring. In some embodiments, $R^4$ is an optionally substituted 5-6 membered monocyclic heteroaryl ring having 1-4 heteroatoms independently selected from nitrogen, oxygen, or sulfur. In some embodiments, $R^4$ is an optionally substituted 8-10 membered bicyclic heteroaryl ring having 1-4 heteroatoms independently selected from nitrogen, oxygen, or sulfur.

In certain embodiments, the present invention provides a compound of formula II:

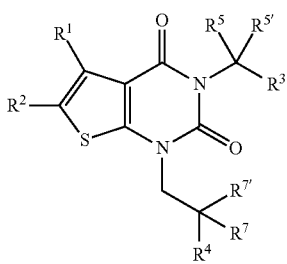

II or a pharmaceutically acceptable salt thereof, wherein:

$R^1$ is hydrogen or $C_{1-4}$ aliphatic, optionally substituted with one or more halogen, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, or —SO$_2$R;

$R^2$ is halogen, —R, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, or —SO$_2$R, or Hy, where Hy is selected from 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; or $R^1$ and $R^2$ are taken together to form an optionally substituted 4-7 membered partially unsaturated carbocyclo-, or heterocyclo-, benzo-, or 5-6 membered heteroarylo-fused ring;

each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring; a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

$R^3$ is hydrogen, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, —SO$_2$R, —B(OH)$_2$, or an optionally substituted ring selected from phenyl or 5-6 membered heteroaryl having 1-4 heteroatoms independently selected from nitrogen, oxygen, or sulfur;

$R^4$ is an optionally substituted phenyl or naphthyl ring;

each of $R^5$ and $R^{5'}$ is independently —R, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, or —SO$_2$R; or $R^5$ and $R^{5'}$ are taken together to form a cyclopropylenyl, cyclobutylenyl, or oxetanyl group; and each of $R^7$ and $R^{7'}$ is independently hydrogen, —R, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, or —SO$_2$R; or $R^7$ and $R^{7'}$ are taken together to form a 3-8 membered saturated or partially unsaturated monocyclic carbocyclic ring, or a 4-8 membered saturated or partially unsaturated monocyclic heterocyclic ring having 1-2 heteroatoms independently selected from nitrogen, oxygen, or sulfur.

As defined generally above, each of $R^5$ and $R^{5'}$ is independently —R, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, or —SO$_2$R; or $R^5$ and $R^{5'}$ are taken together to form a cyclopropylenyl, cyclobutylenyl, or oxetanyl group.

In some embodiments, each of $R^5$ and $R^{5'}$ is —R, wherein —R is not hydrogen. In some embodiments, each of $R^5$ and $R^{5'}$ is methyl. In some embodiments, $R^5$ and $R^{5'}$ are taken together to form a cyclopropylenyl, cyclobutylenyl, or oxetanyl group. In some embodiments, $R^5$ and $R^{5'}$ are taken together to form a cyclobutylenyl group.

As defined generally above, each of $R^7$ and $R^{7'}$ is independently hydrogen, —R, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, or —SO$_2$R; or $R^7$ and $R^{7'}$ are taken together to form a 3-8 membered saturated or partially unsaturated monocyclic carbocyclic ring, or a 4-8 membered saturated or partially unsaturated monocyclic heterocyclic ring having 1-2 heteroatoms independently selected from nitrogen, oxygen, or sulfur.

In certain embodiments, one of $R^7$ and $R^{7'}$ is hydrogen, and the other is —OR. In some embodiments one of $R^7$ and $R^{7'}$ is hydrogen, and the other is isopropoxy. In some embodiments $R^7$ and $R^{7'}$ are taken together to form a 3-6 membered saturated or partially unsaturated monocyclic carbocyclic ring. In some embodiments $R^7$ and $R^{7'}$ are taken together to form a 4-6 membered saturated or partially unsaturated monocyclic heterocyclic ring having 1-2 heteroatoms independently selected from nitrogen, oxygen, or sulfur. In some embodiments, one of $R^7$ and $R^{7'}$ is hydrogen and the other is —OR, where R in this instance is a 4-7 membered saturated heterocyclic ring containing 1-2 heteroatoms independently selected from nitrogen, oxygen and sulfur. In some embodiments, one of $R^7$ and $R^{7'}$ is hydrogen and the other is —OR, where R in this instance is oxetane, tetrahydrofuran, or tetrahydropyran.

In certain embodiments, the present invention provides a compound of formula II, wherein each variable is as described in embodiments for formula I, supra, or described in embodiments herein, both singly and in combination.

In certain embodiments, the present invention provides a compound of formula III:

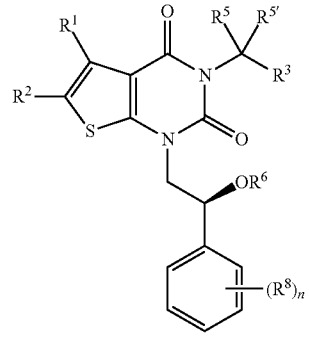

or a pharmaceutically acceptable salt thereof, wherein:
$R^1$ is hydrogen or $C_{1-4}$ aliphatic, optionally substituted with one or more halogen, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, or —SO$_2$R;
$R^2$ is halogen, —R, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, or —SO$_2$R; or $R^1$ and $R^2$ are taken together to form an optionally substituted 4-7 membered partially unsaturated carbocyclo-, or heterocyclo-, benzo-, or 5-6 membered heteroarylo-fused ring;
each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring; a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;
$R^3$ is hydrogen, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, —SO$_2$R, —B(OH)$_2$, or an optionally substituted ring selected from phenyl or 5-6 membered heteroaryl having 1-4 heteroatoms independently selected from nitrogen, oxygen, or sulfur;
each of $R^5$ and $R^{5'}$ is independently —R, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, or —SO$_2$R; or $R^5$ and $R^{5'}$ are taken together to form a cyclopropylenyl, cyclobutylenyl, or oxetanyl group;
$R^6$ is —R, —C(O)N(R)$_2$, or —C(O)R;
each $R^8$ is independently selected from halogen, —R, —OR, —SR, —N(R)$_2$ or deuterium; and
n is 0-5.

In certain embodiments, the present invention provides a compound of formula III, wherein each variable is as described in embodiments for formula I or II, supra.

In certain embodiments $R^6$ is hydrogen. In certain embodiments, $R^6$ is isopropyl.

As defined generally above, each In certain embodiments, each $R^8$ is independently selected from halogen, —R, —OR, —SR, —N(R)$_2$ or deuterium. In certain embodiments, each $R^8$ is halogen.

As defined generally above, n is 0-5. In certain embodiments, n is 0. In some embodiments, n is 1-2.

In certain embodiments, the present invention provides a compound of formula IV:

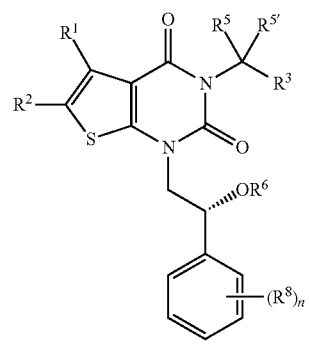

or a pharmaceutically acceptable salt thereof, wherein:
$R^1$ is hydrogen or $C_{1-4}$ aliphatic, optionally substituted with one or more halogen, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$RN(R)$_2$, —C(O)R, —C(O)OR, —OC(O)R, —C(O)OR, —S(O)R, or —SO$_2$R;
$R^2$ is halogen, —R, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, or —SO$_2$R; or $R^1$ and $R^2$ are taken together to form an optionally substituted 4-7 membered partially unsaturated carbocyclo-, or heterocyclo-, benzo-, or 5-6 membered heteroarylo-fused ring;
each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring; a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;
$R^3$ is hydrogen, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, —SO$_2$R, —B(OH)$_2$, or an optionally substituted ring selected from phenyl or 5-6 membered heteroaryl having 1-4 heteroatoms independently selected from nitrogen, oxygen, or sulfur;
each of $R^5$ and $R^{5'}$ is independently —R, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, or —SO$_2$R or $R^5$ and $R^{5'}$ are taken together to form a cyclopropylenyl, cyclobutylenyl, or oxetanyl group; and
$R^6$ is —R, —C(O)N(R)$_2$, or —C(O)R;
each $R^8$ is independently selected from halogen, —R, —OR, —SR, —N(R)$_2$ or deuterium; and
n is 0-5.

In certain embodiments, the present invention provides a compound of formula IV, wherein each variable is as described in embodiments for formula I or II, supra.

In certain embodiments, the present invention provides a compound of formula V-i or V-ii:

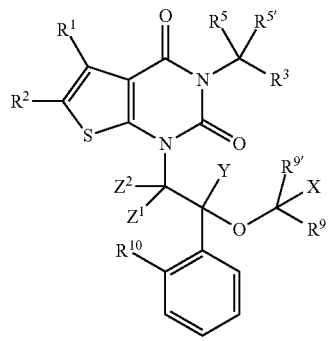

V-i

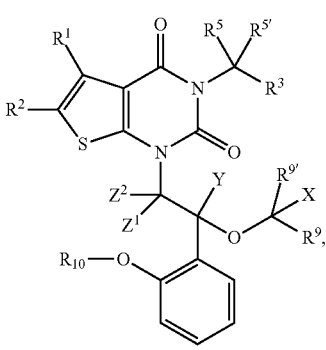

V-ii or a pharmaceutically acceptable salt thereof, wherein $R^2$, $R^3$, $R^5$, $R^{5'}$, are as described in embodiments for formula I, supra; and each of $R^1$, $R^9$, and $R^{9'}$ is independently $CH_3$ or $CD_3$;

each of X, Y, $Z^1$, and $Z^2$ is independently H or D; and $R^{10}$ is $CH_3$, $CD_3$, $CH_2CH_3$, $CH(CH_3)_2$, $CH_2CH(CH_3)_2$, $CF_2H$, $CH_2CD_3$, $CD_2CH_3$, or $CD_2CD_3$.

In certain embodiments, the present invention provides a compound of formula I, wherein $R^2$ is Hy, thereby forming a compound of formula VI:

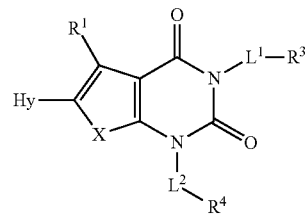

VI or a pharmaceutically acceptable salt thereof, wherein each of X, $L^1$, $L^2$, $R^1$, $R^3$, $R^4$, and Hy is defined above and described in embodiments herein, both singly and in combination.

In certain embodiments, the present invention provides a compound of formula I, wherein $R^2$ is —C(O)OR, thereby forming a compound of formula VII:

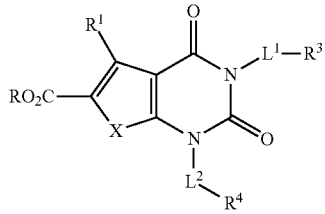

VII or a pharmaceutically acceptable salt thereof, wherein each of X, $L^1$, $L^2$, R, $R^1$, $R^3$, and $R^4$ is defined above and described in embodiments herein, both singly and in combination.

In certain embodiments, the present invention provides a compound of formula II, wherein $R^2$ is Hy, thereby forming a compound of formula VIII:

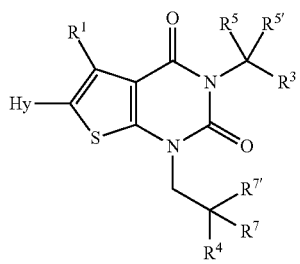

VIII or a pharmaceutically acceptable salt thereof, wherein each of $R^1$, $R^3$, $R^4$, $R^5$, $R^{5'}$, $R^7$, $R^{7'}$, and Hy is defined above and described in embodiments herein, both singly and in combination.

In certain embodiments, the present invention provides a compound of formula II, wherein $R^2$ is —C(O)OR, thereby forming a compound of formula IX:

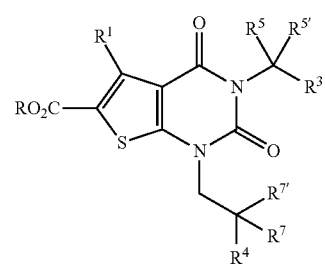

IX or a pharmaceutically acceptable salt thereof, wherein each of R, $R^1$, $R^3$, $R^4$, $R^5$, $R^{5'}$, $R^7$, and $R^{7'}$ is defined above and described in embodiments herein, both singly and in combination.

In certain embodiments, the present invention provides a compound of formula VI, wherein X is S, thereby forming a compound of formula X:

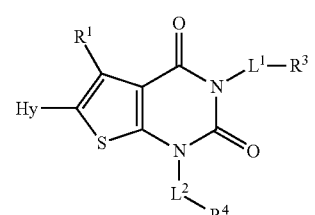

X or a pharmaceutically acceptable salt thereof, wherein each of $L^1$, $L^2$, $R^1$, $R^3$, $R^4$, and Hy is defined above and described in embodiments herein, both singly and in combination.

In certain embodiments, the present invention provides a compound of formula VII, wherein X is S, thereby forming a compound of formula XI:

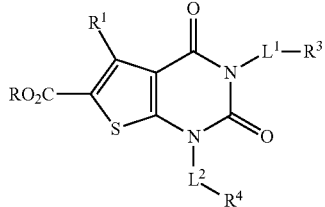

XI or a pharmaceutically acceptable salt thereof, wherein each of $L^1$, $L^2$, R, $R^1$, $R^3$, and $R^4$ is defined above and described in embodiments herein, both singly and in combination.

In certain embodiments, the present invention provides a compound of formula X, wherein $L^1$ is —C($R^5$)($R^{5'}$)—, thereby forming a compound of formula XII:

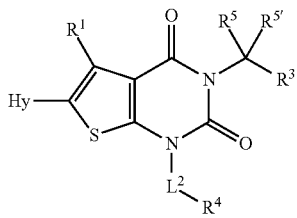

XII or a pharmaceutically acceptable salt thereof, wherein each of $L^2$, $R^1$, $R^3$, $R^4$, $R^5$, $R^{5'}$, and Hy is defined above and described in embodiments herein, both singly and in combination.

In certain embodiments, the present invention provides a compound of formula XI, wherein $L^1$ is —C($R^5$)($R^{5'}$)—, thereby forming a compound of formula XIII:

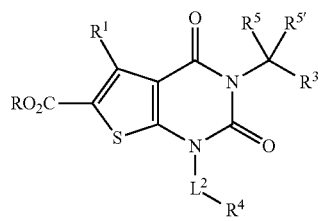

XIII or a pharmaceutically acceptable salt thereof, wherein each of $L^2$, R, $R^1$, $R^3$, $R^4$, $R^5$, $R^{5'}$, and $R^4$ is defined above and described in embodiments herein, both singly and in combination.

In certain embodiments, the present invention provides a compound of formula XIV of the formula:

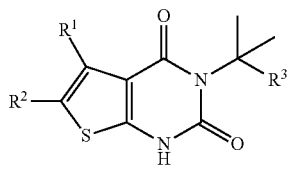

XIV or a pharmaceutically acceptable salt thereof, wherein each of $R^1$, $R^2$, and $R^3$ is defined above and described in embodiments herein, both singly and in combination.

In certain embodiments, the present invention provides a compound of formula XIV, wherein $R^1$ is methyl, and $R^2$ is bromine, thereby forming a compound of formula XV:

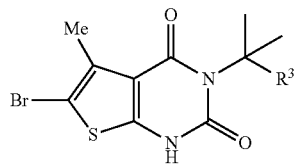

XV or a pharmaceutically acceptable salt thereof, wherein $R^3$ is defined above and described in embodiments herein, both singly and in combination.

In certain embodiments, the present invention provides a compound of formula XIV, wherein $R^1$ is methyl, and $R^2$ is —C(O)OR, thereby forming a compound of formula XVI:

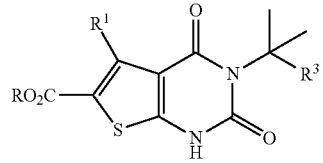

XVI or a pharmaceutically acceptable salt thereof, wherein $R^3$ is defined above and described in embodiments herein, both singly and in combination.

In certain embodiments, the present invention provides a compound of formula XVII of the formula:

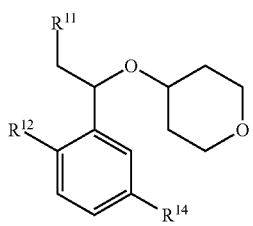

XVII wherein:
$R^{11}$ is selected from the group consisting of —OH, halogen, and —OS(O)$_2$R
$R^{12}$ is —$R^{13}$ or —O$R^{13}$
$R^{13}$ is straight or branched $C_{1-4}$ aliphatic; and
$R^{14}$ is hydrogen or halogen.

In certain embodiments, the present invention provides a compound of formula XVII, wherein $R^{11}$ is —OH, thereby forming a compound of formula XVIII:

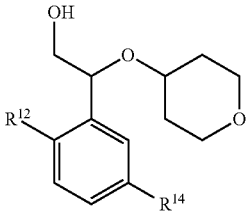

XVIII wherein each of $R^{12}$, $R^{13}$, and $R^{14}$ is defined above for formula XVII and described in embodiments herein, both singly and in combination.

In certain embodiments, the present invention provides a compound of formula XVIII wherein $R^{12}$ is selected from the group consisting of methyl, ethyl, methoxy and ethoxy.

Exemplary compounds of formula I are set forth in Table 1, below:

TABLE 1

Exemplary Compounds of Formula I

| Cmpd # | Compound Structure | m/z |
| --- | --- | --- |
| I-1 | 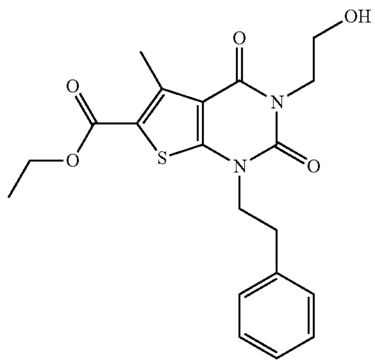 [SMILES: CCOC(=O)c1sc2c(c1C)c(=O)n(CCO)c(=O)n2CCc1ccccc1] | 403 (M + 1) |
| I-2 | 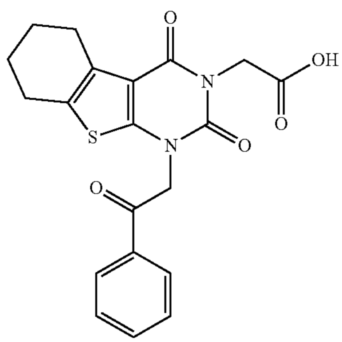 [SMILES: O=C(O)Cn1c(=O)c2c3c(sc2n(CC(=O)c2ccccc2)c1=O)CCCC3] | 399 (M + 1) |
| I-3 | 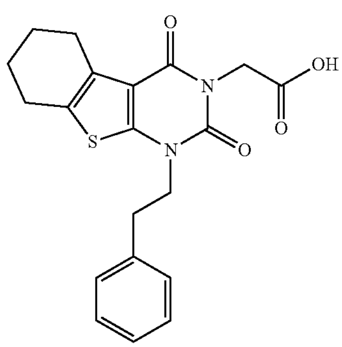 [SMILES: O=C(O)Cn1c(=O)c2c3c(sc2n(CCc2ccccc2)c1=O)CCCC3] | 385 (M + 1) |
| I-4 | 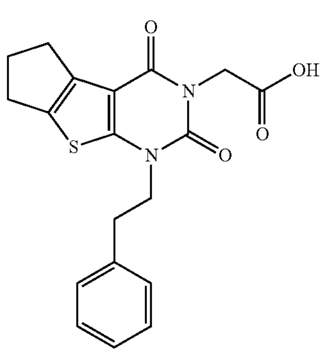 [SMILES: O=C(O)Cn1c(=O)c2c3c(sc2n(CCc2ccccc2)c1=O)CCC3] | 371 (M + 1) |

TABLE 1-continued
Exemplary Compounds of Formula I
| Cmpd # | Compound Structure | m/z |
|---|---|---|
| I-5 | 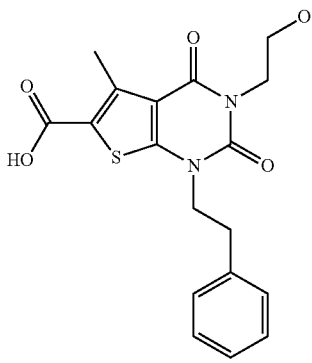 | 375 (M + 1) |
| I-6 | 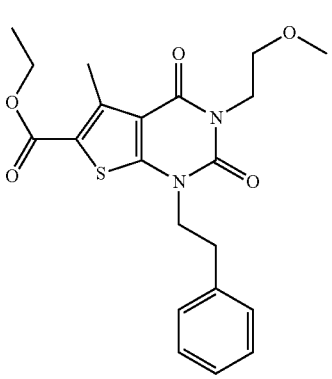 [SMILES: CCOC(=O)c1sc2c(c1C)c(=O)n(CCOC)c(=O)n2CCc1ccccc1] | 417 (M + 1) |
| I-7 | 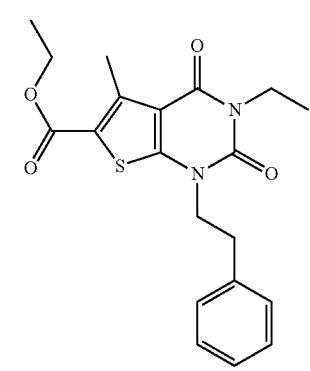 [SMILES: CCOC(=O)c1sc2c(c1C)c(=O)n(CC)c(=O)n2CCc1ccccc1] | 387 (M + 1) |
| I-8 | 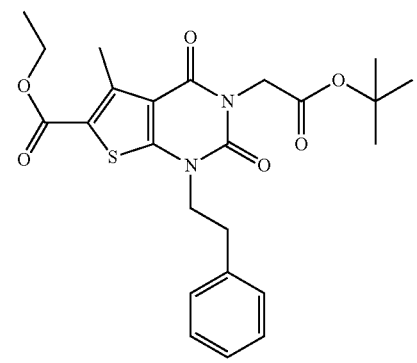 [SMILES: CCOC(=O)c1sc2c(c1C)c(=O)n(CC(=O)OC(C)(C)C)c(=O)n2CCc1ccccc1] | 495 (M + Na) |

TABLE 1-continued

Exemplary Compounds of Formula I

| Cmpd # | Compound Structure | m/z |
| --- | --- | --- |
| I-9 | 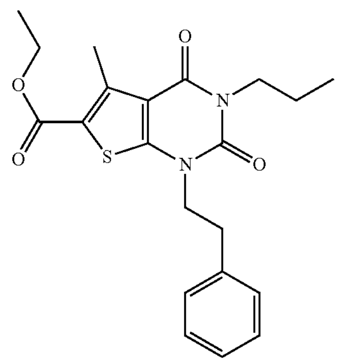 [SMILES: CCCn1c(=O)c2c(C)c(C(=O)OCC)sc2n(CCc2ccccc2)c1=O] | 401 (M + 1) |
| I-10 | 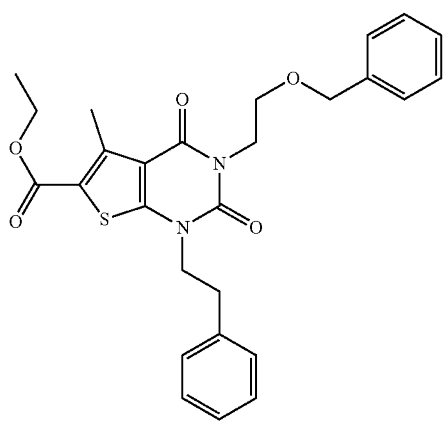 [SMILES: CCOC(=O)c1sc2c(c1C)c(=O)n(CCOCc1ccccc1)c(=O)n2CCc1ccccc1] | 493 (M + 1) |
| I-11 | 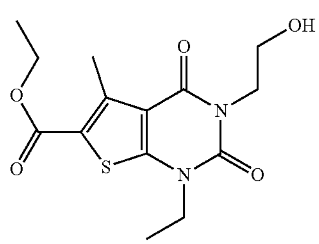 [SMILES: CCOC(=O)c1sc2c(c1C)c(=O)n(CCO)c(=O)n2CC] | 327 (M + 1) |
| I-12 | 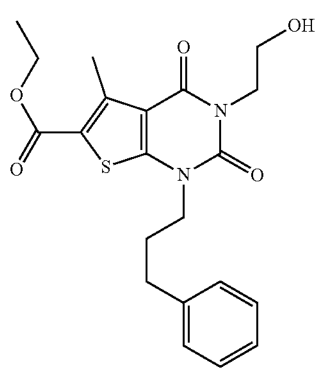 [SMILES: CCOC(=O)c1sc2c(c1C)c(=O)n(CCO)c(=O)n2CCCc1ccccc1] | 417 (M + 1) |

TABLE 1-continued

Exemplary Compounds of Formula I

| Cmpd # | Compound Structure | m/z |
|---|---|---|
| I-13 | 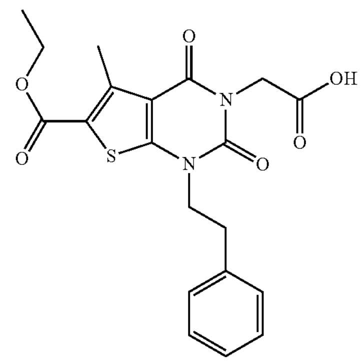 [SMILES: CCOC(=O)c1sc2c(c1C)c(=O)n(CC(=O)O)c(=O)n2CCc1ccccc1] | 417 (M + 1) |
| I-14 | 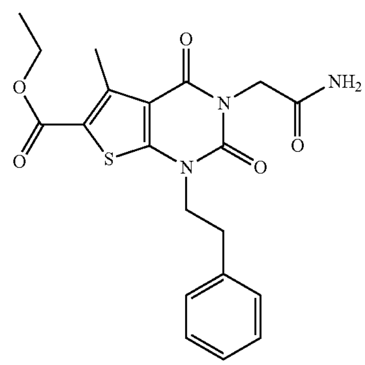 [SMILES: CCOC(=O)c1sc2c(c1C)c(=O)n(CC(N)=O)c(=O)n2CCc1ccccc1] | 416 (M + 1) |
| I-15 | 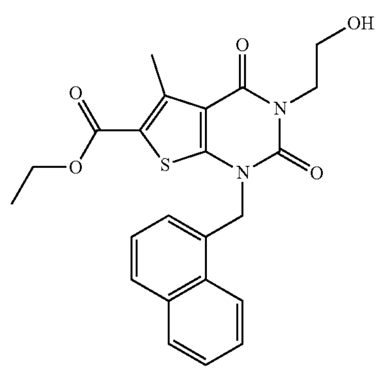 [SMILES: CCOC(=O)c1sc2c(c1C)c(=O)n(CCO)c(=O)n2Cc1cccc2ccccc12] | 439 (M + 1) |
| I-16 | 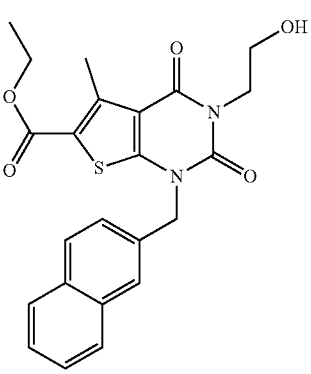 [SMILES: CCOC(=O)c1sc2c(c1C)c(=O)n(CCO)c(=O)n2Cc1ccc2ccccc2c1] | 439 (M + 1) |

TABLE 1-continued

Exemplary Compounds of Formula I

| Cmpd # | Compound Structure | m/z |
|---|---|---|
| I-17 | 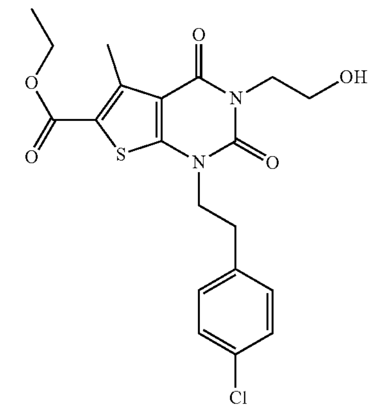 [SMILES: CCOC(=O)c1sc2c(c1C)c(=O)n(CCO)c(=O)n2CCc1ccc(Cl)cc1] | 437 (M + 1) |
| I-18 | 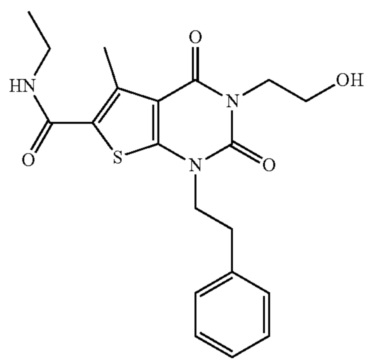 [SMILES: CCNC(=O)c1sc2c(c1C)c(=O)n(CCO)c(=O)n2CCc1ccccc1] | 402 (M + 1) |
| I-19 | 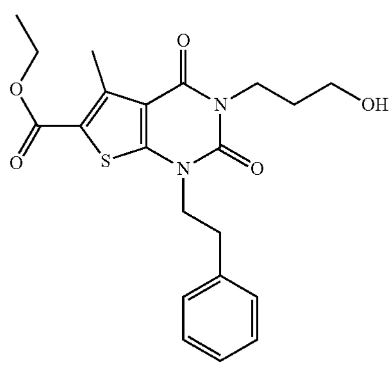 [SMILES: CCOC(=O)c1sc2c(c1C)c(=O)n(CCCO)c(=O)n2CCc1ccccc1] | 417 (M + 1) |
| I-20 | 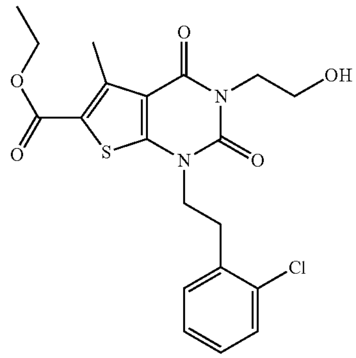 [SMILES: CCOC(=O)c1sc2c(c1C)c(=O)n(CCO)c(=O)n2CCc1ccccc1Cl] | 437 (M + 1) |

TABLE 1-continued

Exemplary Compounds of Formula I

| Cmpd # | Compound Structure | m/z |
|---|---|---|
| I-21 | 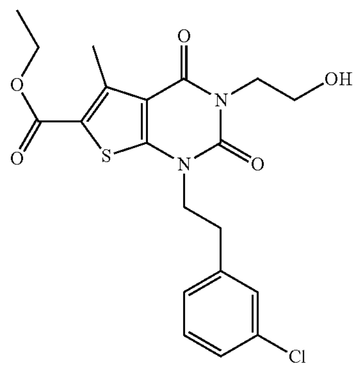 [SMILES: CCOC(=O)c1sc2c(c1C)c(=O)n(CCO)c(=O)n2CCc1cccc(Cl)c1] | 437 (M + 1) |
| I-22 | 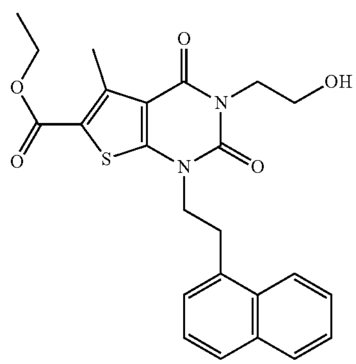 [SMILES: CCOC(=O)c1sc2c(c1C)c(=O)n(CCO)c(=O)n2CCc1cccc2ccccc12] | 453 (M + 1) |
| I-23 | 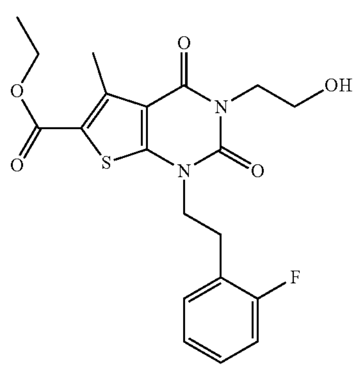 | 421 (M + 1) |
| I-24 | 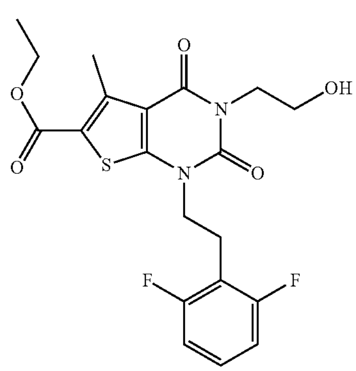 [SMILES: CCOC(=O)c1sc2c(c1C)c(=O)n(CCO)c(=O)n2CCc1c(F)cccc1F] | 439 (M + 1) |

TABLE 1-continued

Exemplary Compounds of Formula I

| Cmpd # | Compound Structure | m/z |
| --- | --- | --- |
| I-25 | 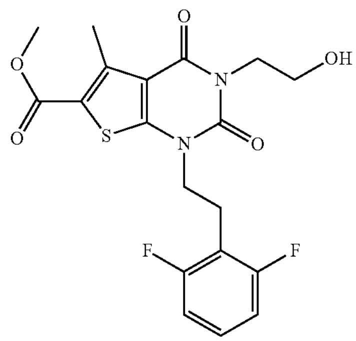 [SMILES: COC(=O)c1sc2c(c1C)c(=O)n(CCO)c(=O)n2CCc1c(F)cccc1F] | 425 (M + 1) |
| I-26 | 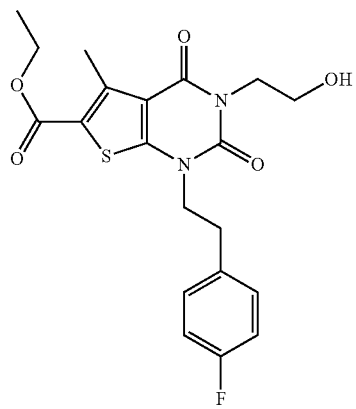 [SMILES: CCOC(=O)c1sc2c(c1C)c(=O)n(CCO)c(=O)n2CCc1ccc(F)cc1] | 421 (M + 1) |
| I-27 | 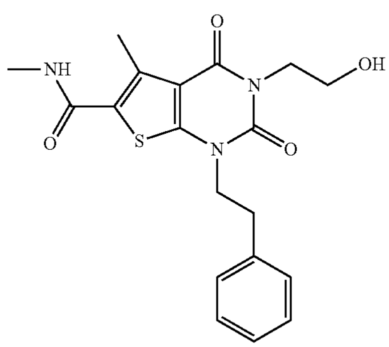 [SMILES: CNC(=O)c1sc2c(c1C)c(=O)n(CCO)c(=O)n2CCc1ccccc1] | 388 (M + 1) |
| I-28 | 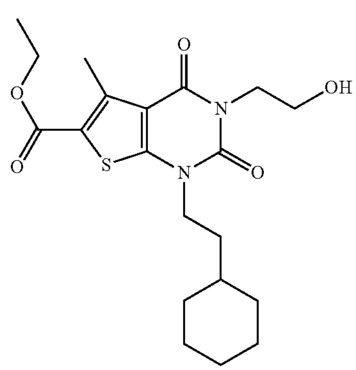 [SMILES: CCOC(=O)c1sc2c(c1C)c(=O)n(CCO)c(=O)n2CCC1CCCCC1] | 409 (M + 1) |

TABLE 1-continued
Exemplary Compounds of Formula I
| Cmpd # | Compound Structure | m/z |
|---|---|---|
| I-29 | 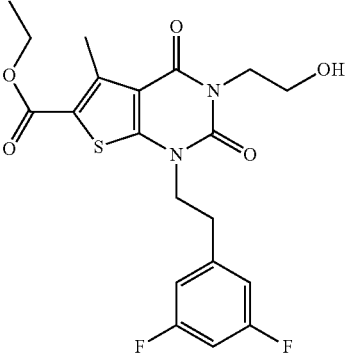 | 439 (M + 1) |
| I-30 | 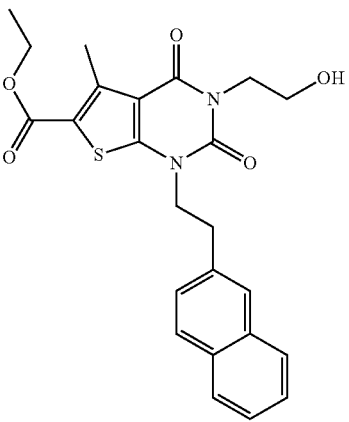 [SMILES: CCOC(=O)c1sc2c(c1C)c(=O)n(CCO)c(=O)n2CCc1ccc2ccccc2c1] | 453 (M + 1) |
| I-31 | 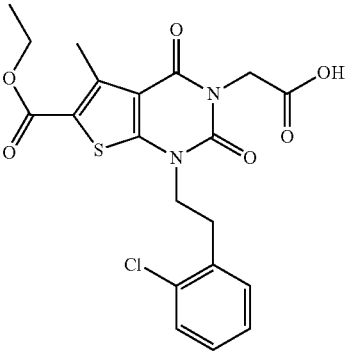 [SMILES: CCOC(=O)c1sc2c(c1C)c(=O)n(CC(=O)O)c(=O)n2CCc1ccccc1Cl] | 451 (M + 1) |
| I-32 | 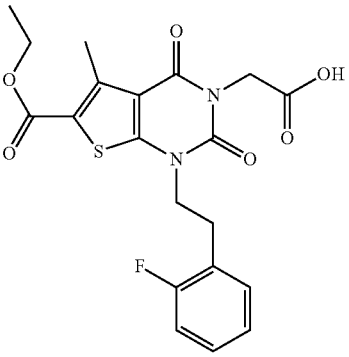 | 435 (M + 1) |

TABLE 1-continued

Exemplary Compounds of Formula I

| Cmpd # | Compound Structure | m/z |
| --- | --- | --- |
| I-33 | 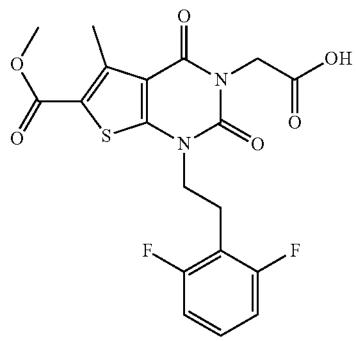 | 453 (M + 1) |
| I-34 | 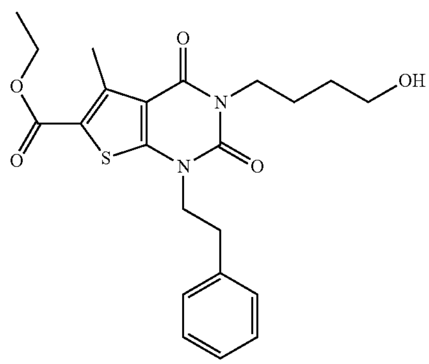 [SMILES: CCOC(=O)c1sc2c(c1C)c(=O)n(CCCCO)c(=O)n2CCc1ccccc1] | 431 (M + 1) |
| I-35 | 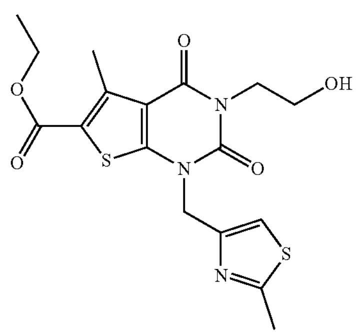 [SMILES: CCOC(=O)c1sc2c(c1C)c(=O)n(CCO)c(=O)n2Cc1csc(C)n1] | 410 (M + 1) |
| I-36 | 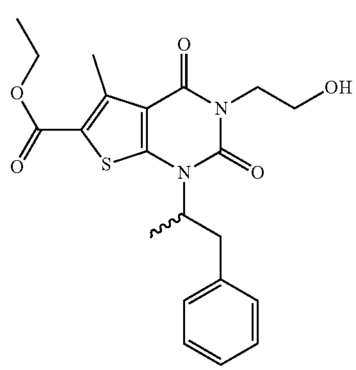 [SMILES: CCOC(=O)c1sc2c(c1C)c(=O)n(CCO)c(=O)n2C(C)Cc1ccccc1] | 417 (M + 1) |

TABLE 1-continued

Exemplary Compounds of Formula I

| Cmpd # | Compound Structure | m/z |
|---|---|---|
| I-37 | 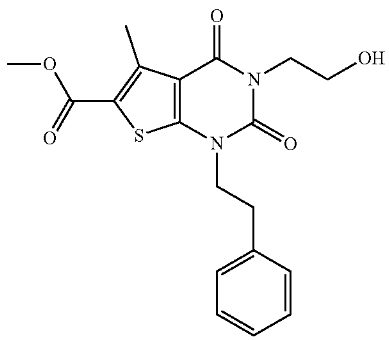 [SMILES: COC(=O)c1sc2c(c1C)c(=O)n(CCO)c(=O)n2CCc1ccccc1] | 389 (M + 1) |
| I-38 | 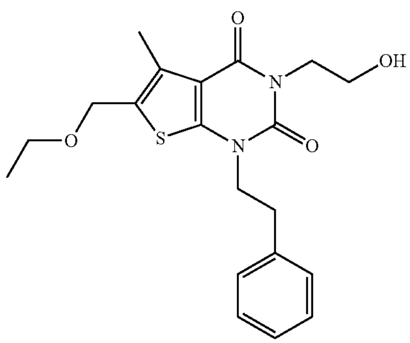 [SMILES: CCOCc1sc2c(c1C)c(=O)n(CCO)c(=O)n2CCc1ccccc1] | 389 (M + 1) |
| I-39 | 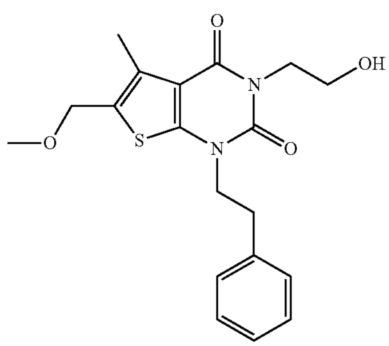 [SMILES: COCc1sc2c(c1C)c(=O)n(CCO)c(=O)n2CCc1ccccc1] | 375 (M + 1) |
| I-40 | 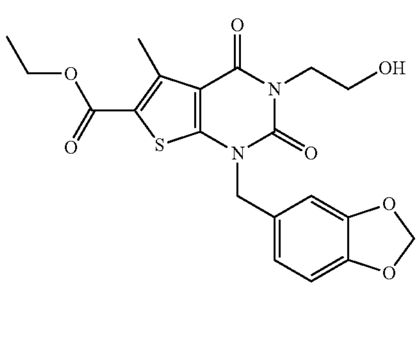 [SMILES: CCOC(=O)c1sc2c(c1C)c(=O)n(CCO)c(=O)n2Cc1ccc2c(c1)OCO2] | 433 (M + 1) |

TABLE 1-continued

Exemplary Compounds of Formula I

| Cmpd # | Compound Structure | m/z |
|---|---|---|
| I-41 | 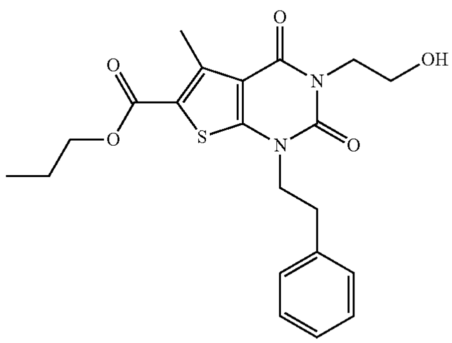 [SMILES: CCCOC(=O)c1sc2c(c1C)c(=O)n(CCO)c(=O)n2CCc1ccccc1] | 417 (M + 1) |
| I-42 | 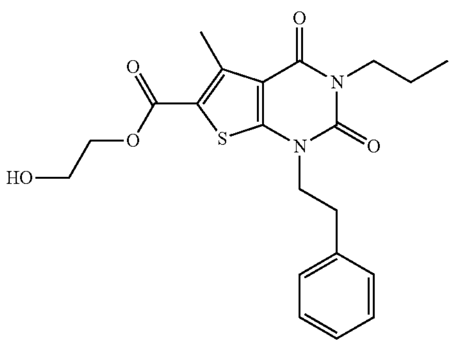 [SMILES: CCCn1c(=O)c2c(C)c(C(=O)OCCO)sc2n(CCc2ccccc2)c1=O] | 419 (M + 1) |
| I-43 | 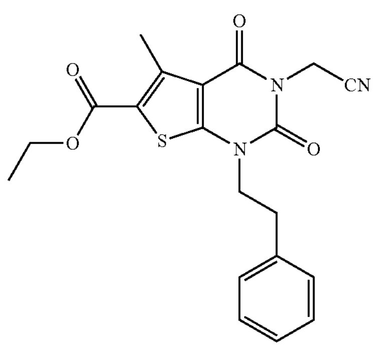 [SMILES: CCOC(=O)c1sc2c(c1C)c(=O)n(CC#N)c(=O)n2CCc1ccccc1] | 398 (M + 1) |
| I-44 | 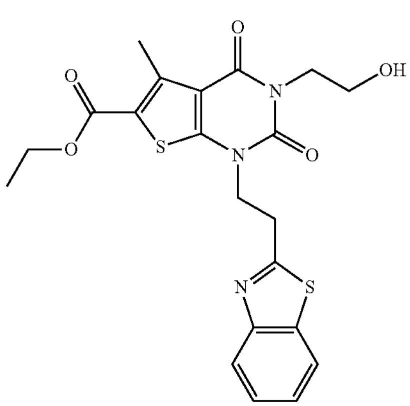 [SMILES: CCOC(=O)c1sc2c(c1C)c(=O)n(CCO)c(=O)n2CCc1nc2ccccc2s1] | 460 (M + 1) |

TABLE 1-continued

Exemplary Compounds of Formula I

| Cmpd # | Compound Structure | m/z |
|---|---|---|
| I-45 | 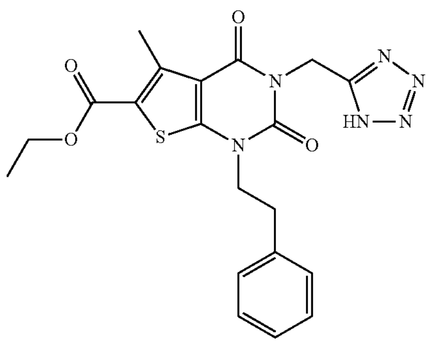 [SMILES: CCOC(=O)c1sc2c(c1C)c(=O)n(Cc1nnn[nH]1)c(=O)n2CCc1ccccc1] | 441 (M + 1) |
| I-46 | 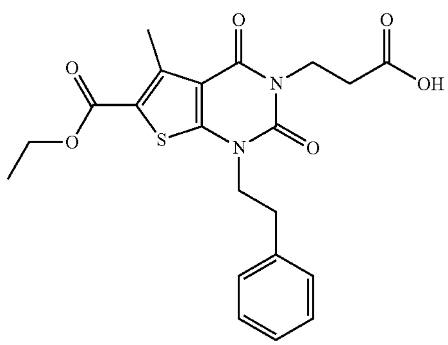 [SMILES: CCOC(=O)c1sc2c(c1C)c(=O)n(CCC(=O)O)c(=O)n2CCc1ccccc1] | 431 (M + 1) |
| I-47 | 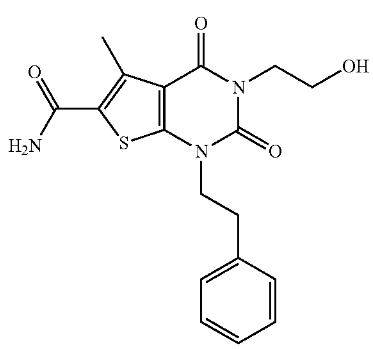 [SMILES: Cc1c(C(N)=O)sc2c1c(=O)n(CCO)c(=O)n2CCc1ccccc1] | 374 (M + 1) |
| I-48 | 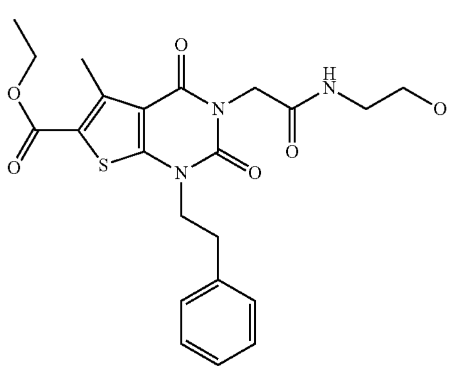 [SMILES: CCOC(=O)c1sc2c(c1C)c(=O)n(CC(=O)NCCO)c(=O)n2CCc1ccccc1] | 460 (M + 1) |

TABLE 1-continued

Exemplary Compounds of Formula I

| Cmpd # | Compound Structure | m/z |
|---|---|---|
| I-49 | 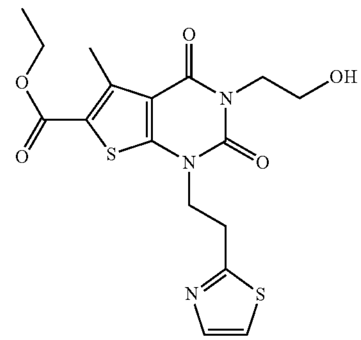 [SMILES: CCOC(=O)c1sc2c(c1C)c(=O)n(CCO)c(=O)n2CCc1nccs1] | 410 (M + 1) |
| I-50 | 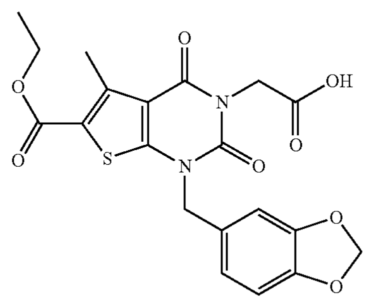 [SMILES: CCOC(=O)c1sc2c(c1C)c(=O)n(CC(=O)O)c(=O)n2Cc1ccc2c(c1)OCO2] | 447 (M + 1) |
| I-51 | 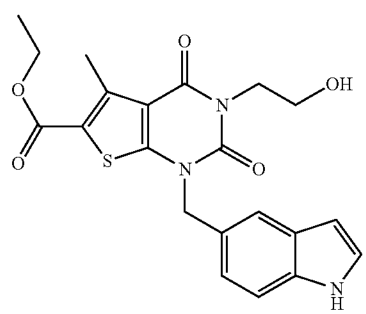 [SMILES: CCOC(=O)c1sc2c(c1C)c(=O)n(CCO)c(=O)n2Cc1ccc2[nH]ccc2c1] | 428 (M + 1) |
| I-52 | 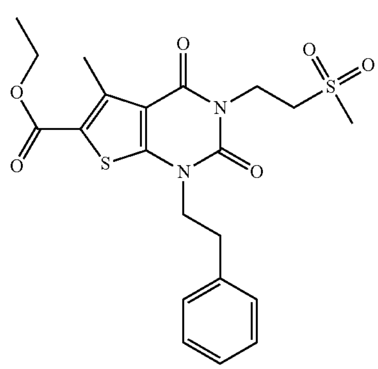 [SMILES: CCOC(=O)c1sc2c(c1C)c(=O)n(CCS(C)(=O)=O)c(=O)n2CCc1ccccc1] | 465 (M + 1) |

TABLE 1-continued

Exemplary Compounds of Formula I

| Cmpd # | Compound Structure | m/z |
| --- | --- | --- |
| I-53 | 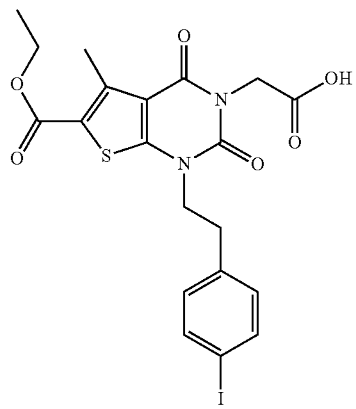 [SMILES: CCOC(=O)c1sc2c(c1C)c(=O)n(CC(=O)O)c(=O)n2CCc1ccc(I)cc1] | 543 (M + 1) |
| I-54 | 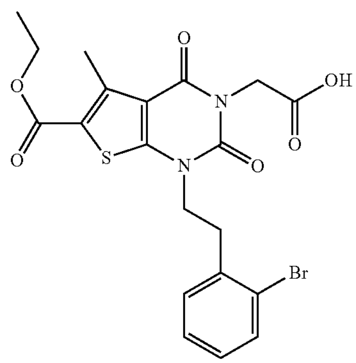 [SMILES: CCOC(=O)c1sc2c(c1C)c(=O)n(CC(=O)O)c(=O)n2CCc1ccccc1Br] | 495 (M + 1) |
| I-55 | 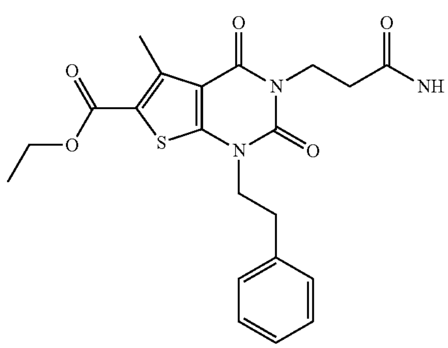 [SMILES: CCOC(=O)c1sc2c(c1C)c(=O)n(CCC(N)=O)c(=O)n2CCc1ccccc1] | 430 (M + 1) |
| I-56 | 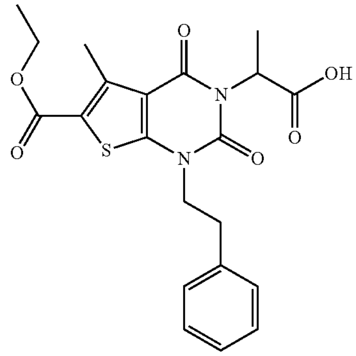 [SMILES: CCOC(=O)c1sc2c(c1C)c(=O)n(C(C)C(=O)O)c(=O)n2CCc1ccccc1] | 431 (M + 1) |

TABLE 1-continued
Exemplary Compounds of Formula I
| Cmpd # | Compound Structure | m/z |
|---|---|---|
| I-57 | 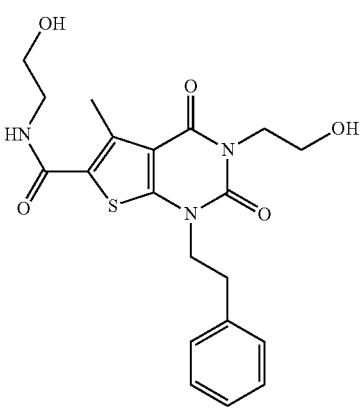 [SMILES: Cc1c(C(=O)NCCO)sc2c1c(=O)n(CCO)c(=O)n2CCc1ccccc1] | 418 (M + 1) |
| I-58 | 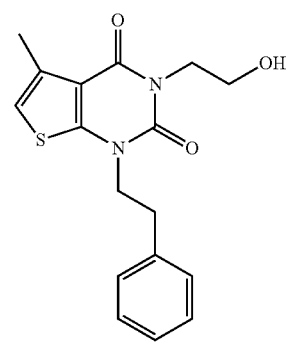 [SMILES: Cc1csc2c1c(=O)n(CCO)c(=O)n2CCc1ccccc1] | 331 (M + 1) |
| I-59 | 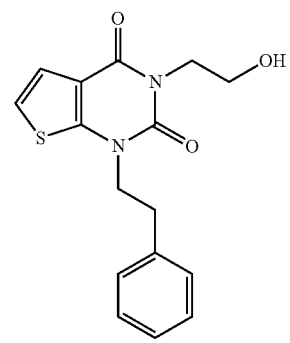 [SMILES: O=c1c2ccsc2n(CCc2ccccc2)c(=O)n1CCO] | 317 (M + 1) |
| I-60 | 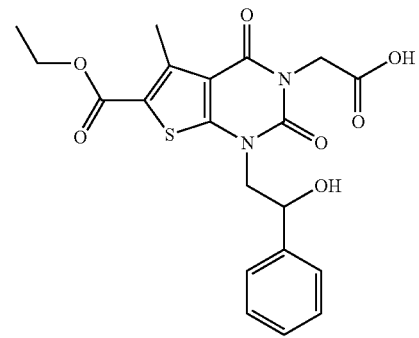 [SMILES: CCOC(=O)c1sc2c(c1C)c(=O)n(CC(=O)O)c(=O)n2CC(O)c1ccccc1] | 433 (M + 1) |

TABLE 1-continued

Exemplary Compounds of Formula I

| Cmpd # | Compound Structure | m/z |
|---|---|---|
| I-61 | 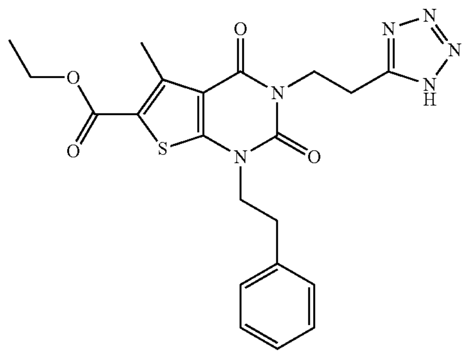 [SMILES: CCOC(=O)c1sc2c(c1C)c(=O)n(CCc1nnn[nH]1)c(=O)n2CCc1ccccc1] | 455 (M + 1) |
| I-62 | 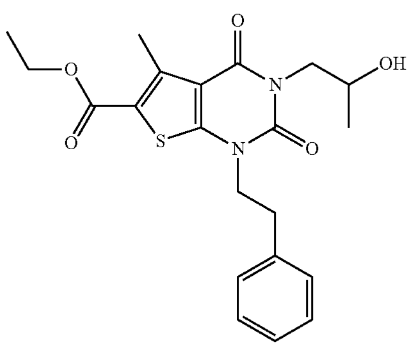 [SMILES: CCOC(=O)c1sc2c(c1C)c(=O)n(CC(C)O)c(=O)n2CCc1ccccc1] | 417 (M + 1) |
| I-63 | 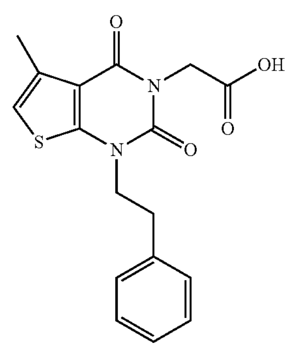 [SMILES: Cc1csc2c1c(=O)n(CC(=O)O)c(=O)n2CCc1ccccc1] | 345 (M + 1) |
| I-64 | 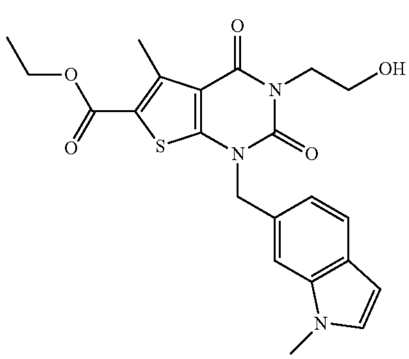 [SMILES: CCOC(=O)c1sc2c(c1C)c(=O)n(CCO)c(=O)n2Cc1ccc2ccn(C)c2c1] | 442 (M + 1) |

TABLE 1-continued

Exemplary Compounds of Formula I

| Cmpd # | Compound Structure | m/z |
| --- | --- | --- |
| I-65 | 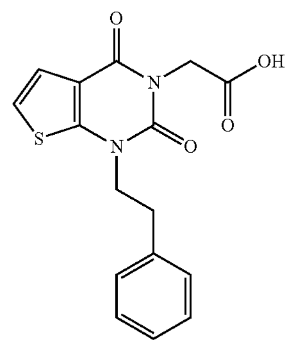 [SMILES: O=C(O)Cn1c(=O)c2ccsc2n(CCc2ccccc2)c1=O] | 331 (M + 1) |
| I-66 | 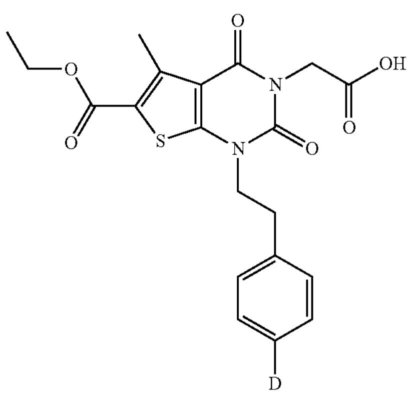 [SMILES: [2H]c1ccc(CCn2c(=O)n(CC(=O)O)c(=O)c3c(C)c(C(=O)OCC)sc32)cc1] | 418 (M + 1) |
| I-67 | 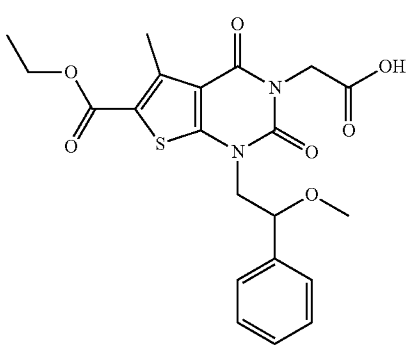 [SMILES: CCOC(=O)c1sc2c(c1C)c(=O)n(CC(=O)O)c(=O)n2CC(OC)c1ccccc1] | 447 (M + 1) |
| I-68 | 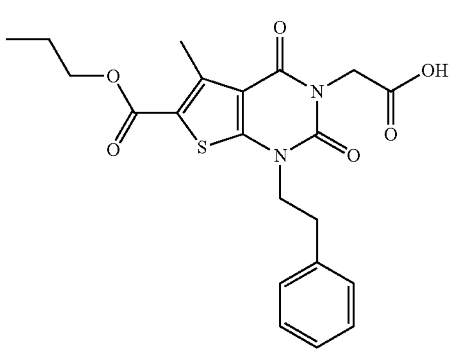 [SMILES: CCCOC(=O)c1sc2c(c1C)c(=O)n(CC(=O)O)c(=O)n2CCc1ccccc1] | 431 (M + 1) |

TABLE 1-continued

Exemplary Compounds of Formula I

| Cmpd # | Compound Structure | m/z |
|---|---|---|
| I-69 | 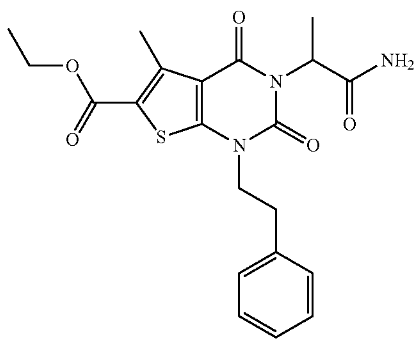 [SMILES: CCOC(=O)c1sc2c(c1C)c(=O)n(C(C)C(N)=O)c(=O)n2CCc1ccccc1] | 430 (M + 1) |
| I-70 | 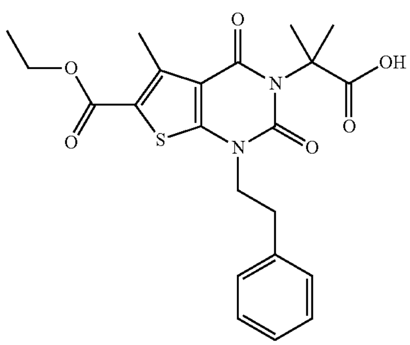 [SMILES: CCOC(=O)c1sc2c(c1C)c(=O)n(C(C)(C)C(=O)O)c(=O)n2CCc1ccccc1] | 445 (M + 1) |
| I-71 | 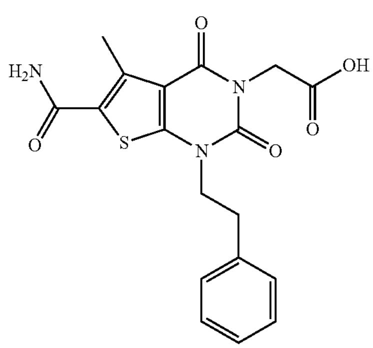 [SMILES: Cc1c(C(N)=O)sc2c1c(=O)n(CC(=O)O)c(=O)n2CCc1ccccc1] | 388 (M + 1) |
| I-72 | 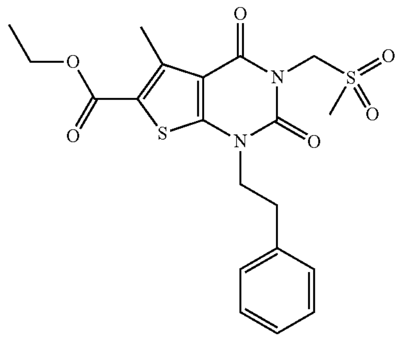 [SMILES: CCOC(=O)c1sc2c(c1C)c(=O)n(CS(C)(=O)=O)c(=O)n2CCc1ccccc1] | 473 (M + Na) |

TABLE 1-continued
Exemplary Compounds of Formula I
| Cmpd # | Compound Structure | m/z |
|---|---|---|
| I-73 | 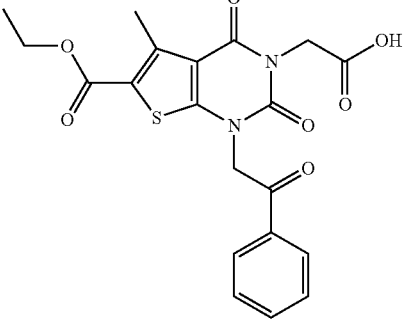 | 431 (M + 1) |
| I-74 | 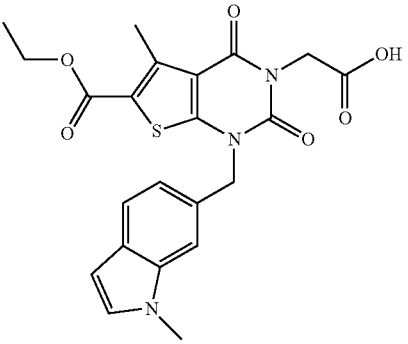 [SMILES: CCOC(=O)c1sc2c(c1C)c(=O)n(CC(=O)O)c(=O)n2Cc1ccc2ccn(C)c2c1] | 456 (M + 1) |
| I-75 | 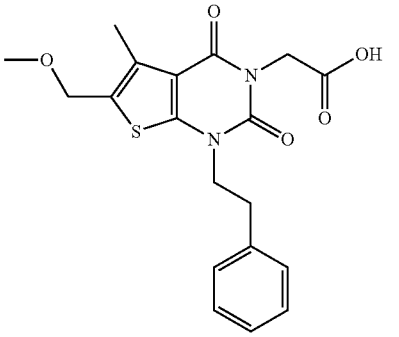 [SMILES: COCc1sc2c(c1C)c(=O)n(CC(=O)O)c(=O)n2CCc1ccccc1] | 389 (M + 1) |
| I-76 | 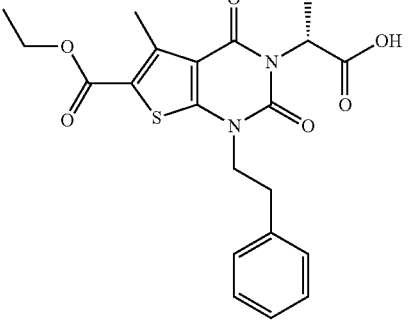 | 431 (M + 1) |

TABLE 1-continued

Exemplary Compounds of Formula I

| Cmpd # | Compound Structure | m/z |
|---|---|---|
| I-77 | 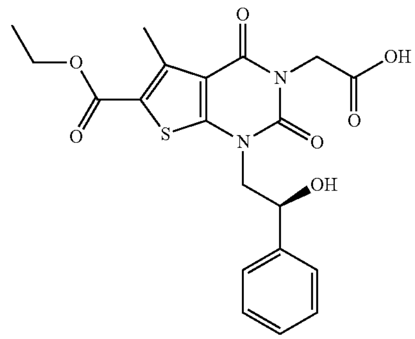 [SMILES: CCOC(=O)c1sc2c(c1C)c(=O)n(CC(=O)O)c(=O)n2C[C@@H](O)c1ccccc1] | 433 (M + 1) |
| I-78 | 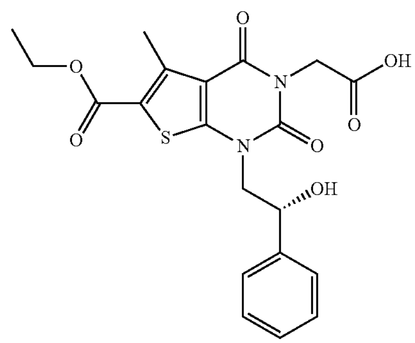 [SMILES: CCOC(=O)c1sc2c(c1C)c(=O)n(CC(=O)O)c(=O)n2C[C@H](O)c1ccccc1] | 433 (M + 1) |
| I-79 | 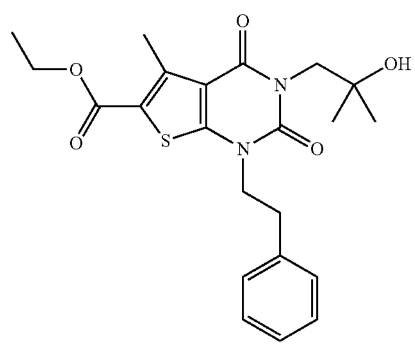 [SMILES: CCOC(=O)c1sc2c(c1C)c(=O)n(CC(C)(C)O)c(=O)n2CCc1ccccc1] | 453 (M + Na) |
| I-80 | 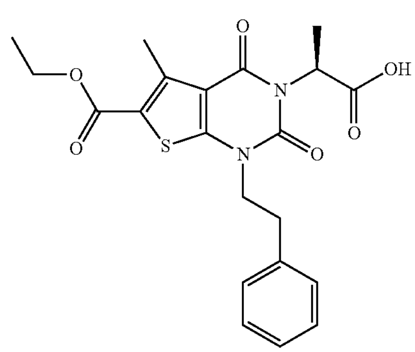 [SMILES: CCOC(=O)c1sc2c(c1C)c(=O)n([C@@H](C)C(=O)O)c(=O)n2CCc1ccccc1] | 431 (M + 1) |

TABLE 1-continued
Exemplary Compounds of Formula I
| Cmpd # | Compound Structure | m/z |
| --- | --- | --- |
| I-81 | 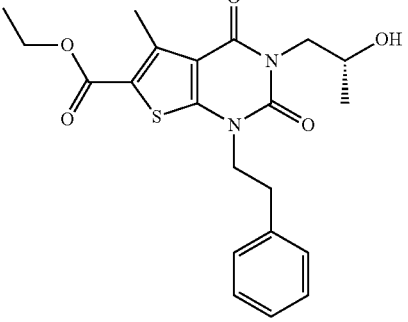 | 417 (M + 1) |
| I-82 | 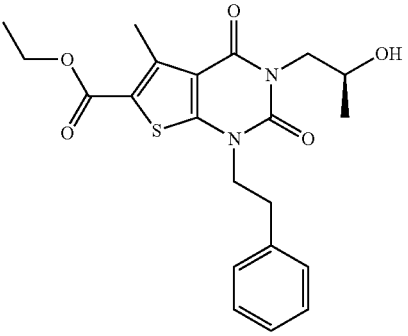 [SMILES: CCOC(=O)c1sc2c(c1C)c(=O)n(C[C@H](C)O)c(=O)n2CCc1ccccc1] | 417 (M + 1) |
| I-83 | 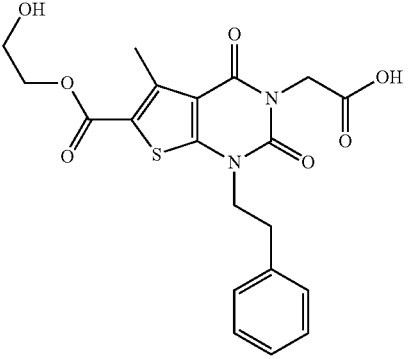 [SMILES: Cc1c(C(=O)OCCO)sc2c1c(=O)n(CC(=O)O)c(=O)n2CCc1ccccc1] | 433 (M + 1) |
| I-84 | 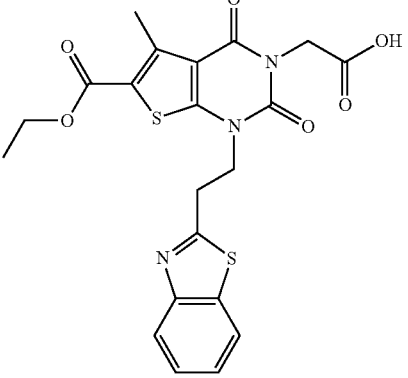 | 474 (M + 1) |

TABLE 1-continued

Exemplary Compounds of Formula I

| Cmpd # | Compound Structure | m/z |
| --- | --- | --- |
| I-85 | 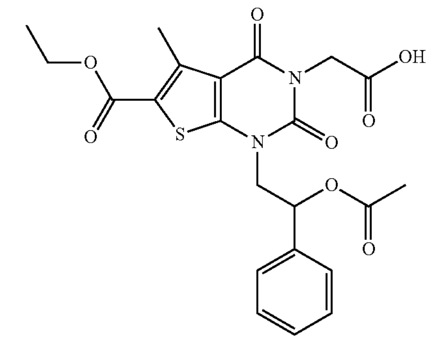 [SMILES: CCOC(=O)c1sc2c(c1C)c(=O)n(CC(=O)O)c(=O)n2CC(OC(C)=O)c1ccccc1] | 475 (M + 1) |
| I-86 | 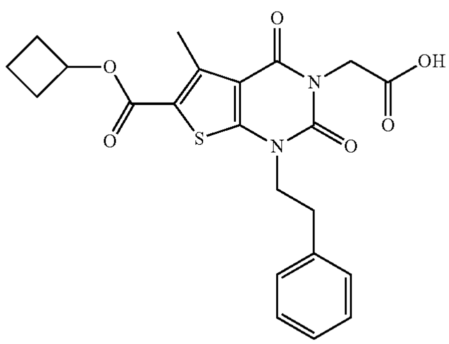 [SMILES: Cc1c(C(=O)OC2CCC2)sc2c1c(=O)n(CC(=O)O)c(=O)n2CCc1ccccc1] | 443 (M + 1) |
| I-87 | 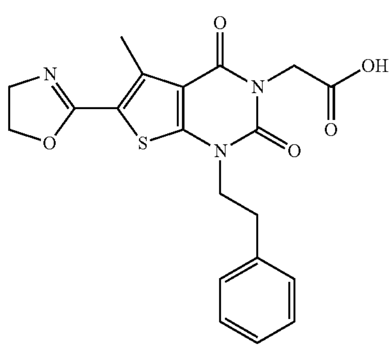 [SMILES: Cc1c(C2=NCCO2)sc2c1c(=O)n(CC(=O)O)c(=O)n2CCc1ccccc1] | 414 (M + 1) |
| I-88 | 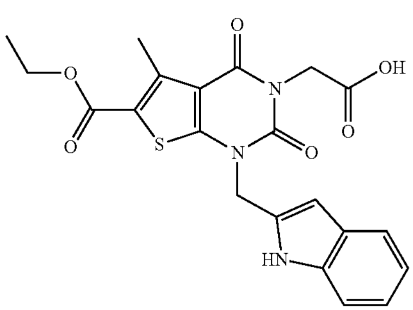 [SMILES: CCOC(=O)c1sc2c(c1C)c(=O)n(CC(=O)O)c(=O)n2Cc1cc2ccccc2[nH]1] | 442 (M + 1) |

TABLE 1-continued

Exemplary Compounds of Formula I

| Cmpd # | Compound Structure | m/z |
|---|---|---|
| I-89 | 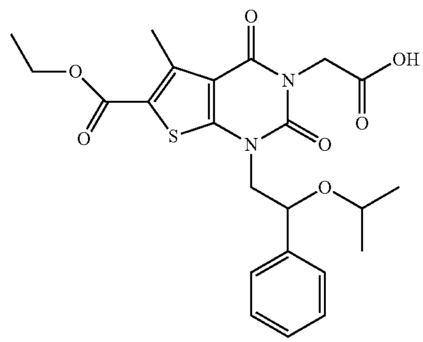 [SMILES: CCOC(=O)c1sc2c(c1C)c(=O)n(CC(=O)O)c(=O)n2CC(OC(C)C)c1ccccc1] | 475 (M + 1) |
| I-90 | 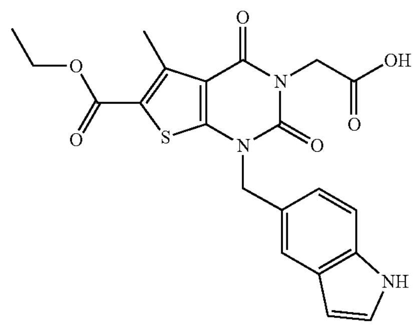 [SMILES: CCOC(=O)c1sc2c(c1C)c(=O)n(CC(=O)O)c(=O)n2Cc1ccc2[nH]ccc2c1] | 442 (M + 1) |
| I-91 | 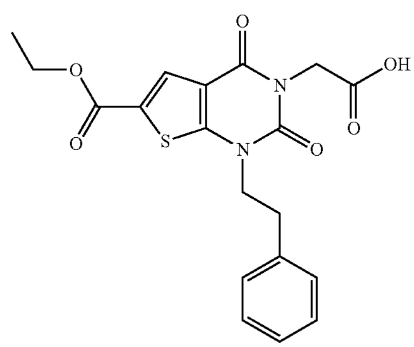 [SMILES: CCOC(=O)c1cc2c(=O)n(CC(=O)O)c(=O)n(CCc3ccccc3)c2s1] | 403 (M + 1) |
| I-92 | 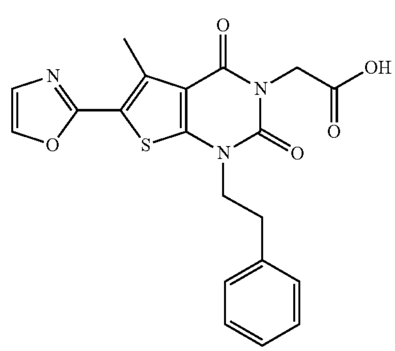 [SMILES: Cc1c(-c2ncco2)sc2c1c(=O)n(CC(=O)O)c(=O)n2CCc1ccccc1] | 412 (M + 1) |

TABLE 1-continued

Exemplary Compounds of Formula I

| Cmpd # | Compound Structure | m/z |
|---|---|---|
| I-93 | 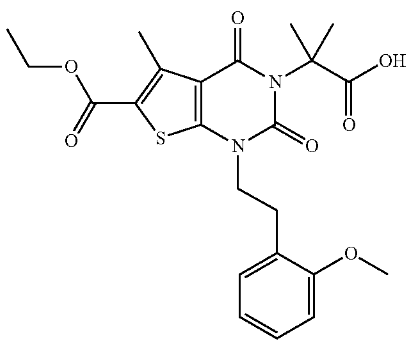 [SMILES: CCOC(=O)c1sc2c(c1C)c(=O)n(C(C)(C)C(=O)O)c(=O)n2CCc1ccccc1OC] | 475 (M + 1) |
| I-94 | 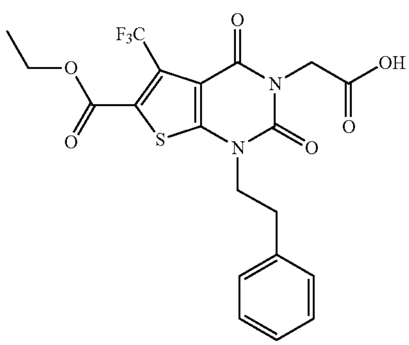 | 471 (M + 1) |
| I-95 | 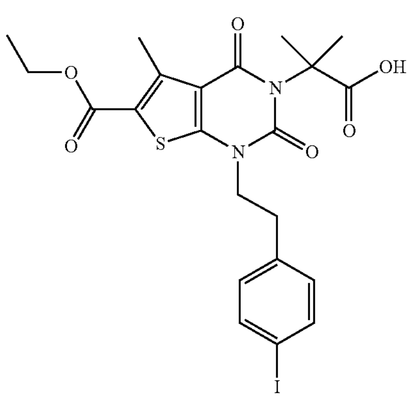 [SMILES: CCOC(=O)c1sc2c(c1C)c(=O)n(C(C)(C)C(=O)O)c(=O)n2CCc1ccc(I)cc1] | 571 (M + 1) |
| I-96 | 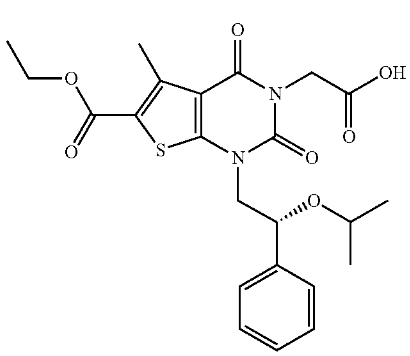 [SMILES: CCOC(=O)c1sc2c(c1C)c(=O)n(CC(=O)O)c(=O)n2C[C@H](OC(C)C)c1ccccc1] | 475 (M + 1) |

TABLE 1-continued
Exemplary Compounds of Formula I
| Cmpd # | Compound Structure | m/z |
|---|---|---|
| I-97 | 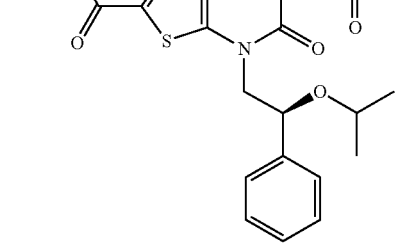 | 475 (M + 1) |
| I-98 | 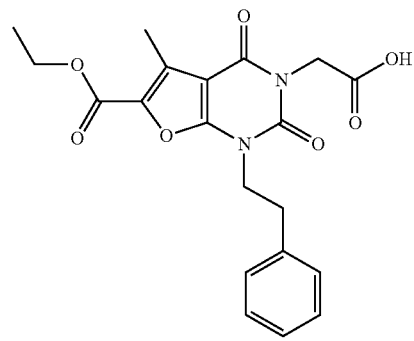 [SMILES: CCOC(=O)c1oc2c(c1C)c(=O)n(CC(=O)O)c(=O)n2CCc1ccccc1] | 400 (M + 1) |
| I-99 | 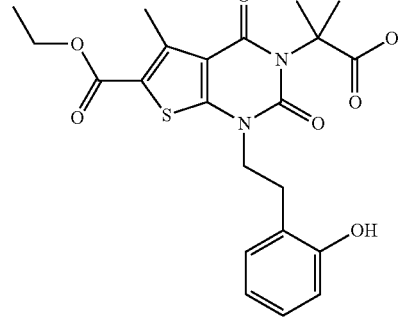 | 461 (M + 1) |
| I-100 | 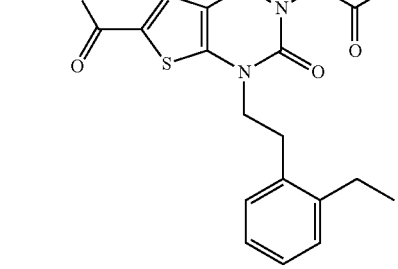 | 473 (M + 1) |

TABLE 1-continued

Exemplary Compounds of Formula I

| Cmpd # | Compound Structure | m/z |
| --- | --- | --- |
| I-101 | 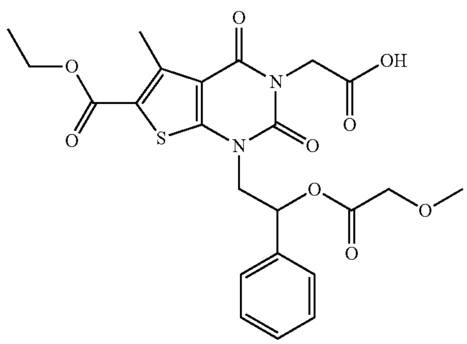 [SMILES: CCOC(=O)c1sc2c(c1C)c(=O)n(CC(=O)O)c(=O)n2CC(OC(=O)COC)c1ccccc1] | 527 (M + Na) |
| I-102 | 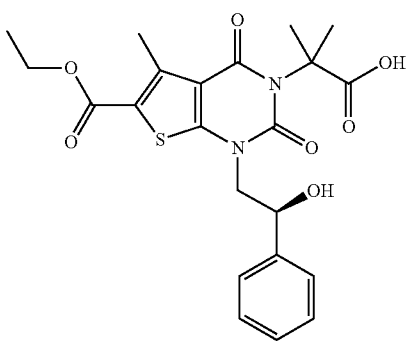 [SMILES: CCOC(=O)c1sc2c(c1C)c(=O)n(C(C)(C)C(=O)O)c(=O)n2C[C@@H](O)c1ccccc1] | 461 (M + 1) |
| I-103 | 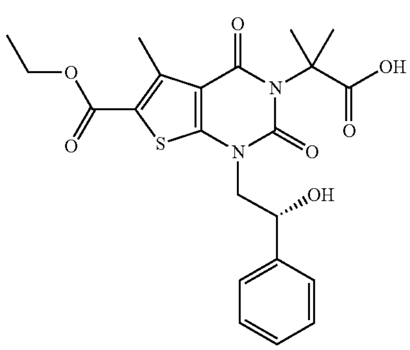 [SMILES: CCOC(=O)c1sc2c(c1C)c(=O)n(C(C)(C)C(=O)O)c(=O)n2C[C@H](O)c1ccccc1] | 461 (M + 1) |
| I-104 | 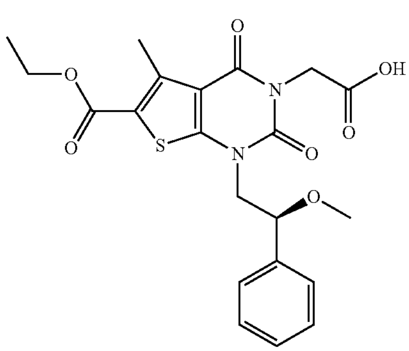 [SMILES: CCOC(=O)c1sc2c(c1C)c(=O)n(CC(=O)O)c(=O)n2C[C@@H](OC)c1ccccc1] | 447 (M + 1) |

TABLE 1-continued

Exemplary Compounds of Formula I

| Cmpd # | Compound Structure | m/z |
| --- | --- | --- |
| I-105 | 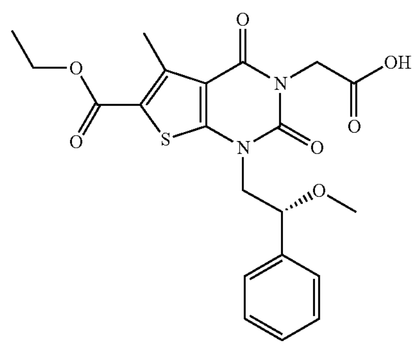 [SMILES: CCOC(=O)c1sc2c(c1C)c(=O)n(CC(=O)O)c(=O)n2C[C@H](OC)c1ccccc1] | 447 (M + 1) |
| I-106 | 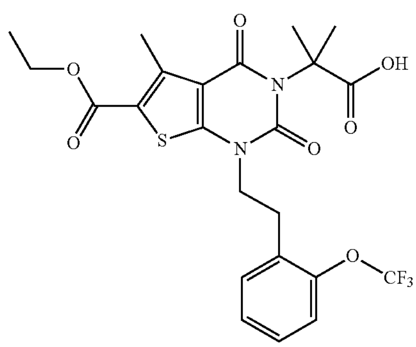 [SMILES: CCOC(=O)c1sc2c(c1C)c(=O)n(C(C)(C)C(=O)O)c(=O)n2CCc1ccccc1OC(F)(F)F] | 529 (M + 1) |
| I-107 | 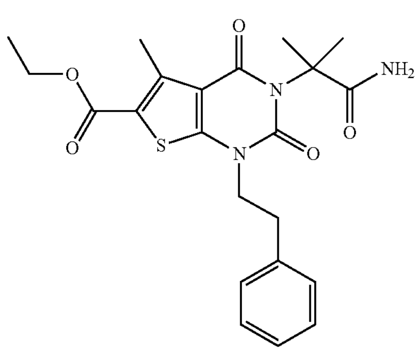 [SMILES: CCOC(=O)c1sc2c(c1C)c(=O)n(C(C)(C)C(N)=O)c(=O)n2CCc1ccccc1] | 466 (M + Na) |
| I-108 | 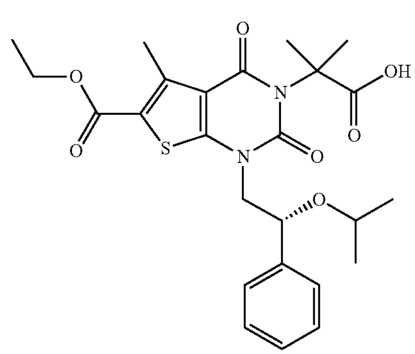 [SMILES: CCOC(=O)c1sc2c(c1C)c(=O)n(C(C)(C)C(=O)O)c(=O)n2C[C@H](OC(C)C)c1ccccc1] | 503 (M + 1) |

TABLE 1-continued

Exemplary Compounds of Formula I

| Cmpd # | Compound Structure | m/z |
|---|---|---|
| I-109 | 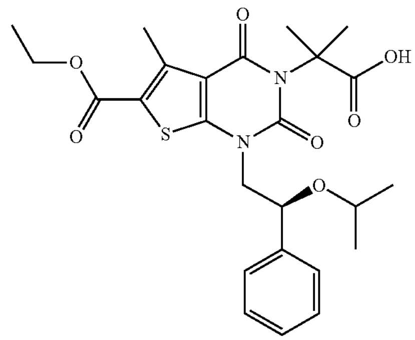 [SMILES: CCOC(=O)c1sc2c(c1C)c(=O)n(C(C)(C)C(=O)O)c(=O)n2C[C@@H](OC(C)C)c1ccccc1] | 503 (M + 1) |
| I-110 | 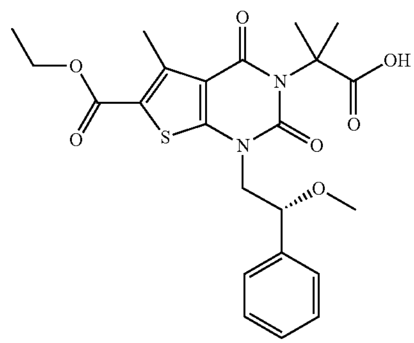 [SMILES: CCOC(=O)c1sc2c(c1C)c(=O)n(C(C)(C)C(=O)O)c(=O)n2C[C@H](OC)c1ccccc1] | 475 (M + 1) |
| I-111 | 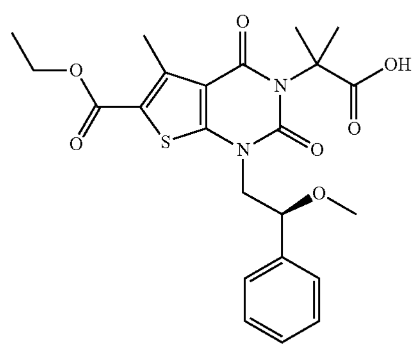 [SMILES: CCOC(=O)c1sc2c(c1C)c(=O)n(C(C)(C)C(=O)O)c(=O)n2C[C@@H](OC)c1ccccc1] | 475 (M + 1) |
| I-112 | 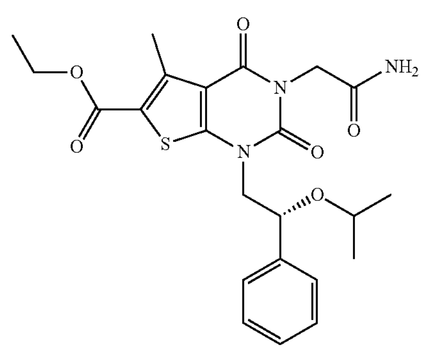 [SMILES: CCOC(=O)c1sc2c(c1C)c(=O)n(CC(N)=O)c(=O)n2C[C@H](OC(C)C)c1ccccc1] | 474 (M + 1) |

TABLE 1-continued

Exemplary Compounds of Formula I

| Cmpd # | Compound Structure | m/z |
|---|---|---|
| I-113 | 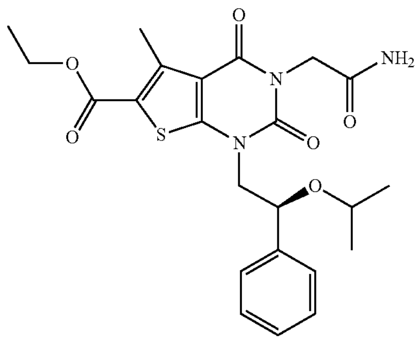 [SMILES: CCOC(=O)c1sc2c(c1C)c(=O)n(CC(N)=O)c(=O)n2C[C@@H](OC(C)C)c1ccccc1] | 474 (M + 1) |
| I-114 | 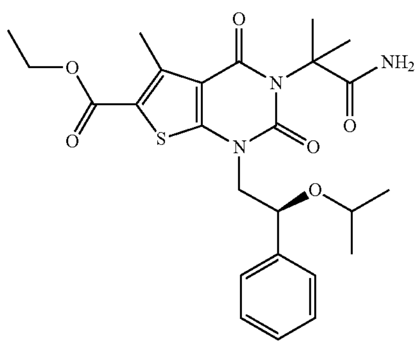 [SMILES: CCOC(=O)c1sc2c(c1C)c(=O)n(C(C)(C)C(N)=O)c(=O)n2C[C@@H](OC(C)C)c1ccccc1] | 524 (M + Na) |
| I-115 | 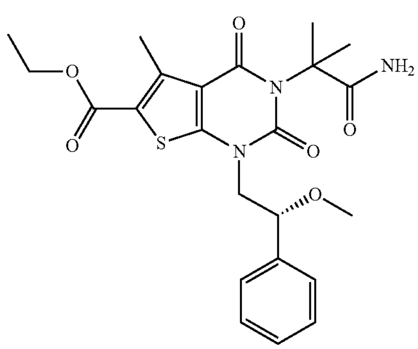 [SMILES: CCOC(=O)c1sc2c(c1C)c(=O)n(C(C)(C)C(N)=O)c(=O)n2C[C@H](OC)c1ccccc1] | 524 (M + Na) |
| I-116 | 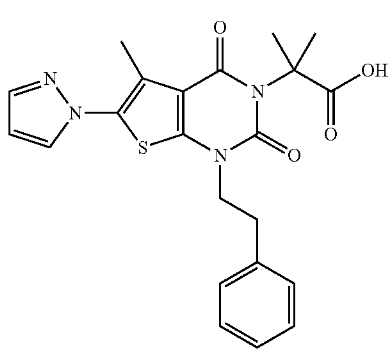 [SMILES: Cc1c(-n2cccn2)sc2c1c(=O)n(C(C)(C)C(=O)O)c(=O)n2CCc1ccccc1] | 439 (M + 1) |

TABLE 1-continued

Exemplary Compounds of Formula I

| Cmpd # | Compound Structure | m/z |
| --- | --- | --- |
| I-117 | 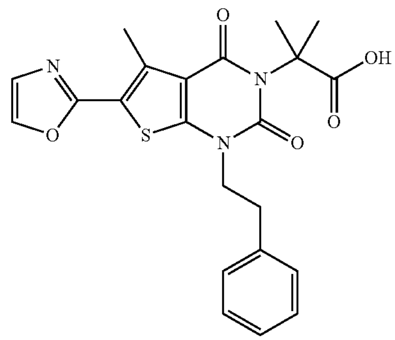 [SMILES: Cc1c(-c2ncco2)sc2c1c(=O)n(C(C)(C)C(=O)O)c(=O)n2CCc1ccccc1] | 440 (M + 1) |
| I-118 | 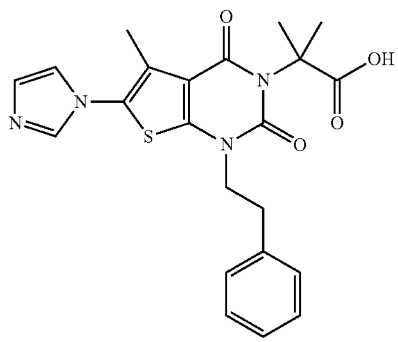 [SMILES: Cc1c(-n2ccnc2)sc2c1c(=O)n(C(C)(C)C(=O)O)c(=O)n2CCc1ccccc1] | 439 (M + 1) |
| I-119 | 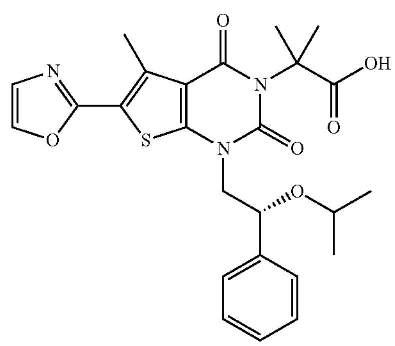 [SMILES: Cc1c(-c2ncco2)sc2c1c(=O)n(C(C)(C)C(=O)O)c(=O)n2C[C@H](OC(C)C)c1ccccc1] | 498 (M + 1) |
| I-120 | 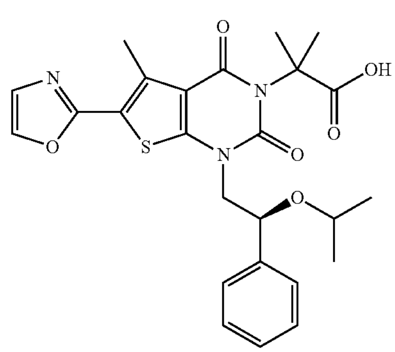 [SMILES: Cc1c(-c2ncco2)sc2c1c(=O)n(C(C)(C)C(=O)O)c(=O)n2C[C@@H](OC(C)C)c1ccccc1] | 498 (M + 1) |

TABLE 1-continued
Exemplary Compounds of Formula I
| Cmpd # | Compound Structure | m/z |
|---|---|---|
| I-121 | 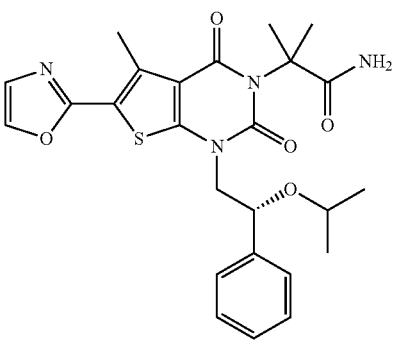 [SMILES: Cc1c(-c2ncco2)sc2c1c(=O)n(C(C)(C)C(N)=O)c(=O)n2C[C@H](OC(C)C)c1ccccc1] | 480 (M − NH$_2$) |
| I-122 | 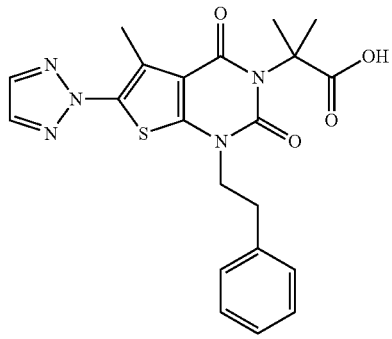 [SMILES: Cc1c(-n2nccn2)sc2c1c(=O)n(C(C)(C)C(=O)O)c(=O)n2CCc1ccccc1] | 440 (M + 1) |
| I-123 | 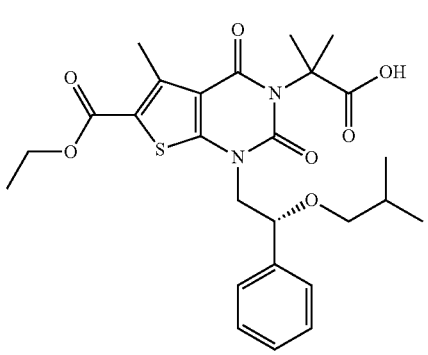 [SMILES: CCOC(=O)c1sc2c(c1C)c(=O)n(C(C)(C)C(=O)O)c(=O)n2C[C@H](OCC(C)C)c1ccccc1] | 517 (M + 1) |
| I-124 | 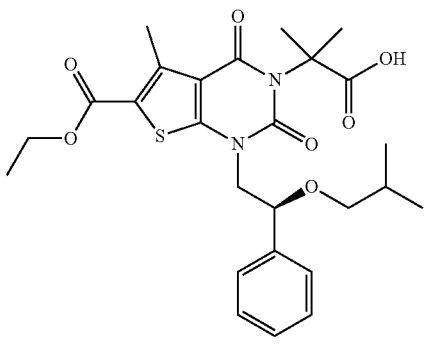 [SMILES: CCOC(=O)c1sc2c(c1C)c(=O)n(C(C)(C)C(=O)O)c(=O)n2C[C@@H](OCC(C)C)c1ccccc1] | 517 (M + 1) |

TABLE 1-continued

Exemplary Compounds of Formula I

| Cmpd # | Compound Structure | m/z |
|---|---|---|
| I-125 | 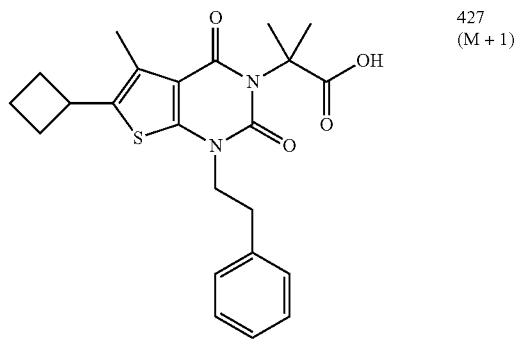 | 427 (M + 1) |
| I-126 | 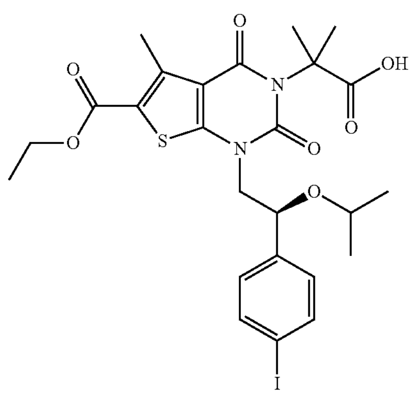 [SMILES: CCOC(=O)c1sc2c(c1C)c(=O)n(C(C)(C)C(=O)O)c(=O)n2C[C@@H](OC(C)C)c1ccc(I)cc1] | 629 (M + 1) |
| I-127 | 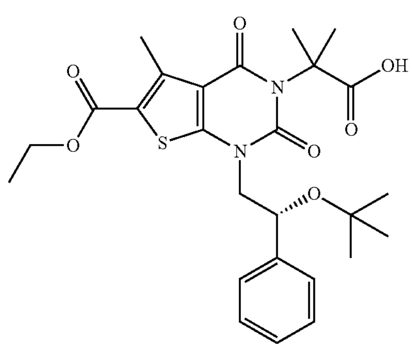 [SMILES: CCOC(=O)c1sc2c(c1C)c(=O)n(C(C)(C)C(=O)O)c(=O)n2C[C@H](OC(C)(C)C)c1ccccc1] | 443 (M − C$_4$H$_9$O) |
| I-128 | 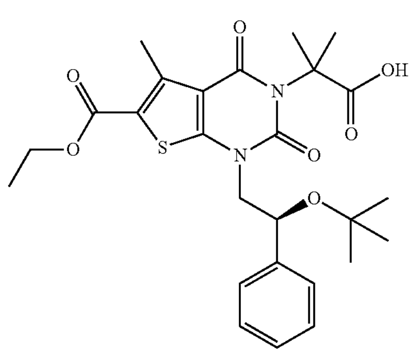 [SMILES: CCOC(=O)c1sc2c(c1C)c(=O)n(C(C)(C)C(=O)O)c(=O)n2C[C@@H](OC(C)(C)C)c1ccccc1] | 445 (M − C$_4$H$_9$O) |

TABLE 1-continued

Exemplary Compounds of Formula I

| Cmpd # | Compound Structure | m/z |
|---|---|---|
| I-129 | 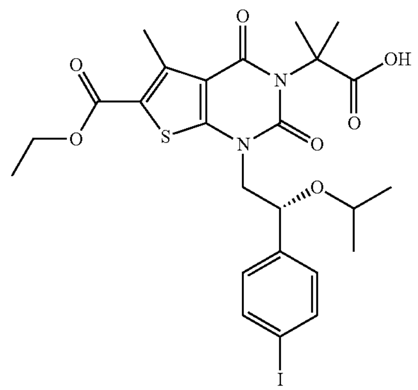 [SMILES: CCOC(=O)c1sc2c(c1C)c(=O)n(C(C)(C)C(=O)O)c(=O)n2C[C@H](OC(C)C)c1ccc(I)cc1] | 629 (M + 1) |
| I-130 | 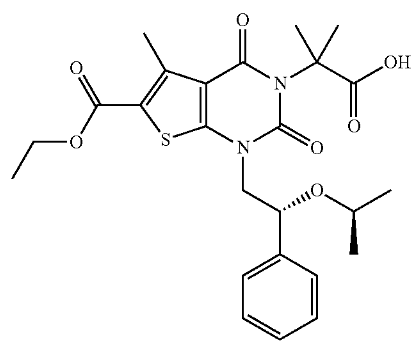 | 517 (M + 1) |
| I-131 | 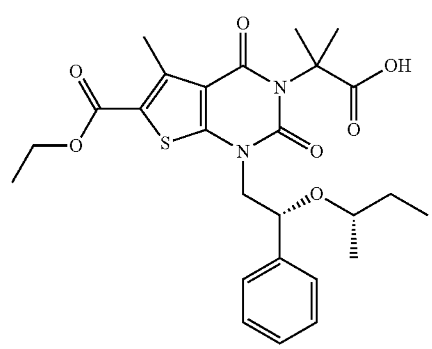 [SMILES: CCOC(=O)c1sc2c(c1C)c(=O)n(C(C)(C)C(=O)O)c(=O)n2C[C@H](O[C@@H](C)CC)c1ccccc1] | 517 (M + 1) |
| I-132 | 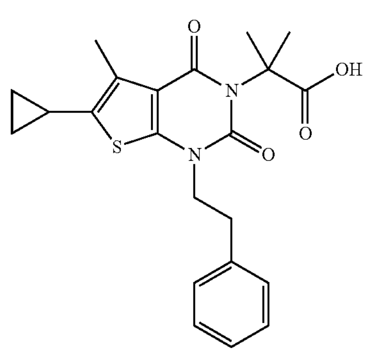 [SMILES: Cc1c(C2CC2)sc2c1c(=O)n(C(C)(C)C(=O)O)c(=O)n2CCc1ccccc1] | 413 (M + 1) |

TABLE 1-continued

Exemplary Compounds of Formula I

| Cmpd # | Compound Structure | m/z |
| --- | --- | --- |
| I-133 | 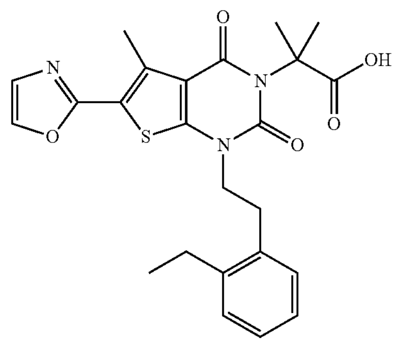 [SMILES: CCc1ccccc1CCn1c(=O)n(C(C)(C)C(=O)O)c(=O)c2c(C)c(-c3ncco3)sc21] | 468 (M + 1) |
| I-134 | 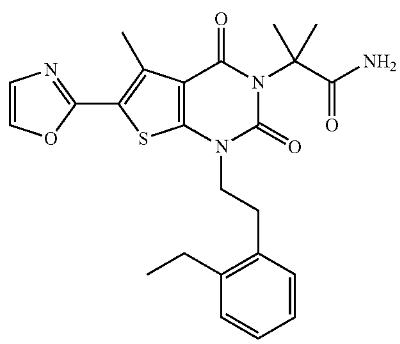 [SMILES: CCc1ccccc1CCn1c(=O)n(C(C)(C)C(N)=O)c(=O)c2c(C)c(-c3ncco3)sc21] | 450 (M − NH₂) |
| I-135 | 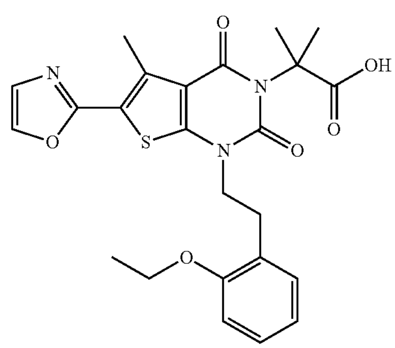 | 484 (M + 1) |
| I-136 | 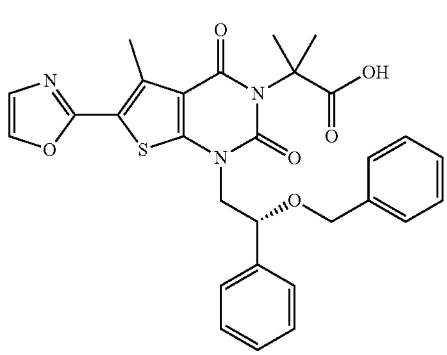 [SMILES: Cc1c(-c2ncco2)sc2c1c(=O)n(C(C)(C)C(=O)O)c(=O)n2C[C@H](OCc1ccccc1)c1ccccc1] | 546 (M + 1) |

TABLE 1-continued

Exemplary Compounds of Formula I

| Cmpd # | Compound Structure | m/z |
|---|---|---|
| I-137 | 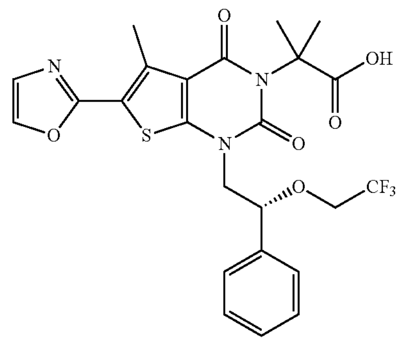 [SMILES: Cc1c(-c2ncco2)sc2c1c(=O)n(C(C)(C)C(=O)O)c(=O)n2C[C@H](OCC(F)(F)F)c1ccccc1] | 538 (M + 1) |
| I-138 | 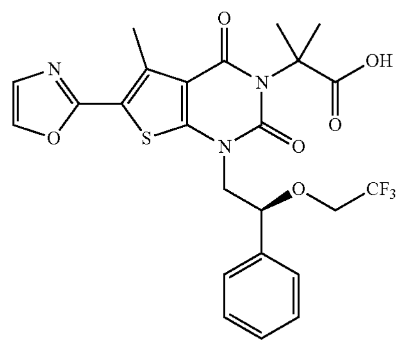 [SMILES: Cc1c(-c2ncco2)sc2c1c(=O)n(C(C)(C)C(=O)O)c(=O)n2C[C@@H](OCC(F)(F)F)c1ccccc1] | 538 (M + 1) |
| I-139 | 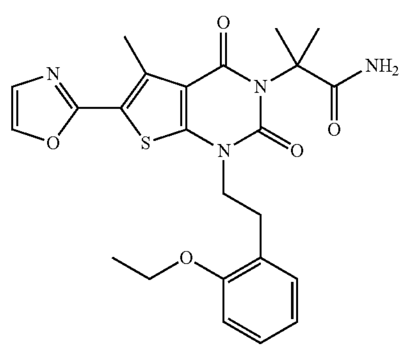 [SMILES: CCOc1ccccc1CCn1c(=O)n(C(C)(C)C(N)=O)c(=O)c2c(C)c(-c3ncco3)sc21] | 505 (M + Na) |
| I-140 | 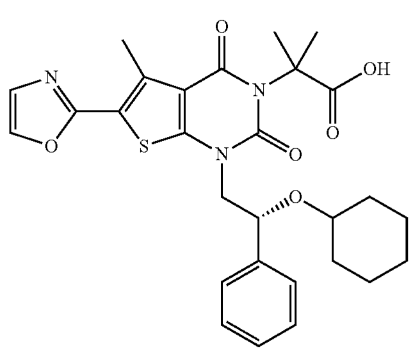 [SMILES: Cc1c(-c2ncco2)sc2c1c(=O)n(C(C)(C)C(=O)O)c(=O)n2C[C@H](OC1CCCCC1)c1ccccc1] | 538 (M + 1) |

TABLE 1-continued
Exemplary Compounds of Formula I
| Cmpd # | Compound Structure | m/z |
|---|---|---|
| I-141 | 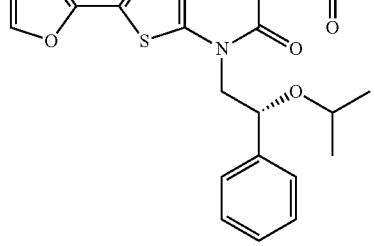 | 514 (M + 1) |
| I-142 | 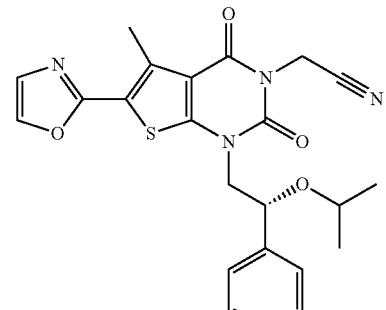 | 451 (M + 1) |
| I-143 | 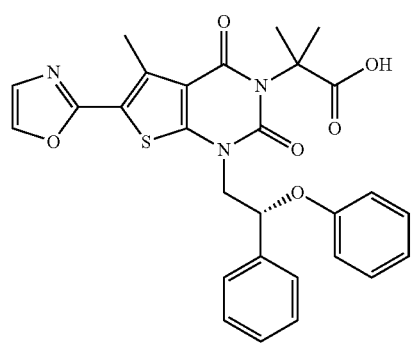 [SMILES: Cc1c(-c2ncco2)sc2c1c(=O)n(C(C)(C)C(=O)O)c(=O)n2C[C@H](Oc1ccccc1)c1ccccc1] | 532 (M + 1) |
| I-144 | 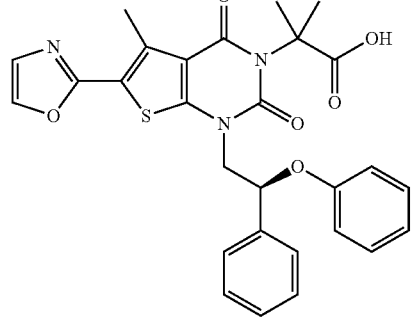 | 532 (M + 1) |

TABLE 1-continued

Exemplary Compounds of Formula I

| Cmpd # | Compound Structure | m/z |
|---|---|---|
| I-145 | 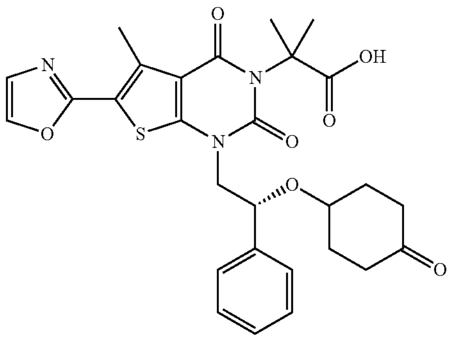 [SMILES: Cc1c(-c2ncco2)sc2c1c(=O)n(C(C)(C)C(=O)O)c(=O)n2C[C@H](OC1CCC(=O)CC1)c1ccccc1] | 552 (M + 1) |
| I-146 | 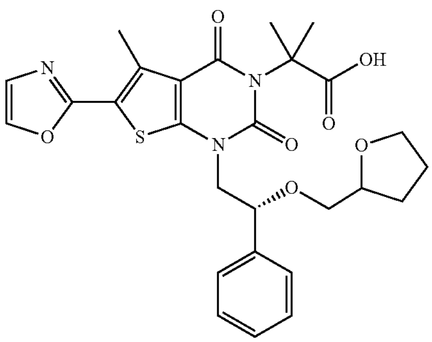 [SMILES: Cc1c(-c2ncco2)sc2c1c(=O)n(C(C)(C)C(=O)O)c(=O)n2C[C@H](OCC1CCCO1)c1ccccc1] | 562 (M + Na) |
| I-147 | 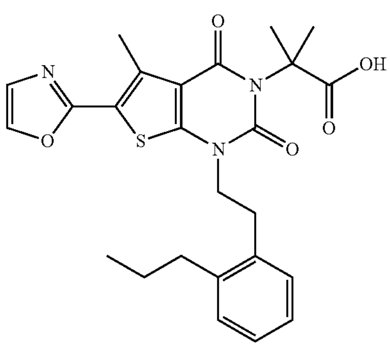 [SMILES: CCCc1ccccc1CCn1c(=O)n(C(C)(C)C(=O)O)c(=O)c2c(C)c(-c3ncco3)sc21] | 482 (M + 1) |
| I-148 | 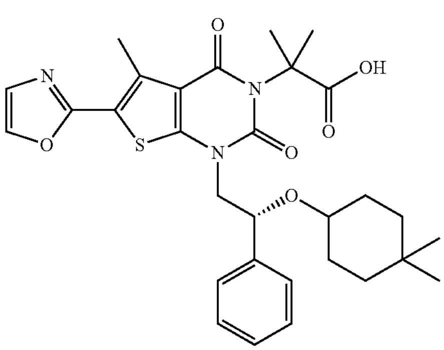 [SMILES: Cc1c(-c2ncco2)sc2c1c(=O)n(C(C)(C)C(=O)O)c(=O)n2C[C@H](OC1CCC(C)(C)CC1)c1ccccc1] | 566 (M + 1) |

TABLE 1-continued

Exemplary Compounds of Formula I

| Cmpd # | Compound Structure | m/z |
|---|---|---|
| I-149 | 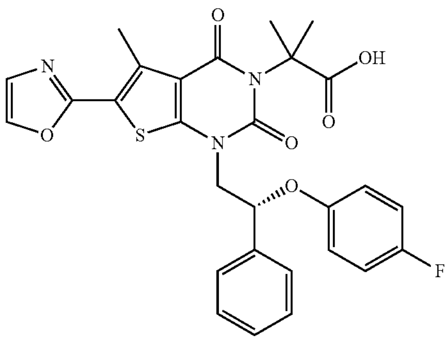 [SMILES: Cc1c(-c2ncco2)sc2c1c(=O)n(C(C)(C)C(=O)O)c(=O)n2C[C@H](Oc1ccc(F)cc1)c1ccccc1] | 550 (M + 1) |
| I-150 | 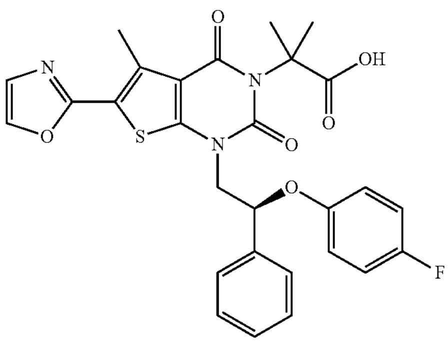 [SMILES: Cc1c(-c2ncco2)sc2c1c(=O)n(C(C)(C)C(=O)O)c(=O)n2C[C@@H](Oc1ccc(F)cc1)c1ccccc1] | 550 (M + 1) |
| I-151 | 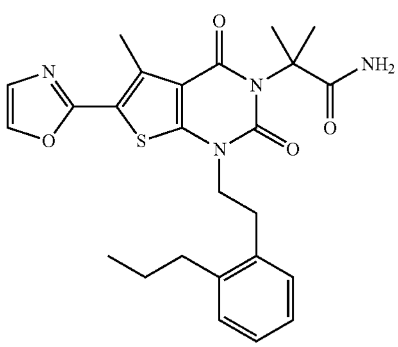 [SMILES: CCCc1ccccc1CCn1c(=O)n(C(C)(C)C(N)=O)c(=O)c2c(C)c(-c3ncco3)sc21] | 464 (M − NH$_2$) |
| I-152 | 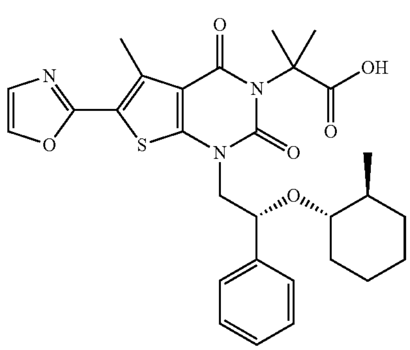 [SMILES: Cc1c(-c2ncco2)sc2c1c(=O)n(C(C)(C)C(=O)O)c(=O)n2C[C@H](O[C@H]1CCCC[C@@H]1C)c1ccccc1] | 552 (M + 1) |

TABLE 1-continued

Exemplary Compounds of Formula I

| Cmpd # | Compound Structure | m/z |
|---|---|---|
| I-153 | 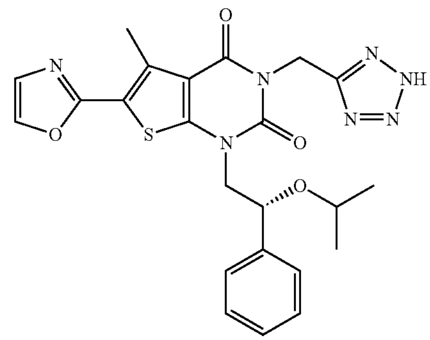 [SMILES: Cc1c(-c2ncco2)sc2c1c(=O)n(Cc1nn[nH]n1)c(=O)n2C[C@H](OC(C)C)c1ccccc1] | 494 (M + 1) |
| I-154 | 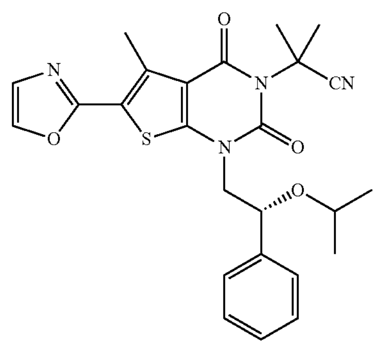 [SMILES: Cc1c(-c2ncco2)sc2c1c(=O)n(C(C)(C)C#N)c(=O)n2C[C@H](OC(C)C)c1ccccc1] | 479 (M + 1) |
| I-155 | 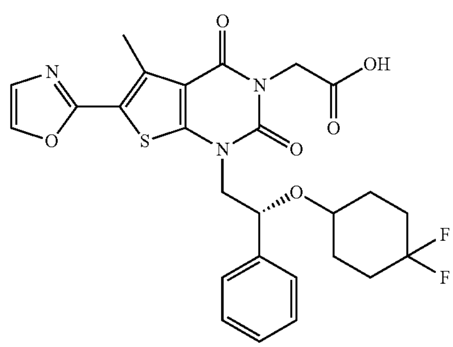 | 574 (M + 1) |
| I-156 | 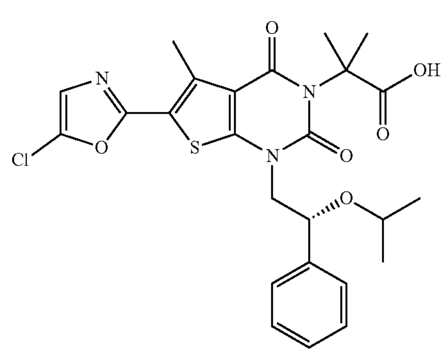 [SMILES: Cc1c(-c2ncc(Cl)o2)sc2c1c(=O)n(C(C)(C)C(=O)O)c(=O)n2C[C@H](OC(C)C)c1ccccc1] | 532 (M + 1) |

TABLE 1-continued
Exemplary Compounds of Formula I
| Cmpd # | Compound Structure | m/z |
|---|---|---|
| I-157 | 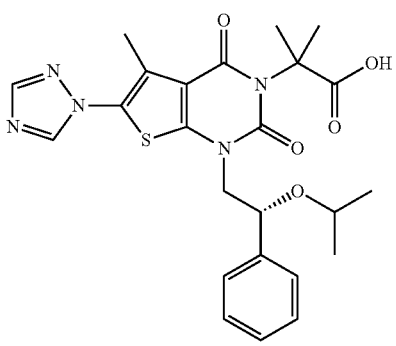 [SMILES: Cc1c(-n2cncn2)sc2c1c(=O)n(C(C)(C)C(=O)O)c(=O)n2C[C@H](OC(C)C)c1ccccc1] | 498 (M + 1) |
| I-158 | 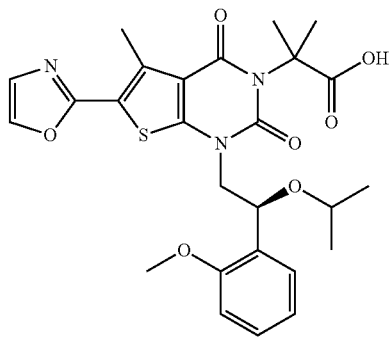 [SMILES: COc1ccccc1[C@@H](Cn1c(=O)n(C(C)(C)C(=O)O)c(=O)c2c(C)c(-c3ncco3)sc21)OC(C)C] | 528 (M + 1) |
| I-159 | 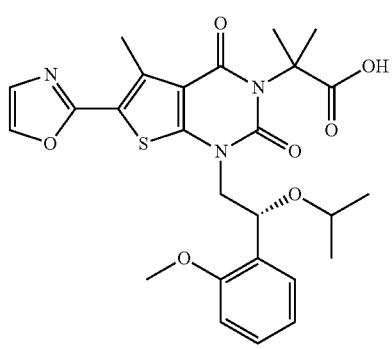 [SMILES: COc1ccccc1[C@H](Cn1c(=O)n(C(C)(C)C(=O)O)c(=O)c2c(C)c(-c3ncco3)sc21)OC(C)C] | 528 (M + 1) |
| I-160 | 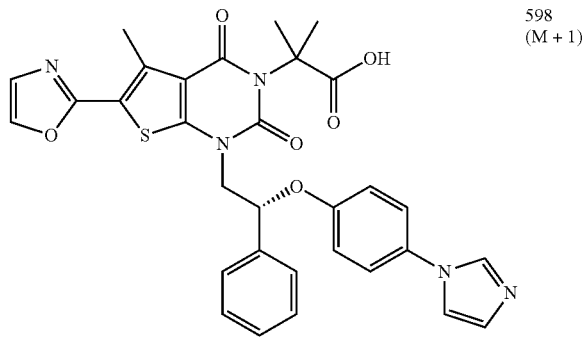 | 598 (M + 1) |

TABLE 1-continued
Exemplary Compounds of Formula I
| Cmpd # | Compound Structure | m/z |
|---|---|---|
| I-161 | 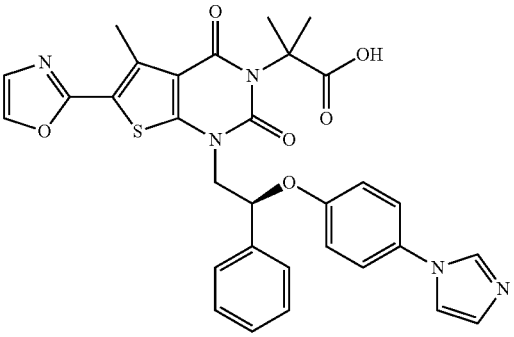 [SMILES: Cc1c(-c2ncco2)sc2c1c(=O)n(C(C)(C)C(=O)O)c(=O)n2C[C@@H](Oc1ccc(-n2ccnc2)cc1)c1ccccc1] | 598 (M + 1) |
| I-162 | 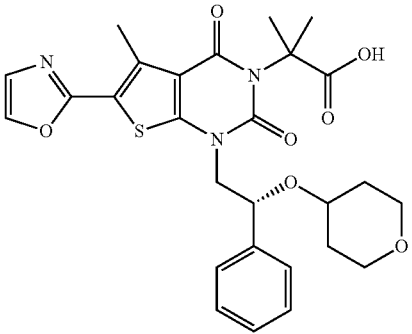 [SMILES: Cc1c(-c2ncco2)sc2c1c(=O)n(C(C)(C)C(=O)O)c(=O)n2C[C@H](OC1CCOCC1)c1ccccc1] | 540 (M + 1) |
| I-163 | 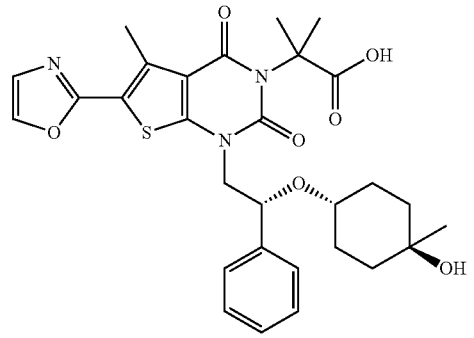 [SMILES: Cc1c(-c2ncco2)sc2c1c(=O)n(C(C)(C)C(=O)O)c(=O)n2C[C@H](O[C@H]1CC[C@](C)(O)CC1)c1ccccc1] | 568 (M + 1) |
| I-164 | 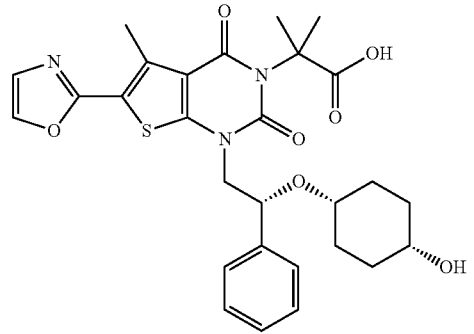 [SMILES: Cc1c(-c2ncco2)sc2c1c(=O)n(C(C)(C)C(=O)O)c(=O)n2C[C@H](O[C@H]1CC[C@@H](O)CC1)c1ccccc1] | 554 (M + 1) |

TABLE 1-continued

Exemplary Compounds of Formula I

| Cmpd # | Compound Structure | m/z |
|---|---|---|
| I-165 | 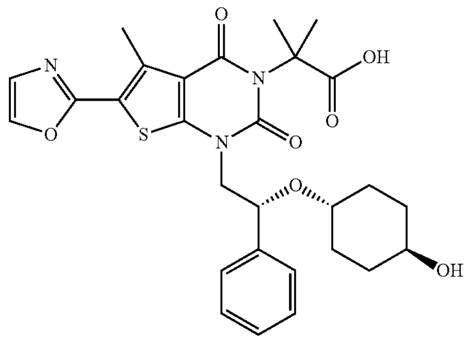 [SMILES: Cc1c(-c2ncco2)sc2c1c(=O)n(C(C)(C)C(=O)O)c(=O)n2C[C@H](O[C@H]1CC[C@H](O)CC1)c1ccccc1] | 554 (M + 1) |
| I-166 | 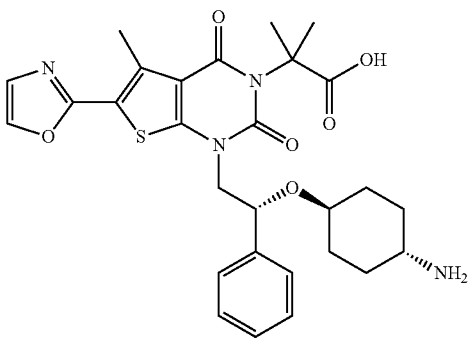 [SMILES: Cc1c(-c2ncco2)sc2c1c(=O)n(C(C)(C)C(=O)O)c(=O)n2C[C@H](O[C@H]1CC[C@H](N)CC1)c1ccccc1] | 553 (M + 1) |
| I-167 | 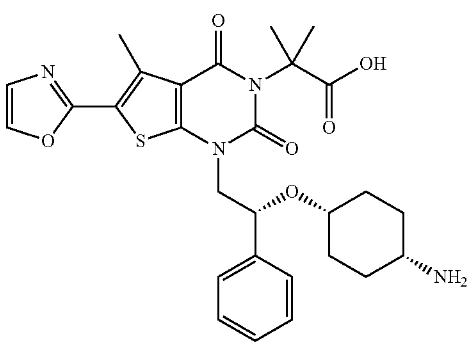 [SMILES: Cc1c(-c2ncco2)sc2c1c(=O)n(C(C)(C)C(=O)O)c(=O)n2C[C@H](O[C@H]1CC[C@@H](N)CC1)c1ccccc1] | 553 (M + 1) |
| I-168 | 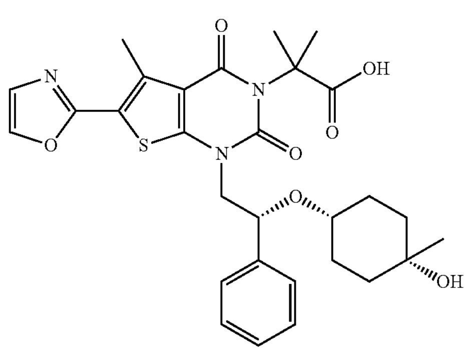 [SMILES: Cc1c(-c2ncco2)sc2c1c(=O)n(C(C)(C)C(=O)O)c(=O)n2C[C@H](O[C@H]1CC[C@@](C)(O)CC1)c1ccccc1] | 568 (M + 1) |

TABLE 1-continued

Exemplary Compounds of Formula I

| Cmpd # | Compound Structure | m/z |
| --- | --- | --- |
| I-169 | 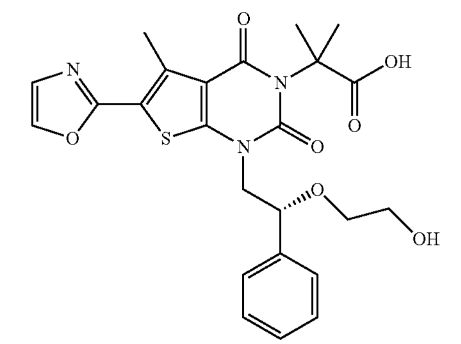 [SMILES: Cc1c(-c2ncco2)sc2c1c(=O)n(C(C)(C)C(=O)O)c(=O)n2C[C@H](OCCO)c1ccccc1] | 500 (M + 1) |
| I-170 | 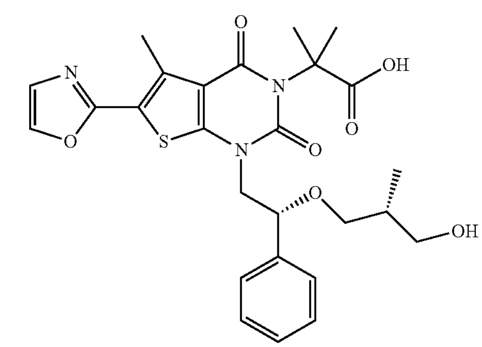 [SMILES: Cc1c(-c2ncco2)sc2c1c(=O)n(C(C)(C)C(=O)O)c(=O)n2C[C@H](OC[C@H](C)CO)c1ccccc1] | 528 (M + 1) |
| I-171 | 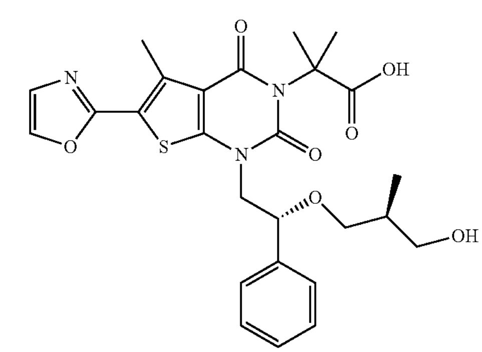 [SMILES: Cc1c(-c2ncco2)sc2c1c(=O)n(C(C)(C)C(=O)O)c(=O)n2C[C@H](OC[C@@H](C)CO)c1ccccc1] | 528 (M + 1) |
| I-172 | 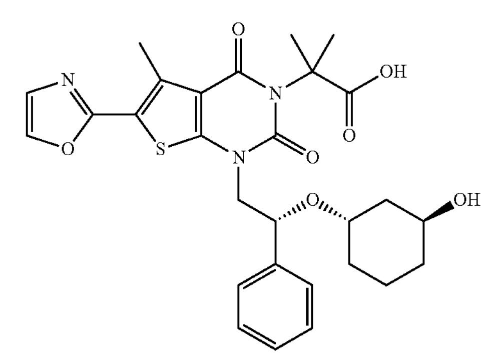 [SMILES: Cc1c(-c2ncco2)sc2c1c(=O)n(C(C)(C)C(=O)O)c(=O)n2C[C@H](O[C@H]1CCC[C@H](O)C1)c1ccccc1] | 554 (M + 1) |

TABLE 1-continued

Exemplary Compounds of Formula I

| Cmpd # | Compound Structure | m/z |
|---|---|---|
| I-173 | 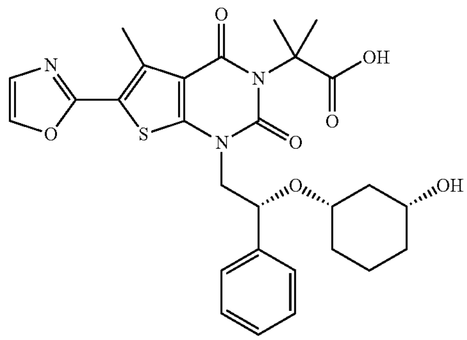 [SMILES: Cc1c(-c2ncco2)sc2c1c(=O)n(C(C)(C)C(=O)O)c(=O)n2C[C@H](O[C@H]1CCC[C@@H](O)C1)c1ccccc1] | 554 (M + 1) |
| I-174 | 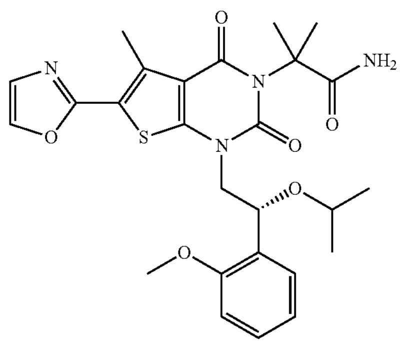 [SMILES: COc1ccccc1[C@H](Cn1c(=O)n(C(C)(C)C(N)=O)c(=O)c2c(C)c(-c3ncco3)sc21)OC(C)C] | 510 (M − NH₂) |
| I-175 | 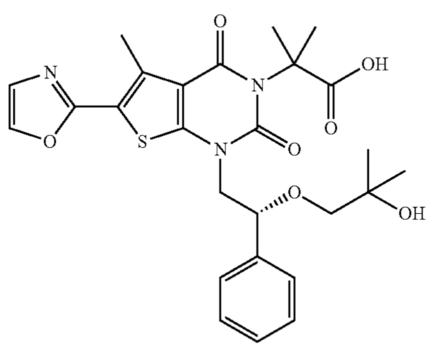 [SMILES: Cc1c(-c2ncco2)sc2c1c(=O)n(C(C)(C)C(=O)O)c(=O)n2C[C@H](OCC(C)(C)O)c1ccccc1] | 528 (M + 1) |
| I-176 | 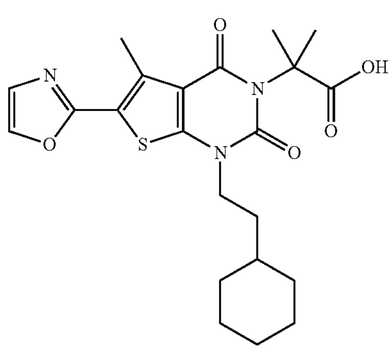 [SMILES: Cc1c(-c2ncco2)sc2c1c(=O)n(C(C)(C)C(=O)O)c(=O)n2CCC1CCCCC1] | 446 (M + 1) |

TABLE 1-continued
Exemplary Compounds of Formula I
| Cmpd # | Compound Structure | m/z |
|---|---|---|
| I-177 | 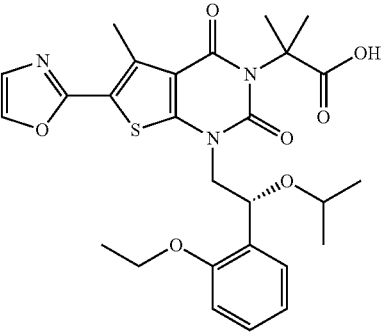 [SMILES: CCOc1ccccc1[C@H](Cn1c(=O)n(C(C)(C)C(=O)O)c(=O)c2c(C)c(-c3ncco3)sc21)OC(C)C] | 542 (M + 1) |
| I-178 | 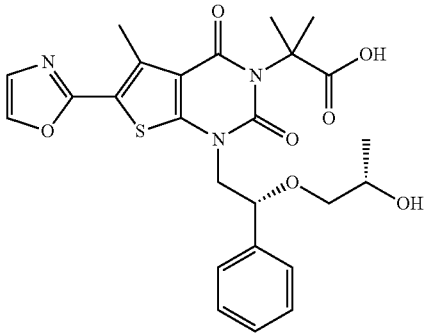 [SMILES: Cc1c(-c2ncco2)sc2c1c(=O)n(C(C)(C)C(=O)O)c(=O)n2C[C@H](OC[C@H](C)O)c1ccccc1] | 514 (M + 1) |
| I-179 | 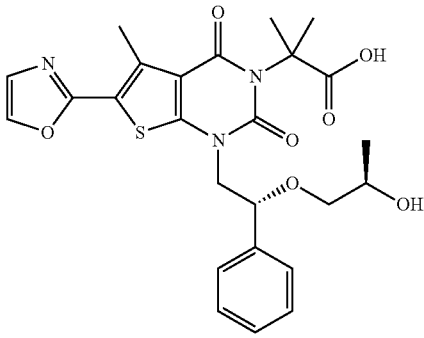 [SMILES: Cc1c(-c2ncco2)sc2c1c(=O)n(C(C)(C)C(=O)O)c(=O)n2C[C@H](OC[C@@H](C)O)c1ccccc1] | 514 (M + 1) |
| I-180 | 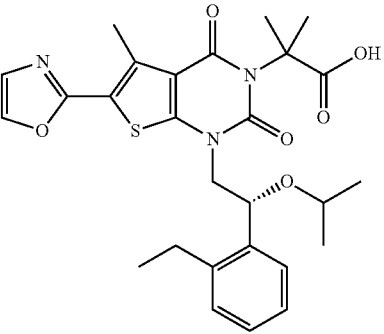 [SMILES: CCc1ccccc1[C@H](Cn1c(=O)n(C(C)(C)C(=O)O)c(=O)c2c(C)c(-c3ncco3)sc21)OC(C)C] | 526 (M + 1) |

TABLE 1-continued

Exemplary Compounds of Formula I

| Cmpd # | Compound Structure | m/z |
| --- | --- | --- |
| I-181 | 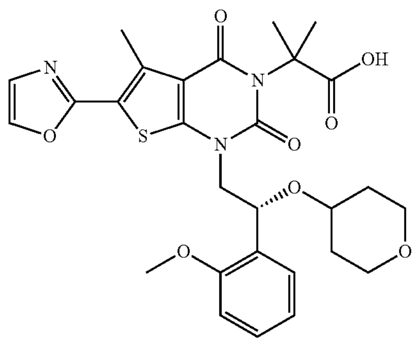 [SMILES: COc1ccccc1[C@H](Cn1c(=O)n(C(C)(C)C(=O)O)c(=O)c2c(C)c(-c3ncco3)sc21)OC1CCOCC1] | 570 (M + 1) |
| I-182 | 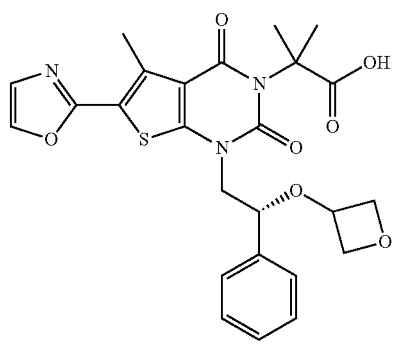 [SMILES: Cc1c(-c2ncco2)sc2c1c(=O)n(C(C)(C)C(=O)O)c(=O)n2C[C@H](OC1COC1)c1ccccc1] | 512 (M + 1) |
| I-183 | 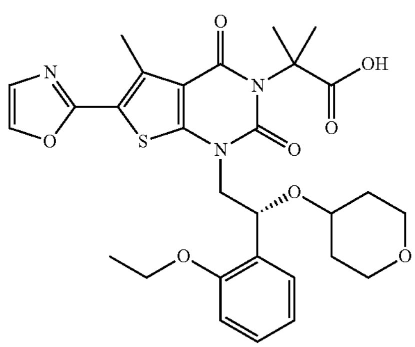 [SMILES: CCOc1ccccc1[C@H](Cn1c(=O)n(C(C)(C)C(=O)O)c(=O)c2c(C)c(-c3ncco3)sc21)OC1CCOCC1] | 606 (M + Na) |
| I-184 | 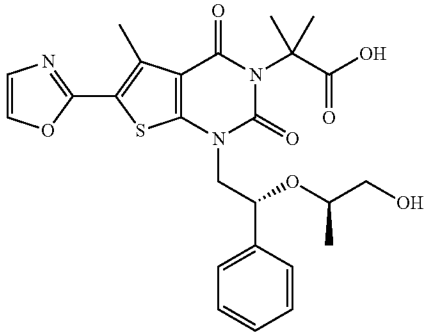 [SMILES: Cc1c(-c2ncco2)sc2c1c(=O)n(C(C)(C)C(=O)O)c(=O)n2C[C@H](O[C@H](C)CO)c1ccccc1] | 514 (M + 1) |

TABLE 1-continued

Exemplary Compounds of Formula I

| Cmpd # | Compound Structure | m/z |
|---|---|---|
| I-185 | 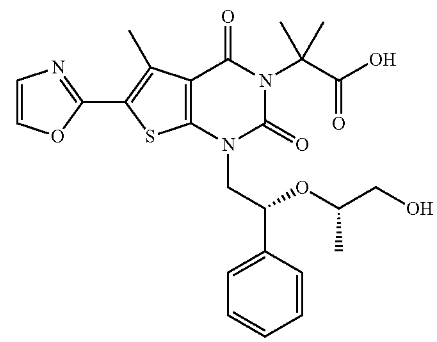 [SMILES: Cc1c(-c2ncco2)sc2c1c(=O)n(C(C)(C)C(=O)O)c(=O)n2C[C@H](O[C@@H](C)CO)c1ccccc1] | 514 (M + 1) |
| I-186 | 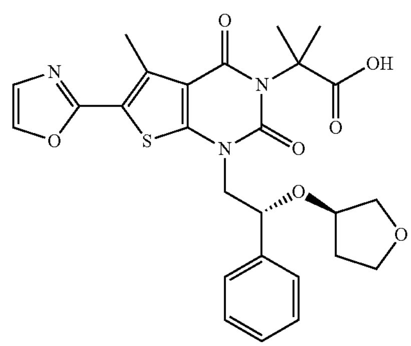 [SMILES: Cc1c(-c2ncco2)sc2c1c(=O)n(C(C)(C)C(=O)O)c(=O)n2C[C@H](O[C@@H]1CCOC1)c1ccccc1] | 526 (M + 1) |
| I-187 | 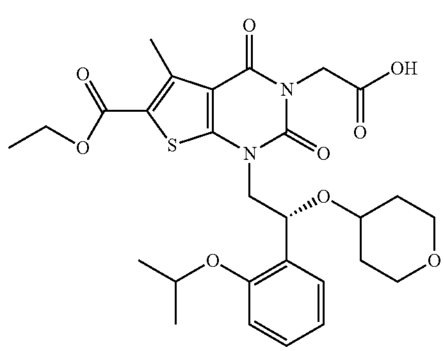 [SMILES: CCOC(=O)c1sc2c(c1C)c(=O)n(CC(=O)O)c(=O)n2C[C@H](OC1CCOCC1)c1ccccc1OC(C)C] | |
| I-188 | 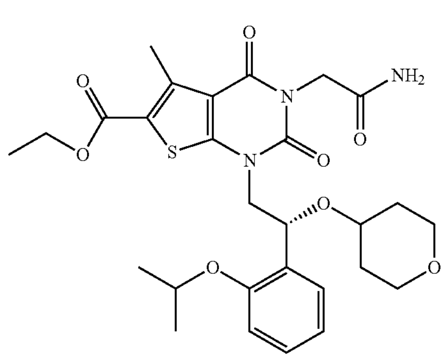 [SMILES: CCOC(=O)c1sc2c(c1C)c(=O)n(CC(N)=O)c(=O)n2C[C@H](OC1CCOCC1)c1ccccc1OC(C)C] | |

TABLE 1-continued

Exemplary Compounds of Formula I

| Cmpd # | Compound Structure | m/z |
|---|---|---|
| I-189 | 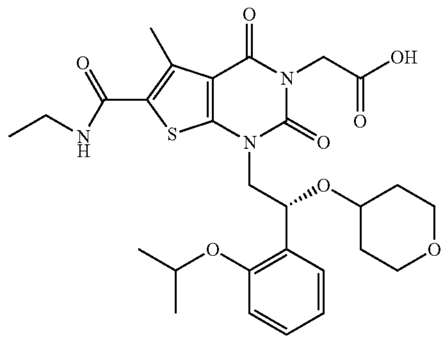 [SMILES: CCNC(=O)c1sc2c(c1C)c(=O)n(CC(=O)O)c(=O)n2C[C@H](OC1CCOCC1)c1ccccc1OC(C)C] | |
| I-190 | 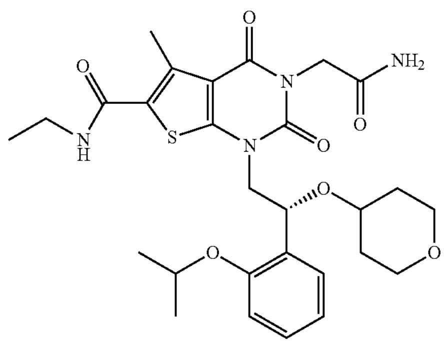 [SMILES: CCNC(=O)c1sc2c(c1C)c(=O)n(CC(N)=O)c(=O)n2C[C@H](OC1CCOCC1)c1ccccc1OC(C)C] | |
| I-191 | 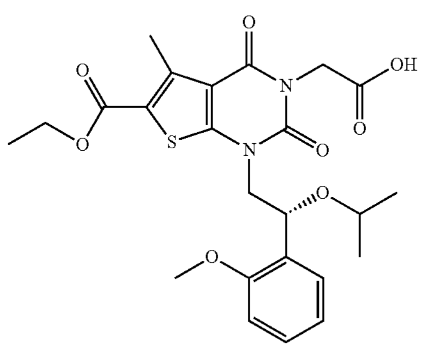 [SMILES: CCOC(=O)c1sc2c(c1C)c(=O)n(CC(=O)O)c(=O)n2C[C@H](OC(C)C)c1ccccc1OC] | |
| I-192 | 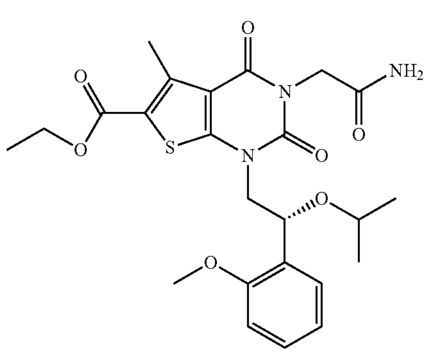 [SMILES: CCOC(=O)c1sc2c(c1C)c(=O)n(CC(N)=O)c(=O)n2C[C@H](OC(C)C)c1ccccc1OC] | |

TABLE 1-continued

Exemplary Compounds of Formula I

| Cmpd # | Compound Structure | m/z |
|---|---|---|
| I-193 | 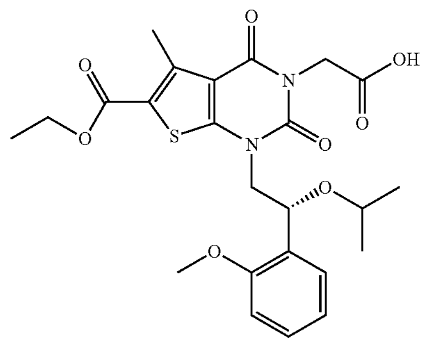 [SMILES: CCOC(=O)c1sc2c(c1C)c(=O)n(CC(=O)O)c(=O)n2C[C@H](OC(C)C)c1ccccc1OC] | |
| I-194 | 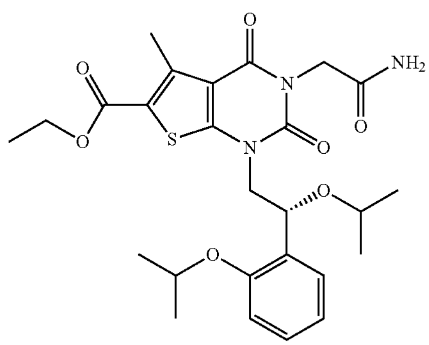 [SMILES: CCOC(=O)c1sc2c(c1C)c(=O)n(CC(N)=O)c(=O)n2C[C@H](OC(C)C)c1ccccc1OC(C)C] | |
| I-195 | 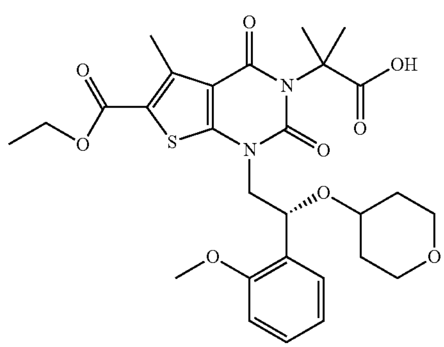 [SMILES: CCOC(=O)c1sc2c(c1C)c(=O)n(C(C)(C)C(=O)O)c(=O)n2C[C@H](OC1CCOCC1)c1ccccc1OC] | |
| I-196 | 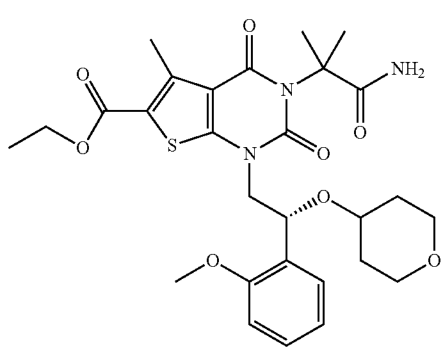 [SMILES: CCOC(=O)c1sc2c(c1C)c(=O)n(C(C)(C)C(N)=O)c(=O)n2C[C@H](OC1CCOCC1)c1ccccc1OC] | |

TABLE 1-continued
Exemplary Compounds of Formula I
| Cmpd # | Compound Structure | m/z |
|---|---|---|
| I-197 | 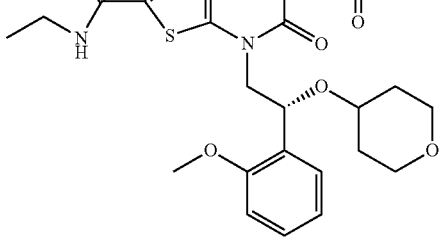 | |
| I-198 | 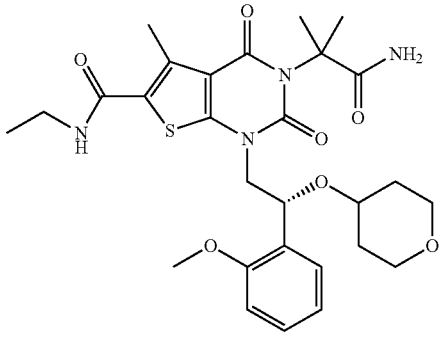 [SMILES: CCNC(=O)c1sc2c(c1C)c(=O)n(C(C)(C)C(N)=O)c(=O)n2C[C@H](OC1CCOCC1)c1ccccc1OC] | |
| I-199 | 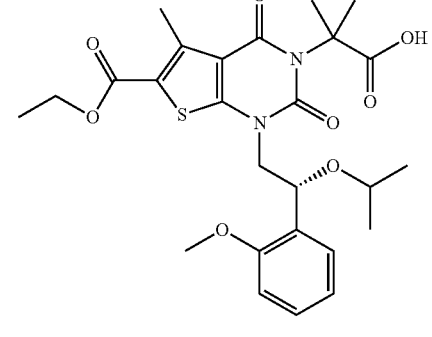 | |
| I-200 | 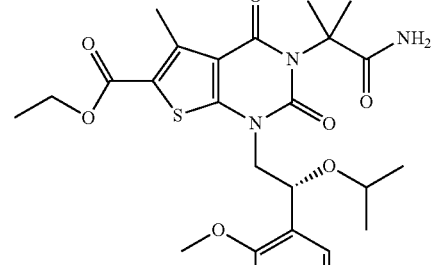 | |

TABLE 1-continued

Exemplary Compounds of Formula I

| Cmpd # | Compound Structure | m/z |
|---|---|---|
| I-201 | 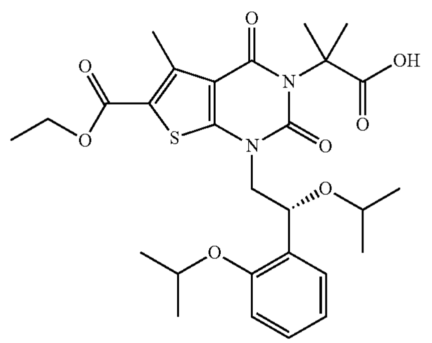 [SMILES: CCOC(=O)c1sc2c(c1C)c(=O)n(C(C)(C)C(=O)O)c(=O)n2C[C@H](OC(C)C)c1ccccc1OC(C)C] | |
| I-202 | 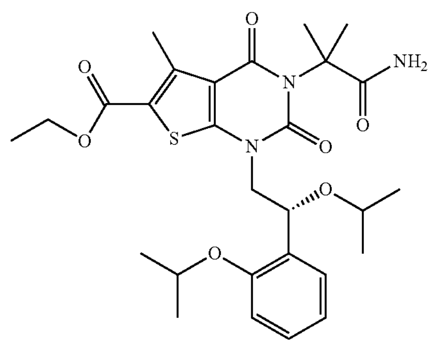 [SMILES: CCOC(=O)c1sc2c(c1C)c(=O)n(C(C)(C)C(N)=O)c(=O)n2C[C@H](OC(C)C)c1ccccc1OC(C)C] | |
| I-203 | 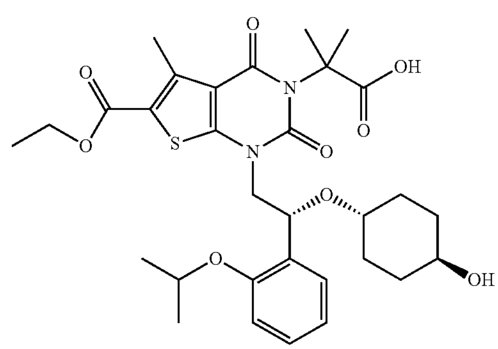 [SMILES: CCOC(=O)c1sc2c(c1C)c(=O)n(C(C)(C)C(=O)O)c(=O)n2C[C@H](O[C@H]1CC[C@H](O)CC1)c1ccccc1OC(C)C] | |
| I-204 | 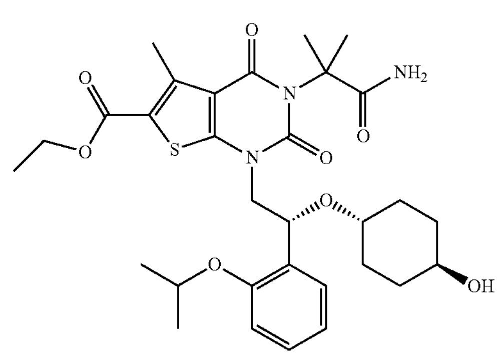 [SMILES: CCOC(=O)c1sc2c(c1C)c(=O)n(C(C)(C)C(N)=O)c(=O)n2C[C@H](O[C@H]1CC[C@H](O)CC1)c1ccccc1OC(C)C] | |

TABLE 1-continued
Exemplary Compounds of Formula I
| Cmpd # | Compound Structure | m/z |
| --- | --- | --- |
| I-205 | 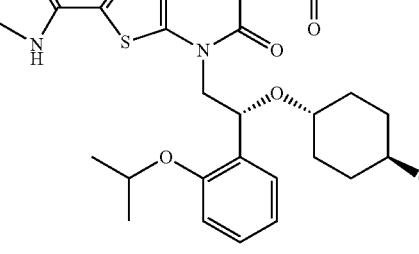 | |
| I-206 | 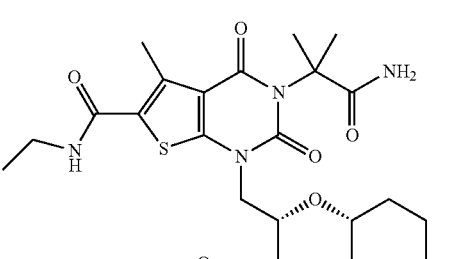 | |
| I-207 | 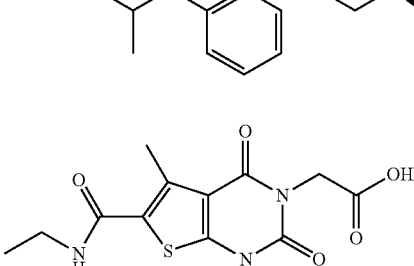 | |
| I-208 | 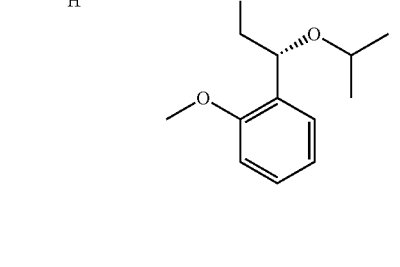 | |

TABLE 1-continued

Exemplary Compounds of Formula I

| Cmpd # | Compound Structure | m/z |
|---|---|---|
| I-209 | 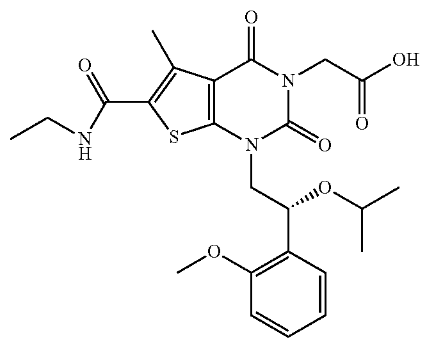 [SMILES: CCNC(=O)c1sc2c(c1C)c(=O)n(CC(=O)O)c(=O)n2C[C@H](OC(C)C)c1ccccc1OC] | |
| I-210 | 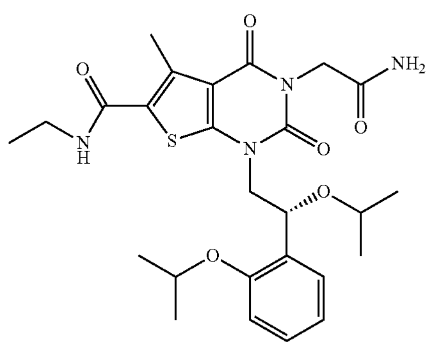 | |
| I-211 | 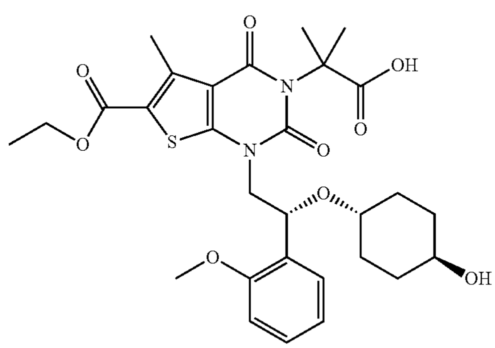 [SMILES: CCOC(=O)c1sc2c(c1C)c(=O)n(C(C)(C)C(=O)O)c(=O)n2C[C@H](O[C@H]1CC[C@H](O)CC1)c1ccccc1OC] | |
| I-212 | 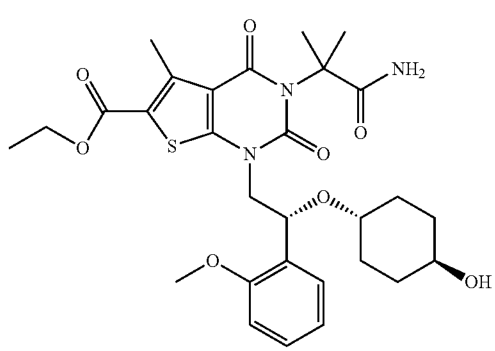 [SMILES: CCOC(=O)c1sc2c(c1C)c(=O)n(C(C)(C)C(N)=O)c(=O)n2C[C@H](O[C@H]1CC[C@H](O)CC1)c1ccccc1OC] | |

TABLE 1-continued

Exemplary Compounds of Formula I

| Cmpd # | Compound Structure | m/z |
|---|---|---|

I-213

I-214

I-215

I-216

TABLE 1-continued

Exemplary Compounds of Formula I

| Cmpd # | Compound Structure | m/z |
| --- | --- | --- |
| I-217 | 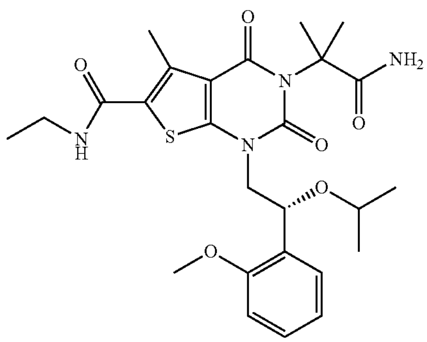 [SMILES: CCNC(=O)c1sc2c(c1C)c(=O)n(C(C)(C)C(N)=O)c(=O)n2C[C@H](OC(C)C)c1ccccc1OC] | |
| I-218 | 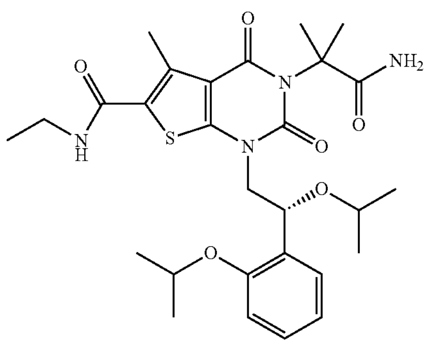 [SMILES: CCNC(=O)c1sc2c(c1C)c(=O)n(C(C)(C)C(N)=O)c(=O)n2C[C@H](OC(C)C)c1ccccc1OC(C)C] | |
| I-219 | 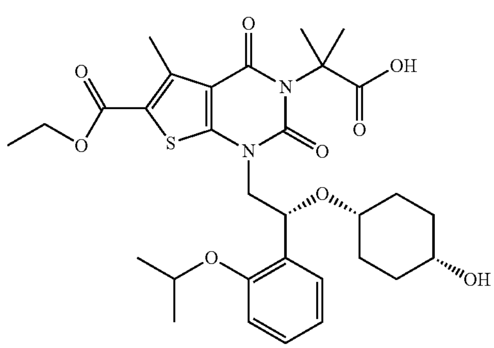 [SMILES: CCOC(=O)c1sc2c(c1C)c(=O)n(C(C)(C)C(=O)O)c(=O)n2C[C@H](O[C@H]1CC[C@@H](O)CC1)c1ccccc1OC(C)C] | |
| I-220 | 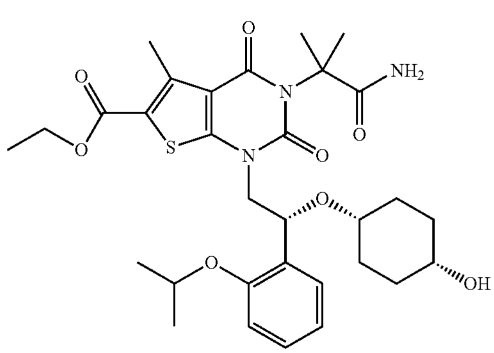 [SMILES: CCOC(=O)c1sc2c(c1C)c(=O)n(C(C)(C)C(N)=O)c(=O)n2C[C@H](O[C@H]1CC[C@@H](O)CC1)c1ccccc1OC(C)C] | |

TABLE 1-continued

Exemplary Compounds of Formula I

| Cmpd # | Compound Structure | m/z |
|---|---|---|
| I-221 | 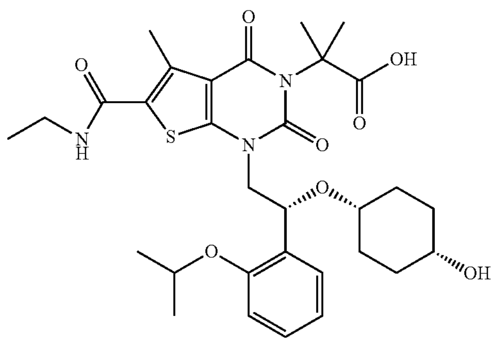 [SMILES: CCNC(=O)c1sc2c(c1C)c(=O)n(C(C)(C)C(=O)O)c(=O)n2C[C@H](O[C@H]1CC[C@@H](O)CC1)c1ccccc1OC(C)C] | |
| I-222 | 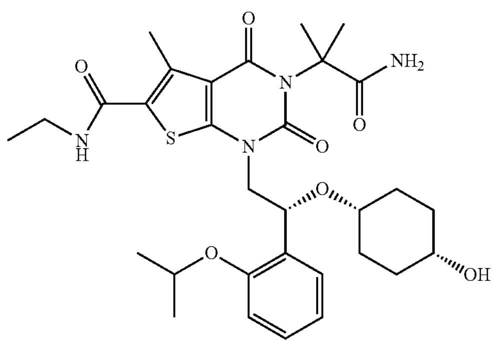 [SMILES: CCNC(=O)c1sc2c(c1C)c(=O)n(C(C)(C)C(N)=O)c(=O)n2C[C@H](O[C@H]1CC[C@@H](O)CC1)c1ccccc1OC(C)C] | |
| I-223 | 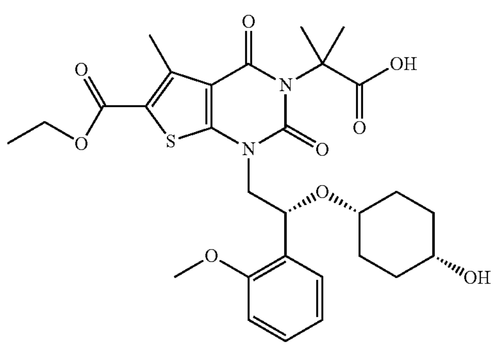 [SMILES: CCOC(=O)c1sc2c(c1C)c(=O)n(C(C)(C)C(=O)O)c(=O)n2C[C@H](O[C@H]1CC[C@@H](O)CC1)c1ccccc1OC] | |
| I-224 | 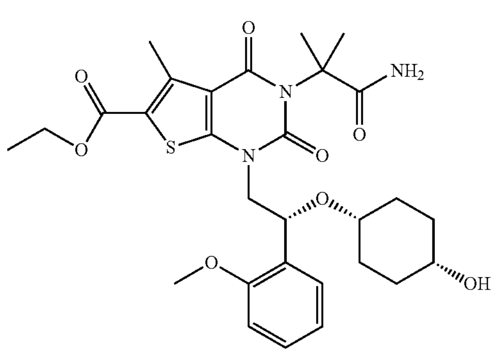 | |

TABLE 1-continued

Exemplary Compounds of Formula I

| Cmpd # | Compound Structure | m/z |
|---|---|---|
| I-225 | 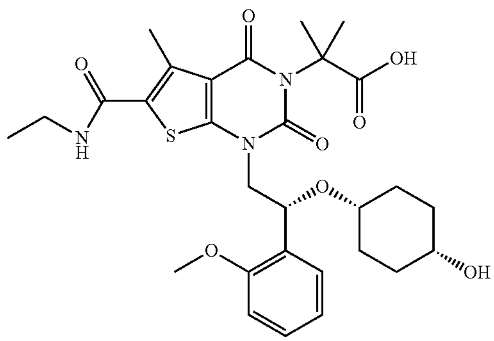 | |
| I-226 | 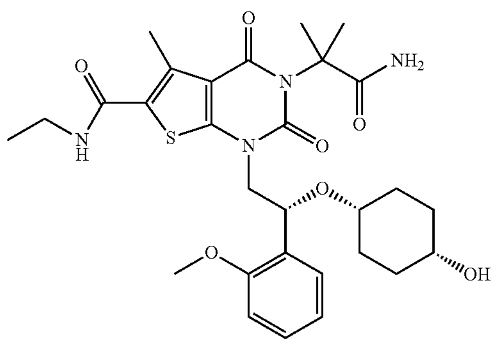 [SMILES: CCOC(=O)c1sc2c(c1C)c(=O)n(C(C)(C)C(N)=O)c(=O)n2C[C@H](O[C@H]1CC[C@@H](O)CC1)c1ccccc1OC] | |
| I-227 | 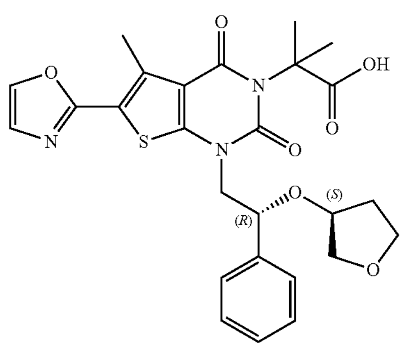 | 526 (M + H)+, |
| I-228 | 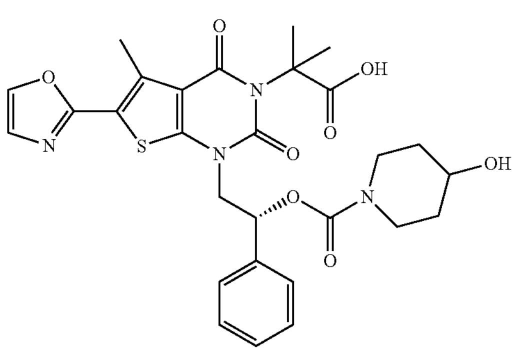 [SMILES: Cc1c(-c2ncco2)sc2c1c(=O)n(C(C)(C)C(=O)O)c(=O)n2C[C@H](OC(=O)N1CCC(O)CC1)c1ccccc1] | 583 (M + H)+ |

TABLE 1-continued

Exemplary Compounds of Formula I

| Cmpd # | Compound Structure | m/z |
| --- | --- | --- |
| I-229 | 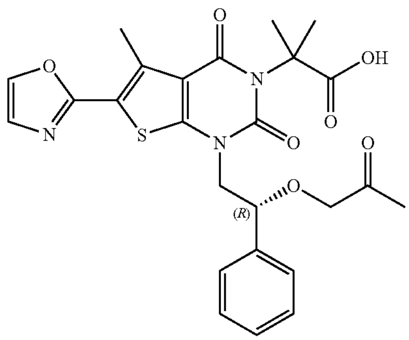 | 512 (M + H)+ |
| I-230 | 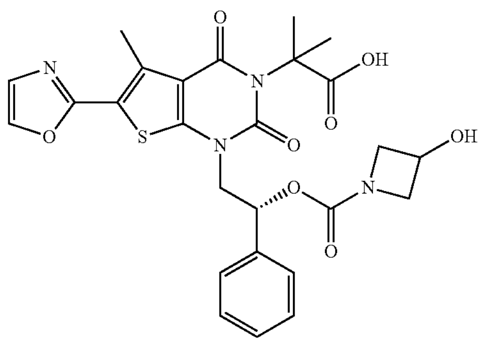 [SMILES: Cc1c(-c2ncco2)sc2c1c(=O)n(C(C)(C)C(=O)O)c(=O)n2C[C@H](OC(=O)N1CC(O)C1)c1ccccc1] | 555 (M + H)+ |
| I-231 | 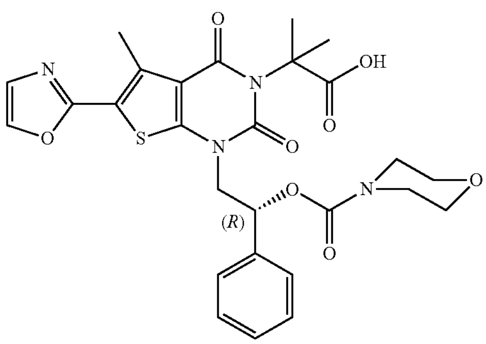 | 569 (M + H)+ |
| I-232 | 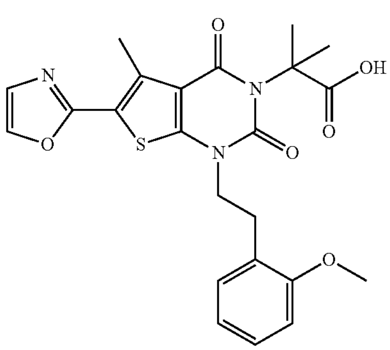 [SMILES: COc1ccccc1CCn1c(=O)n(C(C)(C)C(=O)O)c(=O)c2c(C)c(-c3ncco3)sc21] | 470 (M + H)+ |

TABLE 1-continued
Exemplary Compounds of Formula I
| Cmpd # | Compound Structure | m/z |
|---|---|---|
| I-233 | 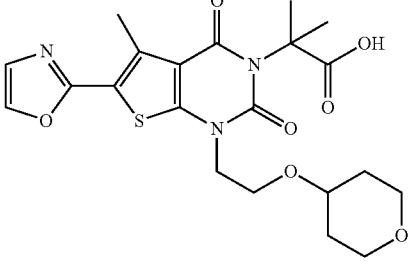 | 464 (M + H)+ |
| I-234 | 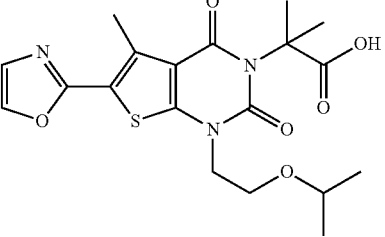 | 423 (M + H)+ |
| I-235 | 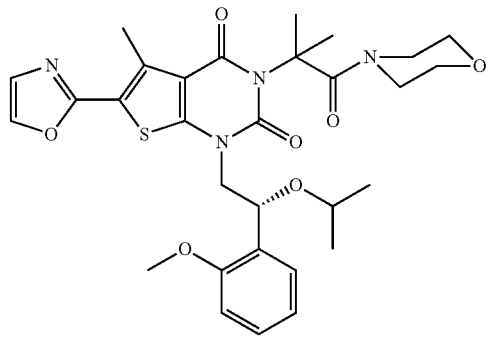 [SMILES: COc1ccccc1[C@H](Cn1c(=O)n(C(C)(C)C(=O)N2CCOCC2)c(=O)c2c(C)c(-c3ncco3)sc21)OC(C)C] | 619 (M + Na)+ |
| I-236 | 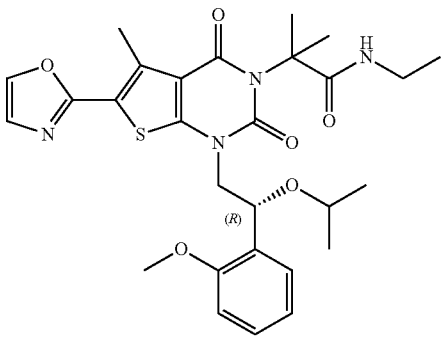 | 577 (M + Na)+ |
| I-237 | 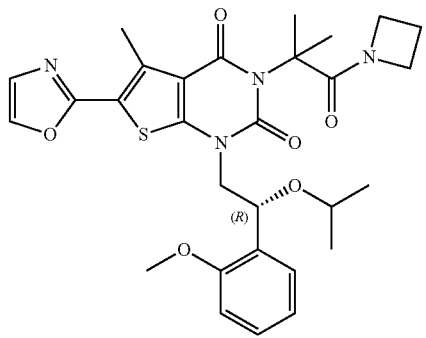 | 568 (M + H)+ |

US 8,969,557 B2
139 140
TABLE 1-continued
Exemplary Compounds of Formula I
| Cmpd # | Compound Structure | m/z |
|---|---|---|
| I-238 | 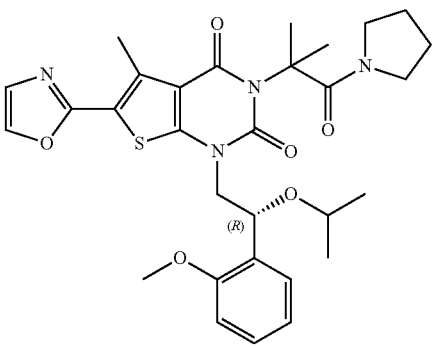 | 603 (M + Na)+ |
| I-239 | 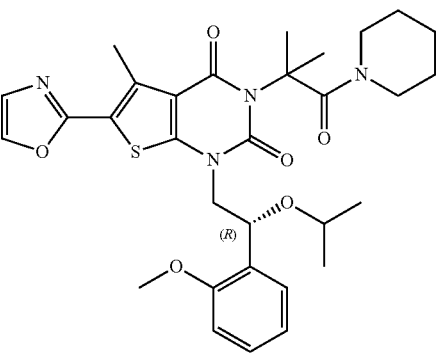 | 617 (M + Na)+ |
| I-240 | 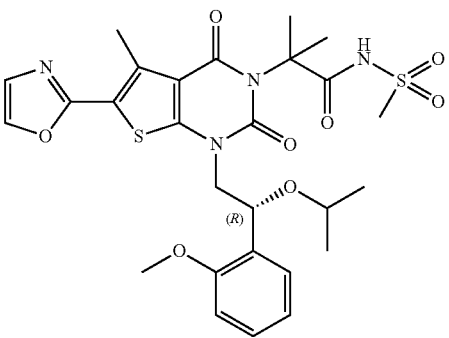 | 605 (M + H)+ |
| I-241 | 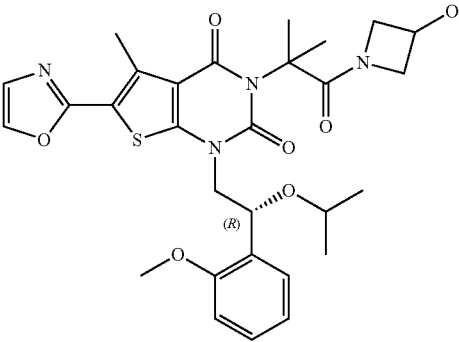 | 605 (M + Na)+ |

TABLE 1-continued

Exemplary Compounds of Formula I

| Cmpd # | Compound Structure | m/z |
| --- | --- | --- |
| I-242 | 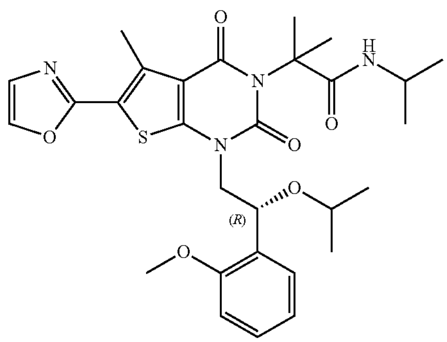 | 591 (M + Na)+ |
| I-243 | 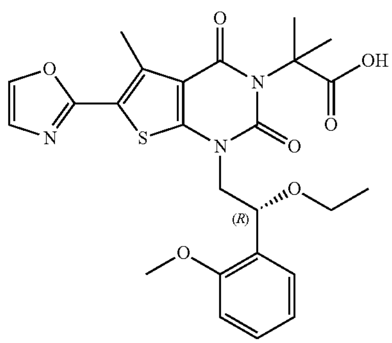 | 514 (M + H)+ |
| I-244 | 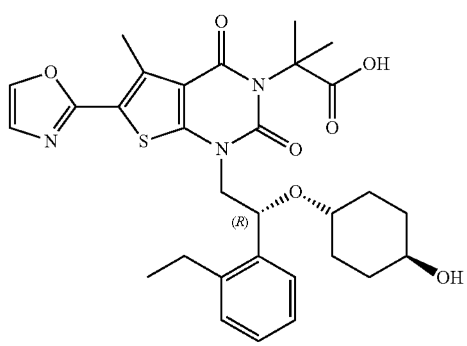 | 582 (M + H)+ |
| I-245 | 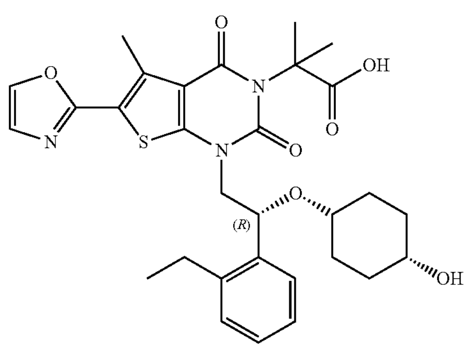 | 582 (M + H)+ |

TABLE 1-continued

Exemplary Compounds of Formula I

| Cmpd # | Compound Structure | m/z |
|---|---|---|
| I-246 | 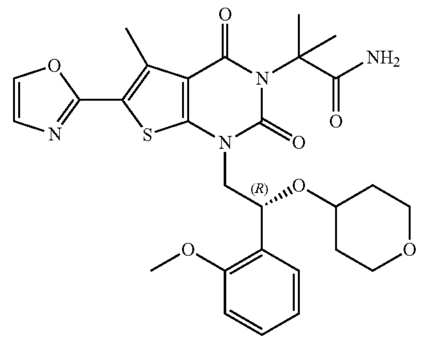 | 591 (M + Na)+ |
| I-247 | 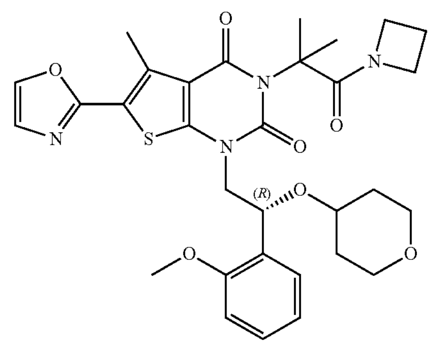 | 609 (M + H)+ |
| I-248 | 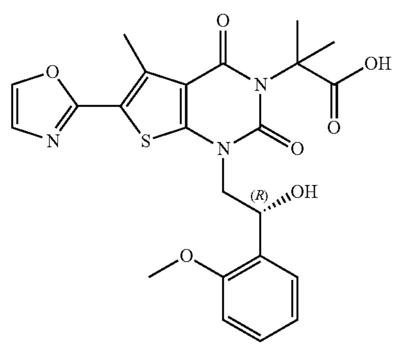 | 586 (M + H)+ |
| I-249 | 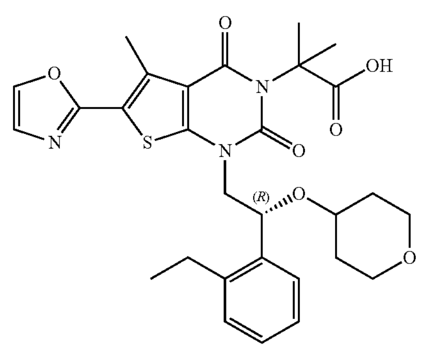 | 568 (M + H)+ |

TABLE 1-continued

Exemplary Compounds of Formula I

| Cmpd # | Compound Structure | m/z |
| --- | --- | --- |
| I-250 | 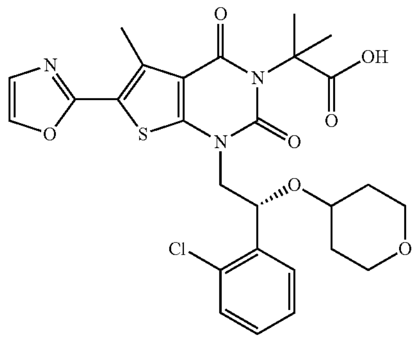 [SMILES: Cc1c(-c2ncco2)sc2c1c(=O)n(C(C)(C)C(=O)O)c(=O)n2C[C@H](OC1CCOCC1)c1ccccc1Cl] | 574 (M + H)⁺ |
| I-251 | 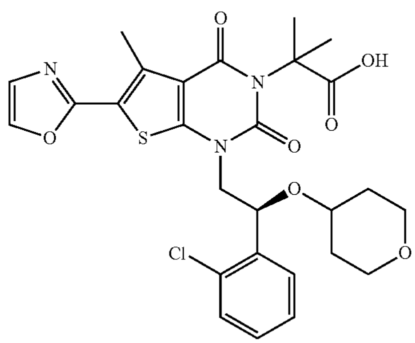 [SMILES: Cc1c(-c2ncco2)sc2c1c(=O)n(C(C)(C)C(=O)O)c(=O)n2C[C@@H](OC1CCOCC1)c1ccccc1Cl] | 574 (M + H)⁺ |
| I-252 | 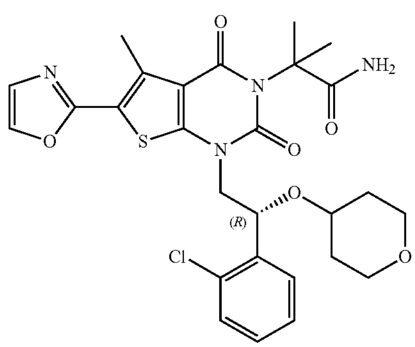 | 595 (M + Na)⁺ |
| I-253 | 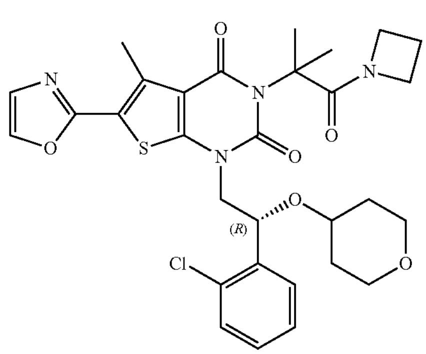 | 613 (M + H)⁺ |

TABLE 1-continued

Exemplary Compounds of Formula I

| Cmpd # | Compound Structure | m/z |
|---|---|---|
| I-254 | 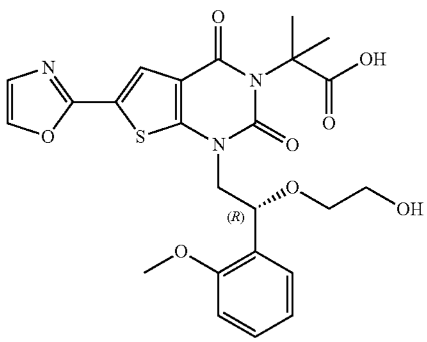 | 530 (M + H)+ |
| I-255 | 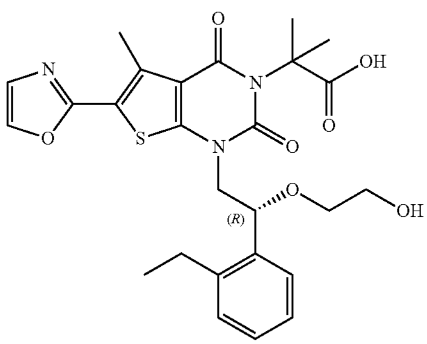 | 528 (M + H)+ |
| I-256 | 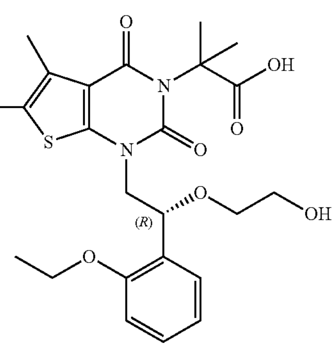 | 544 (M + H)+ |
| I-257 | 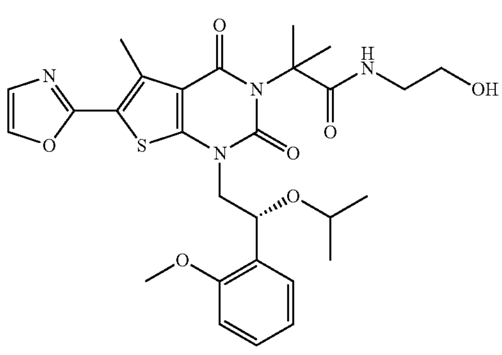 [SMILES: COc1ccccc1[C@H](Cn1c(=O)n(C(C)(C)C(=O)NCCO)c(=O)c2c(C)c(-c3ncco3)sc21)OC(C)C] | 571 (M + H)+ |

TABLE 1-continued
Exemplary Compounds of Formula I
| Cmpd # | Compound Structure | m/z |
|---|---|---|
| I-258 | 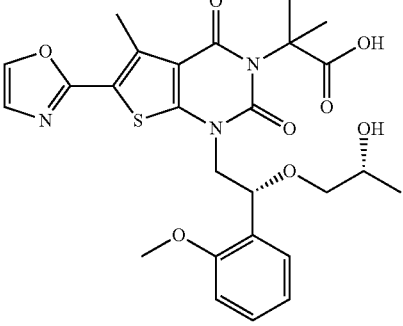 | 544 (M + H)+ |
| I-259 | 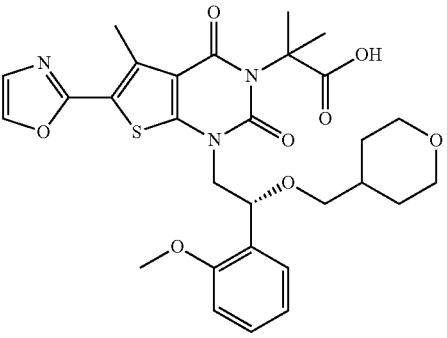 [SMILES: COc1ccccc1[C@H](Cn1c(=O)n(C(C)(C)C(=O)O)c(=O)c2c(C)c(-c3ncco3)sc21)OCC1CCOCC1] | 584 (M + H)+ |
| I-260 | 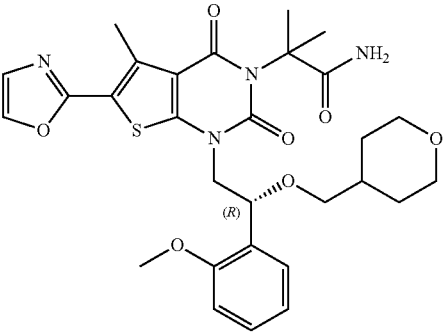 | 583 (M + H)+ |
| I-261 | 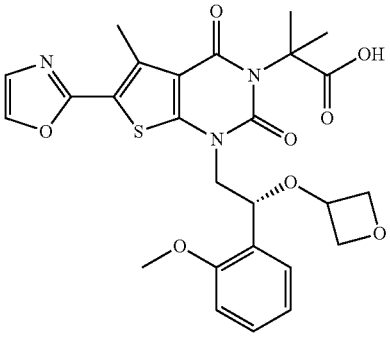 [SMILES: COc1ccccc1[C@H](Cn1c(=O)n(C(C)(C)C(=O)O)c(=O)c2c(C)c(-c3ncco3)sc21)OC1COC1] | 542 (M + H)+ |

TABLE 1-continued

Exemplary Compounds of Formula I

| Cmpd # | Compound Structure | m/z |
|---|---|---|
| I-262 | 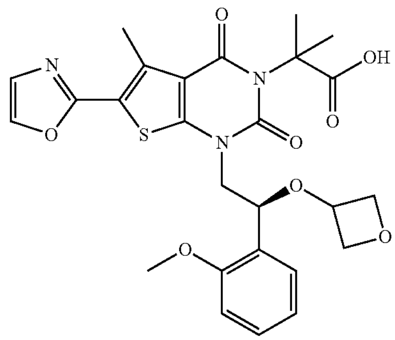 [SMILES: COc1ccccc1[C@@H](Cn1c(=O)n(C(C)(C)C(=O)O)c(=O)c2c(C)c(-c3ncco3)sc21)OC1COC1] | 542 (M + H)+ |
| I-263 | 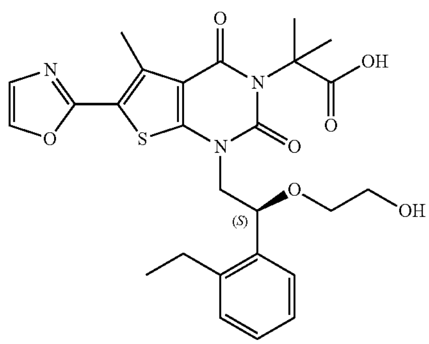 | 528 (M + H)+ |
| I-264 | 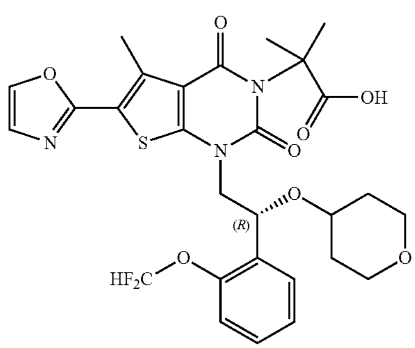 | 607 (M + H)+ |
| I-265 | 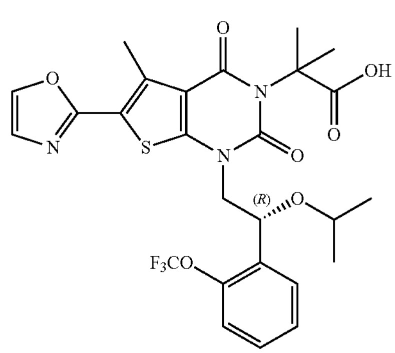 | 582 (M + H)+ |

TABLE 1-continued

Exemplary Compounds of Formula I

| Cmpd # | Compound Structure | m/z |
|---|---|---|
| I-266 | 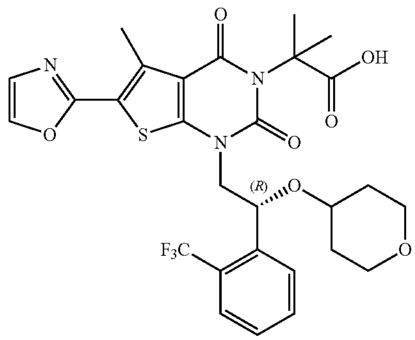 | 608 (M + H)+ |
| I-267 | 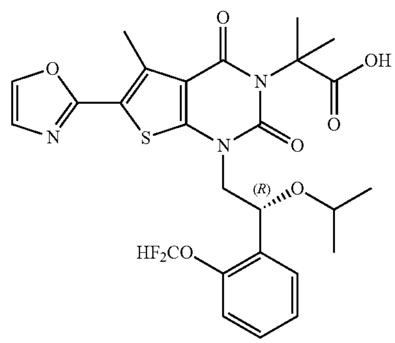 | 564 (M + H)+ |
| I-268 | 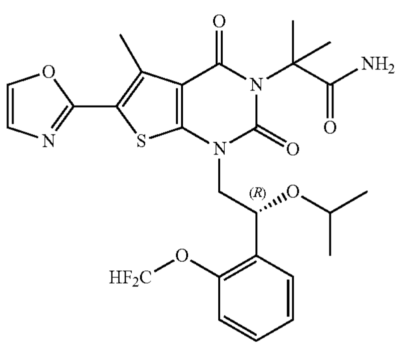 | 563 (M + H)+ |
| I-269 | 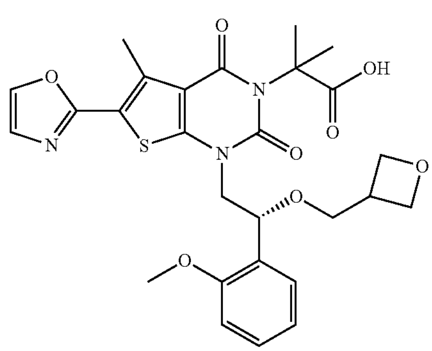 [SMILES: COc1ccccc1[C@H](Cn1c(=O)n(C(C)(C)C(=O)O)c(=O)c2c(C)c(-c3ncco3)sc21)OCC1COC1] | 556 (M + H)+ |

TABLE 1-continued

Exemplary Compounds of Formula I

| Cmpd # | Compound Structure | m/z |
| --- | --- | --- |
| I-270 | 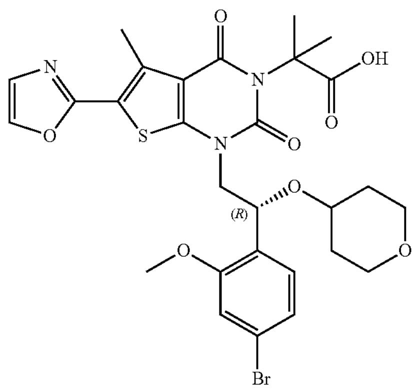 | 650 (M + H)+ |
| I-271 | 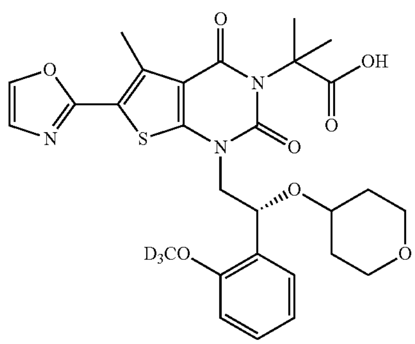 | 573 (M + H)+ |
| I-272 | 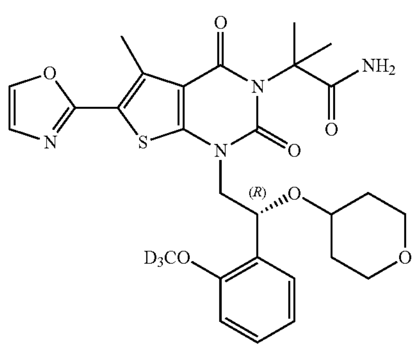 | 594 (M + Na)+ |
| I-273 | 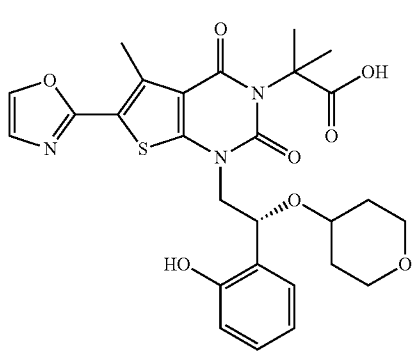 | 556 (M + H)+ |

TABLE 1-continued

Exemplary Compounds of Formula I

| Cmpd # | Compound Structure | m/z |
|---|---|---|
| I-274 | 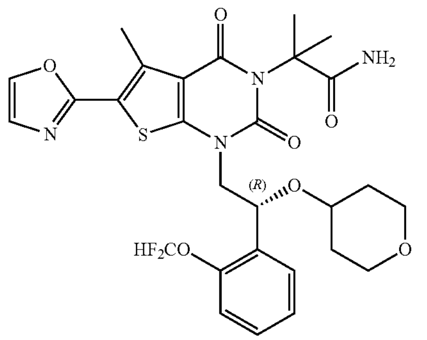 | 627 (M + Na)+ |
| I-275 | 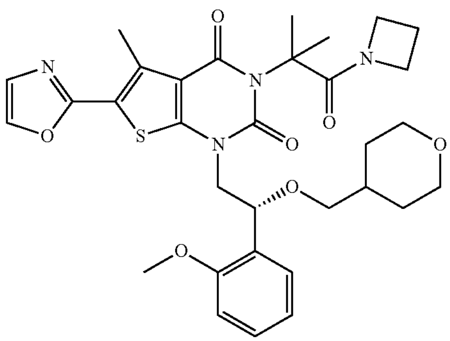 [SMILES: COc1ccccc1[C@H](Cn1c(=O)n(C(C)(C)C(=O)N2CCC2)c(=O)c2c(C)c(-c3ncco3)sc21)OCC1CCOCC1] | 623 (M + H)+ |
| I-276 | 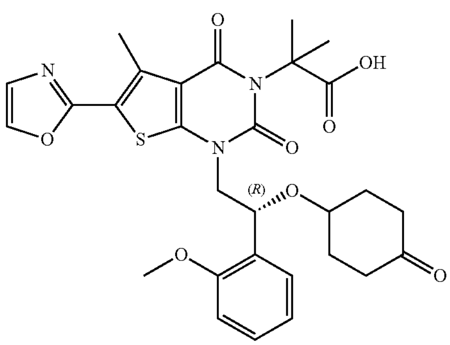 | 582 (M + H)+ |
| I-277 | 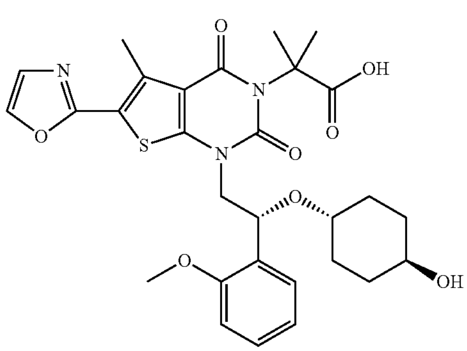 [SMILES: COc1ccccc1[C@H](Cn1c(=O)n(C(C)(C)C(=O)O)c(=O)c2c(C)c(-c3ncco3)sc21)O[C@H]1CC[C@H](O)CC1] | 584 (M + H)+ |

TABLE 1-continued

Exemplary Compounds of Formula I

| Cmpd # | Compound Structure | m/z |
|---|---|---|
| I-278 | 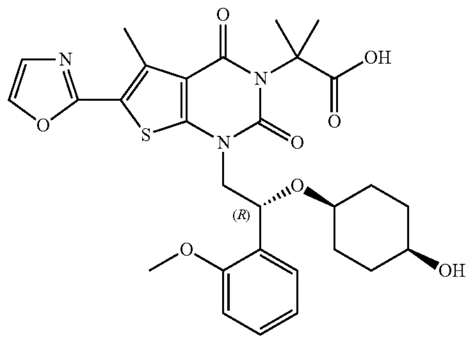 | 584 (M + H)+ |
| I-279 | 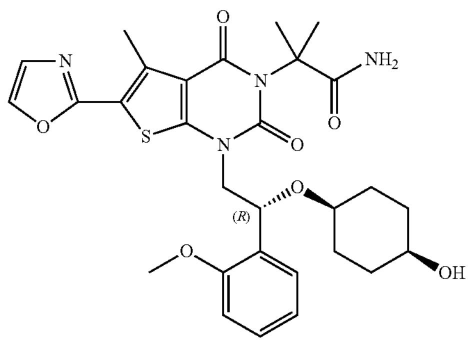 | 605 (M + Na)+ |
| I-280 | 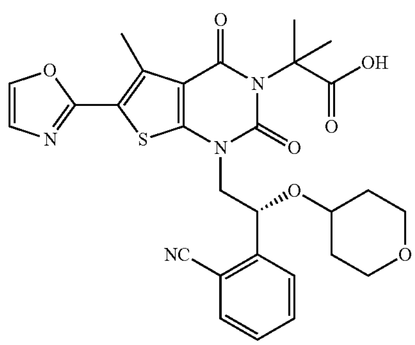 [SMILES: Cc1c(-c2ncco2)sc2c1c(=O)n(C(C)(C)C(=O)O)c(=O)n2C[C@H](OC1CCOCC1)c1ccccc1C#N] | 565 (M + H)+ |
| I-281 | 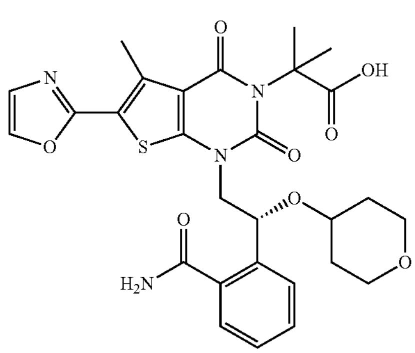 [SMILES: Cc1c(-c2ncco2)sc2c1c(=O)n(C(C)(C)C(=O)O)c(=O)n2C[C@H](OC1CCOCC1)c1ccccc1C(N)=O] | 583 (M + H)+ |

TABLE 1-continued

Exemplary Compounds of Formula I

| Cmpd # | Compound Structure | m/z |
| --- | --- | --- |
| I-282 | 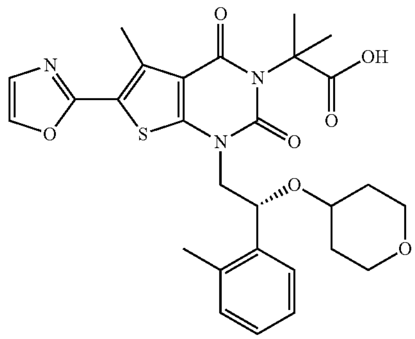 [SMILES: Cc1ccccc1[C@H](Cn1c(=O)n(C(C)(C)C(=O)O)c(=O)c2c(C)c(-c3ncco3)sc21)OC1CCOCC1] | 554 (M + H)+ |
| I-283 | 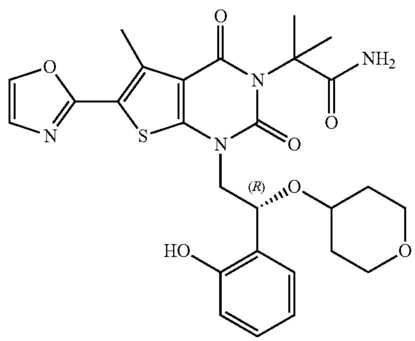 | 577 (M + Na)+ |
| I-284 | 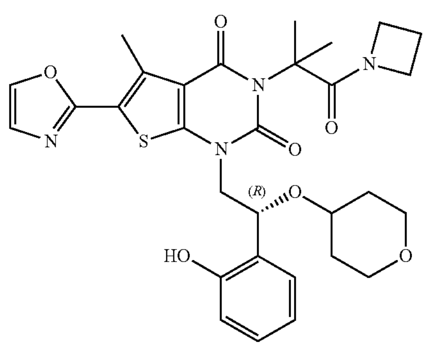 | 595 (M + H)+ |
| I-285 | 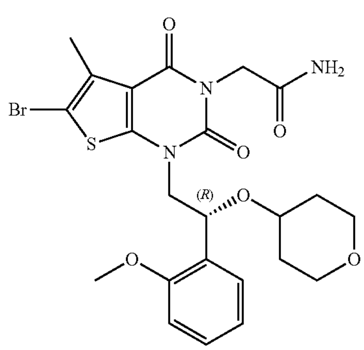 | 554, 552 (M + H+) |

TABLE 1-continued
Exemplary Compounds of Formula I
| Cmpd # | Compound Structure | m/z |
|---|---|---|
| I-286 | 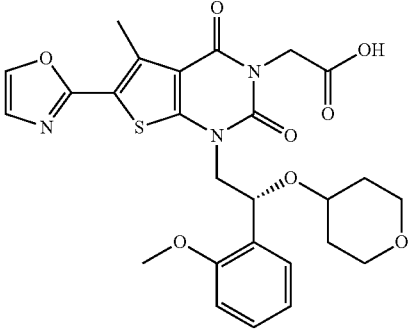 [SMILES: COc1ccccc1[C@H](Cn1c(=O)n(CC(=O)O)c(=O)c2c(C)c(-c3ncco3)sc21)OC1CCOCC1] | 542 (M + H)+ |
| I-287 | 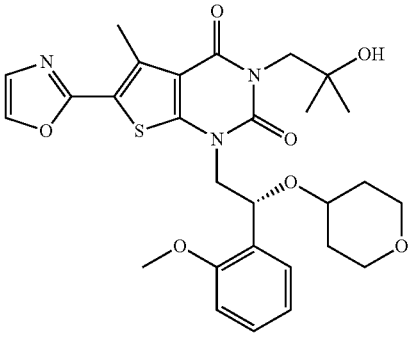 [SMILES: COc1ccccc1[C@H](Cn1c(=O)n(CC(C)(C)O)c(=O)c2c(C)c(-c3ncco3)sc21)OC1CCOCC1] | 556 (M + H)+ |
| I-288 | 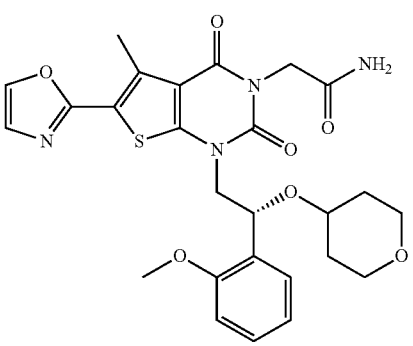 [SMILES: COc1ccccc1[C@H](Cn1c(=O)n(CC(N)=O)c(=O)c2c(C)c(-c3ncco3)sc21)OC1CCOCC1] | 541 (M + H)+ |
| I-289 | 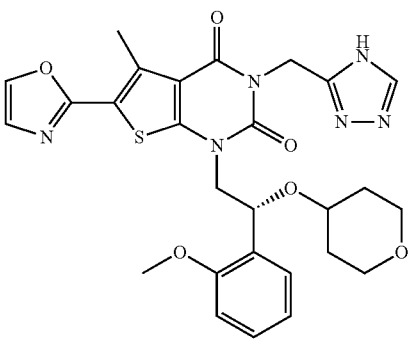 [SMILES: COc1ccccc1[C@H](Cn1c(=O)n(Cc2nnc[nH]2)c(=O)c2c(C)c(-c3ncco3)sc21)OC1CCOCC1] | 565 (M + H)+ |

TABLE 1-continued

Exemplary Compounds of Formula I

| Cmpd # | Compound Structure | m/z |
|---|---|---|
| I-290 | 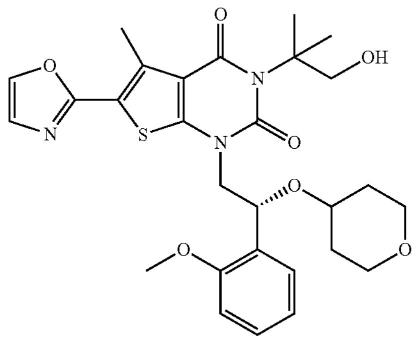 [SMILES: COc1ccccc1[C@H](Cn1c(=O)n(C(C)(C)CO)c(=O)c2c(C)c(-c3ncco3)sc21)OC1CCOCC1] | 556 (M + H)+ |
| I-291 | 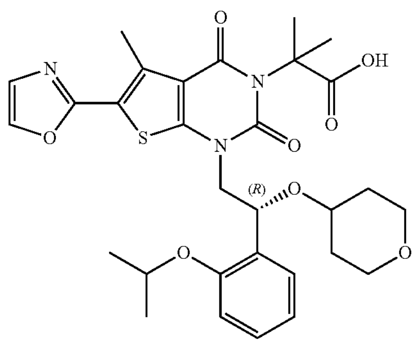 | 598 (M + H)+ |
| I-292 | 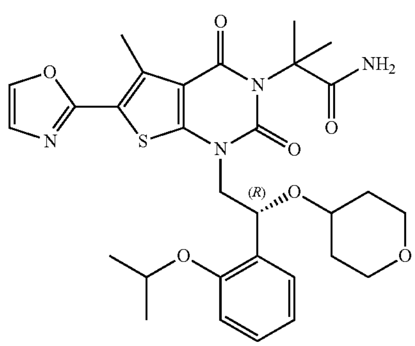 | 619 (M + Na)+ |
| I-293 | 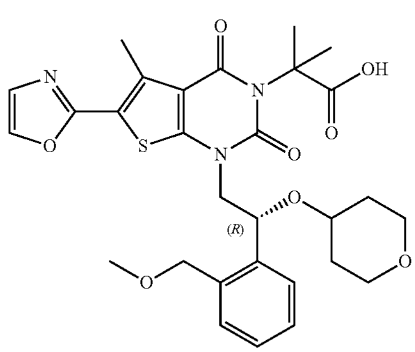 | 606 (M + Na)+ |

TABLE 1-continued

Exemplary Compounds of Formula I

| Cmpd # | Compound Structure | m/z |
| --- | --- | --- |
| I-294 | 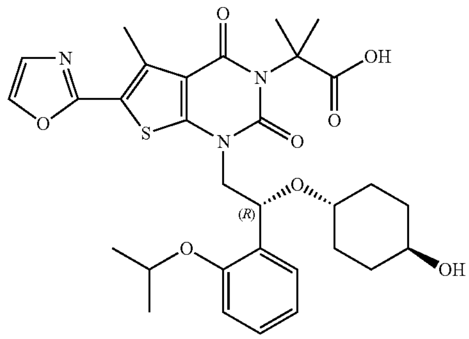 | 612 (M + H)+ |
| I-295 | 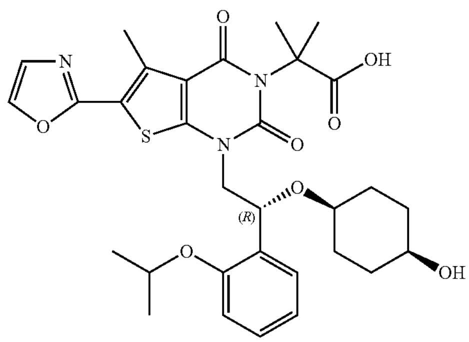 | 612 (M + H)+ |
| I-296 | 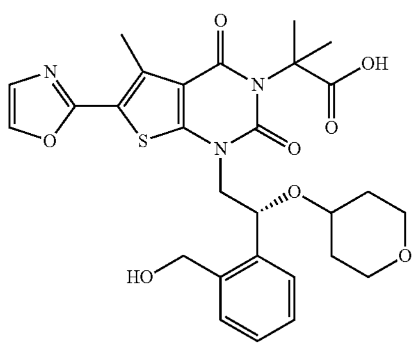 [SMILES: Cc1c(-c2ncco2)sc2c1c(=O)n(C(C)(C)C(=O)O)c(=O)n2C[C@H](OC1CCOCC1)c1ccccc1CC#N] | 592 (M + Na)+ |
| I-297 | 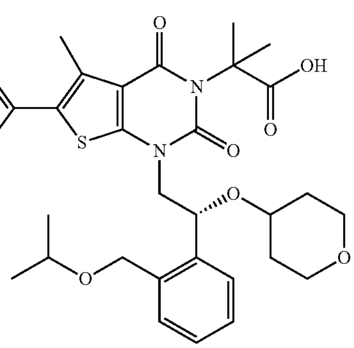 | 634 (M + Na)+ |

TABLE 1-continued

Exemplary Compounds of Formula I

| Cmpd # | Compound Structure | m/z |
|---|---|---|
| I-298 | 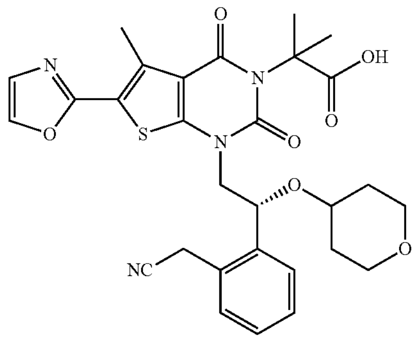 | 579 (M + H)+ |
| I-299 | 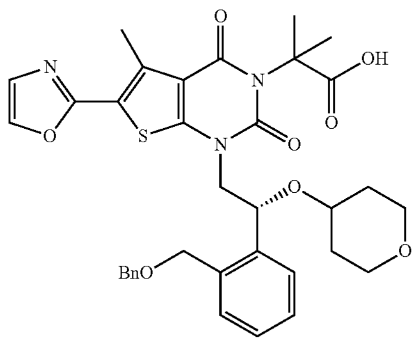 [SMILES: Cc1c(-c2ncco2)sc2c1c(=O)n(C(C)(C)C(=O)O)c(=O)n2C[C@H](OC1CCOCC1)c1ccccc1COCc1ccccc1] | |
| I-300 | 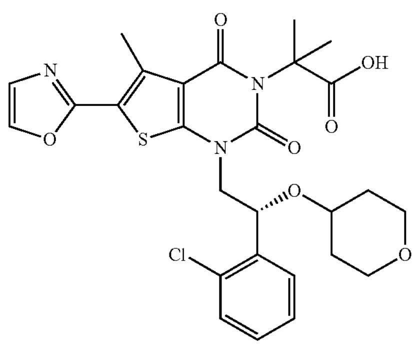 [SMILES: Cc1c(-c2ncco2)sc2c1c(=O)n(C(C)(C)C(=O)O)c(=O)n2C[C@H](OC1CCOCC1)c1ccccc1Cl] | 574 (M + H)+ |
| I-301 | 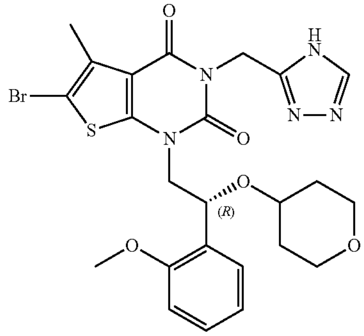 | 576 (M + H)+ |

TABLE 1-continued

Exemplary Compounds of Formula I

| Cmpd # | Compound Structure | m/z |
|---|---|---|
| I-302 | 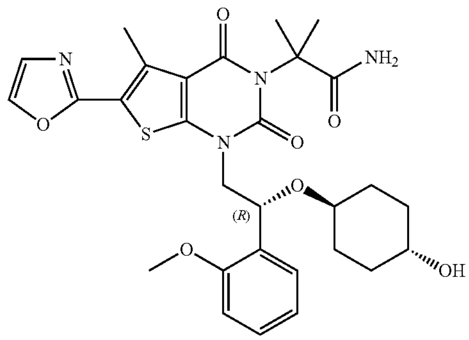 | 605 (M + Na)+ |
| I-303 | 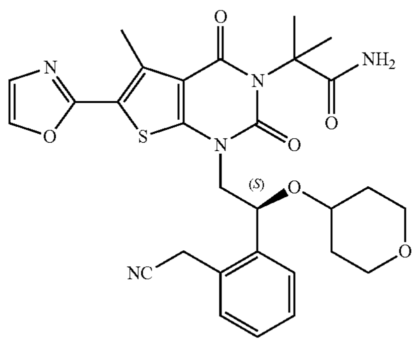 | 579 (M + H)+ |
| I-304 | 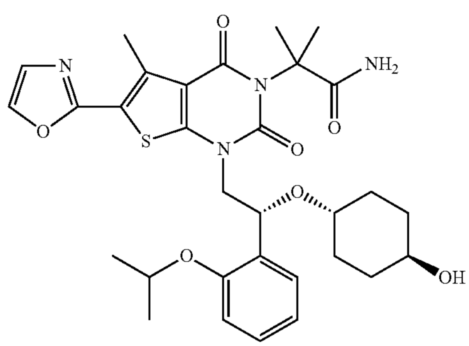 [SMILES: Cc1c(-c2ncco2)sc2c1c(=O)n(C(C)(C)C(N)=O)c(=O)n2C[C@H](O[C@H]1CC[C@H](O)CC1)c1ccccc1OC(C)C] | 633 (M + Na)+ |
| I-305 | 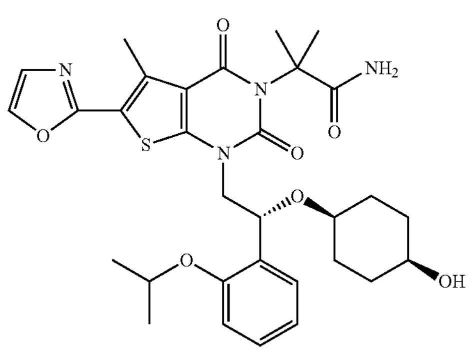 [SMILES: Cc1c(-c2ncco2)sc2c1c(=O)n(C(C)(C)C(N)=O)c(=O)n2C[C@H](O[C@H]1CC[C@@H](O)CC1)c1ccccc1OC(C)C] | 633 (M + Na)+ |

TABLE 1-continued

Exemplary Compounds of Formula I

| Cmpd # | Compound Structure | m/z |
|---|---|---|
| I-306 | 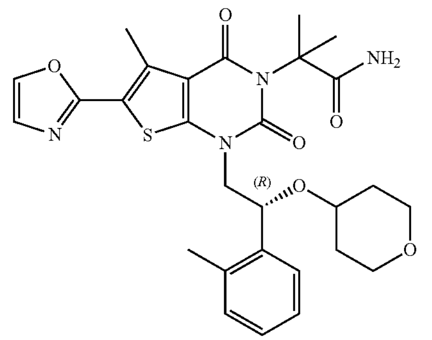 | 575 (M + Na)+ |
| I-307 | 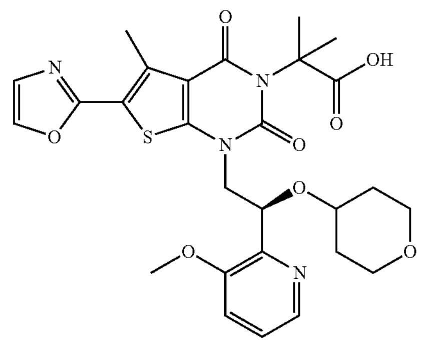 [SMILES: COc1cccnc1[C@@H](Cn1c(=O)n(C(C)(C)C(=O)O)c(=O)c2c(C)c(-c3ncco3)sc21)OC1CCOCC1] | 593 (M + Na)+ |
| I-308 | 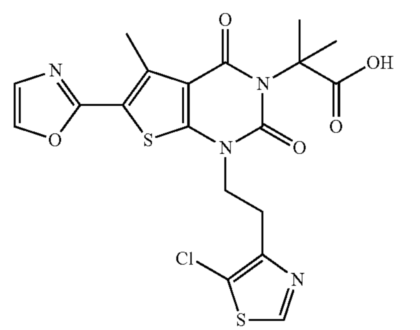 [SMILES: Cc1c(-c2ncco2)sc2c1c(=O)n(C(C)(C)C(=O)O)c(=O)n2CCc1ncsc1Cl] | 481 (M + H)+ |

In certain embodiments, the present invention provides any compound selected from those depicted in Table 1, above, or a pharmaceutically acceptable salt thereof 4. Uses, Formulation and Administration and Pharmaceutically Acceptable Compositions According to another embodiment, the invention provides a composition comprising a compound of this invention or a pharmaceutically acceptable salt, ester, or salt of ester thereof and a pharmaceutically acceptable carrier, adjuvant, or vehicle. The amount of compound in compositions of this invention is such that is effective to measurably inhibit ACC, in a biological sample or in a patient. In certain embodiments, the amount of compound in compositions of this invention is such that is effective to measurably inhibit ACC, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of ACC.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Acetyl-CoA carboxylase (ACC) catalyzes the ATP-dependent carboxylation of acetyl-CoA to form malonyl-CoA. This reaction, which proceeds in two half-reactions, a biotin carboxylase (BC) reaction and a carboxyltransferase (CT) reaction, is the first committed step in fatty acid (FA) biosynthesis and is the rate-limiting reaction for the pathway. In addition to its role as a substrate in FA biosynthesis, malonyl-CoA, the product of the ACC-catalyzed reaction, also plays an important regulatory role in controlling mitochondrial FA uptake through allosteric inhibition of carnitine palmitoyltransferase I (CPT-I), the enzyme catalyzing the first committed step in mitochondrial FA oxidation. Malonyl-CoA, therefore, is a key metabolic signal for the control of FA production and utilization in response to dietary changes and altered nutritional requirements in animals, for example during exercise, and therefore plays a key role in controlling the switch between carbohydrate and fat utilization in liver and skeletal muscle [Harwood, 2005].

In mammals, ACC exists as two tissue-specific isozymes, ACC1 which is present in lipogenic tissues (liver, adipose) and ACC2, which is present in oxidative tissues (liver, heart, skeletal muscle). ACC1 and ACC2 are encoded by separate genes, display distinct cellular distributions, and share 75% overall amino acid sequence identity, except for an extension at the N-terminus of ACC2 that direct ACC2 to the mitochondrial membrane. ACC1, which lacks this targeting sequence, is localized to the cytoplasm. In the heart and skeletal muscle, which have a limited capacity to synthesize fatty acids, the malonyl-CoA formed by ACC2 functions to regulate FA oxidation. In the liver, the malonyl-CoA formed in the cytoplasm through the actions of ACC1 is utilized for FA synthesis and elongation leading to triglyceride formation and VLDL production, whereas the malonyl-CoA formed at the mitochondrial surface by ACC2 acts to regulate FA oxidation [Tong and Harwood, *J. Cellular Biochem.* 99: 1476, 2006]. This compartmentalization of malonyl-CoA results from a combination of synthesis proximity [Abu-Elheiga et al., PNAS (USA) 102: 12011, 2005] and the rapid action of malonyl-CoA decarboxylase [Cheng et al., *J. Med. Chem.* 49:1517, 2006].

Simultaneous inhibition of the enzymatic activities of ACC1 and ACC2 offers the ability to inhibit de novo FA production in lipogenic tissues (e.g. liver & adipose) while at the same time stimulating FA oxidation in oxidative tissues (e.g. liver & skeletal muscle) and therefore offers an attractive modality for favorably affecting, in a concerted manner, a multitude of cardiovascular risk factors associated with obesity, diabetes, insulin resistance, and the metabolic syndrome.

Several lines of evidence strongly support the concept of direct inhibition of ACC activity as an important therapeutic target for treating obesity, diabetes, insulin resistance, and the metabolic syndrome.

Abu-Elheiga et al. [*Proc. Natl. Acad. Sci.* USA 100:10207-10212, 2003] demonstrated that ACC2 knock-out mice exhibit reduced skeletal and cardiac muscle malonyl-CoA, increased muscle FA oxidation, reduced hepatic fat, reduced total body fat, elevated skeletal muscle uncoupling protein-3 (UCP3) which is indicative of increased energy expenditure, reduced body weight, reduced plasma free FAs, reduced plasma glucose, and reduced tissue glycogen, and are protected from diet-induced diabetes and obesity.

Savage et al. [*J. Clin. Invest.* 116: 817, 2006], using ACC1 and ACC2 antisense oligonucleotides, demonstrated stimulation of FA oxidation in isolated rat hepatocytes and in rats fed high-fat diets, and lowering of hepatic triglycerides, improvements in insulin sensitivity, reductions in hepatic glucose production, and increases in UCP1 mRNA in high fat-fed rats. These effects were greater when both ACC1 and ACC2 expression were suppressed than when either ACC1 or ACC2 expression alone was suppressed.

Harwood et al. [*J. Biol. Chem.* 278: 37099, 2003] demonstrated that the isozyme-nonselective ACC inhibitor, CP-640186, which equally inhibits ACC1 and ACC2 ($IC_{50}$=~60 nM) isolated from rat, mouse, monkey and human without inhibiting either pyruvate carboxylase or propionyl-CoA carboxylase, reduced FA synthesis, triglyceride synthesis and secretion in Hep-G2 cells without affecting cholesterol synthesis, and reduced apoB secretion without affecting apoA1 secretion. CP-640186 also stimulated FA oxidation in C2C12 cells and in rat muscle slices and increased CPT-I activity in Hep-G2 cells. In experimental animals, CP-640186 acutely reduced malonyl-CoA concentration in both lipogenic and oxidative tissues in both the fed and fasted state, reduced liver and adipose tissue FA synthesis, and increased whole body FA oxidation. In sucrose-fed rats treated with CP-640186 for three weeks, CP-640186 time- and dose-dependently reduced liver, muscle and adipose triglycerides, reduced body weight due to selective fat reduction without reducing lean body mass, reduced leptin levels, reduced the hyperinsulinemia produced by the high sucrose diet without changing plasma glucose levels, and improved insulin sensitivity.

Saha et al. [*Diabetes* 55:A288, 2006] demonstrated stimulation of insulin sensitivity in insulin-resistant rat muscle tissue by CP-640186 within 30 min of compound administration, and studies by Furler et al. [*Diabetes* 55:A333, 2006] used dual tracer analysis to show that acute (46 min) treatment of rats with CP-640186 stimulated FA clearance without decreasing glucose clearance.

ACC is the rate-limiting enzyme in fatty acid synthesis and its product, malonyl CoA, serves as an important regulator of fatty acid oxidation. Hence, ACC inhibitors both reduce de novo lipid synthesis and promote the oxidation of existing fat. This dual effect on lipid metabolism raises the possibility that ACC inhibitors will be substantially more effective in reducing excess fat than other mechanisms. Furthermore, ACC inhibitors will impact insulin sensitivity, plasma and tissue triglycerides, and fasting plasma glucose as a consequence of whole-body and tissue-specific fat mass reduction without the need for poly-pharmacy.

ACC inhibitors need only access the liver and muscle in the peripheral compartment. Avoiding the CNS will address many of side effects associated with the late-stage obesity programs targeting CNS receptors. ACC inhibitors are also expected to have superior safety profiles to existing metabolic disease agents. For example, it is unlikely that an ACC inhibitor will precipitate life-threatening hypoglycemia as is often seen with insulin mimetics, insulin secretagogues, and insulin degradation inhibitors. Also, since ACC inhibitors will reduce whole-body fat mass, they will be superior to the glitazones that increase whole-body fat mass as part of their mechanism of action.

A peripherally acting agent that causes significant weight loss and improves other metabolic endpoints fits well within the US FDA's requirements for approval of a new obesity agent. However, if an approval for obesity continues to be challenging in 5-7 years, ACC inhibitors could be approved for familial combined hyperlipidemia and non-alcoholic steatohepatitis (NASH). There are currently no marketed ACC inhibitors, so an isozyme-nonselective ACC inhibitor would represent first-in-class therapy for treating obesity and metabolic syndrome.

The activity of a compound utilized in this invention as an inhibitor of ACC or treatment for obesity or metabolic syndrome, may be assayed in vitro or in vivo. An in vivo assessment of the efficacy of the compounds of the invention may be made using an animal model of obesity or metabolic syndrome, e.g., a rodent or primate model. Cell-based assays may be performed using, e.g., a cell line isolated from a tissue that expresses ACC. Additionally, biochemical or mechanism-based assays, e.g., transcription assays using a purified protein, Northern blot, RT-PCR, etc., may be performed. In vitro assays include assays that determine cell morphology, protein expression, and/or the cytotoxicity, enzyme inhibitory activity, and/or the subsequent functional consequences of treatment of cells with compounds of the invention. Alternate in vitro assays quantitate the ability of the inhibitor to bind to protein or nucleic acid molecules within the cell. Inhibitor binding may be measured by radiolabelling the inhibitor prior to binding, isolating the inhibitor/target molecule complex and determining the amount of radiolabel bound. Alternatively, inhibitor binding may be determined by running a competition experiment where new inhibitors are incubated with purified proteins or nucleic acids bound to known radioligands. Detailed conditions for assaying a compound utilized in this invention as an inhibitor of ACC are set forth in the Examples below. The aforementioned assays are exemplary and not intended to limit the scope of the invention. The skilled practitioner can appreciate that modifications can be made to conventional assays to develop equivalent assays that obtain the same result.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The compounds and compositions, according to the method of the present invention, may be administered using any amount and any route of administration effective for treating or lessening the severity of a metabolic disorder or condition, cancer, a bacterial infection, a fungal infection, a parasitic infection (e.g. malaria), an autoimmune disorder, a neurodegenerative or neurological disorder, schizophrenia, a bone-related disorder, liver disease, or a cardiac disorder.

In some embodiments, the compounds and compositions, according to the method of the present invention, may be administered using any amount and any route of administration effective for treating or lessening the severity of a disease associated with ACC (Tong et al. "Acetyl-coenzyme A carboxylase: crucial metabolic enzyme and attractive target for drug discovery" Cell and Molecular Life Sciences (2005) 62, 1784-1803).

In some embodiments, the compounds and compositions, according to the method of the present invention, may be administered using any amount and any route of administration effective for treating or lessening the severity of a metabolic disorder, disease, or condition. In some embodiments, the metabolic disorder is obesity, metabolic syndrome, diabetes or diabetes-related disorders including Type 1 diabetes (insulin-dependent diabetes mellitus, IDDM) and Type 2 diabetes (non-insulin-dependent diabetes mellitus, NIDDM), impaired glucose tolerance, insulin resistance, hyperglycemia, diabetic complications, including, but not limited to atherosclerosis, coronary heart disease, stroke, peripheral vascular disease, nephropathy, hypertension, neuropathy and nephropathy; obesity comorbidities including but not limited to metabolic syndrome, dyslipidemia, hypertension, insulin resistance, diabetes (including Type 1 and Type 2 diabetes), coronary artery disease, and heart failure. In some embodiments, the metabolic disorder, disease or condition is non-alcoholic fatty liver disease or hepatic insulin resistance.

In some embodiments, the present invention provides a method of treating a metabolic disorder, disease, or condition described herein, comprising administering a compound of the invention in conjunction with one or more pharmaceutical agents. Suitable pharmaceutical agents that may be used in combination with the compounds of the present invention include anti-obesity agents (including appetite suppressants), anti-diabetic agents, anti-hyperglycemic agents, lipid lowering agents, and anti-hypertensive agents.

Suitable lipid lowering agents that can be used in conjunction with compounds of the present invention include but are not limited to, bile acid sequestrants, HMG-CoA reductase inhibitors, HMG-CoA synthase inhibitors, cholesterol absorption inhibitors, acyl coenzyme A-cholesterol acyl transferase (ACAT) inhibitors, CETP inhibitors, squalene synthetase inhibitors, PPAR-alpha agonists, FXR receptor modulators, LXR receptor modulators, lipoprotein synthesis inhibitors, renin-angiotensin system inhibitors, PPAR-delta partial agonists, bile acid reabsorption inhibitors, PPAR-gamma agonists, triglyceride synthesis inhibitors, microsomal triglyceride transport inhibitors, transcription modulators, squalene epoxidase inhibitors, low density lipoprotein receptor inducers, platelet aggregation inhibitors, 5-LO or FLAP inhibitors, niacin, and niacin-bound chromium.

Suitable anti-hypertensive agents that can be used in conjunction with compounds of the present invention include but are not limited to diuretics, beta-adrenergic blockers, calcium channel blockers, angiotensin converting enzyme (ACE) inhibitors, neutral endopeptidase inhibitors, endothelin antagonists, vasodilators, angiotensin II receptor antagonists, alpha/beta adrenergic blockers, alpha 1 blockers, alpha 2 agonists, aldosterone inhibitors, mineralocorticoid receptor inhibitors, renin inhibitors, and angiopoietin 2 binding agents.

Suitable anti-diabetic agents that can be used in conjunction with compounds of the present invention include but are not limited to other acetyl-CoA carboxylase (ACC) inhibitors, DGAT-1 inhibitors, AZD7687, LCQ908, DGAT-2 inhibitors, monoacylglycerol O-acyltransferase inhibitors, PDE-10 inhibitors, AMPK activators, sulfonylureas (e.g. acetohexamide, chlorpropamide, diabinese, glibenclamide, glipizide, glyburide, blimipiride, gliclazide, glipentide, gliquidone, glisolamide, tolazamide, tolbutamide), meglitinides, alpha-amylase inhibitors (e.g. tendamistat, treastatin, AL-3688), alpha-glucoside hydrolase inhibitors (e.g. acarbose), alpha-glucosidase inhibitors (e.g. adiposine, camiglibose, emiglitate, miglitol, voglibose, pradimicin-Q, sarbostatin), PPAR-gamma agonists (e.g. balaglitazone, ciglitazone, darglitazone, englitazone, isaglitazone, pioglitazone, rosiglitazone, troglitazone), PPAR-alpha/gamma agonists (e.g. CLX-0940, GW-1536, GW-1929, GW-2433, KRP-297, L-796449, LR-90, MK-0767, SB-219994), biguanides (e.g. metformin, buformin), GLP-1 modulators (exendin-3, exendin-4), liraglutide, albiglutide, exenatide (Byetta), taspoglutide, lixisenatide, dulaglutide, semaglutide, N,N-9924, TTP-054, PTP-1B inhibitors (trodusquemine, hyrtiosal extract), SIRT-1 inhibitors (e.g. resveratrol, GSK2245840, GSK184072), DPP-IV inhibitors (e.g. sitagliptin, vildagliptin, alogliptin, dutogliptin, linagliptin, saxagliptin), insulin secretagogues, fatty acid oxidation inhibitors, A2 antagonists, JNK inhibitors, glucokinase activators (e.g. TTP-399, TTP-355, TTP-547, AZD1656, ARRY403, MK-0599, TAK- 329, AZD5658, GKM-001), insulin, insulin mimetics, glycogen phosphorylase inhibitors (e.g. GSK1362885), VPAC2 receptor agonists, SGLT2 inhibitors (dapagliflozin, canagliflozin, BI-10733, tofogliflozin, ASP-1941, THR1474, TS-071, ISIS388626, LX4211), glucagon receptor modulators, GPR119 modulators (e.g. MBX-2982, GSK1292263, APD597, PSN821), FGF21 derivatives, TGR5 (GPBAR1) receptor agonists (e.g. INT777), GPR40 agonists (e.g. TAK-875), GPR120 agonists, nicotinic acid receptor (HM74A) activators, SGLT1 inhibitors (e.g. GSK1614235), carnitine palmitoyl transferase enzyme inhibitors, fructose 1,6-diphosphatase inhibitors, aldose reductase inhibitors, mineralocorticoid receptor inhibitors, TORC2 inhibitors, CCR2 inhibitors, CCR5 inhibitors, PKC (e.g. PKC-alpha, PKC-beta, PKC-gamma) inhibitors, fatty acid synthetase inhibitors, serine palmitoyl transferase inhibitors, GPR81 modulators, GPR39 modulators, GPR43 modulators, GPR41 modulators, GPR105 modulators, Kv1.3 inhibitors, retinol binding protein 4 inhibitors, glucocorticoid receptor modulators, somatostatin receptor (e.g. SSTR1, SSTR2, SSTR3, SSTR5) inhibitors, PDHK2 inhibitors, PDHK4 inhibitors, MAP4K4 inhibitors, IL1-beta modulators, and RXR-alpha modulators.

Suitable anti-obesity agents include but are not limited to, 11-beta-hydroxysteroid dehydrogenase 1 inhibitors, stearoyl-CoA desaturase (SCD-1) inhibitors, MCR-4 agonists, CCK-A agonists, monoamine reuptake inhibitors (e.g. sibutramine), sympathomimetic agents, beta-3-adrenergic receptor agonists, dopamine receptor agonists (e.g. bromocriptine), melanocyte-stimulating hormone and analogs thereof, 5-HT$_{2C}$ agonists (e.g. lorcaserin/Belviq), melanin concentrating hormone antagonists, leptin, leptin analogs, leptin agonists, galanin antagonists, lipase inhibitors (e.g. tetrahydrolipstatin/Orlistat), anorectic agents (e.g. bombesin agonists), NPY antagonists (e.g. velneperit), PYY$_{3-36}$ (and analogs thereof), BRS3 modulators, opioid receptor mixed antagonists, thyromimetic agents, dehydroepiandrosterone, glucocorticoid agonists or antagonists, orexin antagonists, GLP-1 agonists, ciliary neurotrophic factors (e.g. Axokine), human agouti-related protein (AGRP) inhibitors, H3 antagonists or inverse agonists, neuromedin U agonists, MTP/ApoB inhibitors (e.g. gut-selective MTP inhibitors such as dirlotapide, JTT130, Usistapide, SLX4090), MetAp2 inhibitors (e.g. ZGN-433), agents with mixed modulatory activity at two or more of glucagon, GIP, and GLP1 receptors (e.g. MAR-701, ZP2929), norepinephrine reuptake inhibitors, opioid antagonists (e.g. naltrexone), CB1 receptor antagonists or inverse agonists, ghrelin agonists or antagonists, oxyntomodulin and analogs thereof, monoamine uptake inhibitors (e.g. tesofensine), and combination agents (e.g. buprorion plus zonisamide (Empatic), pramlintide plus metreleptin, buprorion plus naltrexone (Contrave), phentermine plus topiramate (Qsymia).

In some embodiments, the anti-obesity agents used in combination with compounds of the invention are selected from gut-selective MTP inhibitors (e.g. dirlotapide, mitratapide, implitapide, R56918), CCK-A agonists, 5-HT$_{2C}$ agonists (e.g. lorcaserin/Belviq), MCR4 agonists, lipase inhibitors (e.g. Cetilistat), PYY$_{3-36}$ (including analogs and PEGylated analogs thereof), opioid antagonists (e.g. naltrexone), oleoyl estrone, obinepitide, pramlintide, tesofensine, leptin, bromocriptine, orlistat, AOD-9604, and sibutramine.

In some embodiments, the compounds and compositions, according to the method of the present invention, may be administered using any amount and any route of administration effective for treating or lessening the severity of a LKB1 or Kras associated disease. In some embodiments, the LKB1 or Kras associated disease is selected from hepatocellular carcinoma, LKB1 mutant cancers, LKB1 loss of heterozygosity (LOH) driven cancers, Kras mutant cancers, Peutz-Jeghers syndrome (PJS), Cowden's disease (CD), and tubeous sclerosis (TS) (Makowski et al. "Role of LKB1 in Lung Cancer Development" British Journal of Cancer (2008) 99, 683-688). In some embodiments, the LKB1 or Kras associated disease is a Kras positive/LKB1 deficient lung tumor.

In some embodiments, the compounds and compositions, according to the method of the present invention, may be administered using any amount and any route of administration effective for treating or lessening the severity of a cancer, or inhibiting the growth of or inducing apoptosis in cancer cells (Wang et al. "Acetyl-CoA Carboxylase-alpha Inhibitor TOFA Induces Human Cancer Cell Apoptosis" Biochem Biophys Res Commun. (2009) 385(3), 302-306; Chajes et al. "Acetyl-CoA Carboxylase alpha Is Essential to Breast Cancer Cell Survival" Cancer Res. (2006) 66, 5287-5294; Beckers et al. "Chemical Inhibition of Acetyl-CoA Carboxylase Induces Growth Arrest and Cytotoxicity Selectivity in Cancer Cells" Cancer Res. (2007) 8180-8187; Brusselmans et al. "RNA Interference-Mediated Silencing of the Acetyl-CoA-Carboxylase-alpha Gene Induces Growth Inhibition and Apoptosis of Prostate Cancer Cells" Cancer Res. (2005) 65, 6719-6725; Brunet et al. "BRCA1 and Acetyl-CoA Carboxylase: The Metabolic Syndrom of Breast Cancer" Molecular Carcinogenesis (2008) 47, 157-163; Cairns et al. "Regulation of Cancer Cell Metabolism" (2011) 11, 85-95; Chiaradonna et al. "From Cancer Metabolism to New Biomarkers and Drug Targets" Biotechnology Advances (2012) 30, 30-51).

In some embodiments, the compounds and compositions, according to the method of the present invention, may be administered using any amount and any route of administration effective for treating or lessening the severity of a melanoma. In some embodiments, the melanoma is one bearing an activated MAPK pathway (Petti et al. "AMPK activators inhibit the proliferation of human melanomas bearing the activated MAPK pathway" Melanoma Research (2012) 22, 341-350).

Compounds of the present invention find special utility in triple negative breast cancer, as the tumor suppressor protein BRCA1 binds and stabilizes the inactive form of ACC, thus upregulating de novo lipid synthesis, resulting in cancer cell proliferation Brunet et al. "BRCA1 and acetyl-CoA carboxylase: the metabolic syndrome of breast cancer" Mol. Carcinog. (2008) 47(2), 157-163.

In some embodiments, the compounds and compositions, according to the method of the present invention, may be administered using any amount and any route of administration effective for treating or lessening the severity of a liposarcoma. Liposarcomas have been shown to depend on de novo long-chain fatty acid synthesis for growth, and inhibition of ACC by soraphen A inhibited lipogenesis as well as tumor cell growth (Olsen et al. "Fatty acid synthesis is a therapeutic target in human liposarcoma" International J. of Oncology (2010) 36, 1309-1314).

In some embodiments, the compounds and compositions, according to the method of the present invention, may be administered using any amount and any route of administration effective for treating or lessening the severity of a liver disease. In some embodiments, the liver disease is selected from hepatitis C, hepatocellular carcinoma, familial combined hyperlipidemia and non-alcoholic steatohepatitis (NASH), liver cancer, cholangiocarcinoma, angiosarcoma, hemangiosarcoma, and progressive familial intrahepatic cholestasis.

In some embodiments, the compounds and compositions, according to the method of the present invention, may be administered using any amount and any route of administration effective for treating or lessening the severity of a bacterial infection or inhibiting the growth of bacteria.

In some embodiments, the compounds and compositions, according to the method of the present invention, may be administered using any amount and any route of administration effective for treating or lessening the severity of a fungal infection or inhibiting the growth of fungal cells (Shen et al. "A Mechanism for the Potent Inhibition of Eukaryotic Acetyl-Coenzyme A Carboxylase by Soraphen A, a Macrocyclic Polyketide Natural Product" Molecular Cell (2004) 16, 881-891).

In some embodiments, the compounds and compositions, according to the method of the present invention, may be administered using any amount and any route of administration effective for treating or lessening the severity of a bacterial infection (Tong, L. et al. J. Cell. Biochem. (2006) 99, 1476-1488).

In some embodiments, the compounds and compositions, according to the method of the present invention, may be administered using any amount and any route of administration effective for treating or lessening the severity of a viral infection (Munger et al. Nat. Biotechnol. (2008) 26, 1179-1186). In some embodiments, the viral infection is Hepatitis C.

In some embodiments, the compounds and compositions, according to the method of the present invention, may be administered using any amount and any route of administration effective for treating or lessening the severity of a neurological disease (Henderson et al. Neurotherapeutics (2008) 5, 470-480; Costantini et al. Neurosci. (2008) 9 Suppl. 2:S16; Baranano et al. Curr. Treat. Opin. Neurol. (2008) 10, 410-419).

In some embodiments, the compounds and compositions, according to the method of the present invention, may be administered using any amount and any route of administration effective for treating or lessening the severity of a parasitic infection or inhibiting the growth of parasites (e.g. malaria and toxoplasma: Gornicki et al. "Apicoplast fatty acid biosynthesis as a target for medical intervention in apicomplexan parasites" International Journal of Parasitology (2003) 33, 885-896; Zuther et al. "Growth of *Toxoplasma gondii* is inhibited by aryloxyphenoxypropionate herbicides targeting acetyl-CoA carboxylase" PNAS (1999) 96 (23) 13387-13392).

In some embodiments, the compounds and compositions, according to the method of the present invention, may be administered using any amount and any route of administration effective for treating or lessening the severity of a cardiac disorder. In some embodiments, the cardiac disorder is cardiac hypertrophy. In some embodiments the cardiac disorder is treated or its severity lessened by the cardioprotective mechanism resulting from increased fatty acid oxidation via ACC inhibition (Kolwicz et al. "Cardiac-specific deletion of acetyl CoA carboxylase 2 (ACC2) prevents metabolic remodeling during pressure-overload hypertrophy" Circ. Res. (2012); DOI: 10.1161/CIRCRESAHA.112.268128).

In certain embodiments, the compounds and compositions, according to the method of the present invention, may be used as herbicides. In some embodiments, the present invention provides a method to inhibit the growth or viability of plants comprising treating plants with compounds of the present invention. In some embodiments of the present invention, compounds of the present invention can be used to inhibit the growth or viability of plants by inhibiting ACC. In some embodiments, the method of the present invention comprises using compounds of the present invention to inhibit fatty acid production in or increase fatty acid oxidation in plants.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting ACC in a biological sample comprising the step of contacting said biological sample with a compound of this invention, or a composition comprising said compound.

In certain embodiments, the invention relates to a method of modulating fatty acid levels in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of enzymes in a biological sample is useful for a variety of purposes that are known to one of skill in the art. Examples of such purposes include, but are not limited to biological assays, gene expression studies, and biological target identification.

Another embodiment of the present invention relates to a method of inhibiting ACC in a patient comprising the step of administering to said patient a compound of the present invention, or a composition comprising said compound.

According to another embodiment, the invention relates to a method of inhibiting fatty acid production, stimulating fatty acid oxidation, or both, in a patient comprising the step of administering to said patient a compound of the present invention, or a composition comprising said compound.

According to certain embodiments, the invention relates to a method of inhibiting fatty acid production, stimulating fatty acid oxidation, or both in a patient, leading to decreasing obesity or alleviating symptoms of metabolic syndrome, comprising the step of administering to said patient a compound of the present invention, or a composition comprising said compound. In other embodiments, the present invention provides a method for treating a disorder mediated by ACC, in a patient in need thereof, comprising the step of administering to said patient a compound according to the present invention or pharmaceutically acceptable composition thereof. Such disorders are described in detail herein.

In some embodiments the compounds and compositions of the present invention may be used in a method of treating obesity or another metabolic disorder. In certain embodiments the compounds and compositions of the present invention may be used to treat obesity or other metabolic disorder in a mammal. In certain embodiments the mammal is a human patient. In certain embodiments the compounds and compositions of the present invention may be used to treat obesity or other metabolic disorder in a human patient.

In some embodiments the present invention provides a method of treating obesity or another metabolic disorder, comprising administering a compound or composition of the present invention to a patient with obesity or another metabolic disorder. In certain embodiments the method of treating obesity or other metabolic disorder comprises administering compounds and compositions of the present invention to a mammal. In certain embodiments the mammal is a human. In some embodiments the metabolic disorder is dyslipidemia or hyperlipidemia. In some embodiments, the obesity is a symptom of Prader-Willi syndrome, Bardet-Biedl syndrome, Cohen syndrome or MOMO syndrome. In some embodiments, the obesity is a side effect of the administration of another medication, including but not limited to insulin, sulfunylureas, thiazolidinediones, antipsychotics, antidepressants, steroids, anticonvulsants (including phenyloin and valproate), pizotifen, or hormonal contraceptives.

In certain embodiments, the present invention provides a method of treating cancer or another proliferative disorder, comprising administering a compound or composition of the present invention to a patient with cancer or another proliferative disorder. In certain embodiments, the method of treating cancer or another proliferative disorder comprises administering compounds and compositions of the present invention to a mammal. In certain embodiments, the mammal is a human.

As used herein, the terms "inhibition of cancer" and "inhibition of cancer cell proliferation" refer to the inhibition of the growth, division, maturation or viability of cancer cells, and/or causing the death of cancer cells, individually or in aggregate with other cancer cells, by cytotoxicity, nutrient depletion, or the induction of apoptosis.

Examples of tissues containing cancerous cells whose proliferation is inhibited by the compounds and compositions described herein and against which the methods described herein are useful include but are not limited to breast, prostate, brain, blood, bone marrow, liver, pancreas, skin, kidney, colon, ovary, lung, testicle, penis, thyroid, parathyroid, pituitary, thymus, retina, uvea, conjunctiva, spleen, head, neck, trachea, gall bladder, rectum, salivary gland, adrenal gland, throat, esophagus, lymph nodes, sweat glands, sebaceous glands, muscle, heart, and stomach.

In some embodiments, the cancer treated by compounds or compositions of the invention is a melanoma, liposarcoma, lung cancer, breast cancer, prostate cancer, leukemia, kidney cancer, esophageal cancer, brain cancer, lymphoma or colon cancer. In certain embodiments, the cancer is a primary effusion lymphoma (PEL). In certain preferred embodiments the cancer to be treated by compounds or compositions of the invention is one bearing an activated MAPK pathway. In some embodiments the cancer bearing an activated MAPK pathway is a melanoma. In certain preferred embodiments the cancer treated by compounds or compositions of the invention is one associated with BRCA1 mutation. In an especially preferred embodiment, the cancer treated by compounds or compositions of the invention is a triple negative breast cancer.

In certain embodiments, the disease which can be treated by compounds of the invention are neurological disorders. In some embodiments, the neurological disorder is Alzheimer's Disease, Parkinson's Disease, epilepsy, ischemia, Age Associated Memory Impairment, Mild Cognitive Impairment, Friedreich's Ataxia, GLUT1-deficient epilepsy, Leprechaunism, Rabson-Mendenhall Syndrome, Coronary Arterial Bypass Graft dementia, anaesthesia-induced memory loss, amyotrophic lateral sclerosis, gliomaor Huntington's Disease.

In certain embodiments, the disease which can be treated by compounds of the invention is an infectious disease. In some embodiments, the infectious disease is a viral infection. In some embodiments the viral infection is cytomegalovirus infection or influenza infection. In some embodiments, the infectious disease is a fungal infection. In some embodiments, the infectious disease is a bacterial infection.

In some embodiments, compounds of the present invention can be used in the treatment of Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated".

In certain embodiments, a provided compound, or composition thereof, is administered in combination with another inhibitor of ACC or antiobesity agent. In some embodiments, a provided compound, or composition thereof, is administered in combination with one or more other therapeutic agents. Such therapeutic agents agents include, but are not limited to agents such as orlistat (Xenical), CNS stimulants, Qsymia, or Belviq.

In certain embodiments, a provided compound, or a composition thereof, is administered in combination with another anti-cancer, cytotoxin, or chemotherapeutic agent, to a patient in need thereof.

In certain embodiments, the anti-cancer or chemotherapeutic agents used in combination with compounds or compositions of the invention include, but are not limited to metformin, phenformin, buformin, imatinib, nilotinib, gefitinib, sunitinib, carfilzomib, salinosporamide A, retinoic acid, cisplatin, carboplatin, oxaliplatin, mechlorethamine, cyclophosphamide, chlorambucil, ifosfamide, azathioprine, mercaptopurine, doxifluridine, fluorouracil, gemcitabine, methotrexate, tioguanine, vincristine, vinblastine, vinorelbine, vindesine, podophyllotoxin, etoposide, teniposide, tafluposide, paclitaxel, docetaxel, irinotecan, topotecan, amsacrine, actinomycin, doxorubicin, daunorubicin, valrubicin, idarubicin, epirubicin, plicamycin, mitomycin, mitoxantrone, melphalan, busulfan, capecitabine, pemetrexed, epothilones, 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Citrovorum Factor, Cladribine, Cortisone, Cosmegen®, CPT-11, Cytadren®, Cytosar-U®, Cytoxan®, Dacarbazine, Dacogen, Dactinomycin, Darbepoetin Alfa, Dasatinib, Daunomycin, Daunorubicin Hydrochloride, Daunorubicin Liposomal, DaunoXome®, Decadron, Decitabine, Delta-Cortef®, Deltasone®, Denileukin, Diftitox, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, *Erwinia* L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab, ozogamicin, Gemzar Gleevec™, Gliadel® Wafer, GM-CSF, Goserelin, Granulocyte-Colony Stimulating Factor, Granulocyte Macrophage Colony Stimulating Factor, Halotestin®, Herceptin®, Hexadrol, Hexylen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab, Tiuxetan, Idamycin®, Idarubicin Ifex®, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, Kidrolase®, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, Octreotide, Octreotide acetate, Ofatumumab, Oncospar®, Oncovin®, Ontak®, Onxal™, Oprelvekin, Orapred®, Orasone®, Oxaliplatin, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a), Romiplostim, Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, Xeloda®, Zanosar®, Zevalin™, Zinecard®, Zoladex®, Zoledronic acid, Zolinza, Zometa®, or combinations of any of the above.

In certain embodiments, compounds of the present invention may be administered together with a biguanide selected from metformin, phenformin, or buformin, to a patient in need thereof. In certain embodiments, the patient administered a combination of a compound of the invention and a biguanide is suffering from a cancer, obesity, a liver disease, diabetes or two or more of the above.

In certain embodiments, a combination of 2 or more therapeutic agents may be administered together with compounds of the invention. In certain embodiments, a combination of 3 or more therapeutic agents may be administered with compounds of the invention.

Other examples of agents the inhibitors of this invention may also be combined with include, without limitation: vitamins and nutritional supplements, cancer vaccines, treatments for neutropenia (e.g. G-CSF, filgrastim, lenograstim), treatments for thrombocytopenia (e.g. blood transfusion, erythropoietin), PI3 kinase (PI3K) inhibitors, MEK inhibitors, AMPK activators, PCSK9 inhibitors, SREBP site 1 protease inhibitors, HMG CoA-reductase inhibitors, antiemetics (e.g. 5-HT$_3$ receptor antagonists, dopamine antagonists, NK1 receptor antagonists, histamine receptor antagonists, cannabinoids, benzodiazepines, or anticholinergics), treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins, fibrates, cholesterol absorption inhibitors, bile acid sequestrants, and niacin; agents for treating liver disease such as corticosteroids, cholestyramine, interferons, and anti-viral agents; agents for treating blood disorders such as corticosteroids, anti-leukemic agents, and growth factors; agents for treating immunodeficiency disorders such as gamma globulin; and anti-diabetic agents such as biguanides (metformin, phenformin, buformin), thiazolidinediones (rosiglitazone, pioglitazone, troglitazone), sulfonylureas (tolbutamide, acetohexamide, tolazamide, chlorpropamide, glipizide, glyburide, glimepiride, gliclazide), meglitinides (repaglinide, nateglinide), alpha-glucosidase inhibitors (miglitol, acarbose), incretin mimetics (exenatide, liraglutide, taspoglutide), gastric inhibitory peptide analogs, DPP-4 inhibitors (vildagliptin, sitagliptin, saxagliptin, linagliptin, alogliptin), amylin analogs (pramlintide), and insulin and insulin analogs.

In certain embodiments, compounds of the present invention, or a pharmaceutically acceptable composition thereof, are administered in combination with antisense agents, a monoclonal or polyclonal antibody or an siRNA therapeutic.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another, normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula I, an additional therapeutic agent, and a pharmaceutically acceptable carrier, adjuvant, or vehicle.

The amount of both, an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-100 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The invention further refers to an agricultural composition comprising at least one compound of formula I as defined above or an agriculturally acceptable salt thereof and a liquid or solid carrier. Suitable carriers, as well as auxiliaries and further active compounds which may also be contained in the composition of the invention are defined below.

Suitable "agriculturally acceptable salts" include but are not limited to the salts of those cations or the acid addition salts of those acids whose cations and anions, respectively, have no adverse effect on the fungicidal action of the compounds of formula I. Thus, suitable cations are in particular the ions of the alkali metals, preferably sodium and potassium, of the alkaline earth metals, preferably calcium, magnesium and barium, and of the transition metals, preferably manganese, copper, zinc and iron, and also the ammonium ion which, if desired, may carry one to four $C_1$-$C_4$-alkyl substituents and/or one phenyl or benzyl substituent, preferably diisopropylammonium, tetramethylammonium, tetrabutylammonium, trimethylbenzylammonium. Additional agriculturally acceptable salts include phosphonium ions, sulfonium ions, preferably tri($C_1$-$C_4$-alkyl)sulfonium and sulfoxonium ions, preferably tri($C_1$-$C_4$-alkyl)sulfoxonium. Anions of useful acid addition salts are primarily chloride, bromide, fluoride, hydrogen-sulfate, sulfate, dihydrogenphosphate, hydrogenphosphate, phosphate, nitrate, bicarbonate, carbonate, hexafluorosilicate, hexafluorophosphate, benzoate, and also the anions of $C_1$-$C_4$-alkanoic acids, preferably formate, acetate, propionate and butyrate. Such agriculturally acceptable acid addition salts can be formed by reacting compounds of formula I bearing a basic ionizable group with an acid of the corresponding anion, preferably hydrochloric acid, hydrobromic acid, sulfuric acid, phosphoric acid or nitric acid.

The compounds of formula I and the compositions according to the invention, respectively, are suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

In some embodiments, the compounds of formula I and the compositions according to the invention are particularly important in the control of phytopathogenic fungi on various cultivated plants, such as cereals, e.g. wheat, rye, barley, triticale, oats or rice; beet, e.g. sugar beet or fodder beet; fruits, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; natural rubber plants or ornamental and forestry plants, such as flowers, shrubs, broad-leaved trees or evergreens, e.g. conifers; and on the plant propagation material, such as seeds, and the crop material of these plants.

In some embodiments, compounds of formula I and compositions thereof, respectively are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

In some embodiments, treatment of plant propagation materials with compounds of formula I and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, such as hydroxyphenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imida-zolinones (see e.g. U.S. Pat. No. 6,222,100, WO 01/82685, WO 00/026390, WO 97/41218, WO 98/002526, WO 98/02527, WO 04/106529, WO 05/20673, WO 03/014357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A 242 236, EP-A 242 246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox. Genetic engineering methods have been used to render cultivated plants, such as soybean, cotton, corn, beets and rape, tolerant to herbicides such as glyphosate and glufosinate, some of which are commercially available under the trade names RoundupReady® (glyphosate-tolerant, Monsanto, U.S.A.) and LibertyLink® (glufosinate-tolerant, Bayer CropScience, Germany).

Furthermore, plants are also covered that, by the use of recombinant DNA techniques, are capable to synthesize one or more insecticidal proteins, especially those known from the bacterial genus *Bacillus*, particularly from *Bacillus thuringiensis*, such as δ-endotoxins, e.g. CrylA(b), CrylA(c), CrylF, CrylF(a2), CryllA(b), CrylllA, CrylllB(bi) or Cry θc; vegetative insecticidal proteins (VIP), e.g. VIP1, VIP2, VIP3 or VIP3A; insecticidal proteins of bacteria colonizing nematodes, e.g. *Photorhabdus* spp. or *Xenor-habdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or pa-pain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g., in the publications mentioned above. These insecticidal proteins contained in the genetically modified plants impart to the plants producing these proteins tolerance to harmful pests from all taxonomic groups of arthropods, especially to beetles (Coleoptera), two-winged insects (Diptera), and moths (Lepidoptera) and to nematodes (Nematoda). Genetically modified plants capable to synthesize one or more insecticidal proteins are, e.g., described in the publications mentioned above, and some of them are commercially available such as YieldGard® (corn cultivars producing the CryiAb toxin), YieldGard® Plus (corn cultivars producing Cry1 Ab and Cry3Bb1 toxins), Starlink® (corn cultivars producing the Cry9c toxin), Her-culex® RW (corn cultivars producing Cry34Ab1, Cry35Ab1 and the enzyme Phosphi-nothricin-N-Acetyltransferase [PAT]); NuCOTN® 33B (cotton cultivars producing the Cry1 Ac toxin), Bollgard® I (cotton cultivars producing the CryiAc toxin), Bollgard® II (cotton cultivars producing CryiAc and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt 1 1 (e.g. Agrisure® CB) and Bt176 from Syngenta Seeds SAS, France, (corn cultivars producing the CryiAb toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the CryiAc toxin) and 1507 from Pioneer Overseas Corporation, Belgium (corn cultivars producing the Cry1 F toxin and PAT enzyme).

Furthermore, plants are also covered that, by the use of recombinant DNA techniques, are capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392225), plant disease resistance genes (e.g. potato cultivars, which express resistance genes acting against *Phytophthora infestans* derived from the Mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, e.g., in the publications mentioned above.

Furthermore, plants are also covered that, by the use of recombinant DNA techniques, are capable to synthesize one or more proteins to increase the productivity (e.g. biomass production, grain yield, starch content, oil content or protein content), tolerance to drought, salinity or other growth-limiting environmental factors or tolerance to pests and fungal, bacterial or viral pathogens of those plants.

Furthermore, plants are also covered that, by the use of recombinant DNA techniques, contain a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that, by the use of recombinant DNA techniques, contain a modified amount of substances of content or new substances of content, specifically to improve raw material production, e.g. potatoes that produce increased amounts of amylopectin (e.g. Amflora® potato, BASF SE, Germany).

The compounds of formula I and compositions thereof, respectively, are particularly suitable for controlling the following plant diseases:

*Albugo* spp. (white rust) on ornamentals, vegetables (e.g. *A. Candida*) and sunflowers (e.g. *A. tragopogonis*); *Alternaria* spp. (Alternaria leaf spot) on vegetables, rape {*A. brassicola* or *brassicae*), sugar beets (*A. tenuis*), fruits, rice, soybeans, potatoes (e.g. *A. solani* or *A. alternata*), tomatoes (e.g. *A. solani* or *A. alternata*) and wheat; *Aphanomyces* spp. on sugar beets and vegetables; *Ascochyta* spp. on cereals and vegetables, e.g. *A. tritici* (anthracnose) on wheat and *A. hordei* on barley; *Bipolaris* and *Drechslera* spp. (teleomorph: *Cochliobolus* spp.), e.g. Southern leaf blight (*D. maydis*) or Northern leaf blight (β. *zeicola*) on corn, e.g. spot blotch (β. *sorokiniana*) on cereals and e.g. *B. oryzae* on rice and turfs; *Blumeria* (formerly *Erysiphe*) *graminis* (powdery mildew) on cereals (e.g. on wheat or barley); *Botrytis cinerea* (teleomorph: *Botryotinia fuckeliana*: grey mold) on fruits and berries (e.g. strawberries), vegetables (e.g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e.g. *C. ulmi* (Dutch elm disease) on elms; *Cercospora* spp. (Cercospora leaf spots) on corn (e.g. Gray leaf spot: *C. zeaemaydis*), rice, sugar beets (e.g. *C. beticola*), sugar cane, vegetables, coffee, soybeans (e.g. *C. sojina* or *C. kikuchii*) and rice; *Cladosporium* spp. on tomatoes (e.g. *C. fulvum*: leaf mold) and cereals, e.g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e.g. *C. sativus*, anamorph: *B. sorokiniana*) and rice (e.g. *C. miyabeanus*, anamorph: *H. oryzae*); *Colletotrichum* (teleomorph: *Glomerella*) (an-thracnose) on cotton (e.g. *C. gossypii*), corn (e.g. *C. graminicola*: Anthracnose stalk rot), soft fruits, potatoes (e.g. *C. coccodes*: black dot), beans (e.g. *C. lindemuthianum*) and soybeans (e.g. *C. truncatum* or *C. gloeosporioides*); *Corticium* spp., e.g. *C. sasakii* (sheath blight) on rice; *Corynespora cassiicola* (leaf spots) on soybeans and ornamentals; *Cycloconium* spp., e.g. *C. oleaginum* on olive trees; *Cylindrocarpon* spp. (e.g. fruit tree canker or young vine decline, teleomorph: *Nectria* or *Neonectria* spp.) on fruit trees, vines (e.g. *C. liriodendri*, teleomorph: *Neonectria liriodendri*. Black Foot Disease) and ornamentals; Dematophora (teleomorph: *Rosellinia*) necatrix (root and stem rot) on soybeans; *Diaporthe* spp., e.g. *D. phaseolorum* (damping off) on soybeans; *Drechslera* (syn. *Helminthosporium*, teleomorph: *Pyrenophora*) spp. on corn, cereals, such as barley (e.g. *D. teres*, net blotch) and wheat (e.g. *D. tritici-repentis*: tan spot), rice and turf; Esca (dieback, apoplexy) on vines, caused by *Formitiporia* (syn. *Phellinus*) *punctata*, *F. mediterranea*, *Phaeomoniella chlamydospora* (earlier *Phaeo-acremonium chlamydosporum*), *Phaeoacremonium aleophilum* and/or *Botryosphaeria obtusa*; *Elsinoe* spp. on pome fruits (*E. pyri*), soft fruits (*E. veneta*: anthracnose) and vines (*E ampelina*: anthracnose); Entyloma oryzae (leaf smut) on rice; *Epicoccum* spp. (black mold) on wheat; *Erysiphe* spp. (powdery mildew) on sugar beets (*E. betae*), vegetables (e.g. *E. pisi*), such as cucurbits (e.g. *E. cichoracearum*), cabbages, rape (e.g. *E. cruciferarum*); *Eutypa lata* (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e.g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e.g. wheat or barley), *F. oxysporum* on tomatoes, *F. solani* on soybeans and *F. verticillioides* on corn; *Gaeumannomyces graminis* (take-all) on cereals (e.g. wheat or barley) and corn; *Gibberella* spp. on cereals (e.g. *G. zeae*) and rice (e.g. *G. fujikuroi*: Bakanae disease); *Glomerella cingulata* on vines, pome fruits and other plants and *G. gossypii* on cotton; Grain-staining complex on rice; *Guignardia bidwellii* (black rot) on vines; *Gymnosporangium* spp. on rosaceous plants and junipers, e.g. *G. sabinae* (rust) on pears; *Helminthosporium* spp. (syn. *Drechslera*, teleomorph: *Cochliobolus*) on corn, cereals and rice; *Hemileia* spp., e.g. *H. vastatrix* (coffee leaf rust) on coffee; *lsariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e.g. wheat or barley); *Microsphaera diffusa* (powdery mildew) on soybeans; *Monilinia* spp., e.g. *M. laxa, M. fructicola* and *M. fructigena* (bloom and twig blight, brown rot) on stone fruits and other rosaceous plants; *Mycosphaerella* spp. on cereals, bananas, soft fruits and ground nuts, such as e.g. *M. graminicola* (anamorph: *Septoria tritici, Septoria* blotch) on wheat or *M. fijiensis* (black Sigatoka disease) on bananas; *Peronospora* spp. (downy mildew) on cabbage (e.g. *P. brassicae*), rape (e.g. *P. parasitica*), onions (e.g. *P. destructor*), tobacco (*P. tabacina*) and soybeans (e.g. *P. manshurica*); *Phakopsora pachyrhizi* and *P. meibomiae* (soybean rust) on soybeans; *Phialophora* spp. e.g. on vines (e.g. *P. tracheiphila* and *P. tetraspora*) and soybeans (e.g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e.g. *P. viticola*: can and leaf spot) and soybeans (e.g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e.g. *P.*

*capsici*), soybeans (e.g. *P. megasperma*, syn. *P. sojae*), potatoes and tomatoes (e.g. *P. infestans*: late blight) and broad-leaved trees (e.g. *P. ramorum*: sudden oak death); *Plasmodiophora brassicae* (club root) on cabbage, rape, radish and other plants; *Plasmopara* spp., e.g. *P. viticola* (grapevine downy mildew) on vines and *P. halstediiou* sunflowers; *Podosphaera* spp. (powdery mildew) on rosaceous plants, hop, pome and soft fruits, e.g. *P. leucotricha* on apples; *Polymyxa* spp., e.g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e.g. wheat or barley; *Pseudoperonospora* (downy mildew) on various plants, e.g. *P. cubensis* on cucurbits or *P. humili* on hop; *Pseudopezicula tracheiphila* (red fire disease or, rotbrenner', anamorph: Phialophora) on vines; *Puccinia* spp. (rusts) on various plants, e.g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e.g. wheat, barley or rye, and asparagus (e.g. *P. asparagi*); *Pyrenophora* (anamorph: *Drechslera*) *tritici-repentis* (tan spot) on wheat or *P. feres* (net blotch) on barley; *Pyricularia* spp., e.g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e.g. *P. ultimum* or *P. aphanidermatum*); *Ramularia* spp., e.g. *R. collocygni* (Ramularia leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e.g. *R. solani* (root and stem rot) on soybeans, *R. solani* (sheath blight) on rice or *R. cerealis* (Rhizoctonia spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e.g. *S. sclerotiorum*) and soybeans (e.g. *S. rolfsii* or *S. sclerotiorum*); *Septoria* spp. on various plants, e.g. *S. glycines* (brown spot) on soybeans, *S. tritici* (Septoria blotch) on wheat and *S.* (syn. *Stagonospora*) *nodorum* (Stagonospora blotch) on cereals; *Uncinula* (syn. *Erysiphe*) *necator* (powdery mildew, anamorph: *Oidium tuckeri*) on vines; *Setospaeria* spp. (leaf blight) on corn (e.g. *S. turcicum*, syn. *Helminthosporium turcicum*) and turf; *Sphacelotheca* spp. (smut) on corn, (e.g. *S. miliaria*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e.g. *S. nodorum* (Stagonospora blotch, teleomorph: *Leptosphaeria* [syn. *Phaeosphaeria*] *nodorum*) on wheat; *Synchytrium endobioticum* on potatoes (potato wart disease); *Taphrina* spp., e.g. *T. deformans* (leaf curl disease) on peaches and *T. pruni* (plum pocket) on plums; *Thielaviopsis* spp. (black root rot) on tobacco, pome fruits, vegetables, soybeans and cotton, e.g. *T. basicola* (syn. *Chalara elegans*); *Tilletia* spp. (common bunt or stinking smut) on cereals, such as e.g. *T. tritici* (syn. *T. caries*, wheat bunt) and *T. controversa* (dwarf bunt) on wheat; *Typhula incamata* (grey snow mold) on barley or wheat; *Urocystis* spp., e.g. *U. occulta* (stem smut) on rye; *Uromyces* spp. (rust) on vegetables, such as beans (e.g. *U. appendiculatus*, syn. *U. phaseoli*) and sugar beets (e.g. *U. betae*); *Ustilago* spp. (loose smut) on cereals (e.g. *U. nuda* and *U. avaenae*), corn (e.g. *U. maydis*: corn smut) and sugar cane; *Venturia* spp. (scab) on apples (e.g. *V. inaequalis*) and pears; and *Verticillium* spp. (wilt) on various plants, such as fruits and ornamentals, vines, soft fruits, vegetables and field crops, e.g. *V. dahliae* on strawberries, rape, potatoes and tomatoes.

The compounds of formula I and compositions thereof, respectively, are also suitable for controlling harmful fungi in the protection of stored products or harvest and in the protection of materials. The term "protection of materials" is to be understood to denote the protection of technical and non-living materials, such as adhesives, glues, wood, paper and paperboard, textiles, leather, paint dispersions, plastics, colling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pullulans*, *Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichorma* spp., *Alternaria* spp., *Paecilomyces* spp. and Zygomycetes such as *Mucor* spp., and in addition in the protection of stored products and harvest the following yeast fungi are worthy of note: *Candida* spp. and *Saccharomyces cerevisae*.

The compounds of formula I and compositions thereof, respectively, may be used for improving the health of a plant. The invention also relates to a method for improving plant health by treating a plant, its propagation material and/or the locus where the plant is growing or is to grow with an effective amount of compounds of formula I or compositions thereof, respectively.

The term "plant health" is to be understood to denote a condition of the plant and/or its products which is determined by several indicators alone or in combination with each other such as yield (e.g. increased biomass and/or increased content of valuable ingredients), plant vigor (e.g. improved plant growth and/or greener leaves ("greening effect")), quality (e.g. improved content or composition of certain ingredients) and tolerance to abiotic and/or biotic stress. The above identified indicators for the health condition of a plant may be interdependent or may result from each other.

The compounds of formula I can be present in different crystal modifications whose biological activity may differ. They are likewise subject matter of the present invention.

The compounds of formula I are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with compounds of formula I as such or a composition comprising at least one compound of formula I prophylactically either at or before planting or transplanting.

The invention also relates to agrochemical compositions comprising a solvent or solid carrier and at least one compound of formula I and to the use for controlling harmful fungi.

An agrochemical composition comprises a fungicidally effective amount of a compound I and/or II. The term "effective amount" denotes an amount of the composition or of the compound of formula I, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound of formula I used.

The compounds of formula I and salts thereof can be converted into customary types of agrochemical compositions, e.g. solutions, emulsions, suspensions, dusts, powders, pastes and granules. The composition type depends on the particular intended purpose; in each case, it should ensure a fine and uniform distribution of the compound according to the invention.

Examples for composition types are suspensions (SC, OD, FS), emulsifiable concentrates (EC), emulsions (EW, EO, ES), pastes, pastilles, wettable powders or dusts (WP, SP, SS, WS, DP, DS) or granules (GR, FG, GG, MG), which can be water-soluble or wettable, as well as gel formulations for the treatment of plant propagation materials such as seeds (GF).

Usually the composition types (e.g. SC, OD, FS, EC, WG, SG, WP, SP, SS, WS, GF) are employed diluted. Composition types such as DP, DS, GR, FG, GG and MG are usually used undiluted.

The compositions are prepared in a known manner (cf. U.S. Pat. No. 3,060,084, EP-A 707 445 (for liquid concentrates), Browning: "Agglomeration", Chemical Engineering, Dec. 4, 1967, 147-48, Perry's Chemical Engineer's Handbook, 4th Ed., McGraw-Hill, New York, 1963, pp. 8-57 et seq., WO 91/13546, U.S. Pat. Nos. 4,172, 7144,144,050, 3,920,442, 5,180,587, 5,232,701, 5,208,030, GB 2,095,558, U.S. Pat. No. 3,299,566, Klingman: Weed Control as a Science (J. Wiley & Sons, New York, 1961), Hance et al.: Weed Control Handbook (8th Ed., Blackwell Scientific, Oxford, 1989) and Mollet, H. and Grubemann, A.: Formulation technology (Wiley VCH Verlag, Weinheim, 2001).

The agrochemical compositions may also comprise auxiliaries which are customary in agrochemical compositions. The auxiliaries used depend on the particular application form and active substance, respectively.

Examples for suitable auxiliaries are solvents, solid carriers, dispersants or emulsifiers (such as further solubilizers, protective colloids, surfactants and adhesion agents), organic and inorganic thickeners, bactericides, anti-freezing agents, anti-foaming agents, if appropriate colorants and tackifiers or binders (e.g. for seed treatment formulations). Suitable solvents are water, organic solvents such as mineral oil fractions of medium to high boiling point, such as kerosene or diesel oil, furthermore coal tar oils and oils of vegetable or animal origin, aliphatic, cyclic and aromatic hydrocarbons, e.g. toluene, xylene, paraffin, tetrahydronaphthalene, alkylated naphthalenes or their derivatives, alcohols such as methanol, ethanol, propanol, butanol and cyclohexanol, glycols, ketones such as cyclohexanone and gamma-butyrolactone, fatty acid dimethylamides, fatty acids and fatty acid esters and strongly polar solvents, e.g. amines such as N-methylpyrrolidone.

Solid carriers are mineral earths such as silicates, silica gels, talc, kaolins, limestone, lime, chalk, bole, loess, clays, dolomite, diatomaceous earth, calcium sulfate, magnesium sulfate, magnesium oxide, ground synthetic materials, fertilizers, such as, e.g., ammonium sulfate, ammonium phosphate, ammonium nitrate, ureas, and products of vegetable origin, such as cereal meal, tree bark meal, wood meal and nutshell meal, cellulose powders and other solid carriers.

Suitable surfactants (adjuvants, wetters, tackifiers, dispersants or emulsifiers) are alkali metal, alkaline earth metal and ammonium salts of aromatic sulfonic acids, such as lignin-soulfonic acid (Borresperse® types, Borregard, Norway) phenolsulfonic acid, naphthalenesulfonic acid (Morwet® types, Akzo Nobel, U.S.A.), dibutylnaphthalene-sulfonic acid (Nekal® types, BASF, Germany), and fatty acids, alkyl-sulfonates, alkyl-arylsulfonates, alkyl sulfates, laurylether sulfates, fatty alcohol sulfates, and sulfated hexa-, hepta- and octadecanolates, sulfated fatty alcohol glycol ethers, furthermore condensates of naphthalene or of naphthalenesulfonic acid with phenol and formaldehyde, polyoxy-ethylene octylphenyl ether, ethoxylated isooctylphenol, octylphenol, nonylphenol, alkylphenyl polyglycol ethers, tributylphenyl polyglycol ether, tristearyl-phenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and proteins, denatured proteins, polysaccharides (e.g. methylcellulose), hydrophobically modified starches, polyvinyl alcohols (Mowiol® types, Clariant, Switzerland), polycarboxylates (Sokolan® types, BASF, Germany), polyalkoxylates, polyvinyl-amines (Lupasol® types, BASF, Germany), polyvinylpyrrolidone and the copolymers thereof.

Examples for thickeners (i.e. compounds that impart a modified flowability to compositions, i.e. high viscosity under static conditions and low viscosity during agitation) are polysaccharides and organic and anorganic clays such as Xanthan gum (Kelzan®, CP Kelco, U.S.A.), Rhodopol® 23 (Rhodia, France), Veegum® (RT. Vanderbilt, U.S.A.) or Attaclay® (Engelhard Corp., NJ, USA).

Bactericides may be added for preservation and stabilization of the composition. Examples for suitable bactericides are those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie).

Examples for suitable anti-freezing agents are ethylene glycol, propylene glycol, urea and glycerin.

Examples for anti-foaming agents are silicone emulsions (such as e.g. Silikon® SRE, Wacker, Germany or Rhodorsil®, Rhodia, France), long chain alcohols, fatty acids, salts of fatty acids, fluoroorganic compounds and mixtures thereof.

Suitable colorants are pigments of low water solubility and water-soluble dyes. Examples to be mentioned and the designations rhodamin B, C. I. pigment red 112, C. I. solvent red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples for tackifiers or binders are polyvinylpyrrolidons, polyvinylacetates, polyvinyl alcohols and cellulose ethers (Tylose®, Shin-Etsu, Japan).

Powders, materials for spreading and dusts can be prepared by mixing or concomitantly grinding the compounds of formula I and, if appropriate, further active substances, with at least one solid carrier.

Granules, e.g. coated granules, impregnated granules and homogeneous granules, can be prepared by binding the active substances to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, e.g., ammonium sulfate, ammonium phosphate, ammonium nitrate, ureas, and products of vegetable origin, such as cereal meal, tree bark meal, wood meal and nutshell meal, cellulose powders and other solid carriers.

Examples for composition types include, but are not limited to: 1. Composition types for dilution with water, i) Water-soluble concentrates (SL, LS): 10 parts by weight of a compound of formula I according to the invention are dissolved in 90 parts by weight of water or in a water-soluble solvent. As an alternative, wetting agents or other auxiliaries are added. The active substance dissolves upon dilution with water. In this way, a composition having a content of 10% by weight of active substance is obtained. ii) Dispersible concentrates (DC): 20 parts by weight of a compound of formula I according to the invention are dissolved in 70 parts by weight of cyclohexanone with addition of 10 parts by weight of a dispersant, e.g. polyvinylpyrrolidone. Dilution with water gives a dispersion. The active substance content is 20% by weight. iii) Emulsifiable concentrates (EC): 15 parts by weight of a compound of formula I according to the invention are dissolved in 75 parts by weight of xylene with addition of calcium dodecylbenzenesulfonate and castor oil ethoxylate (in each case 5 parts by weight). Dilution with water gives an emulsion. The composition has an active substance content of 15% by weight. iv) Emulsions (EW, EO, ES): 25 parts by weight of a compound of formula I according to the invention are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (Ultraturrax) and made into a homogeneous emulsion. Dilution with water gives an emulsion. The composition has an active substance content of 25% by weight. v) Suspensions (SC, OD, FS): In an agitated ball mill, 20 parts by weight of a compound of formula I according to the invention are comminuted with addition of 10 parts by weight of dispersants and wetting agents and 70 parts by weight of water or an organic solvent to give a fine active sub-stance suspension. Dilution with water gives a stable suspension of the active substance. The active substance content in the composition is 20% by weight. vi) Water-dispersible granules and water-soluble granules (WG, SG) 50 parts by weight of a compound of formula I according to the invention are ground finely with addition of 50 parts by weight of dispersants and wetting agents and prepared as water-dispersible or water-soluble granules by means of technical appliances (e.g. extrusion, spray tower, fluidized bed). Dilution with water gives a stable dispersion or solution of the active substance. The composition has an active substance content of 50% by weight. vii) Water-dispersible powders and water-soluble powders (WP, SP, SS, WS) 75 parts by weight of a compound of formula I according to the invention are ground in a rotor-stator mill with addition of 25 parts by weight of dispersants, wetting agents and silica gel. Dilution with water gives a stable dispersion or solution of the active substance. The active substance content of the composition is 75% by weight. viii) Gel (GF): In an agitated ball mill, 20 parts by weight of a compound of formula I according to the invention are comminuted with addition of 10 parts by weight of dispersants, 1 part by weight of a gelling agent wetters and 70 parts by weight of water or of an organic solvent to give a fine suspension of the active substance. Dilution with water gives a stable suspension of the active substance, whereby a composition with 20% (w/w) of active substance is obtained.

2. Composition types to be applied undiluted: ix) Dustable powders (DP, DS): 5 parts by weight of a compound of formula I according to the invention are ground finely and mixed intimately with 95 parts by weight of finely divided kaolin. This gives a dustable composition having an active substance content of 5% by weight. x) Granules (GR, FG, GG, MG): 0.5 parts by weight of a compound of formula I according to the invention is ground finely and associated with 99.5 parts by weight of carriers. Current methods are extrusion, spray-drying or the fluidized bed. This gives granules to be applied undiluted having an active substance content of 0.5% by weight. xi) ULV solutions (UL) 10 parts by weight of a compound of formula I according to the invention are dissolved in 90 parts by weight of an organic solvent, e.g. xylene. This gives a composition to be applied undiluted having an active substance content of 10% by weight.

The agrochemical compositions generally comprise between 0.01 and 95%, preferably between 0.1 and 90%, most preferably between 0.5 and 90%, by weight of active substance. The active substances are employed in a purity of from 90% to 100%, preferably from 95% to 100% (according to NMR spectrum).

Water-soluble concentrates (LS), flowable concentrates (FS), powders for dry treatment (DS), water-dispersible powders for slurry treatment (WS), water-soluble powders (SS), emulsions (ES) emulsifiable concentrates (EC) and gels (GF) are usually employed for the purposes of treatment of plant propagation materials, particularly seeds. These compositions can be applied to plant propagation materials, particularly seeds, diluted or undiluted. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying or treating agrochemical compounds and compositions thereof, respectively, on to plant propagation material, especially seeds, are known in the art, and include dressing, coating, pelleting, dusting, soaking and in-furrow application methods of the propagation material. In a preferred embodiment, the compounds or the compositions thereof, respectively, are applied on to the plant propagation material by a method such that germination is not induced, e.g. by seed dressing, pelleting, coating and dusting.

In a preferred embodiment, a suspension-type (FS) composition is used for seed treatment. Typically, a FS composition may comprise 1-800 g/l of active substance, 1-200 g/l Surfactant, 0 to 200 g/l antifreezing agent, 0 to 400 g/l of binder, 0 to 200 g/l of a pigment and up to 1 liter of a solvent, preferably water.

The active substances can be used as such or in the form of their compositions, e.g. in the form of directly sprayable solutions, powders, suspensions, dispersions, emulsions, dispersions, pastes, dustable products, materials for spreading, or granules, by means of spraying, atomizing, dusting, spreading, brushing, immersing or pouring. The application forms depend entirely on the intended purposes; it is intended to ensure in each case the finest possible distribution of the active substances according to the invention. Aqueous application forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active substance concentrations in the ready-to-use preparations can be varied within relatively wide ranges. In general, they are from 0.0001 to 10%, preferably from 0.001 to 1% by weight of active substance.

The active substances may also be used successfully in the ultra-low-volume process (ULV), it being possible to apply compositions comprising over 95% by weight of active substance, or even to apply the active substance without additives.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required.

When used in the protection of materials or stored products, the amount of active substance applied depends on the kind of application area and on the desired effect. Amounts customarily applied in the protection of materials are, e.g., 0.001 g to 2 kg, preferably 0.005 g to 1 kg, of active substance per cubic meter of treated material.

Various types of oils, wetters, adjuvants, herbicides, bactericides, other fungicides and/or pesticides may be added to the active substances or the compositions comprising them, if appropriate not until immediately prior to use (tank mix). These agents can be admixed with the compositions according to the invention in a weight ratio of 1:100 to 100:1, preferably 1:10 to 10:1.

Adjuvants which can be used are in particular organic modified polysiloxanes such as Break Thru S 240®; alcohol alkoxylates such as Atplus 245®, Atplus MBA 1303®, Plurafac LF 300® and Lutensol ON 30®; EO/PO block polymers, e.g. Pluronic RPE 2035® and Genapol B®; alcohol ethoxylates such as Lutensol XP 80®; and dioctyl sulfosuccinate sodium such as Leophen RAC).

The compositions according to the invention can, in the use form as fungicides, also be present together with other active substances, e.g. with herbicides, insecticides, growth regulators, fungicides or else with fertilizers, as pre-mix or, if appropriate, not until immediately prior to use (tank mix).

Mixing the compounds of formula I or the compositions comprising them in the use form as fungicides with other fungicides results in many cases in an expansion of the fungicidal spectrum of activity being obtained or in a prevention of fungicide resistance development. Furthermore, in many cases, synergistic effects are obtained.

The following list of active substances, in conjunction with which the compounds according to the invention can be used, is intended to illustrate the possible combinations but does not limit them:

A) strobilurins azoxystrobin, dimoxystrobin, enestroburin, fluoxastrobin, kresoxim-methyl, meto-minostrobin, orysastrobin, picoxystrobin, pyraclostrobin, pyribencarb, trifloxystrobin, 2-(2-(6-(3-chloro-2-methyl-phenoxy)-5-fluoro-pyrimidin-4-yloxy)-phenyl)-2-methoxyimino-N-methyl-acetamide, 3-methoxy-2-(2-(N-(4-methoxy-phenyl)-cyclopropane-carboximidoylsulfanylmethyl)-phenyl)-acrylic acid methyl ester, methyl (2-chloro-5-[1-(3-methylbenzyloxyimino)ethyl]benzyl)carbamate and 2-(2-(3-(2,6-dichlorophenyl)-1-methyl-allylideneaminooxymethyl)-phenyl)-2-methoxyimino-N-methyl-acetamide;

B) carboxamides and carboxanilides: benalaxyl, benalaxyl-M, benodanil, bixafen, boscalid, carboxin, fenfuram, fenhexamid, flutolanil, furametpyr, isopyrazam, isotianil, kiralaxyl, me-pronil, metalaxyl, metalaxyl-M (mefenoxam), ofurace, oxadixyl, oxycarboxin, pen-thiopyrad, sedaxane, tecloftalam, thifluzamide, tiadinil, 2-amino-4-methyl-thiazole-5-carboxanilide, 2-chloro-N-(1,1,3-trimethyl-indan-4-yl)-nicotinamide, N-(3',4',5'-trifluorobiphenyl-2-yl)-3-difluoromethyl-1-methyl-1H-pyrazole-4-carboxamide, N-(4'-trifluoromethylthiobiphenyl-2-yl)-3-difluoromethyl-1-methyl-1H-pyrazole-4-carboxamide, N-(2-(1,3-dimethyl-butyl)-phenyl)-1,3-dimethyl-5-fluoro-1H-pyrazole-4-carboxamide and N-(2-(1,3,3-trimethyl-butyl)-phenyl)-1,3-dimethyl-5-fluoro-1H-pyrazole-4-carboxamide; carboxylic morpholides: dimethomorph, flumorph, pyrimorph; benzoic acid amides: flumetover, fluopicolide, fluopyram, zoxamide, N-(3-Ethyl-3,5,5-trimethyl-cyclohexyl)-3-formylamino-2-hydroxy-benzamide; other carboxamides: carpropamid, dicyclomet, mandiproamid, oxytetracyclin, silthiofarm and N-(6-methoxy-pyridin-3-yl)cyclopropanecarboxylic acid amide;

C) azoles and triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-(4-chloro-phenyl)-2-([1,2,4]triazol-1-yl)-cycloheptanol; imidazoles: cyazofamid, imazalil, pefurazoate, prochloraz, triflumizol; benzimidazoles: benomyl, carbendazim, fuberidazole, thiabendazole; -others: ethaboxam, etridiazole, hymexazole and 2-(4-chloro-phenyl)-N-[4-(3,4-dimethoxy-phenyl)-isoxazol-5-yl]-2-prop-2-ynyloxy-acetamide;

D) heterocyclic compounds pyridines: fluazinam, pyrifenox, 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine, 2,3,5,6-tetra-chloro-4-methane-sulfonyl-pyridine, 3,4,5-trichloropyridine-2,6-dicarbonitrile, N-(1-(5-bromo-3-chloro-pyridin-2-yl)-ethyl)-2,4-dichloronicotinamide, N-[(5-bromo-3-chloro-pyridin-2-yl)-methyl]-2,4-dichloro-nicotinamide; pyrimidines: bupirimate, cyprodinil, diflumetorim, fenarimol, ferimzone, mepanipyrim, nitrapyrin, nuarimol, pyrimethanil; piperazines: triforine; pyrroles: fenpiclonil, fludioxonil; morpholines: aldimorph, dodemorph, dodemorph-acetate, fenpropimorph, tridemorph; piperidines: fenpropidin; -dicarboximides: fluoroimid, iprodione, procymidone, vinclozolin; non-aromatic 5-membered heterocycles: famoxadone, fenamidone, flutianil, octhilinone, probenazole, 5-amino-2-isopropyl-3-oxo-4-ortho-tolyl-2,3-dihydro-pyrazole-1-carbothioic acid S-allyl ester; others: acibenzolar-S-methyl, amisulbrom, anilazin, blasticidin-S, captafol, captan, chinomethionat, dazomet, debacarb, diclomezine, difenzoquat, difenzoquat-methylsulfate, fenoxanil, Folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxy-pyrimidin-2-yl)-2-methyl-1H-benzimidazole, 5-chloro-7-(4-methylpiperidin-1-yl)-6-(2,4,6-trifluorophenyl)-[1,2,4]triazolo[1,5-a]pyrimidine and 5-ethyl-6-octyl-[1,2,4]triazolo[1,5-a]pyrimidine-7-ylamine;

E) carbamates thio- and dithiocarbamates: ferbam, mancozeb, maneb, metam, methasulphocarb, metiram, propineb, thiram, zineb, ziram; carbamates: benthiavalicarb, diethofencarb, iprovalicarb, propamocarb, propamo-carb hydrochlorid, valiphenal and N-(1-(1-(4-cyano-phenyl)ethanesulfonyl)-but-2-yl) carbamic acid-(4-fluorophenyl)ester;

F) other active substances—guanidines: guanidine, dodine, dodine free base, guazatine, guazatine-acetate, iminoctadine, iminoctadine-triacetate, iminoctadine-tris(albesilate); antibiotics: kasugamycin, kasugamycin hydrochloridehydrate, streptomycin, pol-yoxine, validamycin A; nitro phenyl derivates: binapacryl, dinobuton, dinocap, nitrthal-isopropyl, tecna-zen, organometal compounds: fentin salts, such as fentin-acetate, fentin chloride or fentin hydroxide; sulfur-containing heterocyclyl compounds: dithianon, iso-prothiolane; organophosphorus compounds: edifenphos, fosetyl, fosetyl-aluminum, iproben-fos, phosphorous acid and its salts, pyrazophos, tolclofos-methyl; organochlorine compounds: chlorothalonil, dichlofluanid, dichlorophen, flusulfamide, hexachlorobenzene, pencycuron, pentachlorphenole and its salts, phthalide, quintozene, thiophanate-methyl, tolylfluanid, N-(4-chloro-2-nitro-phenyl)-N-ethyl-4-methyl-benzenesulfonamide; inorganic active substances: Bordeaux mixture, copper acetate, copper hydroxide, copper oxychloride, basic copper sulfate, sulfur; biphenyl, bronopol, cyflufenamid, cymoxanil, diphenylamin, metrafenone, mildiomycin, oxin-copper, prohexadione-calcium, spiroxamine, tolylfluanid, N-(cyclopropylmethoxyimino-(6-difluoromethoxy-2,3-difluoro-phenyl)-methyl)-2-phenylacetamide, N'-(4-(4-chloro-3-trifluoromethyl-phenoxy)-2,5-dimethyl-phenyl)-N-ethyl-N-methylformamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methylformamidine, N'-(5-difluoromethyl-2-methyl-4-(3-trimethylsilanyl-propoxy)-phenyl)-N-ethyl-N-methylformamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-S-trifluoromethyl-pyrazole-1-yO-acetyˆ-piperidinˆ-yl]-thiazoleˆ-carboxylic acid methyl-(R)-1,2,3,4-tetrahydro-naphthalen-1-yl-amide, acetic acid 6-tert-butyl-8-fluoro-2,3-dimethyl-quinolin-4-yl ester and methoxy-acetic acid 6-tert-butyl-8-fluoro-2,3-dimethyl-quinolin-4-yl ester.

G) growth regulators abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole;

H) herbicides acetamides: acetochlor, alachlor, butachlor, dimethachlor, dimethenamid, flufen-acet, mefenacet, metolachlor, metazachlor, napropamide, naproanilide, pethoxamid, pretilachlor, propachlor, thenylchlor; amino acid derivatives: bilanafos, glyphosate, glufosinate, sulfosate; aryloxyphenoxypropionates: clodinafop, cyhalofop-butyl, fenoxaprop, fluazifop, haloxyfop, metamifop, propaquizafop, quizalofop, quizalofop-P-tefuryl; Bipyridyls: diquat, paraquat; (thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate; cyclohexanediones: butroxydim, clethodim, cycloxydim, profoxydim, sethoxydim, tepraloxydim, tralkoxydim; -dinitroanilines: benfluralin, ethalfluralin, oryzalin, pendimethalin, prodiamine, trifluralin; diphenyl ethers: acifluorfen, aclonifen, bifenox, diclofop, ethoxyfen, fomesafen, lactofen, oxyfluorfen; hydroxybenzonitriles: bomoxynil, dichlobenil, ioxynil; -imidazolinones: imazamethabenz, imazamox, imazapic, imazapyr, imazaquin, imazethapyr; phenoxy acetic acids: clomeprop, 2,4-dichlorophenoxyacetic acid (2,4-D), 2,4-DB, dichlorprop, MCPA, MCPA-thioethyl, MCPB, Mecoprop; pyrazines: chloridazon, flufenpyr-ethyl, fluthiacet, norflurazon, pyridate; pyridines: aminopyralid, clopyralid, diflufenican, dithiopyr, fluridone, fluoroxypyr, picloram, picolinafen, thiazopyr; sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfu-ron, mesosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b]pyridazin-3-yl)sulfonyl)-3-(4,6-dimethoxy-pyrmidin-2-yl) urea; triazines: ametryn, atrazine, cyanazine, dimethametryn, ethiozin, hexazinone, metamitron, metribuzin, prometryn, simazine, terbuthylazine, terbutryn, triaziflam; ureas: chlorotoluron, daimuron, diuron, fluometuron, isoproturon, linuron, metha-benzthiazuron, tebuthiuron; other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam; others: amicarbazone, aminotriazole, anilofos, beflubutamid, benazolin, bencar-bazone, benfluresate, benzofenap, bentazone, benzobicyclon, bromacil, bromo-butide, butafenacil, butamifos, cafenstrole, carfentrazone, cinidonethlyl, chlor-thal, cinmethylin, clomazone, cumyluron, cyprosulfamide, dicamba, difenzoquat, diflufenzopyr, *Drechslera* monoceras, endothal, ethofumesate, etobenzanid, fen-trazamide, flumiclorac-pentyl, flumioxazin, flupoxam, fluorochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfo-tole, pyrazoxyfen, pyrazolynate, quinoclamine, saflufenacil, sulcotrione, sulfentrazone, terbacil, tefuryltrione, tembotrione, thiencarbazone, topramezone, 4-hydroxy-3-[2-(2-methoxy-ethoxymethyl)-6-trifluoromethyl-pyridine-3-carbonyl]-bicyclo[3.2.1]oct-3-en-2-one, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester.

I) insecticides—organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamido-phos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetra-chlorvinphos, terbufos, triazophos, trichlorfon; carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate; pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin; insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat; nicotinic receptor agonists/antagonists compounds: clothianidin, dinotefuran, imi-dacloprid, thiamethoxam, nitenpyram, acetamiprid, thiacloprid, 1-(2-chloro-thiazol-5-ylmethyl)-2-nitrimino-3,5-dimethyl-[1,3,5]triazinane; GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide; macrocyclic lactone insecticides: abamectin, emamectin, milbemectin, lepimectin, spinosad, spinetoram; mitochondrial electron transport inhibitor (METI) I acaricides: fenazaquin, pyrida-ben, tebufenpyrad, tolfenpyrad, flufenerim; METI II and III compounds: acequinocyl, fluacyprim, hydramethylnon; Uncouplers: chlorfenapyr;—oxidative phosphorylation inhibitors: cyhexatin, diafenthiuron, fenbutatin oxide, propargite; moulting disruptor compounds: cryomazine; mixed function oxidase inhibitors: piperonyl butoxide; sodium channel blockers: indoxacarb, metaflumizone;—others: benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluoron, and pyrifluquinazon.

The present invention furthermore relates to agrochemical compositions comprising a mixture of at least one compound of formula I (component 1) and at least one further active substance useful for plant protection, e.g. selected from the groups A) to I) (component 2), in particular one further fungicide, e.g. one or more fungicide from the groups A) to F), as described above, and if desired one suitable solvent or solid carrier. Those mixtures are of particular interest, since many of them at the same application rate show higher efficiencies against harmful fungi. Furthermore, combating harmful fungi with a mixture of compounds of formula I and at least one fungicide from groups A) to F), as described above, is more efficient than combating those fungi with individual compounds of formula I or individual fungicides from groups A) to F). By applying compounds of formula I together with at least one active substance from groups A) to I) a synergistic effect can be obtained, i.e. more than simple addition of the individual effects is obtained (synergistic mixtures).

According to this invention, applying the compounds of formula I together with at least one further active substance is to be understood to denote that at least one compound of formula I and at least one further active substance occur simultaneously at the site of action (i.e. the harmful fungi to be controlled or their habitats such as infected plants, plant propagation materials, particularly seeds, surfaces, materials or the soil as well as plants, plant propagation materials, particularly seeds, soil, surfaces, materials or rooms to be protected from fungal attack) in a fungicidally effective amount. This can be obtained by applying the compounds of formula I and at least one further active substance simultaneously, either jointly (e.g. as tank-mix) or separately, or in succession, wherein the time interval between the individual applications is selected to ensure that the active substance applied first still occurs at the site of action in a sufficient amount at the time of application of the further active substance(s). The order of application is not essential for working of the present invention.

In binary mixtures, i.e. compositions according to the invention comprising one compound I (component 1) and one further active substance (component 2), e.g. one active substance from groups A) to I), the weight ratio of component 1 and component 2 generally depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:3 to 3:1.

In ternary mixtures, i.e. compositions according to the invention comprising one compound I (component 1) and a first further active substance (component 2) and a second further active substance (component 3), e.g. two active substances from groups A) to I), the weight ratio of component 1 and component 2 depends from the properties of the active substances used, preferably it is in the range of from 1:50 to 50:1 and particularly in the range of from 1:10 to 10:1, and the weight ratio of component 1 and component 3 preferably is in the range of from 1:50 to 50:1 and particularly in the range of from 1:10 to 10:1.

The components can be used individually or already partially or completely mixed with one another to prepare the composition according to the invention. It is also possible for them to be packaged and used further as combination composition such as a kit of parts.

In one embodiment of the invention, the kits may include one or more, including all, components that may be used to prepare a subject agrochemical composition. E. g., kits may include one or more fungicide component(s) and/or an adjuvant component and/or an insecticide component and/or a growth regulator component and/or a herbicide. One or more of the components may already be combined together or pre-formulated. In those embodiments where more than two components are provided in a kit, the components may already be combined together and as such are packaged in a single container such as a vial, bottle, can, pouch, bag or canister. In other embodiments, two or more components of a kit may be packaged separately, i.e., not pre-formulated. As such, kits may include one or more separate containers such as vials, cans, bottles, pouches, bags or canisters, each container containing a separate component for an agrochemical composition. In both forms, a component of the kit may be applied separately from or together with the further components or as a component of a combination composition according to the invention for preparing the composition according to the invention.

The user applies the composition according to the invention usually from a predosage device, a knapsack sprayer, a spray tank or a spray plane. Here, the agrochemical composition is made up with water and/or buffer to the desired application concentration, it being possible, if appropriate, to add further auxiliaries, and the ready-to-use spray liquor or the agrochemical composition according to the invention is thus obtained. In some embodiments, 50 to 500 liters of the ready-to-use spray liquor are applied per hectare of agricultural useful area. In some embodiments 100 to 400 liters of the ready-to-use spray liquor are applied per hectare. In some embodiments, the invention provides a kit for greenhouse application of a ready-to-use composition of the invention.

According to one embodiment, individual components of the composition according to the invention such as parts of a kit or parts of a binary or ternary mixture may be mixed by the user himself in a spray tank and further auxiliaries may be added, if appropriate (tank mix). In a further embodiment, either individual components of the composition according to the invention or partially premixed components, e.g. components comprising compounds of formula I and/or active substances from the groups A) to I), may be mixed by the user in a spray tank and further auxiliaries and additives may be added, if appropriate (tank mix).

In a further embodiment, either individual components of the composition according to the invention or partially premixed components, e.g. components comprising compounds of formula I and/or active substances from the groups A) to I), can be applied jointly (e.g. after tankmix) or consecutively.

In some embodiments the invention provides a mixture comprising a compound of formula I (component 1) and at least one active substance selected from the strobilurines of group A) (component 2) and particularly selected from azoxystrobin, dimoxystrobin, fluoxastrobin, kresoxim-methyl, orysastrobin, picoxystrobin, pyraclostrobin and trifloxystrobin.

In some embodiments the invention provides a mixture comprising a compound of formula I (component 1) and at least one active substance selected from the carboxamides of group B) (component 2). In some embodiments, the carboxamide is selected from the group consisting of bixafen, boscalid, sedaxane, fenhexamid, metalaxyl, isopyrazam, mefenoxam, ofurace, dimethomorph, flumorph, fluopicolid (picobenzamid), zoxamide, carpropamid, mandipropamid and N-(3',4',5'-trifluorobiphenyl-2-yl)-3-difluoromethyl-1-methyl-1H-pyrazole-4-carboxamide.

In some embodiments the invention provides a mixture comprising a compound of formula I (component 1) and at least one active substance selected from the azoles of group C) (component 2). In some embodiments, the azole is selected from the group consisting of cyproconazole, difenoconazole, epoxicona-zole, fluquinconazole, flusilazole, flutriafol, metconazole, myclobutanil, penconazole, propiconazole, prothioconazole, triadimefon, triadimenol, tebuconazole, tetraconazole, triticonazole, prochloraz, cyazofamid, benomyl, carbendazim and ethaboxam.

In some embodiments the invention provides a mixture comprising a compound of formula I (component 1) and at least one active substance selected from the heterocyclic compounds of group D) (component 2). In some embodiments, the heterocyclic compounds of group D) are selected from the group consisting of fluazinam, cyprodinil, fenarimol, mepanipyrim, pyrimethanil, triforine, fludioxonil, dodemorph, fenpropimorph, tridemorph, fenpropidin, iprodione, vinclozolin, famoxadone, fenamidone, probenazole, proquina-zid, acibenzolar-5-methyl, captafol, folpet, fenoxanil, quinoxyfen and 5-ethyl-6-octyl-[1,2,4]triazolo[1,5-a]pyrimidine-7-ylamine.

In some embodiments the invention provides a mixture comprising a compound of formula I (component 1) and at least one active substance selected from the carbamates of group E) (component 2). In some embodiments, the carbamates are selected from the group consisting of mancozeb, metiram, propineb, thiram, iprovalicarb, benthiavalicarb and propamocarb.

In some embodiments the invention provides a mixture comprising a compound of formula I (component 1) and at least one active substance selected from the fungicides given in group F) (component 2). In some embodiments, the fungicides of group F) are selected from the group consisting of dithianon, fentin salts, such as fentin acetate, fosetyl, fosetyl-aluminium, H3PO3 and salts thereof, chlorthalonil, dichlofluanid, thiophanat-methyl, copper acetate, copper hydroxide, copper oxychloride, copper sulfate, sulfur, cymoxanil, metrafenone and spiroxamine.

The active substances referred to as component 2, their preparation and their activity against harmful fungi is known in the art. In some embodiments these substances are commercially available. The compounds described by IUPAC nomenclature, their preparation and their fungicidal activity are also known in the art (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. No. 3,296,272; U.S. Pat. No. 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/1 1853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624).

The mixtures of active substances can be prepared as compositions comprising besides the active ingredients at least one inert ingredient by usual means, e.g. by the means given for the compositions of compounds of formula I.

Concerning usual ingredients of such compositions reference is made to the explanations given for the compositions containing compounds of formula I.

The mixtures of active substances according to the present invention are suitable as fungicides, as are the compounds of formula I. In some embodiments the mixtures and compositions of the present invention are useful for the protection of plants against a broad spectrum of phytopathogenic fungi. In some embodiments, the phytopathogenic fungi are from the classes of the Ascomycetes, Basidiomycetes, Deuteromycetes and Peronosporomycetes (syn. Oomycetes).

The compounds of formula I and pharmaceutically acceptable salts thereof are also suitable for treating diseases in men and animals, especially as antimycotics, for treating cancer and for treating virus infections. The term "antimycotic", as distinguished from the term "fungicide", refers to a medicament for combating zoopathogenic or humanpathogenic fungi, i.e. for combating fungi in animals, especially in mammals (including humans) and birds.

In some embodiments, the present invention provides a medicament comprising at least one compound of formula I or a pharmaceutically acceptable salt thereof and a pharmaceutically acceptable carrier.

In some embodiments, the invention relates to the use of a compound of formula I or a pharmaceutically acceptable salt thereof for preparing an antimycotic medicament; i.e. for preparing a medicament for the treatment and/or prophylaxis of infections with humanpathogenic and/or zoopathogenic fungi.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in

Example 1

Intermediate 1.7

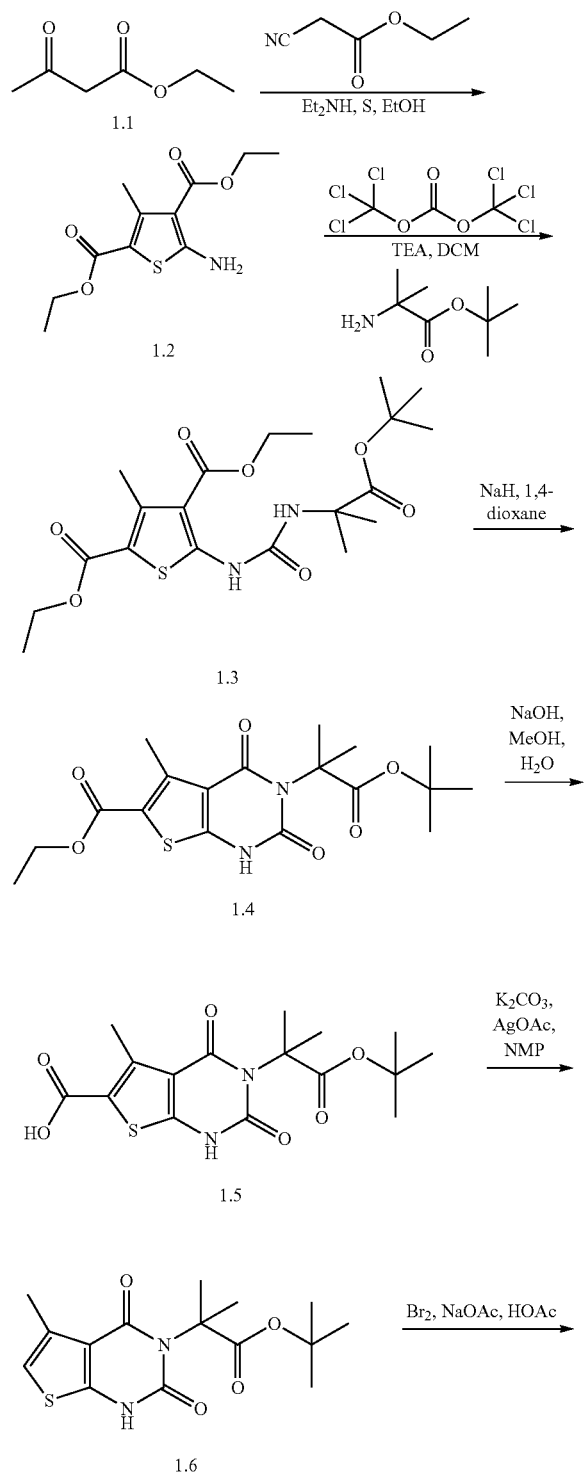

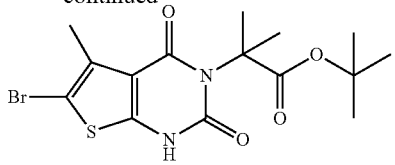

Synthesis of compound 1.2. Into a 2000-mL round-bottom flask was placed a solution of ethyl 3-oxobutanoate (320 g, 2.46 mol, 1.00 equiv), sulfur (80 g, 1.00 equiv) and ethyl 2-cyanoacetate (280 g, 2.48 mol, 1.00 equiv) in ethanol (600 mL). This was followed by the addition of morpholine (235 g, 1.00 equiv) dropwise with stirring at 45° C. over 30 min. The resulting solution was stirred for 5 h at 60° C. The solids were filtered out. The solution was diluted with 3000 mL of $H_2O$. The solids were collected by filtration and the filter cake was washed with 1 L of EtOH (30%). Purification afforded 380 g (60%) of 2,4-diethyl 5-amino-3-methylthiophene-2,4-dicarboxylate as a yellow solid.

Synthesis of compound 1.3. Into a 2000-mL 3-necked round-bottom flask, purged and maintained under an inert atmosphere of nitrogen, was placed 2,4-diethyl 5-amino-3-methylthiophene-2,4-dicarboxylate (200 g, 777.28 mmol, 1.00 equiv) and dichloromethane (1000 mL). This was followed by the addition of ditrichloromethyl carbonate (76.9 g, 259.14 mmol, 0.33 equiv) at 0° C. This was followed by the addition of TEA (314 g, 3.10 mol, 3.99 equiv) dropwise with stirring at 0° C. over 2 hr. The resulting solution was stirred for 3 h at 0° C. To this was added tert-butyl 2-amino-2-methylpropanoate (152 g, 776.70 mmol, 1.00 equiv) at 0° C. The resulting solution was stirred overnight at room temperature. The reaction was then quenched by the addition of 1 L of water. The resulting mixture was concentrated under vacuum. The crude product was re-crystallized from EA/PE in the ratio of 1:10 to afford 105 g (31%) of 1.3 as a yellow solid.

Synthesis of compound 1.4. Into a 1-L 3-necked round-bottom flask, purged and maintained with an inert atmosphere of nitrogen, was placed 1.3 (42 g, 94.91 mmol, 1.00 equiv) and 1,4-dioxane (400 mL). This was followed by the addition of sodium hydride (5.7 g, 142.50 mmol, 1.50 equiv) at 10° C. The resulting solution was stirred for 2 h at 110° C. The reaction was then quenched by the addition of 500 mL of $NH_4Cl$ (sat., aq.). The resulting solution was extracted with 3×200 mL of ethyl acetate and the organic layers combined and concentrated under vacuum. The crude product was re-crystallized from EA/PE in the ratio of 1:10. Purification afforded 24.4 g (65%) of 1.4 as a white solid.

Synthesis of compound 1.5. Into a 500-mL 3-necked round-bottom flask, was placed 1.5 (24.4 g, 61.54 mmol, 1.00 equiv), sodium hydroxide (12.2 g, 305.00 mmol, 4.96 equiv), water (20 mL) and methanol (250 mL). The resulting solution was stirred for 4 h at 50° C. The resulting mixture was concentrated under vacuum. The pH value of the solution was adjusted to 2 with hydrogen chloride (10%). The resulting solution was extracted with 3×300 mL of ethyl acetate and the organic layers combined, dried over anhydrous sodium sulfate and concentrated under vacuum to afford 19.4 g (86%) of 1.5 as a white solid.

Synthesis of compound 1.6. A 1-L 3-necked round-bottom flask was charged with 1.5 (19.4 g, 52.66 mmol, 1.00 equiv), potassium carbonate (8.7 g, 62.95 mmol, 1.20 equiv), $CH_3COOAg$ (10.5 g) and NMP (400 mL). The resulting solution was stirred for 2 h at 110° C. The reaction was then quenched by the addition of 1 L of water. The resulting solution was extracted with 5×200 mL of ethyl acetate and the organic layers combined and concentrated under vacuum. The residue was applied onto a silica gel column with ethyl acetate/petroleum ether (1:20). Purification afforded 15.3 g (90%) of 1.6 as a white solid.

Synthesis of compound 1.7. Into a 1000-mL 3-necked round-bottom flask was placed 1.6 (15.3 g, 47.16 mmol, 1.00 equiv), CH₃COONa (8.5 g, 103.66 mmol, 2.20 equiv) and acetic acid (300 mL). This was followed by the addition of Br₂ (8.3 g, 51.94 mmol, 1.10 equiv) dropwise with stirring. The resulting solution was stirred for 1 h at room temperature, concentrated under vacuum and washed with 500 mL of H₂O to afford 17 g (89%) of 1.7 as a white solid.

Example 2

Synthesis of 2-methyl-2-[5-methyl-6-(1,3-oxazol-2-yl)-2,4-dioxo-1-[(2S)-2-phenyl-2-(propan-2-yloxy)ethyl]-1H,2H,3H,4H-thieno[2,3-d]pyrimidin-3-yl]propanoic acid (I-120)

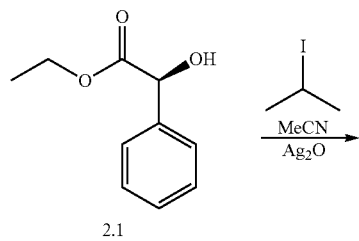

2.1

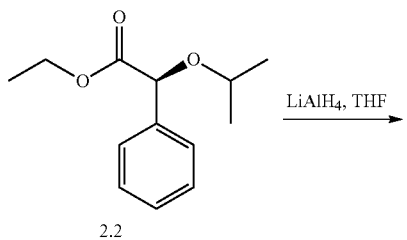

2.2

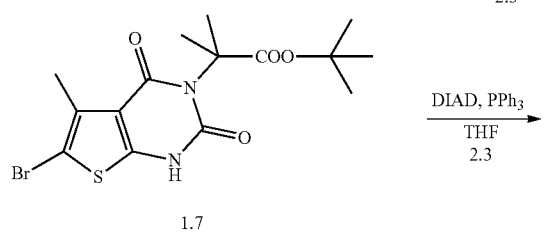

1.7

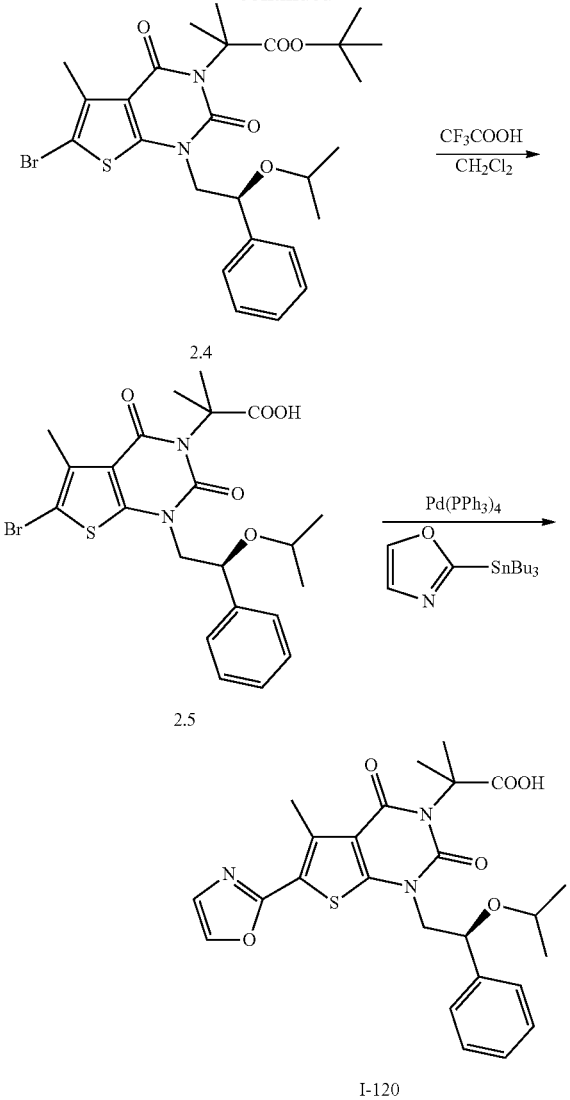

I-120

Synthesis of compound 2.2. A 500-mL round-bottom flask was charged with 2.1 (15 g, 83.24 mmol, 1.00 equiv), prop-1-yne (200 mL), Ag₂O (52 g, 225.11 mmol, 2.70 equiv) and 2-iodopropane (60 g, 352.96 mmol, 4.24 equiv). The resulting solution was stirred overnight at 40° C. in an oil bath. The resulting mixture was concentrated under vacuum. The residue was applied onto a silica gel column with EA/PE (1:50). Purification afforded 3.2 g (crude) of 2.2 as a yellow oil.

Synthesis of compound 2.3. A 100-mL 3-necked round-bottom flask was charged with tetrahydrofuran (10 mL) and 2.2 (300 mg, 1.35 mmol, 1.00 equiv). This was followed by the addition of LiAlH₄ (51 mg, 1.34 mmol, 1.00 equiv) in portions at 0° C. The resulting solution was stirred for 1 h at room temperature. The reaction was then quenched by the addition of 20 mL of NH₄Cl (aq.). The resulting solution was extracted with 3×50 mL of ethyl acetate and the organic layers combined, dried over anhydrous magnesium sulfate and concentrated under vacuum. The residue was applied onto a silica gel column with ethyl acetate/petroleum ether (1:10). Purification afforded 210 mg (86%) of 2.3 as a yellow oil.

Synthesis of compound 2.4. A 100-mL 3-necked round-bottom flask was charged with tetrahydrofuran (10 mL), 2.3 (500 mg, 1.24 mmol, 1.00 equiv), PPh₃ (650 mg, 2.48 mmol, 2.00 equiv), DIAD (362 mg, 1.79 mmol, 1.44 equiv) and 2.3 (268 mg, 1.49 mmol, 1.20 equiv) under an atmosphere of nitrogen. The resulting solution was stirred overnight at room temperature. The resulting mixture was concentrated under vacuum. The residue was applied onto a silica gel column with ethyl acetate/petroleum ether (1:15). Purification afforded 0.430 g (61%) of 2.4 as a colorless oil.

Synthesis of compound 2.5. A 25-mL round-bottom flask was charged with dichloromethane (5 mL), 2.4 (428 mg, 0.76 mmol, 1.00 equiv) and CF$_3$COOH (2 mL). The resulting solution was stirred overnight at room temperature. The resulting mixture was concentrated under vacuum. The residue was applied onto a silica gel column with ethyl acetate/petroleum ether (1:5). Purification afforded 0.282 g (73%) of 2.4 as a colorless oil.

Synthesis of compound I-120. A 100-mL 3-necked round-bottom flask was charged with toluene (10 mL), 2.5 (282 mg, 0.55 mmol, 1.00 equiv), Pd(PPh$_3$)$_4$ (200 mg, 0.17 mmol, 0.31 equiv) and 2-(tripropylstannyl)-1,3-oxazole (238 mg, 0.75 mmol, 1.36 equiv) under an atmosphere of nitrogen. The resulting solution was heated to reflux overnight in an oil bath. The resulting mixture was concentrated under vacuum. The crude product (300 mg) was purified by preparative HPLC under the following conditions (SHIMADZU): column: SunFire Prep C18, 19*150 mm 5 μm; mobile phase: water with 0.05% NH$_4$HCO$_3$ and CH$_3$CN (7.0% CH$_3$CN up to 46.0% in 10 min); detector: 254/220 nm. 0.193 g (70%) of Compound I-120 were obtained as a white solid. MS (ES): m/z 498 (M+H)$^+$. $^1$H NMR (CD$_3$OD, 300 MHz): δ 0.97 (m, 6H), 1.77 (d, J=6.0 Hz, 6H), 3.04 (s, 3H), 3.46 (m, 1H), 3.82 (m, 1H), 4.13 (m, 1H), 4.88 (m, 1H), 7.24-7.44 (m, 6H), 7.94 (d, J=0.9 Hz, 1H).

Example 3

Synthesis of 2-methyl-2-[5-methyl-6-(1,3-oxazol-2-yl)-2,4-dioxo-1-[(2R)-2-phenyl-2-(propan-2-yloxy)ethyl]-1H,2H,3H,4H-thieno[2,3-d]pyrimidin-3-yl]propanoic acid (I-119)

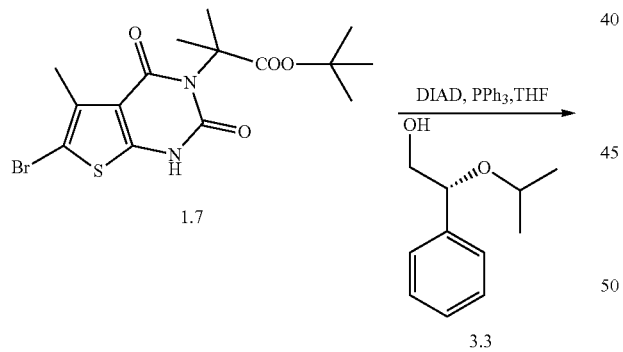

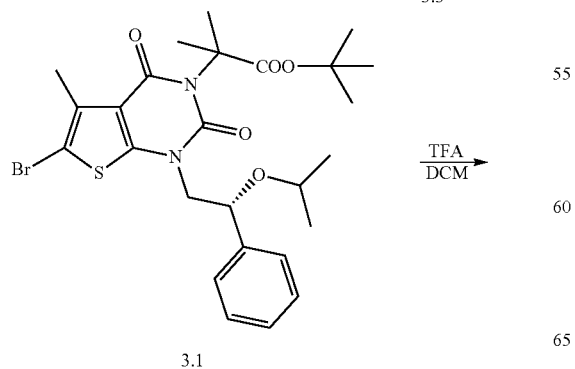

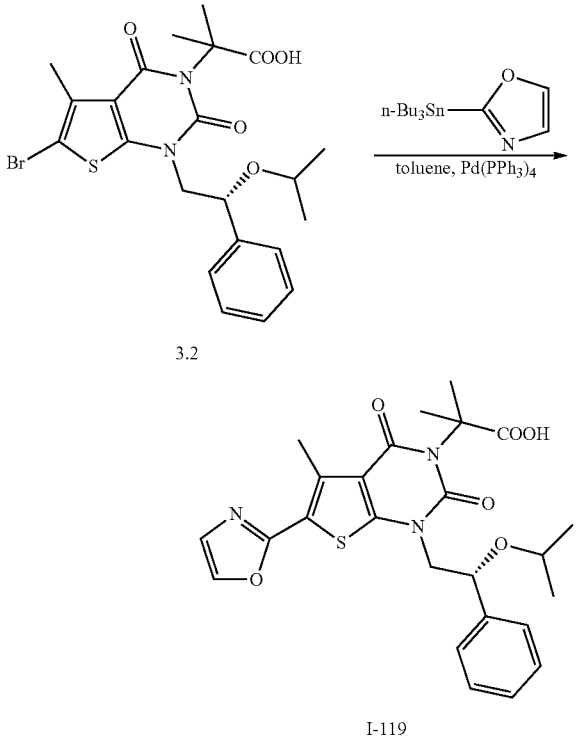

Compound I-119 was synthesized in a manner analogous to Example 2 except that (2R)-2-phenyl-2-(propan-2-yloxy)ethan-1-ol was used rather than (2S)-2-phenyl-2-(propan-2-yloxy)ethan-1-ol. Compound I-119 was obtained in 11% overall yield as a yellow solid. MS (ES): m/z 498 (M+H)$^+$. $^1$H NMR (CD$_3$OD, 300 MHz): δ 0.97 (d, J=6.3 Hz, 3H), 0.99 (d, J=6.3 Hz, 3H), 1.77 (d, J=6.3 Hz, 6H), 2.77 (s, 3H), 3.50 (m, 1H), 3.81 (m, 1H), 4.13 (m, 1H), 4.89 (m, 1H), 7.24-7.45 (m, 6H), 7.94 (d, J=0.9 Hz, 1H).

Example 4

Synthesis of 2-methyl-2-[5-methyl-6-(1,3-oxazol-2-yl)-2,4-dioxo-1-[(2R)-2-phenyl-2-(propan-2-yloxy)ethyl]-1H,2H,3H,4H-thieno[2,3-d]pyrimidin-3-yl]propanamide (I-121)

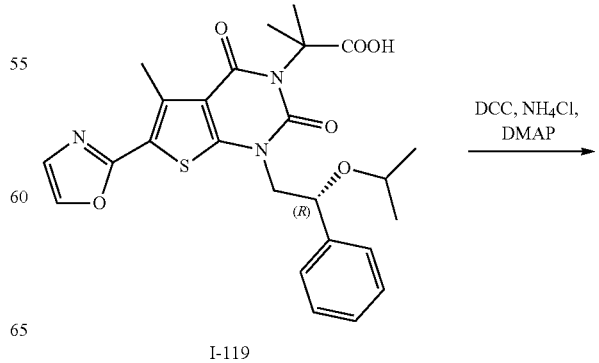

217
-continued

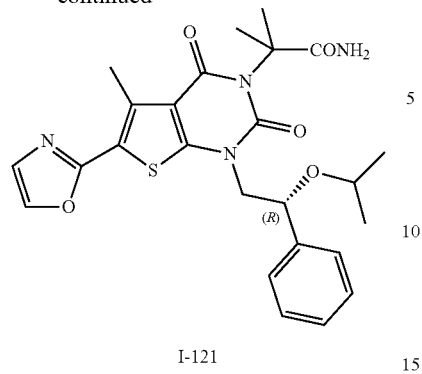

I-121

218
-continued

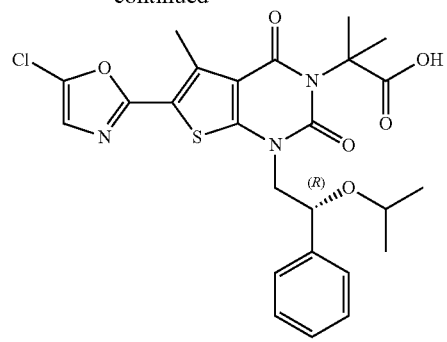

I-156

A 25-mL round-bottom flask was charged with dichloromethane (10 mL), Compound I-119 (70 mg, 0.14 mmol, 1.00 equiv), DCC (39 mg, 0.19 mmol, 1.34 equiv), 4-dimethylaminopyridine (19 mg, 0.16 mmol, 1.11 equiv) and NH$_4$Cl (20 mg, 0.37 mmol, 2.66 equiv). The resulting solution was stirred overnight at 40° C. in an oil bath. The reaction was then quenched by the addition of 10 mL of water. The resulting solution was extracted with 5×20 mL of ethyl acetate and the organic layers combined and concentrated under vacuum. The residue was purified by preparative TLC (DCM:MeOH=15:1). The product (50 mg) thus obtained was repurified by preparative HPLC under the following conditions (SHIMADZU): column: SunFire Prep C18, 19*150 mm 5 μm; mobile phase: water with 0.05% NH$_4$HCO$_3$ and CH$_3$CN (6.0% CH$_3$CN up to 48.0% in 13 min); detector: 254/220 nm. 0.030 g (43%) of Compound I-121 were obtained as a white solid. MS (ES): m/z 497 (M+H)$^+$. $^1$H NMR (CD$_3$OD, 300 MHz): δ 0.90 (m, 6H), 1.79 (d, J=5.1 Hz, 6H), 2.77 (s, 3H), 3.54 (m, 1H), 3.81 (m, 1H), 4.11 (m, 1H), 4.90 (m, 1H), 7.24-7.44 (m, 6H), 7.94 (d, J=0.9 Hz, 1H).

Into a 50-mL round-bottom flask protected by nitrogen was placed CH$_3$CN (10 mL), Compound I-119 (60 mg, 0.12 mmol, 1.00 equiv) and NCS (32 mg, 0.24 mmol, 1.99 equiv). The resulting solution was stirred for 3 days at 50° C. in an oil bath and monitored by LCMS. The resulting mixture was concentrated under vacuum. The crude product (60 mg) was purified by preparative HPLC under the following conditions (Waters): column: Xbridge Prep C18, 5 μm, 19*50 mm; mobile phase: water with 50 mmol NH$_4$HCO$_3$ and CH$_3$CN (10% CH$_3$CN up to 35% in 10 min, up to 95% in 1.5 min, down to 10% in 1.5 min); detector: UV 254/220 nm. 0.010 g (16%) of I-156 were obtained as a white solid. $^1$H NMR (CD$_3$OD, 400 MHz): δ 1.00 (dd, 6H), 1.82 (d, J=8.0 Hz, 6H), 2.79 (s, 3H), 3.54 (m, 1H), 3.85 (dd, J=1H), 4.18 (dd, 1H), 4.93 (dd, 1H), 7.16 (s, 1H), 7.34 (t, J=7.2 Hz, 1H), 7.41 (t, J=7.6 Hz, 2H), 7.47 (d, J=7.2 Hz).

Example 5

Synthesis of 2-[6-(5-chloro-1,3-oxazol-2-yl)-5-methyl-2,4-dioxo-1-[(2R)-2-phenyl-2-(propan-2-yloxy)ethyl]-1H,2H,3H,4H-thieno[2,3-d]pyrimidin-3-yl]-2-methylpropanoic acid (I-156)

Example 6

Synthesis of 2-methyl-2-[5-methyl-6-(1,3-oxazol-2-yl)-2,4-dioxo-1-[(2R)-2-phenyl-2-(propan-2-yloxy)ethyl]-1H,2H,3H,4H-thieno[2,3-d]pyrimidin-3-yl]propanenitrile (I-154)

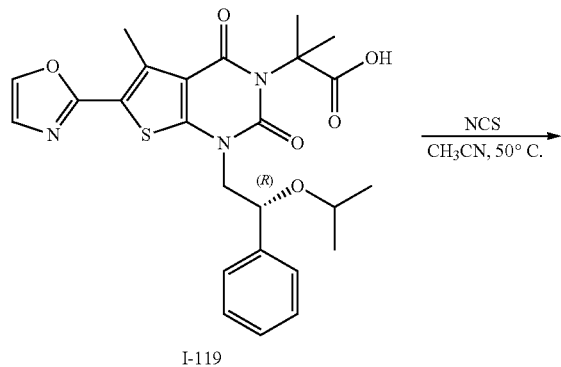

I-119

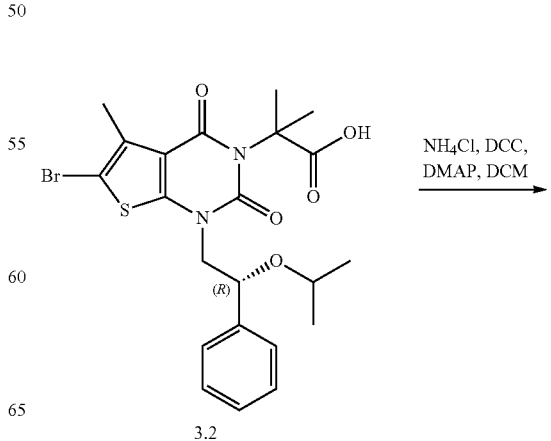

3.2

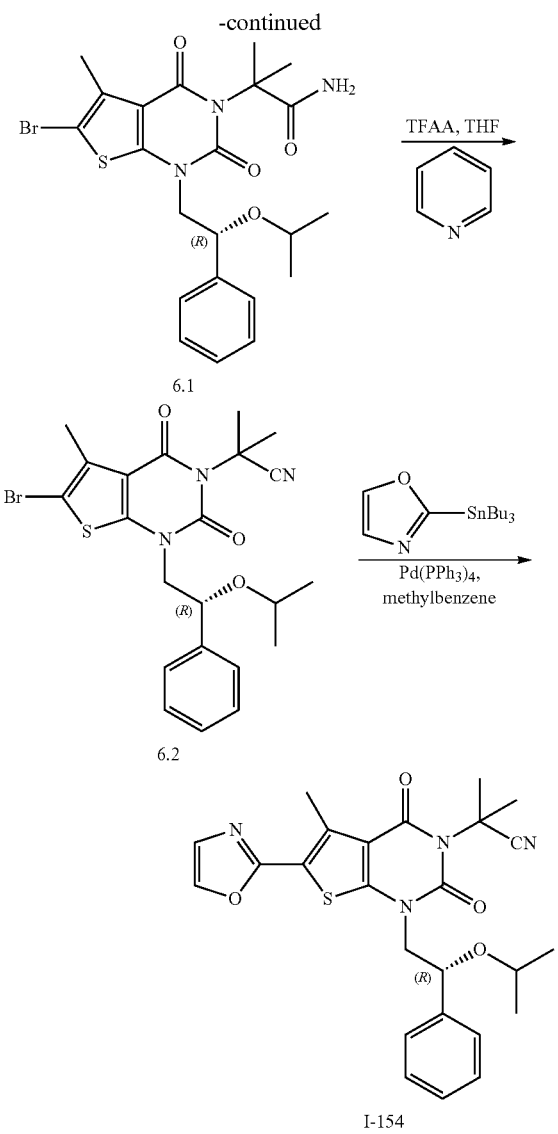

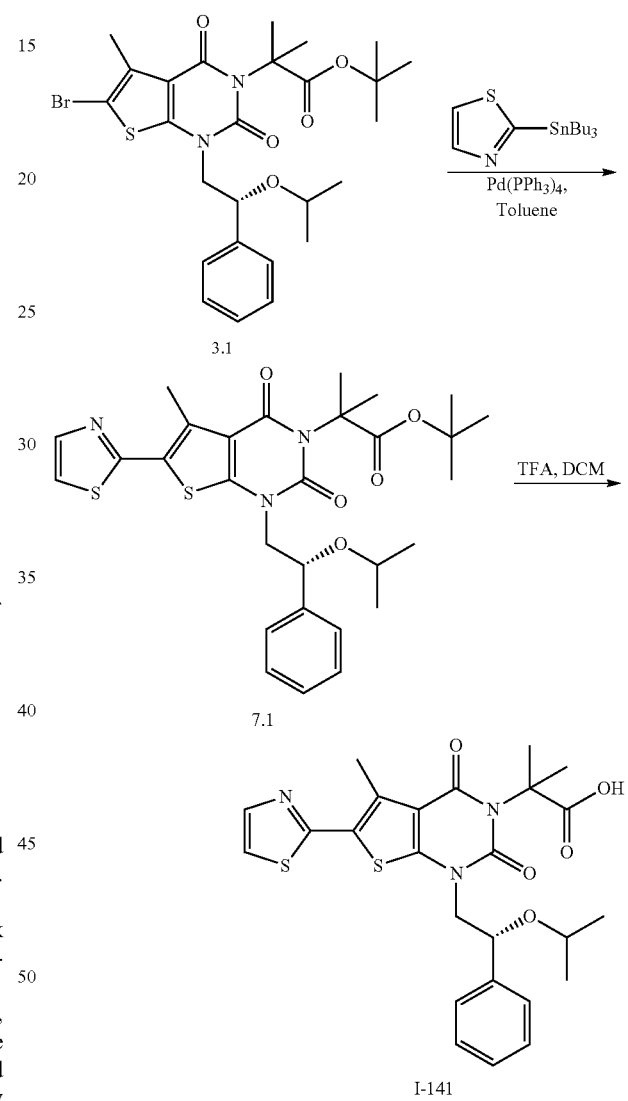

1H), 3.89-3.96 (m, 1H), 4.18-4.25 (m, 1H), 4.94-4.98 (m, 1H), 7.30-7.32 (s, 1H), 7.34-7.49(m, 5H), 8.01 (s, 1H). MS (ES): m/z 479 (M+H)+.

Example 7

Synthesis of 2-methyl-2-[5-methyl-2,4-dioxo-1-[(2R)-2-phenyl-2-(propan-2-yloxy)ethyl]-6-(1,3-thiazol-2-yl)-1H,2H,3H,4H-thieno[2,3-d]pyrimidin-3-yl]propanoic acid (I-141)

Synthesis of compound 6.1. Compound 6.1 was prepared in a manner analogous to Compound I-121 (Example 4). Isolated 100 mg (42%) of 6.1 as a white solid.

Synthesis of compound 6.2. A 25-mL round-bottom flask was charged with 6.1 (100 mg, 0.20 mmol, 1.00 equiv), tetrahydrofuran (5 mL) and pyridine (78 mg, 0.99 mmol, 5.01 equiv). This was followed by the addition of TFAA (103 mg, 0.49 mmol, 2.49 equiv) dropwise with stirring at 0° C. The resulting solution was stirred for 3 h at room temperature and then concentrated under vacuum. The residue was purified by preparative TLC with ethyl acetate/petroleum ether (1:3). Purification afforded 90 mg (93%) of 6.2 as a white solid.

Synthesis of Compound I-154. Into a 25-mL round-bottom flask was placed 6.2 (100 mg, 0.20 mmol, 1.00 equiv), Pd(PPh₃)₄ (60 mg, 0.05 mmol, 0.26 equiv), 2-(tributylstannyl)-1,3-oxazole (153 mg, 0.43 mmol, 2.17 equiv) and methylbenzene (5 mL). The resulting solution was stirred overnight at 110° C. and then concentrated under vacuum. The residue was purified by preparative TLC with ethyl acetate/petroleum ether (1:2). Purification afforded 5.2 mg (6%) of Compound I-154. $^1$H NMR (300 MHz, CD$_3$OD): δ 1.00-1.06 (m, 6H), 2.09-2.10 (d, 6H), 2.84-2.89 (s, 3H), 3.49-3.57 (m, Synthesis of compound 7.1. To a 25-mL round-bottom flask, purged and maintained with an inert atmosphere of nitrogen, was added 3.1 (210 mg, 0.37 mmol, 1.00 equiv), 2-(tributylstannyl)-1,3-thiazole (208 mg, 0.56 mmol, 1.50 equiv), methylbenzene (5 mL) and Pd(PPh₃)₄ (200 mg, 0.17 mmol, 0.47 equiv). The resulting solution was stirred overnight at 110° C. The reaction mixture was cooled to room temperature. The resulting mixture was concentrated under vacuum. The residue was applied onto a silica gel column with ethyl acetate/petroleum ether (1:20). Purification afforded 137 mg (65%) of 7.1 as a white solid.

Synthesis of Compound I-141. A 10-mL round-bottom flask was charged with compound 7.1 (137 mg, 0.24 mmol, 1.00 equiv), trifluoroacetic acid (2 mL) and dichloromethane (3 mL). The resulting solution was stirred overnight at room temperature and then concentrated under vacuum. The crude product (130 mg) was purified by preparative HPLC under the following conditions (SHIMADZU): column: Xbridge Prep Phenyl 5 μm, 19*150 mm; mobile phase: water (0.05% $NH_4HCO_3$) and $CH_3CN$ (6.0% $CH_3CN$ up to 50.0% in 11.5 min); detector: 220/254 nm. 43.9 mg (36%) of Compound I-141 were obtained as a white solid. MS (ES): m/z 514 $(M+H)^+$. $^1H$ NMR ($CD_3OD$, 400 MHz): δ 0.99-1.05 (m, 6H), 1.82-1.84 (d, 6H), 2.76 (s, 3H), 3.49-3.55 (m, 1H), 3.85-3.89 (m, 1H), 4.14-4.19 (m, 1H), 4.92-4.95 (m, 1H), 7.31-7.35 (t, 1H), 7.39-7.43 (t, 2H), 7.47-7.49 (d, 2H), 7.66-7.66 (d, 1H), 7.83-7.84 (d, 1H).

Example 8

Synthesis of 2-methyl-2-[5-methyl-2,4-dioxo-1-[(2R)-2-phenyl-2-(propan-2-yloxy)ethyl]-6-(1H-1,2,4-triazol-1-yl)-1H,2H,3H,4H-thieno[2,3-d]pyrimidin-3-yl]propanoic acid (I-157)

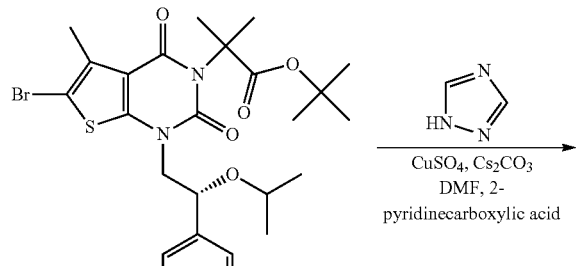

3.1

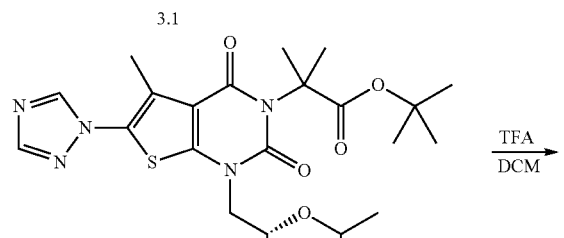

8.1

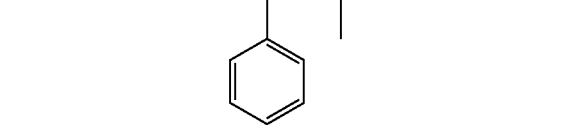

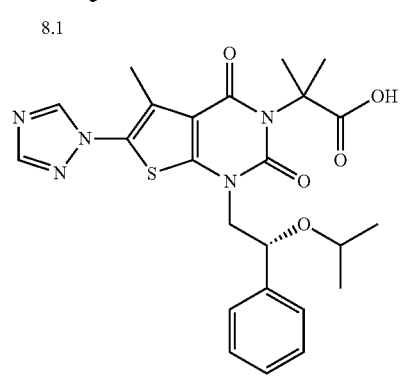

I-157

Synthesis of compound 8.1. An 8-mL sealed tube was charged with 1H-1,2,4-triazole (100 mg, 1.45 mmol, 8.19 equiv), 3.1 (100 mg, 0.18 mmol, 1.00 equiv), pyridine-2-carboxylic acid (70 mg, 0.57 mmol, 3.22 equiv), $CuSO_4$ (5 mL), N,N-dimethylformamide (100 mg, 1.37 mmol, 7.74 equiv) and $Cs_2CO_3$ (70 mg, 3.22 equiv). The reaction mixture was irradiated with microwave radiation for 30 min at 170° C. The reaction was then quenched by the addition of 20 mL of $NH_4Cl$ (sat.). The resulting solution was extracted with 2×20 mL of ethyl acetate and the organic layers combined and concentrated under vacuum. The residue was applied onto a silica gel column with ethyl acetate/petroleum ether (1:10). Purification afforded 30 mg (31%) of 8.1 as a white solid.

Synthesis of compound I-157. A 50-mL round-bottom flask was charged with 8.1 (57 mg, 0.10 mmol, 1.00 equiv), dichloromethane (10 mL) and trifluoroacetic acid (2 mL). The resulting solution was stirred overnight at 30° C. The resulting mixture was concentrated under vacuum. The residue was applied onto a silica gel column with dichloromethane/methanol (50:1). The crude product (60 mg) was purified by preparative HPLC under the following conditions (Waters): column: SunFire Prep C18, 19*150 mm 5 μm; mobile phase: water (50 mM $NH_4HCO_3$) and $CH_3CN$ (5.0% $CH_3CN$ up to 50.0% in 10 min, up to 95.0% in 2 min, down to 5.0% in 2 min); detector: UV 254/220 nm. Purification afforded 9.9 mg (19%) of Compound I-157 as a white solid. $^1H$ NMR ($CD_3OD$, 400 MHz): 1.06 (m, 6H), 1.82 (d, 6H), 2.35 (s, 3H), 3.51 (m, 1H), 3.78 (m, 1H), 4.17 (m, 1H), 4.91 (m, 1H), 7.42 (m, 5H), 8.25 (s, 1H), 8.86 (s, 1H). MS (ES): 498 m/z $(M+H)^+$.

Example 9

Synthesis of 2-[1-[2-(2-ethylphenyl)ethyl]-5-methyl-6-(1,3-oxazol-2-yl)-2,4-dioxo-1H,2H,3H,4H-thieno[2,3-d]pyrimidin-3-yl]-2-methylpropanoic acid (I-133)

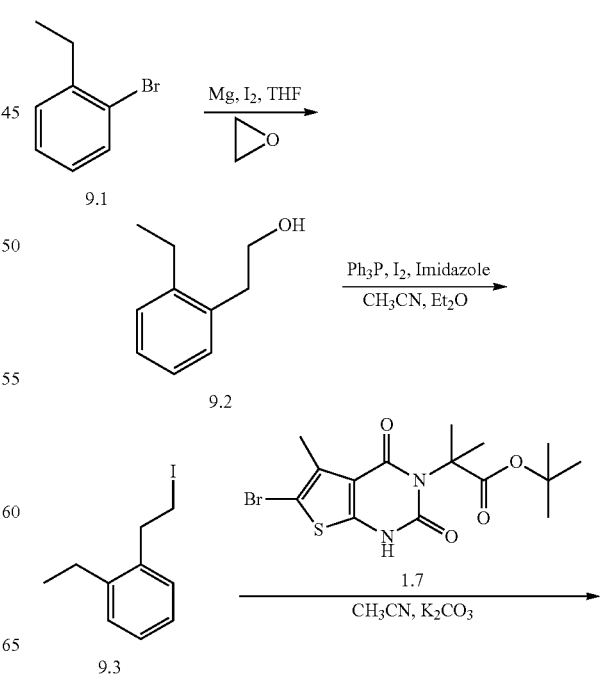

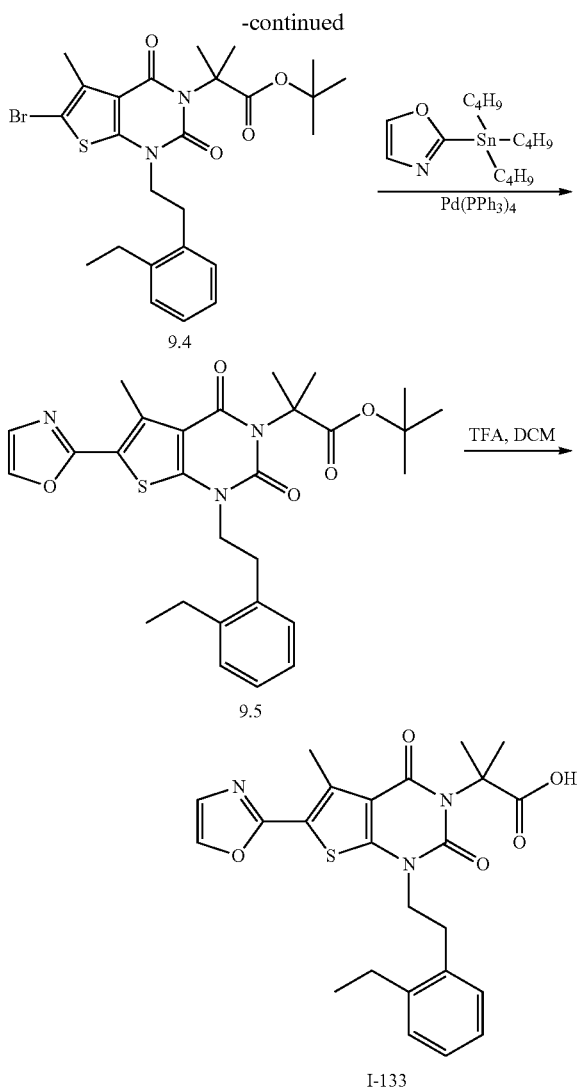

acetate and the organic layers combined, dried over Na₂SO₄ and concentrated under vacuum. The residue was applied onto a silica gel column with ethyl acetate/petroleum ether (1:20). Purification afforded 1.16 g (74%) of 1-ethyl-2-(2-iodoethyl)benzene as a colorless oil.

Synthesis of compound 9.4. A 50-mL round-bottom flask was charged with 9.3 (200 mg, 0.50 mmol, 1.00 equiv), potassium carbonate (205 mg, 1.48 mmol, 2.99 equiv), acetonitrile (20 mL) and 1-ethyl-2-(2-iodoethyl)benzene (258 mg, 0.99 mmol, 2.00 equiv). The resulting solution was heated to reflux overnight in an oil bath. The resulting mixture was concentrated under vacuum. The residue was applied onto a silica gel column with ethyl acetate/petroleum ether (1:50). Purification afforded 220 mg (83%) of compound 9.4 as a white solid.

Synthesis of compound 9.5. A 50-mL round-bottom flask, purged and maintained with an inert atmosphere of nitrogen, was charged with 9.4 (220 mg, 0.41 mmol, 1.00 equiv), toluene (20 mL), 2-(tributylstannyl)-1,3-oxazole (280 mg, 0.78 mmol, 1.90 equiv) and tetrakis(triphenylphosphane) palladium (67 mg, 0.06 mmol, 0.14 equiv). The resulting solution was stirred overnight at 110° C. in an oil bath. The resulting mixture was concentrated under vacuum. The residue was applied onto a silica gel column with ethyl acetate/petroleum ether (1:25). Purification afforded 180 mg (84%) of 9.5 as a white solid.

Synthesis of Compound I-133. Into a 50-mL round-bottom flask was placed compound 9.5 (180 mg, 0.34 mmol, 1.00 equiv), dichloromethane (10 mL) and trifluoroacetic acid (3 mL). The resulting solution was stirred for 3 h at room temperature. The resulting mixture was concentrated under vacuum. The residue was applied onto a silica gel column with ethyl acetate/petroleum ether (1:2). Purification afforded 130 mg (81%) of Compound I-133 as a white solid. ¹H NMR (300 MHz, DMSO-d₆): δ 1.19 (t, J=7.5, 3H), 1.68 (s, 6H), 2.50 (q, J=1.8, 2H), 2.74 (s, 3H), 3.03 (t, J=7.8, 2H), 4.04 (t, J=7.8, 2H), 7.10-7.21 (m, 4H), 7.38 (s, 1H), 8.23 (s, 1H). MS (ES): m/z 468 (M+H)⁺, 509 (M+CH₃CN)⁺.

Synthesis of compound 9.2. Into a 250-mL round-bottom flask protected by N₂ was placed tetrahydrofuran (100 mL), Mg (1.0 g, 41.67 mmol, 2.14 equiv) and I₂ (0.010 g). Then a solution of 1-bromo-2-ethylbenzene (3.6 g, 19.45 mmol, 1.00 equiv) in THF (15 mL) was added dropwise. The resulting mixture was heated to reflux for 1 h. Then it was cooled to 0° C. and oxirane (50 mL) was added. The resulting solution was stirred at room temperature overnight. The reaction was then quenched by the addition of 20 mL of NH₄Cl (aq.). The resulting solution was extracted with 3×50 mL of ethyl acetate and the organic layers combined and concentrated under vacuum. The residue was applied onto a silica gel column with ethyl acetate/petroleum ether (1:5). Purification afforded 1.83 g (63%) of 2-(2-ethylphenyl)ethan-1-ol as a colorless oil.

Synthesis of compound 9.3. Into a 50-mL round-bottom flask was placed ether (10 mL), CH₃CN (5 mL) and 2-(2-ethylphenyl)ethan-1-ol (900 mg, 5.99 mmol, 1.00 equiv). Then imidazole (570 mg, 8.38 mmol, 1.40 equiv), PPh₃ (2.20 g, 8.39 mmol, 1.40 equiv) and I₂ (1.98 g, 7.80 mmol, 1.30 equiv) were added at 0° C. The resulting solution was stirred for 6 h at room temperature. The reaction was then quenched by the addition of 10 mL of saturated Na₂SO₃ solution. The resulting solution was extracted with 3×50 mL of ethyl Example 10

Synthesis of 2-[1-[2-(2-ethylphenyl)ethyl]-5-methyl-6-(1,3-oxazol-2-yl)-2,4-dioxo-1H,2H,3H,4H-thieno[2,3-d]pyrimidin-3-yl]-2-methylpropanamide (I-134)

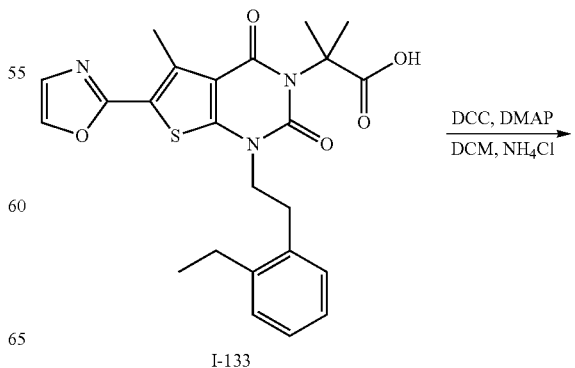

I-133

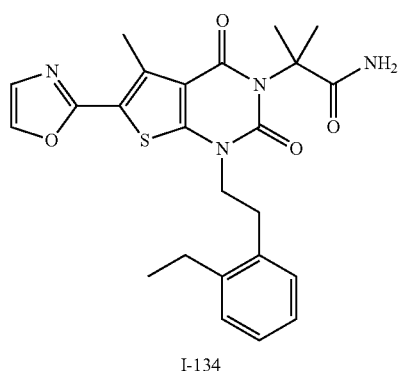

I-134

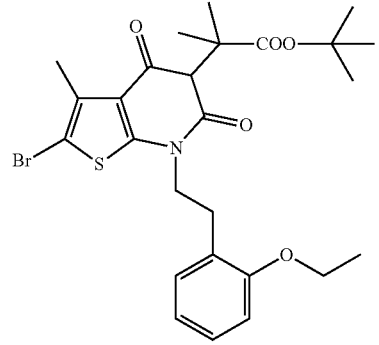

11.5

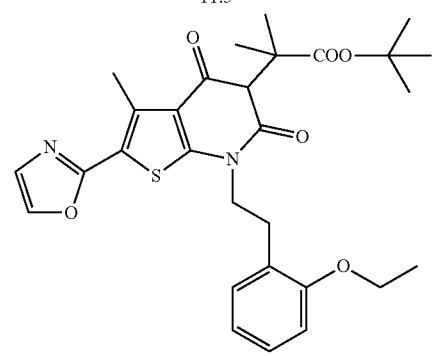

11.6

Compound I-134 was prepared from I-133 in a manner analogous to Compound I-121 (Example 4). Isolated 37.4 mg (42%) of Compound I-134 as a white solid. MS (ES): m/z 467 (M+H)$^+$. $^1$H NMR (DMSO-d$_6$, 300 MHz): δ 1.20 (t, J=7.8 Hz, 3H), 1.66 (s, 6H), 2.67-2.74 (m, 5H), 3.01 (t, J=7.2 Hz, 2H), 4.00 (t, J=7.2 Hz, 2H), 7.14-7.20 (m, 4H), 7.38 (s, 1H), 8.22 (s, 1H).

Example 11

Synthesis of 2-[1-[2-(2-ethoxyphenyl)ethyl]-5-methyl-6-(1,3-oxazol-2-yl)-2,4-dioxo-1H,2H,3H,4H-thieno[2,3-d]pyrimidin-3-yl]-2-methylpropanoic acid (I-135)

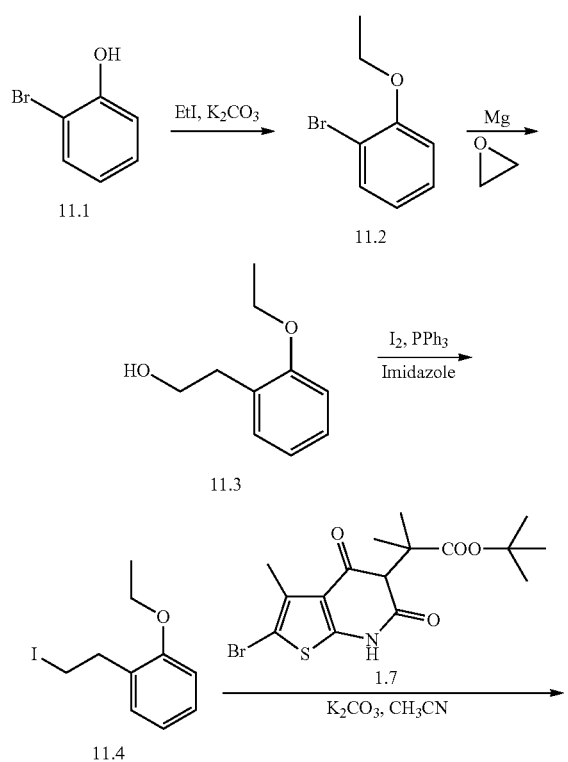

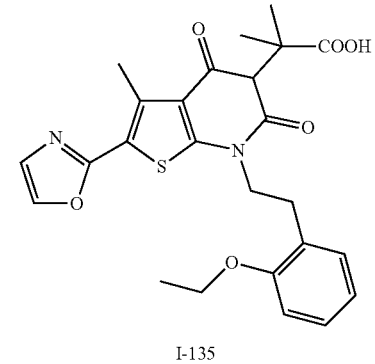

I-135

Synthesis of compound 11.2. Into a 500-mL round-bottom flask was placed CH$_3$COCH$_3$ (200 mL), 2-bromophenol (10.38 g, 60.00 mmol, 1.00 equiv), iodoethane (28.08 g, 180.04 mmol, 3.00 equiv) and potassium carbonate (33.12 g, 239.64 mmol, 3.99 equiv). The resulting solution was heated to reflux overnight in an oil bath. The solids were filtered out. The filtrate was concentrated under vacuum. The residue was applied onto a silica gel column with ethyl acetate/petroleum ether (1:100). Purification afforded 11.48 g (95%) of 1-bromo-2-ethoxybenzene as a colorless oil.

Synthesis of compound 11.3. Into a 250-mL 3-necked round-bottom flask, maintained with an inert atmosphere of nitrogen, was placed Mg (1.0 g, 41.67 mmol, 2.09 equiv) and I$_2$ (10 mg). Then a solution of 1-bromo-2-ethoxybenzene (4.0 g, 19.89 mmol, 1.00 equiv) in 25 mL THF was added dropwise and the resulting mixture was heated to reflux for 0.5 hr. After the reaction was complete, the resulting mixture was cooled to 0° C. and then oxirane (50 mL) was added in one portion. The reaction mixture was stirred overnight at room temperature. The reaction was then quenched by the addition of 50 mL of NH$_4$Cl (aq.) and extracted with 3×50 mL of ethyl acetate. The organic layers were combined, dried over anhydrous sodium sulfate and concentrated under vacuum. The residue was applied onto a silica gel column with ethyl acetate/petroleum ether (1:10). Purification afforded 2.14 g (65%) of 2-(2-ethoxyphenyl)ethan-1-ol as a yellow oil.

Synthesis of compound 11.4. Into a 50-mL round-bottom flask was placed dichloromethane (20 mL) and 2-(2-ethoxyphenyl)ethan-1-ol (1.33 g, 8.00 mmol, 1.00 equiv). The solution was cooled to 0° C. in a water/ice bath. Then PPh$_3$ (2.72 g, 10.37 mmol, 1.30 equiv), imidazole (707 mg, 10.40 mmol, 1.30 equiv) and I$_2$ (2.44 g, 9.61 mmol, 1.20 equiv) were added. The resulting solution was stirred at room temperature overnight. The reaction was then quenched by the addition of 50 mL of NaHSO$_3$ (aq.). The organic layer was separated and concentrated under vacuum. The residue was applied onto a silica gel column with ethyl acetate/petroleum ether (0:100). Purification afforded 1.34 g (61%) of 1-ethoxy-2-(2-iodoethyl)benzene as a colorless oil.

Synthesis of compound I-135. Compound I-135 was prepared from 11.4 and 1.7 in a manner analogous to Example 9. Isolated a white solid in 50% overall yield for the two steps. MS (ES): m/z 484 (M+H)$^+$. $^1$H NMR (DMSO-d$_6$, 300 MHz): δ 1.37 (t, J=7.2 Hz, 3H), 1.64 (s, 6H), 2.73 (s, 3H), 3.00 (t, J=7.2 Hz, 2H), 4.05 (m, 4H), 6.84 (m, 1H), 6.92 (m, 1H), 7.16 (m, 2H), 7.38 (d, J=0.6 Hz, 1H), 8.22 (d, J=0.6 Hz, 1H).

Example 12

Synthesis of 2-[1-[2-(2-ethoxyphenyl)ethyl]-5-methyl-6-(1,3-oxazol-2-yl)-2,4-dioxo-1H,2H,3H,4H-thieno[2,3-d]pyrimidin-3-yl]-2-methylpropanamide (I-139)

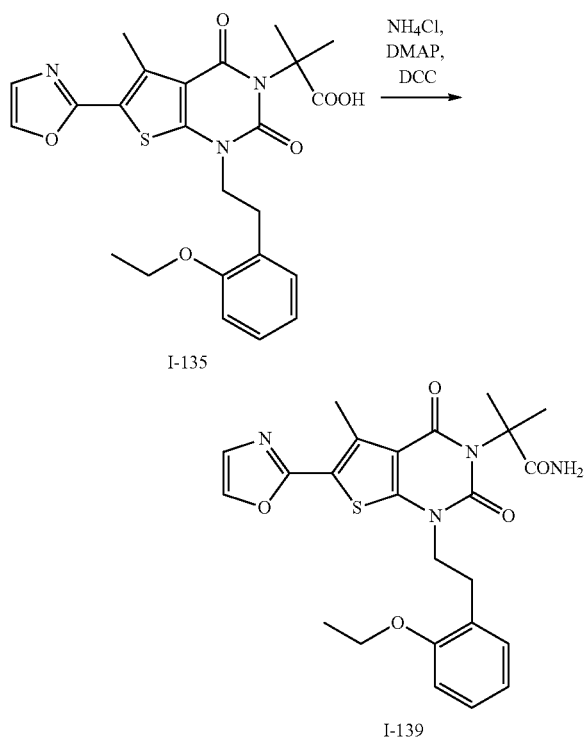

Compound I-139 was prepared from Compound I-135 in a manner analogous to Example 10. Isolated a white solid in 67% yield. MS (ES): m/z 505 (M+Na)$^+$. $^1$H NMR (DMSO-d$_6$, 300 MHz): δ 1.41 (t, J=7.2 Hz, 3H), 1.64 (s, 6H), 2.74 (s, 3H), 2.98 (t, J=7.2 Hz, 2H), 4.05 (m, 4H), 6.65 (s, 1H), 6.86 (t, J=7.2 Hz, 1H), 6.95 (d, J=7.8 Hz, 1H), 7.11 (m, 2H), 7.38 (s, 1H), 8.22 (s, 1H).

Example 13

Synthesis of 2-[1-[(2R)-2-(benzyloxy)-2-phenylethyl]-5-methyl-6-(1,3-oxazol-2-yl)-2,4-dioxo-1H,2H,3H,4H-thieno[2,3-d]pyrimidin-3-yl]-2-methylpropanoic acid (I-136)

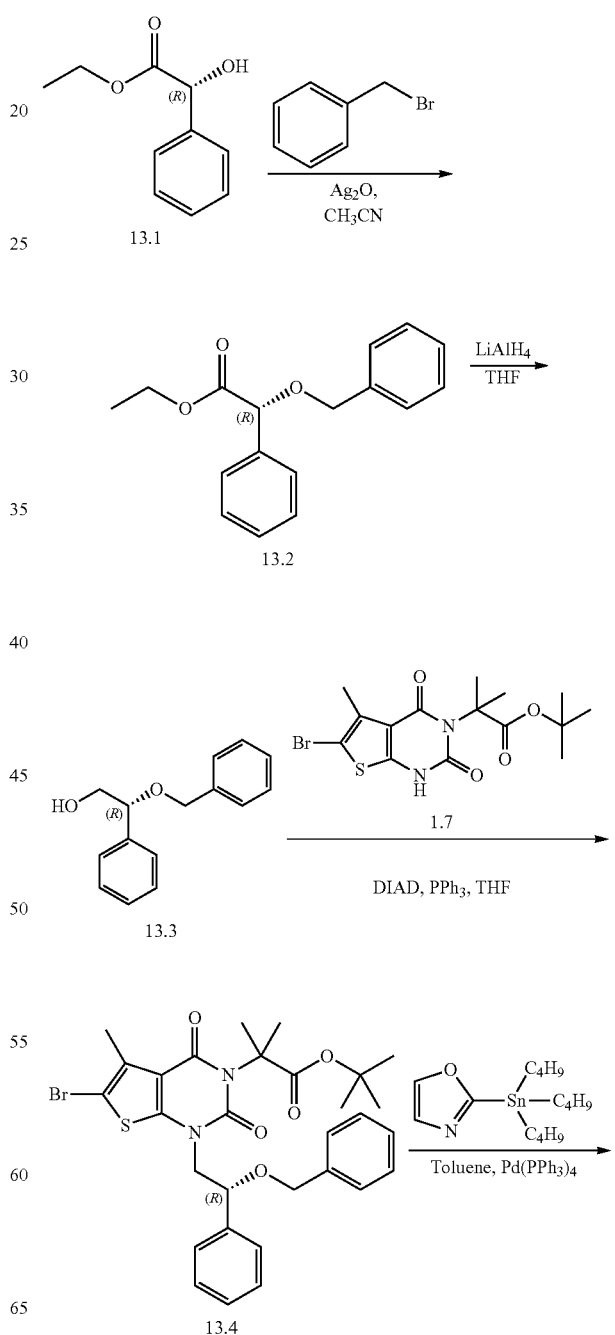

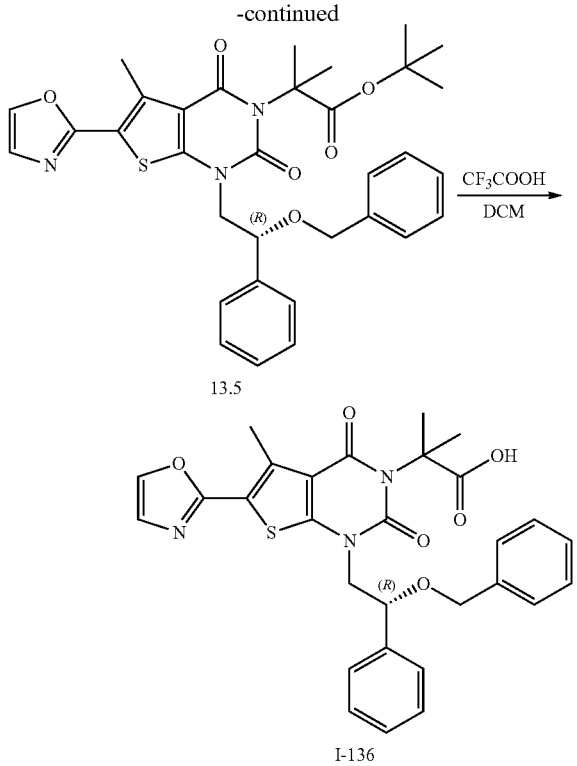

1H), 4.46 (d, J=12.9 Hz, 1H), 4.80 (t, J=6.0 Hz, 1H), 7.08 (d, J=2.1 Hz, 2H), 7.18 (t, J=3.0 Hz, 3H), 7.42 (m, 6H), 8.24 (d, J=0.6 Hz, 1H).

Example 14

Synthesis of 2-methyl-2-[5-methyl-6-(1,3-oxazol-2-yl)-2,4-dioxo-1-[2-phenyl-2-(2,2,2-trifluoroethoxy)ethyl]-1H,2H,3H,4H-thieno[2,3-d]pyrimidin-3-yl] propanoic acid (I-137) and Example 15: (S)-2-methyl-2-(5-methyl-6-(oxazol-2-yl)-2,4-dioxo-1-(2-phenyl-2-(2,2,2-trifluoroethoxy)ethyl)-1,2-dihydrothieno[2,3-d]pyrimidin-3(4H)-yl)propanoic acid (I-138)

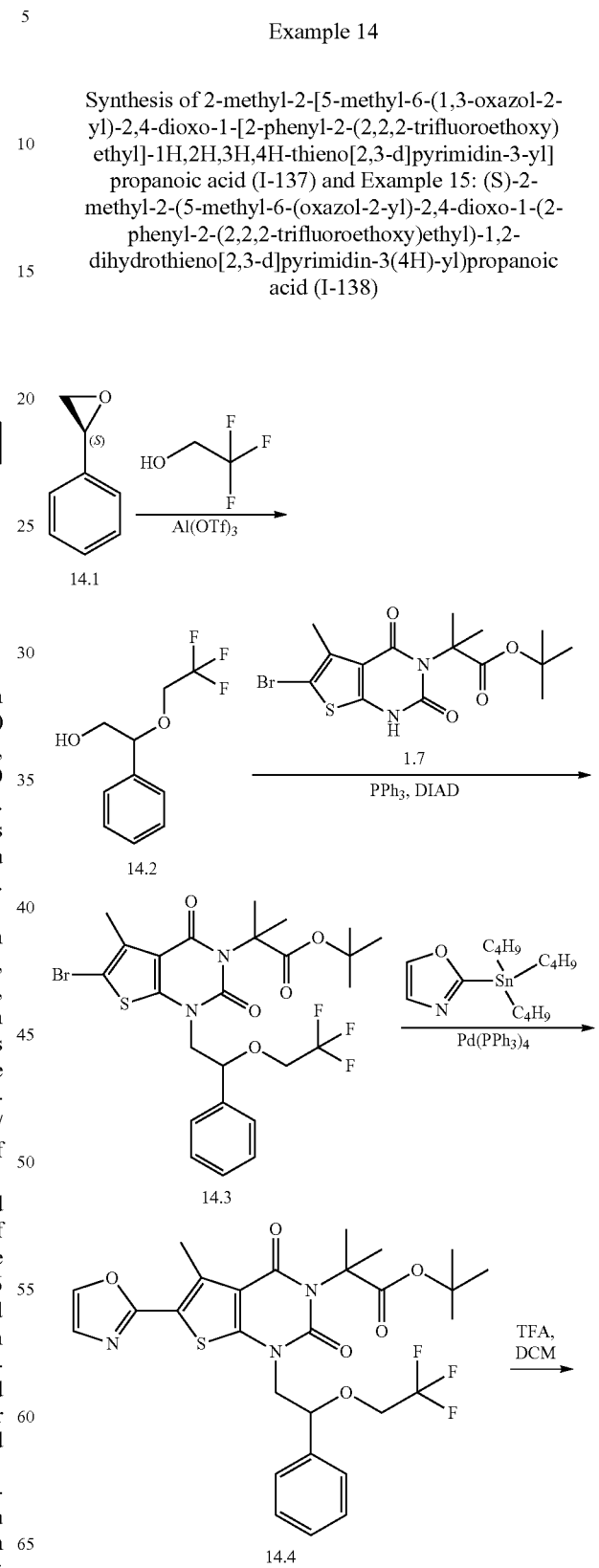

Synthesis of compound 13.2. Into a 500-mL round-bottom flask was placed a solution of 13.1 (5.2 g, 28.86 mmol, 1.00 equiv) in CH$_3$CN (250 mL), (bromomethyl)benzene (14.7 g, 85.95 mmol, 2.98 equiv), Ag$_2$O (10 g, 43.29 mmol, 1.50 equiv). The resulting solution was stirred overnight at 40° C. in an oil bath. The solids were filtered out. The filtrate was concentrated under vacuum. The residue was applied onto a silica gel column with ethyl acetate/petroleum ether (1:10). Purification 6.38 g (crude) of 13.2 as a yellow oil.

Synthesis of compound 13.3. Into a 500-mL round-bottom flask was placed tetrahydrofuran (200 mL) and 13.2 (6.38 g, 23.60 mmol, 1.00 equiv). Then LiAlH (898 mg, 23.66 mmol, 1.00 equiv) was added at 0° C., slowly. The resulting solution was stirred for 2 h at 0° C. in an ice/salt bath. The reaction was then quenched by the addition of 2 mL of NH$_4$Cl (aq.). The resulting mixture was concentrated under vacuum. The residue was applied onto a silica gel column with ethyl acetate/petroleum ether (1:5). Purification afforded 1.80 g (33%) of 13.3 as a yellow oil.

Synthesis of compound 13.4. Into a 100-mL 3-necked round-bottom flask maintained with an inert atmosphere of nitrogen was placed tetrahydrofuran (10 mL), intermediate 1.7 (175 mg, 0.43 mmol, 1.00 equiv), DIAD (133 mg, 0.66 mmol, 1.52 equiv), PPh$_3$ (173 mg, 0.66 mmol, 1.52 equiv) and 13.3 (150 mg, 0.66 mmol, 1.51 equiv). The resulting solution was stirred overnight at room temperature. The resulting mixture was concentrated under vacuum. The residue was applied onto a silica gel column with ethyl acetate/petroleum ether (1:10). Purification afforded 0.422 g (crude) of compound 13.4 as a yellow oil.

Synthesis of compound I-136. Compound I-136 was prepared from 13.4 and 2-(tributylstannyl)-1,3-oxazole in a manner analogous to Example 9. Isolated a white solid in 24% yield for the two steps. $^1$H NMR (DMSO-d$_6$, 300 MHz): δ 1.64 (s, 6H), 2.76 (s, 3H), 4.10 (m, 2H), 4.18 (d, J=12.9 Hz,

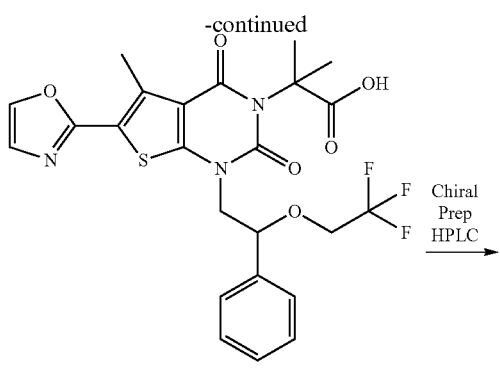

14.5

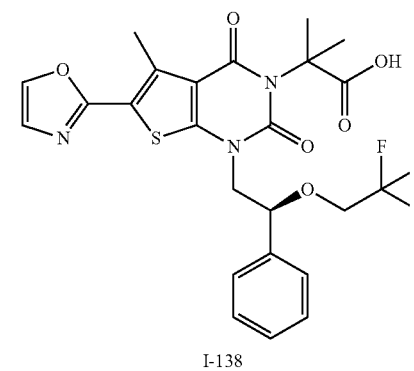

I-137

I-138

Synthesis of compound 14.2. Into a 25-mL round-bottom flask was placed (2S)-2-phenyloxirane (1 g, 8.32 mmol, 1.00 equiv), 2,2,2-trifluoroethan-1-ol (5 mL) and bis[(trifluoromethane)sulfonyloxy]alumanyl trifluoromethanesulfonate (197 mg, 0.42 mmol, 0.05 equiv). The resulting solution was stirred for 2 h at room temperature. The mixture was concentrated under vacuum. The residue was applied onto a silica gel column with ethyl acetate/petroleum ether (1:20). Purification afforded 410 mg (22%) of 2-phenyl-2-(2,2,2-trifluoroethoxy)ethan-1-ol as a colorless oil.

Synthesis of compound 14.3. Into a 25-mL round-bottom flask, purged and maintained with an inert atmosphere of nitrogen, was placed a solution of 1.7 (300 mg, 0.74 mmol, 1.00 equiv), PPh$_3$ (390 mg, 1.49 mmol, 2.00 equiv), 2-phenyl-2-(2,2,2-trifluoroethoxy)ethan-1-ol (310 mg, 1.41 mmol, 1.89 equiv), DIAD (300 mg, 1.48 mmol, 1.99 equiv) in tetrahydrofuran (10 mL). The solution was stirred overnight at room temperature. The resulting mixture was concentrated under vacuum. The residue was applied onto a silica gel column with ethyl acetate/petroleum ether (1:10). Purification afforded 260 mg (58%) of 14.3 as a white solid.

Synthesis of compound 14.4. Into a 50-mL round-bottom flask, purged and maintained with an inert atmosphere of nitrogen, was placed a solution of 14.3 (260 mg, 0.43 mmol, 1.00 equiv), Pd(PPh$_3$)$_4$ (74 mg, 0.06 mmol, 0.14 equiv) and 2-(tributylstannyl)-1,3-oxazole (231 mg, 0.65 mmol, 1.43 equiv) in toluene (10 mL). The solution was stirred overnight at 110° C. in an oil bath. The resulting mixture was concentrated under vacuum. The residue was applied onto a silica gel column with ethyl acetate/petroleum ether (1:10). Purification afforded 150 mg (59%) of 14.4 as a white solid.

Synthesis of compound 14.5. Into a 50-mL round-bottom flask was placed 14.4 (150 mg, 0.25 mmol, 1.00 equiv), dichloromethane (10 mL) and trifluoroacetic acid (2 mL). The resulting solution was stirred for 4 h at room temperature. The resulting mixture was concentrated under vacuum. The residue was applied onto a silica gel column with ethyl acetate/petroleum ether (1:1). Purification afforded 70 mg (52%) of 14.5 as a white solid.

Synthesis of Compounds I-137 and I-138. The enantiomers of the product of the previous step (64 mg) were purified by chiral preparative HPLC under the following conditions (Gilson Gx 281): column: Chiralpak IC, 2*25 cm, 5 μm; mobile phase: hexanes and ethanol (hold at 15.0% ethanol in 25 min); detector: 220/254 nm. 6.8 mg (off-white solid) of Compound I-137 and 20 mg (off-white solid) of Compound I-138 were obtained.

Analytical data for Compound I-137: MS (ES): m/z 538 (M+H)$^+$, 579 (M+CH$_3$CN)$^+$.

$^1$H NMR (400 MHz, CD$_3$OD): δ 1.82 (s, 6H), 2.82 (s, 3H), 3.84 (m, 2H), 4.09 (dd, J=10.8, 6.9, 1H), 4.23 (dd, J=11.1, 2.7, 1H), 5.05 (m, 1H), 7.29 (s, 1H), 7.38-7.50 (m, 5H), 7.99 (s, 1H).

Analytical data for Compound I-138: MS (ES): m/z 538 (M+H)$^+$, 560 (M+Na)$^+$.

$^1$H NMR (400 MHz, CD$_3$OD): δ 1.82 (s, 6H), 2.82 (s, 3H), 3.84 (m, 2H), 4.09 (dd, J=10.8, 6.9, 1H), 4.23 (dd, J=11.1, 2.7, 1H), 5.05 (m, 1H), 7.29 (s, 1H), 7.38-7.50 (m, 5H), 7.99 (s, 1H).

Example 16

Synthesis of 2-[1-[(2R)-2-(cyclohexyloxy)-2-phenylethyl]-5-methyl-6-(1,3-oxazol-2-yl)-2,4-dioxo-1H,2H,3H,4H-thieno[2,3-d]pyrimidin-3-yl]-2-methylpropanoic acid (I-140)

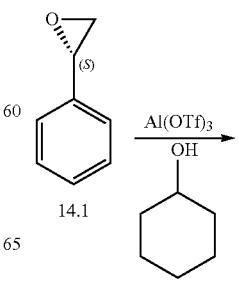

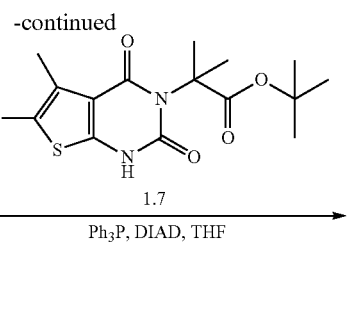
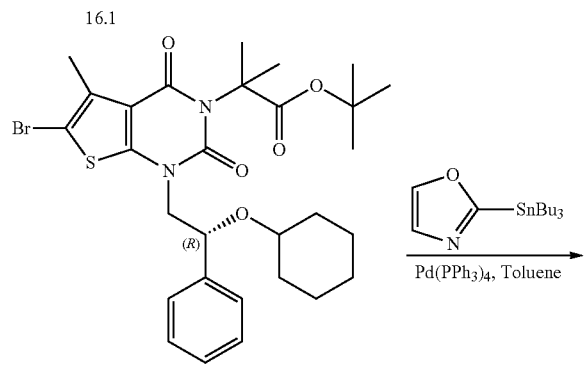
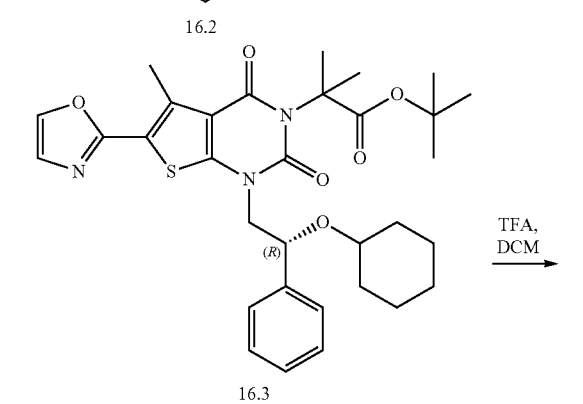
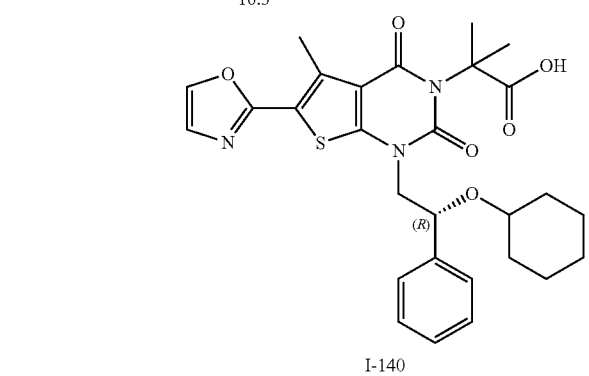

petroleum ether (1:50). This resulted in 1 g (45%) of (2R)-2-(cyclohexyloxy)-2-phenylethan-1-ol as a yellow solid.

Synthesis of compound I-140. Compound I-140 was prepared, in a manner analogous to 14.5, from 16.1 and 1.7. Isolated a white semi-solid in 16% yield from 1.7. MS: (ES): m/z 538 (M+H)$^+$, 579 (M+CH$_3$CN)$^+$. $^1$H NMR (400 MHz, CD$_3$OD): δ 1.17-1.61 (m, 10H), 1.84 (d, J=6.8, 6H), 2.86 (s, 3H), 3.21-3.29 (m, 1H), 3.80-3.88 (m, 1H), 4.22-4.27 (m, 1H), 4.97-5.00 (m, 1H), 7.30 (s, 1H), 7.33-7.50 (m, 5H), 8.00 (s, 1H).

Example 17

Synthesis of 2-methyl-2-[5-methyl-6-(1,3-oxazol-2-yl)-2,4-dioxo-1-[(2S)-2-phenoxy-2-phenylethyl]-1H,2H,3H,4H-thieno[2,3-d]pyrimidin-3-yl]propanoic acid (I-143) and Example 18: Synthesis of 2-methyl-2-[5-methyl-6-(1,3-oxazol-2-yl)-2,4-dioxo-1-[(2S)-2-phenoxy-2-phenylethyl]-1H,2H,3H,4H-thieno[2,3-d]pyrimidin-3-yl]propanoic acid (I-144)

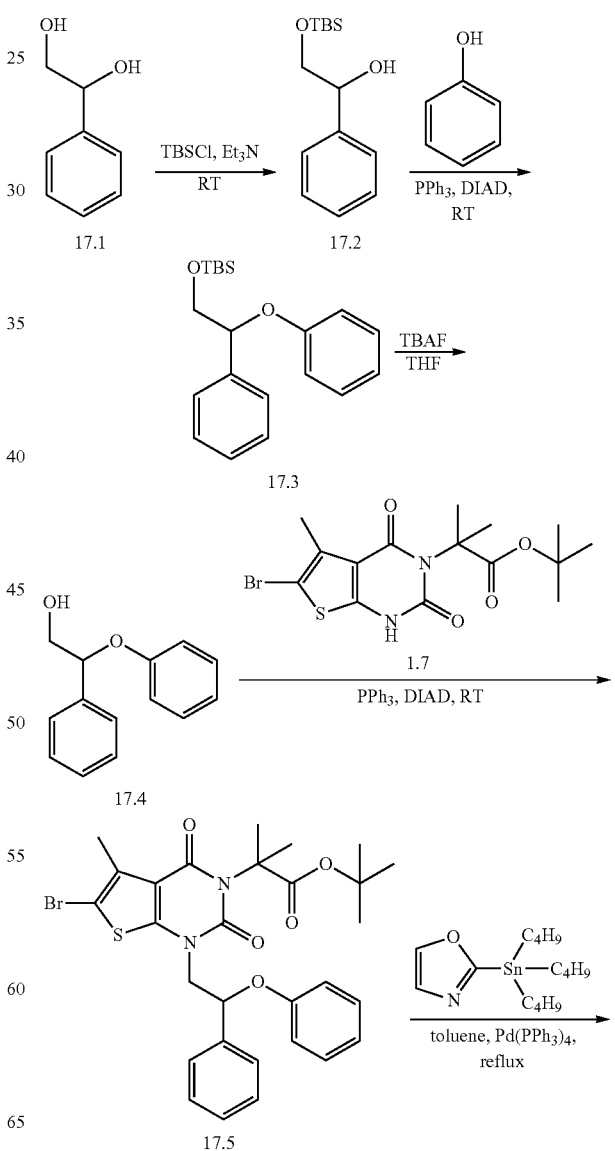

Synthesis of compound 16.1. Into a 50-mL round-bottom flask, was placed Al(OTf)$_3$ (237 mg, 0.50 mmol, 0.05 equiv), cyclohexanol (7 mL). This was followed by the addition of (2S)-2-phenyloxirane (1.2 g, 9.99 mmol, 1.00 equiv) dropwise with stirring. The resulting solution was stirred for 3 h at room temperature. The reaction was then quenched by the addition of 20 mL of water. The resulting solution was extracted with 3×50 mL of ethyl acetate and the organic layers combined. The resulting mixture was washed with water. The resulting mixture was concentrated under vacuum. The residue was applied onto a silica gel column with ethyl acetate/

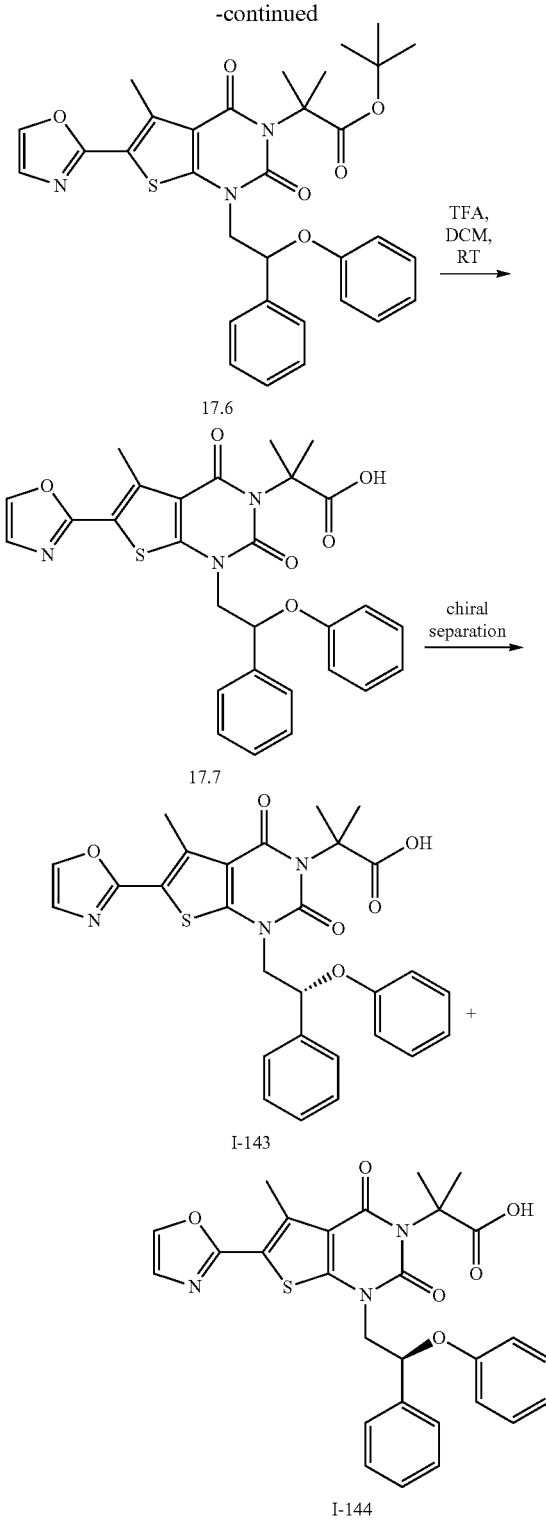

Synthesis of compound 17.2. Into a 250-mL 3-necked round-bottom flask was placed a solution of 1-phenylethane-1,2-diol (10 g, 72.38 mmol, 1.00 equiv), TBSCl (22 g, 145.97 mmol, 2.00 equiv) and triethylamine (14.7 g, 145.27 mmol, 2.00 equiv) in tetrahydrofuran (100 mL). The solution was stirred overnight at room temperature. The next day it was diluted with 150 mL of H$_2$O and the mixture was extracted with 3×80 mL of ethyl acetate. The organic layers were combined, dried over anhydrous sodium sulfate and concentrated under vacuum. The residue was applied onto a silica gel column with ethyl acetate/petroleum ether (1/10). Purification afforded 17 g (93%) of 2-[(tert-butyldimethylsilyl)oxy]-1-phenylethan-1-ol as a white oil.

Synthesis of compound 17.3. Into a 100-mL round-bottom flask, purged and maintained with an inert atmosphere of nitrogen, was placed 17.2 (20 mg, 0.08 mmol, 1.00 equiv), phenol (15 mg, 0.16 mmol, 2.00 equiv), tetrahydrofuran (3 mL), DIAD (32 mg, 0.16 mmol, 2.00 equiv) and PPh$_3$ (41 mg, 0.16 mmol, 2.00 equiv). The resulting solution was stirred for 2 h at room temperature. The resulting mixture was concentrated under vacuum. The residue was applied onto a silica gel column with ethyl acetate/petroleum ether (1:10). This resulted in 15 mg (58%) of tert-butyldimethyl(2-phenoxy-2-phenylethoxy)silane as a white solid.

Synthesis of compound 17.4. Into a 50-mL round-bottom flask, was placed a solution of 17.3 (1.16 g, 3.53 mmol, 1.00 equiv) in tetrahydrofuran (10 mL). Then TBAF (1.8 g, 6.88 mmol, 2.00 equiv) was added at 0° C. The resulting solution was stirred overnight at room temperature. The reaction was then quenched by the addition of 30 mL of water. The resulting solution was extracted with 3×20 mL of ethyl acetate and the organic layers were combined, dried and concentrated under vacuum. The residue was applied onto a silica gel column with PE/EA (10/1). Purification afforded 480 mg (63%) of 17.4 as a white solid.

Synthesis of compound 17.7. Compound 17.7 was prepared, in a manner analogous with 14.5, from 17.4 and 1.7. Isolated the crude product in 32% yield for the three steps.

Synthesis of Compounds I-143 and I-144. The crude product (110 mg) was purified by chiral preparative HPLC under the following conditions (Gilson Gx 281): column: Chiralpak IC, 2*25 cm, 5 μm; mobile phase: hexanes (0.1% TFA) and ethanol (hold at 15.0% ethanol over 5 min); detector: UV 220/254 nm. This purification afforded 6.6 mg (9%) of Compound I-143 as a white solid and 15.9 mg (21%) of Compound I-144 as a white solid.

Analytical data for Compound I-143: MS (ES): m/z 532 (M+H)$^+$. $^1$H NMR (CD$_3$OD, 400 MHz): 1.79 (s, 6H), 2.71 (s, 3H), 4.22 (m, 1H), 4.39 (d, 2H), 5.71 (m, 1H), 6.83 (m, 3H), 7.12 (t, 2H), 7.31 (m, 2H), 7.38 (t, 2H), 7.51 (d, 2H), 8.01 (s, 1H).

Analytical data for Compound I-144: MS (ES): m/z 532 (M+H)$^+$. $^1$H NMR (CD$_3$OD, 400 MHz): 1.79 (s, 6H), 2.71 (s, 3H), 4.22 (m, 1H), 4.39 (d, 1H), 5.71 (m, 1H), 6.83 (m, 3H), 7.12 (t, 2H), 7.31 (m, 2H), 7.38 (t, 2H), 7.51 (d, 2H), 8.01 (s, 1H).

Example 19

Synthesis of (R)-2-methyl-2-(5-methyl-6-(oxazol-2-yl)-2,4-dioxo-1-(2-((4-oxocyclohexyl)oxy)-2-phenylethyl)-1,2-dihydrothieno[2,3-d]pyrimidin-3(4H)-yl)propanoic acid (I-145)

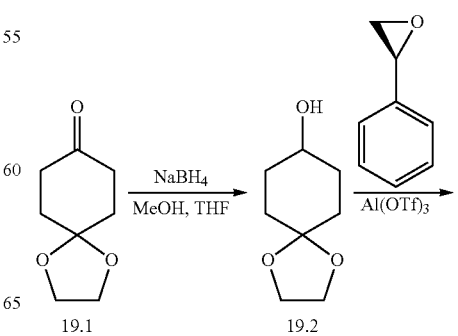

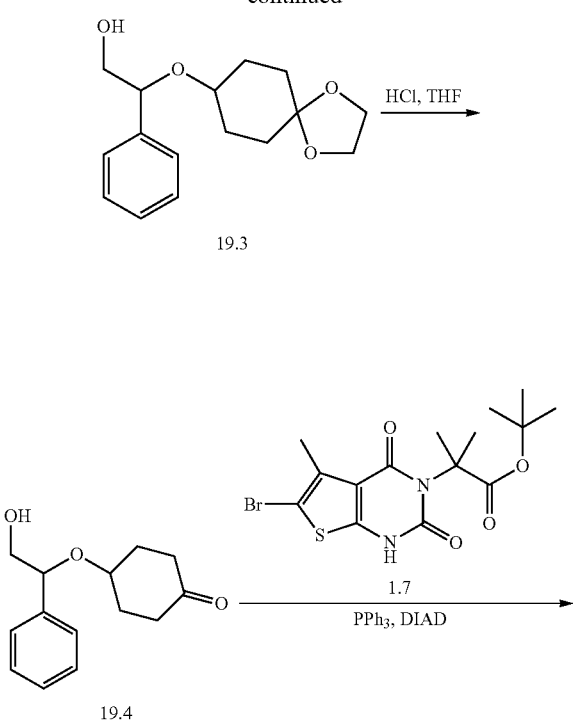

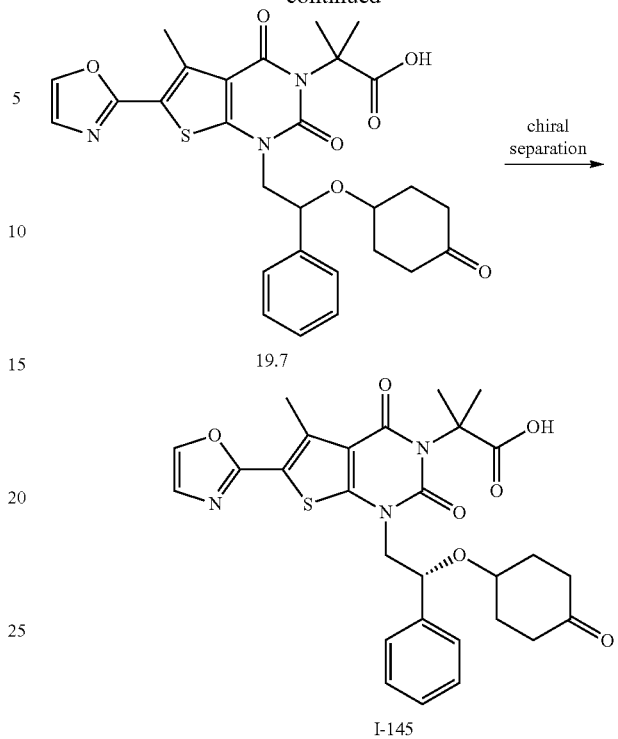

Synthesis of compound 19.2. Into a 500-mL 3-necked round-bottom flask was placed 1,4-dioxaspiro[4.5]decan-8-one (20 g, 128.06 mmol, 1.00 equiv), methanol (250 mL) and NaBH$_4$ (7.3 g, 198.23 mmol, 1.55 equiv). The resulting solution was stirred for 2 h at room temperature. The reaction was then quenched by the addition of 150 mL of NH$_4$Cl (sat., aq.). The resulting solution was extracted with 2×300 mL of ethyl acetate and the organic layers combined and dried over anhydrous sodium sulfate and concentrated under vacuum. The residue was applied onto a silica gel column with ethyl acetate/petroleum ether (1:10). Purification afforded 19.6 g (97%) of 1,4-dioxaspiro[4.5]decan-8-ol as a colorless oil.

Synthesis of compound 19.3. Into a 50-mL round-bottom flask, was placed 1,4-dioxaspiro[4.5]decan-8-ol (10 g, 63.21 mmol, 3.80 equiv), (2S)-2-phenyloxirane (2 g, 16.65 mmol, 1.00 equiv) and Al(OTf)$_3$ (197 mg, 0.42 mmol, 0.02 equiv). The resulting solution was stirred for 2 h at room temperature. The resulting mixture was concentrated under vacuum. The residue was applied onto a silica gel column with ethyl acetate/petroleum ether (1:10). Purification afforded 2.7 g (crude) of 19.3 as a colorless oil.

Synthesis of compound 19.4. Into a 50-mL round-bottom flask was placed 19.3 (2.7 g, 9.70 mmol, 1.00 equiv), tetrahydrofuran (15 mL) and hydrogen chloride (18%) (15 mL). The resulting solution was stirred overnight at 70° C. The reaction was then quenched by the addition of 30 mL of sodium carbonate (aq.). The resulting solution was extracted with 2×50 mL of ethyl acetate and the organic layers combined and dried over anhydrous sodium sulfate and concentrated under vacuum. The residue was applied onto a silica gel column with ethyl acetate/petroleum ether (1:5). Purification afforded 1.6 g (70%) of 19.4 as a colorless oil.

Synthesis of compound 19.7. Compound 19.7 was prepared, in a manner analogous to 14.5, from 19.4 and 1.7. Isolated a light yellow solid in 21% yield for the three steps.

Synthesis of Compound I-145. The crude product (58 mg) was purified by chiral preparative HPLC under the following conditions (Gilson Gx 281): column: Chiralpak IC, 2*25 cm, 5 μm; mobile phase: hexanes and ethanol (hold at 25.0% ethanol for 25 min); detector: UV 220/254 nm. 20.1 mg of a white solid product were obtained. MS (ES): m/z 552 (M+H)+.

$^1$H NMR (300 MHz, CD$_3$OD): δ 1.25 (m, 1H), 1.55 (m, 7H), 1.82 (s, 3H), 1.85 (s, 3H), 2.83 (s, 3H), 3.33 (m, 1H), 3.78 (m, 1H), 4.29 (m, 1H), 4.92 (m, 1H), 7.29 (s, 1H), 7.33-7.51 (m, 5H), 7.99 (s, 1H).

Example 20

Synthesis of 2-methyl-2-[5-methyl-6-(1,3-oxazol-2-yl)-2,4-dioxo-1-[(2R)-2-(oxolan-2-ylmethoxy)-2-phenylethyl]-1H,2H,3H,4H-thieno[2,3-d]pyrimidin-3-yl]propanoic acid (I-146)

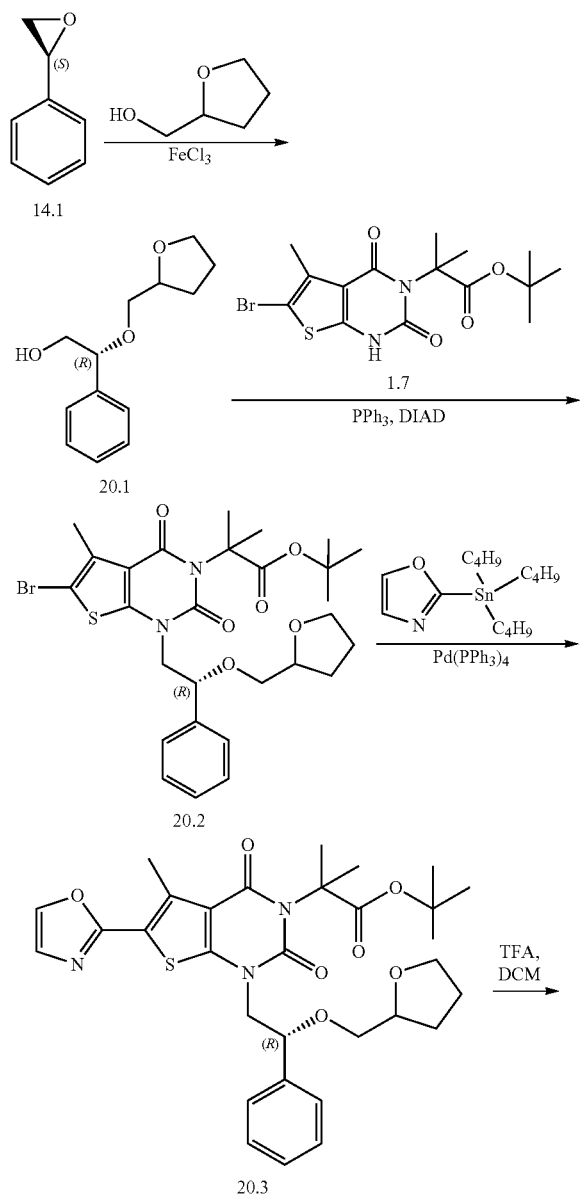

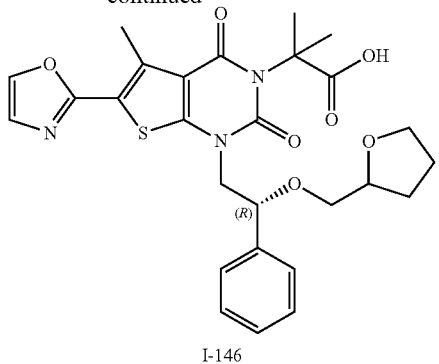

I-146

Synthesis of compound 20.1. Into a 50-mL round-bottom flask, purged and maintained with an inert atmosphere of nitrogen, was placed (2R)-2-phenyloxirane (1 g, 8.32 mmol, 1.00 equiv), oxolan-2-ylmethanol (5 mL) and FeCl$_3$ (68 mg, 0.42 mmol, 0.05 equiv). The resulting solution was stirred overnight at room temperature. The reaction was then quenched by the addition of 20 mL of water. The resulting solution was extracted with 3×10 mL of ethyl acetate, and the organic layers were combined and concentrated under vacuum. The residue was applied onto a silica gel column with ethyl acetate/petroleum ether (1/10). Purification afforded 360 mg (19%) of 20.1 as a white oil.

Synthesis of Compound I-146. Compound I-146 was prepared, in a manner analogous to 14.5, from 20.1 and 1.7. MS (ES): m/z 562 (M+Na)+. $^1$H NMR (CD$_3$OD, 300 MHz): δ 7.99 (s, 1H), 7.48-7.29 (m, 6H), 4.93-4.92 (m, 1H), 4.25-4.19 (m, 1H), 3.99-3.85 (m, 2H), 3.70-3.61 (m, 2H), 3.59-3.41 (m, 1H), 3.32-3.13 (m, 1H), 2.81 (s, 3H), 1.85 (s, 6H), 1.82-1.70 (m, 3H), 1.68-1.47 (m, 1H).

Example 21

Synthesis of 2-methyl-2-[5-methyl-6-(1,3-oxazol-2-yl)-2,4-dioxo-1-[2-(2-propylphenyl)ethyl]-1H,2H,3H,4H-thieno[2,3-d]pyrimidin-3-yl]propanoic acid (I-147)

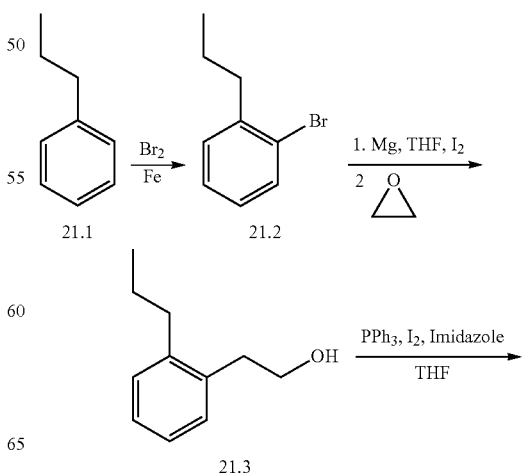

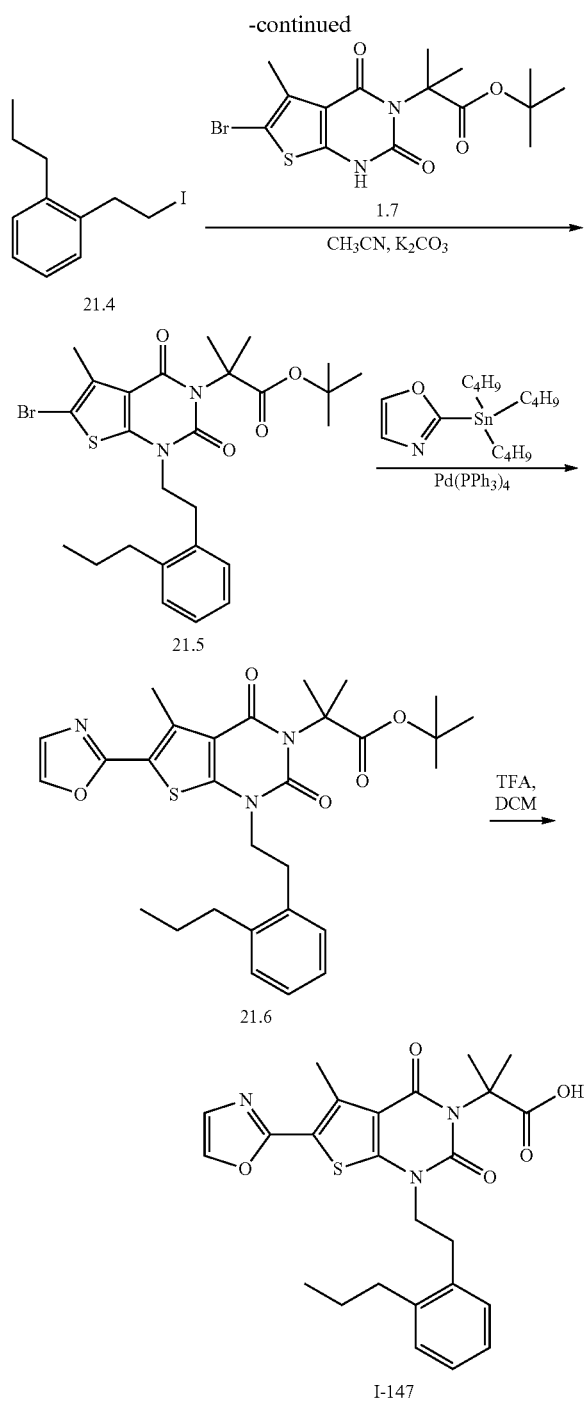

Synthesis of compound 21.3. Into a 250-mL 3-necked round-bottom flask, maintained with a nitrogen atmosphere, was placed $I_2$ (10 mg, 0.04 mmol) and Mg (500 mg, 20.83 mmol, 2.07 equiv). Then 1-bromo-2-propylbenzene (2.0 g, 10.05 mmol, 1.00 equiv) dissolved in tetrahydrofuran (50 mL) was added dropwise into the flask and the mixture was heated to reflux. After the reaction was complete the resulting mixture was cooled to 0° C. and then oxirane (50 mL) was added in one portion. The resulting solution was stirred overnight at room temperature. The reaction was then quenched by the addition of 5 mL of $NH_4Cl$ (aq.). The solids were filtered out. The filtrate was concentrated under vacuum. The residue was applied onto a silica gel column with ethyl acetate/petroleum ether (1:5). Purification afforded 0.24 g (15%) of 2-(2-propylphenyl)ethan-1-ol as a colorless oil.

Synthesis of compound 21.4. Into a 50-mL round-bottom flask was placed 2-(2-propylphenyl)ethan-1-ol (240 mg, 1.46 mmol, 1.00 equiv), $PPh_3$ (498 mg, 1.90 mmol, 1.30 equiv), $I_2$ (446 mg), imidazole (129 mg) and dichloromethane (20 mL). The resulting solution was stirred for 16 h at 30° C. The reaction was then quenched by the addition of 100 mL of $NaHSO_3$ (aq.). The resulting solution was extracted with 2×50 mL of dichloromethane and the organic layers combined and concentrated under vacuum. The residue was applied onto a silica gel column with ethyl acetate/petroleum ether (1:100). Purification afforded 200 mg (50%) of 1-(2-iodoethyl)-2-propylbenzene as a colorless oil.

Synthesis of compound I-147. Compound I-147 was prepared from 21.4 and 1.7 in a manner analogous to Example 9. Isolated a white solid in 45% yield for the three steps. MS (ES): m/z 538 (M+H)$^+$. $^1$H NMR (CD$_3$OD, 300 MHz): 1.30 (t, 3H), 1.70-1.80 (m, 2H), 1.95 (s, 6H), 2.74 (t, 2H), 2.8 (s, 3H), 3.13 (t, 2H), 4.13 (t, 2H), 7.10-7.15 (m, 4H), 7.28 (s, 1H), 7.97 (s, 1H).

Example 22

Synthesis of 2-methyl-2-[5-methyl-6-(1,3-oxazol-2-yl)-2,4-dioxo-1-[2-(2-propylphenyl)ethyl]-1H,2H,3H,4H-thieno[2,3-d]pyrimidin-3-yl]propanamide (I-151)

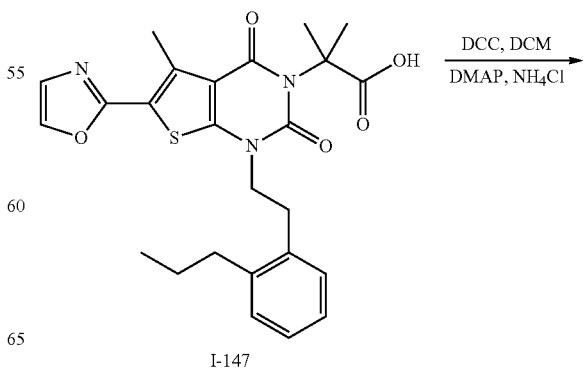

I-147

Synthesis of compound 21.2. Into a 250-mL round-bottom flask was placed propylbenzene (20 g, 166.40 mmol, 1.00 equiv) and Fe (10 g, 178.57 mmol, 1.07 equiv). This was followed by the addition of $Br_2$ (26.6 g, 166.45 mmol, 1.00 equiv) dropwise with stirring. The resulting solution was stirred overnight at room temperature. The reaction was then quenched by the addition of 100 mL of $NaHSO_3$ (aq.). The mixture was extracted with 3×100 mL of ethyl acetate and the organic layers combined and dried over anhydrous sodium sulfate and concentrated under vacuum. Purification afforded 29.4 g (crude) of 1-bromo-2-propylbenzene as a yellow oil.

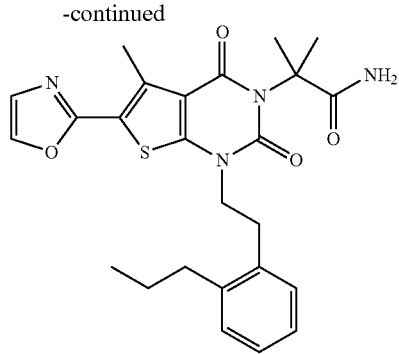

I-151

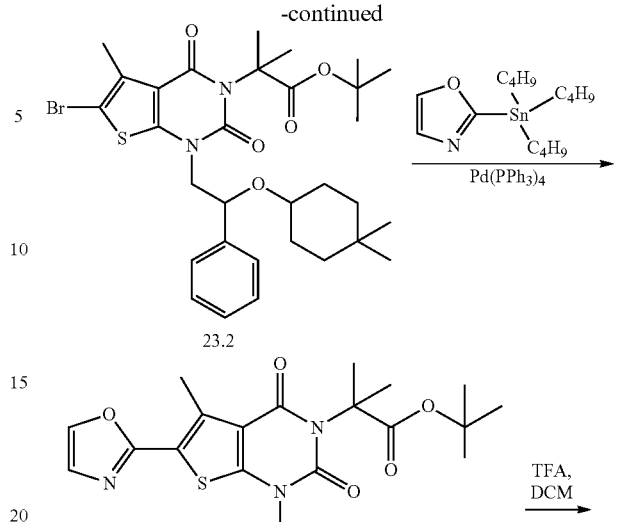

23.2

Compound I-151 was prepared in a manner analogous to Compound I-121 (Example 4). Isolated a white solid in 11% yield. MS (ES): m/z 464 (M−NH$_2$)$^+$. $^1$H(CD$_3$OD, 400 MHz): 1.05 (t, 3H), 1.65 (m, 2H), 1.83 (s, 6H), 2.74 (t, 2H), 2.81 (s, 3H), 3.11 (t, 3H), 4.11 (t, 2H), 7.19 (ArH, 4H), 7.28 (s, 1H), 7.98 (s, 1H).

Example 23

Synthesis of 2-[1-[(2R)-2-[(4,4-dimethylcyclohexyl)oxy]-2-phenylethyl]-5-methyl-6-(1,3-oxazol-2-yl)-2,4-dioxo-1H,2H,3H,4H-thieno[2,3-d]pyrimidin-3-yl]-2-methylpropanoic acid (I-148)

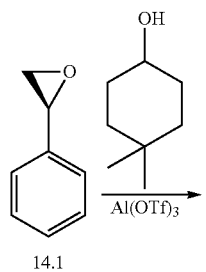

14.1

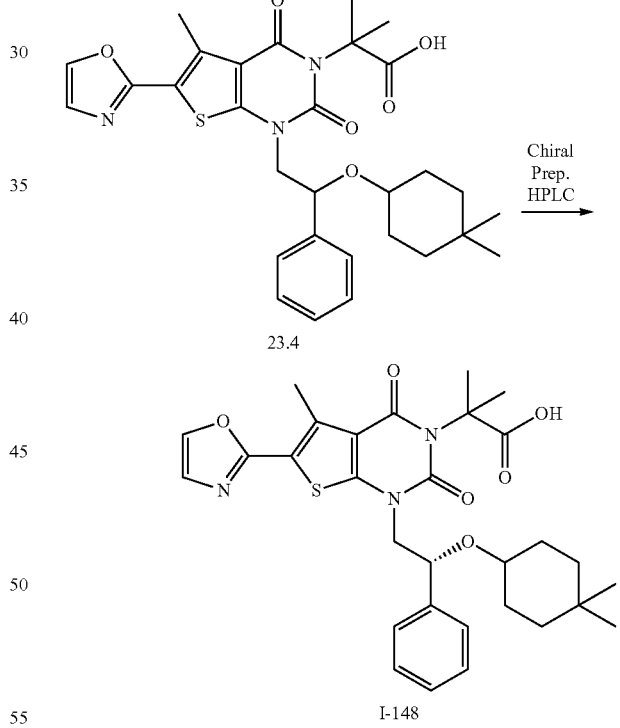

I-148

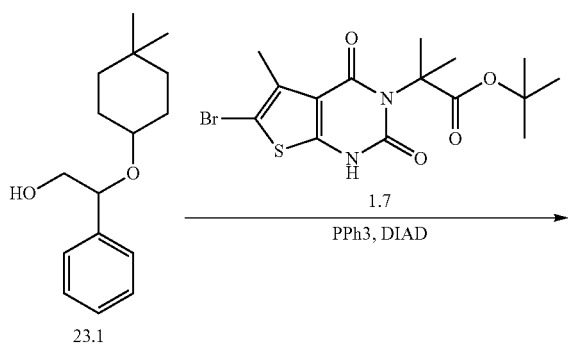

23.1

Synthesis of compound 23.4 Compound 23.4 was prepared in a manner analogous to compound 14.5, substituting 4,4-dimethylcyclohexanol for 2,2,2-trifluoroethan-1-ol. Isolated a white solid in 34% yield from 1.7.

Purification of Compound I-148. Crude 23.4 was purified by chiral preparative HPLC under the following conditions (Gilson Gx 281): column: Chiralpak IC, 2*25 cm, 5 μm; mobile phase: hexanes (0.1% TFA) and ethanol (0.1% TFA) (hold at 5.0% ethanol (0.1% TFA) for 8 min); detector: UV 220/254 nm. Purification afforded 73 mg (36.5%) of Compound I-148 as a white solid. MS (ES): m/z 566 (M+H)$^+$. $^1$H NMR (CD₃OD, 400 MHz): 0.62 (s, 3H), 0.83 (s, 3H), 1.02 (m, 3H), 1.24 (m, 1H), 1.51 (m, 4H), 1.81 (d, 6H), 2.82 (s, 3H), 3.31 (s, 1H), 3.75 (m, 1H), 4.31 (d, 1H), 4.96 (d, 1H), 7.31 (s, 1H), 7.41 (m, 3H), 7.55 (d, 2H), 8.01 (s, 1H).

Example 24

Synthesis of (R)-2-(1-(2-(4-fluorophenoxy)-2-phenylethyl)-5-methyl-6-(oxazol-2-yl)-2,4-dioxo-1,2-dihydrothieno[2,3-d]pyrimidin-3(4H)-yl)-2-methylpropanoic acid (I-149) and Example 25: Synthesis of (S)-2-(1-(2-(4-fluorophenoxy)-2-phenylethyl)-5-methyl-6-(oxazol-2-yl)-2,4-dioxo-1,2-dihydrothieno[2,3-d]pyrimidin-3(4H)-yl)-2-methylpropanoic acid (I-150)

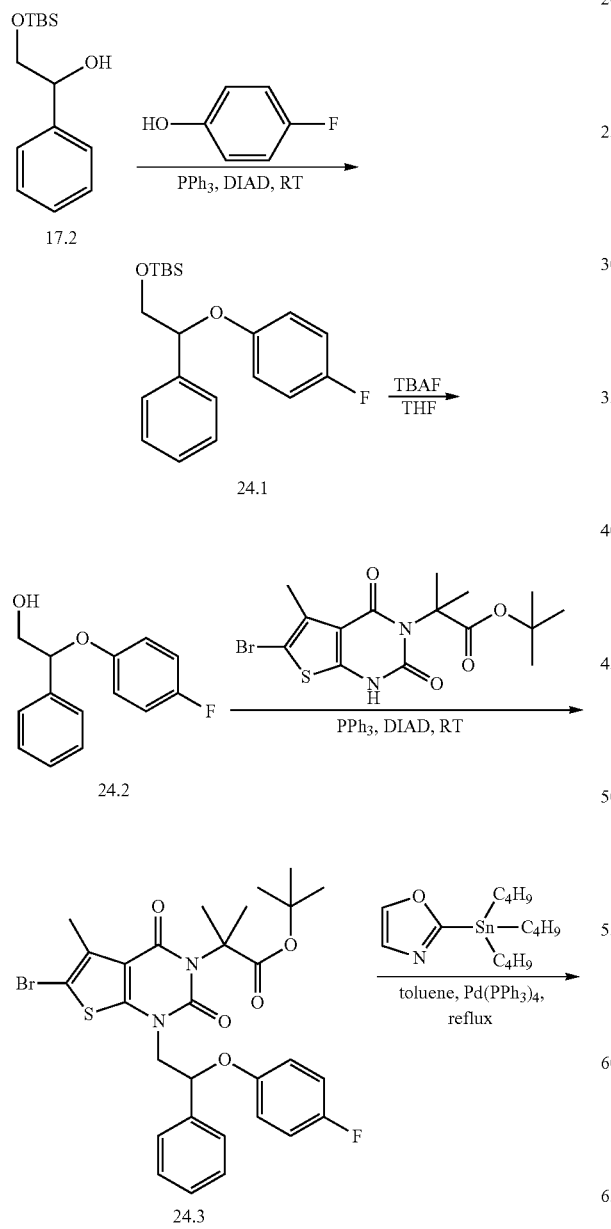

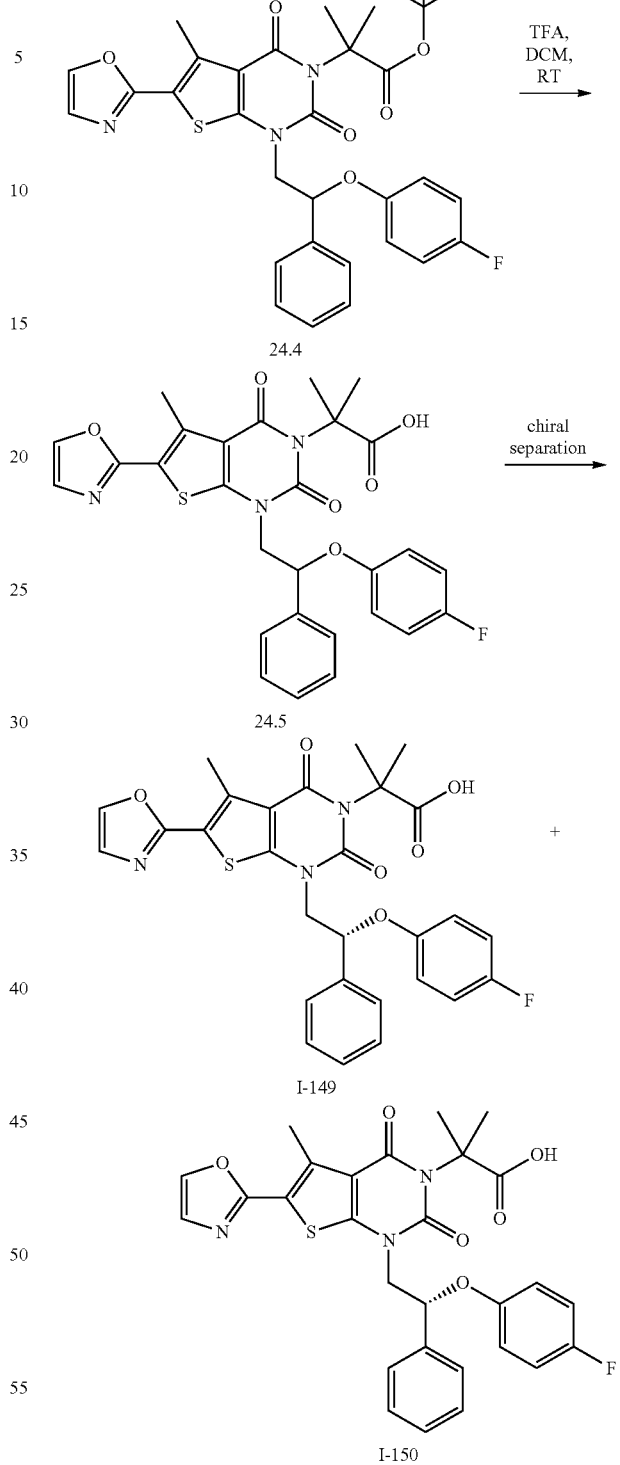

Synthesis of compound 24.2. 2-(4-fluorophenoxy)-2-phenylethan-1-ol (24.2) was prepared in a manner analogous to compound 17.4, substituting 4-fluorophenol for phenol. Isolated a colorless oil in ca. 31% yield (crude).

Synthesis of compound 24.5. 24.5 was prepared in a manner analogous to compound 14.5. Isolated a white solid in 28% yield from 1.7.

Purification of Compound I-149 and Compound I-150. The enantiomers of 24.5 (140 mg) were separated by chiral preparative HPLC under the following conditions (Gilson Gx 281): Column: Chiralpak IC, 2*25 cm, 5 μm; mobile phase: hexanes (0.1% TFA) and ethanol (hold at 15.0% ethanol for 30 min; detector: UV 220/254 nm. 48.1 mg of a white solid product were obtained.

Analytical data for Compound I-149: MS (ES): m/z 550 (M+H)$^+$, 591 (M+CH$_3$CN)$^+$.

$^1$H NMR (300 MHz, CD$_3$OD): 1.79 (s, 6H), 278 (s, 3H), 4.20 (dd, J=14.7, 8.7, 1H), 4.36 (dd, J=14.7, 3.9, 1H), 5.65 (m, 1H), 6.77-6.89 (m, 4H), 7.29-7.53 (m, 6H), 7.99 (s, 1H).

Analytical Data for Compound I-150: MS (ES): m/z 550 (M+H)$^+$, 591 (M+CH$_3$CN)$^+$.

$^1$H NMR (300 MHz, CD$_3$OD): δ 1.79 (s, 6H), 28 (s, 3H), 4.20 (dd, J=14.7, 8.7, 1H), 4.36 (dd, J=14.7, 3.9, 1H), 5.65 (m, 1H), 6.77-6.89 (m, 4H), 7.29-7.53 (m, 6H), 7.99 (s, 1H).

Example 26

Synthesis of 2-methyl-2-[5-methyl-1-[(2R)-2-[[(1S,2S)-2-methylcyclohexyl]oxy]-2-phenylethyl]-6-(1,3-oxazol-2-yl)-2,4-dioxo-1H,2H,3H,4H-thieno[2,3-d]pyrimidin-3-yl]propanoic acid (I-152)

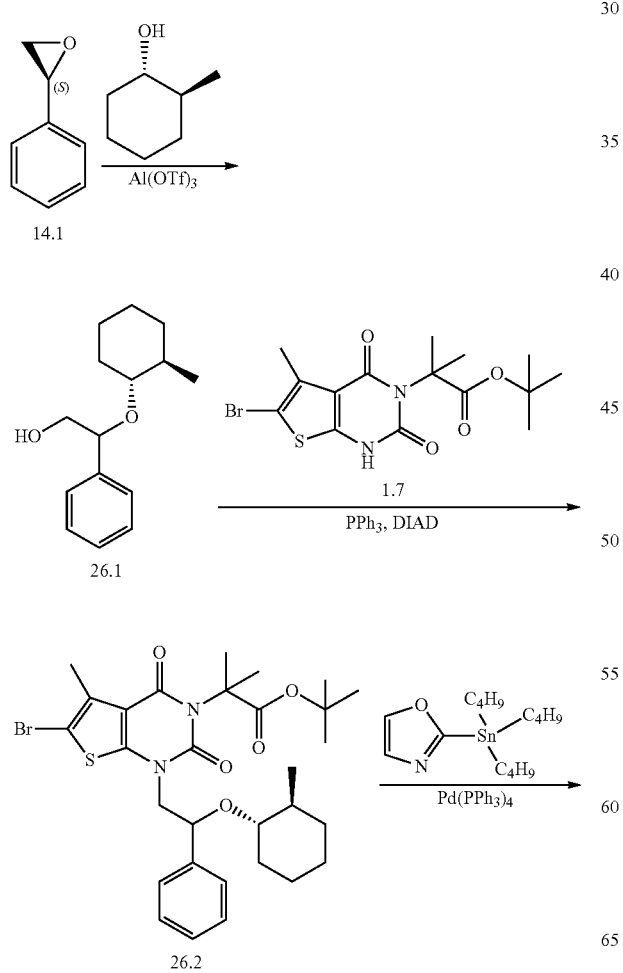

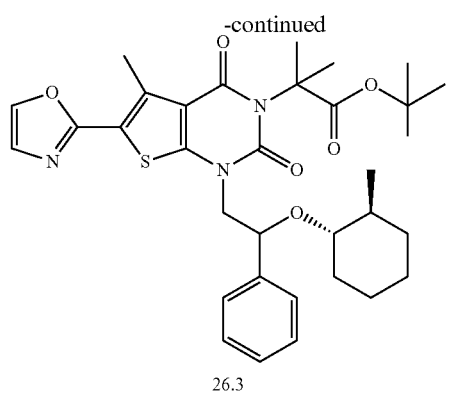

26.3

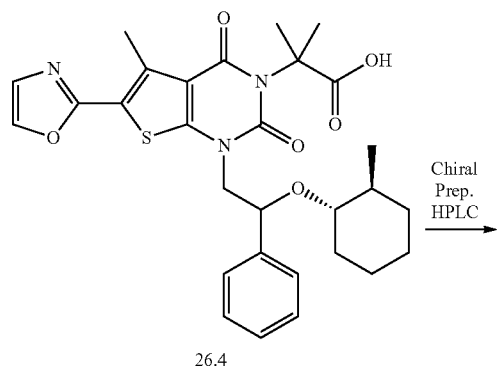

26.4

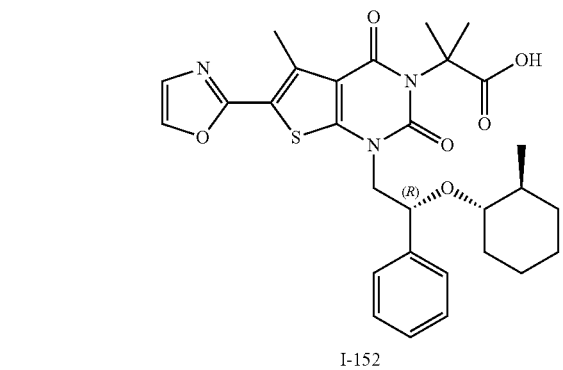

I-152

Synthesis of compound 26.1. 26.1 was prepared in a manner analogous to 14.2, substituting methylcyclohexan-1-ol for 2,2,2-trifluoroethan-1-ol. Isolated a colorless oil in 18% yield.

Synthesis of compound 26.4. 26.4 was prepared in a manner analogous to 14.5. Isolated a white solid in ca. 34% yield from 1.7.

Purification of Compound I-152. The enantiomers of 26.4 (110 mg) were separated by chiral preparative HPLC under the following conditions (Gilson Gx 281): Column: Chiralpak IC, 2*25 cm, 5 μm; mobile phase: hexanes (0.2% TEA) and ethanol (0.2% TEA) (hold at 2.0% ethanol (0.2% TEA) for 20 min); detector: UV 220/254 nm. Purification afforded 58.7 mg (53%) of Compound I-152 as a white solid. MS (ES): m/z 552 (M+H)$^+$, 615 (M+Na+CH$_3$CN)$^+$. $^1$H NMR (300 MHz, CD$_3$OD): δ 0.76 (d, J=6.3, 2H), 0.86 (d, J=6.6 2H), 1.07

(m, 2H), 1.50 (m, 5H), 1.81 (s, 6H), 2.00 (d, J=14.1, 1H), 2.80 (m, 4H), 3.91 (m, 1H), 4.17 (m, 1H), 5.09 (m, 1H), 7.29-7.49 (m, 6H), 8.00 (s, 1H).

Example 27

Synthesis of 2-[1-[(2R)-2-[(4,4-difluorocyclohexyl)oxy]-2-phenylethyl]-5-methyl-6-(1,3-oxazol-2-yl)-2,4-dioxo-1H,2H,3H,4H-thieno[2,3-d]pyrimidin-3-yl]-2-methylpropanoic acid (I-155)

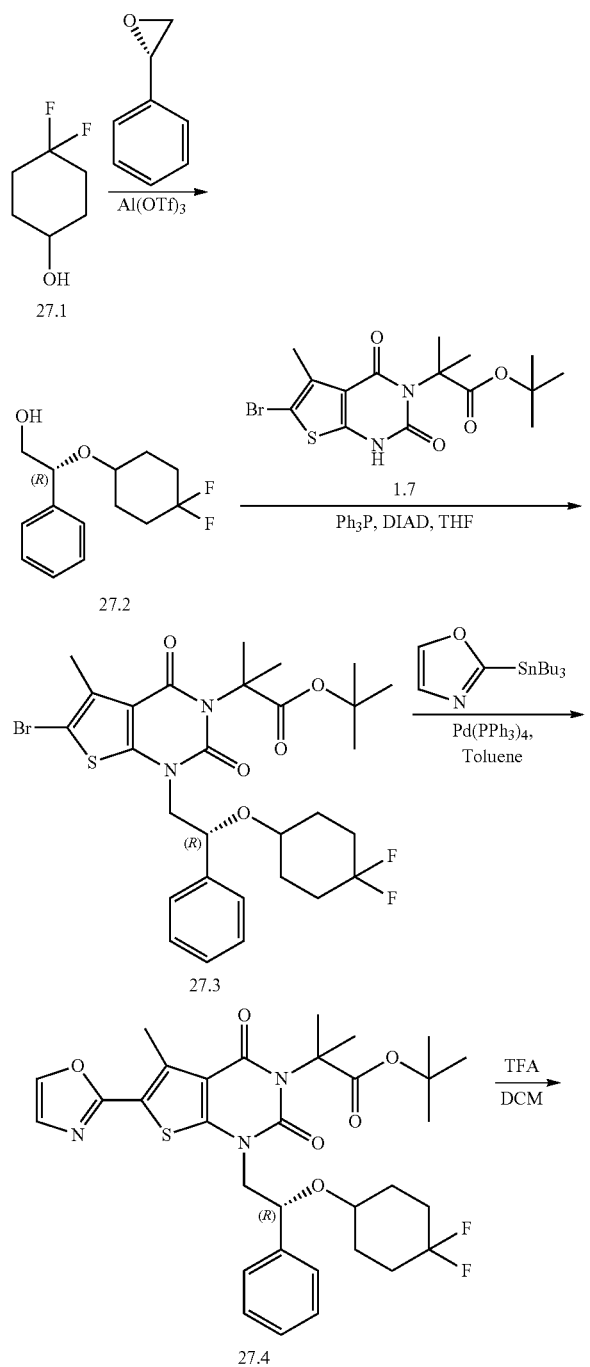

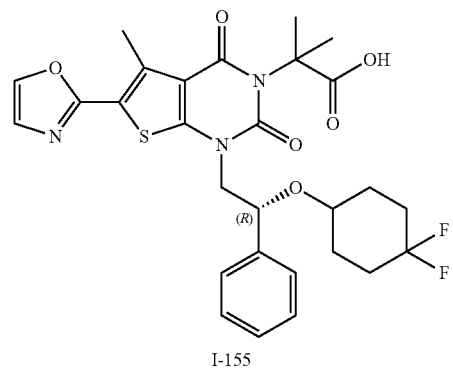

I-155

Synthesis of compound 27.2. Compound 27.2 was prepared in a manner analogous to 14.2, substituting 4,4-difluorocyclohexan-1-ol for 2,2,2-trifluoroethan-1-ol. Isolated a yellow oil in 18% yield.

Synthesis of Compound I-155. Compound I-155 was prepared in a manner analogous to compound 14.5. Isolated a colorless oil in 2% overall yield from 1.7. MS (ES): m/z 574 (M+H)$^+$, 596 (M+Na)$^+$, 637 (M+Na+CH$_3$CN)$^+$. $^1$H NMR (400 MHz, CD$_3$CN): δ 1.54-1.74 (m, 8H), 1.77 (d, 6H), 2.78 (s, 3H), 3.43 (s, 1H), 3.78-3.84 (m, 1H), 4.21-4.25 (m, 1H), 4.91-4.95 (m, 1H), 7.27 (s, 1H), 7.37-7.52 (m, 5H), 7.90 (s, 1H).

Example 28

Synthesis of 2-[1-[(2R)-2-[4-(1H-imidazol-1-yl)phenoxy]-2-phenylethyl]-5-methyl-6-(1,3-oxazol-2-yl)-2,4-dioxo-1H,2H,3H,4H-thieno[2,3-d]pyrimidin-3-yl]-2-methylpropanoic acid (I-160) and Example 29: Synthesis of 2-[1-[(2S)-2-[4-(1H-imidazol-1-yl)phenoxy]-2-phenylethyl]-5-methyl-6-(1,3-oxazol-2-yl)-2,4-dioxo-1H,2H,3H,4H-thieno[2,3-d]pyrimidin-3-yl]-2-methylpropanoic acid (I-161)

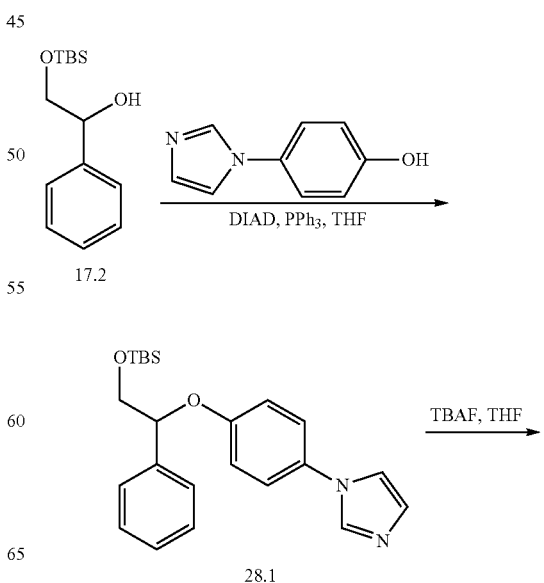

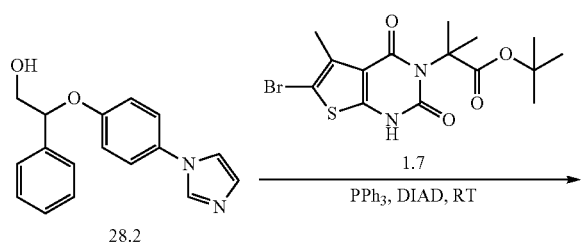

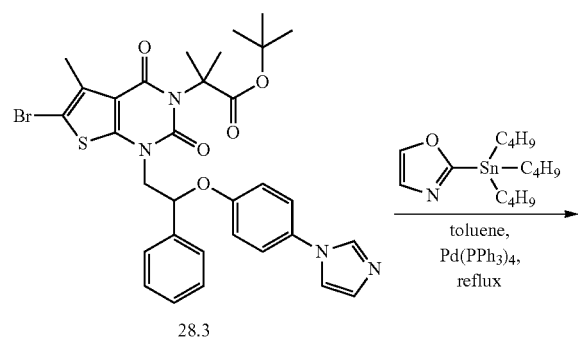

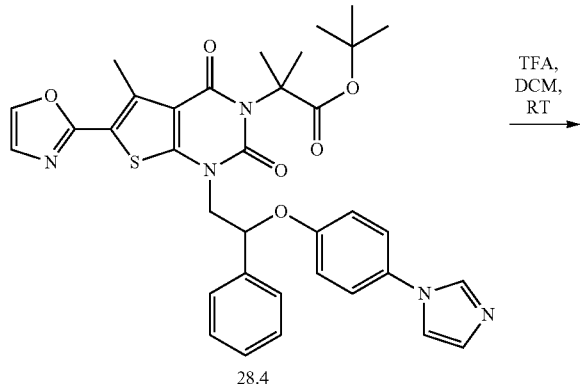

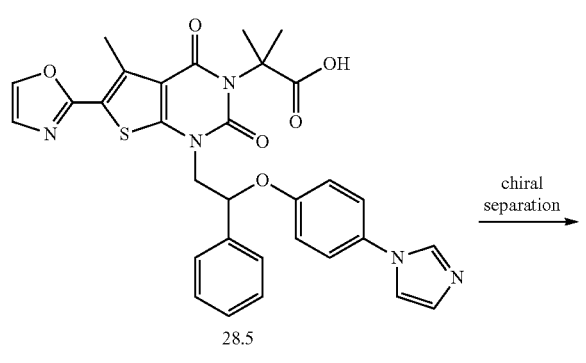

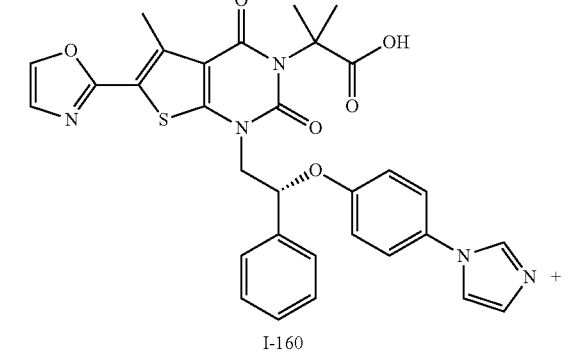

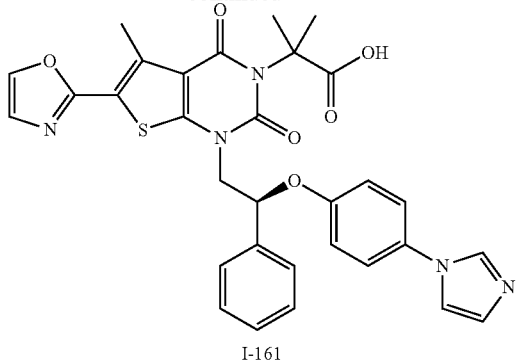

I-161

Synthesis of compound 28.2. 2-[4-(1H-imidazol-1-yl)phenoxy]-2-phenylethan-1-ol (28.2) was prepared in a manner analogous to 17.4, substituting 4-(1H-imidazol-1-yl)phenol for phenol. Isolated a white solid in 25% yield from 17.2.

Synthesis of compound 28.5. Compound 28.5 was prepared in a manner analogous to 14.5, substituting 28.2 for 14.2. Isolated a white solid in ca. 32% yield from 1.7.

Purification of Compounds I-160 and I-161. The enantiomers of 28.5 (148 mg, 0.25 mmol) were separated by chiral preparative HPLC under the following conditions (Gilson Gx 281): Column: Chiralpak IC, 2*25 cm, 5 μm; mobile phase: hexanes (0.1% TFA) and ethanol (0.1% TFA) (hold at 30% ethanol for 70 min); detector: 220/254 nm. The fraction with a retention time of 49.5 min was collected and concentrated in vacuo to afford 0.019 g (26%) of I-160 as a white solid. The fraction with a retention time of 42.0 min was collected and concentrated in vacuo to afford 0.023 g of I-161 as a white solid.

Analytical data for Compound I-160: MS (ES): m/z 598 (M+H)$^+$. $^1$H NMR (CD$_3$OD, 300 MHz): δ 1.76 (s, 6H), 2.75 (s, 3H), 4.22 (m, 1H), 4.45 (m, 1H), 5.80 (d, J=11.1 Hz, 1H), 7.05 (d, J=8.7 Hz, 2H), 7.44 (m, 8H), 7.64 (s, 1H), 7.84 (s, 1H), 7.98 (s, 1H), 9.17 (s, 1H).

Analytical data for Compound I-161: MS (ES): m/z 598 (M+H)$^+$. $^1$H NMR (CD$_3$OD, 300 MHz): δ 1.76 (d, J=1.8 Hz, 6H), 2.74 (s, 3H), 4.26 (dd, J=9.0 Hz, 15.0 Hz, 1H), 4.44 (dd, J=3.9 Hz, 14.7 Hz, 1H), 5.81 (dd, J=3.6 Hz, 8.4 Hz, 1H), 7.06 (m, 2H), 7.27-7.52 (m, 8H), 7.68 (s, 1H), 7.80 (s, 1H), 7.97 (d, J=0.6 Hz, 1H), 9.18 (s, 1H).

Example 29

Synthesis of 2-methyl-2-[5-methyl-1-[(2R)-2-(oxan-4-yloxy)-2-phenylethyl]-6-(1,3-oxazol-2-yl)-2,4-dioxo-1H,2H,3H,4H-thieno[2,3-d]pyrimidin-3-yl] propanoic acid (I-162)

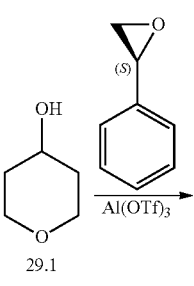

29.1

-continued

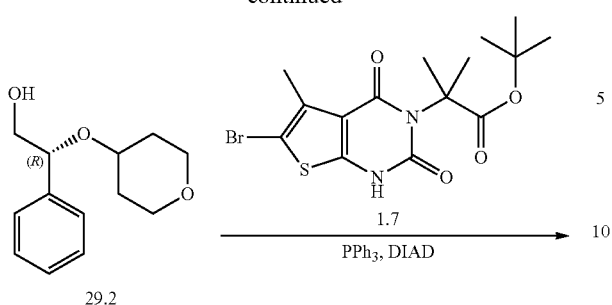

29.2

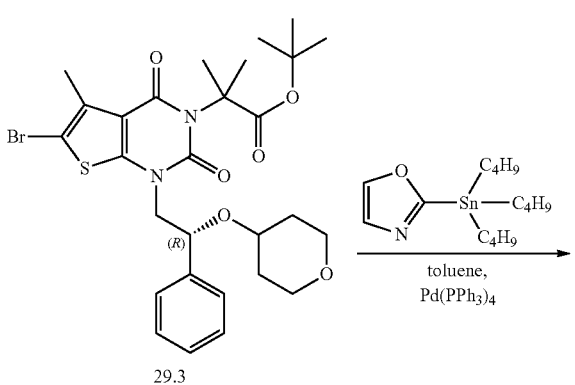

29.3

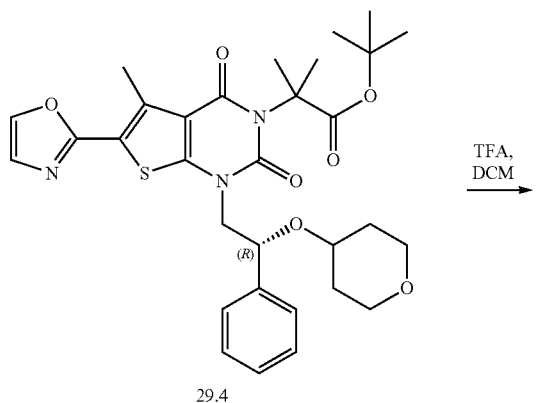

29.4

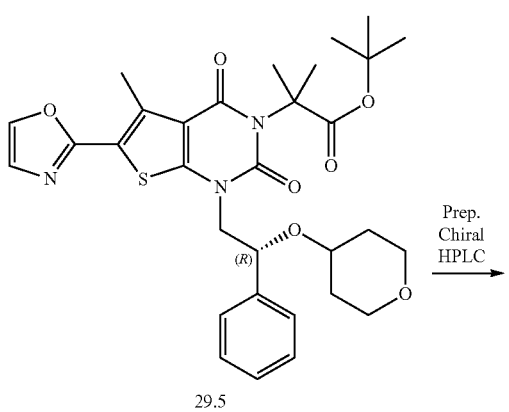

29.5

-continued

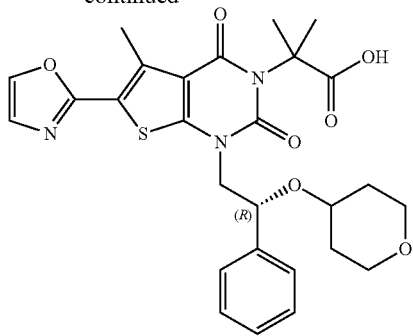

I-162

Synthesis of compound 29.2. (2R)-2-(oxan-4-yloxy)-2-phenylethan-1-ol (29.2) was prepared in a manner analogous to 14.2, substituting oxan-4-ol for 2,2,2-trifluoroethan-1-ol. Isolated a colorless oil in 21% yield.

Synthesis of compound 29.5. 29.5 was prepared in a manner analogous to 14.5, substituting 29.2 for 14.2. Isolated a white solid in 80% yield from 1.7.

Purification of Compound I-162. 29.5 (150 mg, 0.28 mmol, 1.00 equiv) was repurified by chiral preparative HPLC under the following conditions (Gilson Gx 281): column: Chiralpak IC, 2*25 cm, 5 μm; mobile phase: hexanes (0.1% TFA) and ethanol (with 0.1% TFA; hold at 30% ethanol in 13 min); detector: 220/254 nm. The fraction with a retention time of 8.5 min was collected. This fraction afforded 0.050 g of I-162 as a white solid. MS (ES): m/z 540 (M+H)$^+$. $^1$H NMR (DMSO-d$_6$, 400 MHz): δ 1.20 (m, 2H), 1.70 (m, 8H), 2.80 (s, 3H), 3.21-3.50 (m, 5H), 3.82 (s, 1H), 4.17 (d, J=13.6 Hz, 1H), 4.91 (d, J=6.8 Hz, 1H), 7.40 (m, 6H), 8.24 (s, 1H), 12.44 (s, 1H).

Example 30

2-[1-[(2R)-2-(2-hydroxyethoxy)-2-phenylethyl]-5-methyl-6-(1,3-oxazol-2-yl)-2,4-dioxo-1H,2H,3H,4H-thieno[2,3-d]pyrimidin-3-yl]-2-methylpropanoic acid (I-169)

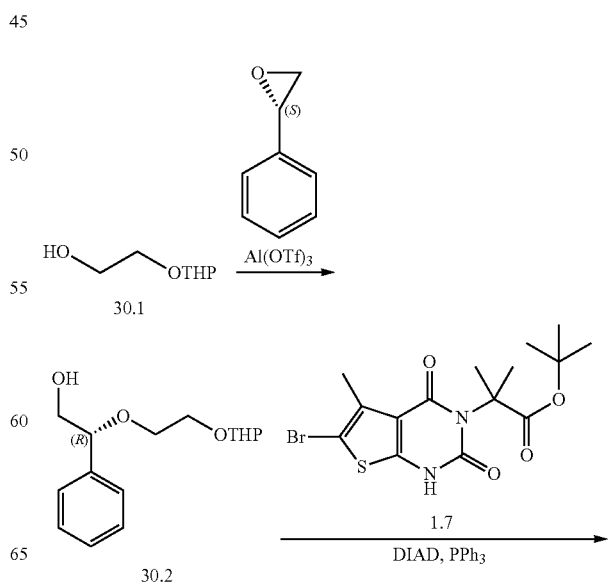

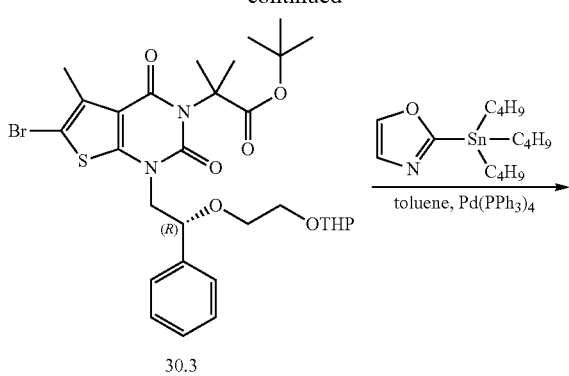

30.3

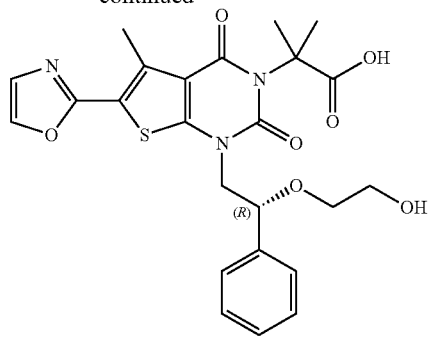

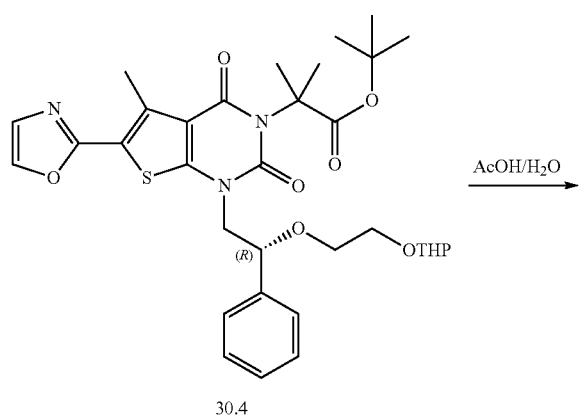

30.4

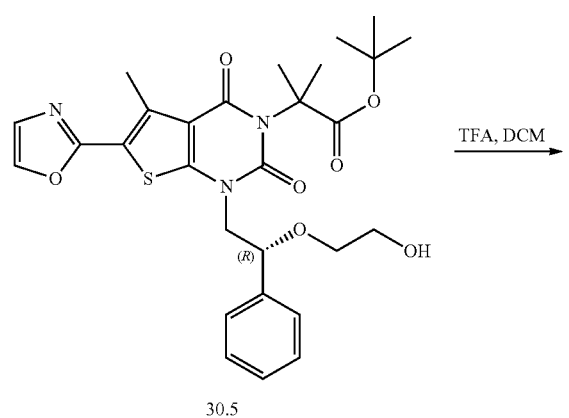

30.5

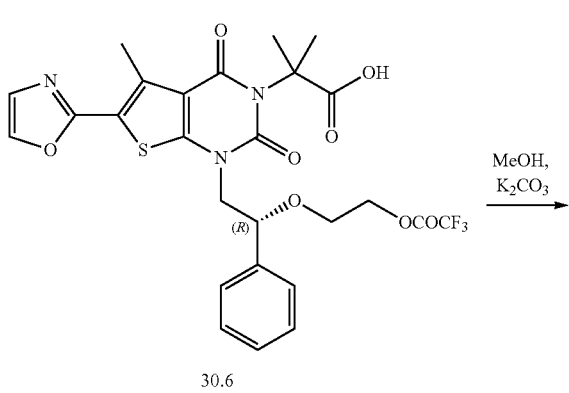

30.6

I-169

Synthesis of compound 30.2. Compound 30.2 was prepared from 2-((tetrahydro-2H-pyran-2-yl)oxy)ethanol in a manner analogous to the synthesis of compound 14.2. Isolated a colorless oil in 5% yield.

Synthesis of compound 30.4. Compound 30.4 was prepared in a manner analogous to compound 14.4. Isolated a yellow solid in 40% overall yield from compounds 30.2 and 1.7.

Synthesis of compound 30.5. Into a 25-mL round-bottom flask was placed 30.4 (150 mg, 0.27 mmol, 1.00 equiv), AcOH (4 mL) and water (1 mL). The resulting solution was stirred overnight at 35° C. in an oil bath. The resulting mixture was concentrated under vacuum. The residue was applied onto a silica gel column with PE/EA (2:1). The crude product (100 mg) was purified by chiral preparative HPLC under the following conditions (Gilson Gx 281): Column: CHIRAL-PAK AD-H SFC, 5*25 cm, 5 μm; mobile phase: hexanes (0.2% TEA and ethanol (0.2% TEA) (hold at 10% ethanol (0.2% TEA) for 17 min); detector: UV 220/254 nm. The fraction with a retention time of 12.9 min was collected. Concentration afforded 25 mg (17%) of 30.5 as a white solid.

Synthesis of compound 30.6. Into a 25-mL round-bottom flask was placed dichloromethane (5 mL), 30.5 (20 mg, 0.04 mmol, 1.00 equiv) and $CF_3COOH$ (1.5 mL). The resulting solution was stirred for 4 h at room temperature. The resulting mixture was concentrated under vacuum. Purification afforded 0.020 g (crude) of 30.6 as a colorless oil.

Synthesis of Compound I-169. Into a 25-mL round-bottom flask was placed methanol (5 mL), 30.6 (20 mg, 0.03 mmol, 1.00 equiv) and potassium carbonate (30 mg, 0.22 mmol, 6.46 equiv). The solution was stirred overnight at room temperature. The resulting mixture was concentrated under vacuum. The crude product (30 mg) was purified by preparative HPLC under the following conditions (Waters): Column: SunFire Prep C18, 19*150 mm 5 μm; mobile phase: water (50 mM $NH_4CO_3$) and $CH_3CN$ (5.0% $CH_3CN$ up to 45.0% in 10 min, up to 95.0% in 2 min, down to 5.0% in 2 min); detector: UV 254/220 nm. This procedure afforded 0.013 g (77%) of Compound I-169 as a white solid. MS (ES): m/z 500 (M+H)$^+$. $^1$H NMR (CD$_3$OD, 400 MHz): δ 1.80 (s, 6H), 2.80 (s, 3H), 3.39-3.49 (m, 3H), 3.59 (q, J=6.0 Hz, 2H), 4.03 (t, J=8.8 Hz, 1H), 4.15 (m, 1H), 7.27 (s, 1H), 7.34 (d, J=8.0 Hz, 1H), 7.41 (t, J=6.8 Hz, 2H), 7.48 (d, J=7.2 Hz, 2H), 7.97 (s, 1H).

Example 31

Synthesis of 2-(1-((R)-2-(R)-3-hydroxy-2-methylpropoxy)-2-phenylethyl)-5-methyl-6-(oxazol-2-yl)-2,4-dioxo-1,2-dihydrothieno[2,3-d]pyrimidin-3(4H)-yl)-2-methylpropanoic acid (I-170) and Example 32: Synthesis of 2-(1-((R)-2-(S)-3-hydroxy-2-methylpropoxy)-2-phenylethyl)-5-methyl-6-(oxazol-2-yl)-2,4-dioxo-1,2-dihydrothieno[2,3-d]pyrimidin-3(4H)-yl)-2-methylpropanoic acid (I-171)

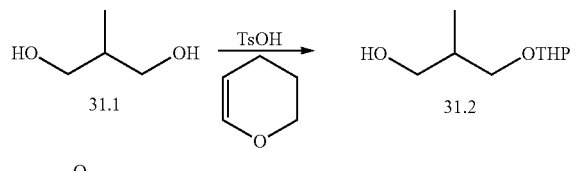

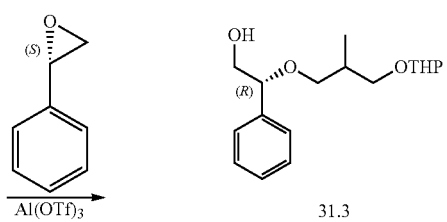

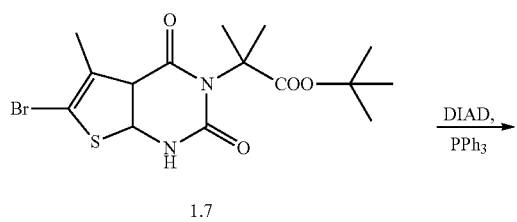

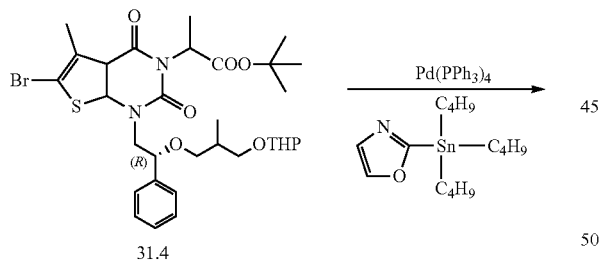

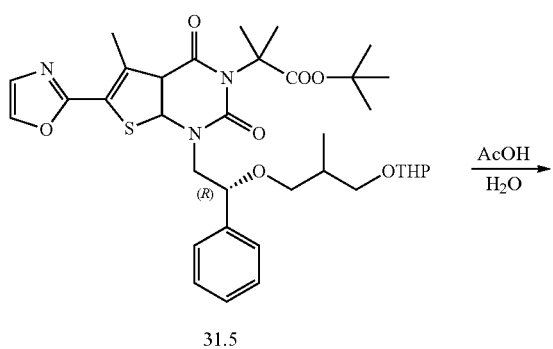

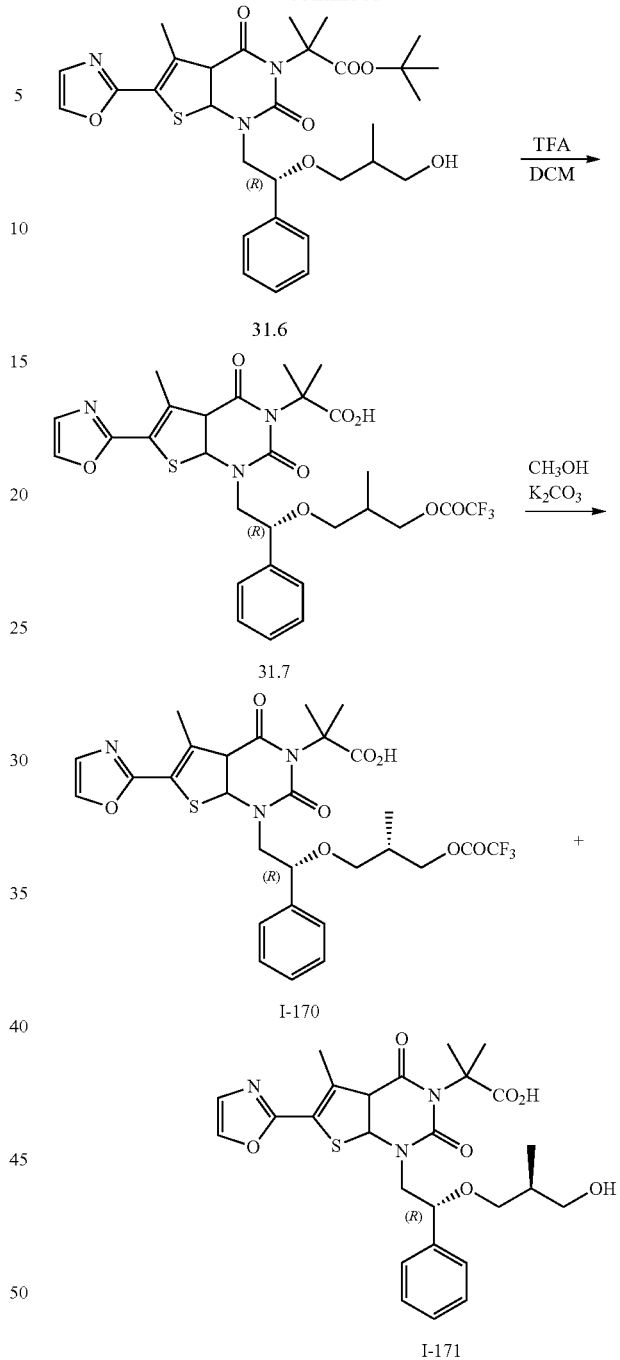

Synthesis of compound 31.2. Into a 50-mL 3-necked round-bottom flask was placed 2-methylpropane-1,3-diol (20 g, 221.92 mmol, 1.00 equiv) and 4-methylbenzene-1-sulfonic acid (11 mg, 0.06 mmol). Then 3,4-dihydro-2H-pyran (5 g, 59.44 mmol, 0.27 equiv) was added at 0° C. The resulting solution was stirred for 3 h at room temperature. The residue was applied onto a silica gel column with ethyl acetate/petroleum ether (1:20). Purification afforded 6.9 g (18%) of 2-methyl-3-(oxan-2-yloxy)propan-1-ol as a light yellow liquid.

Synthesis of compound 31.3. Compound 31.3 was prepared from 31.2 in a manner analogous to the synthesis of compound 14.2. Isolated a colorless oil in 5% yield.

Synthesis of compound 31.7. Compound 31.7 was prepared in a manner analogous to compound 30.6. Isolated a colorless oil in 30% overall yield from 31.3 and 1.7.

Synthesis of Compounds I-170 and I-171. Into a 50-mL round-bottom flask was placed methanol (5 mL), compound 31.7 (100 mg, 0.16 mmol, 1.00 equiv) and potassium methaneperoxoate potassium (50 mg, 0.36 mmol, 2.24 equiv). The resulting solution was stirred overnight at room temperature. The resulting mixture was concentrated under vacuum. The crude product (100 mg) was purified by preparative HPLC under the following conditions (Waters): Column: XBridge Prep C18 OBD column, 5 μm, 19*150 mm; mobile phase: water (50 mM $NH_4HCO_3$) and $CH_3CN$ (10% $CH_3CN$ up to 27% in 2 min, hold at 27% in 15 min, up to 95% in 2 min, down to 10% in 2 min); detector: UV 254/220 nm. Purification afforded 0.024 g (57%) of Compound I-170 as a white solid (tR=10.28 min) and 0.023 g (57%) of Compound I-171, also as a white solid (tR=11.62 min).

Analytical data for Compound I-170: MS (ES): m/z 528 $(M+H)^+$. $^1H$ NMR ($CD_3OD$, 400 MHz): δ 0.74-0.81 (m, 3H), 1.81 (m, 7H), 2.83 (s, 3H), 3.24 (m, 4H), 3.88 (m, 1H), 4.20 (m, 1H), 7.28 (s, 1H), 7.35 (m, 1H), 7.44 (m, 4H), 7.98 (s, 1H).

Analytical data for Compound I-171: MS (ES): m/z 528 $(M+H)^+$. $^1H$ NMR ($CD_3OD$, 400 MHz): δ 0.74-0.81 (m, 3H), 1.81 (m, 7H), 2.83 (s, 3H), 3.24 (m, 4H), 3.88 (m, 1H), 4.20 (m, 1H), 7.28 (s, 1H), 7.35 (m, 1H), 7.44 (m, 4H), 7.98 (s, 1H).

Example 32

Synthesis of 2-(1-((R)-2-(((1S,3S)-3-hydroxycyclohexyl)oxy)-2-phenylethyl)-5-methyl-6-(oxazol-2-yl)-2,4-dioxo-1,2-dihydrothieno[2,3-d]pyrimidin-3(4H)-yl)-2-methylpropanoic acid (I-172) and Example 33: 2-(1-((R)-2-(((1S,3R)-3-hydroxycyclohexyl)oxy)-2-phenylethyl)-5-methyl-6-(oxazol-2-yl)-2,4-dioxo-1,2-dihydrothieno[2,3-d]pyrimidin-3(4H)-yl)-2-methylpropanoic acid (I-173)

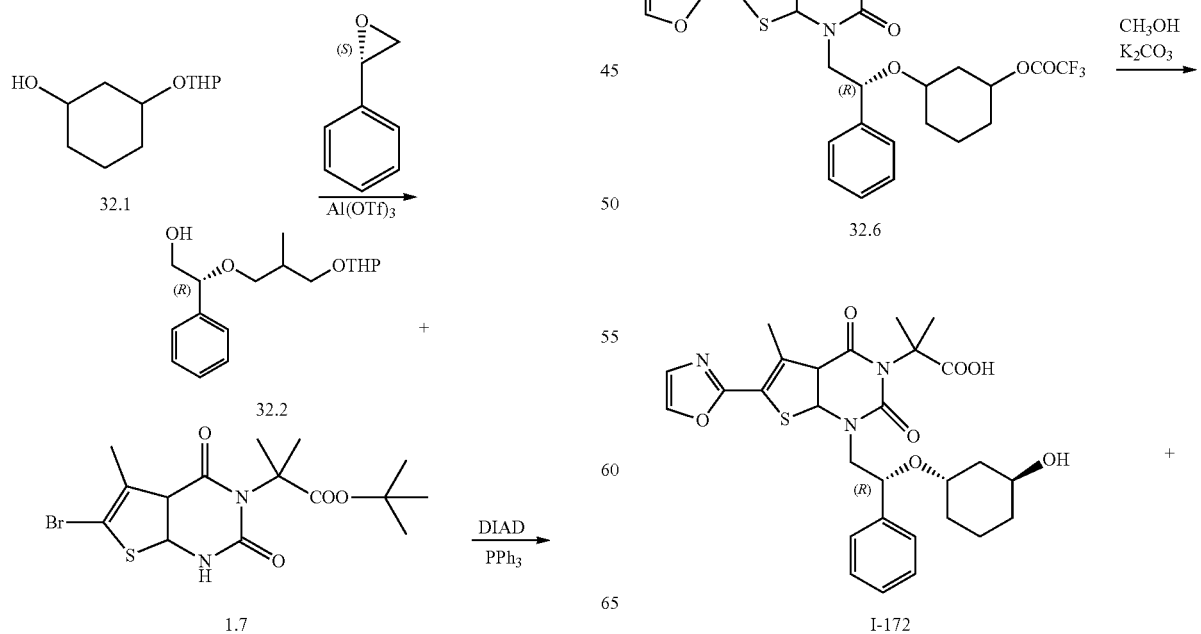

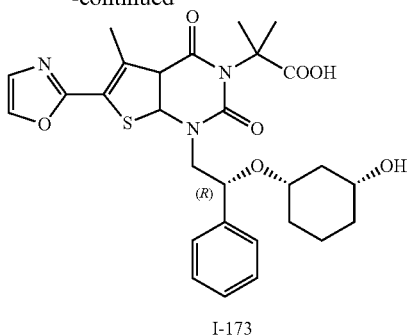

I-173

Synthesis of compound 32.6. Compound 32.6 was prepared from 32.1 and 1.7 in a manner analogous to the synthesis of compound 30.6. Isolated a colorless oil in 14% overall yield from 1.7 (1% from 32.1).

Synthesis of Compounds I-172 and I-173. Into a 50-mL round-bottom flask was placed methanol (5 mL), compound 32.6 (100 mg, 0.15 mmol, 1.00 equiv) and potassium carbonate (80 mg, 0.58 mmol, 3.76 equiv). The solution was stirred overnight at room temperature. The resulting mixture was concentrated under vacuum. The crude product (100 mg) was purified by preparative HPLC under the following conditions (Waters): Column: XBridge Prep C18 OBD, 5 μm, 19*150 mm; mobile phase: water (50 mM $NH_4HCO_3$) and $CH_3CN$ (17.0% $CH_3CN$ up to 40.0% in 10 min, up to 95.0% in 2 min, down to 17.0% in 2 min); detector: UV 254, 220 nm. Purification afforded 17.2 mg (42%) of Compound I-172 as a white solid and 16.1 mg (40%) of Compound I-173, also as a white solid.

Analytical data for Compound I-172: MS (ES): m/z 554 $(M+H)^+$. $^1H$ NMR ($CD_3OD$, 400 MHz): δ 0.88 (m, 1H), 1.20 (m, 3H), 1.35 (m, 1H), 1.60 (m, 2H), 1.80 (m, 6H), 2.10 (m, 1H), 2.83 (s, 3H), 3.20 (m, 1H), 3.60 (m, 1H), 3.80 (m, 1H), 4.20 (m, 1H), 5.00 (m, 1H), 7.29 (d, J=2.4 Hz, 1H), 7.35 (dd, J=6.8, 14.4 Hz, 1H), 7.43 (dd, J=7.6, 15.2 Hz, 2H), 7.50 (t, J=7.6 Hz, 2H), 7.99 (d, J=2.0 Hz, 1H).

Analytical data for Compound I-173: MS (ES): m/z 554 $(M+H)^+$. $^1H$ NMR ($CD_3OD$, 400 MHz): δ 1.20 (m, 3H), 1.35 (m, 2H), 1.55 (m, 2H), 1.82 (m, 6H), 2.04 (m, 1H), 2.84 (s, 3H), 3.47 (d, J=12.0 Hz, 1H), 3.61 (s, 1H), 3.70 (m, 1H), 4.33 (d, J=12.8 Hz, 1H), 5.05 (m, 1H), 7.28 (s, 1H), 7.35 (t, J=6.8 Hz, 1H), 7.43 (t, J=7.6 Hz, 2H), 7.50 (d, J=7.2 Hz, 2H), 7.99 (s, 1H).

Example 33

Synthesis of 2-methyl-2-[5-methyl-6-(1,3-oxazol-2-yl)-2,4-dioxo-1-[(2R)-2-[(3R)-oxolan-3-yloxy]-2-phenylethyl]-1H,2H,3H,4H-thieno[2,3-d]pyrimidin-3-yl]propanoic acid (I-186)

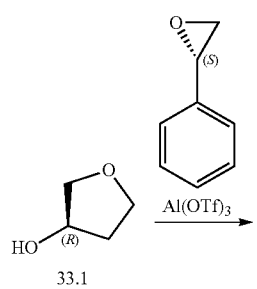

33.1

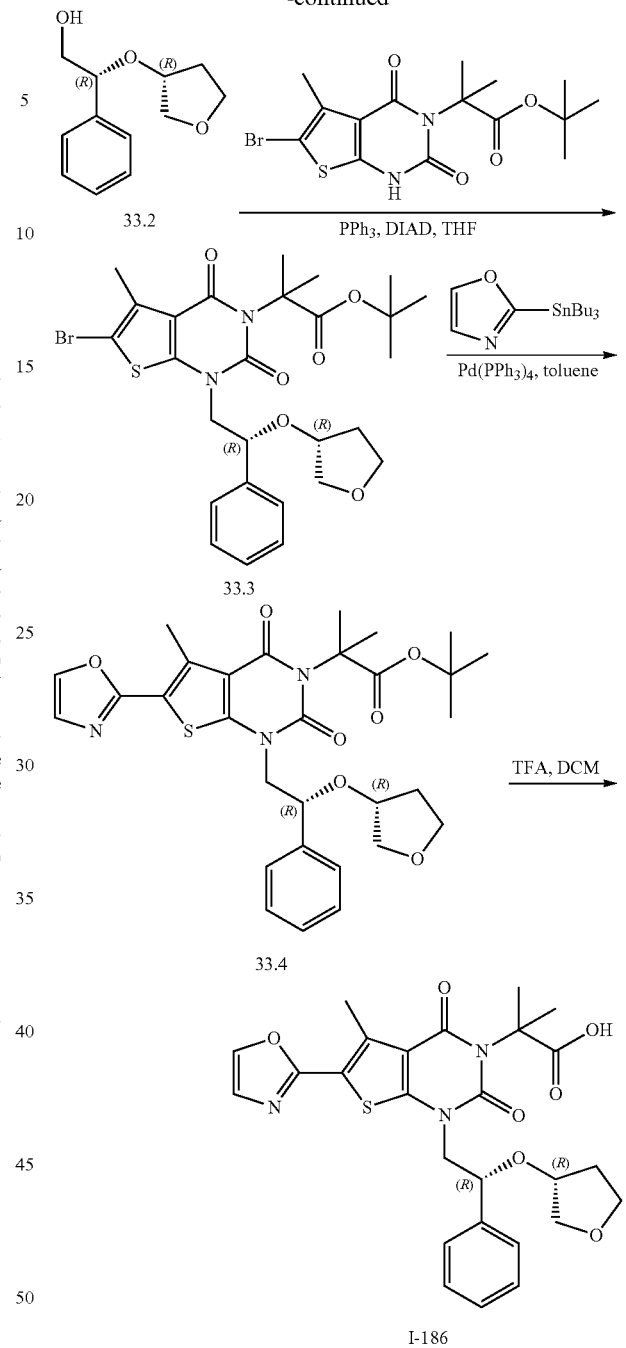

Synthesis of compound 33.4. Compound 33.4 was prepared from 33.1 in a manner analogous to the synthesis of compound 14.4. Isolated a white solid in 6% overall yield from 33.1.

Synthesis of Compound I-186. Into a 50-mL round-bottom flask was placed dichloromethane (5 mL), compound 33.4 (120 mg, 0.21 mmol, 1.00 equiv) and trifluoroacetic acid (1 mL). The solution was stirred for 2 h at room temperature. The resulting mixture was concentrated under vacuum. The residue was applied onto a silica gel column with dichloromethane/methanol (100:1). The product (100 mg) thus obtained was repurified by flash preparative HPLC under the following conditions (IntelFlash-1): Column: C18 silica gel; mobile phase: acetonitrile:water=0:100 increasing to acetonitrile:water=100:0 within 25 min; detector: UV 254 nm. Purification afforded 72.7 mg (67%) of Compound I-186 as a white solid. MS (ES): m/z 526 (M+H)$^+$, 548 (M+Na)$^+$. $^1$H NMR (300 MHz, DMSO-d$_6$): δ 1.59-1.60 (m, 6H), δ 1.64-1.67 (m, 2H), 2.70 (s, 3H), 3.27-3.32 (m, 1H), 3.40-3.43 (m, 1H), 3.49-3.55 (m, 2H), 3.70-3.78 (m, 1H), 3.92 (s, 1H), 4.05-4.11 (m, 1H), 4.77-4.80 (m, 1H), 7.28-7.39 (m, 6H), 8.19 (s, 1H).

Example 34

Synthesis of 2-methyl-2-[5-methyl-6-(1,3-oxazol-2-yl)-2,4-dioxo-1-[(2R)-2-[(3S)-oxolan-3-yloxy]-2-phenylethyl]-1H,2H,3H,4H-thieno[2,3-d]pyrimidin-3-yl]propanoic acid (I-227)

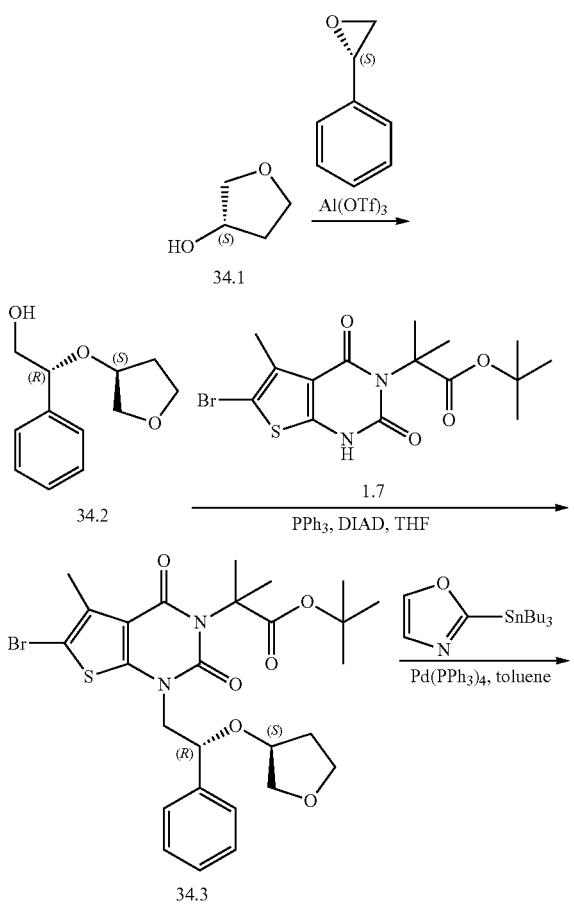

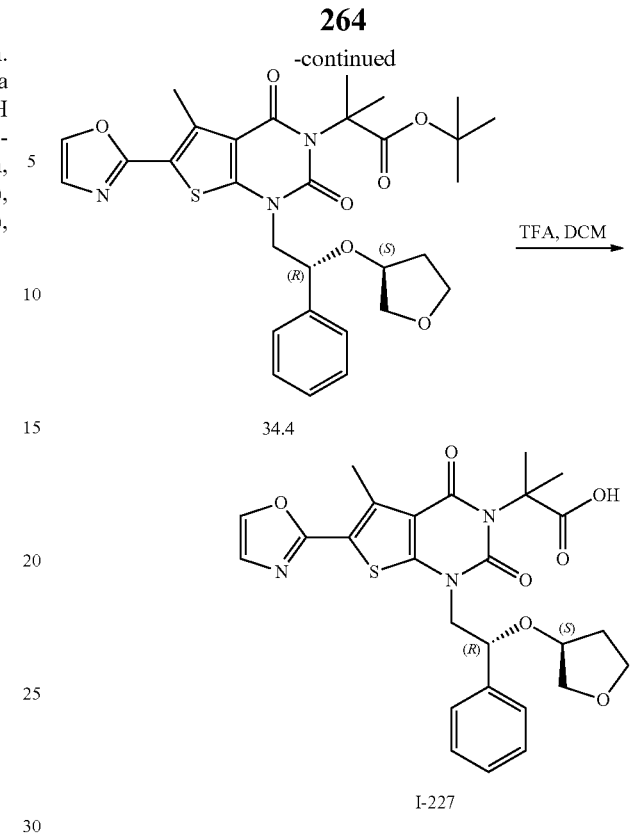

Synthesis of compound 34.4. Compound 34.4 was synthesized in a manner analogous to the synthesis of compound 33.4. Isolated a white solid in 12% overall yield from 34.1.

Synthesis of compound I-227. Into a 50-mL round-bottom flask was placed dichloromethane (5 mL), 34.4 (170 mg, 0.29 mmol, 1.00 equiv) and trifluoroacetic acid (1 mL). The solution was stirred for 2 h at room temperature. The resulting mixture was concentrated under vacuum. The residue was applied onto a silica gel column with dichloromethane/methanol (100:1). The product (120 mg) thus obtained was repurified by flash preparative HPLC under the following conditions (IntelFlash-1): Column: C18 silica gel; mobile phase: acetonitrile:water=0:100 increasing to acetonitrile:water=100:0 within 29 min; Detector, UV 254 nm. Purification afforded 53.3 mg (35%) of Compound I-227 as a white solid. MS (ES): m/z 526 (M+H)$^+$, 548 (M+Na)$^+$. $^1$H NMR (400 MHz, CD$_3$OD): δ 1.59-1.60 (m, 6H), 1.64-1.67 (m, 2H), 2.83 (s, 3H), 3.60-3.72 (m, 4H), 3.81-3.88 (m, 1H), 4.11-4.25 (m, 2H), 4.89-4.95 (m, 1H), 7.28 (s, 1H), 7.33-7.37 (m, 1H), 7.43 (t, J=7.6, 2H), 7.51 (d, J=7.2, 2H), 7.98 (s, 1H).

Example 35

Synthesis of 2-[1-[(2R)-2-[(4-hydroxypiperidin-1-yl)carbonyloxy]-2-phenylethyl]-5-methyl-6-(1,3-oxazol-2-yl)-2,4-dioxo-1H,2H,3H,4H-thieno[2,3-d]pyrimidin-3-yl]-2-methylpropanoic acid (I-228)

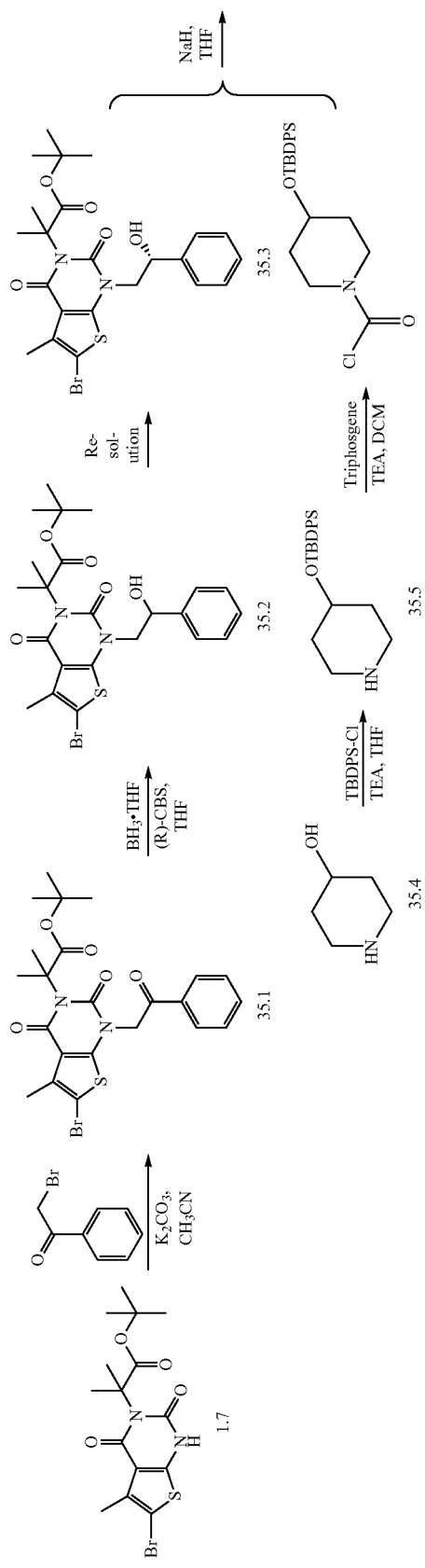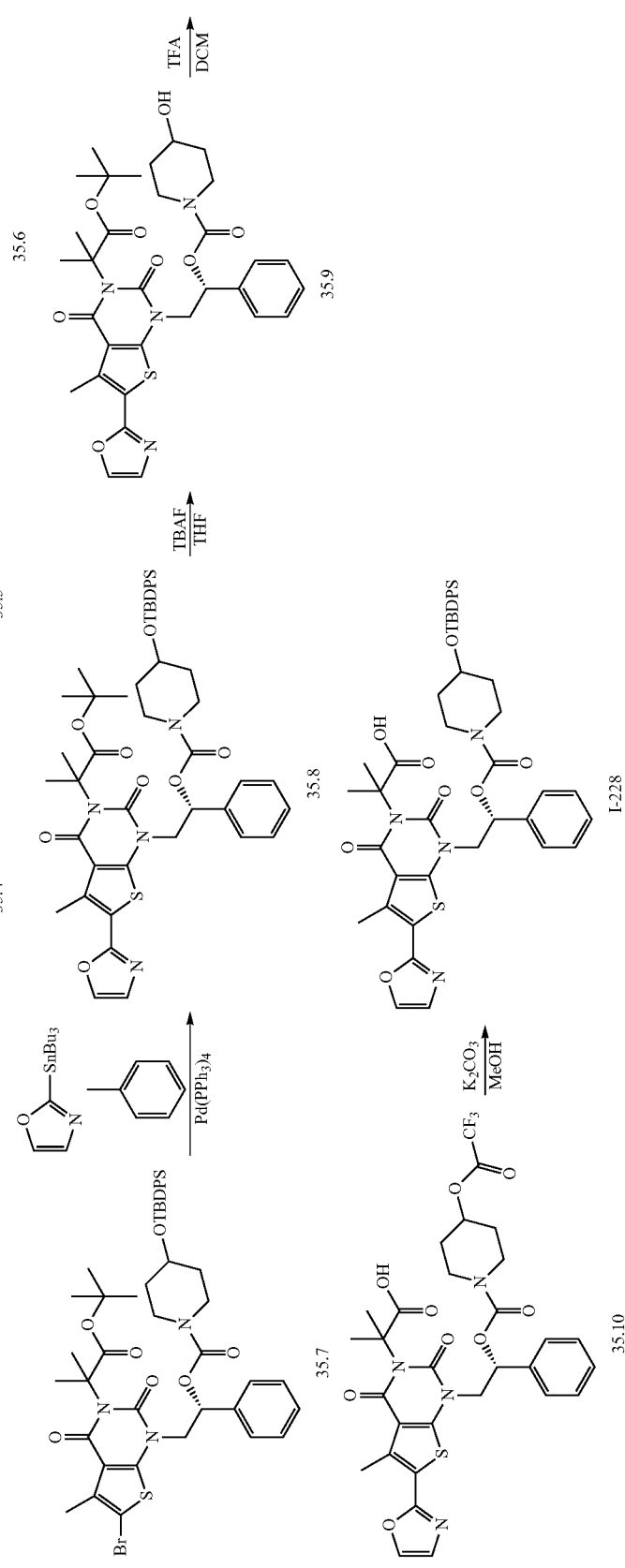

Synthesis of compound 35.5. Into a 250-mL round-bottom flask was placed a solution of piperidin-4-ol (4 g, 39.55 mmol, 1.00 equiv) in tetrahydrofuran (100 mL), TEA (12 g, 118.59 mmol, 3.00 equiv) and tert-butyl(chloro)diphenylsilane (16 g, 58.21 mmol, 1.47 equiv). The resulting solution was stirred for 16 h at room temperature. The solids were filtered out. The filtrate was dried over anhydrous sodium sulfate and concentrated under vacuum. The residue was applied onto a silica gel column with ethyl acetate/petroleum ether (1:2). Purification afforded 1.1 g (8%) of 4-[(tert-butyldiphenylsilyl)oxy]piperidine as a colorless oil.

Synthesis of compound 35.6. Into a 50-mL round-bottom flask was placed a solution of 4-[(tert-butyldiphenylsilyl)oxy]piperidine (1.00 g, 2.95 mmol, 1.00 equiv) in dichloromethane (20 mL), triethylamine (780 mg, 7.71 mmol, 2.62 equiv), ditrichloromethyl carbonate (2.07 g, 6.98 mmol, 2.37 equiv). The resulting solution was stirred overnight at room temperature whereupon it was diluted with 40 mL of DCM and washed with 3×15 mL of water and 2×20 mL of sodium chloride (sat.). The combined organic solutions were dried over anhydrous sodium sulfate and concentrated under vacuum. The residue was applied onto a silica gel column with ethyl acetate/petroleum ether (1:4). Purification afforded 1.15 g (97%) of 35.6 as a light yellow oil.

Synthesis of compound 35.1. To a solution of intermediate 1.7 (1.5 g, 3.72 mmol, 1.00 equiv) in $CH_3CN$ (20 mL) were added potassium carbonate (1.54 g, 11.14 mmol, 3.00 equiv) and 2-bromo-1-phenylethan-1-one (770 mg, 3.87 mmol, 1.05 equiv). The resulting solution was stirred for 3 h at room temperature. The reaction was then quenched by the addition of 20 mL of water. The resulting solution was extracted with 3×30 mL of ethyl acetate and the organic layers combined. The resulting mixture was washed with 2×40 mL of sodium chloride (sat.). The mixture was dried over anhydrous sodium sulfate and concentrated under vacuum. The residue was applied onto a silica gel column with ethyl acetate/petroleum ether (1:5). Purification afforded 1.8 g (93%) of 35.1 as a white solid.

Synthesis of compound 35.2. Into a 50-mL round-bottom flask was placed a solution of 35.1 (1.5 g, 2.88 mmol, 1.00 equiv) in tetrahydrofuran (15 mL) and (R)—CBS (239 mg, 0.86 mmol, 0.30 equiv). This was followed by the addition of a solution of $BH_3$-THF (4 mL, 1.50 equiv) in tetrahydrofuran (5 mL) dropwise with stirring over 8 hr. The resulting solution was stirred overnight at room temperature. The reaction was then quenched by the addition of 15 mL of $NH_4Cl$ (sat.). The resulting solution was extracted with 3×20 mL of ethyl acetate and the organic layers combined. The resulting mixture was washed with 2×30 mL of sodium chloride (sat.). The mixture was dried and concentrated. The residue was applied onto a silica gel column with ethyl acetate/petroleum ether (1:15). Purification afforded 1.4 g (93%) of 35.2 as a white solid.

Synthesis of compound 35.3. The enantiomers of compound 35.2 (1.4 g, 2.67 mmol, 1.00 equiv) were separated by preparative SFC under the following conditions: Column: Phenomenex Lux 5 u Cellulose-3, 5*25 cm, 5 µm; mobile phase: $CO_2$ (80%), methanol (20%); detector: UV 254 nm. Purification afforded 0.98 g of 35.3 as a white solid.

Synthesis of compound 35.7. To a solution of 35.3 (300 mg, 0.57 mmol, 1.00 equiv) in tetrahydrofuran (10 mL) was added sodium hydride (69 mg, 1.73 mmol, 3.00 equiv, 60%) at 0° C. under $N_2$. The mixture was stirred for 30 min and then a solution of 35.6 (238 mg, 0.59 mmol, 1.50 equiv) in tetrahydrofuran (3 mL) was added. The resulting solution was stirred overnight at room temperature. The reaction was then quenched by the addition of 10 mL of water. The resulting solution was extracted with 3×20 mL of ethyl acetate and the organic layers combined. The resulting mixture was washed with 2×20 mL of sodium chloride (sat.). The mixture was dried over anhydrous sodium sulfate and concentrated under vacuum. The residue was applied onto a silica gel column with ethyl acetate/petroleum ether (1:6). Purification afforded 360 mg (71%) of 35.7 as a white solid.

Synthesis of compound 35.8. Into a 25-mL round-bottom flask, purged and maintained with an inert atmosphere of nitrogen, was placed 35.7 (140 mg, 0.16 mmol, 1.00 equiv), $Pd(PPh_3)_4$ (28 mg, 0.02 mmol, 0.15 equiv), 2-(tributylstannyl)-1,3-oxazole (85 mg, 0.24 mmol, 1.51 equiv) and toluene (5 mL). The resulting solution was stirred overnight at 110° C. The resulting mixture was concentrated under vacuum. The residue was applied onto a silica gel column with ethyl acetate/petroleum ether (1:40). Purification afforded 100 mg (72%) of 35.8 as a colorless oil.

Synthesis of compound 35.9. Into a 50-mL round-bottom flask was placed tetrahydrofuran (5 mL) and 35.8 (100 mg, 0.11 mmol, 1.00 equiv). This was followed by the addition of TBAF (33 mg, 0.13 mmol, 1.11 equiv) in portions. The resulting solution was stirred for 2 h at room temperature. The reaction was then quenched by the addition of 0.5 mL of water. The resulting mixture was concentrated under vacuum. The residue was applied onto a silica gel column with ethyl acetate/petroleum ether (1:5). Purification afforded 50 mg (69%) of 35.9 as a yellow oil.

Synthesis of compound 35.10. Into a 50-mL round-bottom flask was placed dichloromethane (5 mL), 35.9 (50 mg, 0.08 mmol, 1.00 equiv) and trifluoroacetic acid (1 mL). The resulting solution was stirred for 2 h at room temperature and then concentrated under vacuum. The residue was applied onto a silica gel column with dichloromethane/methanol (100:1). Purification afforded 40 mg (crude) of 35.10 as a colorless oil.

Synthesis of Compound I-228. Into a 50-mL round-bottom flask was placed 35.10 (40 mg, 0.06 mmol, 1.00 equiv), potassium carbonate (21 mg, 0.15 mmol, 2.58 equiv) and methanol (5 mL). The resulting solution was stirred for 2 h at room temperature. The solids were filtered out. The pH value of the filtrate was adjusted to 6 with TFA. The resulting mixture was concentrated under vacuum. The residue was applied onto a silica gel column with dichloromethane/methanol (100:1). Purification afforded 22.7 mg (66%) of Compound I-228 as a white solid. MS (ES): m/z 583 $(M+H)^+$. $^1H$ NMR (400 MHz, $CD_3OD$): δ 1.05-1.40 (m, 2H), 1.67-1.74 (m, 2H), 1.80 (s, 6H), 2.84 (s, 3H), 3.03-3.23 (m, 2H), 3.50-4.16 (m, 4H), 4.33-4.43 (m, 1H), 6.19-6.22 (m, 1H), 7.29 (s, 1H), 7.36-7.51 (m, 5H), 7.99 (s, 1H).

Example 36

Synthesis of 2-[1-[(2R)-2-[[(2R)-1-hydroxypropan-2-yl]oxy]-2-phenylethyl]-5-methyl-6-(1,3-oxazol-2-yl)-2,4-dioxo-1H,2H,3H,4H-thieno[2,3-d]pyrimidin-3-yl]-2-methylpropanoic acid (I-184)

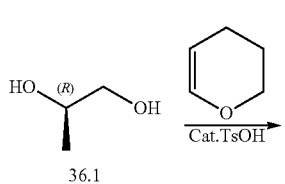

36.1

269
-continued

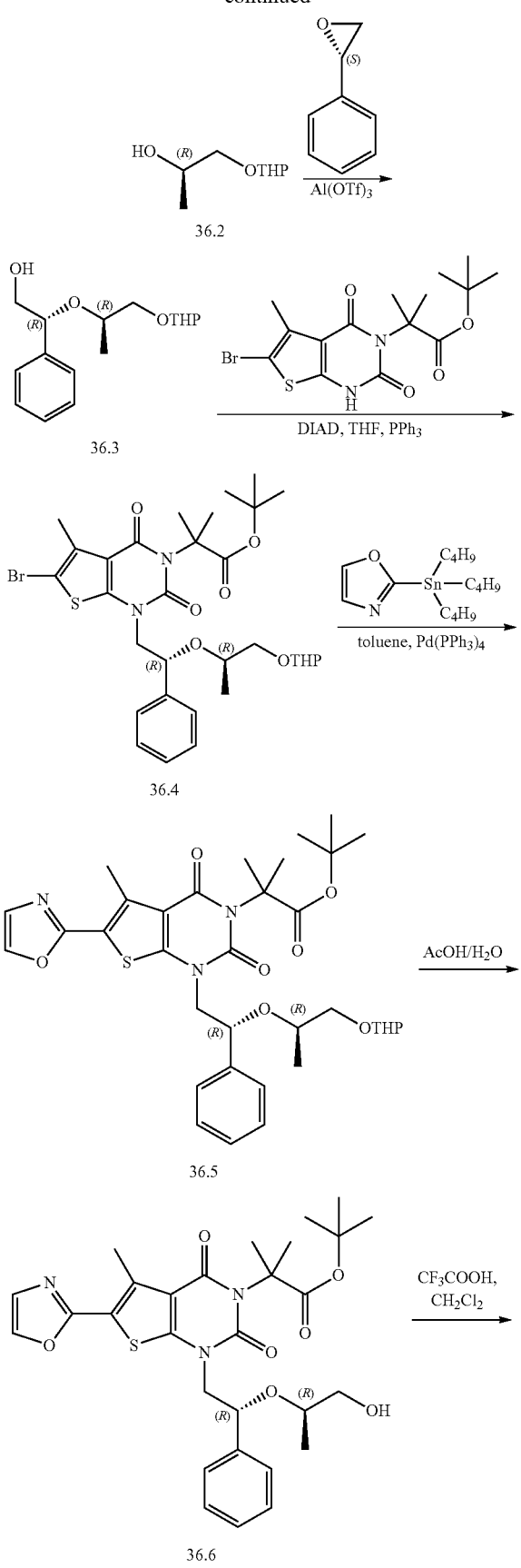

270
-continued

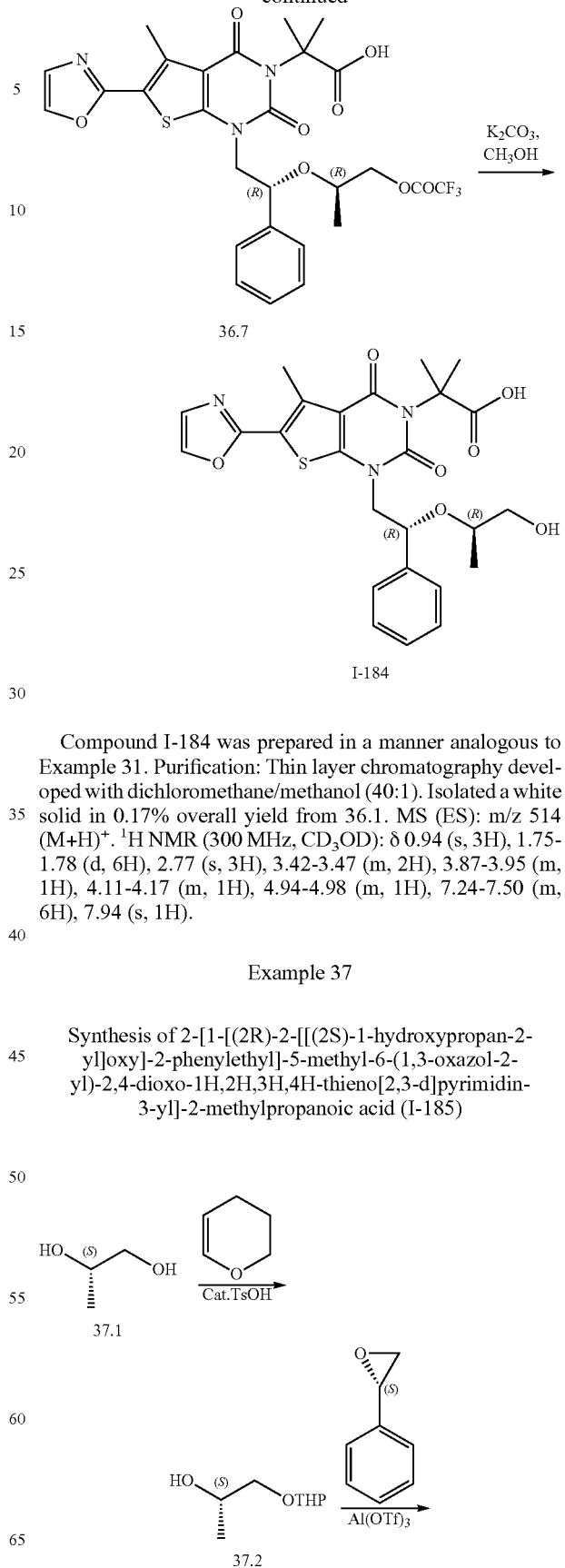

Compound I-184 was prepared in a manner analogous to Example 31. Purification: Thin layer chromatography developed with dichloromethane/methanol (40:1). Isolated a white solid in 0.17% overall yield from 36.1. MS (ES): m/z 514 (M+H)$^+$. $^1$H NMR (300 MHz, CD$_3$OD): δ 0.94 (s, 3H), 1.75-1.78 (d, 6H), 2.77 (s, 3H), 3.42-3.47 (m, 2H), 3.87-3.95 (m, 1H), 4.11-4.17 (m, 1H), 4.94-4.98 (m, 1H), 7.24-7.50 (m, 6H), 7.94 (s, 1H).

Example 37

Synthesis of 2-[1-[(2R)-2-[[(2S)-1-hydroxypropan-2-yl]oxy]-2-phenylethyl]-5-methyl-6-(1,3-oxazol-2-yl)-2,4-dioxo-1H,2H,3H,4H-thieno[2,3-d]pyrimidin-3-yl]-2-methylpropanoic acid (I-185)

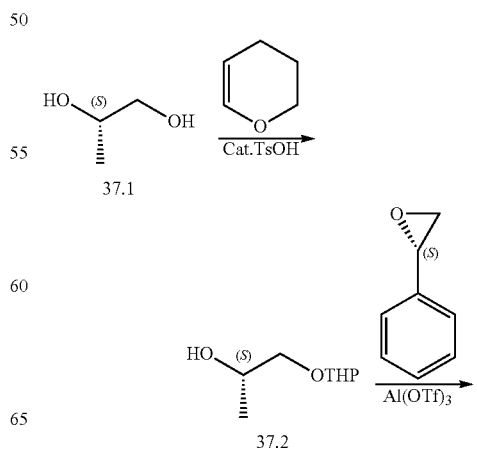

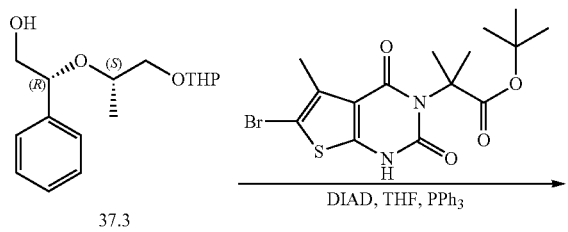
37.3
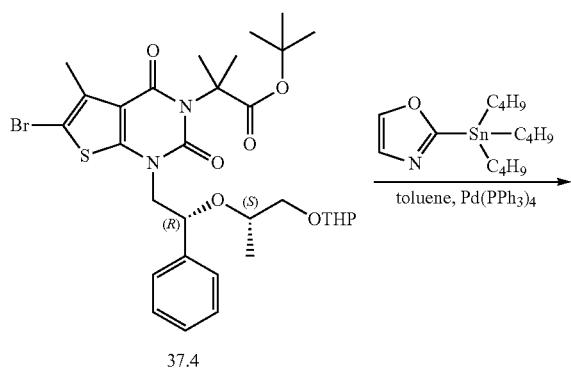
37.4
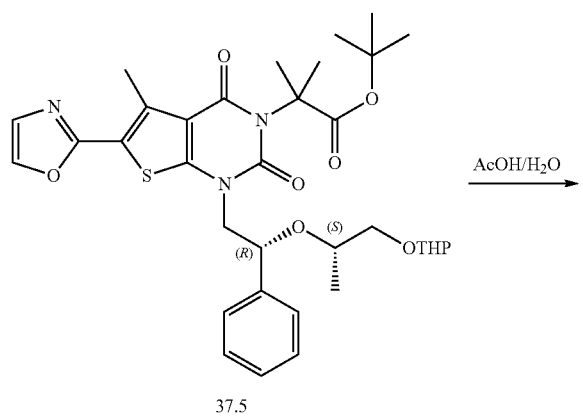
37.5
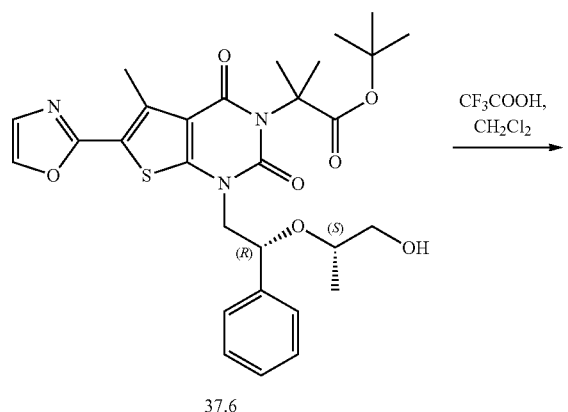
37.6
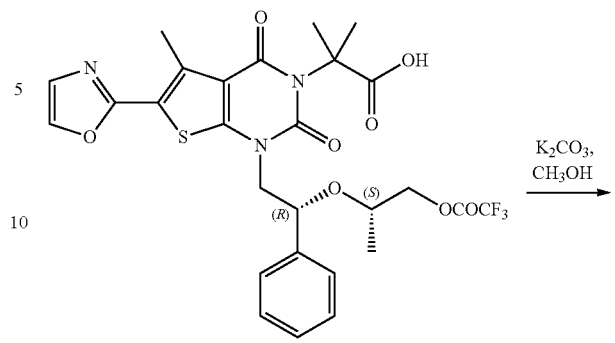
37.7
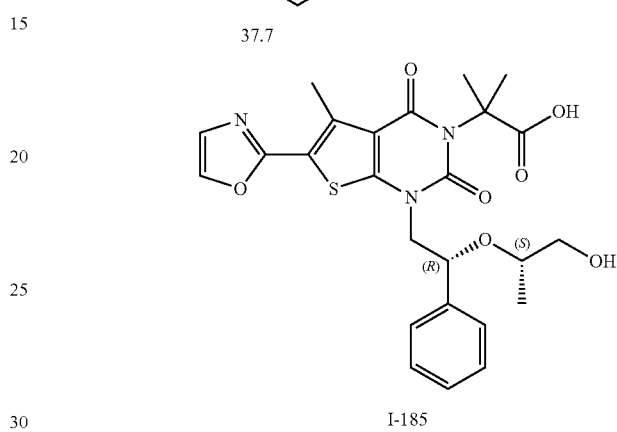
I-185
Compound I-185 was synthesized in a manner analogous to Example 31. Isolated a white solid in 0.061% overall yield from 37.1. MS (ES): m/z 514 (M+H)$^+$. $^1$H NMR (300 MHz, CD$_3$OD): δ 0.94 (s, 3H), 1.76 (s, 6H), 2.76 (s, 3H), 3.42-3.48 (m, 2H), 3.89-3.97 (m, 1H), 4.08-4.14 (m, 1H), 5.03-5.08 (m, 1H), 7.24-7.45 (m, 6H), 7.94 (s, 1H).
Example 38
Synthesis of Intermediate 38.6
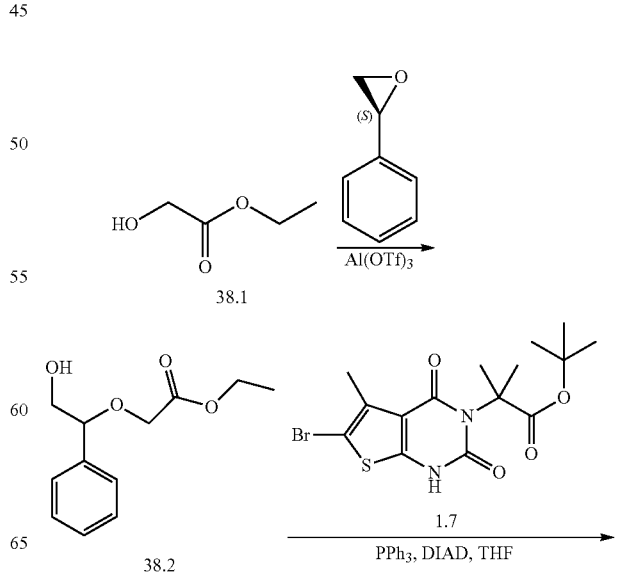
38.1
38.2

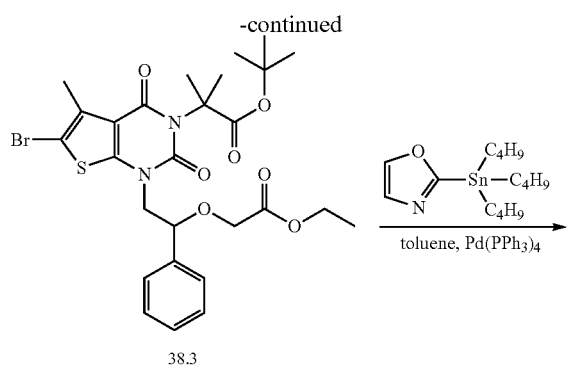

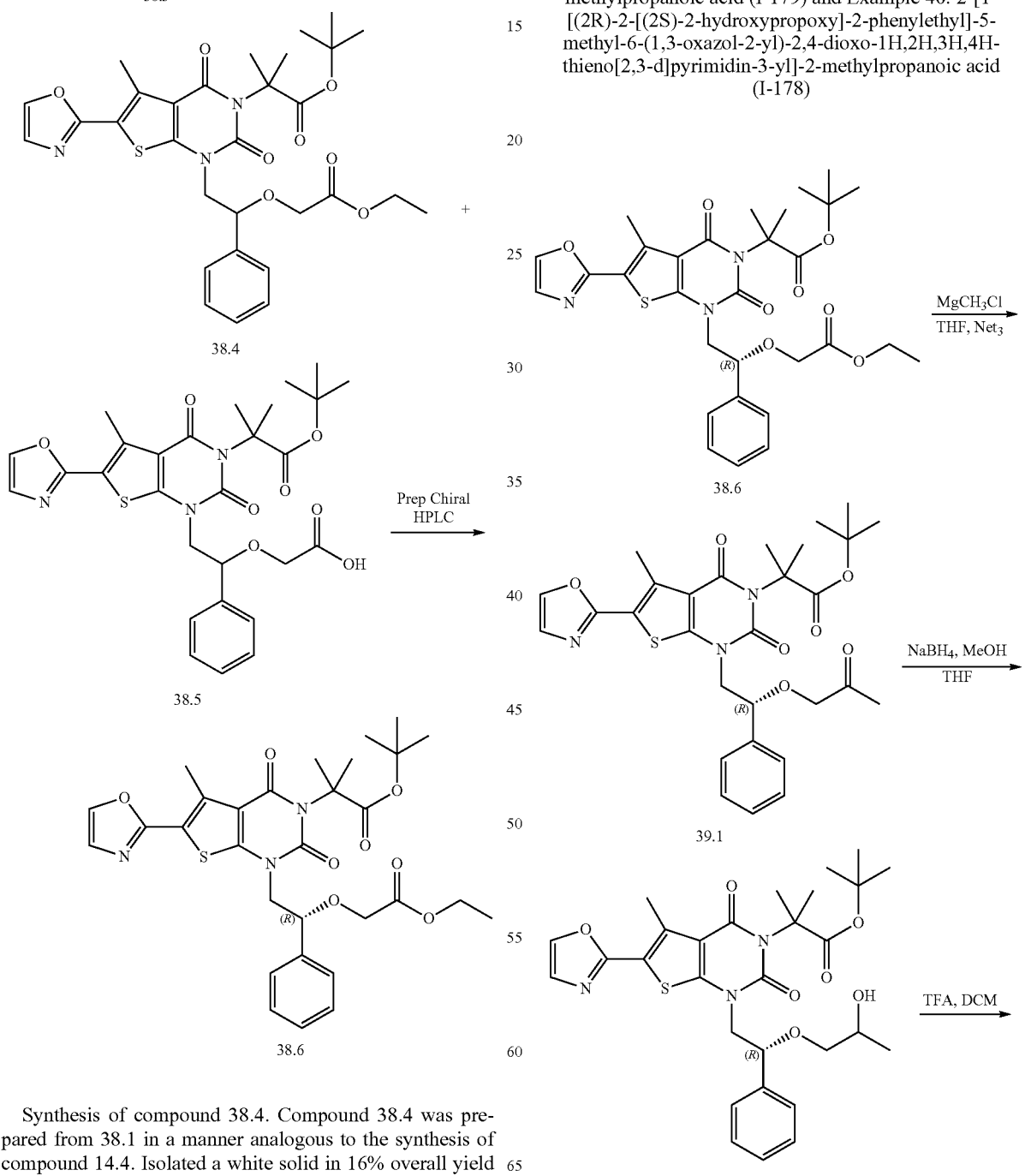

Synthesis of compound 38.4. Compound 38.4 was prepared from 38.1 in a manner analogous to the synthesis of compound 14.4. Isolated a white solid in 16% overall yield from 1.7 (1.1% from 38.1). The by-product 38.5 was also isolated.

Synthesis of compound 38.6. The enantiomers of 38.4 (240 mg) were separated by chiral preparative HPLC under the following conditions (Gilson Gx 281): Column: Chiralpak IC(SFC), 2*25 cm, 5 μm; mobile phase: hexanes and ethanol (hold at 25.0% ethanol for 25 min); detector: UV 220/254. 160 mg of a white solid product were obtained.

Example 39

Synthesis of 2-[1-[(2R)-2-[(2R)-2-hydroxypropoxy]-2-phenylethyl]-5-methyl-6-(1,3-oxazol-2-yl)-2,4-dioxo-1H,2H,3H,4H-thieno[2,3-d]pyrimidin-3-yl]-2-methylpropanoic acid (I-179) and Example 40: 2-[1-[(2R)-2-[(2S)-2-hydroxypropoxy]-2-phenylethyl]-5-methyl-6-(1,3-oxazol-2-yl)-2,4-dioxo-1H,2H,3H,4H-thieno[2,3-d]pyrimidin-3-yl]-2-methylpropanoic acid (I-178)

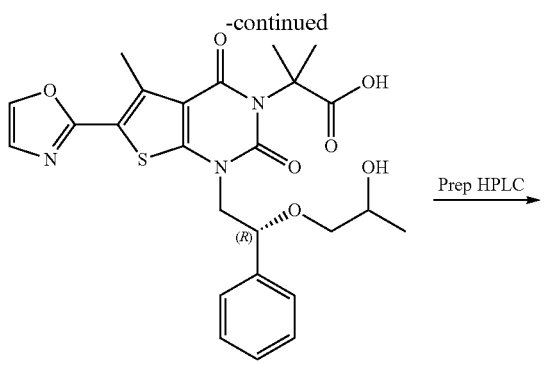

39.3

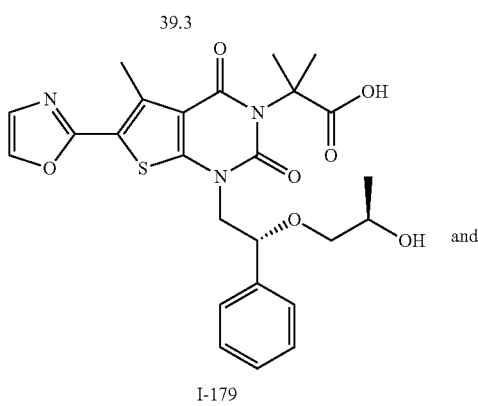

I-179

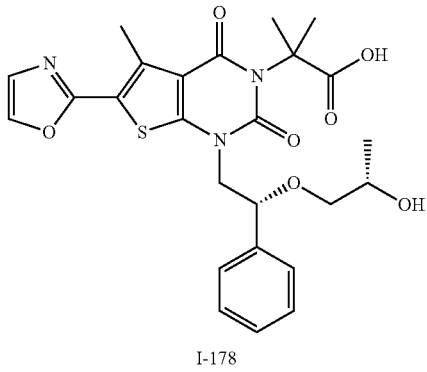

I-178

Synthesis of compound 39.1. Into a 100-mL 3-necked round-bottom flask was placed 38.6 (160 mg, 0.27 mmol, 1.00 equiv), tetrahydrofuran (20 mL) and Et₃N (54.1 mg, 0.54 mmol, 2.00 equiv). This was followed by the addition of chloro(methyl)magnesium (0.26 mL, 3M) in portions. The resulting solution was stirred for 3 h at −50° C. The reaction was then quenched by the addition of 20 mL of NH₄Cl (sat., aq). The resulting solution was extracted with 2×30 mL of ethyl acetate and the organic layers combined and dried over anhydrous sodium sulfate and concentrated under vacuum. The residue was applied onto a silica gel column with ethyl acetate/petroleum ether (1:15). Purification afforded 40 mg (26%) of 39.1 as a white solid.

Synthesis of compound 39.2. Into a 25-mL round-bottom flask was placed 39.1 (40 mg, 0.07 mmol, 1.00 equiv), methanol (10 mL) and NaBH₄ (2.6 mg, 0.07 mmol, 0.98 equiv). The resulting solution was stirred for 3 h at room temperature. The reaction was then quenched by the addition of 10 mL of water. The resulting solution was extracted with 2×15 mL of ethyl acetate and the organic layers combined and dried in an oven under reduced pressure. The residue was applied onto a silica gel column with ethyl acetate/petroleum ether (1:2). Purification afforded 30 mg (75%) of 39.2 as a white solid.

Synthesis of compound 39.3. Into a 25-mL round-bottom flask was placed 39.2 (30 mg, 0.05 mmol, 1.00 equiv), dichloromethane (5 mL) and trifluoroacetic acid (1 mL). The resulting solution was stirred overnight at room temperature. The resulting mixture was concentrated under vacuum. The residue was purified by thin layer chromatography developed with dichloromethane/methanol (20:1) to afford 20 mg (74%) of 39.3 as a white solid.

Resolution of Compounds I-179 and I-178. The enantiomers of 39.3 (20 mg) were purified by preparative HPLC under the following conditions (Waters): Column: XBridge Prep Phenyl OBD 5 μm, 19*150 mm; mobile phase: water (50 mM NH₄HCO₃) and CH₃CN (5.0% CH₃CN up to 95.0% in 10 min, hold at 95.0% in 2 min then down to 5.0% in 2 min); detector: UV 254/220 nm. Purification afforded 6.7 mg (34%; tR=8.55 min) of Compound I-179 as a white solid and 2.3 mg (12%, tR=9.47 min) of Compound I-178 as a white solid.

Analytical Data for Compound I-179: MS (ES): m/z 514 (M+H)⁺. ¹H NMR (300 MHz, CD₃OD): δ 0.94 (d, J=6.3 Hz, 3H), 1.75 (s, 6H), 2.76 (s, 3H), 3.05 (m, 1H), 3.76 (m, 1H), 3.92 (m, 1H), 4.16 (m, 1H), 7.22-7.46 (m, 6H), 7.92 (s, 1H).

Analytical Data for Compound I-178: MS (ES): m/z 514 (M+H)⁺. ¹H NMR (300 MHz, CD₃OD): δ 0.94 (d, J=6.3 Hz, 3H), 1.75 (s, 6H), 2.76 (s, 3H), 3.05 (m, 1H), 3.76 (m, 1H), 3.94 (m, 1H), 4.16 (m, 1H), 7.22-7.48 (m, 6H), 7.93 (s, 1H).

Example 40

Synthesis of 2-[1-[(2R)-2-(2-hydroxy-2-methylpropoxy)-2-phenylethyl]-5-methyl-6-(1,3-oxazol-2-yl)-2,4-dioxo-1H,2H,3H,4H-thieno[2,3-d]pyrimidin-3-yl]-2-methylpropanoic acid (I-175)

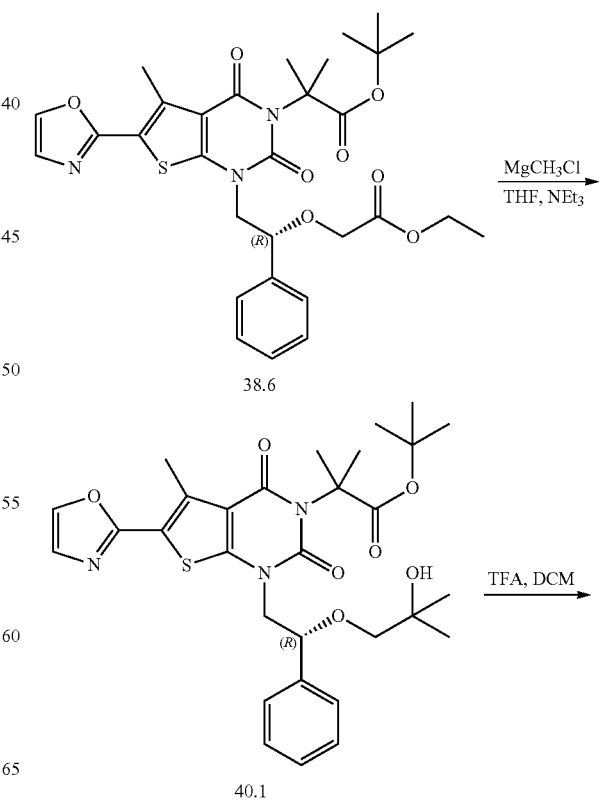

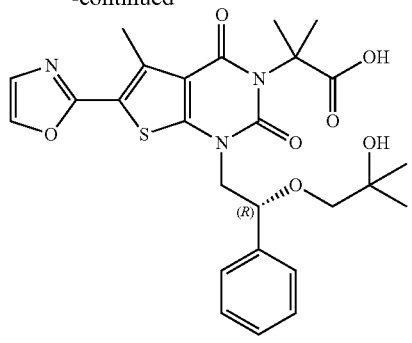

I-175

Synthesis of compound 40.1. Into a 25-mL round-bottom flask, purged and maintained with an inert atmosphere of nitrogen, was placed intermediate 38.6 (160 mg, 0.27 mmol, 1.00 equiv), tetrahydrofuran (10 mL), Et$_3$N (54.1 mg, 0.54 mmol, 2.00 equiv). This was followed by the addition of chloro(methyl)magnesium (0.26 mL, 3 M) dropwise with stirring at −78° C. The resulting solution was stirred for 3 h at −50° C. The reaction was then quenched by the addition of 10 mL of NH$_4$Cl (sat., aq.). The resulting solution was extracted with 3×15 mL of ethyl acetate and the organic layers combined and dried over anhydrous sodium sulfate and concentrated under vacuum. The residue was applied onto a silica gel column with ethyl acetate/petroleum ether (1:10). Purification afforded 40 mg (26%) of 40.1 as a white solid.

Synthesis of Compound I-175. Into a 25-mL round-bottom flask was placed compound 40.1 (40 mg, 0.07 mmol, 1.00 equiv), dichloromethane (5 mL) and trifluoroacetic acid (1 mL). The resulting solution was stirred for 2 h at room temperature. The resulting mixture was concentrated under vacuum. The residue was applied onto a silica gel column with dichloromethane/methanol (20:1). Purification afforded 23.4 mg (65%) of Compound I-175 as a white solid. MS (ES): m/z 528 (M+H)$^+$. $^1$H NMR (300 MHz, CD$_3$OD): δ 0.97 (s, 3H), 1.03 (s, 3H), 1.77 (s, 6H), 2.76 (s, 6H), 3.00 (d, J=9.0 Hz, 1H), 3.13 (d, J=9.0 Hz, 1H), 3.91 (dd, J=14.4, 9.0 Hz, 1H), 4.19 (dd, J=14.4, 3.9 Hz, 1H), 7.24-7.44 (m, 6H), 7.92 (s, 1H).

Example 41

Synthesis of 2-methyl-2-[5-methyl-6-(1,3-oxazol-2-yl)-2,4-dioxo-1-[(2R)-2-(2-oxopropoxy)-2-phenylethyl]-1H,2H,3H,4H-thieno[2,3-d]pyrimidin-3-yl] propanoic acid (I-229)

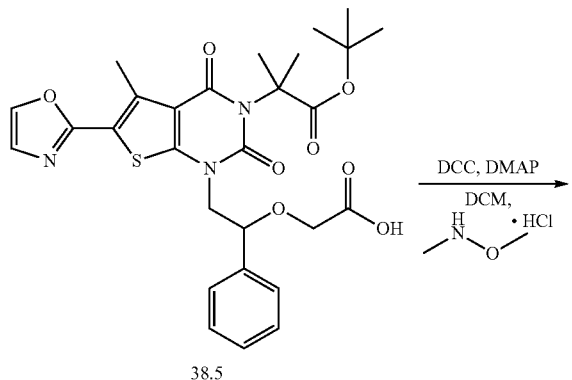

38.5

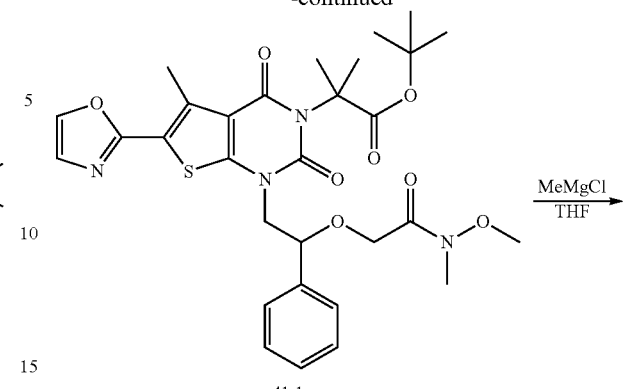

41.1

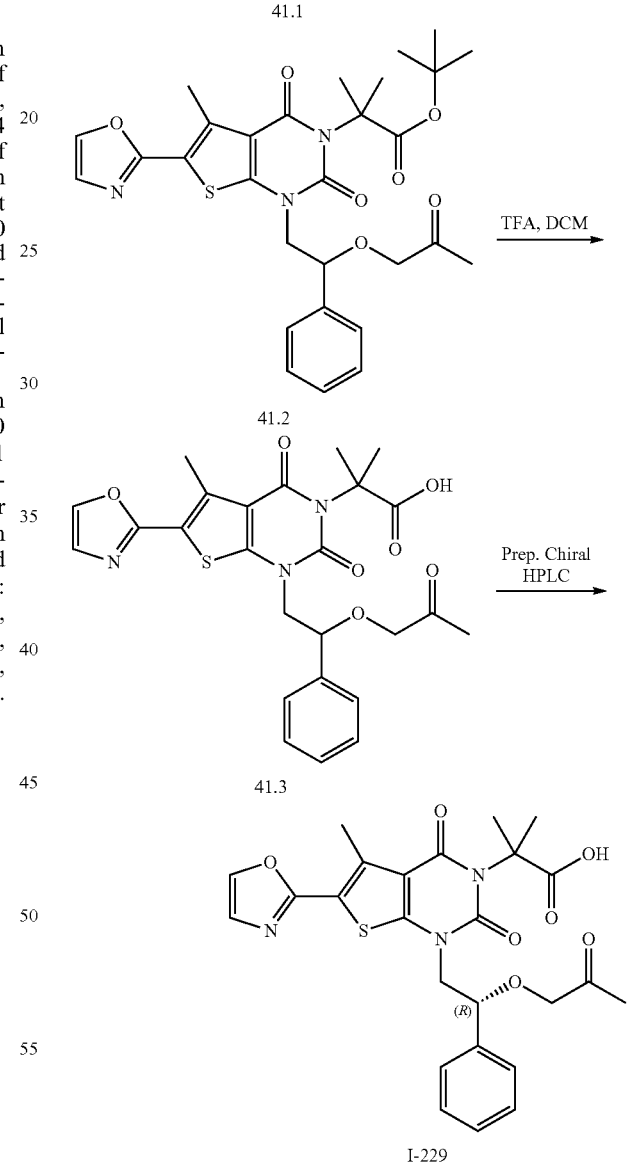

Synthesis of compound 41.1. Compound I-229 was prepared in a manner analogous to Compound I-121 (Example 4). Isolated 100 mg (46%) of 41.1 as a white solid.

Synthesis of compound 41.2. Into a 50-mL 3-necked round-bottom flask, purged and maintained with an inert atmosphere of nitrogen, was placed 41.1 (100 mg, 0.16 mmol, 1.00 equiv) and tetrahydrofuran (10 mL). This was followed by the addition of chloro(methyl)magnesium (3 M) (0.05 mL, 2.00 equiv) dropwise with stirring at −50° C. The resulting solution was stirred for 2 h at room temperature. The resulting mixture was concentrated under vacuum. The residue was applied onto a silica gel column with ethyl acetate/petroleum ether (1:2). Purification afforded 55 mg (59%) of 41.2 as a white solid.

Synthesis of compound 41.3. Into a 10-mL round-bottom flask was placed trifluoroacetic acid (1 mL), 41.2 (55 mg, 0.10 mmol, 1.00 equiv) and dichloromethane (5 mL). The solution was stirred overnight at room temperature. The resulting mixture was concentrated under vacuum. The residue was applied onto a silica gel column with dichloromethane/methanol (40:1). Purification afforded 10 mg (20%) of 41.3 as a white solid.

Synthesis of Compound I-229. The crude product (1 g) was purified by chiral preparative HPLC under the following conditions (Gilson Gx 281): Column: Chiralpak IC, 2*25 cm, 5 μm; mobile phase: hexanes (0.1% TFA) and ethanol (0.1% TFA) (hold at 15% ethanol (0.1% TFA) in 30 min); detector: UV 220/254 nm. Purification afforded 3.0 mg (30%) of Compound I-229 as a white solid. MS (ES): m/z 512 (M+H)$^+$. $^1$H NMR (300 MHz, CD$_3$OD): δ 1.82 (s, 6H), 1.98 (s, 3H), 2.81 (s, 3H), 3.88-4.07 (m, 3H), 4.26 (d, 1H), 4.94 (m, 1H), 7.37 (s, 1H), 7.38-7.49 (m, 5H), 7.98 (s, 1H).

Example 42

Synthesis of Intermediate 42.1

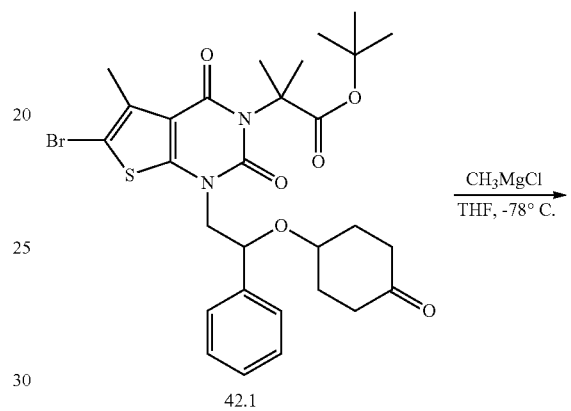

Synthesis of Intermediate 42.1. Into a 250-mL 3-necked round-bottom flask, purged and maintained with an inert atmosphere of nitrogen, was placed 19.2 (1.6 g, 6.83 mmol, 1.84 equiv), tetrahydrofuran (60 mL), DIAD (1.5 g, 7.42 mmol, 1.99 equiv), PPh$_3$ (1.9 g, 7.24 mmol, 1.95 equiv) and 1.7 (1.5 g, 3.72 mmol, 1.00 equiv). The resulting solution was stirred for 4 h at room temperature and then concentrated under vacuum. The residue was applied onto a silica gel column with ethyl acetate/petroleum ether (1:50). Purification afforded 1 g (43%) of intermediate 42.1 as a white solid.

Example 43

Synthesis of 2-(1-((R)-2-(((1r,4R)-4-hydroxy-4-methylcyclohexyl)oxy)-2-phenylethyl)-5-methyl-6-(oxazol-2-yl)-2,4-dioxo-1,2-dihydrothieno[2,3-d]pyrimidin-3(4H)-yl)-2-methylpropanoic acid (I-163)

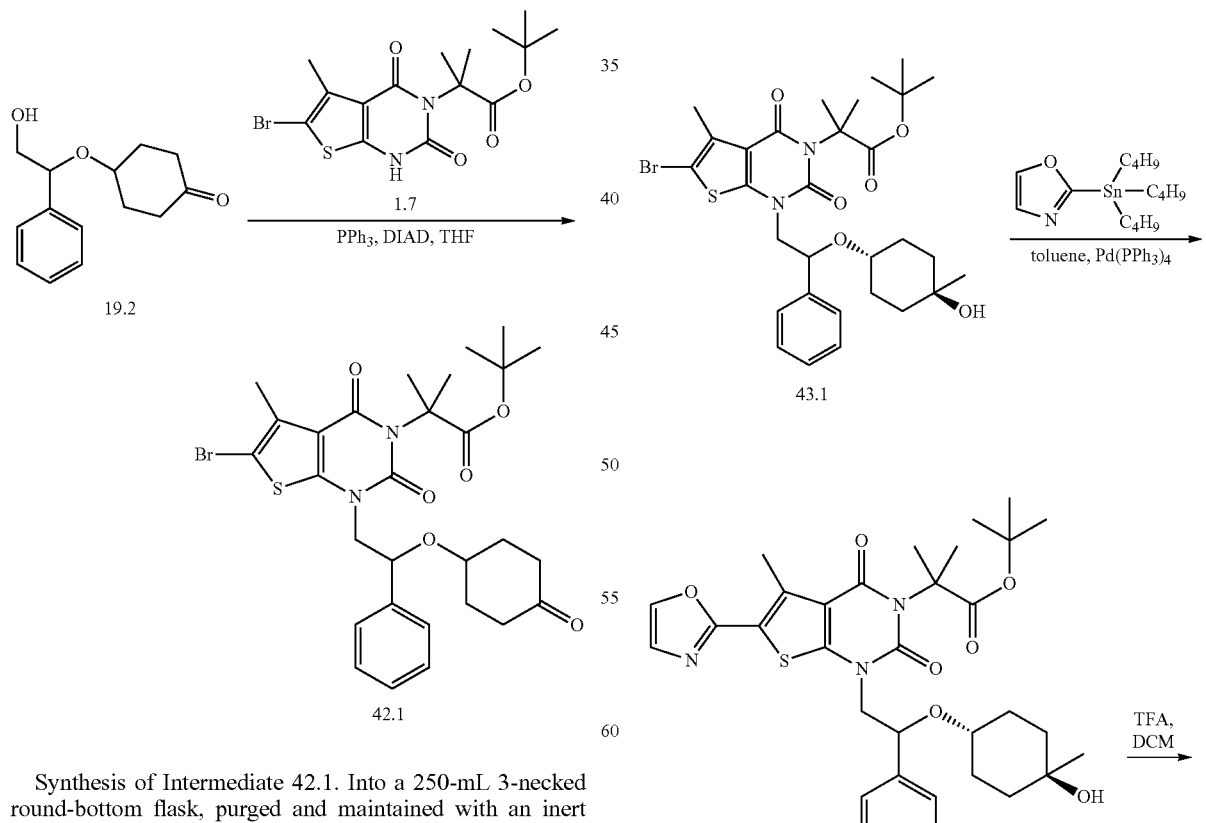

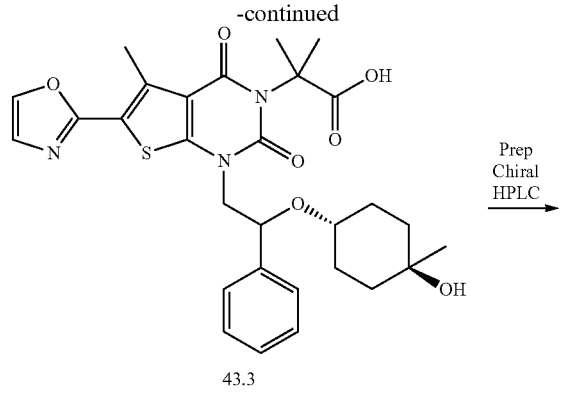

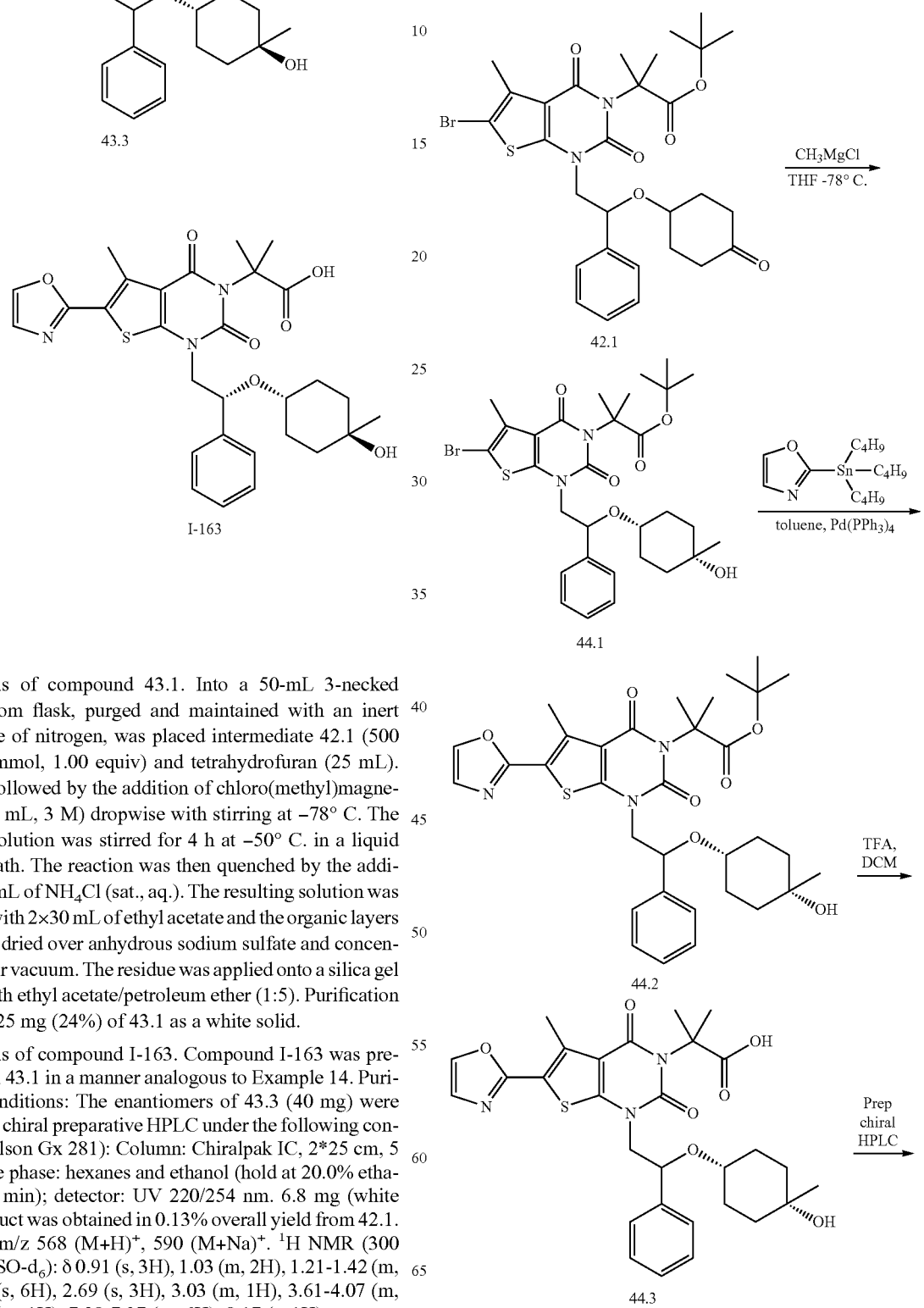

Example 44

Synthesis of 2-(1-((R)-2-(((1s,4S)-4-hydroxy-4-methylcyclohexyl)oxy)-2-phenylethyl)-5-methyl-6-(oxazol-2-yl)-2,4-dioxo-1,2-dihydrothieno[2,3-d]pyrimidin-3(4H)-yl)-2-methylpropanoic acid (I-168)

Synthesis of compound 43.1. Into a 50-mL 3-necked round-bottom flask, purged and maintained with an inert atmosphere of nitrogen, was placed intermediate 42.1 (500 mg, 0.81 mmol, 1.00 equiv) and tetrahydrofuran (25 mL). This was followed by the addition of chloro(methyl)magnesium (0.52 mL, 3 M) dropwise with stirring at −78° C. The resulting solution was stirred for 4 h at −50° C. in a liquid nitrogen bath. The reaction was then quenched by the addition of 10 mL of NH$_4$Cl (sat., aq.). The resulting solution was extracted with 2×30 mL of ethyl acetate and the organic layers combined, dried over anhydrous sodium sulfate and concentrated under vacuum. The residue was applied onto a silica gel column with ethyl acetate/petroleum ether (1:5). Purification afforded 125 mg (24%) of 43.1 as a white solid.

Synthesis of compound I-163. Compound I-163 was prepared from 43.1 in a manner analogous to Example 14. Purification conditions: The enantiomers of 43.3 (40 mg) were purified by chiral preparative HPLC under the following conditions (Gilson Gx 281): Column: Chiralpak IC, 2*25 cm, 5 µm; mobile phase: hexanes and ethanol (hold at 20.0% ethanol for 12 min); detector: UV 220/254 nm. 6.8 mg (white solid) product was obtained in 0.13% overall yield from 42.1. MS (ES): m/z 568 (M+H)$^+$, 590 (M+Na)$^+$. $^1$H NMR (300 MHz, DMSO-d$_6$): δ 0.91 (s, 3H), 1.03 (m, 2H), 1.21-1.42 (m, 6H), 1.61 (s, 6H), 2.69 (s, 3H), 3.03 (m, 1H), 3.61-4.07 (m, 3H), 4.82 (m, 1H), 7.28-7.37 (m, 6H), 8.17 (s, 1H).

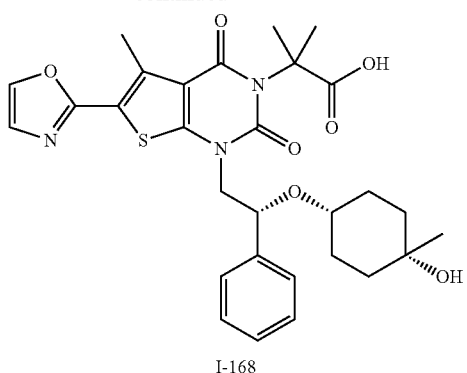

I-168

Compound I-168 was prepared in a manner analogous to Example 43. Isolated a white solid in 5.1% overall yield from 42.1. MS (ES): m/z 568 (M+H)$^+$, 590 (M+Na)$^+$. $^1$H NMR (300 MHz, CD$_3$OD): δ 0.81 (s, 3H), 0.99 (m, 1H), 1.14 (m, 2H), 1.25-1.61 (m, 5H), 1.78 (m, 6H), 2.77 (s, 3H), 3.51 (m, 1H), 3.71 (m, 1H), 4.33 (m, 1H), 4.92 (m, 1H), 7.25-7.47 (m, 6H), 7.95 (s, 1H).

Example 45

Synthesis of Intermediate 45.2

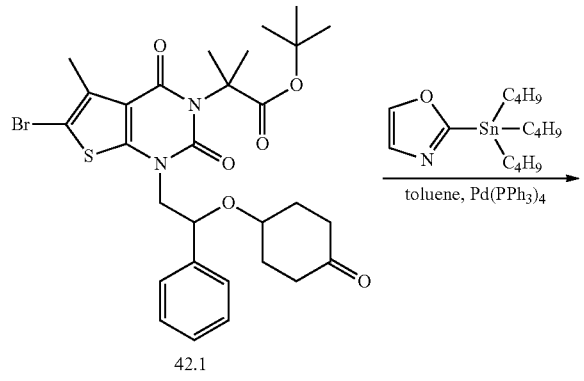

Synthesis of compound 45.1. Compound 45.1 was prepared from 2-(tributylstannyl)oxazole and 42.1 in a manner analogous to the synthesis of I-120 (Example 2). Isolated a white solid in 45% yield.

Synthesis of Intermediate 45.2. The enantiomers of racemic 45.1 (220 mg) were separated by chiral preparative HPLC under the following conditions (Gilson Gx 281): Column: Chiralpak IC, 2*25 cm, 5 μm; mobile phase: hexanes (0.1% TEA) and IPA (hold at 25.0% IPA for 40 min); detector: UV 220/254 nm. 80 mg (white solid) of the product were obtained.

Example 46

Synthesis of 2-[1-[(2R)-2-[(4-hydroxycyclohexyl)oxy]-2-phenylethyl]-5-methyl-6-(1,3-oxazol-2-yl)-2,4-dioxo-1H,2H,3H,4H-thieno[2,3-d]pyrimidin-3-yl]-2-methylpropanoic acid (I-164)

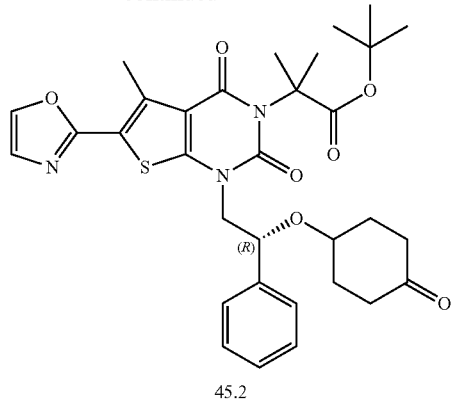

45.2

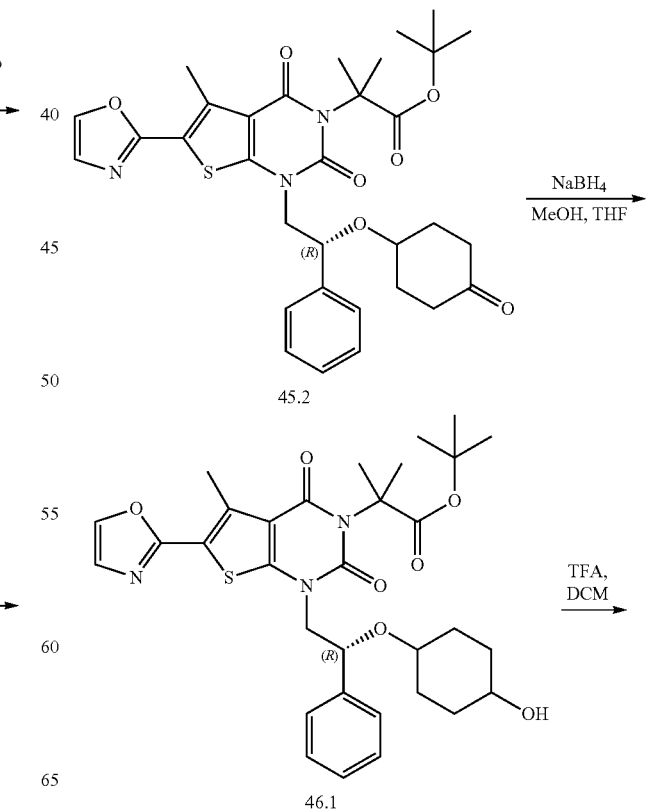

285
-continued

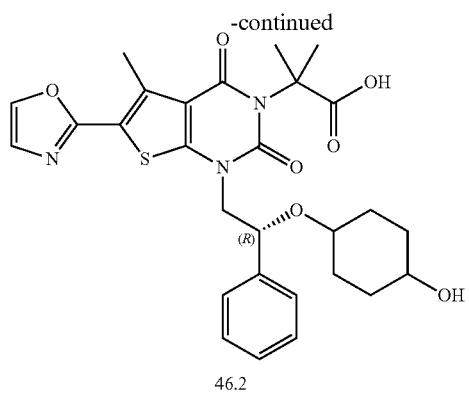

46.2

Prep.
HPLC
→

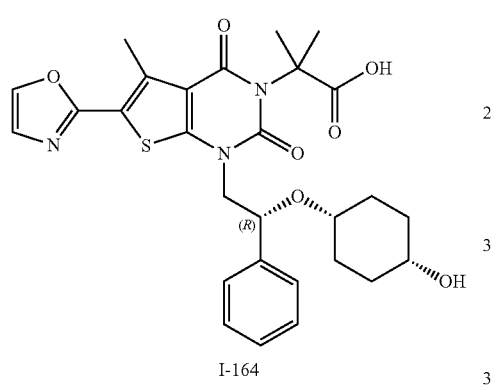

I-164

Synthesis of 46.1. Into a 50-mL round-bottom flask was placed intermediate 45.2 (40 mg, 0.07 mmol, 1.00 equiv), methanol (10 mL) and NaBH$_4$ (3.7 mg, 0.10 mmol, 1.53 equiv). The resulting solution was stirred for 3 h at room temperature whereupon it was concentrated under vacuum. The residue was purified by preparative TLC with ethyl acetate/petroleum ether (1:5) to afford 35 mg (87%) of 46.1 as a white solid.

Synthesis of Compound I-164. Compound I-164 was prepared from 46.1 in a manner analogous to compound 2.5. Isolated a white solid in 28% yield from 46.1. Purification conditions: The crude product (30 mg) was purified by preparative HPLC under the following conditions (Waters): Column: XBridge Shield RP18 OBD column, 5 μm, 19*150 mm; mobile phase: water (50 mM NH$_4$HCO$_3$) and CH$_3$CN (6.0% CH$_3$CN up to 50.0% in 14 min); detector: UV 254/220 nm. Purification afforded 9 mg of Compound I-164 (tR=7.86 min) as a white solid. MS (ES): m/z 554 (M+H)$^+$, 576 (M+Na)$^+$, 617 (M+Na+CH$_3$CN)$^+$.

286

Example 47

Synthesis of 2-(1-((R)-2-(((1r,4R)-4-aminocyclohexyl)oxy)-2-phenylethyl)-5-methyl-6-(oxazol-2-yl)-2,4-dioxo-1,2-dihydrothieno[2,3-d]pyrimidin-3(4H)-yl)-2-methylpropanoic acid (I-166) and Example 48: Synthesis of 2-(1-((R)-2-(((1s,4S)-4-aminocyclohexyl)oxy)-2-phenylethyl)-5-methyl-6-(oxazol-2-yl)-2,4-dioxo-1,2-dihydrothieno[2,3-d]pyrimidin-3(4H)-yl)-2-methylpropanoic acid (I-167)

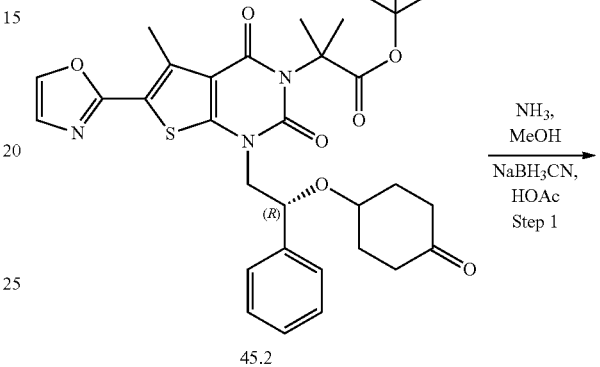

45.2

NH$_3$,
MeOH
NaBH$_3$CN,
HOAc
Step 1
→

47.1

TFA,
DCM
Step 2
→

47.2

Prep.
HPLC
Step 3
→

3.45-3.51 (m, 1H), 3.92-3.96 (m, 1H), 4.23 (m, 1H), 4.85-5.04 (m, 1H), 7.25-7.57 (m, 6H), 7.95 (s, 1H).

Example 49

Synthesis of Intermediate 49.4

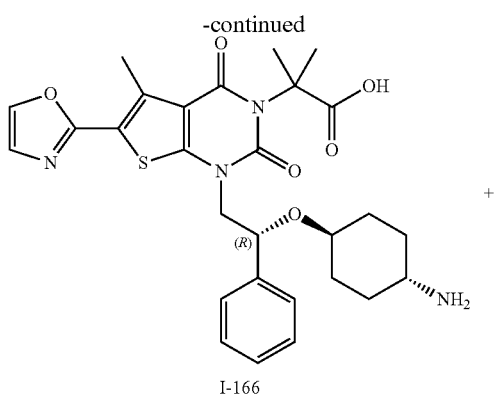

I-166

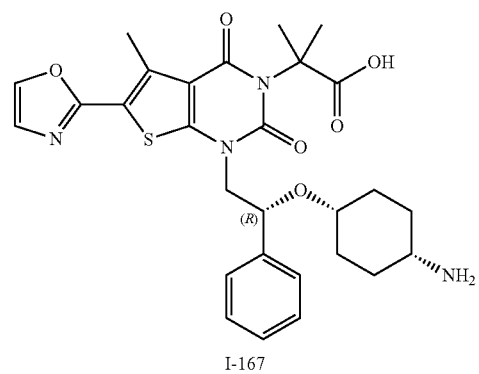

I-167

Synthesis of compound 47.1. Into a 50-mL round-bottom flask was placed intermediate 45.2 (40 mg, 0.07 mmol, 1.00 equiv), methanol/NH₃ (10 mL), acetic acid (4 mg, 0.07 mmol, 1.01 equiv) and NaBH₃CN (8 mg, 0.13 mmol, 1.93 equiv). The resulting solution was stirred overnight at room temperature whereupon it was concentrated under vacuum. The residue was purified by preparative TLC with DCM/methanol (1:20) to afford 26 mg (65%) of 47.1 as a white solid.

Synthesis of compound 47.2. Compound 47.2 was prepared from 47.1 in a manner analogous to compound 2.5. Isolated a white solid in 64% yield.

Synthesis of Compounds I-166 and I-167. The enantiomers of 47.2 (15 mg) were separated by preparative HPLC under the following conditions (Waters): Column: XBridge Shield RP18 OBD Column, 5 μm, 19*150 mm; mobile phase: water (with 50 mM NH₄HCO₃) and CH₃CN (20.0% CH₃CN up to 80.0% in 25 min); detector: UV 254/220 nm. 0.6 mg of Compound I-166 (tR=18.73 min; white solid, 5.1% yield from 47.2) and 0.5 mg of Compound I-167 (tR=22.06 min; white solid, 1.9% yield from 47.2) were obtained.

Analytical Data for Compound I-166: MS (ES): m/z 553 (M+H)⁺. ¹H NMR (300 MHz, CD₃OD): δ 0.82-0.86 (m, 2H), 1.09-1.26 (m, 12H), 1.76-1.95 (m, 10H), 2.77 (s, 3H), 3.41-3.70 (m, 2H), 4.96-5.01 (m, 2H), 7.23-7.47 (m, 6H), 7.93 (s, 1H).

Analytical Data for Compound I-167: MS (ES): m/z 553 (M+H)⁺. ¹H NMR (300 MHz, CD₃OD): δ 1.18-1.78 (m, 14H), 1.90-1.95 (m, 1H), 2.79 (s, 3H), 2.86-2.91 (m, 1H),

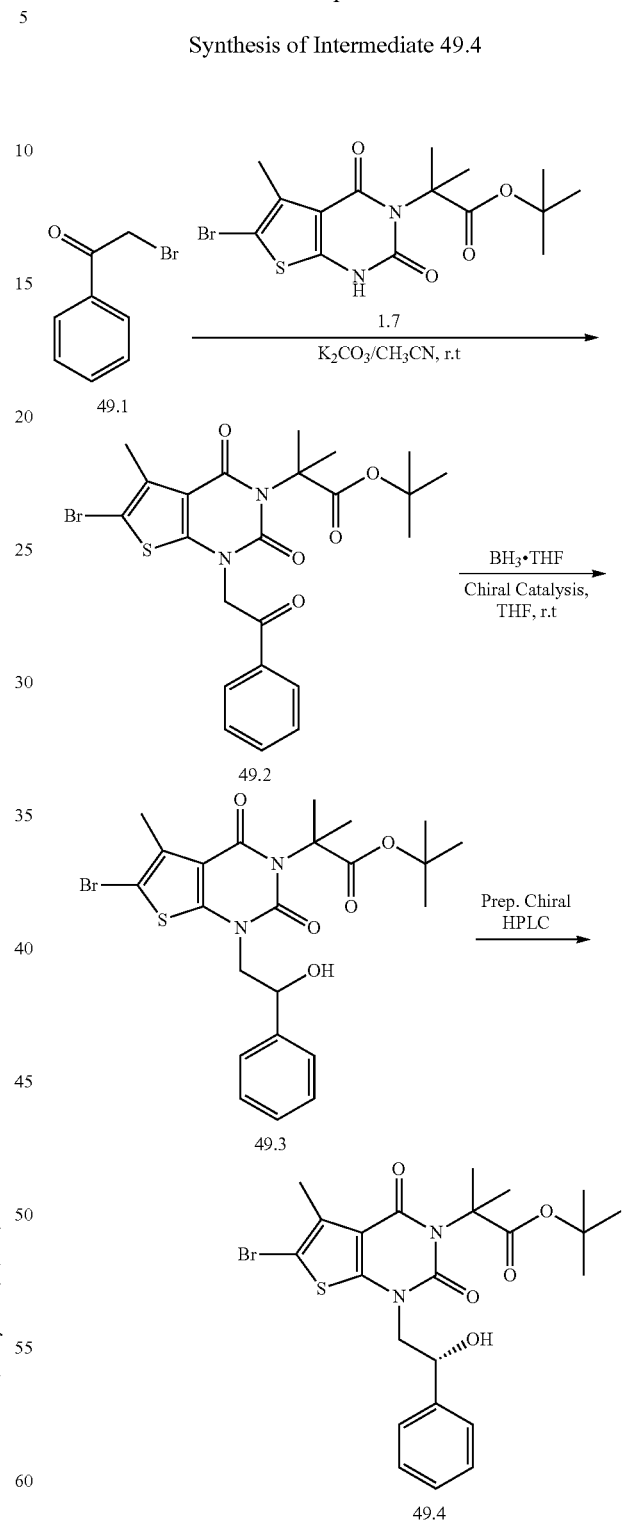

Synthesis of compound 49.2. To a solution of 1.7 (1.5 g, 3.72 mmol, 1.00 equiv) in CH₃CN (20 mL) were added potassium carbonate (1.54 g, 11.14 mmol, 3.00 equiv) and 2-bromo-1-phenylethan-1-one (770 mg, 3.87 mmol, 1.05 equiv). The resulting solution was stirred for 3 h at room temperature. The reaction was then quenched by the addition of 20 mL of water. The mixture was extracted with 3×30 mL of ethyl acetate and the organic layers combined, washed with 2×40 mL of sodium chloride (sat.), dried over anhydrous sodium sulfate and concentrated under vacuum. The residue was applied onto a silica gel column with ethyl acetate/petroleum ether (1:5). Purification afforded 1.8 g (93%) of 49.2 as a white solid.

Synthesis of compound 49.3. Into a 50-mL round-bottom flask was placed a solution of 49.2 (1.5 g, 2.88 mmol, 1.00 equiv) and (R)—CBS (239 mg, 0.86 mmol, 0.30 equiv) in tetrahydrofuran (15 mL). This was followed by the addition of a solution of BH$_3$-THF (4 mL, 1.50 equiv) in tetrahydrofuran (5 mL) dropwise with stirring in 8 hr. The resulting solution was stirred overnight at room temperature. The reaction was then quenched by the addition of 15 mL of NH$_4$Cl (sat., aq.). The mixture was extracted with 3×20 mL of ethyl acetate and the organic layers combined and washed with 2×30 mL of sodium chloride (sat.). The solid was dried in an oven under reduced pressure. The residue was applied onto a silica gel column with ethyl acetate/petroleum ether (1:15). Purification afforded 1.4 g (93%) of 49.3 as a white solid.

Synthesis of compound 49.4. The enantiomers of 49.3 (1.4 g, 2.67 mmol, 1.00 equiv) were separated by preparative SFC under the following conditions: Column: Phenomenex Lux 5 u Cellulose-3, 5*25 cm, 5 μm; mobile phase: CO$_2$ (80%), methanol (20%); detector: UV 254 nm. Purification afforded 0.98 g of 49.4 as a white solid as well as 0.3 g of tert-butyl 2-[6-bromo-1-[(2S)-2-hydroxy-2-phenylethyl]-5-methyl-2,4-dioxo-1H,2H,3H,4H-thieno[2,3-d]pyrimidin-3-yl]-2-methylpropanoate, also as a white solid.

Example 50

Synthesis of 2-[1-[(2R)-2-[(3-hydroxyazetidin-1-yl)carbonyloxy]-2-phenylethyl]-5-methyl-6-(1,3-oxazol-2-yl)-2,4-dioxo-1H,2H,3H,4H-thieno[2,3-d]pyrimidin-3-yl]-2-methylpropanoic acid (I-230)

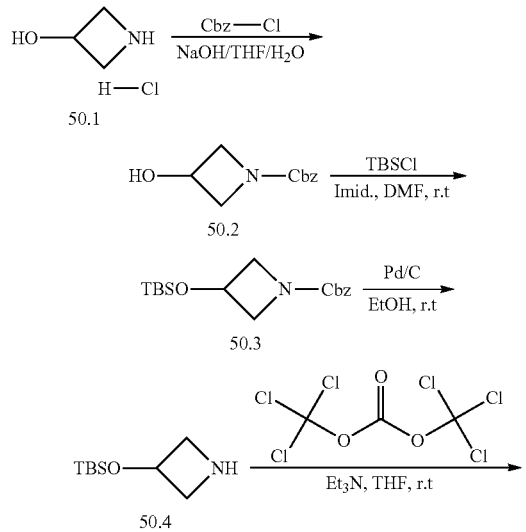

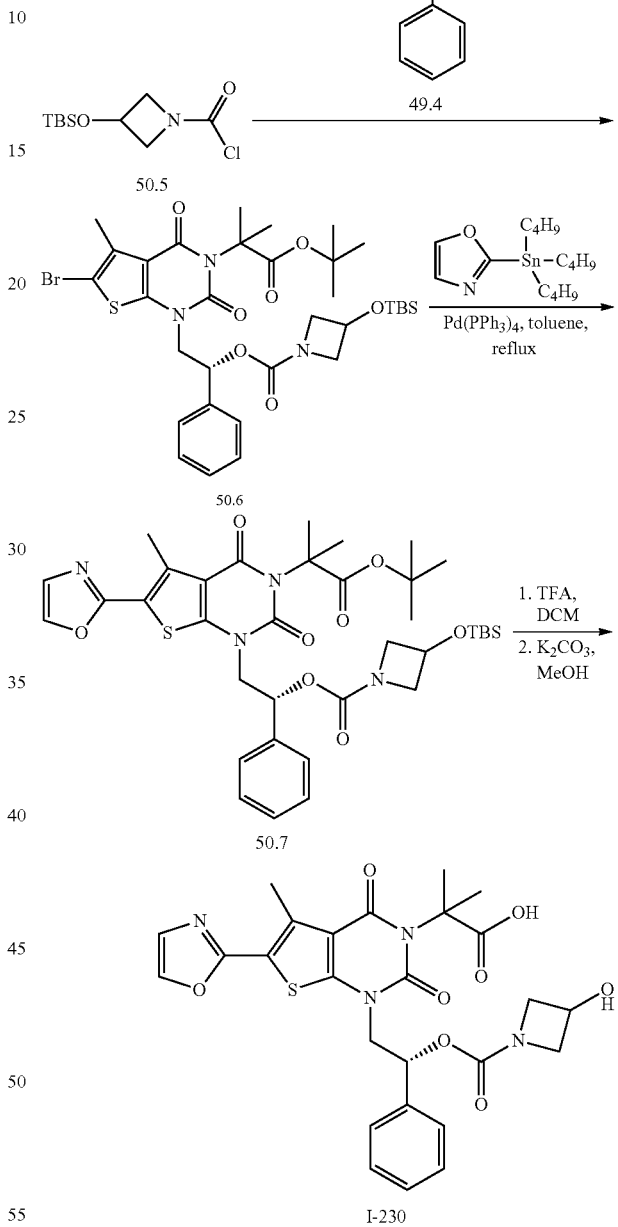

Synthesis of compound 50.2. To a solution of azetidin-3-ol hydrochloride (2 g, 18.26 mmol, 1.00 equiv) and sodium hydroxide (1.53 g, 38.25 mmol, 2.10 equiv) in water (10 mL) and tetrahydrofuran (25 mL) was added Cbz-Cl (3.27 g, 19.17 mmol, 1.05 equiv) dropwise with stirring at 0° C. over 30 min. The resulting solution was stirred for 3 h at room temperature. The reaction was then quenched by the addition of 20 mL of water. The mixture was extracted with 3×30 mL of ethyl acetate and the organic layers combined. The resulting mixture was washed with 2×40 mL of sodium chloride (sat.). The mixture was dried over anhydrous sodium sulfate and concentrated under vacuum. The residue was applied onto a silica gel column with ethyl acetate/petroleum ether (1:1). Purification afforded 2.0 g (53%) of benzyl 3-hydroxyazetidine-1-carboxylate (50.2) as a light yellow liquid.

Synthesis of compound 50.3. Into a 50-mL round-bottom flask was placed benzyl 3-hydroxyazetidine-1-carboxylate (2.15 g, 10.38 mmol, 1.00 equiv), TBSCl (2.34 g, 15.60 mmol, 1.50 equiv), imidazole (1.27 g, 18.68 mmol, 1.80 equiv) and N,N-dimethylformamide (15 mL). The resulting solution was stirred overnight at room temperature. The reaction was then quenched by the addition of 30 mL of water. The mixture was extracted with 3×40 mL of ethyl acetate and the organic layers combined. The resulting mixture was washed with 2×50 mL of sodium chloride (sat.). The mixture was dried over anhydrous sodium sulfate and concentrated under vacuum. The residue was applied onto a silica gel column with ethyl acetate/petroleum ether (1:5). Purification afforded 3.0 g (90%) of benzyl 3-[(tert-butyldimethylsilyl)oxy]azetidine-1-carboxylate (50.3) as a light yellow liquid.

Synthesis of compound 50.4. Into a solution of benzyl 3-[(tert-butyldimethylsilyl)oxy]azetidine-1-carboxylate (4.2 g, 13.06 mmol, 1.00 equiv) in ethanol (15 mL) was added palladium carbon (1.3 g, 0.30 equiv) at 0° C. in water/ice bath. The resulting solution was stirred overnight at room temperature. The solids were filtered off. The resulting mixture was concentrated under vacuum to afford 2.2 g (90%) of 3-[(tert-butyldimethylsilyl)oxy]azetidine (50.4) as a light yellow liquid.

Synthesis of compound 50.5. To a solution of ditrichloromethyl carbonate (2.38 g, 8.02 mmol, 1.50 equiv) in dichloromethane (20 mL) was added a solution of 3-[(tert-butyldimethylsilyl)oxy]azetidine (1 g, 5.34 mmol, 1.00 equiv) in dichloromethane (5 mL) dropwise with stirring at 0° C. over 30 min. Stirring was continued for 30 min whereupon a solution of triethylamine (810 mg, 8.00 mmol, 1.50 equiv) in dichloromethane (5 mL) was added dropwise with stirring at 0° C. in 30 min. The resulting solution was stirred overnight at room temperature. The reaction was then quenched by the addition of 20 mL of sodium bicarbonate (sat.). The resulting solution was extracted with 3×20 mL of ethyl acetate and the organic layers combined, washed with 2×40 mL of sodium chloride (sat.), dried over anhydrous sodium sulfate and concentrated under vacuum. The residue was applied onto a silica gel column with ethyl acetate/petroleum ether (1:15). Purification afforded 1.3 g (97%) of 3-[(tert-butyldimethylsilyl)oxy]azetidine-1-carbonyl chloride as a light yellow liquid.

Synthesis of compound 50.6. Into a 50-mL 3-necked round-bottom flask was placed a solution of 49.4 (200 mg, 0.38 mmol, 1.00 equiv) in tetrahydrofuran (10 mL). This was followed by the addition of sodium hydride (46 mg, 1.15 mmol, 3.00 equiv, 60%) at 0° C. The resulting solution was stirred for 0.5 h at 0° C. To this was added a solution of 3-[(tert-butyldimethylsilyl)oxy]azetidine-1-carbonyl chloride (142 mg, 0.57 mmol, 1.50 equiv) in tetrahydrofuran (3 mL) dropwise with stirring at 0° C. The resulting solution was allowed to react, with stirring, overnight at room temperature. The reaction was then quenched by the addition of 10 mL of water. The resulting solution was extracted with 3×20 mL of ethyl acetate and the organic layers combined. The resulting mixture was washed with 2×20 mL of brine. The mixture was dried over sodium sulfate and concentrated under vacuum. The residue was applied onto a silica gel column with PE/EA (6/1). Purification afforded 220 mg (78%) of 50.6 as a white solid.

Synthesis of compound 50.7. Into a 50-mL round-bottom flask flushed with nitrogen was placed toluene (10 mL), 50.6 (310 mg, 0.42 mmol, 1.00 equiv), Pd(PPh$_3$)$_4$ (97 mg, 0.08 mmol, 0.20 equiv) and 2-(tributylstannyl)-1,3-oxazole (181 mg, 0.51 mmol, 1.20 equiv). The resulting solution was heated to reflux overnight in an oil bath. The resulting mixture was concentrated under vacuum. The residue was applied onto a silica gel column with ethyl acetate/petroleum ether (1:10). Purification afforded 0.190 g (62%) of 50.7 as a white solid.

Synthesis of Compound I-230. Into a 50-mL round-bottom flask was placed dichloromethane (20 mL), 50.7 (190 mg, 0.26 mmol, 1.00 equiv) and trifluoroacetic acid (4 mL). The resulting solution was stirred for 4 h at room temperature whereupon it was concentrated under vacuum. The residue was dissolved in 5 mL of methanol. The pH value of the solution was adjusted to 10 with potassium carbonate. The resulting mixture was concentrated under vacuum. The crude product (150 mg) was purified by preparative HPLC under the following conditions (Waters): Column: XBridge Prep C18 OBD, 5 μm, 19*150 mm; mobile phase: water (50 mM NH$_4$HCO$_3$) and CH$_3$CN (5% CH$_3$CN up to 23% in 3 min, hold at 23% for 11.5 min, then up to 95% in 2 min, then down to 5% in 2 min); detector: UV 254/220 nm. 56.5 mg (39.5%) of I-230 were obtained as a white solid. MS (ES): m/z 555 (M+H)$^+$. $^1$H NMR (300 MHz, CD$_3$OD): δ 1.72-1.75 (d, 6H), 2.79 (s, 3H), 3.37-3.80 (m, 2H), 3.97-4.41 (m, 4H), 6.05-6.09 (m, 1H), 7.24 (s, 1H), 7.29-7.46 (m, 5H), 7.95 (s, 1H).

Example 51

Synthesis of 2-methyl-2-[5-methyl-1-[(2R)-2-[(morpholin-4-yl)carbonyloxy]-2-phenylethyl]-6-(1,3-oxazol-2-yl)-2,4-dioxo-1H,2H,3H,4H-thieno[2,3-d]pyrimidin-3-yl]propanoic acid (I-231)

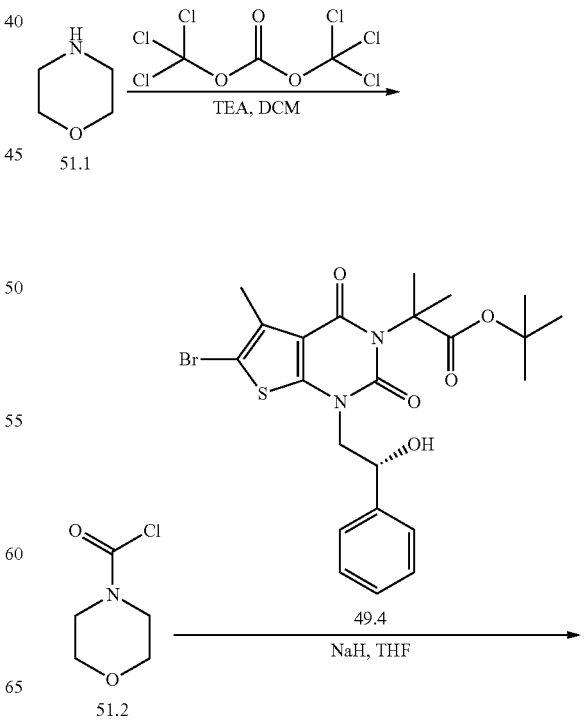

3.15-3.64 (m, 8H), 4.11-4.17 (m, 1H), 4.41-4.45 (m, 1H), 6.27-6.30 (m, 1H), 7.32 (s, 1H), 7.38-7.52 (m, 5H), 8.03 (s, 1H).

Example 52

Synthesis of 2-[1-[2-(2-methoxyphenyl)ethyl]-5-methyl-6-(1,3-oxazol-2-yl)-2,4-dioxo-1H,2H,3H,4H-thieno[2,3-d]pyrimidin-3-yl]-2-methylpropanoic acid (I-232)

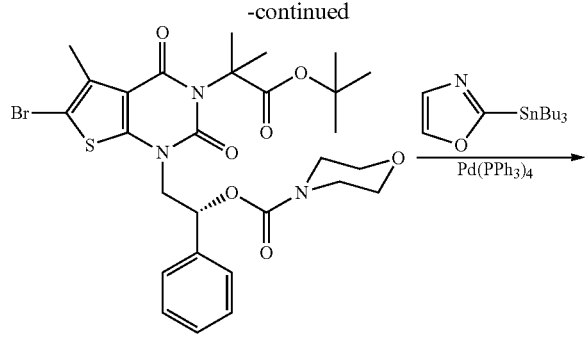

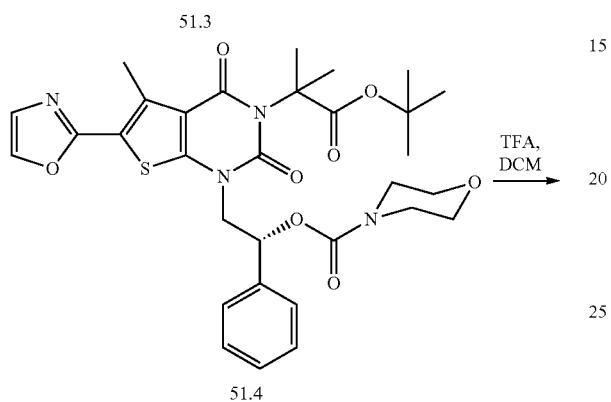

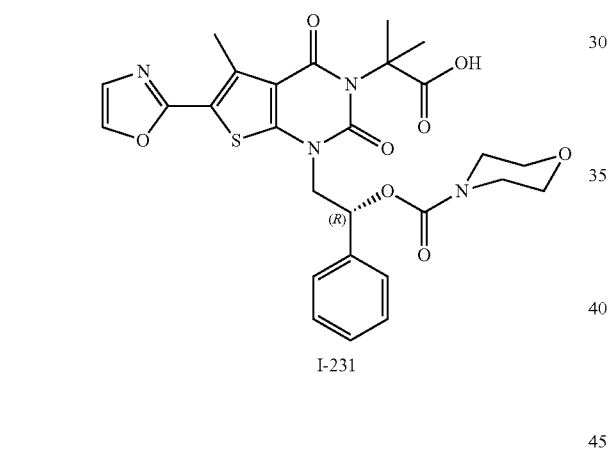

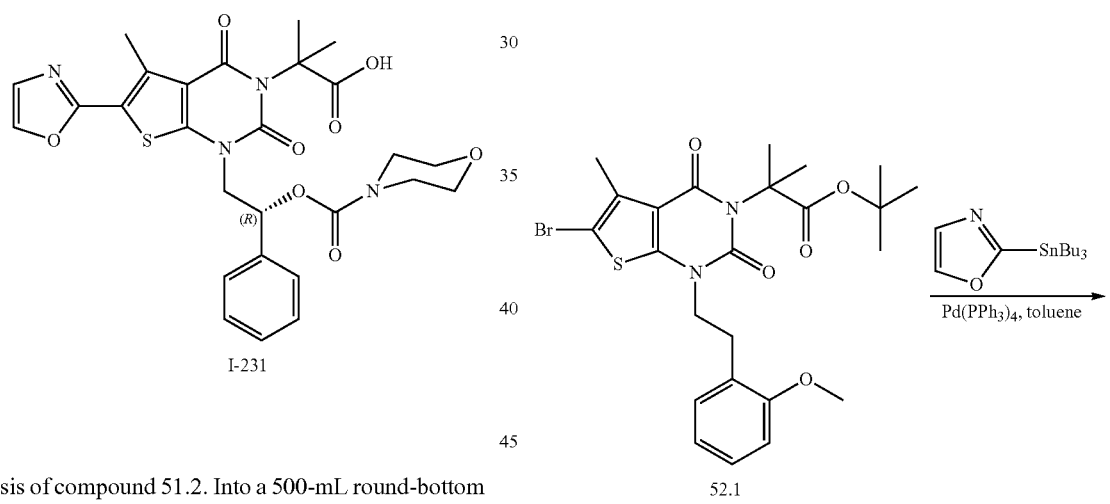

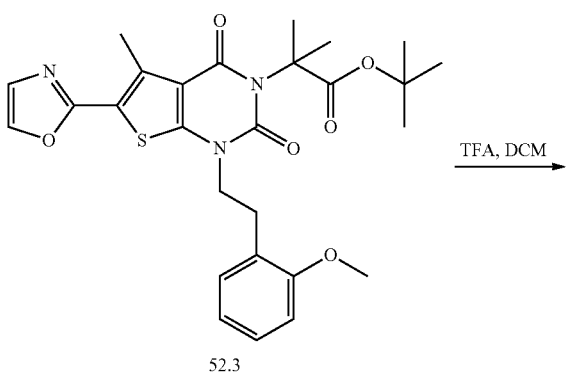

Synthesis of compound 51.2. Into a 500-mL round-bottom flask was placed ditrichloromethyl carbonate (10.2 g, 34.37 mmol, 1.50 equiv) and dichloromethane (100 mL). This was followed by the addition of morpholine (2 g, 22.96 mmol, 1.00 equiv) dropwise with stirring at 0° C. in 2 min. To this was added TEA (4.2 g, 41.51 mmol, 1.81 equiv) dropwise with stirring at 0° C. in 3 min. The resulting solution was stirred for 3 h at room temperature. The reaction was then washed by the addition of 100 mL of water. The mixture was dried over anhydrous sodium sulfate. The solids were filtered out. The resulting mixture was concentrated under vacuum. The residue was applied onto a silica gel column with ethyl acetate/petroleum ether (1:10). Purification afforded 2.238 g (65%) of morpholine-4-carbonyl chloride as a light yellow oil.

Synthesis of Compound I-231. Compound I-231 was prepared from 51.3 and 2-(tributylstannyl)-1,3-oxazole in a manner analogous to I-133 (Example 9). Isolated a white solid in 9% overall yield. MS (ES): m/z 569 (M+H)+. 1H NMR (400 MHz, CD3OD): δ 1.84 (d, J=6 Hz), 2.87 (s, 3H),

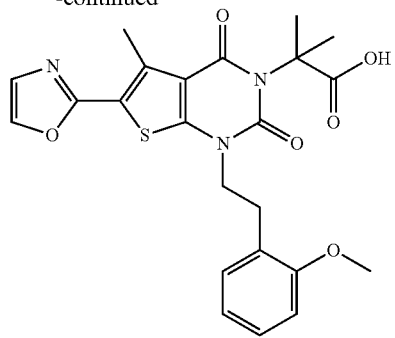

I-232

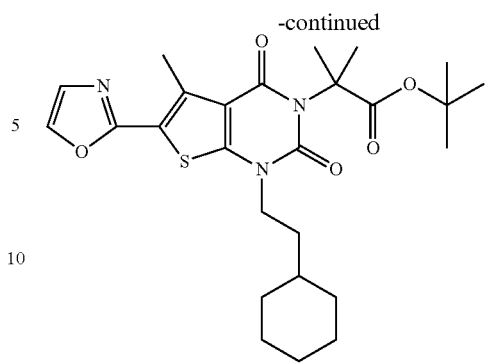

53.4

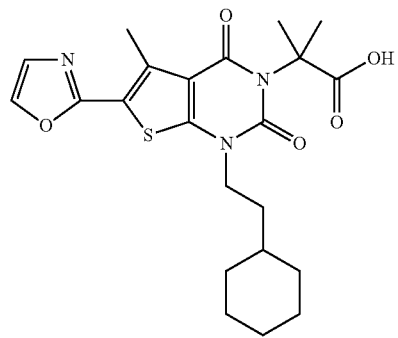

I-176

Compound I-232 was prepared in a manner analogous to I-133 (Example 9). Isolated a white solid in 33% overall yield from 1.7. MS (ES): m/z 470 (M+H)$^+$. $^1$H NMR (400 MHz, CD$_3$OD): δ 1.79 (s, 6H), 2.78(s, 3H), 3.11-3.16 (t, 2H), 3.84 (s, 1H), 4.16-4.19 (t, J=6.8 Hz, 2H), 6.83-6.89 (m, 2H), 6.71-6.27 (m, 2H), 7.27 (s, 1H), 7.97 (s, 1H).

Example 53

Synthesis of 2-[1-(2-cyclohexylethyl)-5-methyl-6-(1, 3-oxazol-2-yl)-2,4-dioxo-1H,2H,3H,4H-thieno[2,3-d]pyrimidin-3-yl]-2-methylpropanoic acid (I-176)

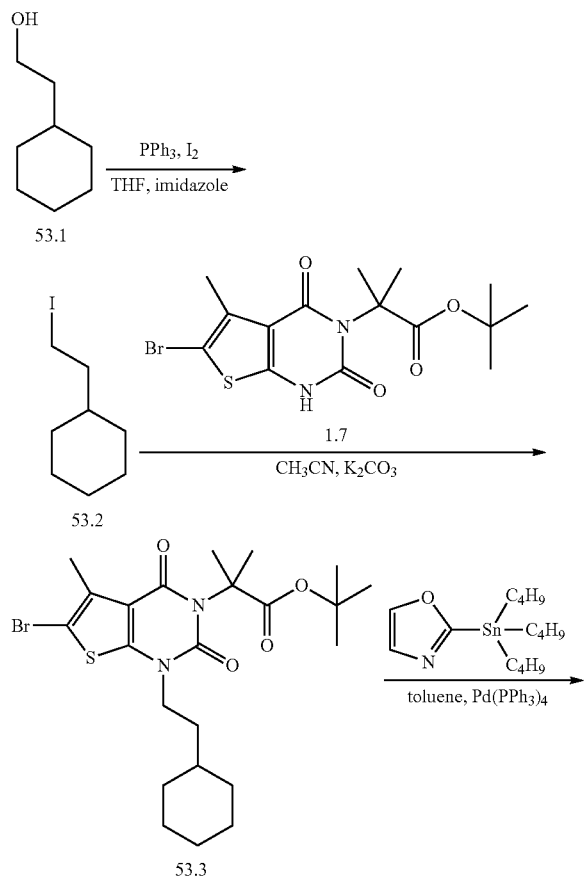

Synthesis of compound 53.2. Into a 250-mL 3-necked round-bottom flask was placed 2-cyclohexylethan-1-ol (3 g, 23.40 mmol, 1.00 equiv), imidazole (2 g, 29.41 mmol, 1.26 equiv), PPh$_3$ (8 g, 30.50 mmol, 1.30 equiv), tetrahydrofuran (60 mL) and I$_2$ (7.7 g, 30.31 mmol, 1.30 equiv). The resulting solution was stirred for 4 h at room temperature. The reaction was then quenched by the addition of 100 mL of sodium bicarbonate (sat.). The resulting solution was extracted with 2×100 mL of ethyl acetate and the organic layers combined and concentrated under vacuum. The residue was applied onto a silica gel column with petroleum ether. Purification afforded 4.4 g (79%) of (2-iodoethyl)cyclohexane as a colorless oil.

Synthesis of Compound I-176. Compound I-176 was synthesized in a manner analogous to I-133 Example 9. Isolated a white solid in 34% overall yield from 1.7. MS (ES): m/z 446 (M+H)$^+$. $^1$H NMR (DMSO-d$_6$, 300 MHz): δ 0.94 (m, 2H), 1.27 (m, 5H), 1.63 (m, 12H), 2.73 (s, 3H), 3.85 (t, 2H), 7.36 (s, 1H), 8.19 (s, 1H), 12.34 (brs, 1H).

Example 54

Synthesis of 2-methyl-2-[5-methyl-1-[2-(oxan-4-yloxy)ethyl]-6-(1,3-oxazol-2-yl)-2,4-dioxo-1H,2H, 3H,4H-thieno[2,3-d]pyrimidin-3-yl]propanoic acid (I-233)

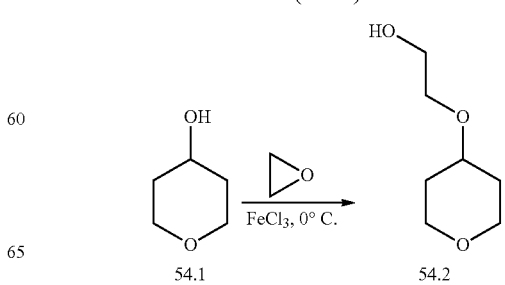

-continued

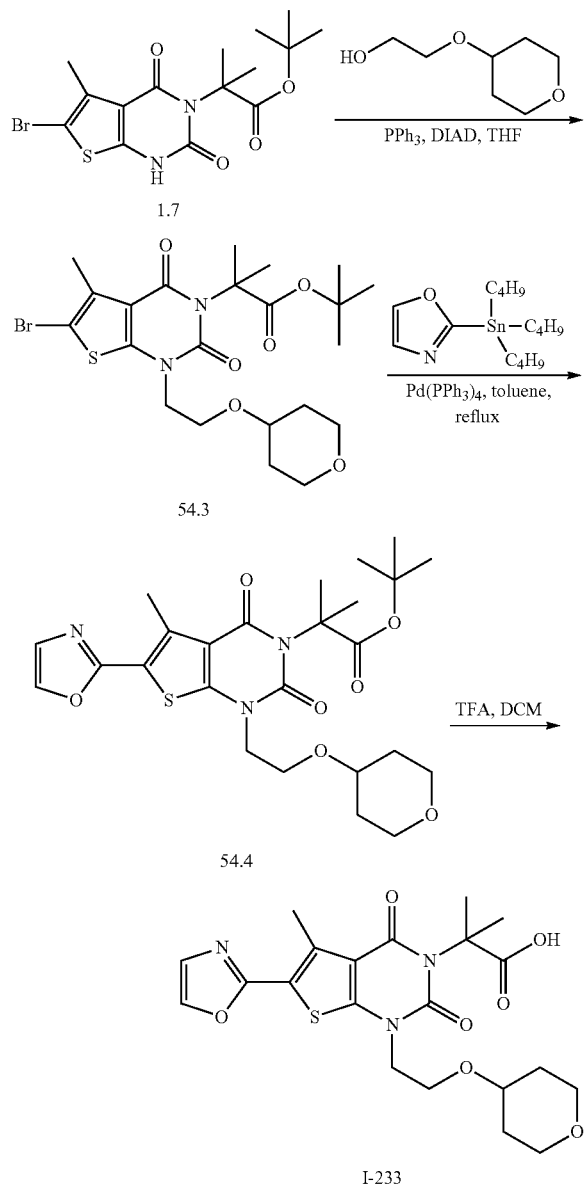

54.3

54.4

I-233

Synthesis of compound 54.2. Into a 50-mL 3-necked round-bottom flask, was placed FeCl₃ (800 mg, 4.94 mmol, 0.10 equiv). This was followed by the addition of oxan-4-ol (5 g, 48.96 mmol, 1.00 equiv) at 0° C. To this was added oxirane (20 mL) dropwise with stirring at 0° C. The resulting solution was stirred overnight at room temperature. The reaction was then quenched by the addition of 10 mL of water. The resulting solution was extracted with 2×50 mL of ethyl acetate and the organic layers combined. The residue was applied onto a silica gel column with ethyl acetate/petroleum ether (1:30-1:1). Purification afforded 2.25 g (crude) of 2-(oxan-4-yloxy)ethan-1-ol (54.2) as a colorless oil.

Synthesis of Compound I-233. Compound I-233 was prepared in a manner analogous to compound 14.5. Isolated a white solid in 11% overall yield from 1.7. Purification: thin layer chromatography developed with dichloromethane/methanol (30:1:0.15). MS (ES): m/z 464 (M+H)⁺. ¹H NMR (400 MHz, CD₃OD): δ 7.99 (1H, s), 7.29 (1H, s), 4.17-4.15 (2H, t, J=4.4 Hz), 3.87-3.85 (2H, t, J=4.4 Hz), 3.79-3.75 (2H, m), 3.61-3.58 (1H, m), 3.50-3.33 (2H, m), 2.82 (3H, s), 1.81 (8H, s), 1.53-1.31 (2H, m).

Example 55

Synthesis of 2-methyl-2-[5-methyl-6-(1,3-oxazol-2-yl)-2,4-dioxo-1-[2-(propan-2-yloxy)ethyl]-1H,2H,3H,4H-thieno[2,3-d]pyrimidin-3-yl]propanoic acid (I-234)

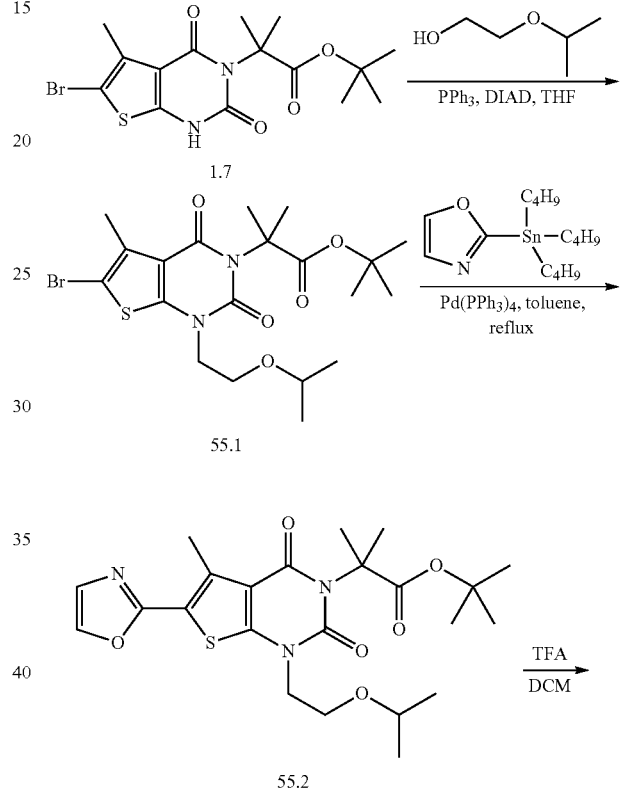

55.1

55.2

I-234

Compound I-234 was prepared from 1.7 and 2-(propan-2-yloxy)ethan-1-ol in a manner analogous to compound 14.5. Isolated a white solid in 12% overall yield from 1.7. Purification: preparative TLC with dichloromethane/methanol (40:1). MS (ES): m/z 423 (M+H)⁺.

¹H NMR (300 MHz, CDCl₃): δ 1.09-1.11 (d, 6H), 1.87 (s, 6H), 2.84 (s, 3H), 3.57-3.63 (m, 1H), 3.72-3.76 (t, 2H), 4.03-4.10 (t, 2H), 7.26(s, 1H), 7.68 (s, 1H).

Example 56

Synthesis of Intermediate 56.2

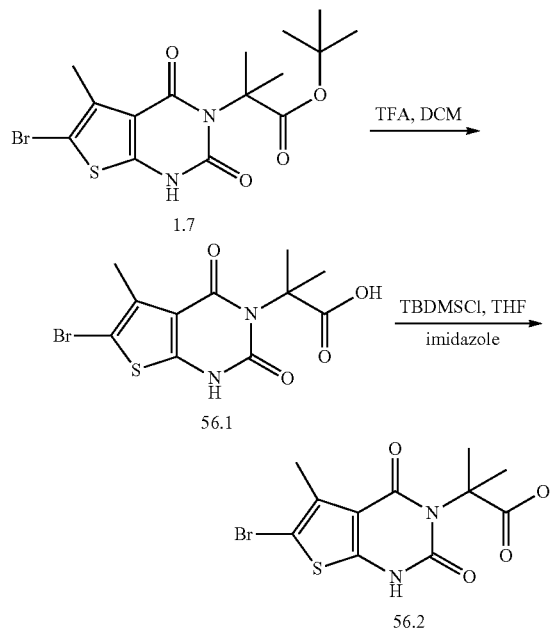

Synthesis of compound 56.1. Into a 250-mL round-bottom flask, was placed 1.7 (4 g, 9.92 mmol, 1.00 equiv), dichloromethane (100 mL) and trifluoroacetic acid (20 mL). The resulting solution was stirred overnight at room temperature. The mixture was concentrated under vacuum. Purification afforded 3.3 g (crude) of 56.1 as a white solid.

Synthesis of Intermediate 56.2. Into a 250-mL round-bottom flask was placed 56.1 (3.3 g, 9.51 mmol, 1.00 equiv), tetrahydrofuran (60 mL), imidazole (775 mg, 10.37 mmol, 1.2 equiv) and TBDMSCl (1.7 g, 11.26 mmol, 1.18 equiv). The resulting solution was stirred for 3 h at room temperature. The solids were filtered off. The filtrate was concentrated under vacuum. The residue was applied onto a silica gel column and eluted with PE/EA (10/1) to afford 3.9 g (89%) of 56.2 as a white solid.

Example 57

Synthesis of 2-[1-[(2R)-2-(2-methoxyphenyl)-2-(propan-2-yloxy)ethyl]-5-methyl-6-(1,3-oxazol-2-yl)-2,4-dioxo-1H,2H,3H,4H-thieno[2,3-d]pyrimidin-3-yl]-2-methylpropanoic acid (I-159)

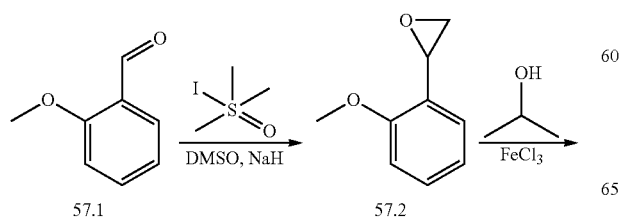

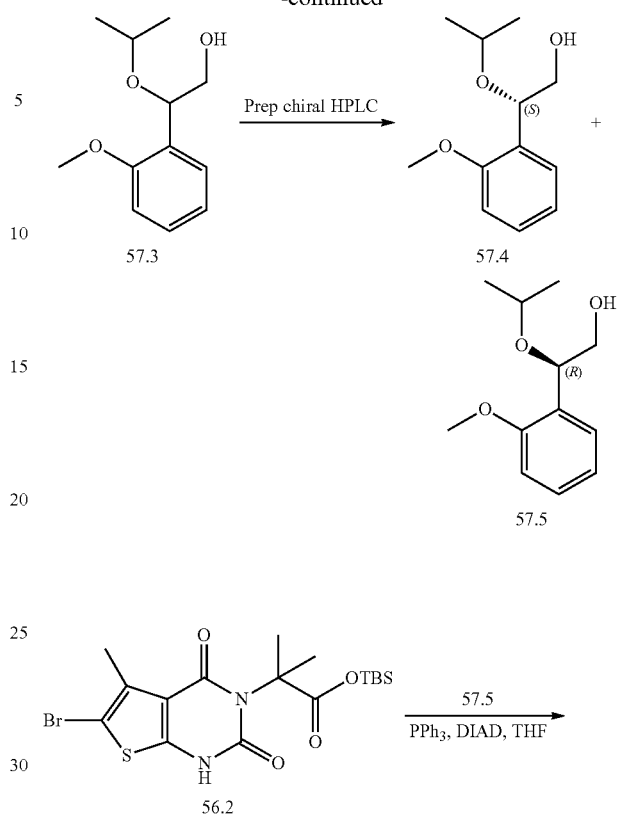

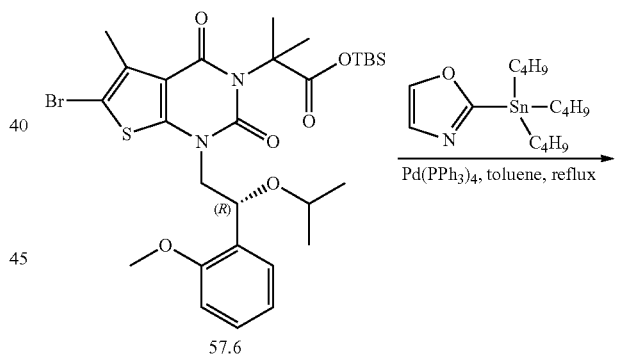

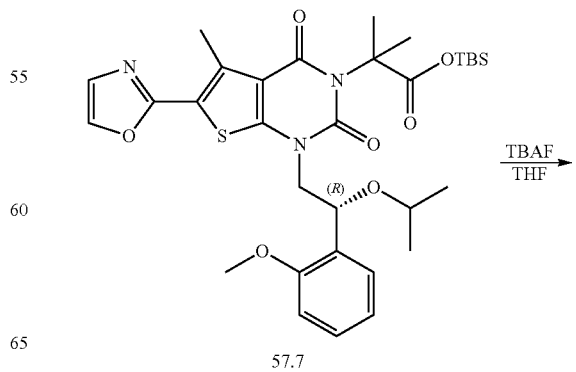

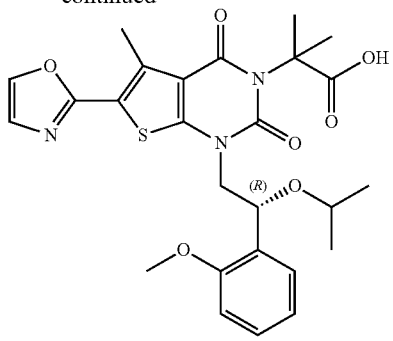

I-159

Synthesis of compound 57.2. Into a 1000-mL 3-necked round-bottom flask was placed DMSO (400 mL) and sodium hydride (7 g, 175.00 mmol, 1.19 equiv, 60%). This was followed by the addition of S,S-dimethylmethanesulfinyl iodide (38 g, 172.67 mmol, 1.18 equiv). The mixture was stirred for 1 h at 40° C. To this was added a solution of 2-methoxybenzaldehyde (20 g, 146.90 mmol, 1.00 equiv) in DMSO (100 mL) dropwise with stirring at 15° C. The resulting solution was stirred for 1 h at room temperature. The reaction was then quenched by the addition of 400 mL of $NH_4Cl$ (aq.). The resulting solution was extracted with 1000 mL of ethyl acetate and the organic layers combined. The resulting mixture was washed with 1000 mL of $H_2O$. The mixture was dried over anhydrous sodium sulfate and concentrated under vacuum. Purification afforded 14 g (63%) of 2-(2-methoxyphenyl)oxirane as a yellow oil.

Synthesis of compound 57.3. 57.3 was prepared using the same method as for the preparation of 54.2. Isolated a white solid in 33% yield.

Synthesis of compound 57.5. The enantiomers of 57.3 (8.5 g) were separated by chiral preparative HPLC under the following conditions (Gilson Gx 281): Column: Venusil Chiral OD-H, 21.1*25 cm, 5 μm; mobile phase: hexanes and HPLC-grade ethanol (hold at 5% ethanol for 12 min); detector: UV 220/254 nm. 3.3 g of 57.5 (tR=8 min) were obtained.

Synthesis of compound 57.6. Into a 500-mL 3-necked round-bottom flask was placed 56.2 (3 g, 6.50 mmol, 1.00 equiv), 57.5 (2.73 g, 12.98 mmol, 2.00 equiv), tetrahydrofuran (150 mL) and DIAD (1.97 g, 9.74 mmol, 1.50 equiv). This was followed by the addition of a solution of $PPh_3$ (2.55 g, 9.72 mmol, 1.50 equiv) in tetrahydrofuran (50 mL) dropwise with stirring at 0° C. The resulting solution was stirred overnight at room temperature and then concentrated under vacuum. The residue was applied onto a silica gel column with ethyl acetate/petroleum ether (1:50). Purification afforded 4.2 g (crude) of 57.6 as a yellow solid.

Synthesis of compound 57.7. Into a 500-mL 3-necked round-bottom flask, purged and maintained with an inert atmosphere of nitrogen, was placed 57.6 (4.2 g, 6.42 mmol, 1.00 equiv), toluene (100 mL), 2-(tributylstannyl)-1,3-oxazole (3.44 g, 9.61 mmol, 1.50 equiv) and $Pd(PPh_3)_4$ (740 mg, 0.64 mmol, 0.10 equiv). The resulting solution was stirred overnight at 110° C. in an oil bath. The resulting mixture was concentrated under vacuum. The residue was applied onto a silica gel column with ethyl acetate/petroleum ether (1:25). Purification afforded 1.15 g (impure) of 57.7 as a yellow solid.

Synthesis of Compound I-159. Into a 100-mL round-bottom flask was placed 57.7 (1.15 g, 1.79 mmol, 1.00 equiv), tetrahydrofuran (20 mL) and $TBAF.3H_2O$ (306 mg, 0.97 mmol, 0.54 equiv). The resulting solution was stirred for 15 min at room temperature and then concentrated under vacuum. The residue was applied onto a silica gel column with ethyl acetate/petroleum ether (1:2). Purification afforded 583 mg (62%) of Compound I-159 as a white solid. MS (ES): m/z 528 (M+H)+, 550 (M+Na)+, 591 (M+Na+$CH_3CN$)+. 1H NMR (300 MHz, $CD_3OD$): δ 0.98 (d, 3H), 1.01 (d, 3H), 1.72 (s, 3H), 1.76 (s, 3H), 1.77 (s, 3H), 3.47 (m, 1H), 3.78 (s, 3H), 4.04 (m, 2H), 4.84 (m, 1H), 6.95-7.93 (m, 6H).

Example 58

Synthesis of 2-[1-[(2R)-2-(2-methoxyphenyl)-2-(propan-2-yloxy)ethyl]-5-methyl-6-(1,3-oxazol-2-yl)-2,4-dioxo-1H,2H,3H,4H-thieno[2,3-d]pyrimidin-3-yl]-2-methylpropanamide (I-174)

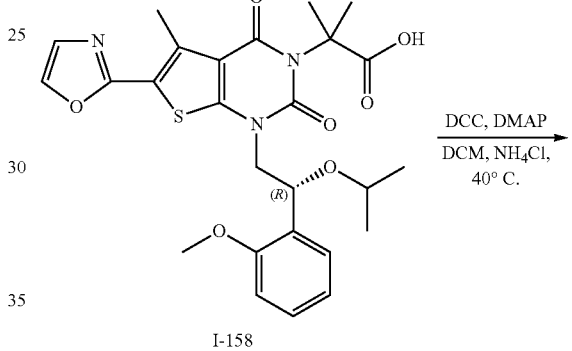

I-158

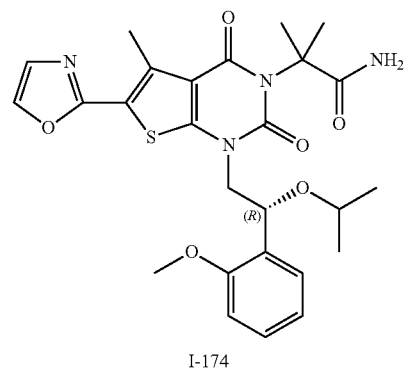

I-174

Compound I-174 was prepared from Compound I-158 using the method of Example 4. Purification: thin layer chromatography developed with dichloromethane/methanol (20:1). Isolated a white solid in 52% yield. MS (ES): m/z 527 (M+H)+, 549 (M+Na)+. 1H NMR (300 MHz, $CD_3OD$): δ 1.07 (m, 6H), 1.76-1.77 (d, 6H), 2.75 (s, 3H), 3.41-3.51 (m, 1H), 3.77 (s, 3H), 3.97-4.12 (m, 2H), 5.28-5.33 (m, 1H), 6.85-6.88 (d, 1H), 6.94-6.99 (t, 1H), 7.19-7.24 (m, 2H), 7.47-7.50 (d, 1H), 7.93 (s, 1H).

Example 59

Synthesis of 1-[(2R)-2-(2-methoxyphenyl)-2-(propan-2-yloxy)ethyl]-5-methyl-3-[2-methyl-1-(morpholin-4-yl)-1-oxopropan-2-yl]-6-(1,3-oxazol-2-yl)-1H,2H,3H,4H-thieno[2,3-d]pyrimidine-2,4-dione (I-235)

Example 60

Synthesis of N-ethyl-2-[1-[(2R)-2-(2-methoxyphenyl)-2-(propan-2-yloxy)ethyl]-5-methyl-6-(1,3-oxazol-2-yl)-2,4-dioxo-1H,2H,3H,4H-thieno[2,3-d]pyrimidin-3-yl]-2-methylpropanamide (I-236)

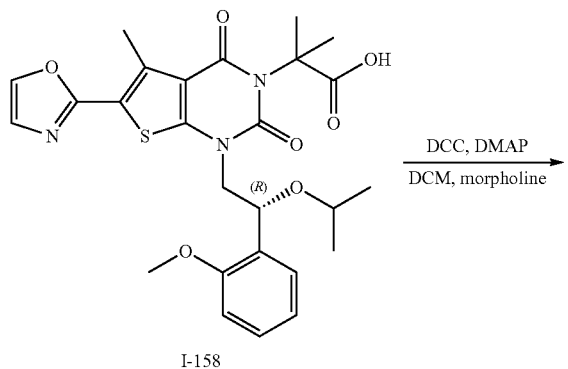

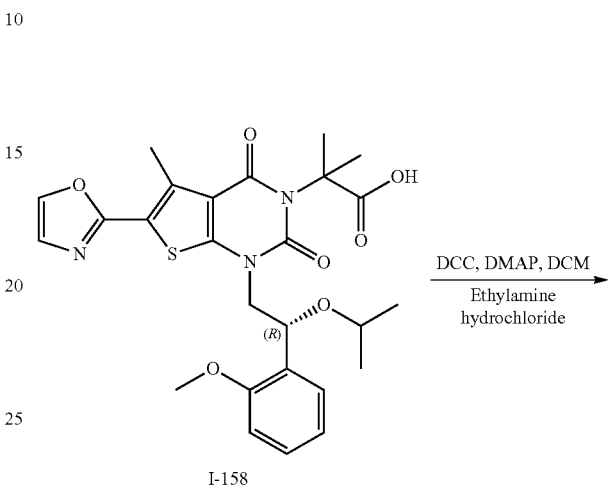

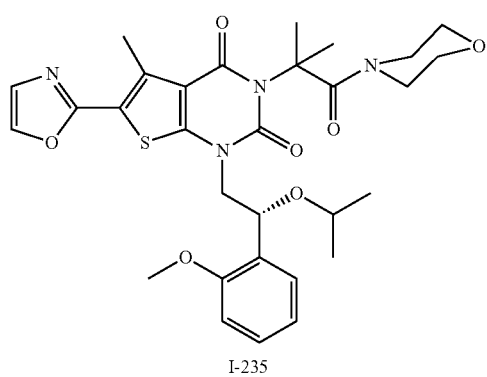

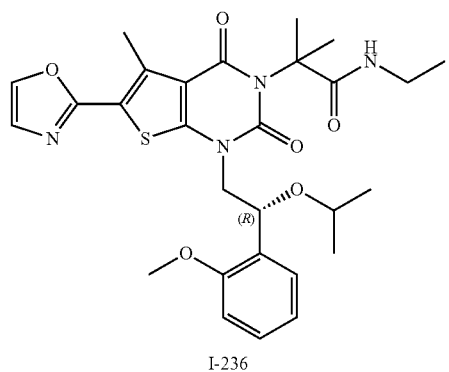

Compound I-235 was prepared from Compound I-158 and morpholine using the method of Example 4. Purification: Preparative HPLC (Waters) under the following conditions: Column: XBridge Prep Phenyl OBD, 5 μm, 19*150 mm; mobile phase, water (50 mM NH$_4$HCO$_3$) and CH$_3$CN (5.0% CH$_3$CN up to 95.0% in 10 min, hold at 95.0% in 2 min, down to 5.0% in 2 min); detector: UV 254, 220 nm. 34.2 mg (60%) of Compound I-235 were obtained.

$^1$H NMR (400 MHz, CD$_3$OD): δ 1.03-1.08 (m, 6H), 1.77 (s, 6H), 2.82 (s, 3H), 3.44-3.66 (m, 9H), 3.85 (s, 3H), 4.08-4.24 (m, 2H), 5.38 (m, 1H), 6.89-7.03 (m, 2H), 7.29 (m, 2H), 7.51 (m, 1H), 7.99 (s, 1H). MS (ES): m/z 619 (M+Na)$^+$.

Compound I-236 was prepared from Compound I-158 and ethylamine hydrochloride using the method of Example 4. Purification: Preparative HPLC (Waters) under the following conditions: Column: XBridge Prep Phenyl OBD, 5 μm, 19*150 mm; mobile phase, water (50 mM NH$_4$HCO$_3$) and CH$_3$CN (5.0% CH$_3$CN up to 95.0% in 10 min, hold at 95.0% in 2 min, down to 5.0% in 2 min); detector: UV 254, 220 nm. MS (ES): m/z 577 (M+Na)$^+$. $^1$H NMR (400 MHz, CD$_3$OD): δ 1.13-1.15 (m, 9H), 1.77 (d, 6H), 2.79 (s, 3H), 3.26 (m, 2H), 3.52 (m, 1H), 3.81 (s, 3H), 4.10 (m, 2H), 5.34 (m, 1H), 6.89-7.01 (m, 2H), 7.29 (m, 2H), 7.51 (m, 1H), 7.97 (s, 1H).

Example 61

Synthesis of 3-[1-(azetidin-1-yl)-2-methyl-1-oxopropan-2-yl]-1-[(2R)-2-(2-methoxyphenyl)-2-(propan-2-yloxy)ethyl]-5-methyl-6-(1,3-oxazol-2-yl)-1H,2H,3H,4H-thieno[2,3-d]pyrimidine-2,4-dione (I-237)


Compound I-237 was prepared from Compound I-158 and azetidine using the method of Example 4. Purification: The reaction mixture was concentrated under vacuum. The residue was applied onto a silica gel column with dichloromethane/methanol (40:1). Purification afforded 38.3 mg (48%) of Compound I-237 as a white solid. MS (ES): m/z 568 (M+H)$^+$, 589 (M+Na)$^+$. $^1$H NMR (300 MHz, CD$_3$OD): δ 1.05 (t, 6H), 1.76 (s, 6H), 2.19-2.27 (m, 2H), 2.83 (s, 3H), 3.41-3.55 (m, 1H), 3.85 (s, 3H), 4.06-4.17 (m, 6H), 5.35-5.39 (t, 1H), 6.94-7.04 (m, 2H), 7.26-7.32 (m, 2H), 7.50-7.51 (d, 1H), 7.99 (s, 1H).

Example 62

Synthesis of 1-[(2R)-2-(2-methoxyphenyl)-2-(propan-2-yloxy)ethyl]-5-methyl-3-[2-methyl-1-oxo-1-(pyrrolidin-1-yl)propan-2-yl]-6-(1,3-oxazol-2-yl)-1H,2H,3H,4H-thieno[2,3-d]pyrimidine-2,4-dione (I-238)

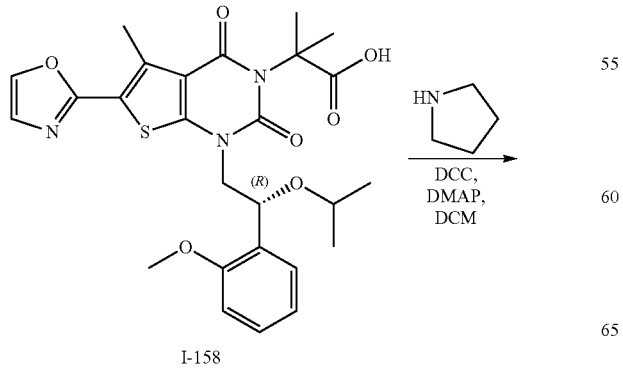

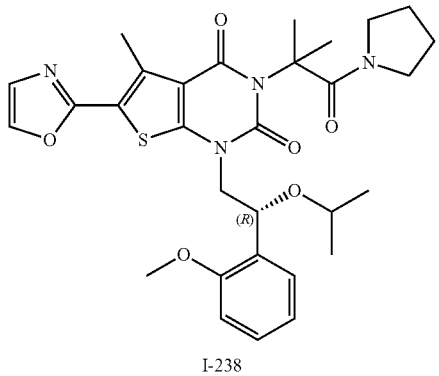

Compound I-238 was prepared from Compound I-158 and pyrrolidine using the method of Example 4. Purification: The reaction mixture was concentrated under vacuum. The residue was applied onto a silica gel column with dichloromethane/methanol (40:1). Purification afforded 41.6 mg (50%) of Compound I-238 as a white solid. MS (ES): m/z 603 (M+Na)$^+$. $^1$H NMR (300 MHz, CD$_3$OD): δ 1.03-1.07 (m, 6H), 1.77-1.82 (m, 10H), 2.80 (s, 3H), 3.09-3.15 (m, 2H), 3.46-3.56 (m, 3H), 3.86 (s, 3H), 4.15 (br s, 2H), 5.35-5.39 (t, 1H), 6.95-7.04 (m, 2H), 7.26-7.32 (m, 2H), 7.50-7.52 (d, 1H), 7.99 (s, 1H).

Example 63

Synthesis of 1-[(2R)-2-(2-methoxyphenyl)-2-(propan-2-yloxy)ethyl]-5-methyl-3-[2-methyl-1-oxo-1-(piperidin-1-yl)propan-2-yl]-6-(1,3-oxazol-2-yl)-1H,2H,3H,4H-thieno[2,3-d]pyrimidine-2,4-dione (I-239)

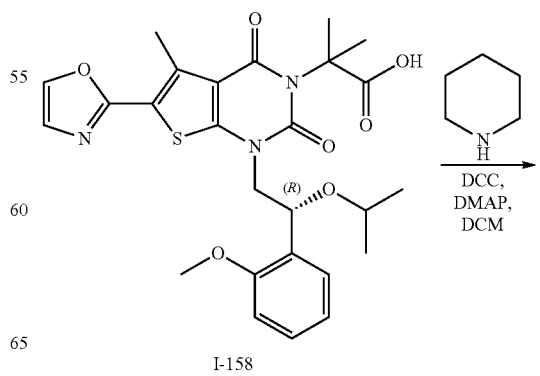

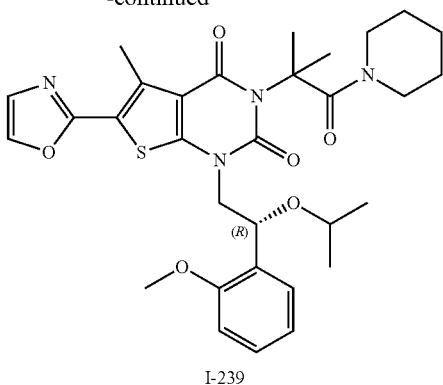

I-239

Compound I-239 was prepared from Compound I-158 and piperidine using the method of Example 4. Purification: The reaction mixture was concentrated under vacuum. The residue was applied onto a silica gel column with dichloromethane/methanol (40:1). Purification afforded 41.6 mg (49%) of Compound I-239 as a white solid. MS (ES): m/z 617 (M+Na)$^+$. $^1$H NMR (300 MHz, CD$_3$OD): δ 1.02 (m, 6H), 1.29-1.41 (m, 2H), 1.41-1.95 (m, 10H), 2.81 (s, 3H), 3.45-3.61 (m, 3H), 3.87 (s, 3H), 4.10-4.24 (m, 1H), 5.38-5.39 (m, 1H), 6.95-7.04 (m, 2H), 7.27-7.32 (m, 2H), 7.43-7.65 (m, 1H), 8.03 (s, 1H).

Example 64

Synthesis of N-methanesulfonyl-2-[1-[(2R)-2-(2-methoxyphenyl)-2-(propan-2-yloxy)ethyl]-5-methyl-6-(1,3-oxazol-2-yl)-2,4-dioxo-1H,2H,3H,4H-thieno[2,3-d]pyrimidin-3-yl]-2-methylpropanamide (I-240)

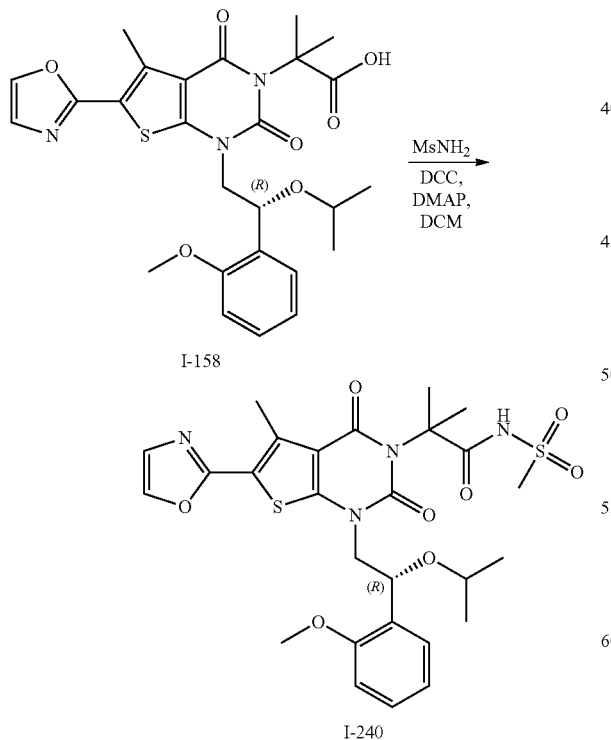

Compound I-240 was prepared from Compound I-158 and methanesulfonamide using the method of Example 4. Purification: The reaction mixture was concentrated under vacuum. The residue was applied onto a silica gel column with dichloromethane/methanol (40:1). Purification afforded 13.6 mg (16%) of Compound I-240 as a white solid. MS (ES): m/z 605 (M+H)$^+$, 627 (M+Na)$^+$. $^1$H NMR (300 MHz, CD$_3$OD): δ 0.80-0.94 (m, 6H), 1.67-1.68 (d, 6H), 2.75 (s, 3H), 3.15 (s, 3H), 3.35-3.43 (m, 1H), 3.70 (s, 3H), 3.97-3.99 (m, 1H), 5.20-5.26 (m, 1H), 6.79-6.82 (d, 1H), 6.88-6.93 (t, 1H), 7.13-7.17 (m, 2H), 7.41-7.43 (d, 2H), 7.87 (s, 1H).

Example 65

3-[1-(3-hydroxyazetidin-1-yl)-2-methyl-1-oxopropan-2-yl]-1-[(2R)-2-(2-methoxyphenyl)-2-(propan-2-yloxy)ethyl]-5-methyl-6-(1,3-oxazol-2-yl)-1H,2H,3H,4H-thieno[2,3-d]pyrimidine-2,4-dione (I-241)

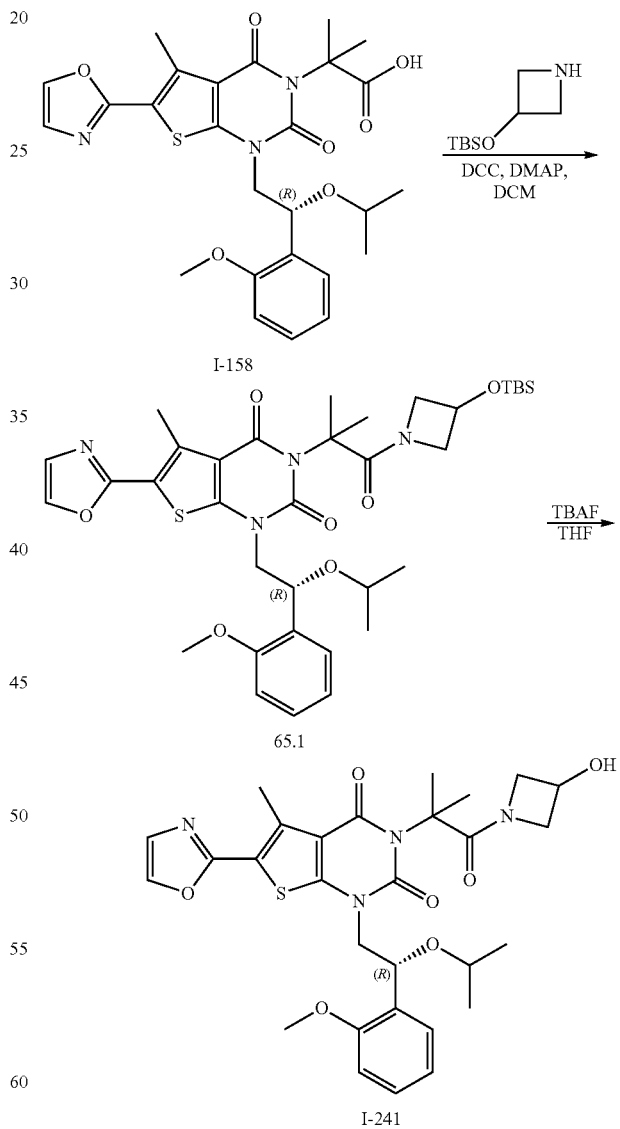

Synthesis of compound 65.1. Compound 65.1 was prepared from Compound I-158 and 3-[(tert-butyldimethylsilyl)oxy]azetidine using the method of Example 4, except that microwave irradiation at 50° C. was the heat source. Purification: The resulting mixture was concentrated under vacuum. The residue was applied onto a silica gel column with ethyl acetate/petroleum ether (1:2). Purification afforded 100 mg (50%) of Compound 65.1 as a white solid.

Synthesis of compound I-241. Into a 50-mL round-bottom flask was 65.1 (100 mg, 0.14 mmol, 1.00 equiv), oxolane (10 mL) and TBAF (37.4 mg, 0.14 mmol, 1.00 equiv). The resulting solution was stirred for 2 h at room temperature and then concentrated under vacuum. The residue was applied onto a silica gel column with dichloromethane/methanol (30:1). Purification afforded 53.6 mg (64%) of Compound I-241 as a white solid. MS (ES): m/z 605 (M+Na)+. 1H NMR (300 MHz, CD3OD): δ 1.03-1.07 (m, 6H), 1.74-1.75 (d, 6H), 2.83 (s, 3H), 3.47-3.55 (m, 1H), 3.76-3.80 (m, 2H), 3.85 (s, 3H), 4.16-4.24 (m, 4H), 4.47-4.55 (m, 1H), 5.35-5.39 (t, 1H), 6.94-7.04 (m, 2H), 7.26-7.32 (m, 2H), 7.50-7.53 (d, 1H), 7.99 (s, 1H).

Example 66

Synthesis of 2-[1-[(2R)-2-(2-methoxyphenyl)-2-(propan-2-yloxy)ethyl]-5-methyl-6-(1,3-oxazol-2-yl)-2,4-dioxo-1H,2H,3H,4H-thieno[2,3-d]pyrimidin-3-yl]-2-methyl-N-(propan-2-yl)propanamide (I-242)

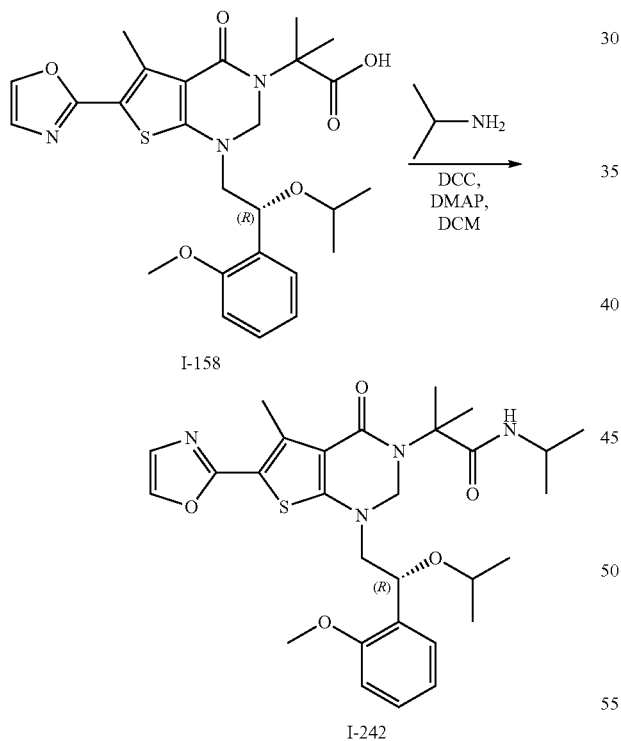

Compound I-242 was prepared from Compound I-158 and propan-2-amine using the method of Example 4. Purification: The reaction mixture was concentrated under vacuum. The residue was applied onto a silica gel column with dichloromethane/methanol (40:1). Purification afforded 31.5 mg (39%) of Compound I-242 as a white solid. MS (ES): m/z 591 (M+Na)+. 1H NMR (300 MHz, CD3OD): δ 1.03-1.07 (m, 6H), 1.10-1.20 (m, 6H), 1.77-1.83 (d, 6H), 2.85 (s, 3H), 3.46-3.56 (m, 1H), 3.81 (s, 3H), 3.97-4.10 (m, 3H), 5.33-5.38 (t, 1H), 6.89-6.92 (d, 1H), 6.99-7.04 (t, 1H), 7.23-7.32 (m, 2H), 7.52-7.55 (m, 1H), 7.98 (s, 1H).

Example 67

Synthesis of 2-[1-[(2R)-2-(2-ethoxyphenyl)-2-(propan-2-yloxy)ethyl]-5-methyl-6-(1,3-oxazol-2-yl)-2,4-dioxo-1H,2H,3H,4H-thieno[2,3-d]pyrimidin-3-yl]-2-methylpropanoic acid (I-177)

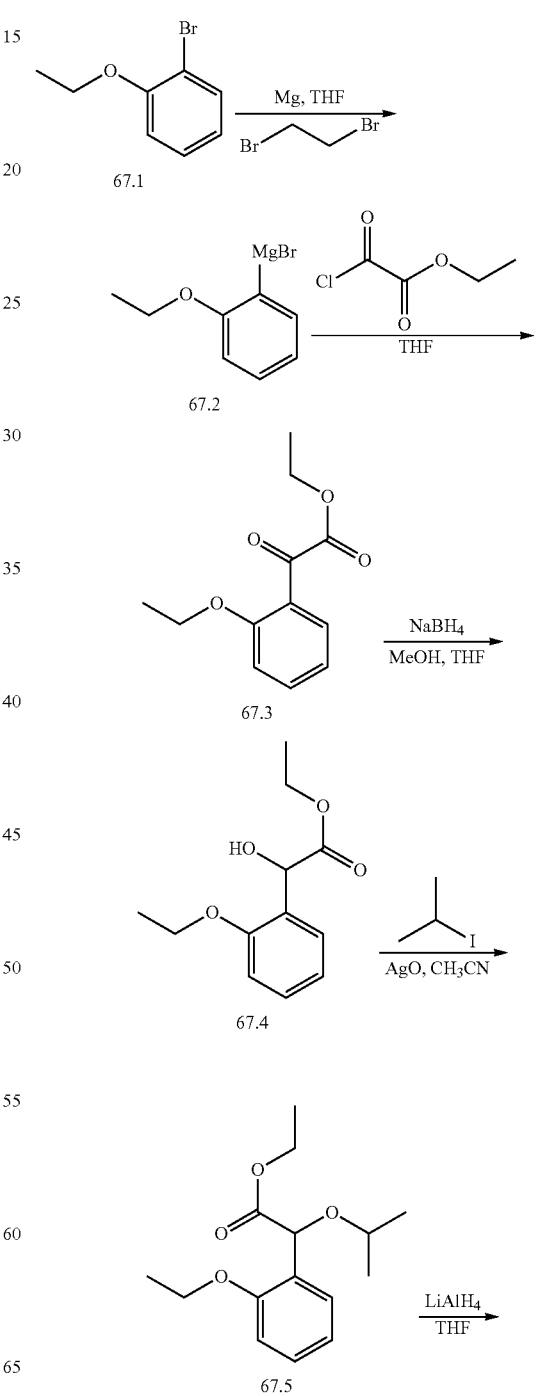

-continued

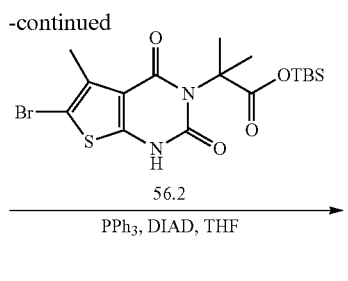

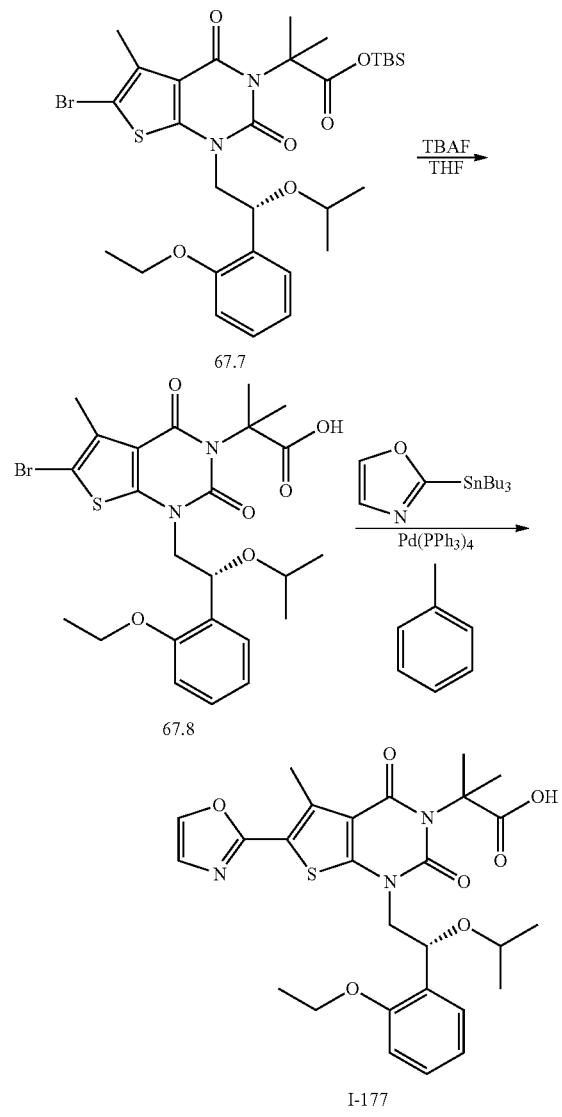

Synthesis of compound 67.2. Into a 100-mL 3-necked round-bottom flask was placed Mg (1.55 g) and 10 mL of tetrahydrofuran. Then 1-bromo-2-ethoxybenzene (1 g) and 1,2-dibromoethane (100 mg, 0.53 mmol, 0.01 equiv) were added to initiate the reaction. Then a second batch of 1-bromo-2-ethoxybenzene (9 g) were dissolved in 40 mL THF was added dropwise. The resulting solution was stirred for 2 h at room temperature. The mixture was directly used in the next step.

Synthesis of compound 67.3. Into a 100-mL 3-necked round-bottom flask was placed tetrahydrofuran (20 mL) and ethyl 2-chloro-2-oxoacetate (17 g, 124.51 mmol, 2.51 equiv). This was followed by the addition of bromo(2-ethoxyphenyl) magnesium (20 mL, 1.00 equiv) dropwise with stirring at −80° C. The resulting solution was stirred for 30 min at −80° C. The reaction was then quenched by the addition of 50 mL of water. The resulting solution was extracted with 3×100 mL of ethyl acetate and the organic layers combined and concentrated under vacuum. The residue was applied onto a silica gel column with ethyl acetate/petroleum ether (1:20). Purification afforded 8.5 g (77%) of 67.3 as a colorless oil.

Synthesis of compound 67.4. Into a 100-mL 3-necked round-bottom flask was placed methanol (10 mL), ethyl 2-(2-ethoxyphenyl)-2-oxoacetate (8.5 g, 38.25 mmol, 1.00 equiv) and tetrahydrofuran (50 mL). This was followed by the addition of NaBH$_4$ (730 mg, 19.30 mmol, 0.50 equiv), in portions at 0° C. The resulting solution was stirred for 30 min at room temperature. The reaction was then quenched by the addition of 50 mL of water. The resulting solution was extracted with 3×100 mL of ethyl acetate and the organic layers combined and concentrated under vacuum. The residue was applied onto a silica gel column with ethyl acetate/petroleum ether (1:20). Purification afforded 7.1 g (83%) of 67.4 as a colorless oil.

Synthesis of compound 67.5. Into a 250-mL round-bottom flask was placed ethyl 2-(2-ethoxyphenyl)-2-hydroxyacetate (7.1 g, 31.66 mmol, 1.00 equiv), CH$_3$CN (50 mL), Ag$_2$O (22.1 g) and 2-iodopropane (27 g, 158.83 mmol, 5.02 equiv). The resulting solution was stirred overnight at 40° C. The solids were filtered out. The filtrate was concentrated under vacuum. The residue was applied onto a silica gel column with ethyl acetate/petroleum ether (1:100). Purification afforded 1.3 g (15%) of 67.5 as a colorless oil.

Synthesis of compound 67.6. Into a 50-mL 3-necked round-bottom flask was placed tetrahydrofuran (20 mL) and 67.5 (1.3 g, 4.88 mmol, 1.00 equiv). Then LiAlH$_4$ (186 mg, 4.90 mmol, 1.00 equiv) was added at 0° C. The resulting solution was stirred for 30 min at 0° C. The reaction was then quenched by the addition of 20 mL of NH$_4$Cl (aq.). The resulting solution was extracted with 3×100 mL of ethyl acetate and the organic layers combined and concentrated under vacuum. The residue was applied onto a silica gel column with ethyl acetate/petroleum ether (1:20). The crude product was purified by chiral preparative HPLC under the following conditions (Gilson Gx 281): Column: Venusil Chiral OD-H, 21.1*25 cm, 5 μm; mobile phase: hexanes and ethanol (hold at 2.0% ethanol for 11 min); detector: UV 220/254 nm. Purification afforded 0.35 g (32%) of 67.6 as a yellow solid.

Synthesis of compound 67.7. Into a 50-mL round-bottom flask was placed Ph$_3$P (545 mg, 2.08 mmol, 2.00 equiv), 67.6 (350 mg, 1.56 mmol, 1.50 equiv), tetrahydrofuran (10 mL), 56.2 (480 mg, 1.04 mmol, 1.00 equiv) and DIAD (420 mg, 2.08 mmol, 2.00 equiv). The resulting solution was stirred overnight at room temperature and then concentrated under vacuum. The residue was applied onto a silica gel column with ethyl acetate/petroleum ether (1:50). Purification afforded 400 mg (crude) of 67.7 as a yellow oil.

Synthesis of compound 67.8. Into a 50-mL round-bottom flask was placed tetrahydrofuran (5 mL), 67.7 (400 mg, 0.60 mmol, 1.00 equiv) and TBAF (172 mg, 0.66 mmol, 1.10 equiv). The resulting solution was stirred for 2 h at room temperature. The reaction was then quenched by the addition of 0.5 mL of water. The resulting mixture was concentrated under vacuum. The residue was applied onto a silica gel column with ethyl acetate/petroleum ether (1:10). Purification afforded 350 mg (crude) of 67.8 as a yellow oil.

Synthesis of Compound I-177. Compound I-177 was prepared from 67.8 and 2-(tributylstannyl)-1,3-oxazole according to the method of Example 2. Purification: The residue was applied onto a silica gel column with ethyl acetate/petroleum ether (1:10). Purification afforded 106.1 mg (31%) of Compound I-177 as a white solid. MS (ES): m/z 542 (M+H)+, 564 (M+Na)+. 1H NMR (400 MHz, CD3OD): δ 0.99-1.04 (m, 6H), 1.44 (t, J=7.2, 3H), 1.75-1.76 (m, 6H), 2.83 (s, 3H), 3.43-3.51 (m, 1H), 4.05-4.13 (m, 4H), 5.37-5.41 (m, 1H), 6.93 (d, J=8.4, 1H), 7.00 (t, J=7.2, 1H), 7.23-7.28 (m, 2H), 7.53 (d, J=7.6, 1H), 7.97 (s, 1H).

Example 68

Synthesis of 2-[1-[(2S)-2-(2-methoxyphenyl)-2-(propan-2-yloxy)ethyl]-5-methyl-6-(1,3-oxazol-2-yl)-2,4-dioxo-1H,2H,3H,4H-thieno[2,3-d]pyrimidin-3-yl]-2-methylpropanoic acid (I-158)

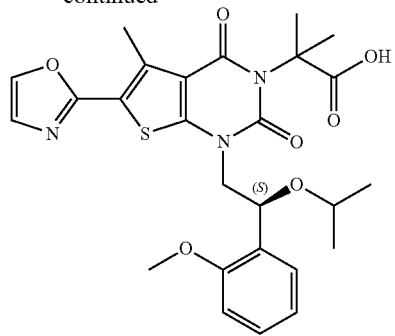

I-158

Compound I-158 was prepared from 57.4 and intermediate 56.2 using the same procedure as for Example 57. Purification: silica gel column with ethyl acetate/petroleum ether (1:5). Isolated 541 mg (20%) of Compound I-158 as a white solid. MS (ES): m/z 528 (M+H)+, 550 (M+Na)+, 591 (M+Na+CH3CN)+. 1H NMR (300 MHz, CD3OD): δ 1.02 (d, 3H), 1.05 (d, 3H), 1.76 (s, 3H), 1.81 (s, 3H), 2.80 (s, 3H), 3.46 (m, 1H), 3.83 (s, 3H), 4.09 (m, 2H), 5.32 (m, 1H), 6.91-7.04 (m, 2H), 7.25 (m, 2H), 7.53 (d, 1H), 7.97 (s, 1H).

Example 69

Synthesis of 2-[1-[(2R)-2-(2-ethylphenyl)-2-(propan-2-yloxy)ethyl]-5-methyl-6-(1,3-oxazol-2-yl)-2,4-dioxo-1H,2H,3H,4H-thieno[2,3-d]pyrimidin-3-yl]-2-methylpropanoic acid (I-180)

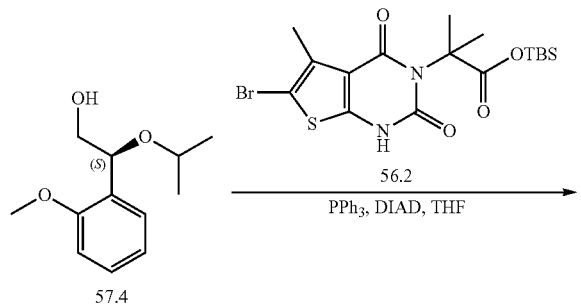

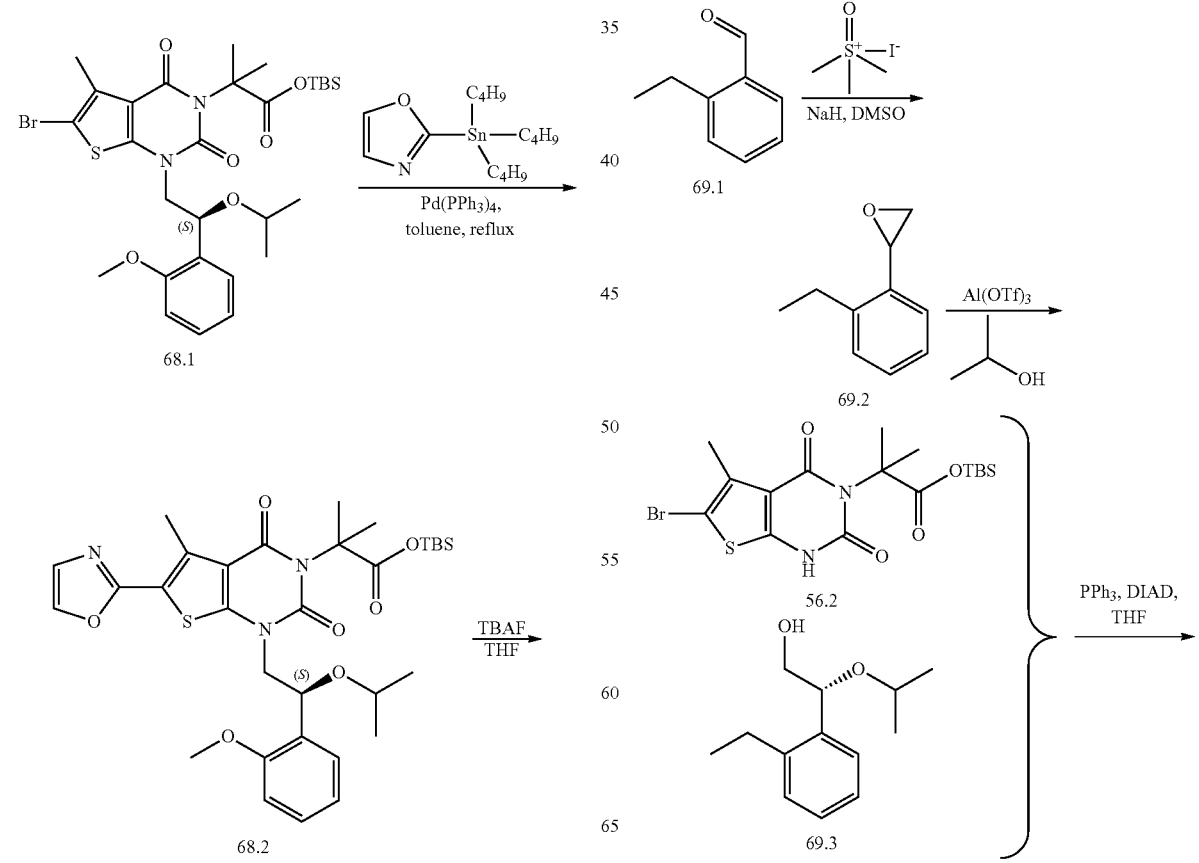

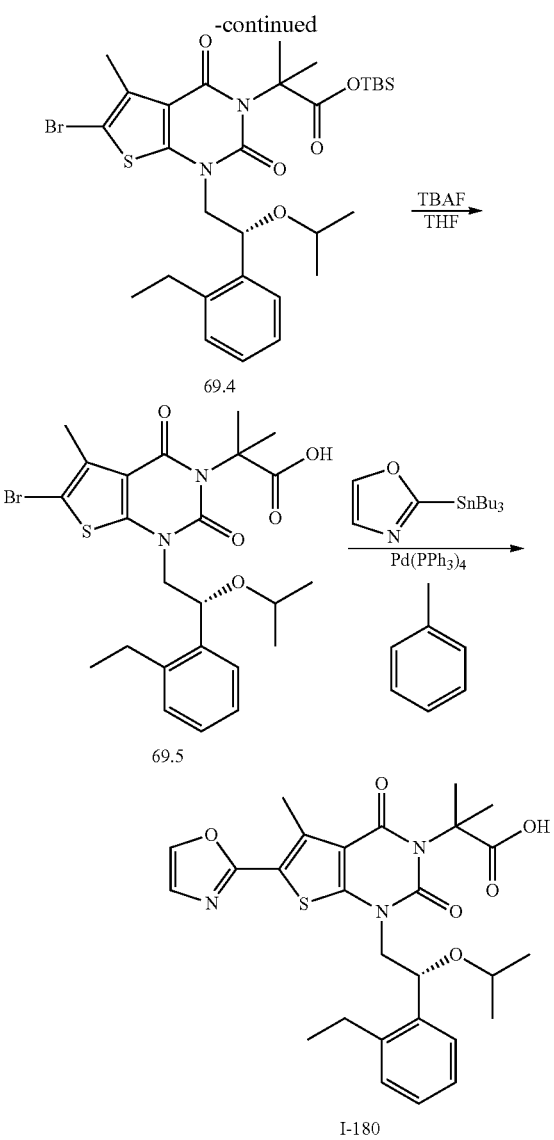

were isolated as a white solid. MS (ES): m/z 526 (M+Na)⁺, 589 (M+H+CH$_3$CN)⁺. $^1$H NMR (300 MHz, CD$_3$OD): δ 0.95 (t, J=6.3 Hz, 6H), 1.25 (t, J=7.5 Hz, 3H), 1.78-1.80 (m, 6H), 2.68-2.75 (m, 1H), 2.79 (s, 3H), 2.89-2.94 (m, 1H), 3.37-3.45 (m, 1H), 3.65-3.70 (m, 1H), 4.18-4.24 (m, 1H), 5.14-5.18 (m, 1H), 7.19-7.27 (m, 4H), 7.57-7.60 (m, 1H), 7.95 (s, 1H).

Example 70

Synthesis of Intermediate 70.1

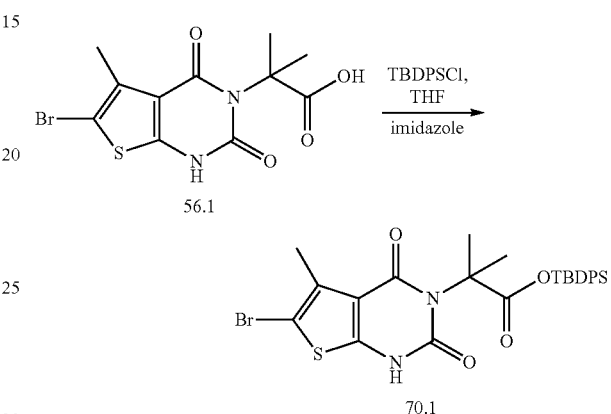

Intermediate 70.1 was prepared in a manner analogous to intermediate 56.2. Isolated a white solid in 84%.

Example 71

Synthesis of 2-[1-[(2R)-2-(2-ethoxyphenyl)-2-(oxan-4-yloxy)ethyl]-5-methyl-6-(1,3-oxazol-2-yl)-2,4-dioxo-1H,2H,3H,4H-thieno[2,3-d]pyrimidin-3-yl]-2-methylpropanoic acid (I-183)

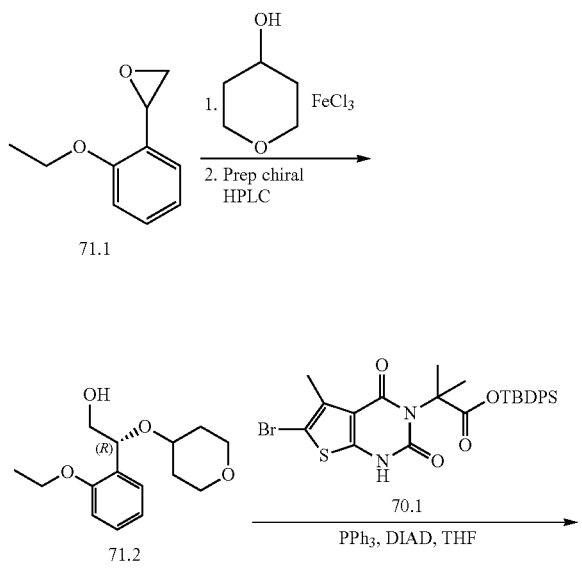

Synthesis of compound 69.2. Compound 69.2 was prepared from 69.1 using the same method as for the synthesis of 57.2. Isolated a colorless oil in quantitative yield.

Synthesis of compound 69.3. Into a 50-mL round-bottom flask was placed Al(OTf)$_3$ (641 mg, 1.35 mmol, 0.05 equiv), propan-2-ol (20 mL) and 69.2 (4 g, 26.99 mmol, 1.00 equiv). The resulting solution was stirred for 1 h at room temperature. The reaction was then quenched by the addition of 1 mL of water. The resulting mixture was concentrated under vacuum. The residue was applied onto a silica gel column with ethyl acetate/petroleum ether (1:100). From the purified racemate the desired enantiomer was isolated by chiral preparative HPLC under the following conditions (Gilson GX 281): Column: Venusil Chiral OD-H, 21.1*25 cm, 5 μm; mobile phase: hexanes (0.2% TEA) and IPA (hold at 2.0% IPA in 11 min); detector: UV 220/254 nm. The second peak to elute was collected. Concentration afforded 1.2 g (21%) of 69.3 as a yellow oil.

Synthesis of Compound I-180. Compound I-180 was prepared in a manner analogous with Example 67. Purification: silica gel column with ethyl acetate/petroleum ether (1:10). 47.8 mg (11% overall yield from 56.2) of Compound I-180

3.50-3.70 (m, 2H), 3.90 (m, 1H), 4.02 (m, 2H), 4.20 (m, 1H), 5.40 (dd, J=4.2 Hz, 9.0 Hz, 1H), 6.95 (m, 2H), 7.23 (m, 2H), 7.49 (dd, J=1.5 Hz, 7.5 Hz, 1H), 7.93 (s, 1H).

Example 72

Synthesis of 2-[1-[(2R)-2-ethoxy-2-(2-methoxyphenyl)ethyl]-5-methyl-6-(1,3-oxazol-2-yl)-2,4-dioxo-1H,2H,3H,4H-thieno[2,3-d]pyrimidin-3-yl]-2-methylpropanoic acid (I-243)

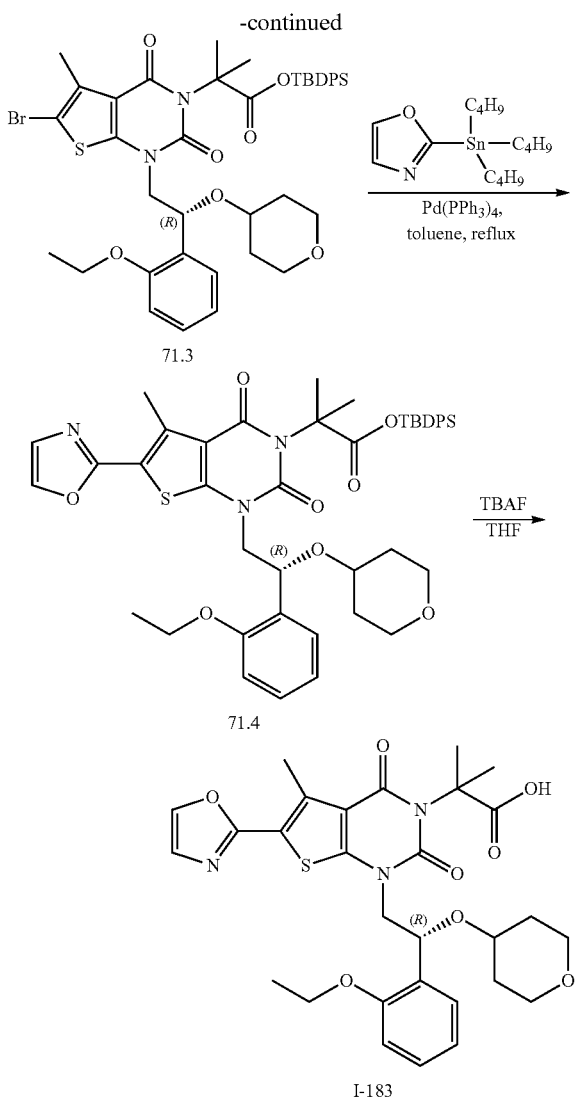

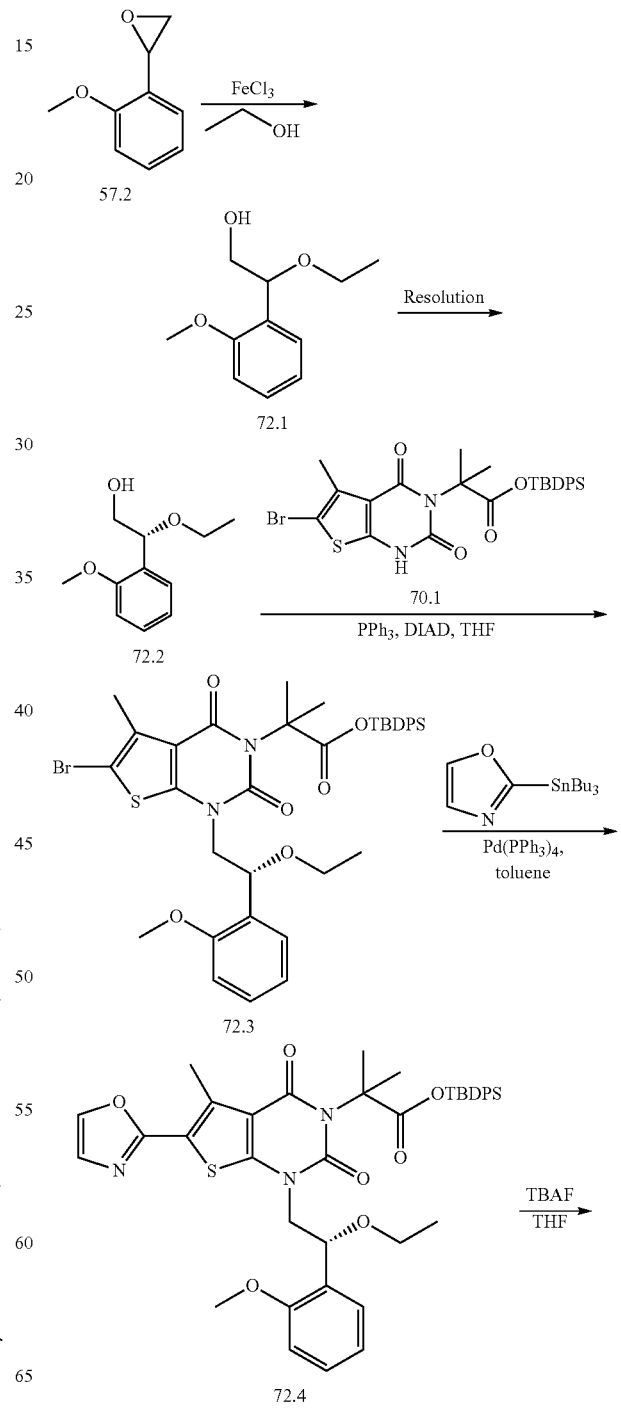

Synthesis of compound 71.2. Compound 71.2 was synthesized using the method for the synthesis of 20.1. Purification: The residue obtained after work-up was applied onto a silica gel column with ethyl acetate/petroleum ether (1:10) to obtain a pure racemic product. The enantiomers were then separated by chiral preparative HPLC under the following conditions (Gilson Gx 281): Column: Lichrom OD-H 2*25 cm, 5 μm; mobile phase: hexanes and IPA (hold at 5% IPA for 15 min); detector: UV 220/254 nm. 0.870 g (8%) of 71.2 were obtained as a colorless oil.

Synthesis of Compound I-183. Compound I-183 was prepared following the same procedure as for Example 57. Purification: The crude material was applied onto a silica gel column with ethyl acetate/petroleum ether (1:2, 0.5%, AcOH). The product (100 mg) thus obtained was further purified by preparative HPLC under the following conditions ((Waters): Column: XBridge Prep C18 OBD column, 5 μm, 19*150 mm; mobile phase: water (with 50 mM $NH_4HCO_3$) and $CH_3CN$ (20.0% $CH_3CN$ up to 50.0% in 10 min, up to 95.0% in 2 min, down to 20.0% in 2 min); detector: UV 254, 220 nm. Purification afforded 0.046 g (12% from 70.1) of Compound I-183 as a white solid. MS (ES): m/z 606 (M+Na)$^+$ 606. $^1$H NMR ($CD_3OD$, 300 MHz): δ 1.41 (m, 5H), 1.73 (m, 8H), 2.77 (s, 3H), 3.34 (m, 2H), 3.41 (m, 1H),

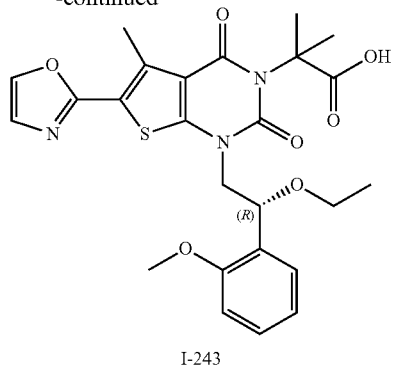

I-243

Synthesis of compound 72.2. Compound 72.2 was prepared in a manner analogous to compound 57.5, substituting ethanol for isopropanol in the epoxide-opening step. Purification: The crude product (1.5 g) was purified by chiral preparative HPLC under the following conditions (Gilson Gx 281): Column: Venusil Chiral OD-H, 21.1*25 cm, 5 μm; mobile phase: hexanes and ethanol (hold at 5.0% ethanol for 12 min); detector: UV 220/254 nm. The second peak was collected. 0.59 g (36% from 57.2) of 72.2 were obtained as a white solid.

Synthesis of Compound I-243. Compound I-243 was prepared in a manner analogous to the synthesis of compound I-158 (Example 57). Purification: silica gel column with dichloromethane/methanol (100:1). Isolated a white solid in 37% overall yield from 70.1. MS (ES): m/z 514 (M+H)$^+$. $^1$H NMR (300 MHz, CD$_3$OD): δ 1.13 (t, J=6.9 Hz, 3H), 1.75 (s, 3H), 1.79 (s, 3H), 2.79 (s, 3H), 3.32-3.53 (m, 2H), 3.80 (s, 3H), 4.06-4.10 (m, 1H), 4.21-4.28 (m, 1H), 5.21-5.26 (m, 1H), 6.91 (d, J=8.4 Hz, 1H), 7.02 (t, J=7.8, 1H), 7.24-7.29 (m, 2H), 7.46-7.49 (m, 1H), 7.97 (s, 1H).

Example 73

Synthesis of 2-methyl-2-[5-methyl-6-(1,3-oxazol-2-yl)-1-[(2R)-2-(oxetan-3-yloxy)-2-phenylethyl]-2,4-dioxo-1H,2H,3H,4H-thieno[2,3-d]pyrimidin-3-yl]propanoic acid (I-182)

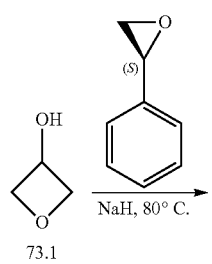

73.1

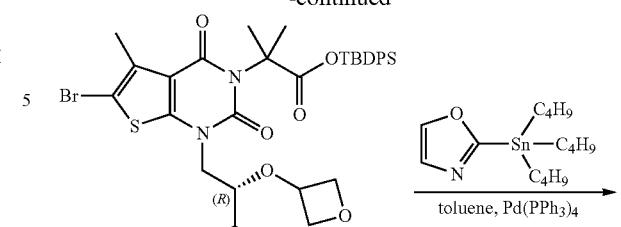

73.3

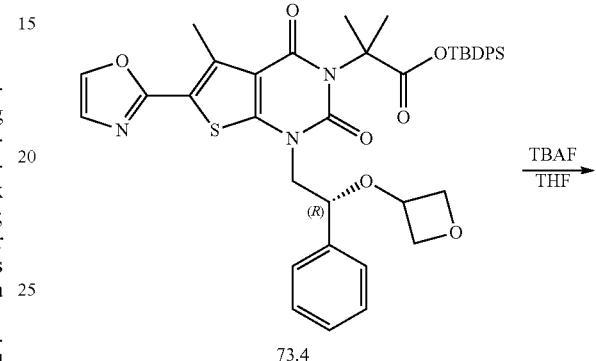

73.4

I-182

Synthesis of compound 73.2. Into a 50-mL round-bottom flask was placed (2S)-2-phenyloxirane (4 g, 33.29 mmol, 1.00 equiv) and oxetan-3-ol (16 mL). This was followed by the addition of sodium hydride (1.3 g, 32.50 mmol, 1.00 equiv, 60%) in several batches. The resulting solution was stirred for 1 h at 80° C. in an oil bath. The reaction was then quenched by the addition of 50 mL of NH$_4$Cl (sat., aq.). The resulting solution was extracted with 2×50 mL of ethyl acetate and the organic layers combined and concentrated under vacuum. The residue was applied onto a silica gel column with PE/EA (8:1). Purification afforded 1.6 g (25%) of (2R)-2-(oxetan-3-yloxy)-2-phenylethan-1-ol (73.2) as a yellow oil.

Synthesis of Compound I-182. Compound I-182 was prepared in a manner analogous to Example 57. Purification: The crude product was applied onto a silica gel column with dichloromethane/methanol (20:1). 23.6 mg (27%) of Compound I-182 were obtained as a white solid. MS (ES): m/z 512 (M+H)$^+$. $^1$H NMR (300 MHz, CD$_3$OD): δ 1.83 (s, 6H), 2.85 (s, 3H), 3.41-3.45 (t, 1H), 3.47-3.56 (t, 1H), 3.89-3.99 (m, 2H), 4.07-4.23 (m, 3H), 4.57-4.61 (m, 1H), 7.27-7.38 (m, 6H), 7.99 (s, 1H).

Example 74
Synthesis of 2-(1-((R)-2-(2-ethylphenyl)-2-(((1r,4R)-4-hydroxycyclohexyl)oxy)ethyl)-5-methyl-6-(oxazol-2-yl)-2,4-dioxo-1,2-dihydrothieno[2,3-d]pyrimidin-3(4H)-yl)-2-methylpropanoic acid (I-244) and Example 75: Synthesis of 2-(1-((R)-2-(2-ethylphenyl)-2-(((1s,4S)-4-hydroxycyclohexyl)oxy)ethyl)-5-methyl-6-(oxazol-2-yl)-2,4-dioxo-1,2-dihydrothieno[2,3-d]pyrimidin-3(4H)-yl)-2-methylpropanoic acid (I-245)
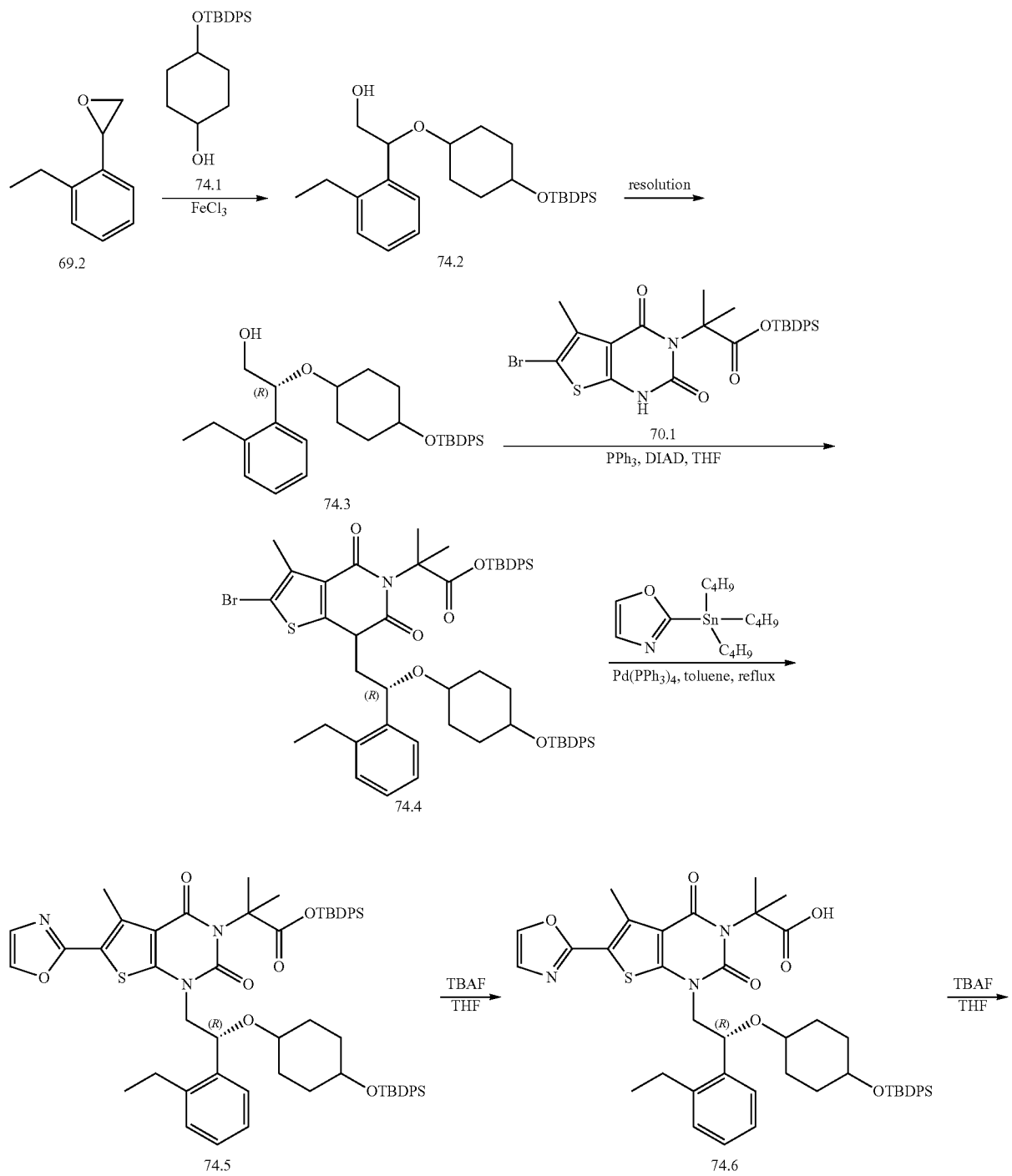

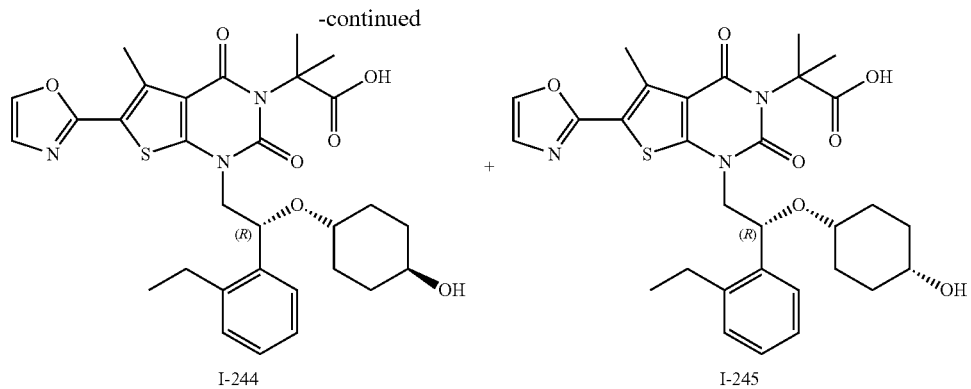

I-244        I-245

Synthesis of compound 74.1. Into a 1000-mL 3-necked round-bottom flask was placed cyclohexane-1,4-diol (20 g, 172.18 mmol, 1.00 equiv), 1,4-dioxane (500 mL) and 1H-imidazole (17.58 g, 258.24 mmol, 1.50 equiv). This was followed by the addition of a solution of tert-butyl(chloro)diphenylsilane (49.69 g, 180.78 mmol, 1.05 equiv) in dioxane (100 mL) dropwise with stirring at 15° C. The resulting solution was stirred for 15 h at 15-20° C. The solids were filtered out. The filtrate was diluted with 200 mL of water. The resulting solution was extracted with 3×200 mL of ethyl acetate and the organic layers combined and concentrated under vacuum. The residue was applied onto a silica gel column with ethyl acetate/petroleum ether (0:1-1:60-1:50-1:30-1:20). Purification afforded 32.98 g (54%) of 4-[(tert-butyldiphenylsilyl)oxy]cyclohexan-1-ol (74.1) as a white semi-solid.

Synthesis of compound 74.2. Compound 74.2 was prepared in a manner analogous to compounds 57.4 and 57.5, substituting 74.1 for isopropanol in the epoxide-opening step. Purification: The crude product was applied onto a silica gel column with ethyl acetate/petroleum ether (1/10). The material thus obtained (1.8 g) was repurified by flash preparative HPLC under the following conditions (IntelFlash-1): Column: C18 silica gel; mobile phase: acetonitrile/water=3/1 increasing to acetonitrile/water=19/1 within 30 min; detector: UV 220 nm. 1.64 g of 74.2 were obtained as a colorless oil.

Resolution of Compound 74.3. The enantiomers of 74.2 (2.09 g) were separated by chiral preparative HPLC under the following conditions (Gilson Gx 281): Column: Venusil Chiral OD-H, 21.1*25 cm, 5 µm; mobile phase: hexanes and IPA.

Synthesis of compound 74.4. Compound 74.4 was prepared in a manner analogous to compound 57.7. Isolated a light yellow oil in 54% yield from 70.1.

Synthesis of Compound 74.6. Into a 100-mL round-bottom flask was placed 74.5 (486 mg, 0.46 mmol, 1.00 equiv), tetrahydrofuran (10 mL) and TBAF (120 mg, 0.46 mmol, 1.00 equiv). The resulting solution was stirred overnight at room temperature and then concentrated under vacuum. The residue was purified by thin layer chromatography developed with DCM/MeOH/HOAc (30/1/0.15). 78 mg (21%) of 74.7 were obtained as a white solid.

Synthesis of Compounds I-244 and I-245. Into a 25-mL round-bottom flask was placed compound 74.7 (78 mg, 0.10 mmol, 1.00 equiv), tetrahydrofuran (2 mL) and TBAF (100 mg, 0.38 mmol, 4.02 equiv). The resulting solution was stirred for 4 days at room temperature and then concentrated under vacuum. The residue was applied onto a silica gel column with DCM/MeOH/HOAc (1:16:0.1). The product (70 mg) thus obtained was further purified by preparative HPLC under the following conditions (Waters): Column: SunFire Prep C18, 19*150 mm 5 µm; mobile phase: water (with 50 mM $NH_4CO_3$) and $CH_3CN$ (5.0% $CH_3CN$ up to 42.0% in 10 min, up to 95.0% in 2 min, down to 5.0% in 2 min); detector: UV 254/220 nm. 10.5 mg (38%) of Compound I-244 and 4.6 mg (16%) of Compound I-245 were obtained, both as white solids. MS (ES): m/z 582 (M+H)$^+$.

Analytical Data for Compound I-244: $^1$H NMR (CD$_3$OD, 300 MHz): δ 7.99 (1H, s), 7.63-7.60 (1H, m), 7.23-7.22 (4H, m), 5.26-5.22 (1H, dd, J$_1$=9.0 Hz, J$_2$=3.0 Hz), 4.30-4.25 (1H, d, J=12.0 Hz), 3.70-3.62 (1H, t, J=12.0 Hz), 3.50-3.47 (1H, m), 3.20-3.19 (1H, m), 3.08-2.90 (1H, m), 2.82 (3H, s), 2.80-2.69 (1H, m), 1.83 (3H, s), 1.81 (3H, s), 1.73-1.62 (4H, m), 1.36-1.31 (4H, m), 1.25-1.10 (3H, m).

Analytical Data for Compound I-245: MS (ES): m/z 582 (M+H)$^+$; 604 (M+Na)$^+$. $^1$H NMR (CD$_3$OD, 300 MHz): δ 7.97 (1H, s), 7.65-7.62 (1H, m), 7.32-7.25 (4H, m), 5.29-5.26 (1H, m), 4.30-4.26 (1H, m), 3.70-3.63 (1H, m), 3.54-3.45 (1H, m), 3.19-2.96 (1H, m), 2.82 (3H, s), 2.76-2.63 (1H, m), 1.94 (3H, s), 1.91 (3H, s), 1.81-1.67 (2H, m), 1.53-1.38 (9H, m).

Example 76

Synthesis of 2-[1-[2-(2-methoxyphenyl)-2-(oxan-4-yloxy)ethyl]-5-methyl-6-(1,3-oxazol-2-yl)-2,4-dioxo-1H,2H,3H,4H-thieno[2,3-d]pyrimidin-3-yl]-2-methylpropanoic acid (I-181)

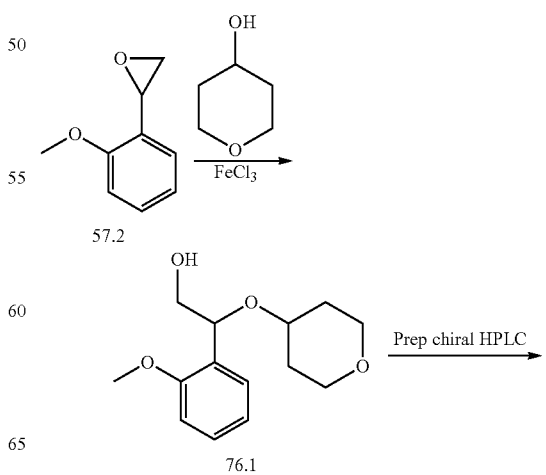

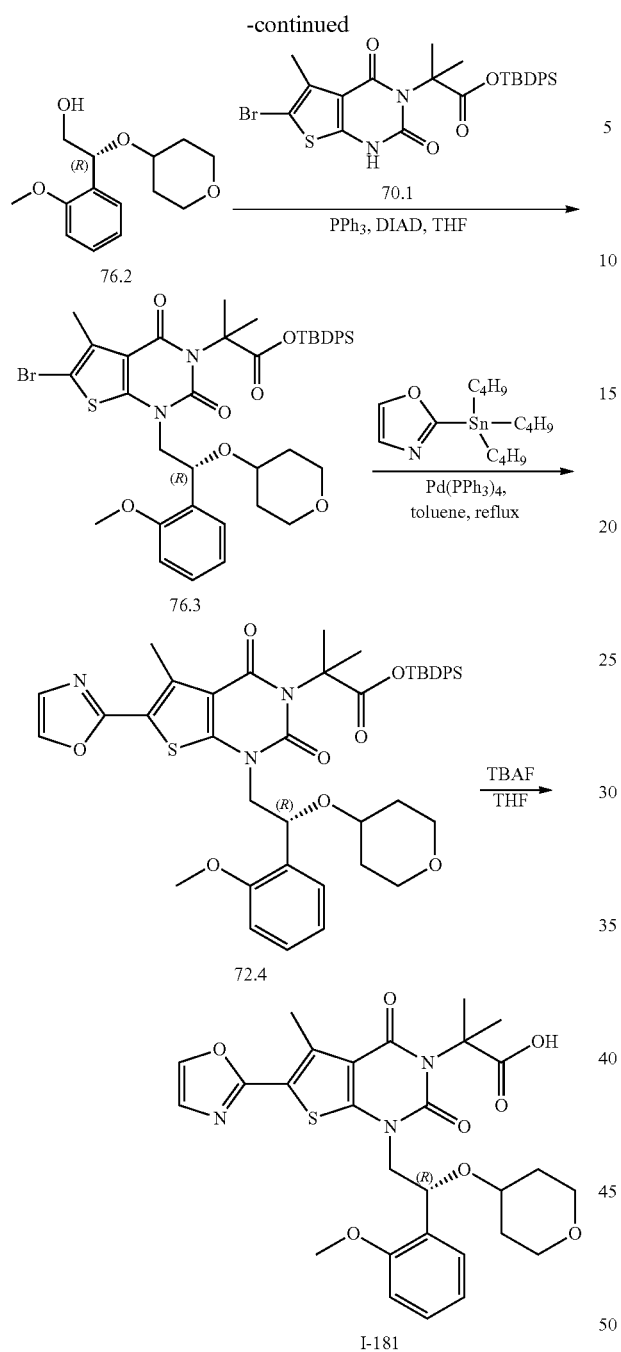

lowing conditions (Gilson Gx 281): Column: Venusil Chiral OD-H, 21.1*25 cm, 5 μm; mobile phase: hexanes (0.2% TEA) and ethanol (0.2% TEA) (hold at 10% ethanol (0.2% TEA) for 13 min); detector: UV 220/254 nm. 11.4 g (52%) of 76.2 were obtained as a white solid.

Synthesis of compound 76.3. Into a 500-mL 3-necked round-bottom flask, purged and maintained with an inert atmosphere of nitrogen, was placed 70.1 (12 g, 20.49 mmol, 1.00 equiv), tetrahydrofuran (200 mL), 76.2 (6.2 g, 24.57 mmol, 1.20 equiv) and DIAD (6.5 g, 32.18 mmol, 1.57 equiv). This was followed by the addition of a solution of triphenylphosphane (8.4 g, 32.03 mmol, 1.56 equiv) in tetrahydrofuran (100 mL) dropwise with stirring at 0° C. in 60 min. The resulting solution was stirred overnight at room temperature. The resulting mixture was concentrated under vacuum. The residue was applied onto a silica gel column with ethyl acetate/petroleum ether (1:5). This resulted in 17 g (crude) of 76.3 as a white solid.

Synthesis of compound 76.4. Into a 500-mL 3-necked round-bottom flask, purged and maintained with an inert atmosphere of nitrogen, was placed 76.3 (17 g, crude), toluene (300 mL), Pd(PPh$_3$)$_4$ (1.7 g, 1.47 mmol, 0.07 equiv) and 2-(tributylstannyl)-1,3-oxazole (8.6 g, 24.02 mmol, 1.16 equiv). The resulting solution was stirred overnight at 110° C. The resulting mixture was concentrated under vacuum. The residue was applied onto a silica gel column with ethyl acetate/petroleum ether (1:10). Purification afforded 6 g of 76.4 as a white solid.

Synthesis of compound I-181. Into a 250-mL 3-necked round-bottom flask, was placed 76.4 (6 g, 7.43 mmol, 1.00 equiv), tetrahydrofuran (100 mL), TBAF (2.3 g, 8.80 mmol, 1.18 equiv). The resulting solution was stirred for 1 h at room temperature. The resulting mixture was concentrated under vacuum. The residue was applied onto a silica gel column with dichloromethane/methanol (50:1). This resulted in 3.4 g (80%) of Compound I-181 as a white solid.

Purification: MS (ES): m/z 570 (M+H)$^+$, 592 (M+Na)$^+$. $^1$H NMR (300 MHz, DMSO-d$_6$): δ 1.22-1.36 (m, 2H), 1.62 (m, 8H), 2.75 (s, 3H), 3.20-3.39 (m, 3H), 3.48-3.58 (m, 2H), 3.80 (s, 3H), 3.85-4.20 (m, 2H), 5.30 (m, 1H), 7.03 (m, 2H), 7.33-7.50 (m, 3H), 8.2 (s, 1H).

Example 77

Synthesis of 2-[1-[(2R)-2-(2-methoxyphenyl)-2-(oxan-4-yloxy)ethyl]-5-methyl-6-(1,3-oxazol-2-yl)-2,4-dioxo-1H,2H,3H,4H-thieno[2,3-d]pyrimidin-3-yl]-2-methylpropanamide (I-246)

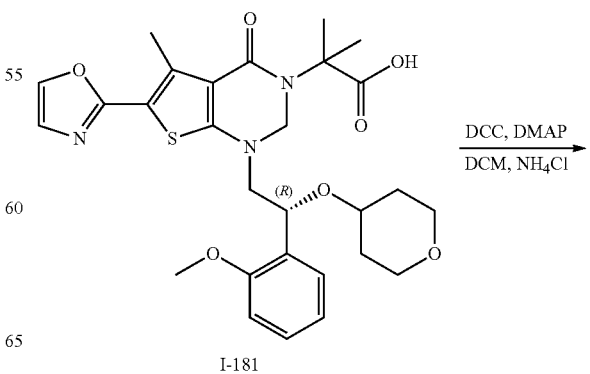

I-181

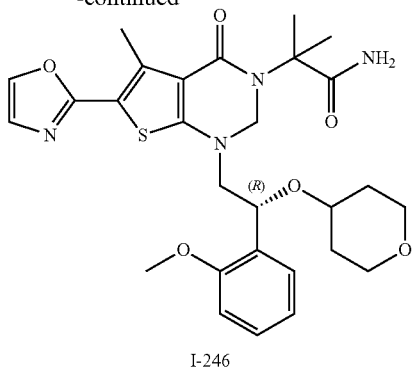

I-246

Compound I-246 was prepared from Compound I-181 according to the method of Example 4. Purification: silica gel column with dichloromethane/methanol (40:1). Isolated a white solid in 37% yield. MS (ES): m/z 591 (M+Na)+. 1H NMR (300 MHz, CD3OD): δ 1.29-1.36 (m, 2H), 1.65-1.67 (m, 8H), 2.75 (s, 3H), 3.20-3.26 (m, 2H), 3.50-3.59 (m, 2H), 3.79 (s, 3H), 3.95-4.09 (m, 2H), 5.26-5.31 (t, 1H), 6.78 (brs, 1H), 6.97-7.10 (m, 3H), 7.27-7.33 (m, 1H), 7.39 (s, 1H), 7.47-7.49 (m, 1H), 8.22 (s, 1H).

Example 78

Synthesis of 3-[1-(azetidin-1-yl)-2-methyl-1-oxopropan-2-yl]-1-[(2R)-2-(2-methoxyphenyl)-2-(oxan-4-yloxy)ethyl]-5-methyl-6-(1,3-oxazol-2-yl)-1H,2H,3H,4H-thieno[2,3-d]pyrimidine-2,4-dione (I-247)

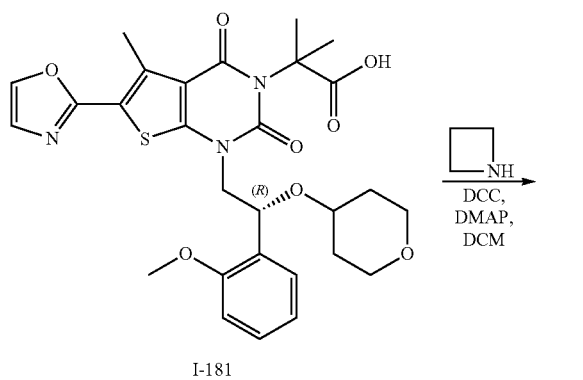

I-247

Compound I-247 was prepared from Compound I-181 and azetidine according to the method of Example 4. Purification: MS (ES): m/z 609 (M+H)+. 1H NMR (DMSO-d6, 300 MHz): δ 8.24 (1H, s), 7.48-7.46 (1H, d), 7.40 (1H, s), 7.31-7.29 (1H, t), 7.06-7.00 (2H, m), 5.31-5.29 (1H, m), 3.91-3.89 (2H, m), 3.86-3.81 (4H, m), 3.81 (3H, s), 3.70-3.58 (2H, m), 3.38-3.24 (1H, m), 3.23-3.21 (2H, m), 2.78 (3H, s), 2.14-2.09 (2H, t), 1.64-1.63 (8H, m), 1.40-1.15 (2H, m).

Example 79

Synthesis of 2-[1-[(2R)-2-hydroxy-2-(2-methoxyphenyl)ethyl]-5-methyl-6-(1,3-oxazol-2-yl)-2,4-dioxo-1H,2H,3H,4H-thieno[2,3-d]pyrimidin-3-yl]-2-methylpropanoic acid (I-248)

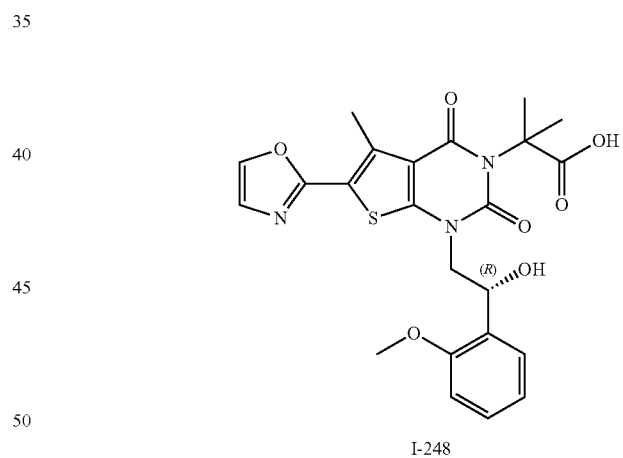

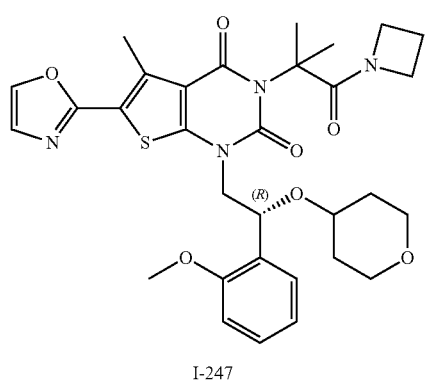

I-248

Into a 50-mL round-bottom flask was placed I-181 (100 mg, 0.18 mmol, 1.00 equiv), sodium bicarbonate (798 mg, 9.50 mmol, 50.11 equiv) and dichloromethane (10 mL). This was followed by the addition of BBr3 (476 mg, 10.03 equiv) dropwise with stirring at 0° C. The resulting solution was stirred for 0.5 h at room temperature and then concentrated under vacuum. The residue was purified by thin layer chromatography developed with methanol/DCM (1:20). 9.6 mg (11%) of Compound I-248 were obtained as a white solid. MS (ES): m/z 586 (M+H)+. 1H NMR (400 MHz, CD3OD): δ 1.79-1.82 (d, 6H), 2.78 (s, 3H), 3.33 (s, 3H), 4.00-4.05 (m, 1H), 4.25-4.31 (m, 1H), 5.14-5.17 (t, 1H), 6.71-6.73 (d, 1H), 6.87-6.90 (t, 1H), 7.07-7.11 (t, 1H), 7.25 (s, 1H), 7.35-7.36 (d, 1H), 7.96 (s, 1H).

Example 80

Synthesis of 2-[1-[(2R)-2-(2-ethylphenyl)-2-(oxan-4-yloxy)ethyl]-5-methyl-6-(1,3-oxazol-2-yl)-2,4-dioxo-1H,2H,3H,4H-thieno[2,3-d]pyrimidin-3-yl]-2-methylpropanoic acid (I-249)

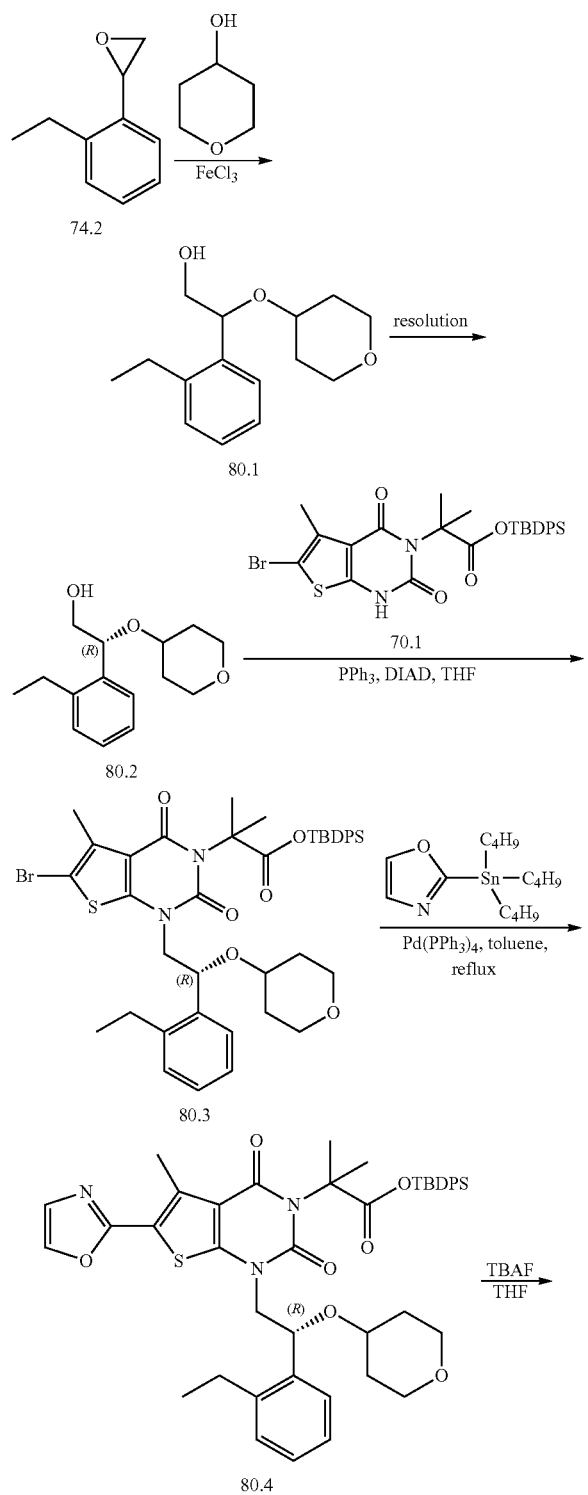

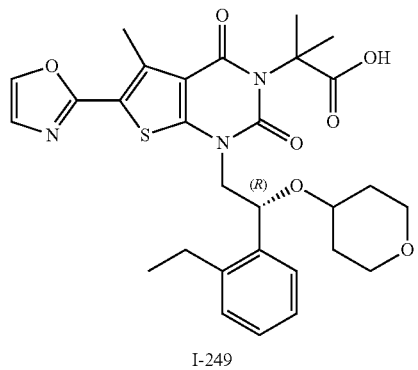

I-249

Synthesis of compound 80.2. Compound 80.2 was prepared according to the method for the preparation of compound 57.5. Purification: The enantiomers of the racemic product (550 mg) were separated by chiral preparative HPLC under the following conditions (Gilson Gx 281): column: Venusil Chiral OD-H, 21.1*25 cm, 5 μm; mobile phase: hexanes and ethanol (hold at 5% ethanol for 7 min); detector: UV 220/254 nm. 300 mg product were obtained (0.05% yield from 74.2).

Synthesis of Compound I-249. Compound I-249 was prepared according to the method of Example 57. Purification: silica gel column with dichloromethane/methanol (40:1). 56.6 mg (80%) of Compound I-249 were obtained as a white solid. MS (ES): m/z 568 (M+H)$^+$.

$^1$H NMR (300 MHz, CD$_3$OD): δ 1.23-1.28 (t, 3H), 1.40-1.42 (m, 2H), 1.64-1.68 (m, 2H), 1.77-1.81 (d, 6H), 2.72-2.76 (m, 1H), 2.80 (s, 3H), 2.89-2.94 (m, 1H), 3.32-3.62 (m, 6H), 4.26-4.27 (d, 1H), 5.22-5.26 (d, 1H), 7.22-7.27 (m, 4H), 7.59-7.62 (m, 1H), 7.96(s, 1H).

Example 81

Synthesis of 2-[1-[(2R)-2-(2-chlorophenyl)-2-(oxan-4-yloxy)ethyl]-5-methyl-6-(1,3-oxazol-2-yl)-2,4-dioxo-1H,2H,3H,4H-thieno[2,3-d]pyrimidin-3-yl]-2-methylpropanoic acid (I-250) and Example 82: Synthesis of 2-[1-[(2S)-2-(2-chlorophenyl)-2-(oxan-4-yloxy)ethyl]-5-methyl-6-(1,3-oxazol-2-yl)-2,4-dioxo-1H,2H,3H,4H-thieno[2,3-d]pyrimidin-3-yl]-2-methylpropanoic acid (I-251)

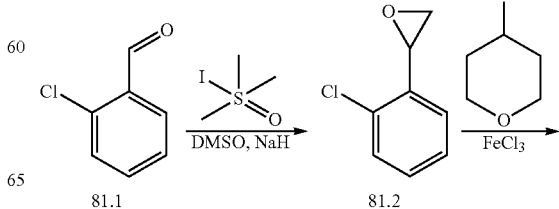

331
-continued

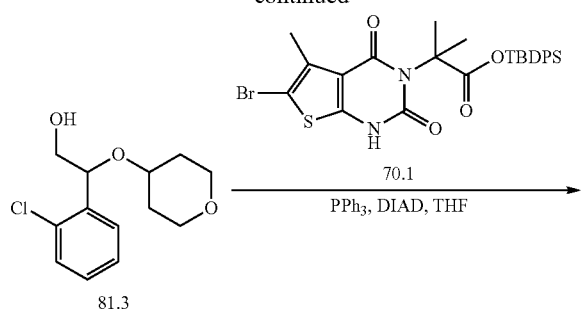

81.3

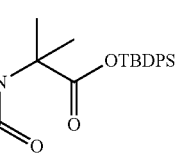

81.4

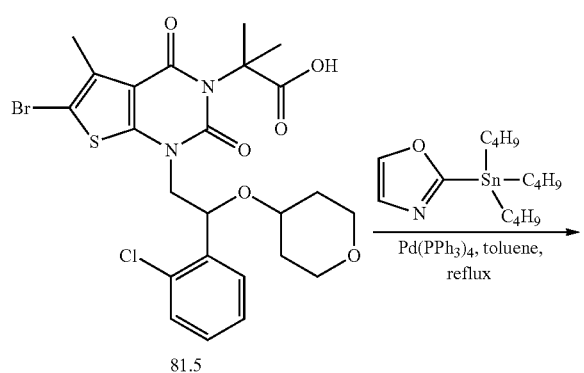

81.5

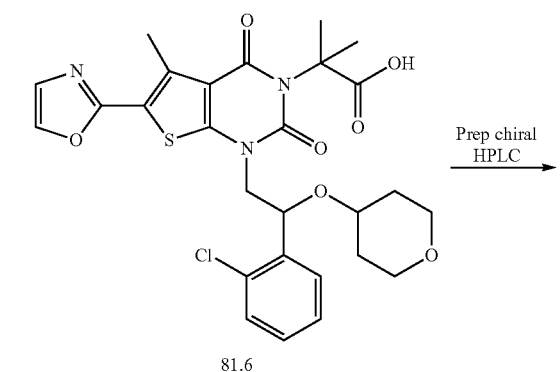

81.6

332
-continued

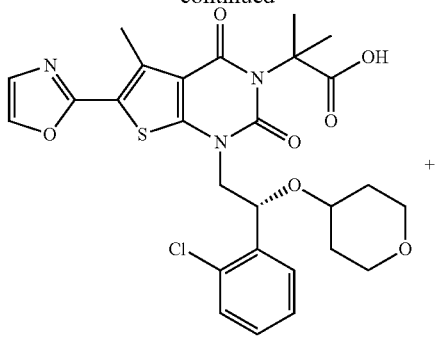

I-250

+

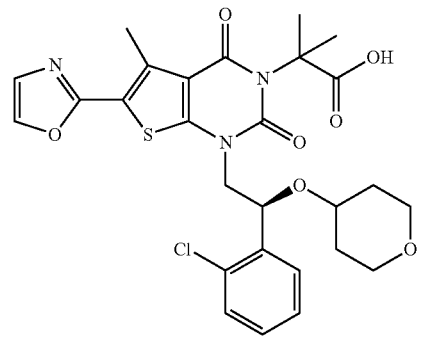

I-251

Synthesis of compound 81.3. Compound 81.3 was prepared according to the method used for the preparation of 57.3, substituting 4-hydroxypyran for isopropanol in the epoxide-opening step. Isolated a light yellow liquid in 5% overall yield.

Synthesis of compound 81.6. Compound 81.6 was prepared from 81.3 and 70.1 following the procedure for Example 67. Purification: The residue obtained after work-up was applied onto a silica gel column and eluted with DCM/MeOH=100:1. The product thus obtained was repurified by flash preparative HPLC under the following conditions (IntelFlash-1): Column: C18 silica gel; mobile phase: acetonitrile:water=0:100 increasing to acetonitrile:water=100:0 within 16 min; detector: UV 220 nm. 40 mg (23%) of 81.6 were obtained as a colorless oil.

Synthesis of Compounds I-250 and I-251. The enantiomers of 81.6 were separated by chiral preparative HPLC under the following conditions (Gilson Gx 281): Column: Chiralpak IA, 2*25 cm, 5 μm; mobile phase: hexanes and IPA (hold at 20% IPA for 22 min); detector: UV 220/254 nm. 2.8 mg (7%) of Compound I-250 and 3.5 mg (9%) of I-251 were obtained as white solids.

Analytical Data for Compound I-250: MS (ES): m/z 574 (M+H)$^+$. $^1$H NMR (300 MHz, CD$_3$OD): δ 8.00 (s, 1H), 7.75 (d, 1H, J=6.0 Hz), 7.45 (m, 2H), 7.35 (d, 1H, J=5.1 Hz), 7.29 (s, 1H), 5.49 (q, 1H, J=5.1 Hz), 4.32 (m, 1H), 3.99 (m, 1H), 3.70 (m, 2 H), 3.50 (m, 1H), 3.40 (m, 2H), 2.83 (s, 3H), 1.82 (s, 3H), 1.80 (s, 3H), 1.75 (m, 2H), 1.52 (m, 2H).

Analytical Data for Compound I-251: MS (ES): m/z 574 (M+H)$^+$. $^1$H NMR (300 MHz, CD$_3$OD): δ 7.99 (s, 1 H), 7.75 (d, 1 H, J=6.0 Hz), 7.45 (m, 3 H), 7.29 (s, 1 H), 5.49 (q, 1 H, J=3.3 Hz), 4.32 (m, 1 H), 3.99 (m, 1 H), 3.71-3.49 (m, 3 H), 3.38 (m, 2H), 2.83 (s, 3 H), 1.82(s, 3 H), 1.80 (s, 3 H), 1.74 (m, 2H), 1.50 (m, 2H).

Example 83

Synthesis of 2-[1-[(2R)-2-(2-chlorophenyl)-2-(oxan-4-yloxy)ethyl]-5-methyl-6-(1,3-oxazol-2-yl)-2,4-dioxo-1H,2H,3H,4H-thieno[2,3-d]pyrimidin-3-yl]-2-methylpropanamide (I-252)

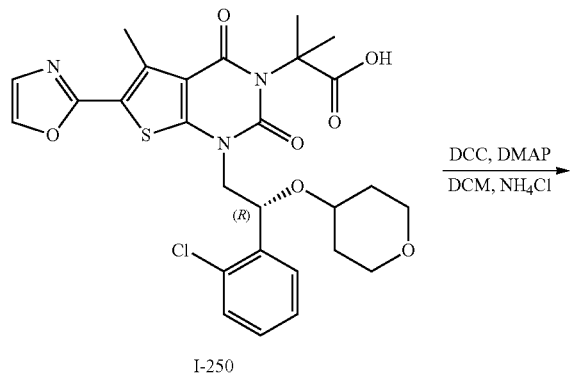

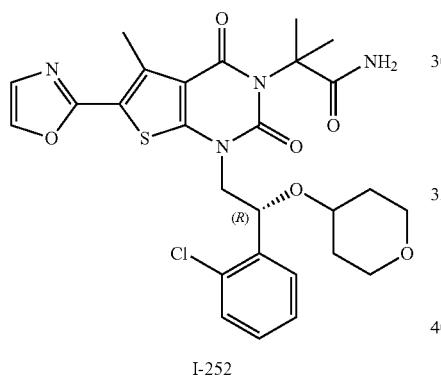

Compound I-252 was prepared from Compound I-250 (Example 81) and ammonium chloride according to the method of Example 4. Isolated a white solid in 60% yield. MS (ES): m/z 595 (M+Na)+. $^1$H NMR (300 MHz, DMSO-$d_6$): δ 8.22 (1H, s), 7.70-7.67 (1H, d), 7.49-7.37 (4H, m), 7.30-6.70 (2H, m), 5.35-5.30 (1H, m), 4.30-4.15 (1H, m), 3.90-3.80 (1H, m), 3.54-3.52 (2H, m), 3.40-3.36 (1H, m), 3.32-3.21 (2H, m), 2.75 (3H, s), 1.66-1.60 (8H, m), 1.32-1.24 (2H, m).

Example 84

Synthesis of 3-[1-(azetidin-1-yl)-2-methyl-1-oxopropan-2-yl]-1-[(2R)-2-(2-chlorophenyl)-2-(oxan-4-yloxy)ethyl]-5-methyl-6-(1,3-oxazol-2-yl)-1H,2H,3H,4H-thieno[2,3-d]pyrimidine-2,4-dione (I-253)

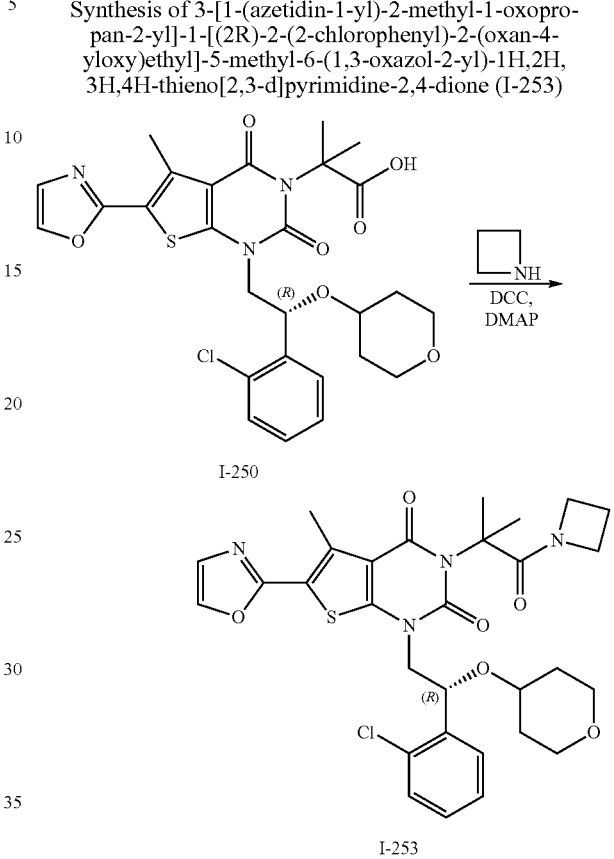

Compound I-253 was prepared from Compound I-250 (Example 81) and azetidine according to the method of Example 4. Isolated a white solid in 49% yield. MS (ES): m/z 613 (M+H)+. $^1$H NMR (300 MHz, DMSO-$d_6$): δ 8.24 (1H, s), 7.69-7.66 (1H, d), 7.48-7.38 (4H, m), 5.35-5.30 (1H, m), 4.30-4.21 (1H, m), 3.90-3.88 (4H, m), 3.57-3.48 (2H, m), 3.33-3.30 (1H, m), 3.27-3.24 (3H, m), 2.77 (3H, s), 2.12 (2H, m), 1.70-1.61 (8H, m), 1.38-1.25 (2H, m).

Example 85

Synthesis of 2-[1-[(2R)-2-(2-hydroxyethoxy)-2-(2-methoxyphenyl)ethyl]-5-methyl-6-(1,3-oxazol-2-yl)-2,4-dioxo-1H,2H,3H,4H-thieno[2,3-d]pyrimidin-3-yl]-2-methylpropanoic acid (I-254)

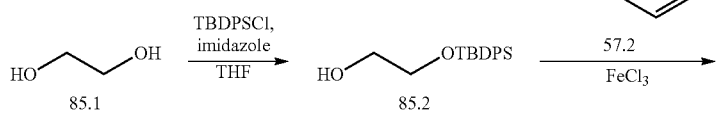

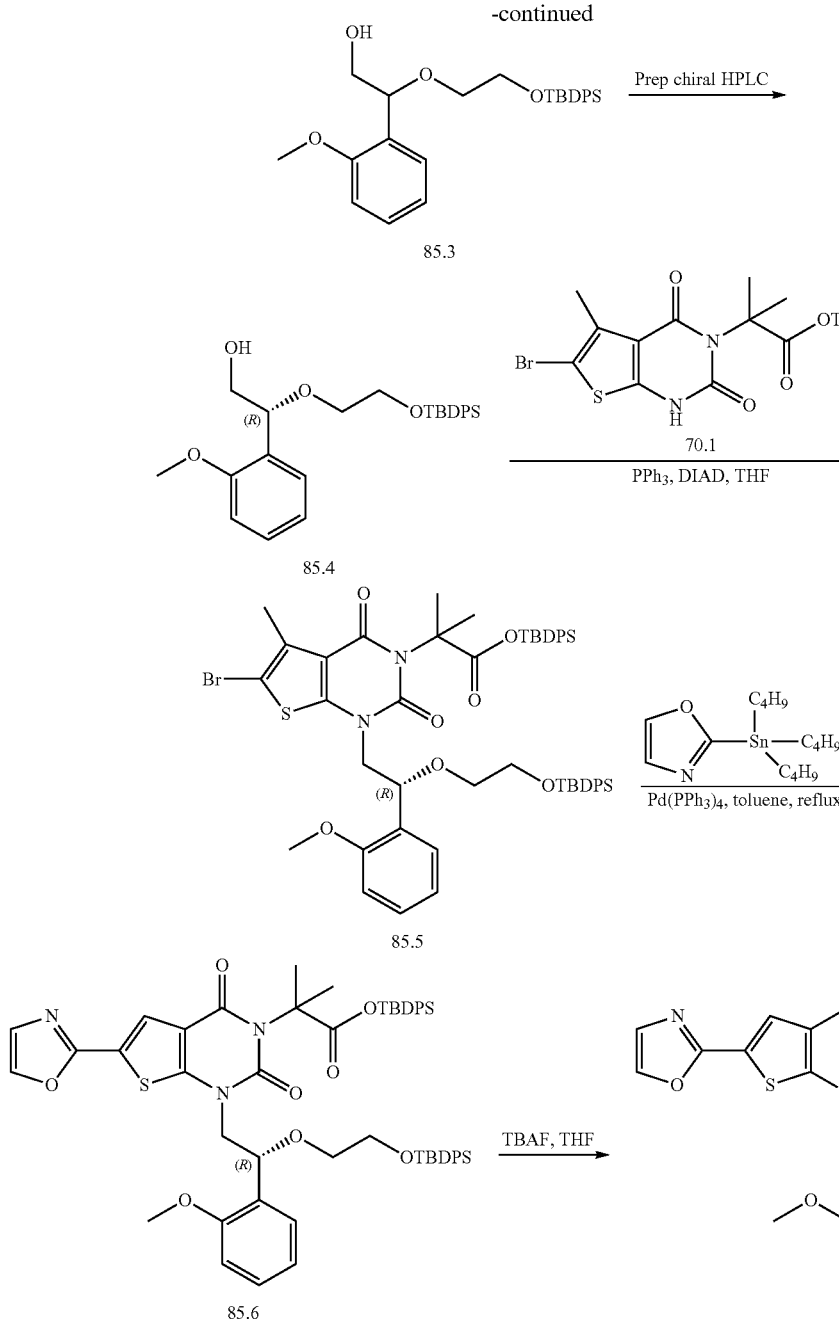

Synthesis of compound 85.2. Into a 2-L 3-necked round-bottom flask was placed tetrahydrofuran (800 mL), ethane-1,2-diol (40 g, 644.46 mmol, 1.00 equiv) and imidazole (61.4 g, 901.92 mmol, 1.40 equiv). This was followed by the addition of TBDPSCl (186.3 g) dropwise with stirring at 0° C. in 30 min. The resulting solution was stirred overnight at room temperature. The solids were filtered out, and the filtrate cake was washed with 200 mL of EA. The resulting mixture was washed with 200 mL of brine and concentrated under vacuum. The residue was applied onto a silica gel column with ethyl acetate/petroleum ether (1:25). Purification afforded 83 g (43%) of 2-[(tert-butyldiphenylsilyl)oxy]ethan-1-ol (85.2) as a colorless oil.

Synthesis of compound 85.3. Compound 85.3 was prepared according to the method used for the synthesis of 57.3, substituting 85.2 for isopropanol. Isolated a yellow oil in 5% yield.

Synthesis of Compound 85.4. The enantiomers of 85.3 were separated by chiral preparative HPLC under the following conditions (Gilson Gx 281): Column: Venusil Chiral OD-H, 21.1*25 cm, 5 μm; mobile phase: hexanes and IPA (hold at 2.0% IPA for 16 min); detector: UV 220/254 nm. 270 mg (39%) of 85.4 were obtained as a yellow oil.

Synthesis of Compound I-254. Compound I-254 was prepared according to the method of Example 57. Purification: The residue obtained after work-up was applied onto a silica gel column with dichloromethane/methanol (40:1). Purification afforded 14 mg (4% from 70.1) of Compound I-254 as a white solid. MS (ES): m/z 468 (M–C$_2$H$_5$O$_2$)$^+$, 530 (M+H)$^+$. $^1$H NMR (300 MHz, CD$_3$OD): δ 1.65-1.67 (d, 6H), 2.69 (s, 3H), 3.20-3.39 (m, 1H), 3.41-3.49 (m, 1H), 3.51-3.57 (m, 2H), 3.68 (s, 3H), 3.88-3.95 (m, 1H), 4.20-4.27 (m, 1H), 5.16-5.21 (t, 1H), 6.78-6.81 (d, 1H), 6.88-6.93 (t, 1H), 7.13-7.18 (m, 2H), 7.41-7.44 (d, 1H), 7.95 (s, 1H).
Example 86
Synthesis of 2-[1-[(2R)-2-(2-ethylphenyl)-2-(2-hydroxyethoxy)ethyl]-5-methyl-6-(1,3-oxazol-2-yl)-2,4-dioxo-1H,2H,3H,4H-thieno[2,3-d]pyrimidin-3-yl]-2-methylpropanoic acid (I-255)
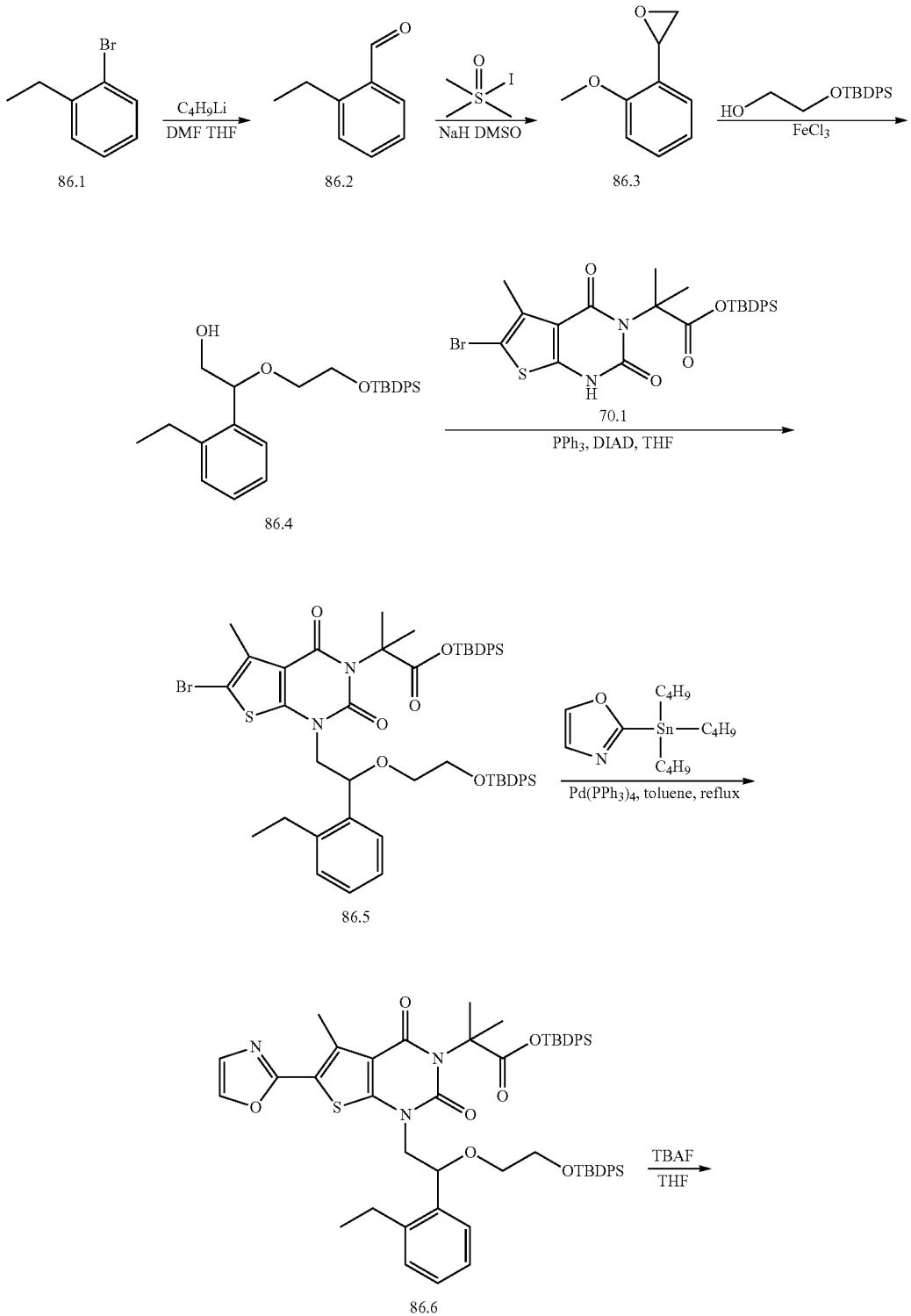

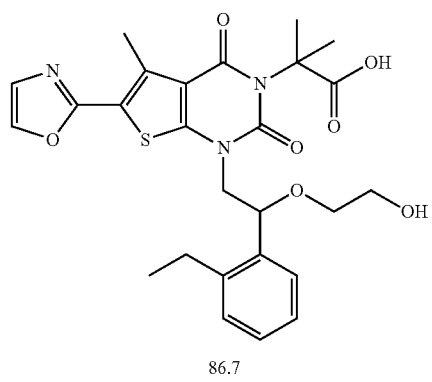

86.7

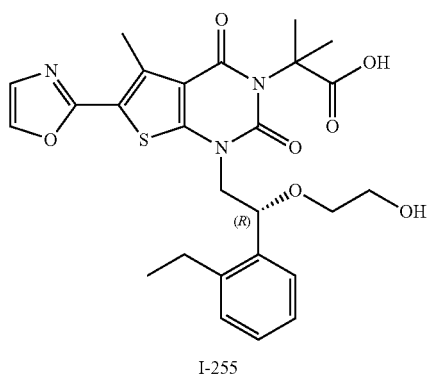

I-255

Synthesis of compound 86.5. Compound 86.5 was prepared in a manner analogous to compound 85.3. Isolated a colorless oil in 2% yield.

Synthesis of compound 86.7. Compound 86.7 was prepared according to the method of Example 57. Purification: The residue obtained after work-up was applied onto a TLC plate with dichloromethane/methanol/HOAc (40:1:0.1). Purification afforded 406 mg (57% from 70.1) of 86.7 as a white powder.

Synthesis of Compound I-255. The (R) enantiomer was isolated from 406 mg of 86.7 by chiral preparative HPLC under the following conditions: Column: CHIRALPAK IA; mobile phase: hexanes (0.1% acetic acid):IPA=75:25; detector: UV 254 nm. 44.5 mg of Compound I-255 were obtained as a white solid. MS (ES): m/z 528 (M+H)$^+$. $^1$H NMR (CD$_3$OD, 300 MHz): δ 7.98 (1H, d, J=0.6 Hz), 7.62-7.59 (1H, m), 7.31-7.21 (4H, m), 5.19-5.15 (1H, dd, J$_1$=9 Hz, J$_2$=3.3 Hz), 4.26-4.20 (1H, dd, J$_1$=14.7 Hz, J$_2$=3.3 Hz), 3.93-3.85 (1H, dd, J$_1$=14.7 Hz, J$_2$=9 Hz), 3.57-3.53 (2H, m), 3.49-3.40 (1H, m), 2.96-2.87 (1H, m), 2.80-2.70 (4H, m), 1.81 (3H, s), 1.80 (3H, s), 1.30-1.25 (3H, t, J=7.5 Hz).

Example 87

Synthesis of 2-[1-[(2R)-2-(2-ethoxyphenyl)-2-(2-hydroxyethoxy)ethyl]-5-methyl-6-(1,3-oxazol-2-yl)-2,4-dioxo-1H,2H,3H,4H-thieno[2,3-d]pyrimidin-3-yl]-2-methylpropanoic acid (I-256)

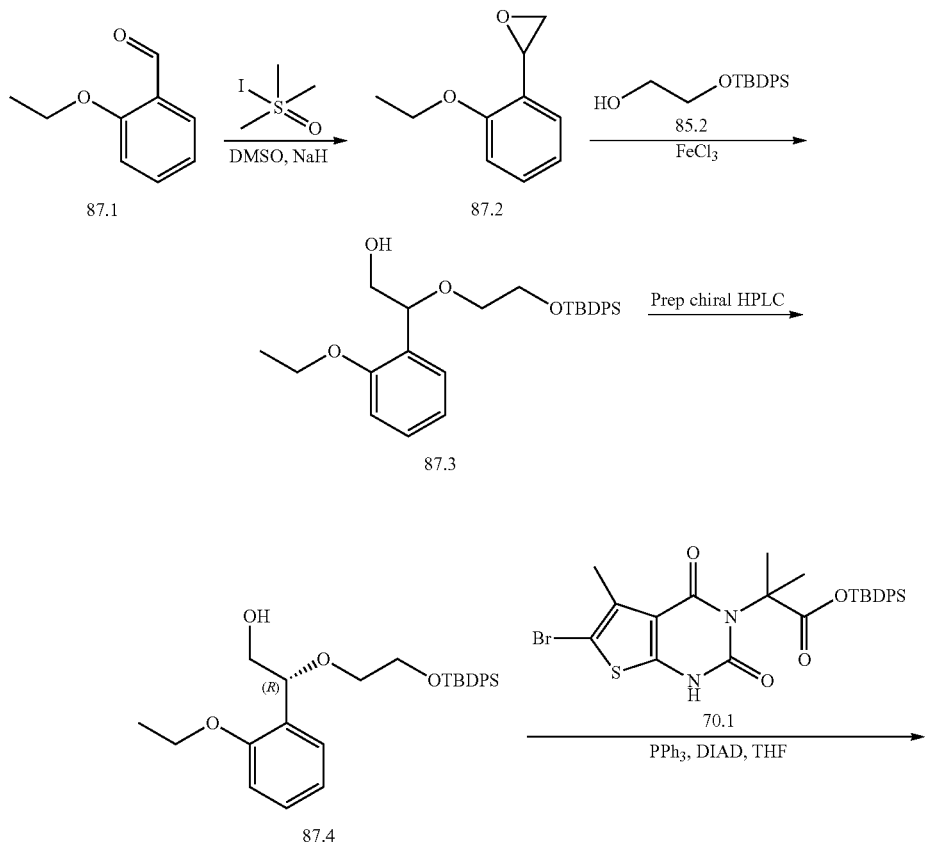

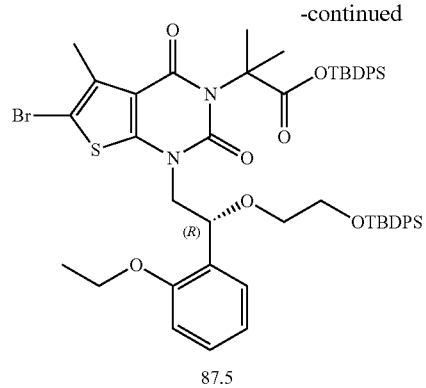 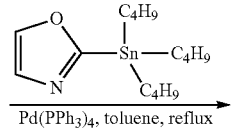

87.5

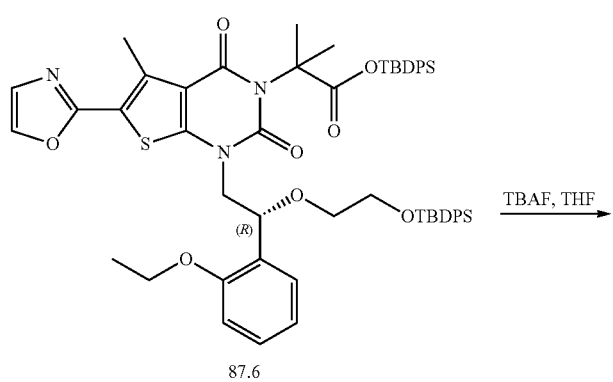

87.6 → I-256

Synthesis of compound 87.4. Compound 87.4 was prepared from 87.1 in a manner analogous to compound 57.5. Isolated a yellow oil in 2% overall yield.

Synthesis of Compound I-256. Compound I-256 was prepared from 87.4 and 70.1 in a manner analogous to the synthesis of compound I-158 (Example 57). MS (ES): m/z 482 $(M-C_2H_5O_2)^+$, 544 $(M+H)^+$. $^1H$ NMR (300 MHz, $CD_3OD$): δ 1.31-1.41 (t, 3H), 1.72-1.74 (d, 2H), 2.77-2.81 (s, 3H), 3.32-3.68 (m, 4H), 4.02-4.11 (m, 2H), 4.21-4.23 (m, 2H), 5.30-5.35 (t, 1H), 6.93-7.31 (m, 2H), 7.24-7.30 (m, 2H), 7.52-7.54 (d, 1H), 7.98 (s, 1H).

Example 88

Synthesis of N-(2-hydroxyethyl)-2-[1-[(2R)-2-(2-methoxyphenyl)-2-(propan-2-yloxy)ethyl]-5-methyl-6-(1,3-oxazol-2-yl)-2,4-dioxo-1H,2H,3H,4H-thieno[2,3-d]pyrimidin-3-yl]-2-methylpropanamide (I-257)

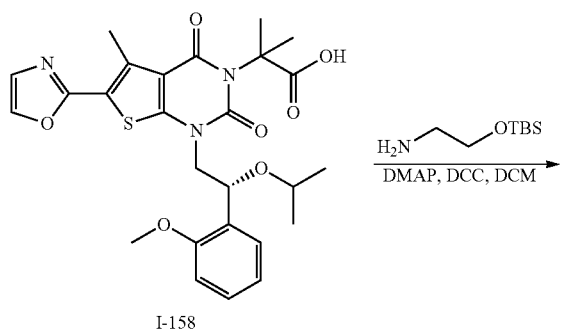

I-158

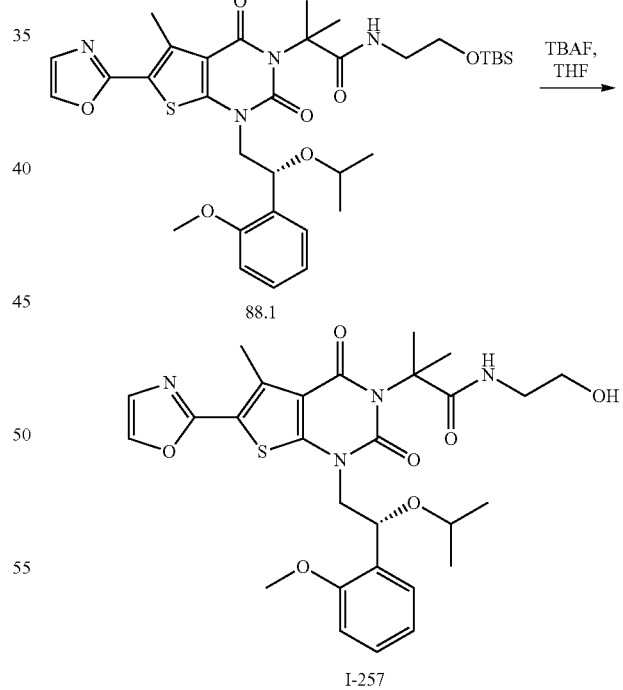

Synthesis of 88.1. Compound 88.1 was prepared from Compound I-158 (Example 57) in a manner analogous to Example 4. Isolated a white solid in 48% yield.

Synthesis of Compound I-257. Into a 50-mL round-bottom flask was placed 88.1 (50 mg, 0.07 mmol, 1.00 equiv), TBAF (20 mg, 0.08 mmol, 1.05 equiv) and tetrahydrofuran (5 mL). The resulting solution was stirred for 3 h at room temperature and then concentrated under vacuum. The residue was purified by TLC with ethyl acetate/petroleum ether (1:1) to afford 8 mg (19%) of Compound I-257 as a light yellow solid. MS (ES): m/z 571 (M+H)+. $^1$H NMR (400 MHz, CD$_3$OD): δ 1.14-1.15 (m, 6H), 1.71-1.96 (m, 6H), 2.41 (s, 3H), 3.33 (m, 1H), 3.46 (m, 1H), 3.56 (m, 1H), 3.74 (m, 4H), 3.93 (s, 3H), 5.13 (s, 1H), 7.00 (t, J=7.6 Hz, 2H), 7.19 (s, 1H), 7.28-7.33 (t, J=7.2 Hz, 1H), 7.46-7.48 (d, J=7.6 Hz, 1H), 7.87 (s, 1H).
Example 89
Synthesis of 2-[1-[(2R)-2-[(2R)-2-hydroxypropoxy]-2-(2-methoxyphenyl)ethyl]-5-methyl-6-(1,3-oxazol-2-yl)-2,4-dioxo-1H,2H,3H,4H-thieno[2,3-d]pyrimidin-3-yl]-2-methylpropanoic acid (I-258)
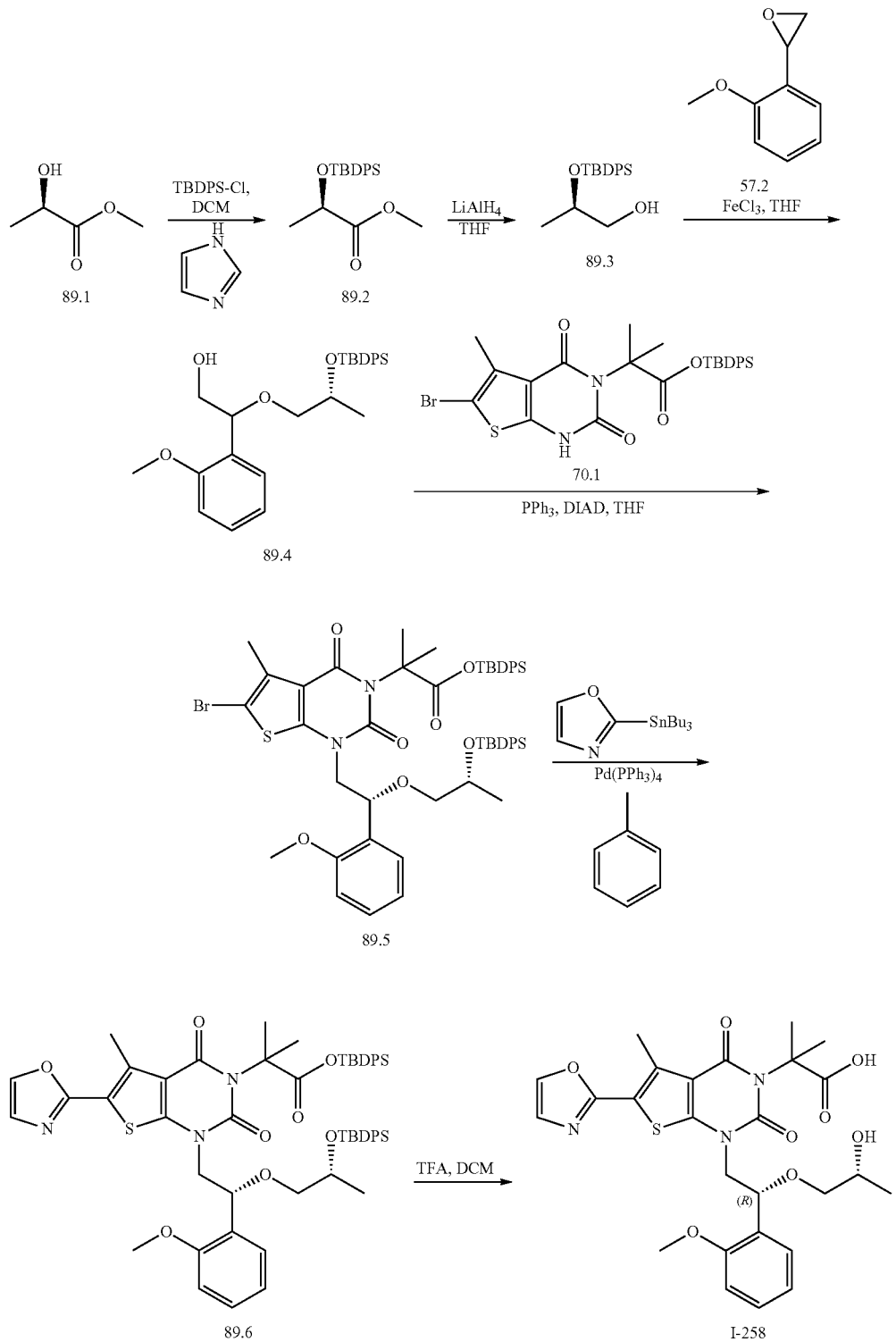

345

Synthesis of compound 89.2. Into a 250-mL 3-necked round-bottom flask was placed dichloromethane (100 mL), methyl (2R)-2-hydroxypropanoate (10 g, 96.06 mmol, 1.00 equiv) and 1H-imidazole (9.8 g, 143.95 mmol, 1.50 equiv). This was followed by the addition of TBDPSCl (29.1 g, 112.45 mmol, 1.17 equiv) dropwise with stirring at 0° C. The resulting solution was stirred for 2 h at room temperature and then concentrated under vacuum. The residue was applied onto a silica gel column with ethyl acetate/petroleum ether (1:50). Purification afforded 32 g (97%) of 89.2 as a colorless oil.

Synthesis of compound 89.3. Into a 500-mL 3-necked round-bottom flask was placed tetrahydrofuran (200 mL) and 89.2 (28 g, 81.75 mmol, 1.00 equiv). This was followed by the addition of LiAlH$_4$ (1.56 g, 41.11 mmol, 0.50 equiv) in portions at −30° C. The resulting solution was stirred for 30 min at −30° C. The reaction was then quenched by the addition of 100 mL of NH$_4$Cl (sat., aq.). The resulting solution was extracted with 3×200 mL of ethyl acetate and the organic layers combined and concentrated under vacuum. The residue was applied onto a silica gel column with ethyl acetate/petroleum ether (1:30). This resulted in 11.8 g (46%) of (2R)-2-[(tert-butyldiphenylsilyl)oxy]propan-1-ol (89.3) as a colorless oil.

Synthesis of compound 89.4. Compound 89.4 was prepared from 57.2 and compound 89.3 in a manner analogous to compound 57.3. Isolated a colorless oil in 1% yield.

Synthesis of Compound I-258. Compound I-258 was prepared from 89.4 and 70.1 in a manner analogous to the preparation of compound 14.5. Isolated a white solid in 22% yield from 70.1. MS (ES): m/z 544 (M+H)$^+$. $^1$H NMR (400 MHz, CD$_3$OD): δ 1.05 (d, J=7.2 Hz, 3H), 1.79-1.80 (m, 6H), 2.81 (s, 3H), 3.13-3.18 (m, 1H), 3.83-3.87 (m, 4H), 4.01-4.06 (m, 1H), 4.28-4.34 (m, 1H), 5.27-5.31 (m, 1H), 6.94 (d, J=8.4, 1H), 7.03 (t, J=7.6, 1H), 7.26-7.30 (m, 2H), 7.54 (d, J=7.6, 1H), 7.98 (s, 1H).

Example 90

Synthesis of 2-[1-[(2R)-2-(2-methoxyphenyl)-2-(oxan-4-ylmethoxy)ethyl]-5-methyl-6-(1,3-oxazol-2-yl)-2,4-dioxo-1H,2H,3H,4H-thieno[2,3-d[pyrimidin-3-yl]-2-methylpropanoic acid (I-259)

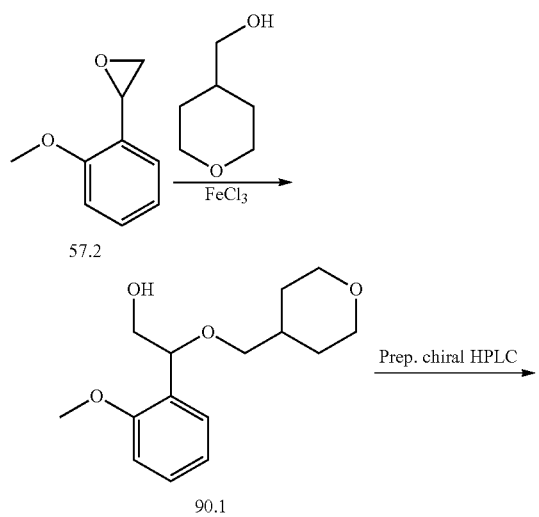

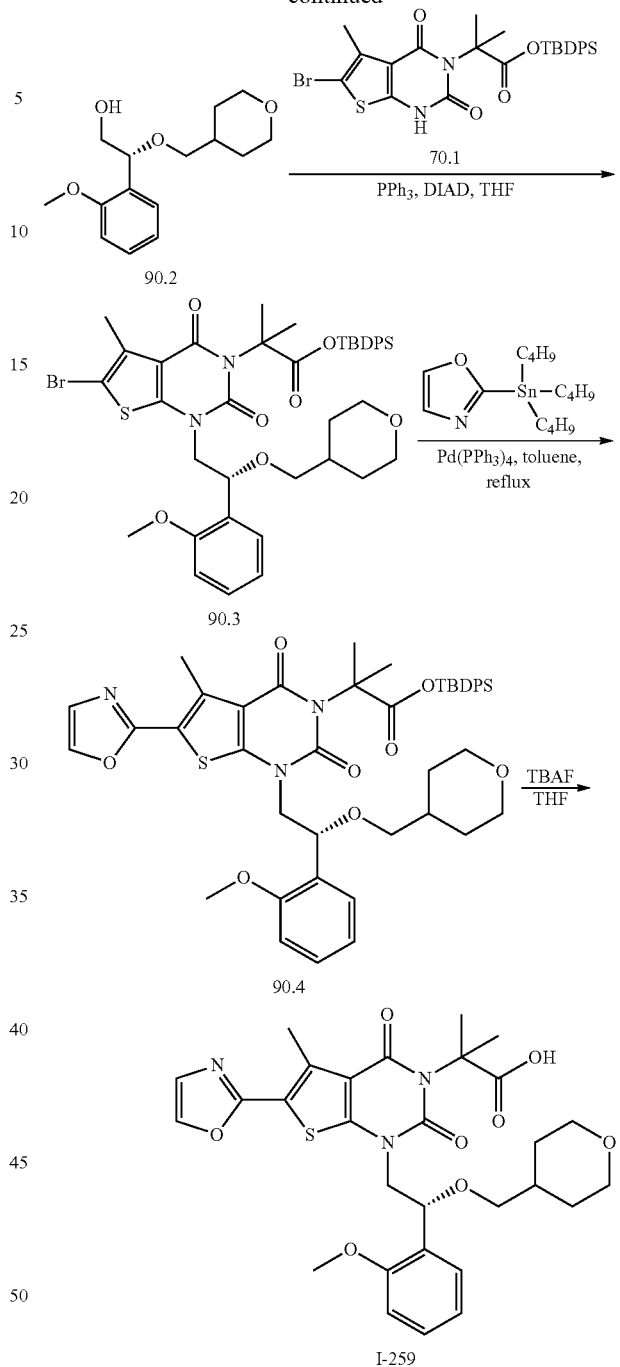

Synthesis of compound 90.2. Compound 90.2 was prepared from 57.2 and (tetrahydro-2H-pyran-4-yl)methanol in a manner analogous to the synthesis of 57.5. Chiral separation: Gilson Gx 281; Column: Venusil Chiral OD-H, 0.46*25 cm, 5 μm; mobile phase: hexanes and EtOH (hold at 5.0% EtOH for 18 min); detector: UV 254 nm. Isolated 970 mg (12%) of a colorless oil.

Synthesis of Compound I-259. Compound I-259 was prepared from 90.2 and 70.1 in a manner analogous to the preparation of Compound I-158, Example 57. MS (ES): m/z 584 (M+H)$^+$. $^1$H NMR (300 MHz, CD$_3$OD): δ 1.13-1.46 (m, 2H), 1.51-1.57 (m, 2H), 1.62-1.80 (m, 7H), 2.76-2.81 (s, 3H), 3.07-3.12 (t, 1H), 3.25-3.56 (m, 3H), 3.82-3.92 (m, 5H), 4.09-4.21 (m, 2H, 5.21-5.26 (t, 1H), 6.95-7.05 (m, 2H), 7.32-7.32 (m, 2H), 7.44-7.47 (m, 1H), 8.00 (s, 1H).

Example 91

Synthesis of 2-[1-[(2R)-2-(2-methoxyphenyl)-2-(oxan-4-ylmethoxy)ethyl]-5-methyl-6-(1,3-oxazol-2-yl)-2,4-dioxo-1H,2H,3H,4H-thieno[2,3-d]pyrimidin-3-yl]-2-methylpropanamide (I-260)

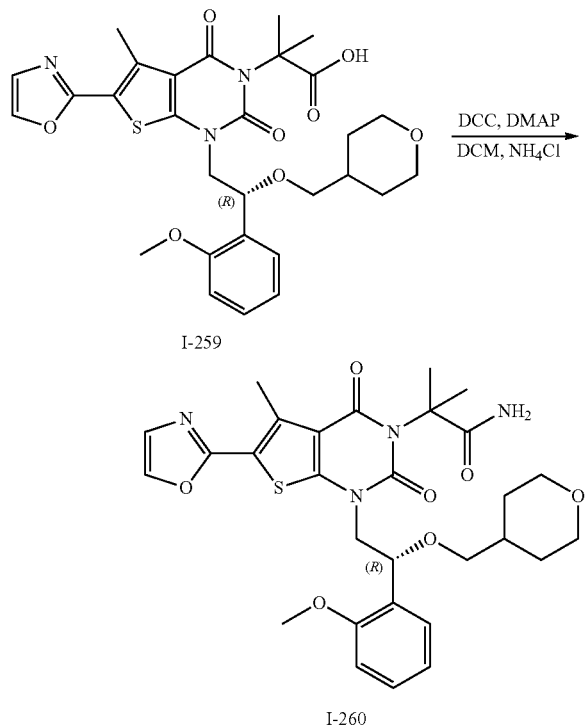

Compound I-260 was prepared from Compound I-259 (Example 90) according to the method of Example 4. Isolated a white solid in 43% yield. MS (ES): m/z 583 (M+H)$^+$, 605 (M+Na)$^+$. $^1$H NMR (DMSO-d$_6$, 300 MHz): δ 8.22 (1H, s), 7.39-7.26 (3H, m), 7.05-6.97 (3H, m), 6.70 (1H, br s), 5.12-5.08 (1H, m), 4.07-3.94 (2H, m), 3.78-3.70 (5H, m), 3.19-3.00 (4H, m), 2.73 (3H, s), 1.65-1.64 (7H, m), 1.44-1.36 (2H, m), 1.20-0.99 (2H, m).

Example 92

Synthesis of (R)-2-(1-(2-(2-methoxyphenyl)-2-(oxetan-3-yloxy)ethyl)-5-methyl-6-(oxazol-2-yl)-2,4-dioxo-1,2-dihydrothieno[2,3-d]pyrimidin-3(4H)-yl)-2-methylpropanoic acid (I-261) and Example 93: Synthesis of (S)-2-(1-(2-(2-methoxyphenyl)-2-(oxetan-3-yloxy)ethyl)-5-methyl-6-(oxazol-2-yl)-2,4-dioxo-1,2-dihydrothieno[2,3-d]pyrimidin-3(4H)-yl)-2-methylpropanoic acid (I-262)

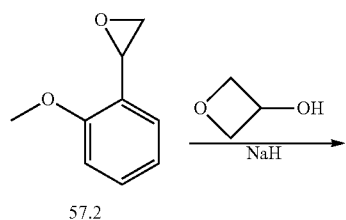

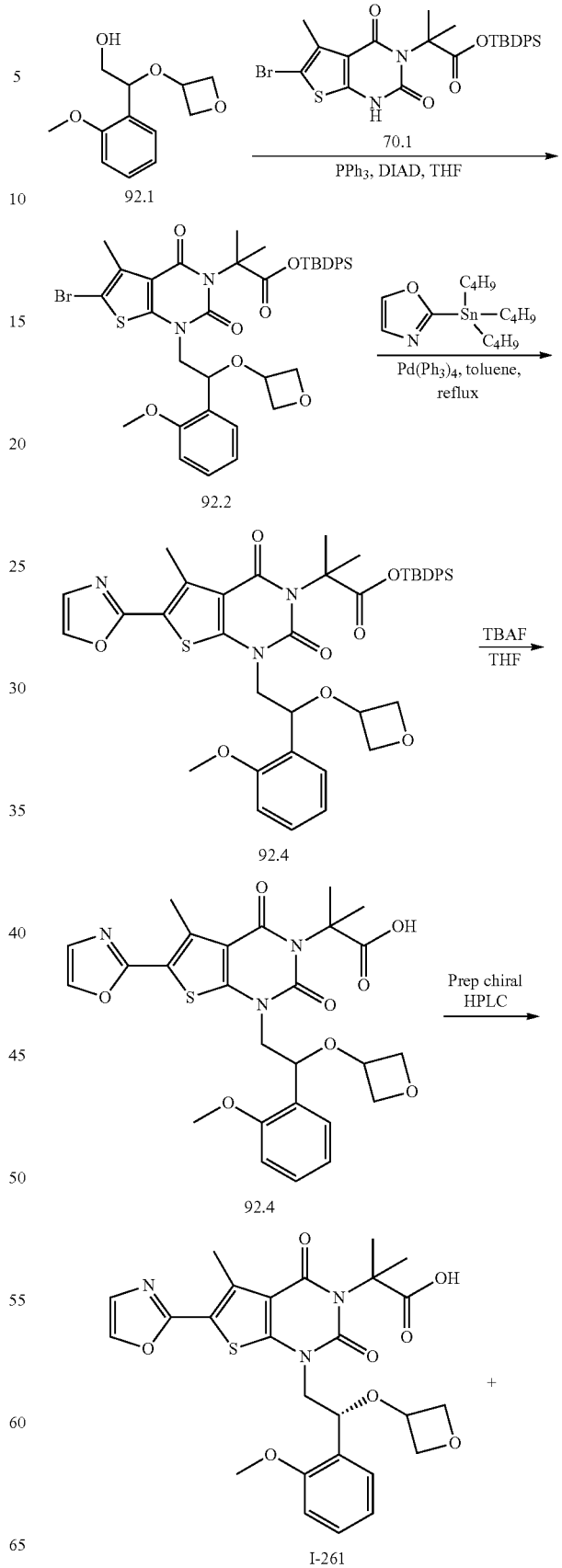

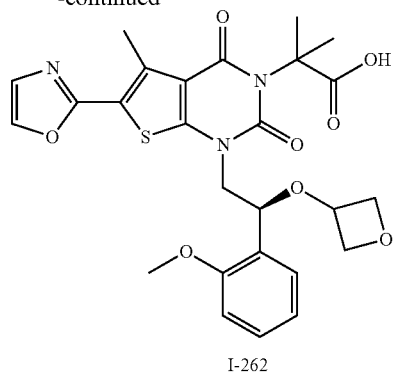

I-262

Synthesis of compound 92.1. Compound 92.1 was prepared from 57.2 in a manner analagous to the preparation of 73.2. Isolated a yellow oil in 8% yield.

Synthesis of compound 92.4. Compound 92.4 was prepared from 92.1 and 70.1 in a manner analogous to the synthesis of Compound I-158, Example 57. Isolated a white solid in 15% yield from 70.1.

Synthesis of Compounds I-261 and I-262. The enantiomers of 92.4 (100 mg) were separated by chiral preparative HPLC under the following conditions (Gilson Gx 281): Column: Chiralpak IC, 2*25 cm, 5 μm; mobile phase: hexanes (0.1% DEA) and ethanol (0.2% DEA) (hold at 25.0% ethanol (0.2% DEA) for 8 min); detector: UV 220/250 nm. 11.1 mg of Compound I-261 and 10.2 mg of Compound I-262 were obtained.

Analytical Data for Compound I-261: MS (ES): m/z 542 (M+H)$^+$. $^1$H NMR (300 MHz, CD$_3$OD): δ 1.68-1.69 (d, 6H), 2.73 (s, 3H), 3.70 (s, 3H), 4.10-4.16 (m, 1H), 4.26-4.38 (m, 3H), 4.61-4.71 (m, 3H), 6.02 (br s, 1H), 7.00-7.08 (m, 2H), 7.32 (s, 1H), 7.37-7.40 (m, 1H), 7.42-7.56 (m, 1H), 8.17 (s, 1H), 12.4 (br s, 1H).

Analytical Data for Compound I-262: MS (ES): m/z 542 (M+H)$^+$. $^1$H NMR (300 MHz, CD$_3$OD): δ 1.68-1.69 (d, 6H), 2.73 (s, 3H), 3.70 (s, 3H), 4.10-4.16 (m, 1H), 4.26-4.38 (m, 3H), 4.61-4.71 (m, 3H), 6.01 (br s, 1H), 7.00-7.08 (m, 2H), 7.32 (s, 1H), 7.37-7.40 (m, 1H), 7.42-7.56 (m, 1H), 8.17 (s, 1H), 12.40 (br s, 1H).

Example 94

Synthesis of 2-[1-[(2S)-2-(2-ethylphenyl)-2-(2-hydroxyethoxy)ethyl]-5-methyl-6-(1,3-oxazol-2-yl)-2,4-dioxo-1H,2H,3H,4H-thieno[2,3-d]pyrimidin-3-yl]-2-methylpropanoic acid (I-263)

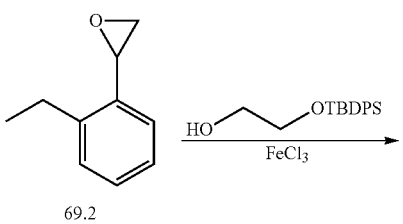

69.2

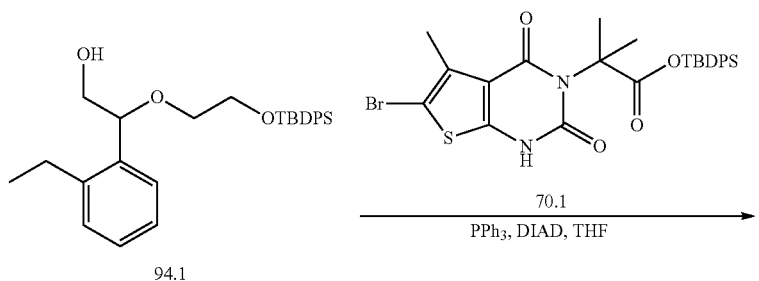

94.1

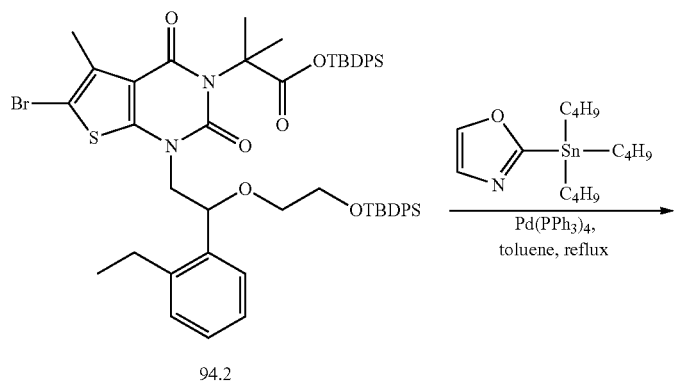

94.2

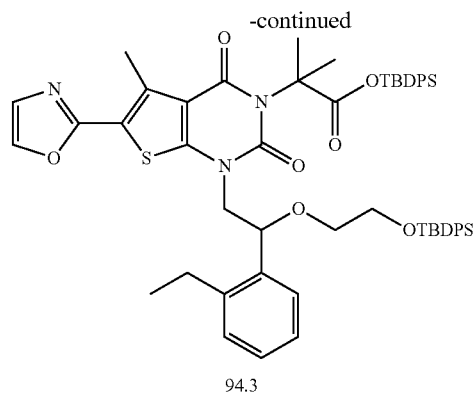

94.3

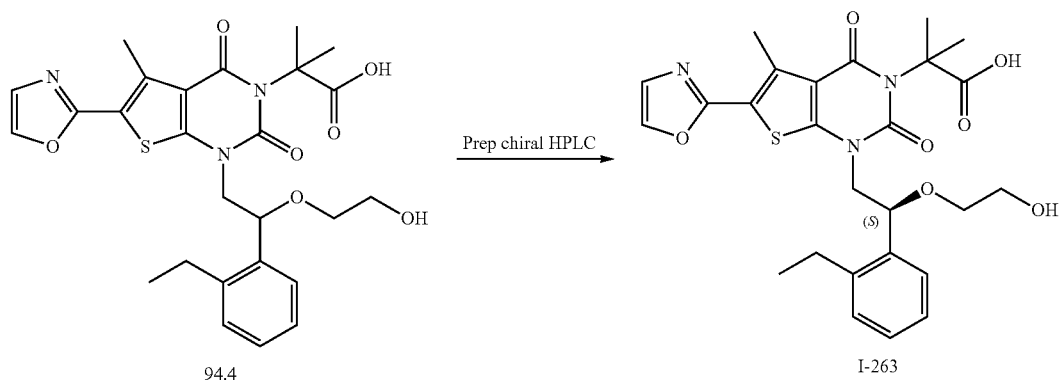

94.4 → I-263

Synthesis of compound 94.1. Compound 94.1 was prepared from 69.2 using the same method as for 57.3. Isolated a colorless oil in 2% yield.

Synthesis of compound 94.4. Compound 94.4 was prepared from 94.1 and 70.1 using the same procedure as for Compound I-158, Example 57. Isolated a white powder in 57% yield.

Isolation of Compound I-263. The enantiomers of 94.4 (406 mg) were separated by chiral preparative HPLC under the following conditions: Column: CHIRALPAK IA; mobile: hexanes (0.1% acetic acid):IPA=75:25; detector: UV 254 nm. 34.2 mg of Compound I-263 were obtained as a white solid. MS (ES): m/z 528 (M+H)+. $^1$H NMR (300 MHz, CD$_3$OD): 7.98 (1H, d, J=0.6 Hz), 7.62-7.59 (1H, m), 7.31-7.21 (4H, m), 5.19-5.15 (1H, dd, J$_1$=9 Hz, J$_2$=3.3 Hz), 4.26-4.20 (1H, dd, J$_1$=14.7 Hz, J$_2$=3.3 Hz), 3.93-3.85 (1H, dd, J$_1$=14.7 Hz, J$_2$=9 Hz), 3.57-3.53 (2H, m), 3.49-3.40 (1H, m), 2.96-2.87 (1H, m), 2.80-2.70 (4H, m), 1.81 (3H, s), 1.80 (3H, s), 1.30-1.25 (3H, t, J=7.5 Hz).

Example 95

Synthesis of Intermediate 95.4

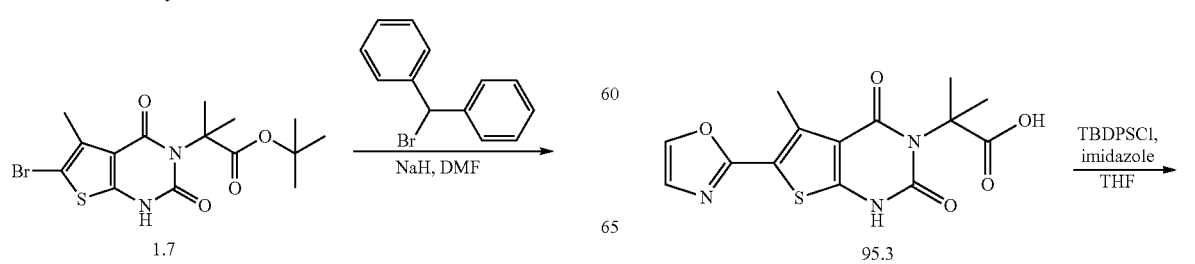

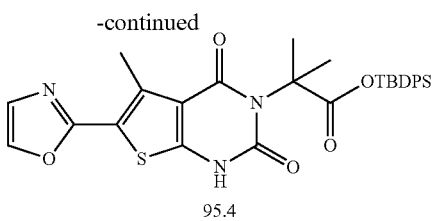

95.4

Synthesis of Compound 95.1. Into a 250-mL 3-necked round-bottom flask was placed 1.7 (5 g, 12.40 mmol, 1.00 equiv), N,N-dimethylformamide (60 mL), [bromo(phenyl)methyl]benzene (3.966 g, 16.05 mmol, 1.29 equiv) and sodium hydride (644.8 mg, 16.12 mmol, 1.30 equiv, 60%). The resulting solution was stirred overnight at room temperature. The reaction was then quenched by the addition of 300 mL of water. The resulting solution was extracted with 4×200 mL of ethyl acetate and the organic layers combined, washed with 200 mL of brine, dried over anhydrous sodium sulfate and concentrated under vacuum. The residue was applied onto a silica gel column with ethyl acetate/petroleum ether (1:30). Purification afforded 1.93 g (27%) of 95.1 as a yellow solid.

Synthesis of compound 95.2. Into a 250-mL 3-necked round-bottom flask, purged and maintained with an inert atmosphere of nitrogen, was placed 95.1 (8.15 g, 14.31 mmol, 1.00 equiv), toluene (40 mL), 2-(tributylstannyl)-1,3-oxazole (10.024 g, 27.99 mmol, 1.96 equiv) and Pd(PPh$_3$)$_4$ (2.426 g, 2.10 mmol, 0.15 equiv). The resulting solution was stirred under N$_2$ atmosphere overnight at 110° C. in an oil bath and then concentrated under vacuum. The residue was applied onto a silica gel column with ethyl acetate/petroleum ether (1:20). Purification afforded 5.5 g (69%) of 95.2 as a brown solid.

Synthesis of compound 95.3. Into a 250-mL 3-necked round-bottom flask was placed 95.2 (5.5 g, 9.86 mmol, 1.00 equiv), trifluoroacetic acid (30 mL) and CF$_3$SO$_3$H (2.97 g). The resulting solution was stirred for 3 h at 0° C. in a water/ice bath and then diluted with 300 mL of water. The solids were collected by filtration and then dissolved in 100 mL of ethanol. The resulting mixture was concentrated under vacuum. The solids were collected by filtration to afford 2.5 g (76%) of 95.3 as a white solid.

Synthesis of compound 95.4. Into a 100-mL 3-necked round-bottom flask was placed 95.3 (2.556 g, 7.58 mmol, 1.00 equiv), tetrahydrofuran (20 mL), tert-butyl(chloro)diphenylsilane (4.181 g, 15.21 mmol, 2.00 equiv) and imidazole (1.038 g, 15.26 mmol, 2.01 equiv). The resulting solution was stirred overnight at room temperature and then concentrated under vacuum. The residue was applied onto a silica gel column with ethyl acetate/petroleum ether (1:30). Purification afforded 4 g (92%) of 95.4 as a white solid.

Example 96

Synthesis of 2-[1-[(2R)-2-[2-(difluoromethoxy)phenyl]-2-(oxan-4-yloxy)ethyl]-5-methyl-6-(1,3-oxazol-2-yl)-2,4-dioxo-1H,2H,3H,4H-thieno[2,3-d]pyrimidin-3-yl]-2-methylpropanoic acid (I-264)

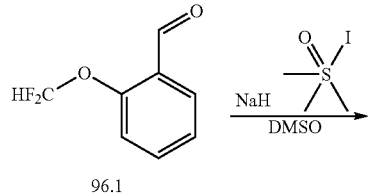

96.1

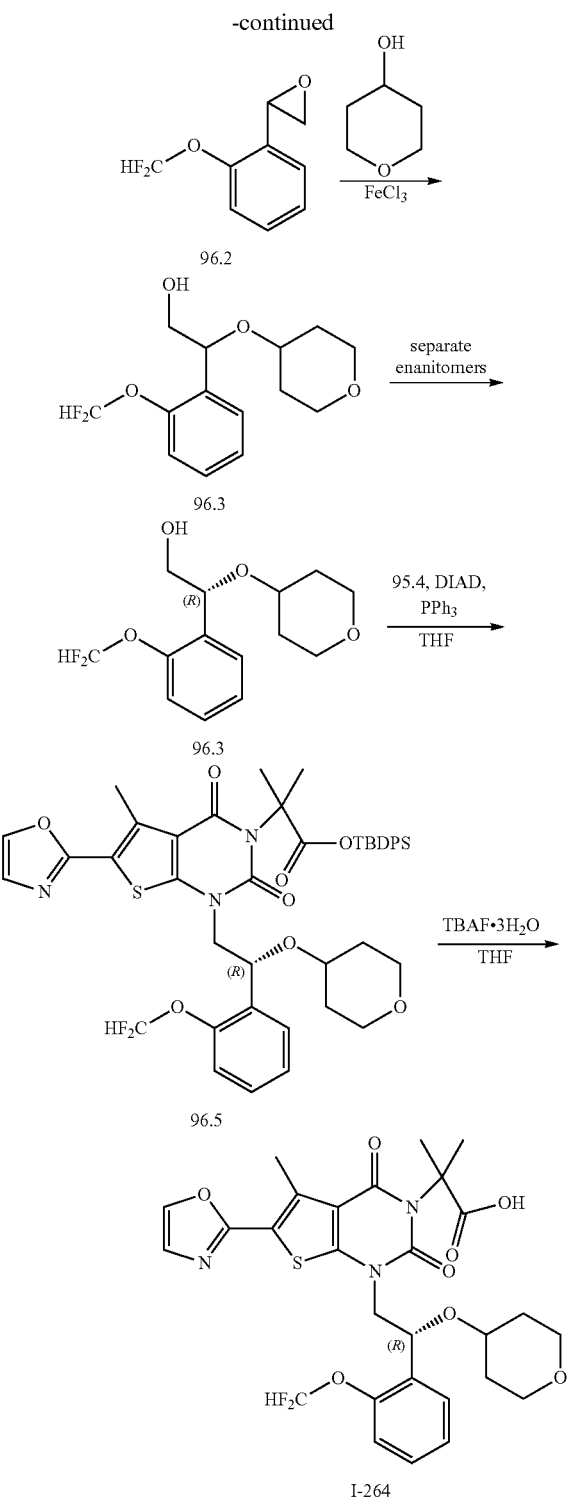

Synthesis of compound 96.4. Compound 96.4 was prepared from 2-(difluoromethoxy)benzaldehyde according to the procedure for the synthesis of 57.5. Chiral separation: Gilson Gx 281; column: Venusil Chiral OD-H, 21.1*25 cm, 5 μm; mobile phase: hexanes and ethanol (hold at 2% ethanol for 13 min); detector: UV 254/220 nm. Isolated 248 mg (2% overall yield from 96.1) of a colorless oil.

Synthesis of Compound I-264. Compound I-264 was prepared from intermediate 95.4 and 96.4 in a manner analogous to compound 67.8. Isolated a white solid in 20% yield from 95.4. MS (ES): m/z 607 (M+H)+. 1H NMR (300 MHz, DMSO-$d_6$): δ 1.23-1.30 (m, 2H), 1.65 (m, 8H), 2.75 (s, 3H), 3.24-3.27 (m, 2H), 3.50-3.53 (m, 2H), 3.96-4.18 (m, 2H), 5.26-5.27 (m,1H), 7.00-7.65 (m,5H), 8.24 (s,1H), 12.42 (s,1H).

Example 97

Synthesis of (R)-2-(1-(2-isopropoxy-2-(2-(trifluoromethoxy)phenyl)ethyl)-5-methyl-6-(oxazol-2-yl)-2,4-dioxo-1,2-dihydrothieno[2,3-d]pyrimidin-3(4H)-yl)-2-methylpropanoic acid (I-265)

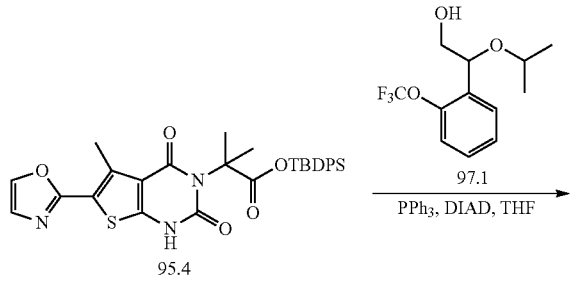

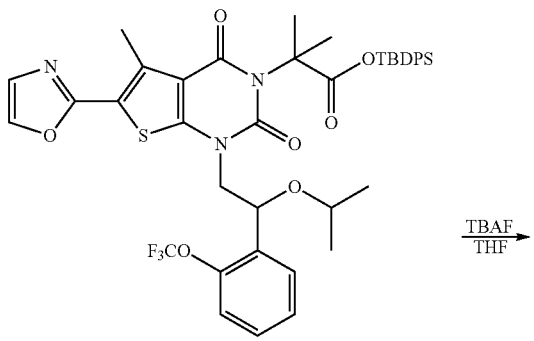

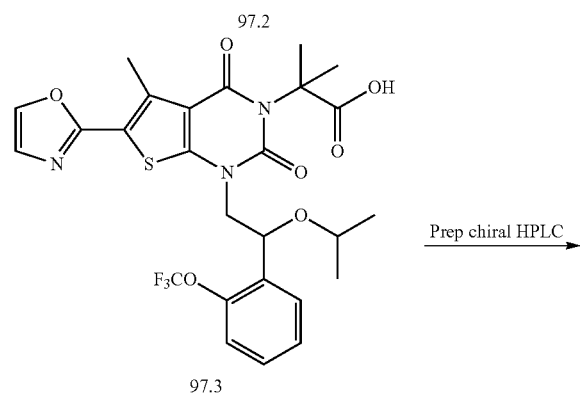

Synthesis of compound 97.1. Compound 97.1 was prepared from 2-(trifluoromethoxy)benzaldehyde and isopropanol using the same method as for compound 57.3. Isolated a colorless oil in 17% overall yield.

Synthesis of compound 97.3. Compound 97.3 was prepared 95.4 and 97.1 in a manner analogous to Example 96. Isolated a white solid in 23% yield from 95.4.

Synthesis of Compound I-265. The R enantiomer was isolated from 390 mg of 97.3 by chiral preparative HPLC under the following conditions: Gilson Gx 281; column: Chiralpak IC, 2*25 cm, 5 μm; mobile phase: hexanes (0.1% TFA) and IPA (0.1% TFA) (hold at 4% IPA (0.1% TFA) in 10 min); detector: UV 254/220 nm. 56.2 mg of a white solid were obtained. MS (ES): m/z 582 (M+H)+. 1H NMR (300 MHz, CD$_3$OD): δ 8.23 (s, 1 H), 7.72-7.68 (m, 1 H), 7.52-7.45 (m, 2 H), 7.38-7.34 (m, 2 H), 5.16 (t, 1 H, J=6.6 Hz), 4.06-3.97 (m, 2 H), 3.46-3.32 (m, 1 H), 2.74 (s, 3H), 1.65 (d, 6 H, J=1.2 Hz), 0.95 (t, 6H, J=6.0 Hz).

Example 98

Synthesis of 2-methyl-2-[5-methyl-1-[(2R)-2-(oxan-4-yloxy)-2-[2-(trifluoromethyl)phenyl]ethyl]-6-(1,3-oxazol-2-yl)-2,4-dioxo-1H,2H,3H,4H-thieno[2,3-d]pyrimidin-3-yl]propanoic acid (I-266)

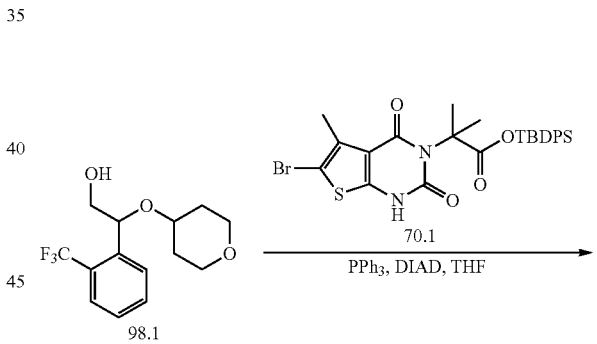

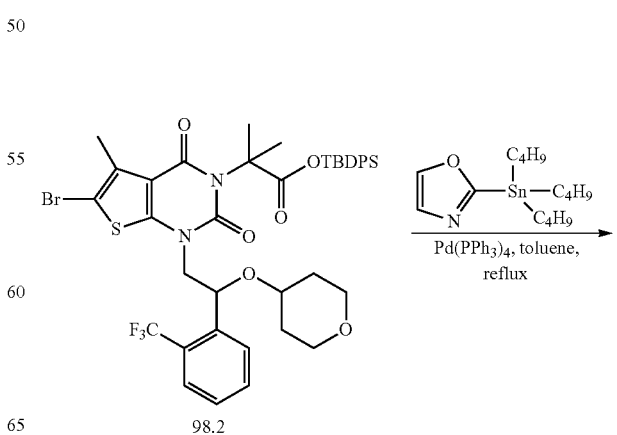

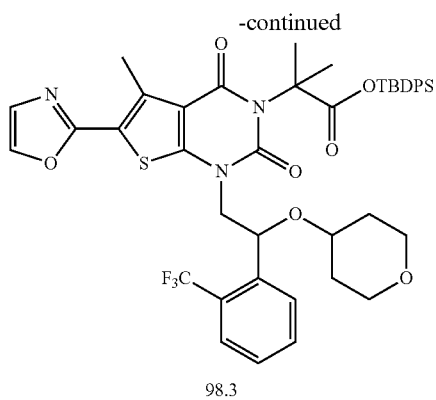

98.3

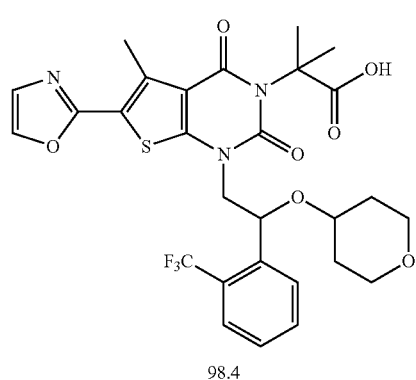

98.4

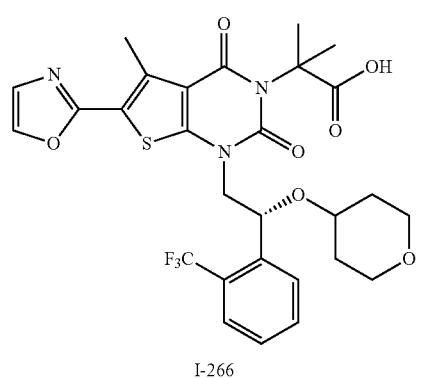

I-266

Synthesis of compound 98.1. Compound 98.1 was prepared from 2-(trifluoromethoxy)benzaldehyde and oxan-4-ol using the same method as for compound 57.3. Isolated a colorless oil in 5% yield from 2-(trifluoromethoxy)benzaldehyde.

Synthesis of Compound I-266. Compound I-266 was prepared from 98.1 and 70.1 in a manner analogous to Example 97. MS (ES): m/z 608 (M+H)+. 1H NMR (CD3OD, 300 MHz): 7.90 (2H, m), 771-7.63 (2H, m), 7.48-7.43 (1H, m), 7.20 (1H, s), 5.35-5.34 (1H, m), 4.30-4.24 (1H, m), 3.89-3.70 (1H, m), 3.55-3.34 (2H, m), 3.33-3.20 (2H, m), 2.73 (3H, s), 1.71-1.50 (8H, m), 1.37-1.20 (2H, m).

Example 99

Synthesis of 2-[1-[(2R)-2-[2-(difluoromethoxy)phenyl]-2-(propan-2-yloxy)ethyl]-5-methyl-6-(1,3-oxazol-2-yl)-2,4-dioxo-1H,2H,3H,4H-thieno[2,3-d]pyrimidin-3-yl]-2-methylpropanoic acid (I-267)

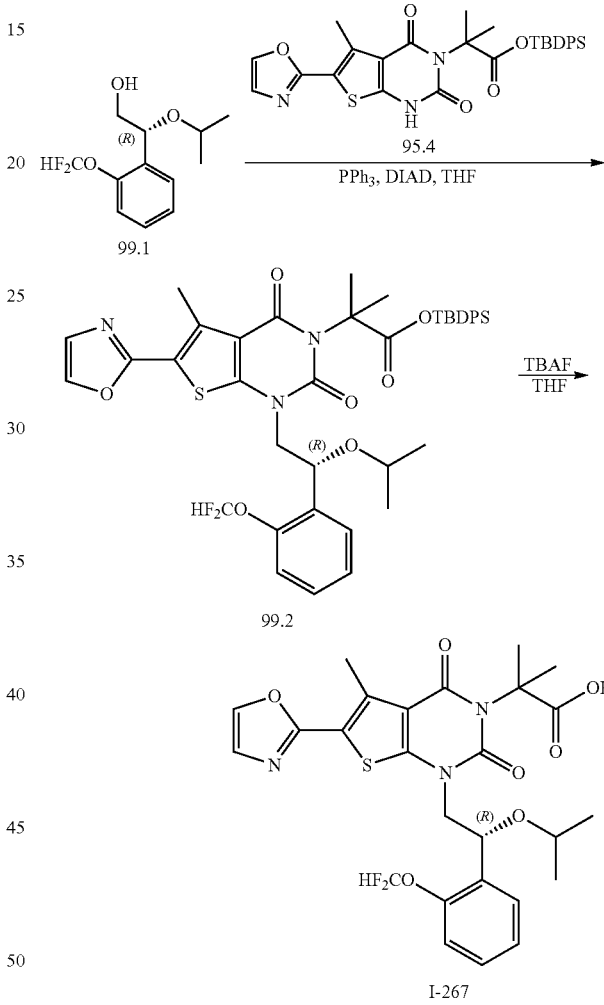

Synthesis of compound 99.1. Compound 99.1 was prepared from 2-(difluoromethoxy)benzaldehyde and isopropanol using the same method as for compound 57.5. Purification: Venusil chiral OD-H column, 0.46*25 cm, 5 μm; mobile phase: hexanes:IPA=98:2; detector: UV 220 nm. Isolated a white solid in 13% yield from 2-(difluoromethoxy)benzaldehyde.

Synthesis of Compound I-267. Compound I-267 was prepared from 99.1 and 95.4 in a manner analogous to compound I-264 (Example 96). Isolated a white solid in 37% yield from 95.4. MS (ES): m/z 564 (M+H)+. 1H NMR (DMSO-d6, 300 MHz): δ 12.38 (1H, br s), 8.23 (1H, s), 7.62-7.61 (1H, d, J=1.8 Hz), 7.60-7.22 (3H, m), 7.20-6.97 (2H, m), 5.20-5.16 (1H, t), 4.04 (2H, m), 3.47-3.33 (1H, m), 2.74 (3H, s), 1.65-1.64 (6H, d, J=2.1 Hz), 0.98-0.93 (6H, m).

Example 100

Synthesis of 2-[1-[(2R)-2-[2-(difluoromethoxy)phenyl]-2-(propan-2-yloxy)ethyl]-5-methyl-6-(1,3-oxazol-2-yl)-2,4-dioxo-1H,2H,3H,4H-thieno[2,3-d]pyrimidin-3-yl]-2-methylpropanamide (I-268)

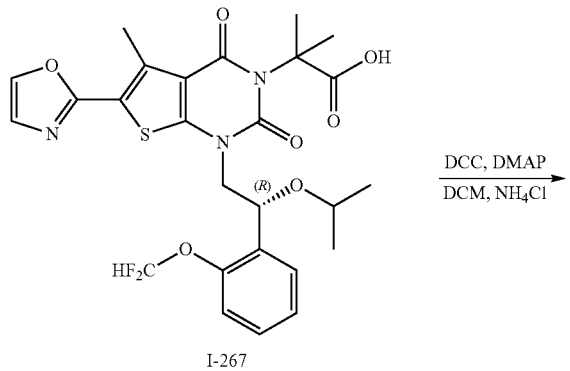

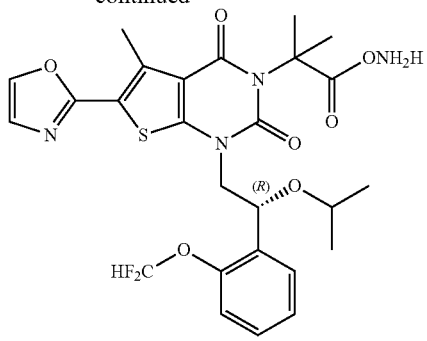

Compound I-268 was prepared from I-267 and ammonium chloride using the same method as Example 4. Isolated a white solid in 80% yield. MS (ES): m/z 563 (M+H)$^+$. $^1$H NMR (DMSO-d$_6$, 300 MHz): δ 8.22 (1H, s), 7.62-7.60 (1H, m), 7.31 (1H, m), 7.39-7.32 (3H, m), 7.21-6.96 (3H, m), 5.18 (1H, m), 4.03 (2H, m), 3.45-3.41 (1H, m), 2.73 (3H,$), 1.63 (6H, d), 0.96 (6H, d).

Example 101

Synthesis of (R)-2-(1-(2-(2-methoxyphenyl)-2-(oxetan-3-ylmethoxy)ethyl)-5-methyl-6-(oxazol-2-yl)-2,4-dioxo-1,2-dihydrothieno[2,3-d]pyrimidin-3(4H)-yl)-2-methylpropanoic acid (I-269)

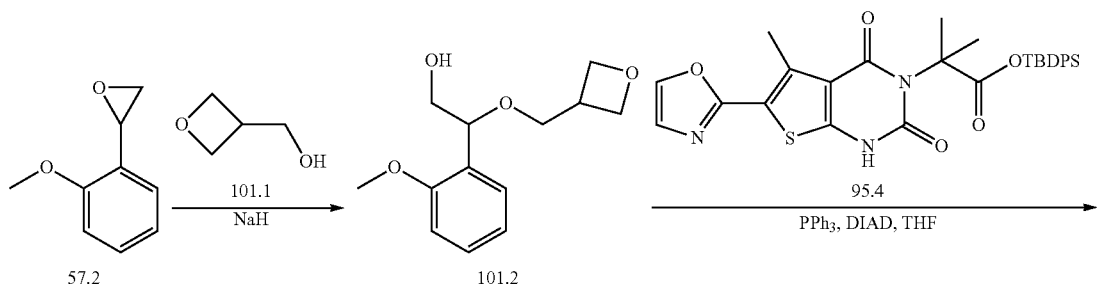

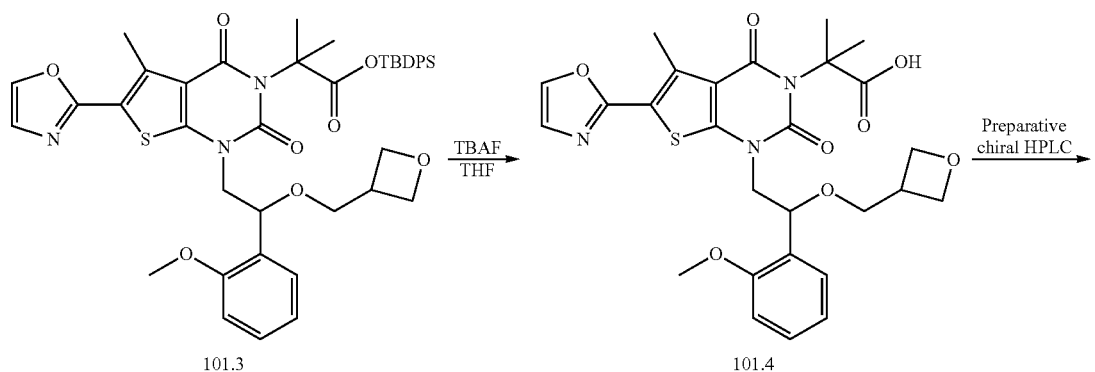

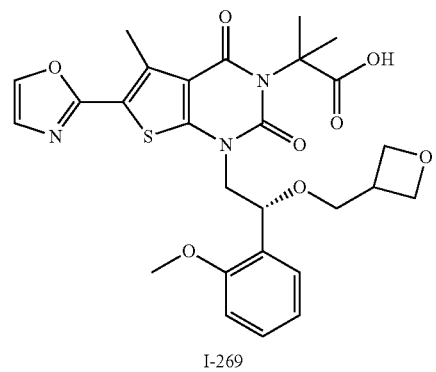

I-269

Synthesis of compound 101.2. Compound 101.1 was prepared from 57.2 and commercially-available 101.1 in a manner analogous to 73.2. Isolated a colorless oil in 38% yield.

Synthesis of Compound I-269. Compound I-269 was prepared from 95.4 and 101.2 in a manner analogous to I-265 (Example 97). Isolated a white solid in 2% overall yield from 95.4. MS (ES): m/z 556 (M+H)+. $^1$H NMR (300 MHz, DMSO-$d_6$): δ 1.70 (d, 6H), 2.69 (s, 3H), 3.08-3.12 (m, 1H), 3.62-3.81 (m, 5H), 4.16-4.23 (m, 3H), 4.32-4.28 (m, 1H), 4.48-4.54 (m, 2H), 6.09 (m, 1H), 6.99-7.09 (m, 2H), 7.32 (s, 1H), 7.38-7.40 (m, 1H), 7.43-7.57 (m, 1H), 8.17 (s, 1H).

Example 102

2-[1-[(2R)-2-(4-bromo-2-methoxyphenyl)-2-(oxan-4-yloxy)ethyl]-5-methyl-6-(1,3-oxazol-2-yl)-2,4-dioxo-1H,2H,3H,4H-thieno[2,3-d]pyrimidin-3-yl]-2-methylpropanoic acid (I-270)

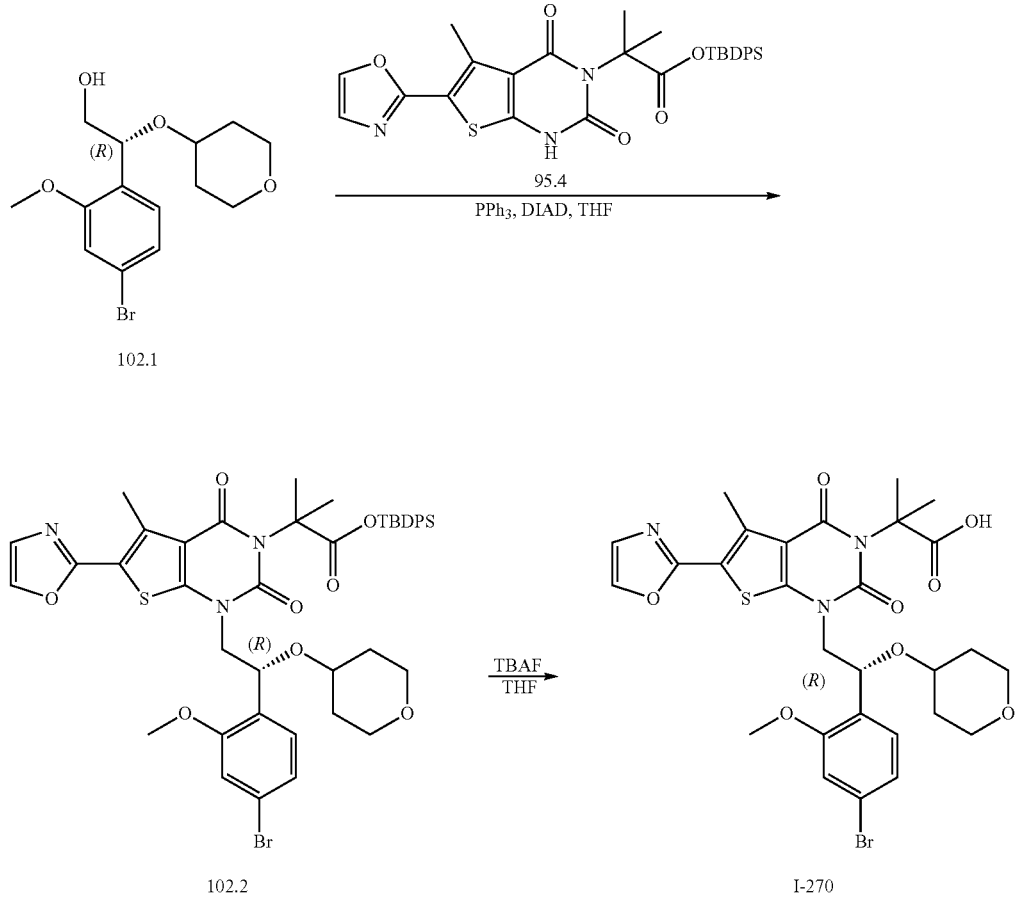

Synthesis of compound 102.1. Compound 102.1 was prepared from 4-bromo-2-methoxybenzaldehyde and oxan-4-ol in a manner analogous to 57.5. The R enantiomer was isolated by chiral preparative HPLC under the following conditions: Column: Chiralcel OJ-H, 0.46*25 cm, 5 μm; mobile phase, hexanes:EtOH=75:25; detector: 254 nm. Isolated a white solid in 2% overall yield.

Synthesis of Compound I-270. Compound I-270 was prepared from 95.4 and 102.1 in a manner analogous to I-264 (Example 96). Isolated a white solid in 27% overall yield from 95.4. MS (ES): m/z 650 (M+H)$^+$. $^1$H NMR (DMSO-$d_6$, 300 MHz): δ 8.24 (1H, s), 7.43-7.39 (2H, m), 7.25-7.21 (2H, m), 5.23-5.19 (1H, m), 4.07-3.95 (2H, m), 3.83 (3H, s), 3.59-3.49 (2H, m), 3.32-3.20 (2H, m), 2.75 (3H, s), 1.67-1.64 (8H, m), 1.35-1.31 (2H, m).

Example 103

Synthesis of 2-[1-[(2R)-2-[2-($d_3$)methoxyphenyl]-2-(oxan-4-yloxy)ethyl]-5-methyl-6-(1,3-oxazol-2-yl)-2,4-dioxo-1H,2H,3H,4H-thieno[2,3-d]pyrimidin-3-yl]-2-methylpropanoic acid (I-271)

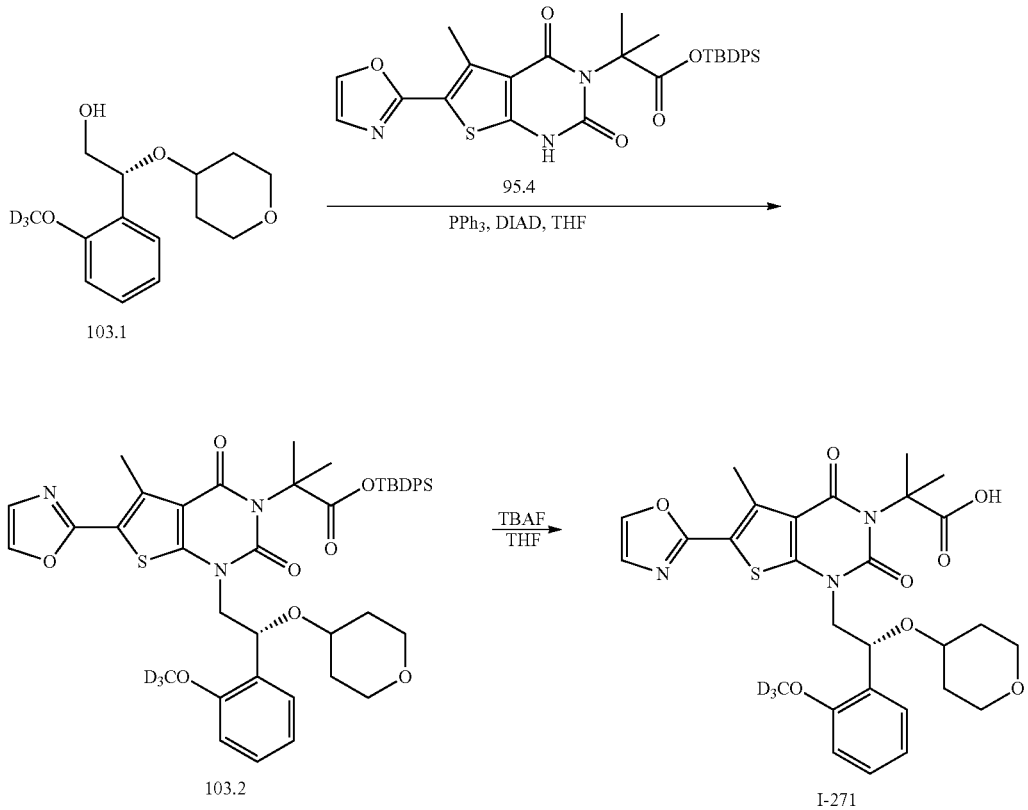

Synthesis of compound 103.1. Compound 103.1 was prepared from 2-($d_3$)methoxybenzaldehyde and oxan-4-ol in a manner analogous to 57.5. The R enantiomer was isolated by chiral preparative HPLC under the following conditions (Gilson Gx 281): Column: Venusil Chiral OD-H, 21.1*25 cm, 5 μm; mobile phase, hexanes and EtOH (5% EtOH for 12 min); detector: 220/254 nm. Isolated a white solid in 9% overall yield.

Synthesis of Compound I-271. Compound I-271 was prepared from 95.4 and 103.1 in a manner analogous to Example 96. Isolated a white solid in 42% overall yield from 95.4. MS (ES): m/z 573 (M+H)$^+$. $^1$H NMR (DMSO-$d_6$, 300 MHz): δ 12.4 (1H, br s), 8.25 (1H, s), 7.50-7.49 (1H, d), 7.39 (1H, m), 7.34-7.28 (1H, m), 7.06-6.99 (2H, m), 5.30-5.26 (1H, m), 4.07-3.80 (2H, m), 3.59-3.48 (2H, m), 3.39-3.32 (1H, m), 3.27-3.20 (2H, m), 2.75 (3H, s), 1.69-1.67 (8H, m), 1.38-1.21 (2H, m).

Example 104

Synthesis of 2-[1-[(2R)-2-[2-(d₃)methoxyphenyl]-2-(oxan-4-yloxy)ethyl]-5-methyl-6-(1,3-oxazol-2-yl)-2,4-dioxo-1H,2H,3H,4H-thieno[2,3-d]pyrimidin-3-yl]-2-methylpropanamide (I-272)

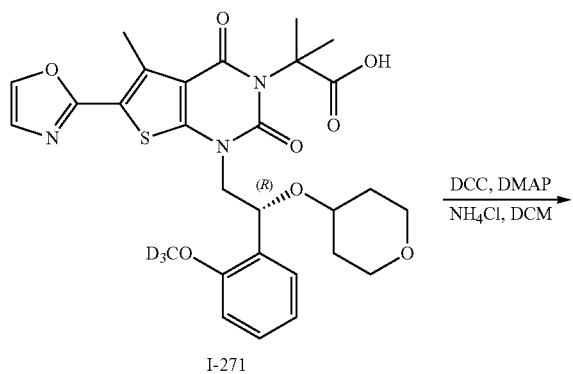

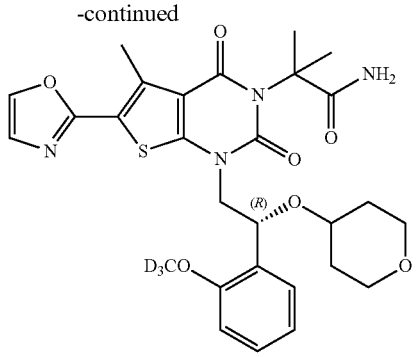

Compound I-272 was prepared from I-271 (Example 103) and ammonium chloride using the same method as for Example 4. Isolated a white solid in 57% yield. MS (ES): m/z 594 (M+Na)⁺. ¹H NMR (DMSO-$d_6$, 300 MHz): δ1.20-1.33 (m, 2H), 1.65-1.67 (m, 8H), 2.75 (s, 3H), 3.20-3.26 (m, 2H), 3.33-3.37 (m, 1H), 3.50-3.58 (m, 2H), 3.94-4.04 (m, 2H), 5.26-5.31 (s, 1H), 6.99-7.06 (m, 4H), 7.27-7.29 (m, 1H), 7.32 (s, 1H), 7.47-7.50 (d, 1H), 8.22 (s, 1H).

Example 105

Synthesis of 2-[1-[(2R)-2-(2-hydroxyphenyl)-2-(oxan-4-yloxy)ethyl]-5-methyl-6-(1,3-oxazol-2-yl)-2,4-dioxo-1H,2H,3H,4H-thieno[2,3-d]pyrimidin-3-yl]-2-methylpropanoic acid (I-273)

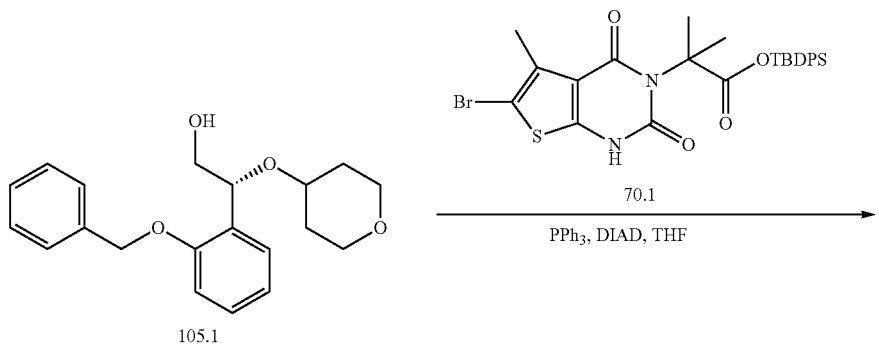

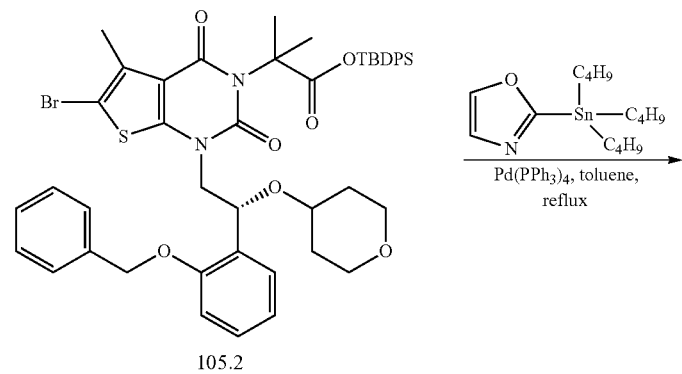

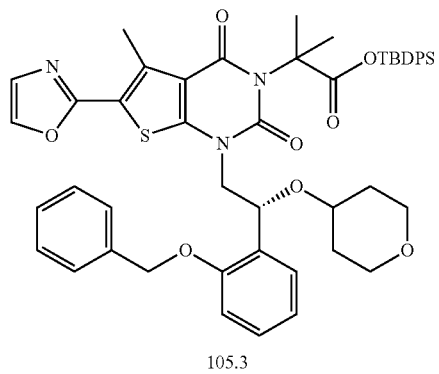

105.3

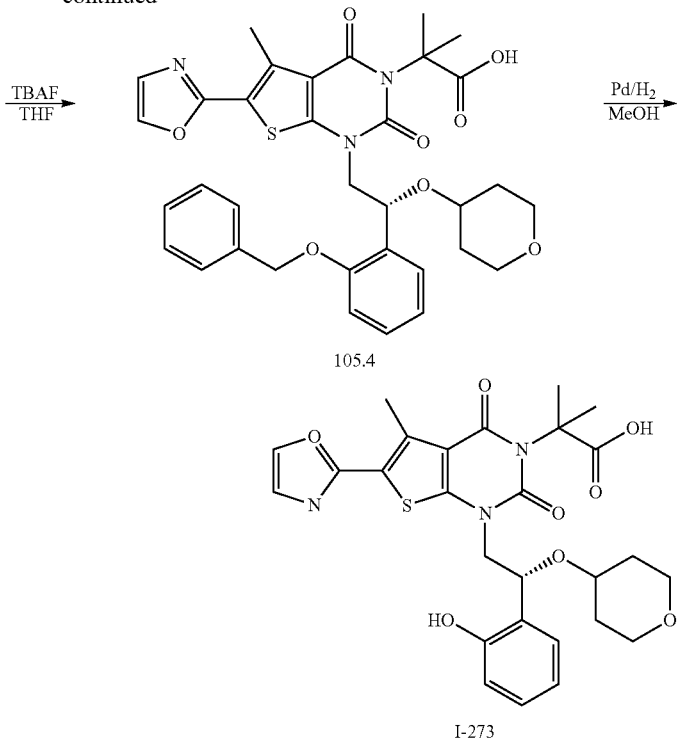

Synthesis of compound 105.1. Compound 105.1 was prepared from 2-(benzyloxy)benzaldehyde and oxan-4-ol in a manner analogous to 57.5. The R enantiomer was isolated by preparative SFC under the following conditions: Column: Chiralpak AD-H, 2*25 cm; mobile phase: $CO_2$ (75%), ethanol (25%); detector: UV 254 nm. Isolated the product in 10% overall yield from 2-(benzyloxy)benzaldehyde.

Synthesis of compound 105.4. Compound 105.4 was prepared from 70.1 and 105.1 in a manner analogous to Example 57. Isolated a white solid in 25% overall yield from 70.1.

Synthesis of Compound I-273. Into a 100-mL round-bottom flask was placed 105.4 (100 mg, 0.15 mmol, 1.00 equiv) and methanol (20 mL). This was followed by the addition of palladium on carbon (20 mg). The flask was evacuated and flushed three times with nitrogen, followed by flushing with hydrogen. The mixture was stirred overnight at room temperature under an atmosphere of hydrogen. The solids were collected by filtration. The filtrate was concentrated under vacuum. The residue was purified by thin layer chromatography developed with dichloromethane/MeOH/HOAc (30:1: 0.15). 35.7 mg (41%) of I-273 were obtained as a white solid. MS (ES): m/z 556 (M+H)+. $^1$H NMR (300 MHz, DMSO-$d_6$): δ 1.18-1.34 (m, 2H), 1.57-1.62 (m, 2H), 1.62 (s, 3H), 1.70 (s, 3H), 2.75 (s, 3H), 3.12-3.35 (m, 3H), 3.50-3.70 (m, 2H), 3.78 (m, 1H), 4.11-4.14 (m, 1H), 5.23-5.28 (m, 1H), 6.81-6.85 (m, 2H), 7.06-7.11 (m, 1H), 7.36-7.37 (m, 1H).

Example 106

Synthesis of 2-[1-[(2R)-2-[2-(difluoromethoxy)phenyl]-2-(oxan-4-yloxy)ethyl]-5-methyl-6-(1,3-oxazol-2-yl)-2,4-dioxo-1H,2H,3H,4H-thieno[2,3-d]pyrimidin-3-yl]-2-methylpropanamide (I-274)

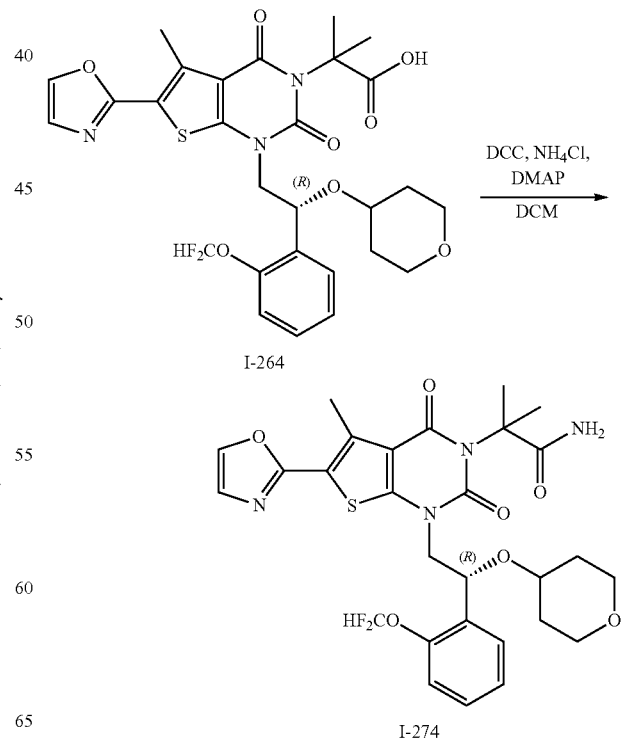

Compound I-274 was prepared from I-264 (Example 96) and ammonium chloride in a manner analogous to Example 4. Isolated 63.4 mg of a white solid in 57% yield. MS (ES): m/z 627 (M+Na)⁺. ¹H NMR (DMSO-d₆, 300 MHz): δ 1.24-1.34 (m, 2H), 1.63-1.65 (m, 8H), 2.74 (s, 3H), 3.20-3.26 (m, 2H), 3.32 (m, 1H), 3.53 (m, 2H), 4.01-4.10 (m, 2H), 5.27 (m, 1H), 6.98 (br s, 1H), 6.98 (br s,1H), 7.18 (br s,1H), 7.21-7.32 (m, 1H), 7.34-7.47 (m, 3H), 7.62-7.64 (m, 1H), 8.22 (s, 1H).

Example 107

Synthesis of 3-[1-(azetidin-1-yl)-2-methyl-1-oxopropan-2-yl]-1-[(2R)-2-(2-methoxyphenyl)-2-(oxan-4-ylmethoxy)ethyl]-5-methyl-6-(1,3-oxazol-2-yl)-1H,2H,3H,4H-thieno[2,3-d]pyrimidine-2,4-dione (I-275)

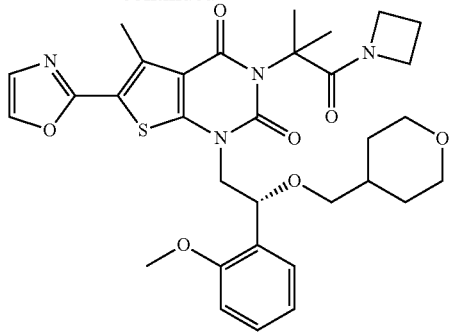

I-275

Compound I-275 was prepared from I-259 (Example 90) and azetidine in a manner analogous to Example 4. A sealed tube was used rather than a round-bottom flask. Isolated 46.8 mg of a white solid in 44% yield. MS (ES): m/z 623 (M+H)⁺. ¹H NMR (DMSO-d₆, 300 MHz): δ 8.23 (1H, s), 7.40-7.28 (3H, m), 7.06-7.00 (2H, m), 5.14-5.09 (1H, t), 4.09 (1H, m), 3.87-3.84 (4H, m), 3.80 (3H, s), 3.78-3.69 (2H, m), 3.19-3.11 (3H, m), 3.06-3.00 (1H, m), 2.76 (3H, s), 2.14-2.09 (2H, m), 1.63-1.61 (6H, d), 1.44-1.35 (2H, m), 1.10-1.03 (2H, m).

Example 108

Synthesis of (R)-2-(1-(2-(2-methoxyphenyl)-2-((4-oxocyclohexyl)oxy)ethyl)-5-methyl-6-(oxazol-2-yl)-2,4-dioxo-1,2-dihydrothieno[2,3-d]pyrimidin-3(4H)-yl)-2-methylpropanoic acid (I-276)

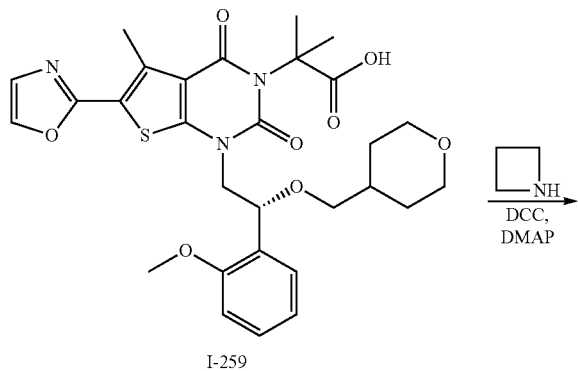

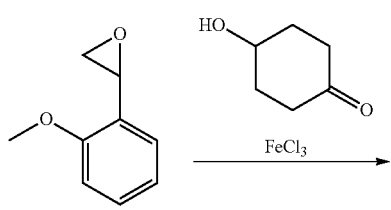

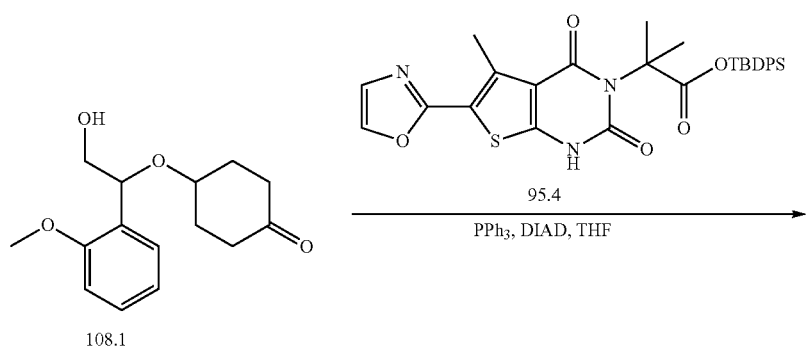

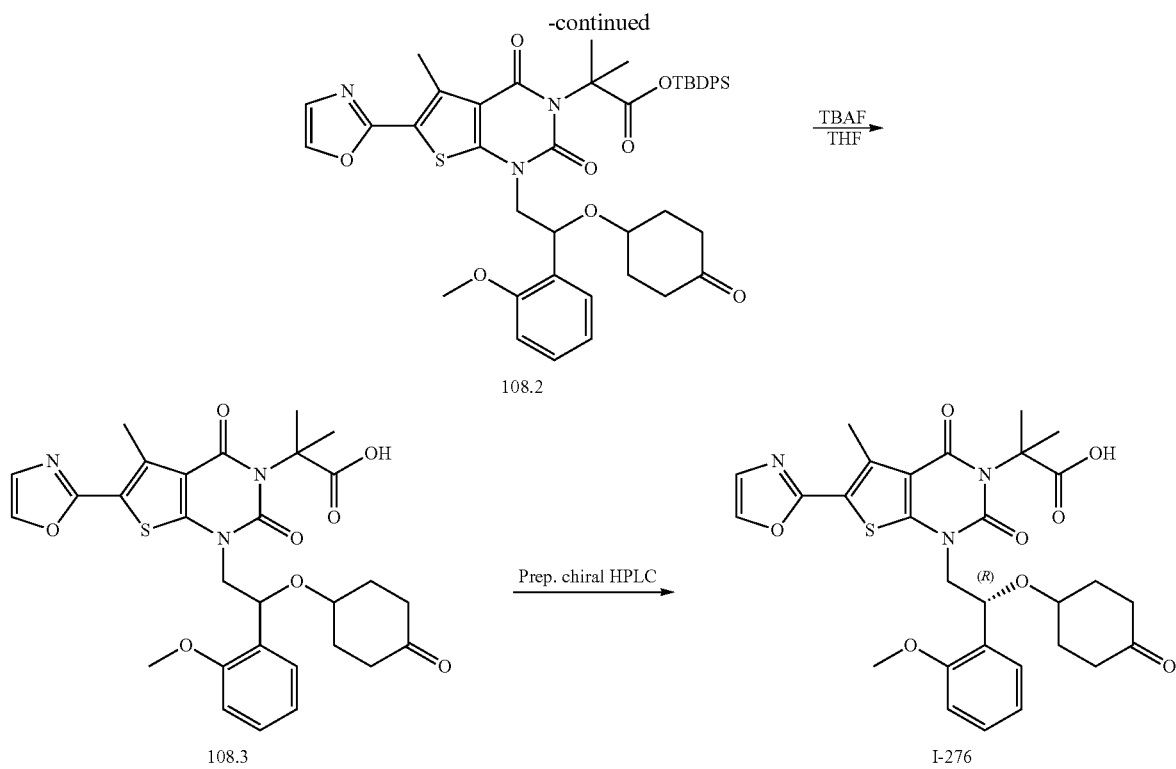

Synthesis of compound 108.1. Compound 108.1 was synthesized from 57.2 and 4-hydroxycyclohexan-1-one using the method for the synthesis of compound 57.3. Isolated 400 mg of a colorless oil in 5% yield.

Synthesis of Compound I-276. Compound I-276 was prepared from 108.1 and 95.4 in a manner analogous to Example 97. Isolated 7.7 mg (1% from 95.4) of a white solid (MS (ES): m/z 582 (M+H)$^+$. $^1$H NMR (300 MHz, DMSO-d$_6$): δ 1.64-1.78 (m, 10H), 2.06-2.20 (m, 3H), 2.22-2.27 (m, 1H), 2.73 (s, 3H), 3.56 (m, 1H), 3.83 (s, 3H), 4.09 (m, 2H), 5.31-5.35 (m, 1H), 7.02-7.09 (m, 2H), 7.30-7.39 (m, 2H), 7.52-7.42 (d, 1H), 8.23 (s, 6H), 12.42 (s, 1H).

Example 109

2-[1-[(2R)-2-[(4-hydroxycyclohexyl)oxy]-2-(2-methoxyphenyl)ethyl]-5-methyl-6-(1,3-oxazol-2-yl)-2,4-dioxo-1H,2H,3H,4H-thieno[2,3-d]pyrimidin-3-yl]-2-methylpropanoic acid (I-277)

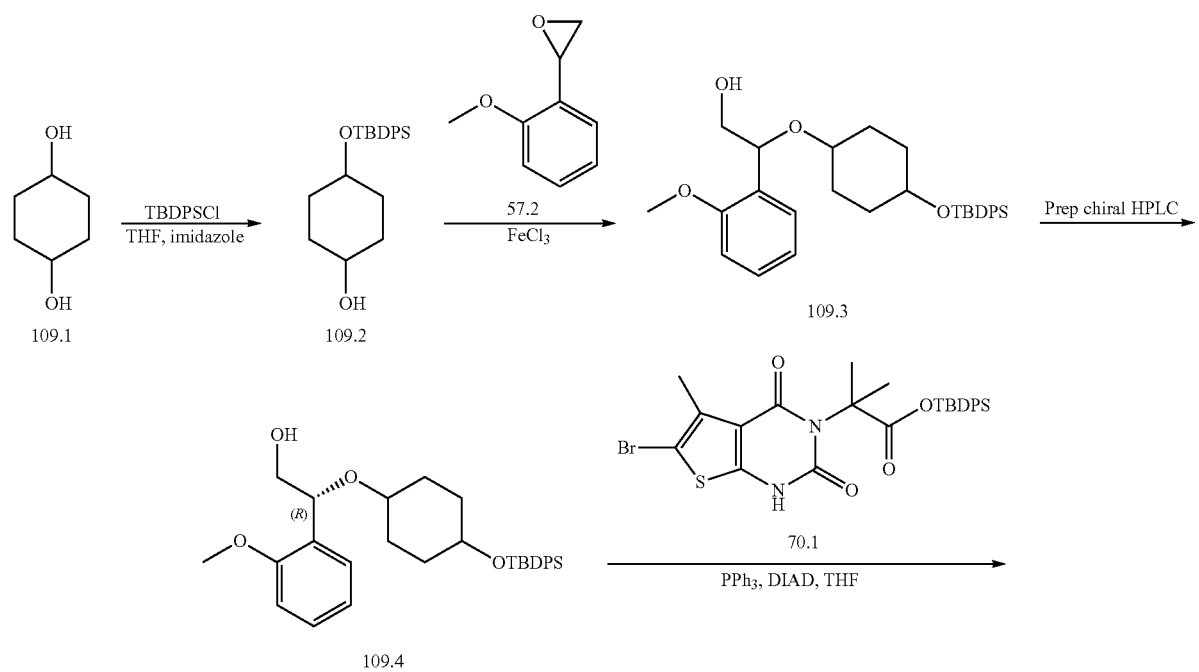

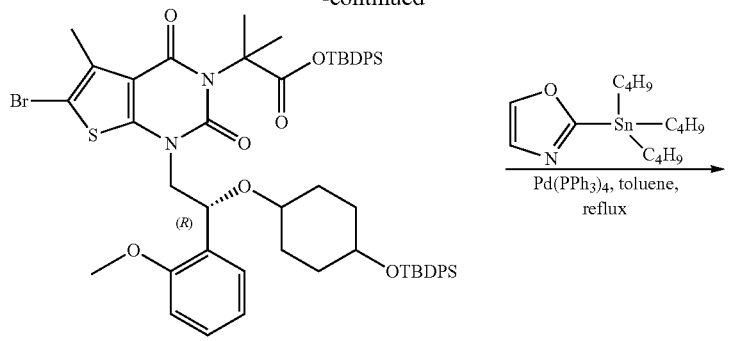

109.5

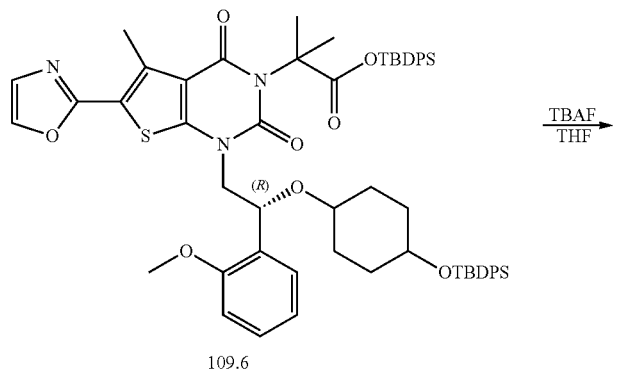

109.6

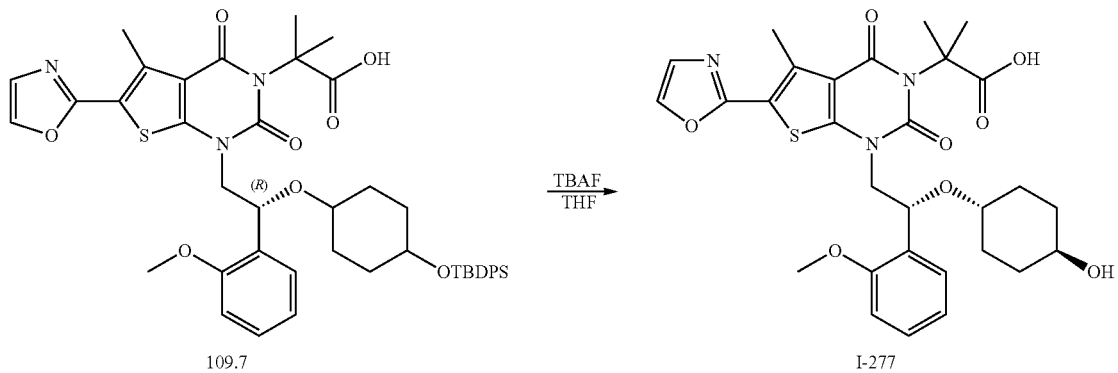

109.7                                    I-277

Synthesis of compound 109.2. Into a 1000-mL 3-necked round-bottom flask was placed cyclohexane-1,4-diol (20 g, 172.18 mmol, 1.00 equiv), 1,4-dioxane (500 mL) and 1H-imidazole (17.58 g, 258.24 mmol, 1.50 equiv). This was followed by the addition of a solution of tert-butyl(chloro) diphenylsilane (49.69 g, 180.78 mmol, 1.05 equiv) in dioxane (100 mL) dropwise with stirring at 15° C. The resulting solution was stirred for 15 h at 15-20° C. The solids were filtered out. The filtrate was diluted with 200 mL of water. The resulting solution was extracted with 3×200 mL of ethyl acetate and the organic layers combined and concentrated under vacuum. The residue was applied onto a silica gel column with ethyl acetate/petroleum ether (0:1-1:60-1:50-1:30-1:20). Purification afforded 32.98 g (54%) of 109.2 as a white semi-solid.

Synthesis of compound 109.4. Compound 109.4 was prepared from 109.2 and 57.2 using the procedure for the synthesis of 57.5. Purification: Chiral preparative HPLC under the following conditions (Gilson): Column: Venusil Chiral OD-H, 21.1*25 cm, 5 μm; mobile phase: hexanes and ethanol (hold at 5% ethanol for 15 min); detector: UV 220/254 nm.

Synthesis of compound 109.7. Compound 109.7 was prepared from 70.1 and 109.4 in a manner analogous to Example 57. Isolated a white solid in 14% yield from 70.1.

Synthesis of Compound I-277. Into a 10-mL round-bottom flask was placed a solution of 109.7 (100 mg, 0.12 mmol, 1.00 equiv) in tetrahydrofuran (5 mL). TBAF (127 mg) was added and the resulting solution was stirred for 3 days at room temperature. The resulting mixture was concentrated under vacuum. The residue was purified by preparative TLC, eluting with methanol/DCM/HOAc (10:200:1). 7.8 mg (11%) of Compound I-277 were obtained as a white solid. MS (ES): m/z 584 (M+H)$^+$. $^1$H NMR (300 MHz, CD$_3$OD): δ 0.88-0.94 (m, 1H), 1.01-1.29 (m, 3H), 1.48-1.84 (m, 10H), 2.70 (s, 3H), 2.97-3.22 (m, 1H), 3.38-3.44 (m,1H), 3.75 (m, 3H), 3.98 (m, 1H), 5.24-5.29 (t, 1H), 6.83-6.94 (m, 2H), 7.15-7.20 (t, 2H), 7.41-7.44 (d, 1H), 7.86 (s, 1H).

Example 110

Synthesis of Intermediate 110.3

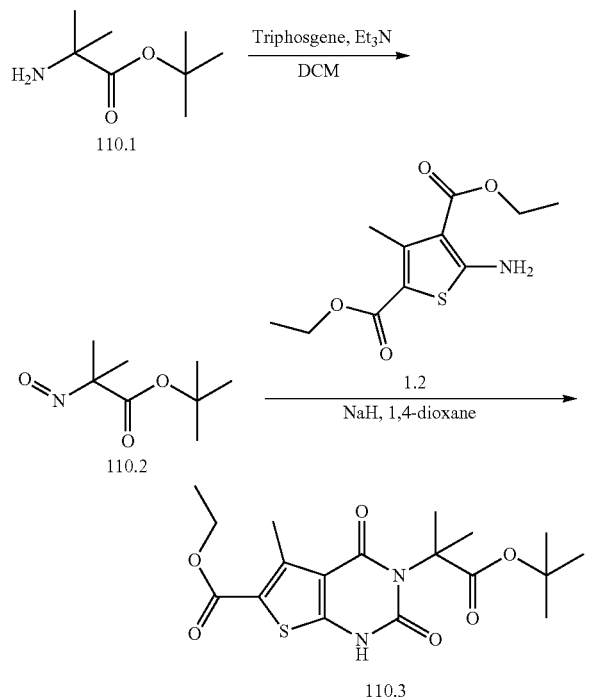

Synthesis of compound 110.2. Into a 100-mL 3-necked round-bottom flask was placed a solution of tert-butyl 2-amino-2-methylpropanoate (1.2 g, 7.54 mmol, 1.00 equiv) in dichloromethane (20 mL). This was followed by the addition of ditrichloromethyl carbonate (750 mg, 2.53 mmol, 0.34 equiv), in portions at 0° C. After 30 min, triethylamine (2.3 g, 22.73 mmol, 3.02 equiv) was added dropwise with stirring. The resulting solution was stirred for 5 h at room temperature and then concentrated under vacuum. The residue was diluted with 20 mL of ethyl ether. The solids were filtered out. The filtrate was concentrated under vacuum. Purification afforded 1.4 g (crude) of tert-butyl 2-isocyanato-2-methylpropanoate (110.2) as a yellow oil.

Synthesis of Intermediate 110.3. Into a 100-mL 3-necked round-bottom flask was placed a solution of 1.2 (1.62 g, 6.30 mmol, 1.00 equiv) in 1,4-dioxane (20 mL). This was followed by the addition of sodium hydride (280 mg, 7.00 mmol, 1.11 equiv, 60%) at 10° C., and the mixture was stirred at room temperature for 15 min. To this was added a solution of 110.2 (1.4 g, 7.56 mmol, 1.20 equiv) in 1,4-dioxane (10 mL) dropwise with stirring at 10° C. The resulting solution was stirred at room temperature for 30 min then heated to 100° C. with stirring overnight. The reaction was then quenched by the addition of 30 mL of NH₄Cl (aq.). The resulting solution was extracted with 3×50 mL of ethyl acetate and the organic layers combined and dried over anhydrous magnesium sulfate and concentrated under vacuum. The residue was applied onto a silica gel column with ethyl acetate/petroleum ether (1:10). Purification afforded 0.2 g (crude) of intermediate 110.3 as a yellow oil.

Example 111

2-[6-(ethoxycarbonyl)-5-methyl-1-[(2R)-2-(2-methylpropoxy)-2-phenylethyl]-2,4-dioxo-1H,2H,3H,4H-thieno[2,3-d]pyrimidin-3-yl]-2-methylpropanoic acid (I-123)

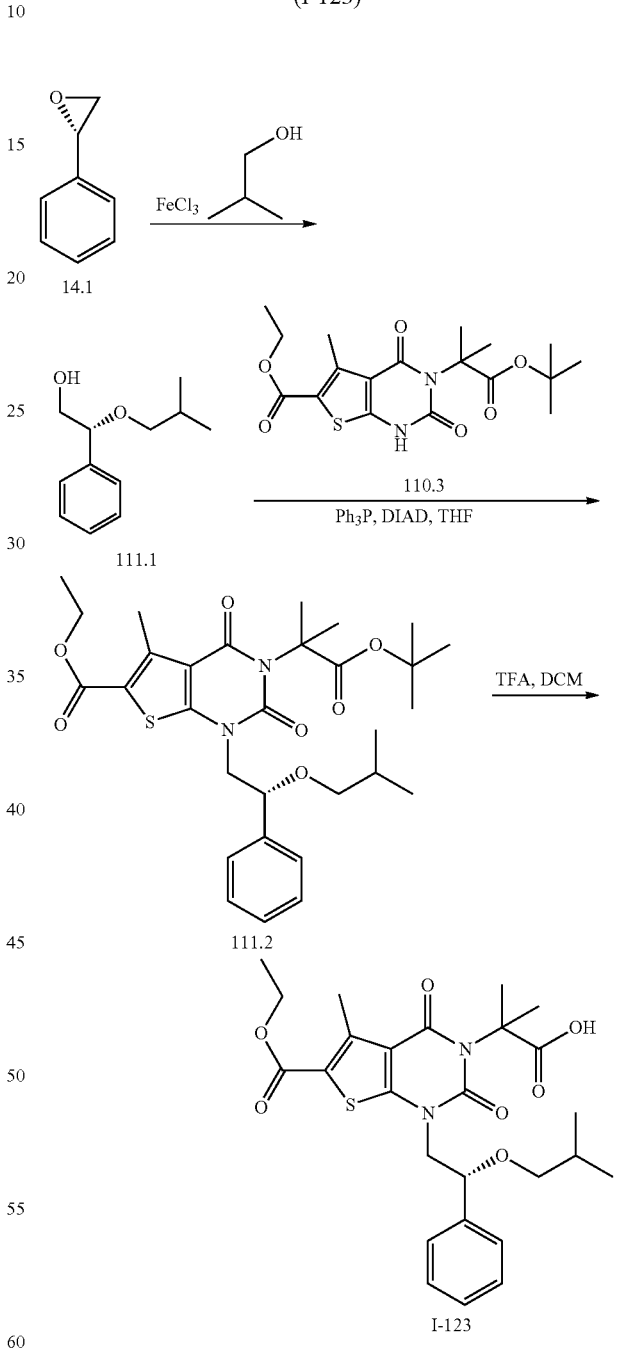

Synthesis of compound 111.1. Compound 111.1 was prepared from methylpropan-1-ol and 14.1 in a manner analogous to the synthesis of compound 57.3. Isolated 111.1 as a colorless oil in 68% yield.

Synthesis of Compound I-123. Compound I-123 was prepared from 111.1 and 110.3 in a manner analogous to compound 2.5. The crude product (150 mg) was purified by chiral preparative HPLC under the following conditions (Gilson Gx 281): Column: Chiralpak IC, 2*25 cm, 5 μm; mobile phase: hexanes and ethanol (0.1% TFA) (hold at 5.0% ethanol (0.1% TFA) for 15 min); detector: UV 220/254 nm. Isolated 33.7 mg of a light brown solid in 12% yield from 110.3. MS (ES): m/z 517 (M+H)$^+$, 539 (M+Na)$^+$, 580 (M+Na+CH$_3$CN)$^+$. $^1$H NMR (300 MHz, CD$_3$CN): δ 0.67-0.73 (m, 6H), 1.31 (t, J=6.9, 3H), 1.60-1.67 (m, 1H), 1.70 (s, 6H), 2.71 (s, 3H), 2.93-3.09 (m, 2H), 3.79-3.87 (m, 1H), 4.08-4.13 (m, 1H), 4.28 (q, J=7.2, 2H), 4.69-4.73 (m, 1H), 7.32-7.39 (m, 5H).

Example 112

2-[6-(ethoxycarbonyl)-5-methyl-1-[(2S)-2-(2-methylpropoxy)-2-phenylethyl]-2,4-dioxo-1H,2H,3H,4H-thieno[2,3-d]pyrimidin-3-yl]-2-methylpropanoic acid (I-124)

Compound I-124 was prepared from 112.1 and 110.3 in a manner analogous to Example 111. Isolated 22.2 mg (10% from 110.3) as a light brown solid. MS (ES): m/z 517 (M+H)$^+$, 539 (M+Na)$^+$, 580 (M+Na+CH$_3$CN)$^+$. $^1$H NMR (300 MHz, DMSO-d$_6$): δ 0.64-0.72 (m, 6H), 1.31 (t, J=6.9, 3H), 1.65 (s, 6H), 2.68 (s, 3H), 2.89-3.03 (m, 2H), 3.80-3.88 (m, 1H), 4.05-4.11 (m, 1H), 4.25 (q, J=7.2, 2H), 4.64-4.68 (m, 1H), 7.31-7.41 (m, 5H).

Example 113

Synthesis of (R)-2-(6-(ethoxycarbonyl)-1-(2-(4-iodophenyl)-2-isopropoxyethyl)-5-methyl-2,4-dioxo-1,2-dihydrothieno[2,3-d]pyrimidin-3(4H)-yl)-2-methylpropanoic acid (I-129) and Example 114: Synthesis of (S)-2-(6-(ethoxycarbonyl)-1-(2-(4-iodophenyl)-2-isopropoxyethyl)-5-methyl-2,4-dioxo-1,2-dihydrothieno[2,3-d]pyrimidin-3(4H)-yl)-2-methylpropanoic acid (I-126)

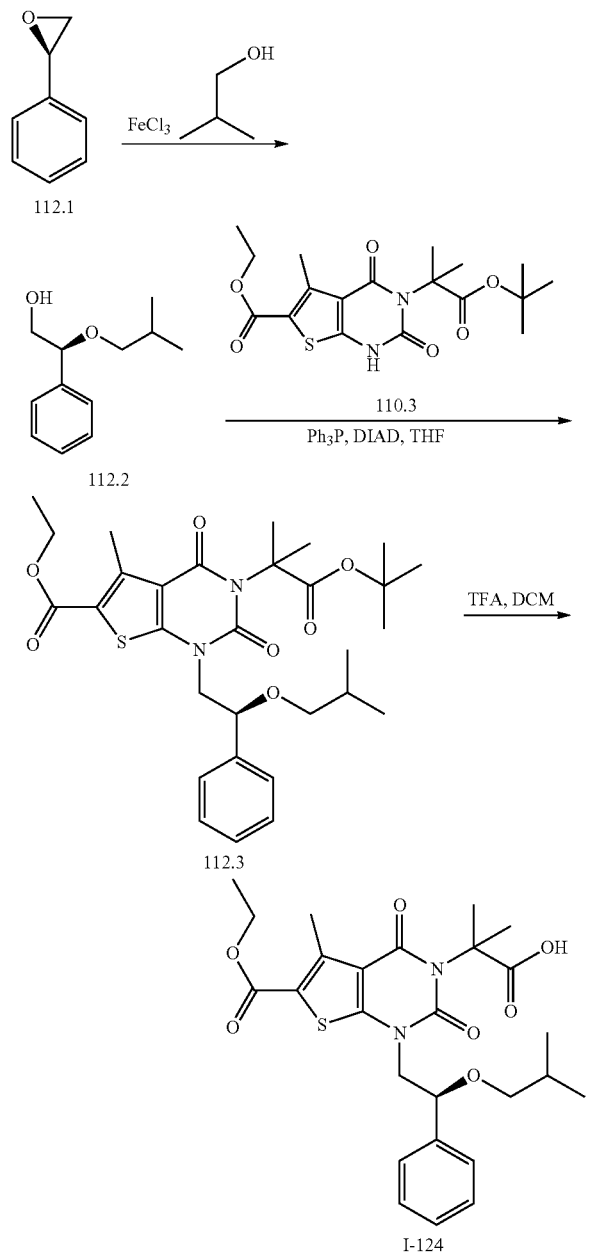

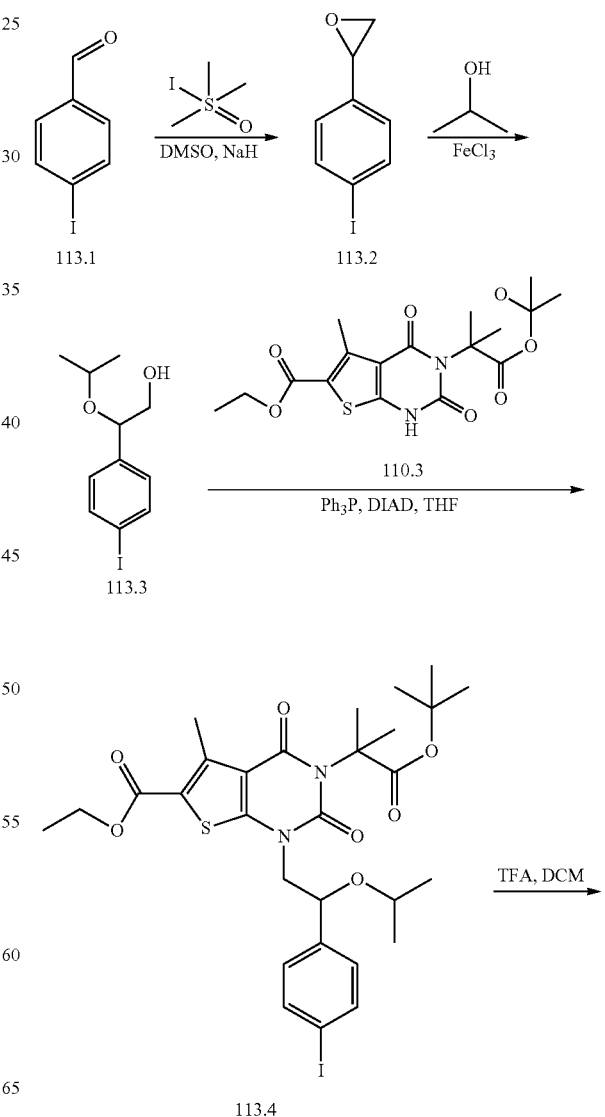

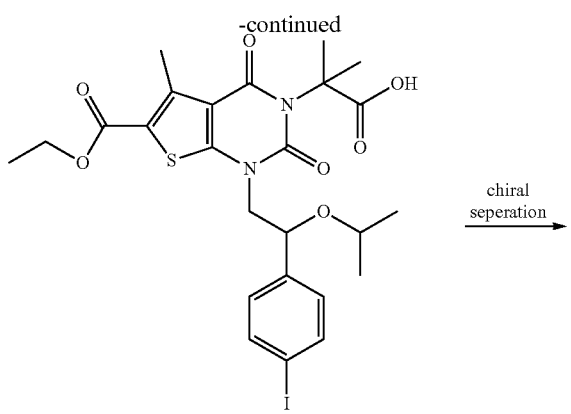

113.5

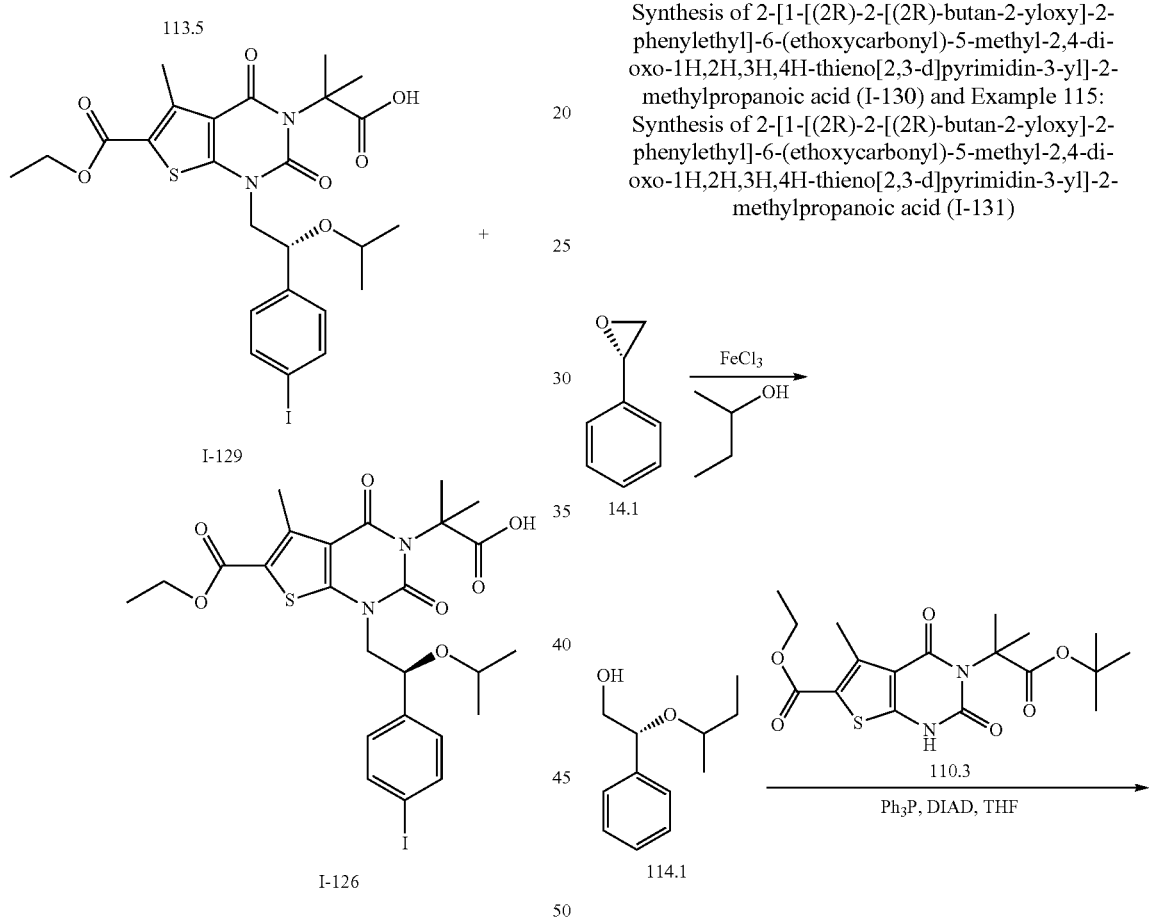

Synthesis of compound 113.3. Compound 113.3 was prepared in a manner analogous to compound 57.3. Isolated 1.036 g (59% from 113.1) as a colorless oil.

Synthesis of compound 113.5. Compound 113.5 was prepared in a manner analogous to compound 2.5. Isolated 1.2 g of a white solid in 79% yield from 110.3.

Synthesis of Compounds I-129 and I-126. The enantiomers of 113.5 (1.2 g) were separated by chiral preparative HPLC under the following conditions (Gilson Gx 281): Column: Chiralpak IC, 2*25 cm, 5 μm; mobile phase: hexanes and ethanol (hold at 15.0% ethanol for 23 min); detector: UV 220/254 nm. 325.8 mg of I-129 (tR=18.56 min) and 325.7 mg of I-126 (tR=13.09 min) were obtained as white solids.

Analytical Data for Compound I-129: MS (ES): m/z 629 (M+H)$^+$, 692 (M+Na+CH$_3$CN)$^+$.

$^1$H NMR (300 MHz, DMSO-d$_6$): δ 0.89 (d, 3H), 0.91 (d, 3H), 1.28 (t, 3H), 1.62 (s, 6H), 2.68 (s, 3H), 3.41 (m, 1H), 3.76 (m, 1H), 4.01 (d, 1H), 4.26 (q, 2H), 4.73 (m, 1H), 7.19 (d, 2H), 7.73 (d, 2H), 12.3 (br s, 1H).

Analytical Data for Compound I-126: MS (ES): m/z 629 (M+H)$^+$, 692 (M+Na+CH$_3$CN)$^+$.

$^1$H NMR (300 MHz, DMSO-d$_6$): δ 0.89 (d, 3H), 0.91 (d, 3H), 1.28 (t, 3H), 1.62 (s, 6H), 2.68 (s, 3H), 3.41 (m, 1H), 3.76 (m, 1H), 4.0 (d, 1H), 4.26 (q, 2H), 4.73 (m, 1H), 7.18 (d, 2H), 7.73 (d, 2H), 12.3 (br s, 1H).

Example 114

Synthesis of 2-[1-[(2R)-2-[(2R)-butan-2-yloxy]-2-phenylethyl]-6-(ethoxycarbonyl)-5-methyl-2,4-dioxo-1H,2H,3H,4H-thieno[2,3-d]pyrimidin-3-yl]-2-methylpropanoic acid (I-130) and Example 115: Synthesis of 2-[1-[(2R)-2-[(2R)-butan-2-yloxy]-2-phenylethyl]-6-(ethoxycarbonyl)-5-methyl-2,4-dioxo-1H,2H,3H,4H-thieno[2,3-d]pyrimidin-3-yl]-2-methylpropanoic acid (I-131)

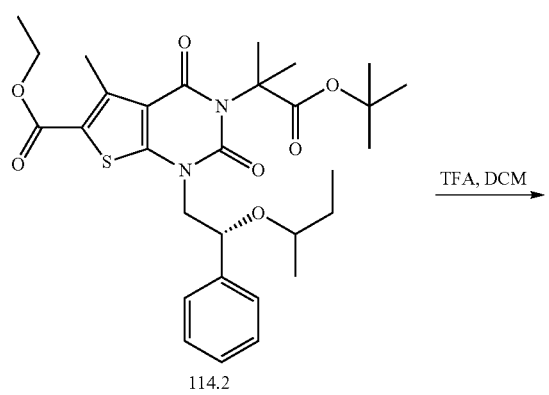

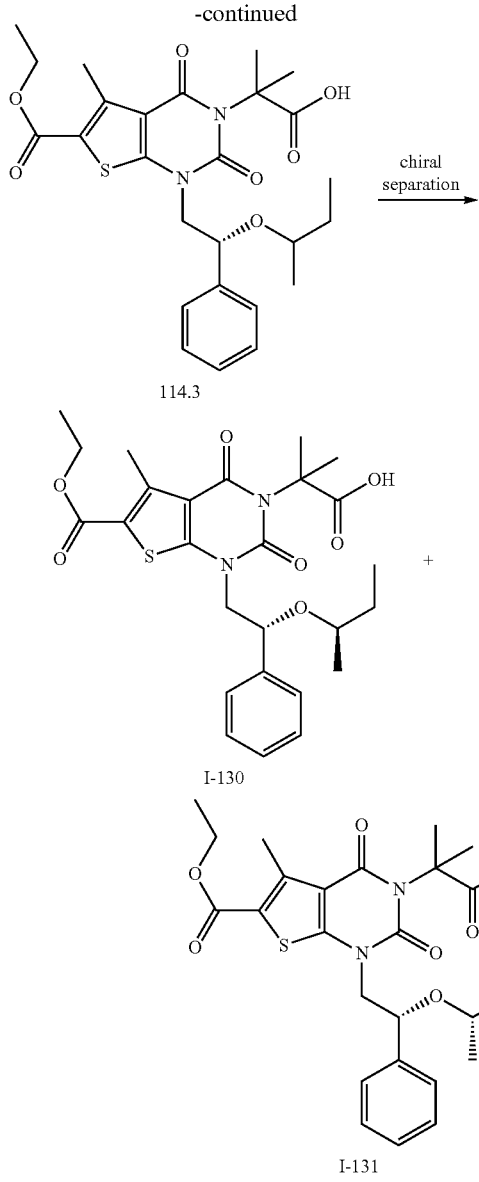

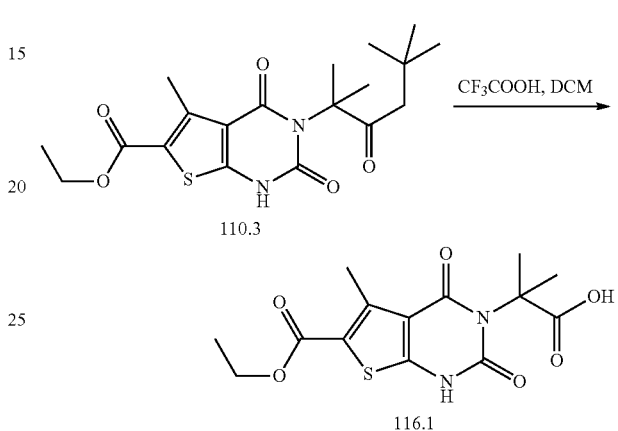

Synthesis of compound 114.1. Compound 114.1 was prepared from 14.1 in a manner analogous to compound 57.3. Isolated 1.3 g (40%) of a colorless oil.

Synthesis of compound 114.3. Compound 114.3 was prepared in a manner analogous to compound 2.5. Isolated 320 mg of a white solid in 77% yield from 110.3.

Synthesis of Compounds I-130 and I-131. The enantiomers of 114.3 were separated by chiral preparative HPLC under the following conditions (Gilson): Column: Phenomenex Lux 5 u Cellulose-4, 2.12*25, 5 μm; mobile phase: hexanes (0.1% TFA) and ethanol (hold at 5.0% ethanol in 22 min); detector: UV 220/254 nm. Compound I-130 was the first compound to elute and was isolated in 65% yield (117.4 mg) as a white solid. Compound I-131 was the second to elute and was isolated in 54% yield (97.2 mg) as a white solid.

Analytical Data for Compound I-130: MS (ES): m/z 517 (M+H)$^+$, 539 (M+Na)$^+$, 580 (M+Na+CH$_3$CN)$^+$. $^1$H NMR (300 MHz, CD$_3$OD): δ 0.66 (t, J=6.9, 3H), 0.91 (d, J=6.3, 3H), 1.26-1.35 (m, 2H), 1.40 (t, J=7.5, 3H), 1.75-1.77 (m, 6H), 2.75 (s, 3H), 3.28-3.34 (m, 1H), 3.80-3.83 (m, 1H), 4.09-4.15 (m, 1H), 4.31 (q, J=7.2, 2H), 7.29-7.43 (m, 5H).

Analytical Data for Compound I-131: MS (ES): m/z 517 (M+H)$^+$, 539 (M+Na)$^+$, 580 (M+Na+CH$_3$CN)$^+$. $^1$H NMR (300 MHz, CD$_3$OD): δ 0.66 (t, J=6.9, 3H), 0.91 (d, J=6.3, 3H), 1.26-1.35 (m, 2H), 1.40 (t, J=7.5, 3H), 1.75-1.77 (m, 6H), 2.75 (s, 3H), 3.28-3.34 (m, 1H), 3.80-3.83 (m, 1H), 4.09-4.15 (m, 1H), 4.31 (q, J=7.2, 2H), 7.29-7.43 (m, 5H).

Example 116

Synthesis of Intermediate 116.1

Into a 25-mL round-bottom flask was placed 110.3 (500 mg, 1.26 mmol, 1.00 equiv), dichloromethane (10 mL) and CF$_3$COOH (3 mL). The resulting solution was stirred for 3 h at room temperature and then concentrated under vacuum. The residue was applied onto a silica gel column with ethyl acetate/petroleum ether (1:20). Purification afforded 0.409 g (95%) of intermediate 116.1 as a white solid.

Example 117

Synthesis of 2-[1-[(2R)-2-(tert-butoxy)-2-phenyl-ethyl]-6-(ethoxycarbonyl)-5-methyl-2,4-dioxo-1H,2H,3H,4H-thieno[2,3-d]pyrimidin-3-yl]-2-methyl-propanoic acid (I-127)

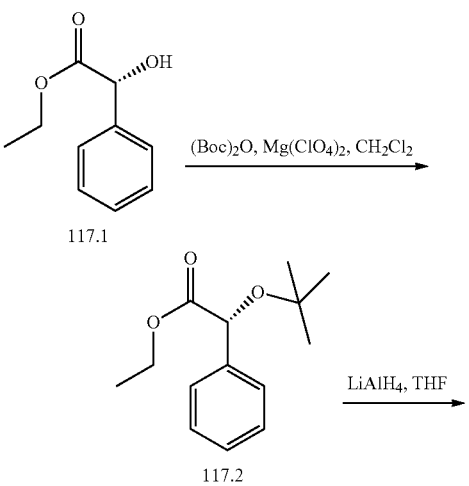

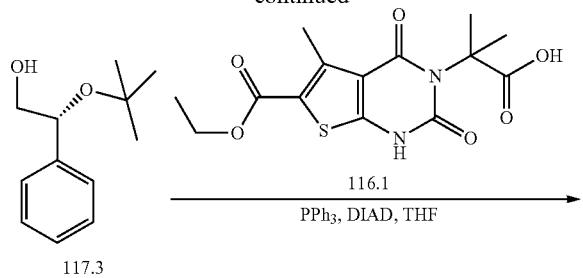

Synthesis of compound 117.2. Into a 100-mL 3-necked round-bottom flask was placed ethyl (2R)-2-hydroxy-2-phenylacetate (117.1, 5 g, 27.75 mmol, 1.00 equiv), dichloromethane (50 mL), Mg(ClO$_4$)$_2$ (0.619 g, 0.10 equiv) and (Boc)$_2$O (13.912 g, 63.74 mmol, 2.30 equiv). The resulting solution was stirred overnight at 40° C. The reaction was then quenched by the addition of water. The resulting solution was extracted with ethyl acetate and the organic layers combined, dried, and concentrated under vacuum. The residue was applied onto a silica gel column with EA/PE (1:25). Purification afforded 2.5 g (38%) of ethyl (2R)-2-(tert-butoxy)-2-phenylacetate (117.2) as a light yellow liquid.

Synthesis of compound 117.3. Into a 50-mL round-bottom flask was placed tetrahydrofuran (10 mL), 117.2 (500 mg, 2.12 mmol, 1.00 equiv) and LiAlH$_4$ (81 mg, 2.13 mmol, 1.01 equiv). The resulting solution was stirred for 2 h at 0° C. in a water/ice bath. The reaction was then quenched by the addition of 20 mL of ethyl acetate. The resulting mixture was concentrated under vacuum. The residue was applied onto a silica gel column with ethyl acetate/petroleum ether (1:5). Purification afforded 0.38 g (92%) of (2R)-2-(tert-butoxy)-2-phenylethan-1-ol (117.3) as a white solid.

Synthesis of Compound I-127. Into a 100-mL 3-necked round-bottom flask purged and maintained with an inert atmosphere of nitrogen was placed 116.1 (200 mg, 0.59 mmol, 1.00 equiv), tetrahydrofuran (30 mL), DIAD (238 mg, 1.18 mmol, 2.00 equiv), PPh$_3$ (309 mg, 1.18 mmol, 2.00 equiv) and 117.3 (114 mg, 0.59 mmol, 1.00 equiv). The resulting solution was stirred overnight at room temperature and then concentrated under vacuum. The residue was applied onto a silica gel column with ethyl acetate/hexane (1:25). The product thus obtained (100 mg) was purified by preparative HPLC under the following conditions (Waters): Column: Xbridge Prep Phenyl 5 μm, 19*150 mm; mobile phase: water (0.05% NH$_4$HCO$_3$) and CH$_3$CN (6.0% CH$_3$CN up to 50.0% in 10 min); detector: 220/254 nm. 24.9 mg (8%) of Compound I-127 were obtained as a white solid. MS (ES): m/z 517 (M+H)$^+$; 443 (M−C$_4$H$_9$O)$^+$. $^1$H NMR (300 MHz, DMSO-d$_6$): δ 0.94 (s, 9H), 1.22-1.27 (t,3H), 1.58-1.61 (d, 6H), 2.61 (s,3H), 3.80-3.86 (q, 2H), 4.19-4.24 (m, 2H), 4.66-4.70 (m, 1H), 7.09-7.46 (m, 5H), 12.38-12.51 (s, 1H).

Example 118

Synthesis of 2-[1-[(2S)-2-(tert-butoxy)-2-phenylethyl]-6-(ethoxycarbonyl)-5-methyl-2,4-dioxo-1H,2H,3H,4H-thieno[2,3-d]pyrimidin-3-yl]-2-methylpropanoic acid (I-128)

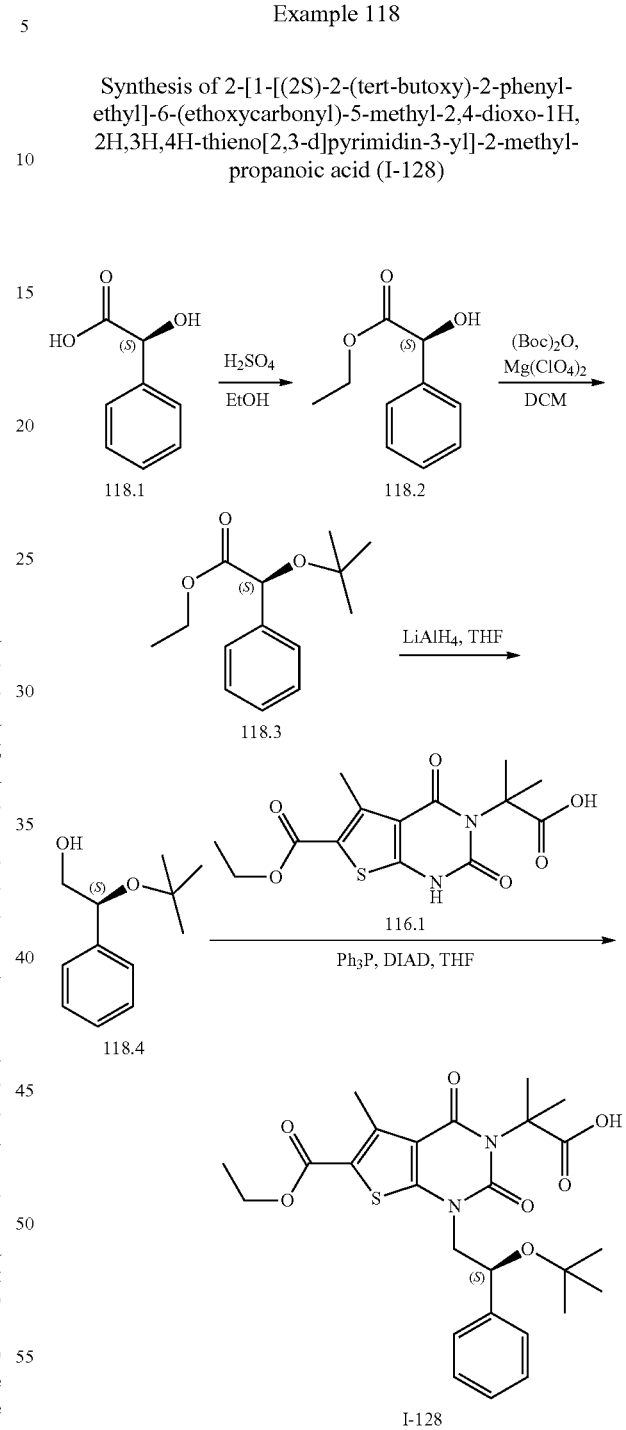

Synthesis of compound 118.4. Compound 118.4 was prepared from 118.1 in a manner analogous to compound 117.3. Isolated 220 mg of a white solid in 16% overall yield.

Synthesis of compound I-128. Compound I-128 was prepared from 118.4 and 116.1 in a manner analogous to Example 117. MS (ES): m/z 517 (M+H)$^+$, 443 (M−C$_4$H$_9$O)$^+$. $^1$H NMR (300 MHz, DMSO-d$_6$): δ 0.94 (s, 9H), 1.22-1.27 (t, 3H), 1.59-1.61 (d, 6H), 2.61 (s, 3H), 3.79-3.82 (q, 2H), 4.19-4.26 (q, 2H), 4.66-4.70 (m, 1H), 7.09-7.43 (m, 5H), 12.382 (s,1H).

Example 119

Synthesis of Intermediate 119.1

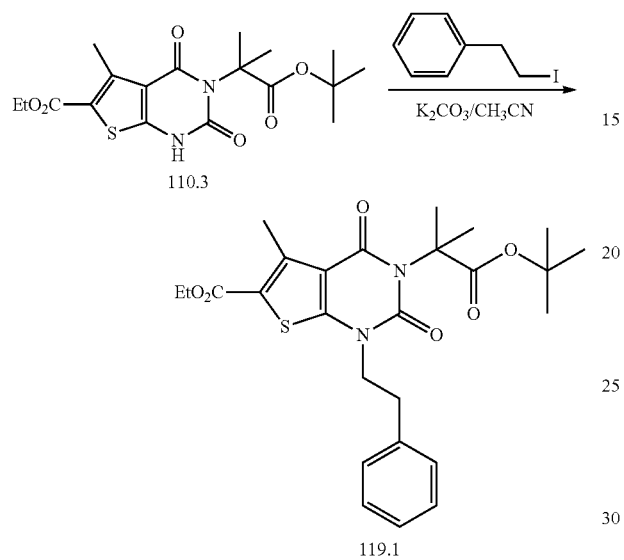

Synthesis of compound 119.1. Into a 100-mL 3-necked round-bottom flask was placed 110.3 (1 g, 2.52 mmol, 1.00 equiv), CH$_3$CN (50 mL), potassium carbonate (1.045 g, 7.56 mmol, 3.00 equiv) and (2-iodoethyl)benzene (1.172 g, 5.05 mmol, 2.00 equiv). The resulting solution was stirred for 4 h at 80° C. The resulting mixture was concentrated under vacuum. The residue was applied onto a silica gel column with EA/PE (1:100-1:15). Purification afforded 1.24 g (98%) of 119.1 as a white solid.

Example 120

Synthesis of 2-[6-(ethoxycarbonyl)-5-methyl-2,4-dioxo-1-(2-phenylethyl)-1H,2H,3H,4H-thieno[2,3-d]pyrimidin-3-yl]-2-methylpropanoic acid (I-70)

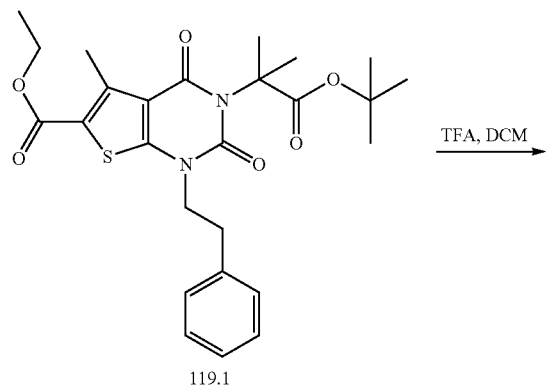

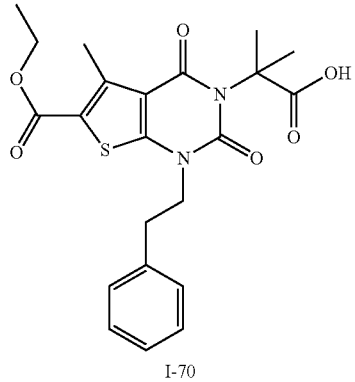

Compound I-70 was synthesized following the procedure of intermediate 116.1. Isolated 50 mg of a white solid in 38% yield. MS (ES): m/z 445 (M+H)$^+$. $^1$H NMR (DMSO-d$_6$, 300 MHz): δ 1.29 (t, J=9.6 Hz, 3H), 1.63 (s, 6H), 2.70 (s, 3H), 2.98 (t, J=9.6 Hz, 2H), 4.07 (t, J=9.6 Hz, 2H), 4.27 (q, J=9.6 Hz, 2H), 7.19-7.31 (m, 5H), 12.40 (s, 1H).

Example 121

Synthesis of Intermediate 121.3

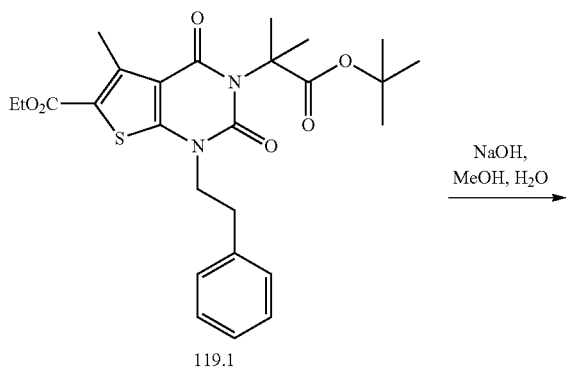

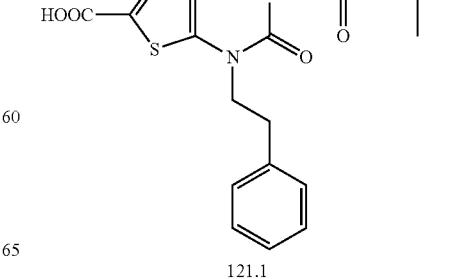

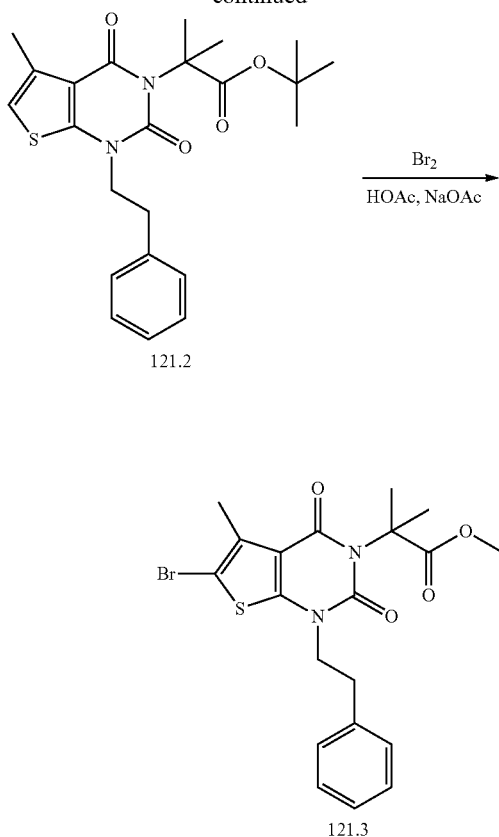

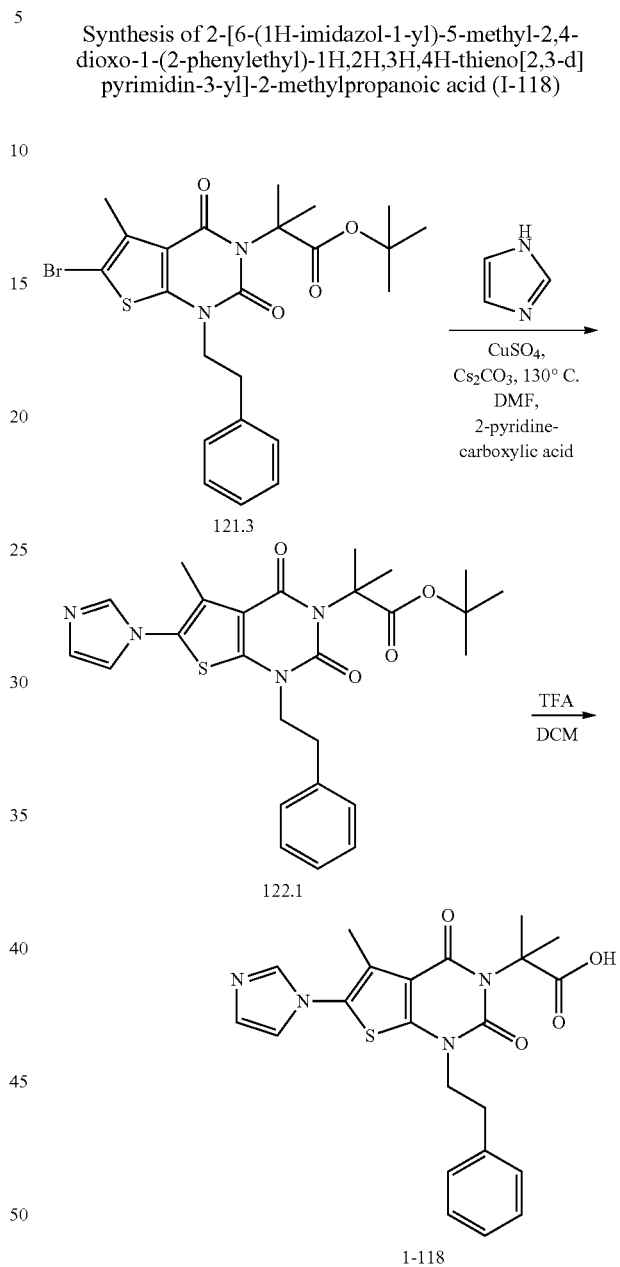

Example 122

Synthesis of 2-[6-(1H-imidazol-1-yl)-5-methyl-2,4-dioxo-1-(2-phenylethyl)-1H,2H,3H,4H-thieno[2,3-d]pyrimidin-3-yl]-2-methylpropanoic acid (I-118)

Synthesis of compound 121.1. Into a 100-mL 3-necked round-bottom flask was placed 119.1 (1.017 g, 2.03 mmol, 1.00 equiv) and methanol (40 mL). Then a solution of sodium hydroxide (162 mg, 4.05 mmol, 2.00 equiv) in water (5 mL) was added dropwise. The resulting solution was stirred overnight at room temperature. The reaction was then quenched by the addition of HCl (aq.). The resulting solution was extracted with ethyl acetate and the organic layers combined and concentrated under vacuum. The crude product was purified by re-crystallization from EA/PE in the ratio of 1:4. 0.578 g (60%) of 121.1 were obtained as a white solid.

Synthesis of compound 121.2. Into a 100-mL 3-necked round-bottom flask was placed 121.1 (578 mg, 1.22 mmol, 1.00 equiv), NMP (40 mL), potassium carbonate (169 mg, 1.22 mmol, 1.00 equiv) and AgOAc (0.204 g). The resulting solution was stirred for 2 h at 110° C. The reaction was then quenched by the addition of water. The resulting solution was extracted with ethyl acetate and the organic layers combined and concentrated under vacuum. The residue was applied onto a silica gel column with EA/PE (1:25). Purification afforded 0.445 g (85%) of 121.2 as a white solid.

Synthesis of compound 121.3. Into a 50-mL round-bottom flask was placed 121.2 (445 mg, 1.04 mmol, 1.00 equiv), acetic acid (5 mL) and CH₃COONa (0.170 g). Then Br₂ (167 mg, 1.04 mmol, 1.01 equiv) was added dropwise. The resulting solution was stirred for 15 min at room temperature and then concentrated under vacuum. The residue was applied onto a silica gel column with EA/PE (1:25). Purification afforded 0.502 g (95%) of intermediate 121.3 as a white solid.

Synthesis of compound 122.1. Into a 10-mL sealed tube, purged and maintained with an inert atmosphere of nitrogen, was placed a solution of 121.3 (200 mg, 0.39 mmol, 1.00 equiv) in N,N-dimethylformamide (5 mL), 1H-imidazole (200 mg, 2.94 mmol, 7.45 equiv), pyridine-2-carboxylic acid (50 mg, 0.41 mmol, 1.03 equiv), CuSO₄ (100 mg, 0.63 mmol, 1.60 equiv) and Cs₂CO₃ (400 mg, 1.23 mmol, 3.11 equiv). The resulting solution was stirred overnight at 140° C. The reaction was then quenched by the addition of 5 mL of NH₄Cl (aq.). The resulting solution was extracted with 3×5 mL of ethyl acetate and the organic layers combined and concentrated under vacuum. The residue was applied onto a silica gel column with ethyl acetate/petroleum ether (1:2). Purification afforded 166 mg (85%) of 122.1 as a brown oil.

Synthesis of Compound I-118. Into a 100-mL round-bottom flask was placed 122.1 (166 mg, 0.34 mmol, 1.00 equiv), dichloromethane (10 mL) and trifluoroacetic acid (2 mL). The resulting solution was stirred for 4 h at room temperature and then concentrated under vacuum. The residue was applied onto a silica gel column with dichloromethane/methanol (50:1). Purification afforded 121.7 mg (83%) of I-118 was a yellow solid. MS (ES): m/z 439 (M+H)$^+$.

$^1$H NMR (DMSO-d$_6$, 300 MHz): δ 1.61 (s, 6 H), 2.13 (s, 3 H), 2.95 (t, J=7.2 Hz, 2 H), 4.00 (t, J=7.2 Hz, 2 H), 7.47-7.16 (m, 5 H), 7.47 (s, 1 H), 8.09 (s, 1 H), 12.38 (br s, 1 H).

Example 123

Synthesis of 2-methyl-2-[5-methyl-2,4-dioxo-1-(2-phenylethyl)-6-(2H-1,2,3-triazol-2-yl)-1H,2H,3H,4H-thieno[2,3-d]pyrimidin-3-yl]propanoic acid (I-122)

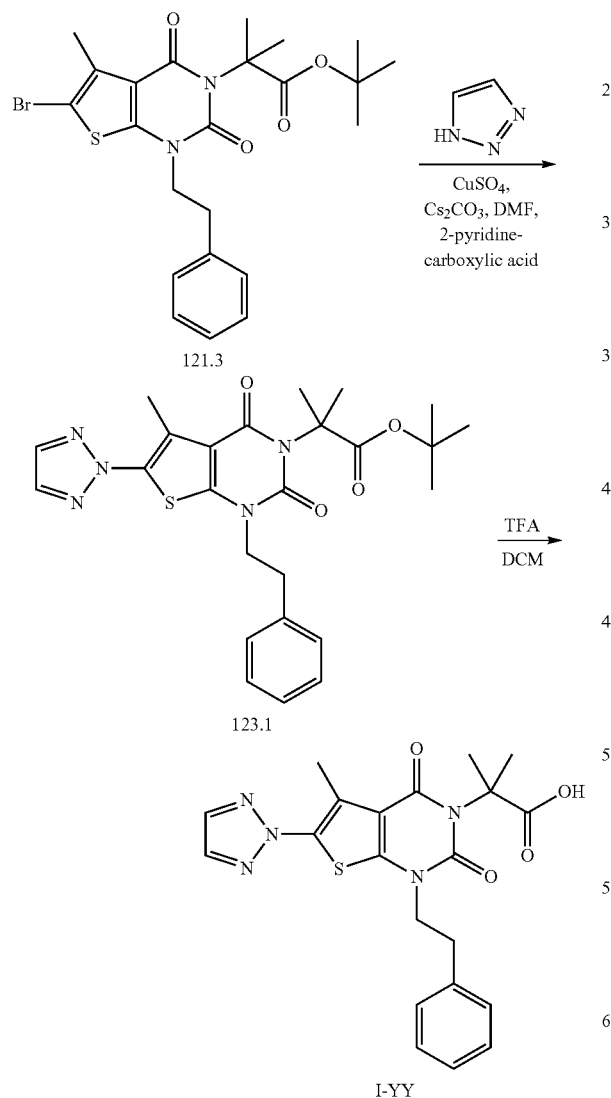

(ES): m/z 440 (M+H)$^+$. $^1$H NMR (CD$_3$OD, 300 MHz): δ 1.75 (s, 6H), 2.51 (s, 3H), 3.05 (t, J=7.2 Hz, 2H), 4.08 (t, J=7.2 Hz, 2H), 7.26-7.12 (m, 5H), 7.91 (s, 1H).

Example 124

Synthesis of 2-methyl-2-[5-methyl-6-(1,3-oxazol-2-yl)-2,4-dioxo-1-(2-phenylethyl)-1H,2H,3H,4H-thieno[2,3-d]pyrimidin-3-yl]propanoic acid (I-117)

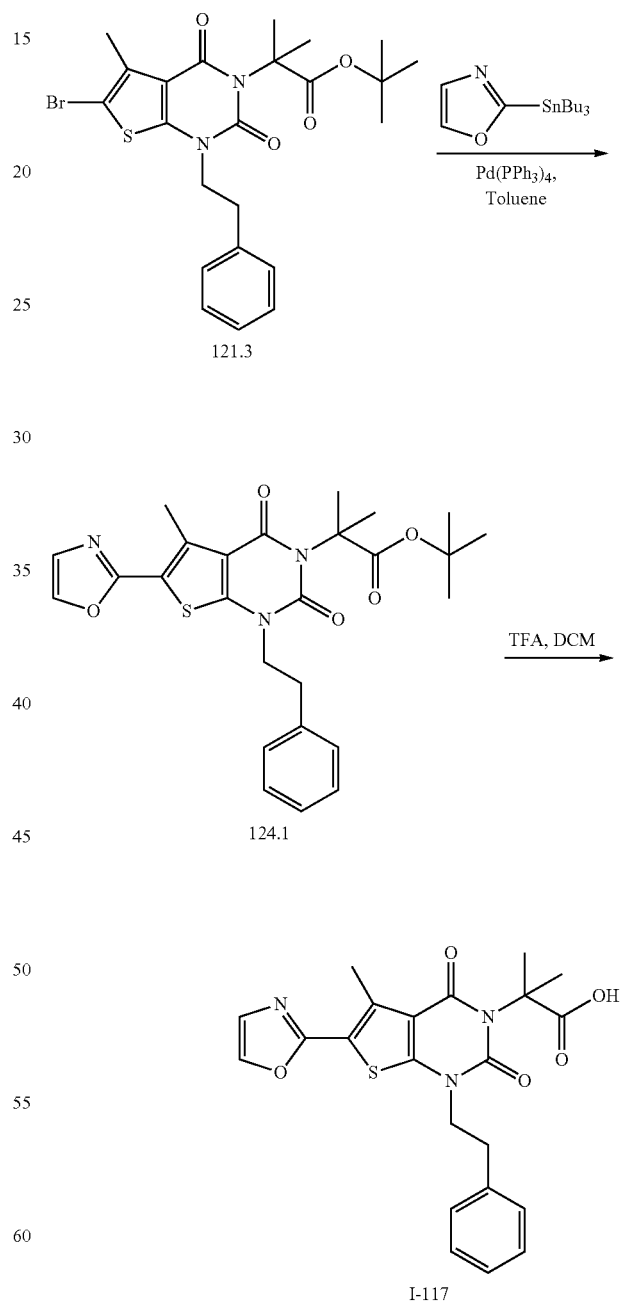

Compound I-122 was prepared from 1H-1,2,3-triazole and intermediate 121.3 following the procedure of Example 122. Isolated 20.6 mg of a white solid in 5% yield from 123.1. MS Compound I-117 was prepared from 121.3 in a manner analogous to the procedure of Example 7. MS (ES): m/z 440 (M+H)$^+$. $^1$H NMR (400 MHz, CD$_3$OD): δ 1.79 (s, 6 H), 2.78

(s, 3H), 3.11 (t, J=7.2 Hz, 2 H), 4.15 (t, J=7.2 Hz, 2 H), 7.19-7.23 (m, 1 H), 7.25-7.31 (m, 5 H), 7.96 (s, 1 H).

Example 125

Synthesis of 2-[6-cyclopropyl-5-methyl-2,4-dioxo-1-(2-phenylethyl)-1H,2H,3H,4H-thieno[2,3-d]pyrimidin-3-yl]-2-methylpropanoic acid (I-132)

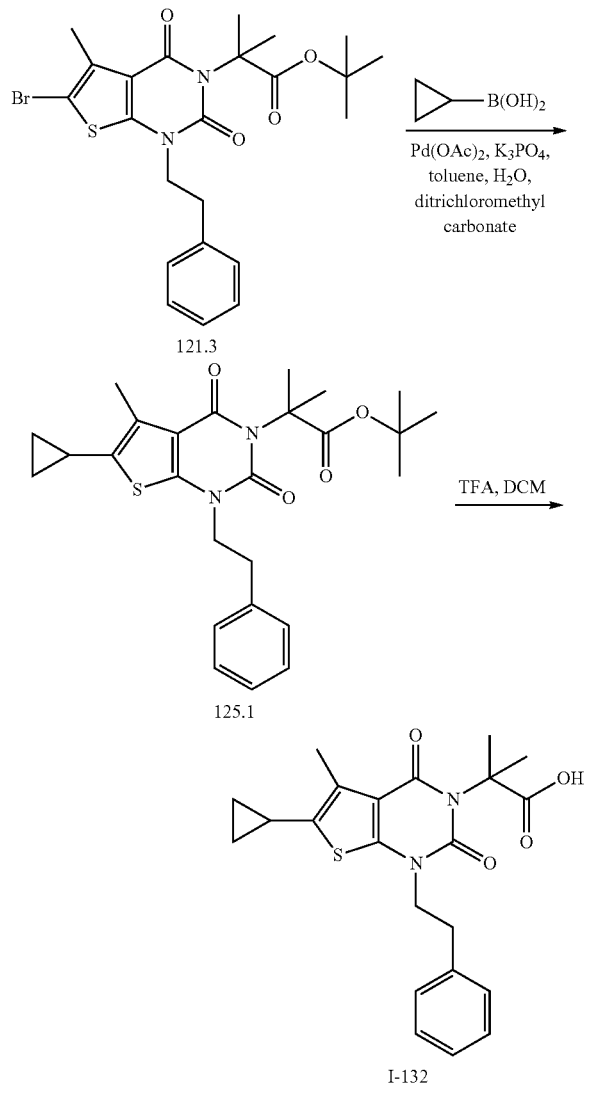

applied onto a silica gel column with dichloromethane/methanol (20:1). Purification afforded 22 mg (15%) of I-132 as a white solid. MS (ES): m/z 413 (M+H)$^+$.

$^1$H NMR (CD$_3$OD, 400 MHz): δ 0.67 (t, J=5.2 Hz, 2H), 0.97 (t, J=8 Hz, 2H), 1.80 (s, 6H), 1.90-2.00 (m, 1H), 2.41 (s, 3H), 3.03 (t, J=6.8 Hz, 2H), 4.08 (t, J=6.8 Hz, 2H), 7.29-7.18 (m, 5H).

Example 126

Synthesis of 2-[6-cyclobutyl-5-methyl-2,4-dioxo-1-(2-phenylethyl)-1H,2H,3H,4H-thieno[2,3-d]pyrimidin-3-yl]-2-methylpropanoic acid (I-125)

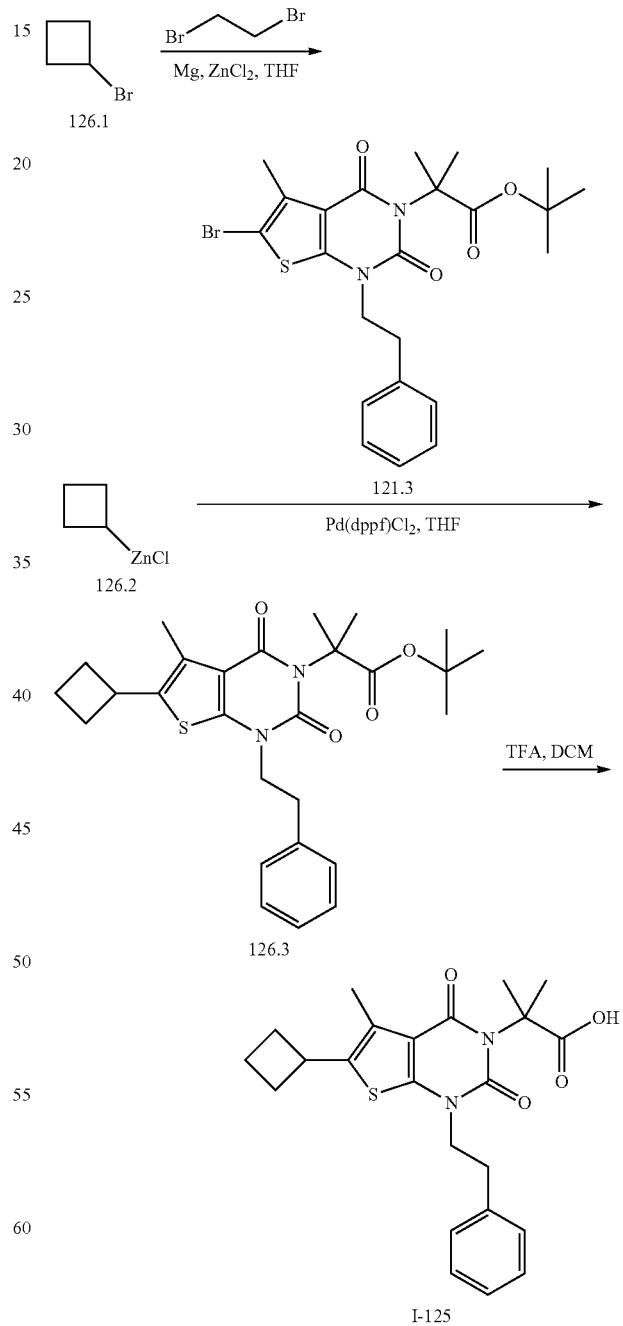

Synthesis of compound 125.1. Into a 100-mL 3-necked round-bottom flask, purged and maintained with an inert atmosphere of nitrogen, was placed 121.3 (200 mg, 0.39 mmol, 1.00 equiv), cyclopropylboronic acid (200 mg, 2.33 mmol, 5.91 equiv), ditrichloromethyl carbonate (20 mg, 0.07 mmol, 0.17 equiv), K$_3$PO$_4$ (300 mg, 1.41 mmol, 3.59 equiv), Pd(OAc)$_2$ (10 mg, 0.04 mmol, 0.11 equiv), water (0.5 mL) and toluene (20 mL). The resulting solution was heated to reflux for 2 hr and then concentrated under vacuum. The residue was applied onto a silica gel column with ethyl acetate/petroleum ether (1:10). Purification afforded 170 mg of a white solid.

Synthesis of Compound I-132. Into a 50-mL round-bottom flask was placed 125.1 (170 mg, 0.36 mmol, 1.00 equiv), trifluoroacetic acid (1 mL) and dichloromethane (5 mL). The resulting solution was stirred overnight at room temperature and then concentrated under vacuum. The residue was Synthesis of compound 126.2. Into a 100-mL 3-necked round-bottom flask was placed a suspension of Mg (0.46 g) in tetrahydrofuran (10 mL), followed by a roughly 10% portion of a 2-g batch of bromocyclobutane (14.81 mmol, 1.00 equiv). Then several drops of 1,2-dibromoethane were added to initiate the reaction. This was followed by the addition of a solution of the remaining bromocyclobutane (2 g, 14.81 mmol, 1.00 equiv) in THF dropwise. The resulting solution was stirred for 2 h at room temperature. After cooling to 0° C., $ZnCl_2$ (2.22 g, 16.29 mmol, 1.10 equiv) was added in portions. The resulting solution was stirred for 2 h at room temperature and directly used for the next step.

Synthesis of compound 126.3. A solution of $Pd(dppf)Cl_2$ (72 mg, 0.10 mmol, 0.10 equiv) and 121.3 (500 mg, 0.99 mmol, 1.00 equiv) in tetrahydrofuran (5 mL) was added to a flask of chloro(cyclobutyl)zinc (126.2, crude solution). The resulting solution was stirred overnight at room temperature. The reaction was then quenched by the addition of 50 mL of $NH_4Cl$ (aq.). The resulting solution was extracted with 3×100 mL of ethyl acetate and the organic layers combined and concentrated under vacuum. The residue was applied onto a silica gel column with ethyl acetate/petroleum ether (1:40). Purification afforded 240 mg (50%) of 126.3 as a colorless oil.

Synthesis of Compound I-125. Into a 50-mL round-bottom flask was placed dichloromethane (5 mL), 126.3 (240 mg, 0.50 mmol, 1.00 equiv) and trifluoroacetic acid (2 mL). The resulting solution was stirred for 2 h at room temperature and then concentrated under vacuum. The residue was applied onto a silica gel column with dichloromethane/methanol (50:1). Purification afforded 43.5 mg (21%) of Compound I-125 as a white solid. MS (ES): m/z 426 (M+H)$^+$, 449 (M+Na)$^+$, 490 (M+Na+$CH_3CN$)$^+$. $^1$H NMR (300 MHz, DMSO-$d_6$): δ 1.59 (s, 6H), 1.77-1.81 (m, 1H), 1.90-2.00 (m, 3H), 2.18 (s, 3H), 2.31-2.34 (m, 2H), 2.93 (t, J=7.5, 2H), 3.71-3.77 (m, 1H), 3.99 (t, J=7.5, 2H), 7.15-7.28 (m, 5H).

Example 127

Synthesis of Intermediate 127.3

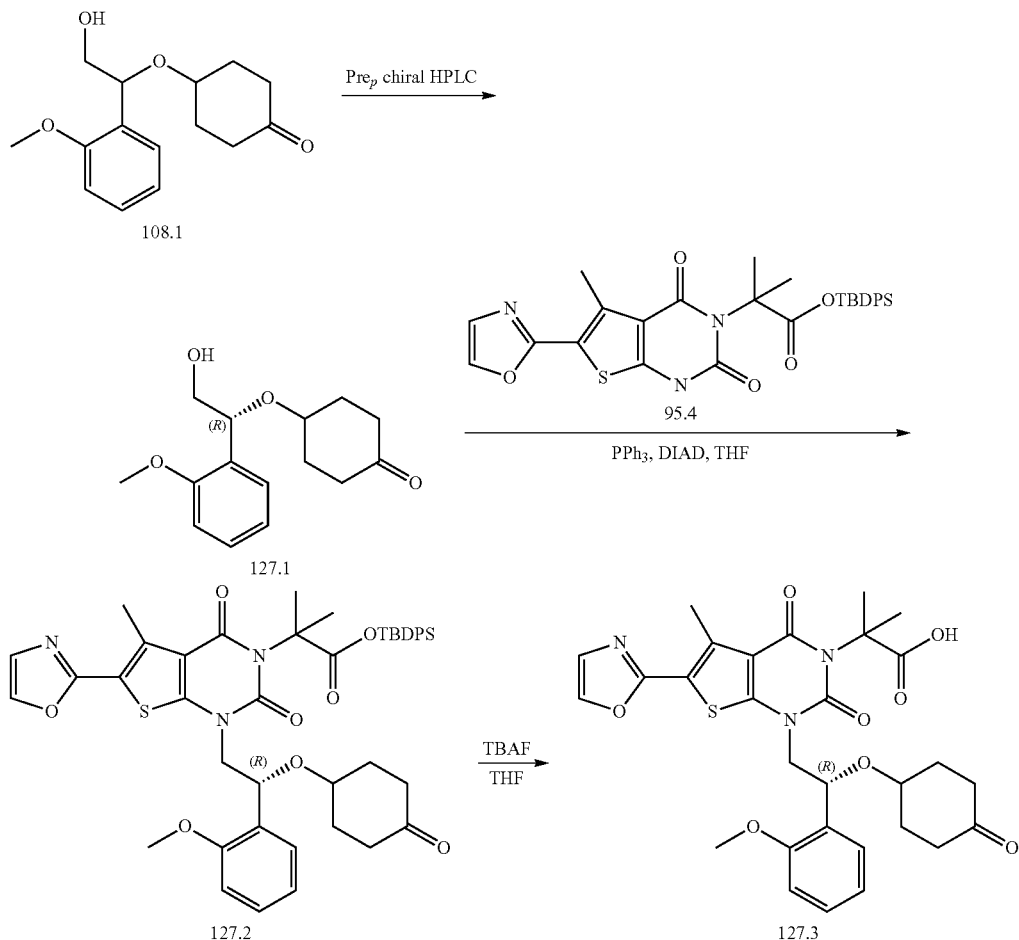

Synthesis of compound 127.1. The enantiomers of racemic 108.1 (400 mg) were separated by chiral preparative HPLC under the following conditions (Gilson Gx 281): Column: Venusil Chiral OD-H, 21.1*25 cm, 5 μm; mobile phase: hexanes and IPA (hold at 5% IPA for 36 min); detector: UV 254/220 nm. 180 mg of 127.1 were obtained.

Synthesis of compound 127.3. Compound 127.3 was prepared from 95.4 and 127.1 in a manner analogous to the procedure Example 96. Isolated a white solid in 53% yield from 95.4.

Example 128

Synthesis of 2-[1-[(2R)-2-[(4-hydroxycyclohexyl)oxy]-2-(2-methoxyphenyl)ethyl]-5-methyl-6-(1,3-oxazol-2-yl)-2,4-dioxo-1H,2H,3H,4H-thieno[2,3-d]pyrimidin-3-yl]-2-methylpropanoic acid (I-278)

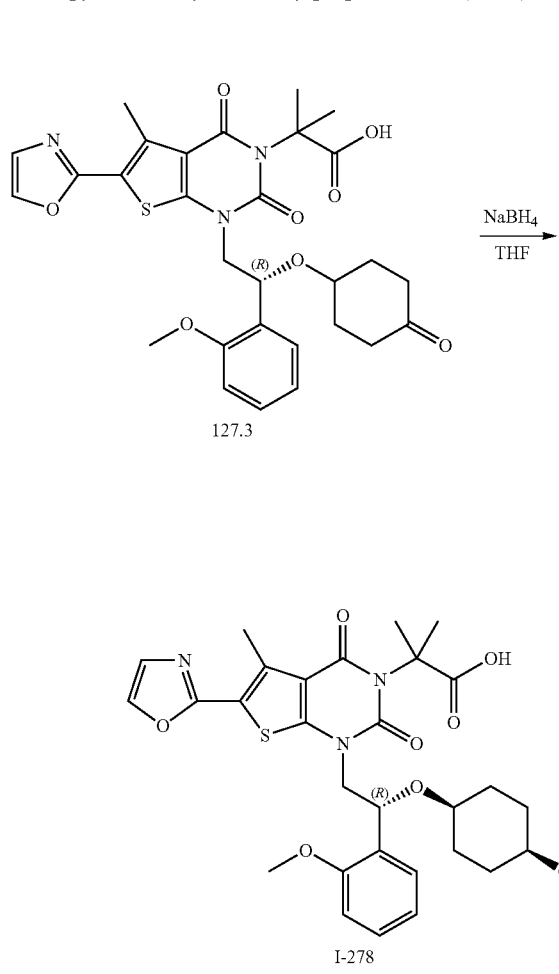

Into a 25-mL round-bottom flask was placed 127.3 (600 mg, 1.03 mmol, 1.00 equiv) and methanol (5 mL). Then sodium borohydride (40 mg, 1.09 mmol, 1.00 equiv) was added at 0° C. The resulting solution was stirred overnight at room temperature and then concentrated under vacuum. The crude product (400 mg) was purified by preparative HPLC under the following conditions (Waters): Column: Xbridge Prep Phenyl 5 μm, 19*150 mm; mobile phase: water (50 mM NH$_4$HCO$_3$) and CH$_3$CN (40.0% CH$_3$CN up to 60.0% in 20 min); detector: UV 254/220 nm. 93.5 mg (16%) of Compound I-278 were obtained as a white solid. MS (ES): m/z 584 (M+H)$^+$, 606 (M+Na)$^+$. $^1$H NMR (300 MHz, DMSO-d$_6$): δ 1.21-1.40 (m, 6H), 1.56 (m, 2H), 1.68 (d, 6H), 2.74 (s, 3H), 3.17 (m, 2H), 3.78 (s, 3H), 3.89-4.03 (m,2H), 5.24 (t, 1H), 6.99 (m,2H), 7.26 (m,1H), 7.38 (s,1H), 7.47 (m,1H), 8.21 (s, 1H).

Example 129

Synthesis of 2-[1-[(2R)-2-[(4-hydroxycyclohexyl)oxy]-2-(2-methoxyphenyl)ethyl]-5-methyl-6-(1,3-oxazol-2-yl)-2,4-dioxo-1H,2H,3H,4H-thieno[2,3-d]pyrimidin-3-yl]-2-methylpropanamide (I-279)

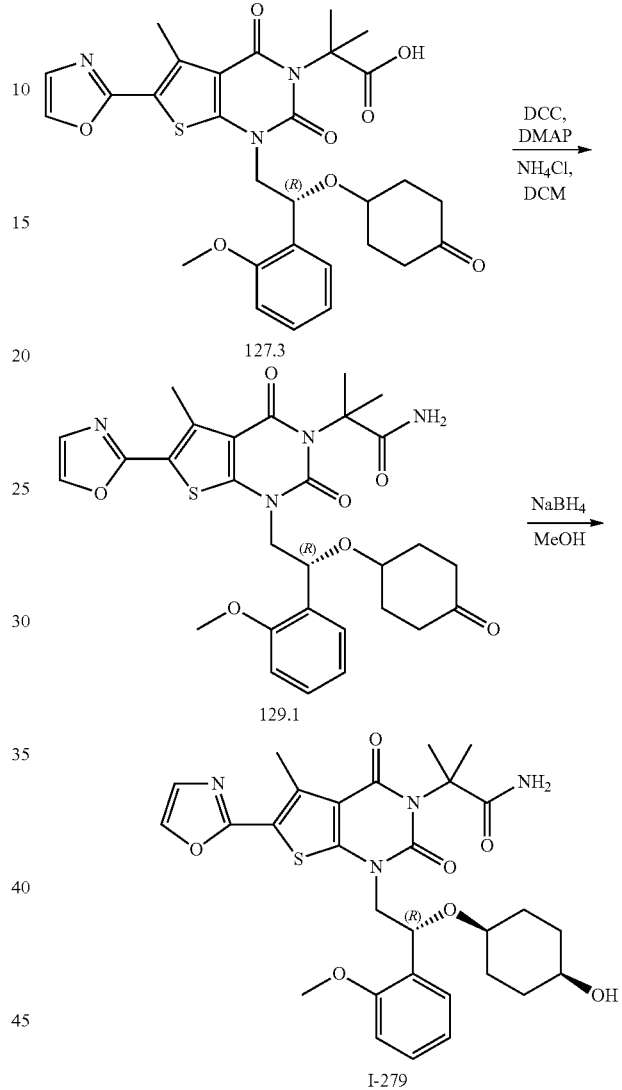

Synthesis of compound 129.1. Compound 129.1 was prepared from 127.3 and ammonium chloride following the procedure of Example 4. Isolated 530 mg of a white solid in quantitative yield.

Synthesis of Compound I-279. Into a 50-mL round-bottom flask was placed 129.1 (530 mg, 0.91 mmol, 1.00 equiv), methanol (10 mL) and sodium borohydride (35 mg, 0.95 mmol, 1.04 equiv). The resulting solution was stirred overnight at room temperature and concentrated under vacuum. The crude product (150 mg) was purified by preparative HPLC under the following conditions (Waters): Column: HPrepC-012(T) Xbridge Prep Phenyl 5 μm, 19*150 mm; mobile phase: Water (50 mM NH$_4$HCO$_3$) and CH$_3$CN (30.0% CH$_3$CN up to 70.0% in 15 min); detector: 254/220 nm. Purification afforded 39.1 mg (7%) of Compound I-279 (tR=8.21 min) as a white solid. MS (ES): m/z 605 (M+Na)$^+$. $^1$H NMR (300 MHz, DMSO-d$_6$): δ 1.17-1.30 (m, 6H), 1.53 (m, 2H), 1.66 (d, 6H), 2.74 (s, 3H), 3.17 (m, 1H), 3.31 (m, 1H), 3.78 (s, 3H), 3.99 (m, 2H), 4.29 (s, 1H), 5.28 (t, 1H), 6.79-7.28 (m, 4H), 7.30 (m, 1H), 7.37 (s, 1H), 7.47 (m, 1H), 8.21 (s, 1H).

Example 130

Synthesis of 2-[1-[(2R)-2-(2-cyanophenyl)-2-(oxan-4-yloxy)ethyl]-5-methyl-6-(1,3-oxazol-2-yl)-2,4-dioxo-1H,2H,3H,4H-thieno[2,3-d]pyrimidin-3-yl]-2-methylpropanoic acid (I-280)

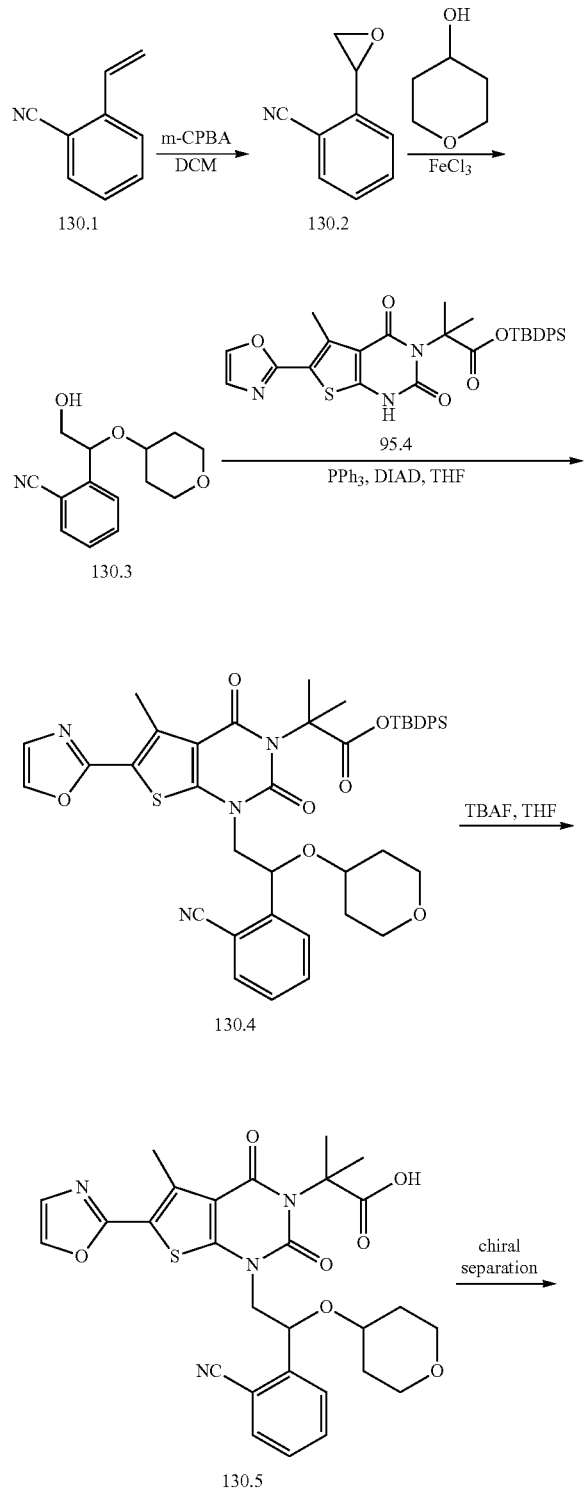

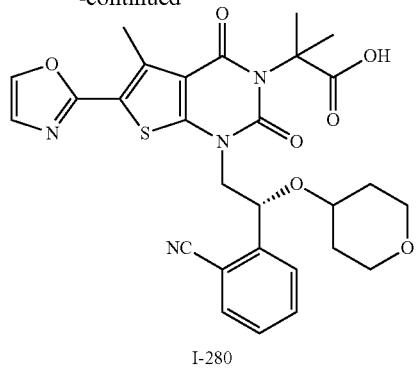

Synthesis of compound 130.2. Into a 100-mL round-bottom flask was placed 2-ethenylbenzonitrile (2.73 g, 21.14 mmol, 1.00 equiv), sodium bicarbonate (1.77 g, 21.07 mmol, 4.61 equiv), dichloromethane (20 mL) and water (20 mL). Then m-CPBA (10.9 g, 63.16 mmol, 2.25 equiv) was added at 0° C. in several batches. The resulting solution was stirred overnight at room temperature and then concentrated under vacuum. The residue was applied onto a silica gel column with PE/EA (50:1). Purification afforded 400 mg (13%) of 2-(oxiran-2-yl)benzonitrile as a yellow oil.

Synthesis of compound 130.3. Compound 130.3 was prepared from 130.2 in a manner analogous to the synthesis of 57.3. Isolated a yellow oil in 59% yield.

Synthesis of Compound I-280. Compound I-280 was prepared from 95.4 and 130.3 according to the procedure for Example 97. Purification: The enantiomers of 130.5 were separated by chiral preparative HPLC under the following conditions: Gilson Gx 281; column: Chiralpak IA, 2*25 cm, 5 μm; mobile phase: hexanes and IPA (hold at 20.0% IPA for 4 min); detector: UV 254/220 nm. MS (ES): m/z 565 (M+H)$^+$, 587 (M+Na)$^+$. $^1$H NMR (300 MHz, CD$_3$OD): δ 1.41-1.45 (m, 2H), 1.61-1.72 (m, 8H), 2.70 (s, 3H), 3.20-3.33 (m, 3H), 3.43-3.59 (m, 1H), 3.60-3.62 (m, 2H), 4.08-4.19 (m, 2H), 5.19-5.24 (m,1H), 7.17-7.17 (s, 1H), 7.42-7.45 (m, 1H), 7.63-7.68 (m, 3H), 7.87 (s, 1H).

Example 131

Synthesis of 2-[1-[(2R)-2-(2-carbamoylphenyl)-2-(oxan-4-yloxy)ethyl]-5-methyl-6-(1,3-oxazol-2-yl)-2,4-dioxo-1H,2H,3H,4H-thieno[2,3-d]pyrimidin-3-yl]-2-methylpropanoic acid (I-281)

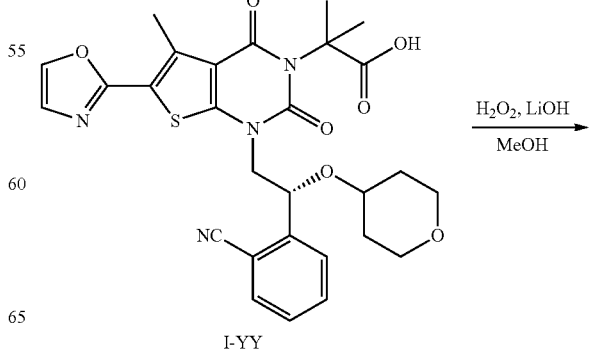

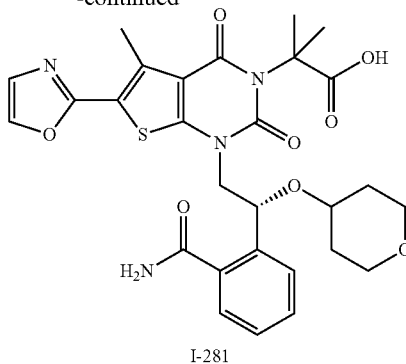

I-281

Into a 50-mL round-bottom flask was placed I-280 (30 mg, 0.05 mmol, 1.00 equiv), LiOH.H₂O (7 mg, 0.17 mmol, 5.50 equiv), H₂O₂ (8 mg, 30%) and methanol (10 mL). The resulting solution was stirred overnight at 35° C. The resulting mixture was concentrated under vacuum. The residue was purified by thin layer chromatography developed with dichloromethane/methanol (30:1). 2.8 mg (9%) of Compound I-281 were obtained as a white solid. MS (ES): m/z 583 (M+H)⁺. ¹H NMR (300 MHz, CD₃OD): δ 1.24-1.25 (m, 2H), 1.57-1.67 (m, 8H), 2.76 (s, 3H), 3.22-3.34 (m, 3H), 3.44-3.48 (m, 2H), 4.09-4.25 (m, 2H), 5.36-5.37 (m, 1H), 7.38-7.42 (m, 3H), 7.54 (s, 2H), 7.65-7.66 (m, 1H), 7.92 (s, 1H), 8.24 (s, 1H).

Example 132

Synthesis of 2-methyl-2-[5-methyl-1-[(2R)-2-(2-methylphenyl)-2-(oxan-4-yloxy)ethyl]-6-(1,3-oxazol-2-yl)-2,4-dioxo-1H,2H,3H,4H-thieno[2,3-d]pyrimidin-3-yl]propanoic acid (I-282)

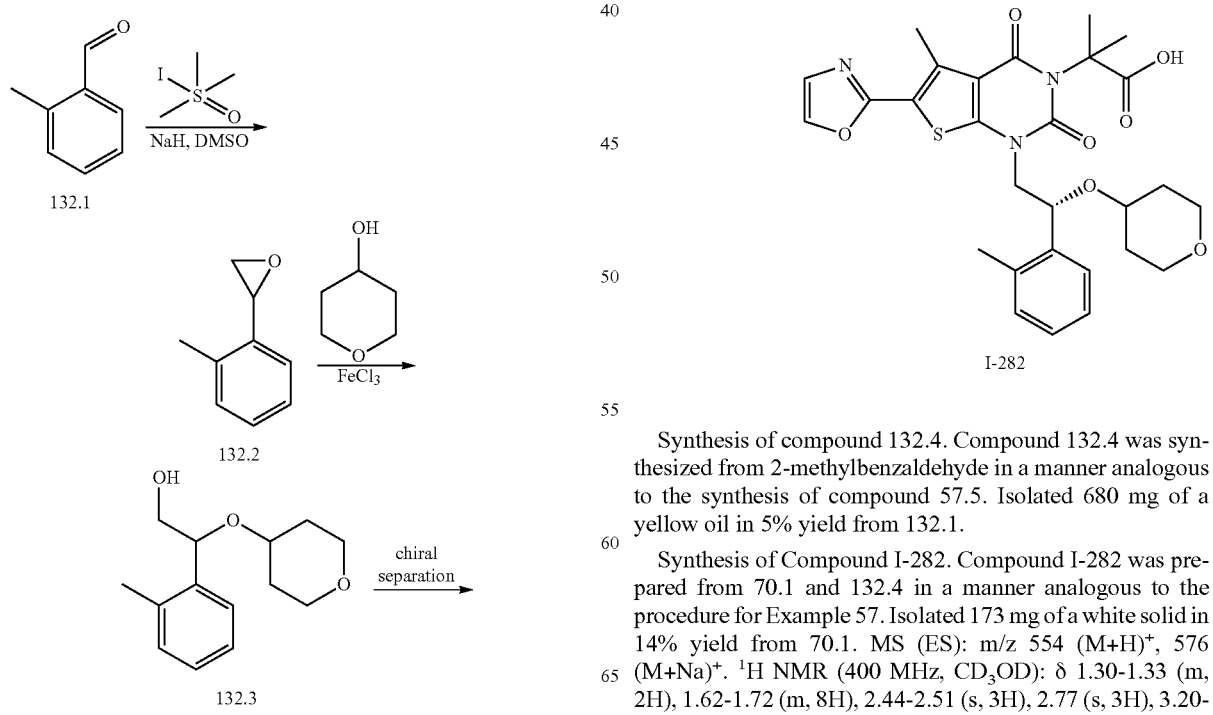

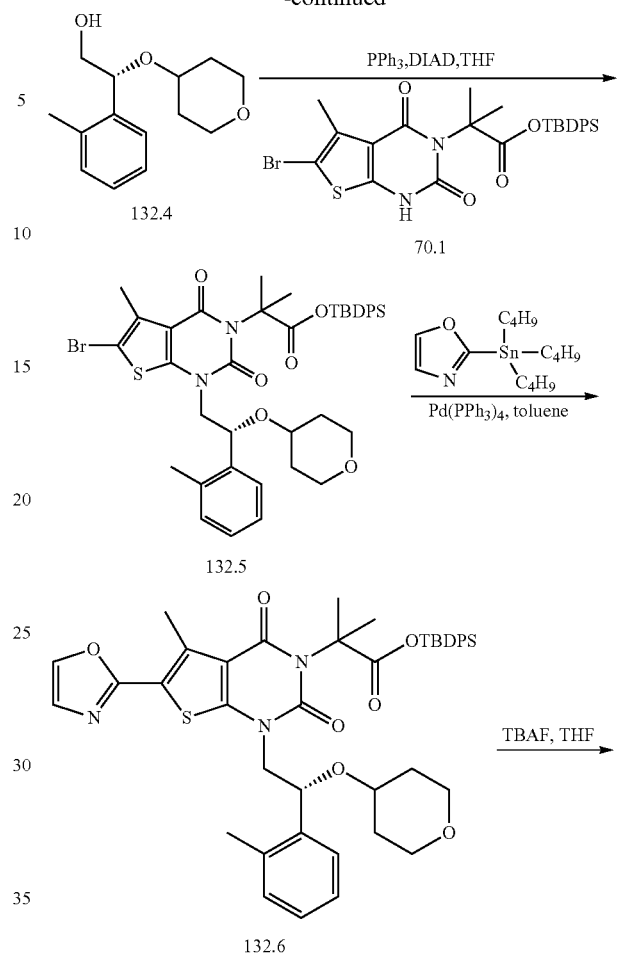

Synthesis of compound 132.4. Compound 132.4 was synthesized from 2-methylbenzaldehyde in a manner analogous to the synthesis of compound 57.5. Isolated 680 mg of a yellow oil in 5% yield from 132.1.

Synthesis of Compound I-282. Compound I-282 was prepared from 70.1 and 132.4 in a manner analogous to the procedure for Example 57. Isolated 173 mg of a white solid in 14% yield from 70.1. MS (ES): m/z 554 (M+H)⁺, 576 (M+Na)⁺. ¹H NMR (400 MHz, CD₃OD): δ 1.30-1.33 (m, 2H), 1.62-1.72 (m, 8H), 2.44-2.51 (s, 3H), 2.77 (s, 3H), 3.20-3.24 (m, 2H), 3.33-3.39 (m, 2H), 3.41-3.64 (m, 2H), 4.21-

4.24 (m, 1H), 5.10-5.13 (m, 1H), 7.21-7.32 (m, 3H), 7.41 (s, 1H), 7.54-7.56 (m, 1H), 8.25 (s, 1H), 12.49 (s, 1H).

Example 133

Synthesis of 2-[1-[(2R)-2-(2-hydroxyphenyl)-2-(oxan-4-yloxy)ethyl]-5-methyl-6-(1,3-oxazol-2-yl)-2,4-dioxo-1H,2H,3H,4H-thieno[2,3-d]pyrimidin-3-yl]-2-methylpropanamide (I-283)

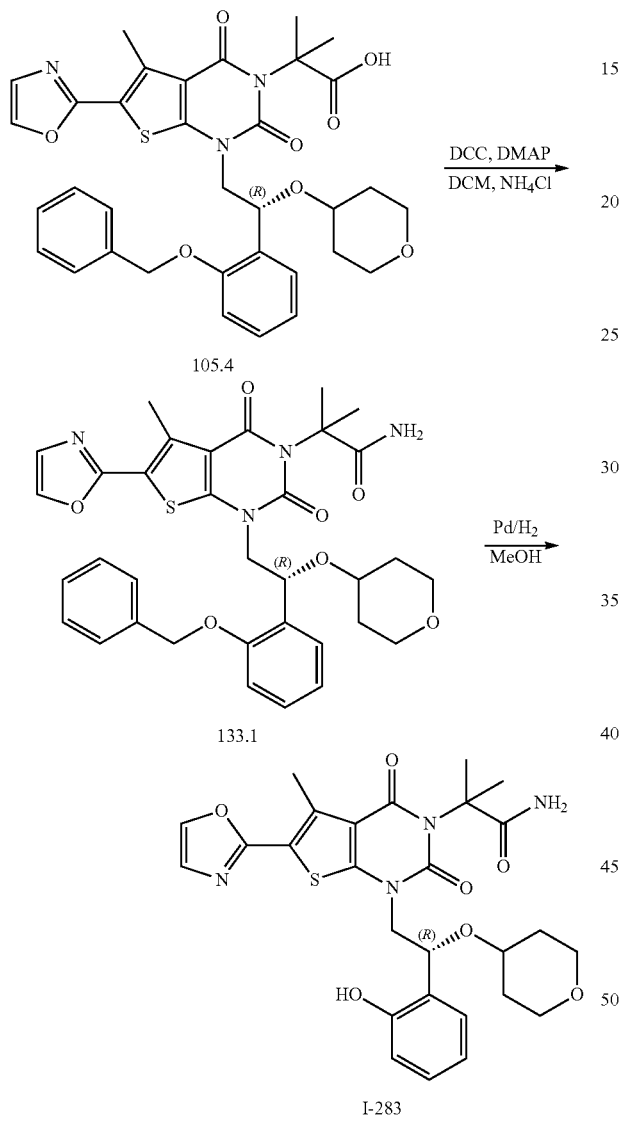

Synthesis of compound 133.1. Compound 133.1 was prepared from 105.4 according to the procedure for Example 4. Isolated a white solid in 70% yield.

Synthesis of Compound I-283. Into a 100-mL round-bottom flask was placed 133.1 (290 mg, 0.45 mmol, 1.00 equiv) and methanol (30 mL). This was followed by the addition of palladium on carbon (50 mg). The flask was evacuated and flushed three times with nitrogen, followed by flushing with hydrogen. The mixture was stirred overnight at room temperature under an atmosphere of hydrogen. The solids were filtered out. The filtrate was concentrated under vacuum. The residue was purified by thin layer chromatography developed with dichloromethane/MeOH/HOAc (30:1:0.15). 91.6 mg (37%) of Compound I-283 were obtained as a white solid. MS (ES): m/z 577 (M+Na)$^+$. $^1$H NMR (300 MHz, DMSO-d$_6$): δ 1.23 (m, 2H), 1.65-1.68 (m, 8H), 2.75 (s, 3H), 3.21 (m, 2H), 3.50 (m, 2H), 3.90 (m, 1H), 4.13 (m, 1H), 5.29 (t,1H), 6.79-6.89 (m, 3H), 7.10 (m, 2H), 7.38 (m, 2H), 8.23 (s, 1H), 9.72 (s, 1H).

Example 134

Synthesis of 3-[1-(azetidin-1-yl)-2-methyl-1-oxopropan-2-yl]-1-[(2R)-2-(2-hydroxyphenyl)-2-(oxan-4-yloxy)ethyl]-5-methyl-6-(1,3-oxazol-2-yl)-1H,2H,3H,4H-thieno[2,3-d]pyrimidine-2,4-dione (I-284)

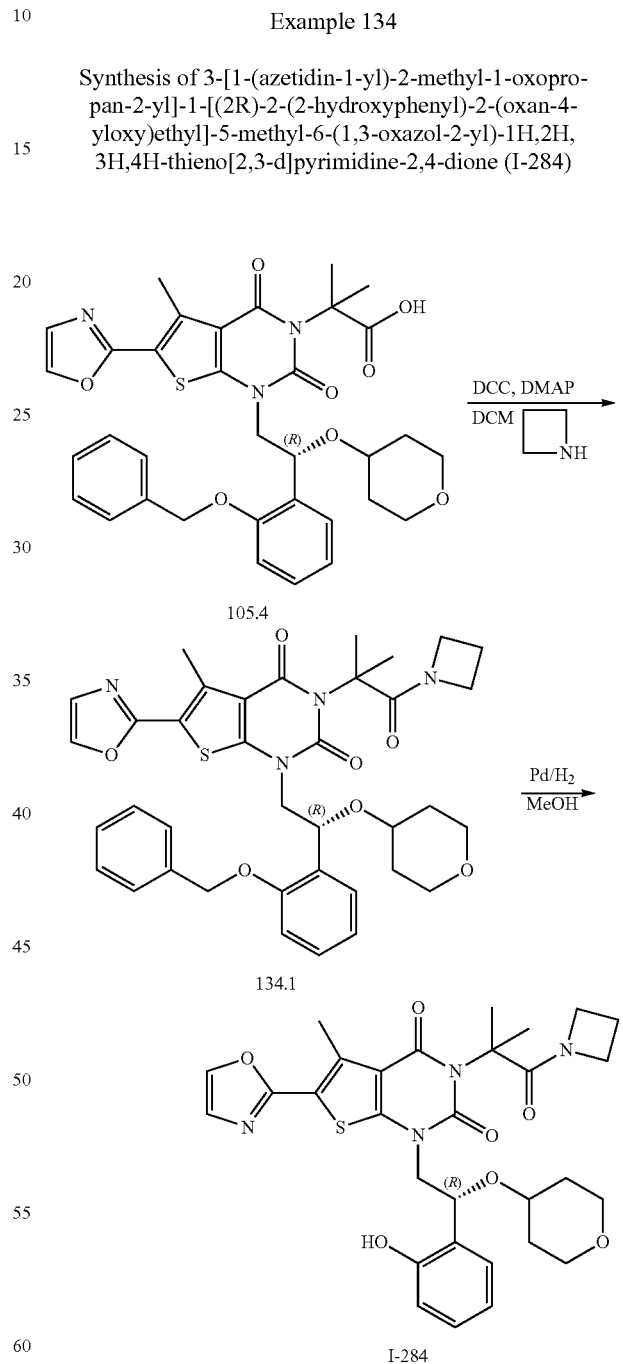

Compound I-284 was prepared according to the procedure for Example 133, substituting azetidine for ammonium chloride in the first step. MS (ES): m/z 595 (M+H)$^+$, 617 (M+Na)$^+$. $^1$H NMR (300 MHz, DMSO-d$_6$): δ 1.18-1.32 (m, 2H), 1.63-1.70 (m, 8H), 2.08-2.16 (m, 2H), 2.77 (s, 3H), 3.20

(m, 2H), 3.50 (m, 1H), 3.50-3.60 (m, 2H), 3.76-4.13 (br m, 6H), 5.29 (t, 1H), 6.79-6.89 (m, 2H), 7.10 (m, 1H), 7.37 (m, 2H), 8.23 (s, 1H), 9.74 (s, 1H).

Example 135

Synthesis of Intermediate 135.3

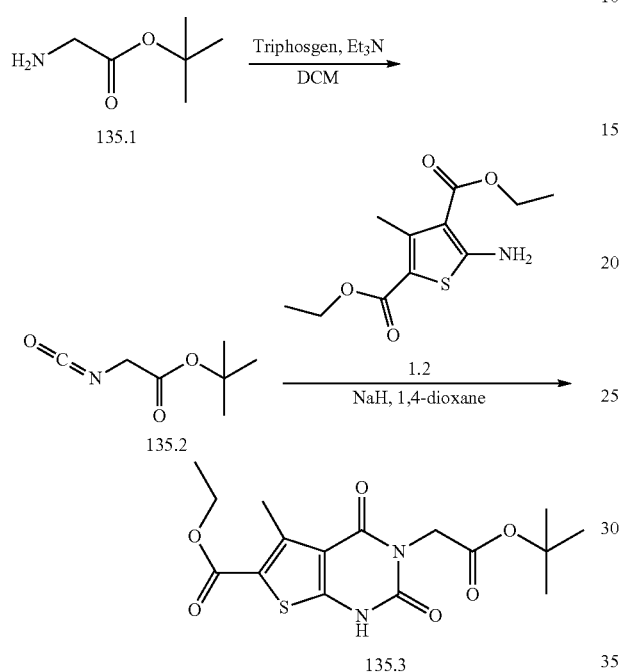

Synthesis of compound 135.2. Into a 500-mL 3-necked round-bottom flask was placed tert-butyl 2-aminoacetate (135.1, 5.9 g, 44.98 mmol, 1.00 equiv). Then dichloromethane (180 mL) and ditrichloromethyl carbonate (4.43 g, 14.93 mmol, 0.33 equiv) were added at 0° C. After 30 min triethylamine (13.65 g, 134.89 mmol, 3.00 equiv) was added to the above mixture. The resulting solution was stirred for 4 h at 5-10° C. in a water/ice bath. The solids were filtered out. The filtrate was concentrated under vacuum. The resulting solution was diluted with 50 mL of ethyl ether. The solids were filtered out. The resulting mixture was concentrated under vacuum. Purification afforded 7.1 g (crude) of tert-butyl 2-isocyanatoacetate (135.2) as a yellow oil.

Synthesis of Intermediate 135.3. Into a 250-mL 3-necked round-bottom flask was placed 1.2 (7.9 g, 30.70 mmol, 1.00 equiv) and 1,4-dioxane (80 mL). Then sodium hydride (1.32 g, 33.00 mmol, 1.07 equiv, 60%) was added at 0° C. The mixture was stirred for 15 min at room temperature. Then a solution of tert-butyl 2-isocyanatoacetate (7.1 g, 45.17 mmol, 1.47 equiv) in 1,4-dioxane (20 mL) was added dropwise with stirring at 0° C. in 15 min. The resulting solution was stirred for 30 min at 10-15° C. in a water/ice bath. The resulting solution was allowed to react, with stirring, overnight while the temperature was maintained at 100° C. in an oil bath. The reaction mixture was cooled to 20° C. with a water bath. The reaction was then quenched by the addition of 80 mL of $NH_4Cl$ (aq.). The resulting solution was extracted with 3×200 mL of ethyl acetate, the organic layers combined and dried over anhydrous magnesium sulfate and concentrated under vacuum. The residue was applied onto a silica gel column with ethyl acetate/petroleum ether (1:7). Purification afforded 5.1 g (45%) of intermediate 135.3 as a white solid.

Example 136

Synthesis of ethyl 5-methyl-2,4-dioxo-1-(2-phenylethyl)-3-(1H-1,2,3,4-tetrazol-5-ylmethyl)-1H,2H,3H,4H-thieno[2,3-d]pyrimidine-6-carboxylate (I-45)

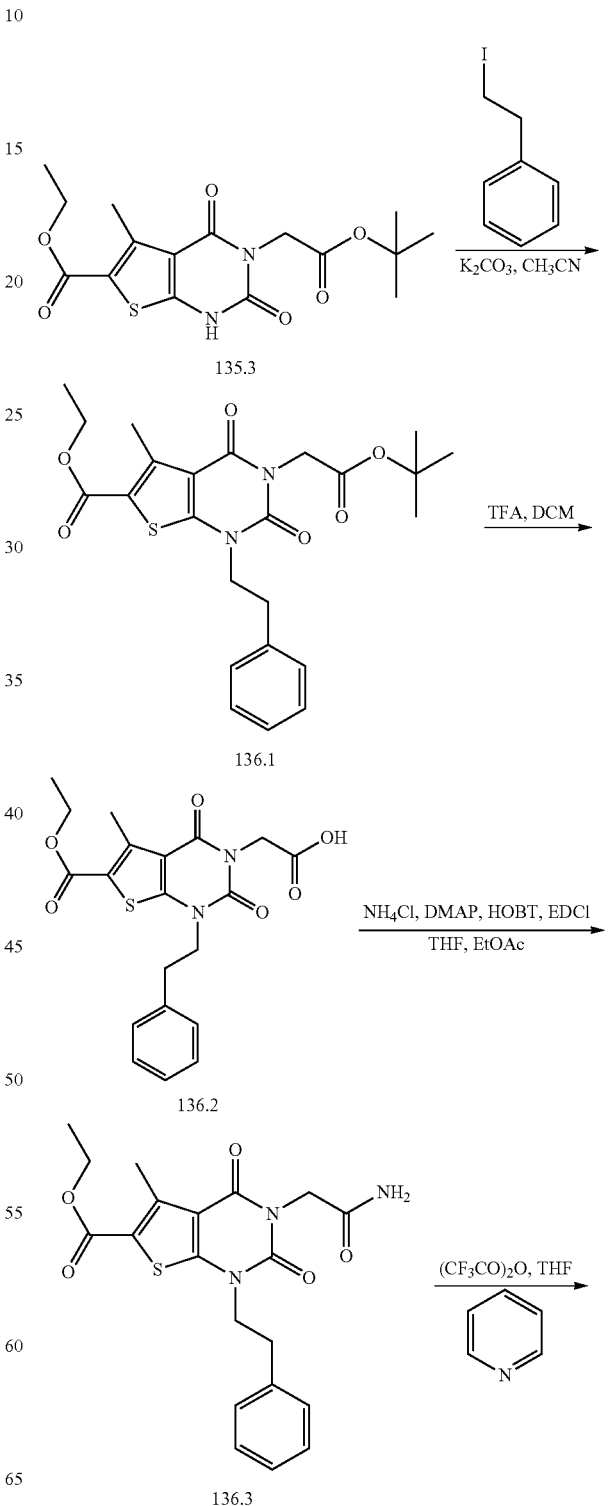

-continued

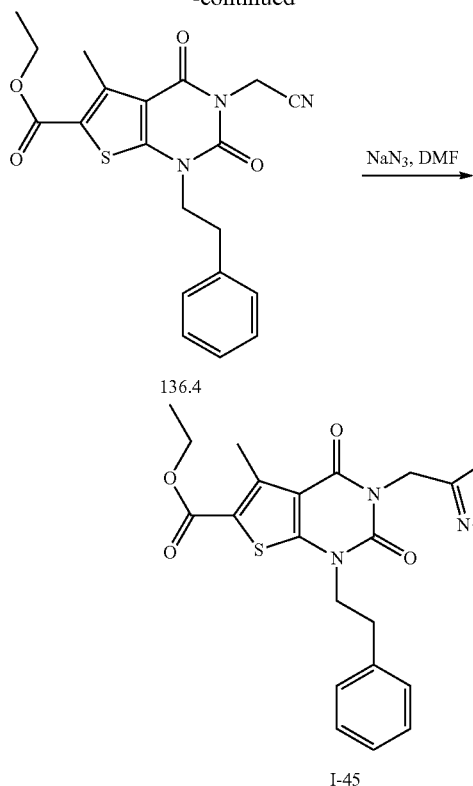

Synthesis of compound 136.1. Compound 136.1 was prepared from 135.3 and (2-iodoethyl)benzene in a manner analogous to the synthesis of compound 9.1. Isolated 1.7 g (66%) of 136.1 as a white solid.

Synthesis of compound 136.2 (I-13). Into a 50-mL round-bottom flask was placed a solution of 136.1 (2.4 g, 5.08 mmol, 1.00 equiv) in dichloromethane (20 mL). Then CF$_3$COOH (3 mL) was added dropwise. The resulting solution was stirred for 30 min at room temperature. The resulting mixture was concentrated under vacuum. The residue was applied onto a silica gel column with dichloromethane/methanol (10:1). Purification afforded 1.7 g (80%) of 136.2 (I-13) as a white solid. MS (ES): m/z: (M+H)+ calcd for $C_{20}H_{21}N_2O_6S$ 417. found 417; $^1$H-NMR (300 MHz, DMSO-d6) δ13.08 (1H, br s), 7.22-7.34 (5H, m), 4.57 (2H, s), 4.27-4.34 (2H, q), 4.13-4.18 (2H, t), 3.00-3.05 (2H, t), 2.77 (3H, s),1.27-1.34 (3H,t).

Synthesis of compound 136.3. Into a 250-mL 3-necked round-bottom flask was placed HOBt (220 mg, 1.63 mmol, 1.13 equiv), 136.2 (600 mg, 1.44 mmol, 1.00 equiv), NH$_4$Cl (1.5 g, 28.04 mmol, 19.46 equiv), EDCI (310 mg, 1.62 mmol, 1.12 equiv), CH$_3$CN (20 mL), ethyl acetate (20 mL) and 4-dimethylaminopyridine (200 mg, 1.64 mmol, 1.14 equiv). The resulting solution was stirred overnight at room temperature. The reaction was then quenched by the addition of 20 mL of water. The resulting solution was extracted with 3×50 mL of ethyl acetate and the organic layers combined and dried over anhydrous magnesium sulfate and concentrated under vacuum. The residue was applied onto a silica gel column with dichloromethane/methanol (50:1). Purification afforded 0.3 g (50%) of 136.3 as an off-white solid.

Synthesis of compound 136.4. Into a 100-mL 3-necked roundbottom flask was placed 136.3 (300 mg, 0.72 mmol, 1.00 equiv), pyridine (280 mg, 3.54 mmol, 4.90 equiv) and tetrahydrofuran (10 mL). This was followed by the addition of (CF$_3$CO)$_2$O (0.38 g, 1.75 mmol, 2.50 equiv) dropwise with stirring at 0-10° C. The resulting solution was stirred for 3 h at room temperature. The resulting mixture was concentrated under vacuum. The residue was applied onto a silica gel column with ethyl acetate/petroleum ether (1:5). Purification afforded 250 mg (87%) of 136.4 as a white solid.

Synthesis of Compound I-45. Into an 8-mL sealed tube was placed 136.4 (50 mg, 0.13 mmol, 1.00 equiv), NaN$_3$ (13 mg, 0.20 mmol, 1.57 equiv) and N,N-dimethylformamide (3 mL). The resulting solution was stirred overnight at 120° C. in an oil bath. The reaction was then quenched by the addition of 5 mL of water. The resulting solution was extracted with 3×20 mL of ethyl acetate and the organic layers were combined, dried over anhydrous magnesium sulfate and concentrated under vacuum. The residue was applied onto a silica gel column with ethyl acetate/petroleum ether (1:2). Purification afforded 2.5 mg (5%) of Compound I-45 as a white solid. MS (ES): m/z 441 (M+H)+. $^1$H NMR (400 MHz, CD$_3$OD): δ 1.43 (t, J=7.2 Hz, 3H), 2.83 (s, 3H), 3.12 (t, J=8.0 Hz, 2H), 4.19 (t, J=8.0 Hz, 2H), 4.35 (q, J=4.8 Hz, 2H), 5.43 (s, 2H), 7.23-7.33 (m, 5H).

Example 137

Synthesis of Intermediate 137.3

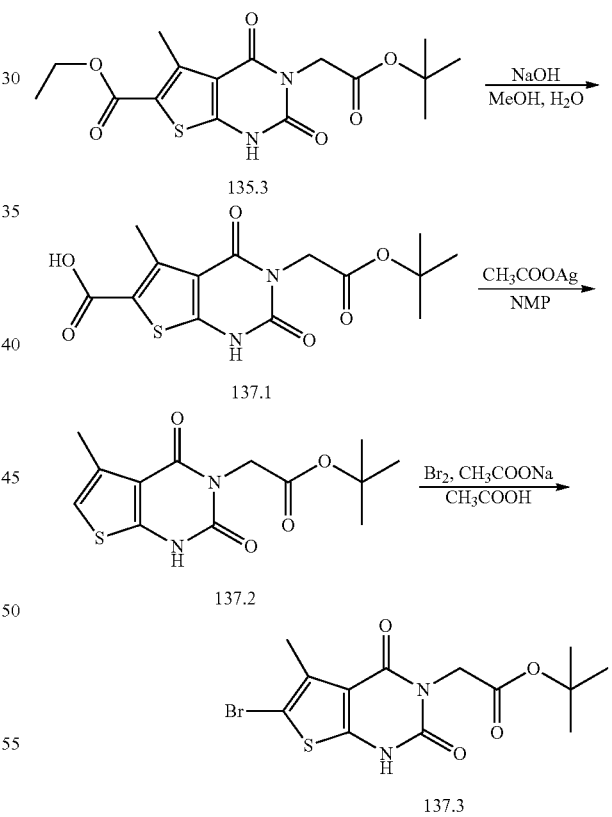

Synthesis of compound 137.1. Into a 250-mL 3-necked round-bottom flask was placed 135.3 (5 g, 13.57 mmol, 1.00 equiv), water (50 mL), sodium hydroxide (1.63 g, 40.75 mmol, 3.00 equiv) and methanol (50 mL). The resulting solution was stirred for 5 h at 50° C. The pH value of the solution was adjusted to 4 with hydrogen chloride (10%). The resulting mixture was concentrated under vacuum. The residue was extracted with 3×50 mL of ethyl acetate and the organic layers combined, washed with 100 mL of brine and dried over anhydrous magnesium sulfate and concentrated under vacuum. 4.6 g (crude) of 137.1 were obtained as a white solid.

Synthesis of compound 137.2. Into a 30-mL round-bottom flask was placed 137.2 (4.6 g, 13.52 mmol, 1.00 equiv), CH₃COOAg (2.48 g, 14.85 mmol, 1.10 equiv) and NMP (30 mL). The resulting solution was stirred for 2 h at 110° C. The reaction was then quenched by the addition of 50 mL of water. The resulting solution was extracted with 3×100 mL of ethyl acetate and the organic layers were combined, washed with 150 mL of water and concentrated under vacuum. The residue was applied onto a silica gel column with ethyl acetate/petroleum ether (1:5). Purification afforded 1.3 g (32%) of 137.2 as a white solid.

Synthesis of Intermediate 137.3. Into a 50-mL round-bottom flask, was placed CH₃COONa (720 mg, 8.78 mmol, 2.00 equiv), 137.2 (1.3 g, 4.39 mmol, 1.00 equiv) and acetic acid (20 mL). This was followed by the addition of Br₂ (780 mg, 4.88 mmol, 1.11 equiv) dropwise with stirring. The resulting solution was stirred for 30 min at room temperature and then concentrated under vacuum. The residue was applied onto a silica gel column with ethyl acetate/petroleum ether (1:5). Purification afforded 1.6 g (97%) of 137.3 as a white solid.

Example 138

Synthesis of 2-(1-((R)-2-isopropoxy-2-phenylethyl)-5-methyl-6-(oxazol-2-yl)-2,4-dioxo-1,2-dihydrothieno[2,3-d]pyrimidin-3(4H)-yl)acetonitrile (I-142)

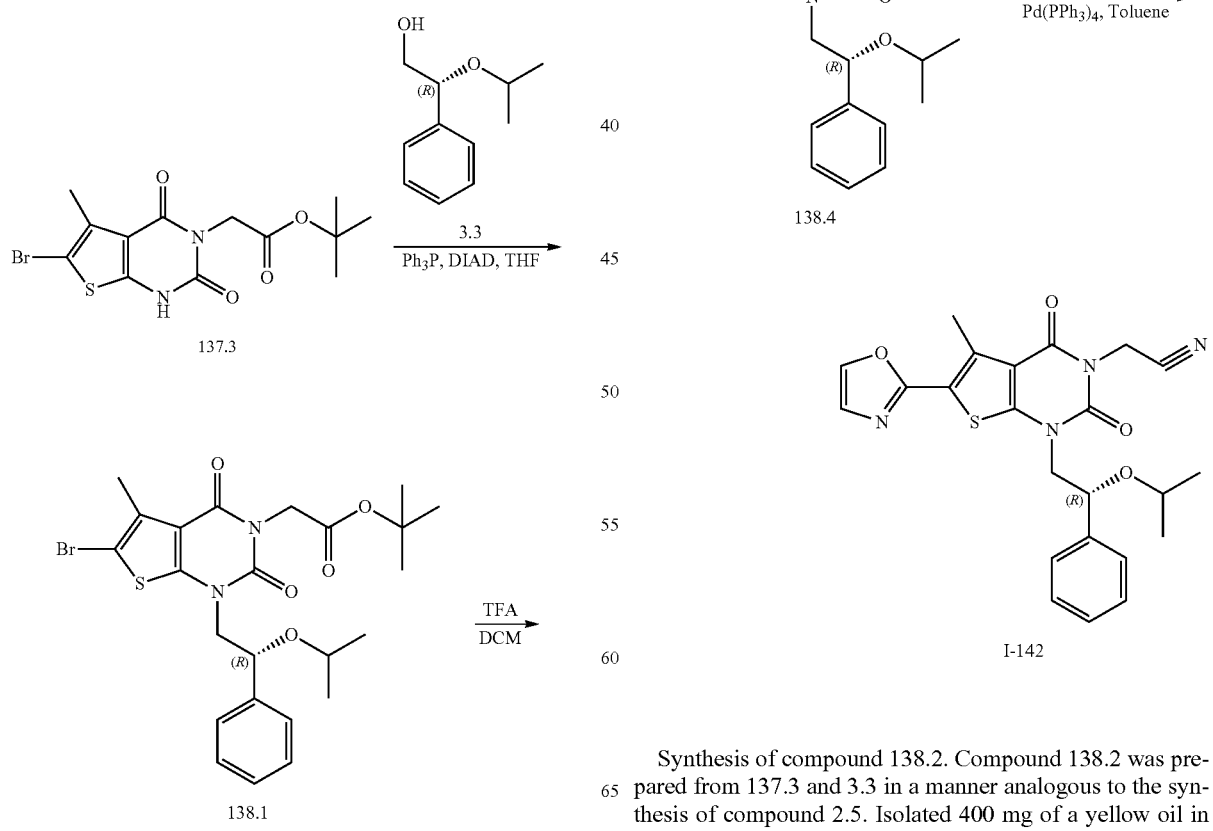

Synthesis of compound 138.2. Compound 138.2 was prepared from 137.3 and 3.3 in a manner analogous to the synthesis of compound 2.5. Isolated 400 mg of a yellow oil in 78% yield from 137.3.

Synthesis of compound 138.3. Into a 50-mL round-bottom flask was placed 138.2 (400 mg, 0.83 mmol, 1.00 equiv), NH₄Cl (90 mg, 1.68 mmol, 2.02 equiv), HOBT (169 mg, 1.25 mmol, 1.51 equiv), 4-dimethylaminopyridine (152 mg, 1.24 mmol, 1.50 equiv), EDCI (240 mg, 1.25 mmol, 1.51 equiv) and N,N-dimethylformamide (10 mL). The resulting solution was stirred for 3 h at room temperature. The reaction was then quenched by the addition of 30 mL of water. The resulting solution was extracted with 3×50 mL of ethyl acetate and the organic layers combined and concentrated under vacuum. The residue was applied onto a silica gel column with dichloromethane/methanol (100:1). Purification afforded 390 mg (98%) of 138.3 as a white solid.

Synthesis of compound 138.4. Into a 50-mL round-bottom flask was placed a solution of 138.3 (390 mg, 0.81 mmol, 1.00 equiv) in tetrahydrofuran (10 mL) and pyridine (321 mg, 4.06 mmol, 5.00 equiv). This was followed by the addition of TFAA (426 mg, 2.03 mmol, 2.50 equiv) dropwise with stirring at 0° C. The resulting solution was stirred for 2 h at room temperature and then concentrated under vacuum. The residue was applied onto a silica gel column with ethyl acetate/petroleum ether (1:5). Purification afforded 360 mg (96%) of 138.4 as a yellow solid.

Synthesis of Compound I-142. Into a 50-mL round-bottom flask, maintained with an inert atmosphere of nitrogen, was placed 138.4 (360 mg, 0.78 mmol, 1.00 equiv), Pd(PPh₃)₄ (90 mg, 0.08 mmol, 0.10 equiv), 2-(tributylstannyl)-1,3-oxazole (560 mg, 1.56 mmol, 2.00 equiv) and toluene (10 mL). The resulting solution was stirred overnight at 110° C. and then concentrated under vacuum. The residue was applied onto a silica gel column with ethyl acetate/petroleum ether (1:5). Purification afforded 60 mg (17%) of Compound I-142 as a yellow solid. MS (ES): m/z 451 (M+H)⁺, 473 (M+Na)⁺, 492 (M+H+CH₃CN)⁺. ¹H NMR (400 MHz, CD₃CN): δ 0.93-1.00 (m, 6H), 2.85 (s, 3H), 3.47-3.53 (m, 1H), 3.93-3.99 (m, 1H), 4.16-4.20 (m, 1H), 4.91 (s, 2H), 4.92-4.94 (m, 1H), 7.28 (s, 1H), 7.35-7.51 (m, 5H), 7.92 (s, 1H).

Example 139

Synthesis of 5-methyl-6-(1,3-oxazol-2-yl)-1-[(2R)-2-phenyl-2-(propan-2-yloxy)ethyl]-3-(1H-1,2,3,4-tetrazol-5-ylmethyl)-1H,2H,3H,4H-thieno[2,3-d]pyrimidine-2,4-dione (I-153)

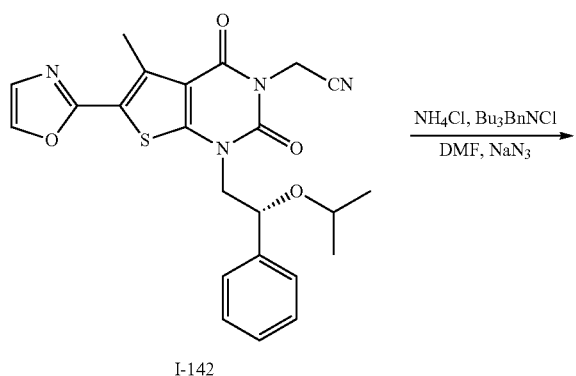

I-142

NH₄Cl, Bu₃BnNCl
―――――――――→
DMF, NaN₃

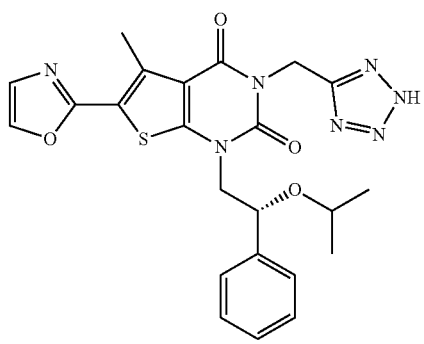

I-153

Into a 50-mL round-bottom flask was placed I-142 (Example 138) (60 mg, 0.13 mmol, 1.00 equiv), NH₄Cl (29 mg, 0.54 mmol, 4.07 equiv), N,N-dimethylformamide (5 mL), Bu₃BnNCl (42 mg) and NaN₃ (35 mg, 0.54 mmol, 4.04 equiv). The resulting solution was stirred overnight at 135° C. The solids were filtered out. The crude product (50 mg) was purified by flash preparative HPLC under the following conditions (IntelFlash-1): Column: C18 silica gel; mobile phase: acetonitrile:water=0:100 increasing to acetonitrile:water=100:0 within 29 min; detector: UV 220 nm. 16 mg (24%) of Compound I-153 were obtained as an off-white solid. MS (ES): m/z 494 (M+H)⁺, 535 (M+H+CH₃CN)⁺. ¹H NMR (400 MHz, CD₃CN): δ 0.90-0.91 (d, J=6.0, 3H), 0.97-0.99 (d, J=6.4, 3H), 2.85 (s, 3H), 3.45-3.51 (m, 1H), 3.92-3.98 (m, 1H), 4.14-4.19 (m, 1H), 4.89-4.92 (d, 1H), 5.47 (s, 2H), 7.28 (s, 1H), 7.33-7.49 (m, 5H), 7.91 (s, 1H).

Example 140

Synthesis of Intermediate 140.1

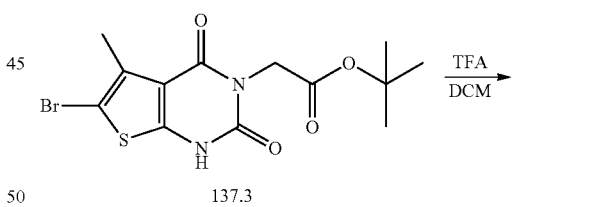

137.3

TFA
――→
DCM

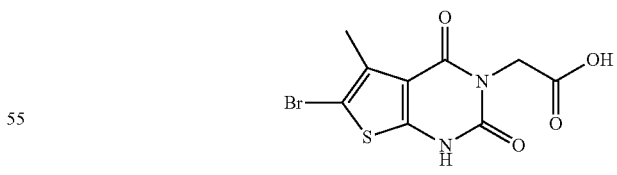

140.1

Synthesis of compound 140.1. Into a 250-mL round-bottom flask was placed 137.3 (2.3 g, 6.13 mmol, 1.00 equiv), dichloromethane (100 mL), trifluoroacetic acid (20 mL). The resulting solution was stirred for 6 h at room temperature and then concentrated under vacuum. The crude product was re-crystallized from ethyl acetate/hexane in the ratio of 1:10 to afford 1.9 g (97%) of 140.1 as a white solid.

Example 141

Synthesis of 2-[6-bromo-1-[(2R)-2-(2-methoxyphenyl)-2-(oxan-4-yloxy)ethyl]-5-methyl-2,4-dioxo-1H,2H,3H,4H-thieno[2,3-d]pyrimidin-3-yl]acetamide (I-285)

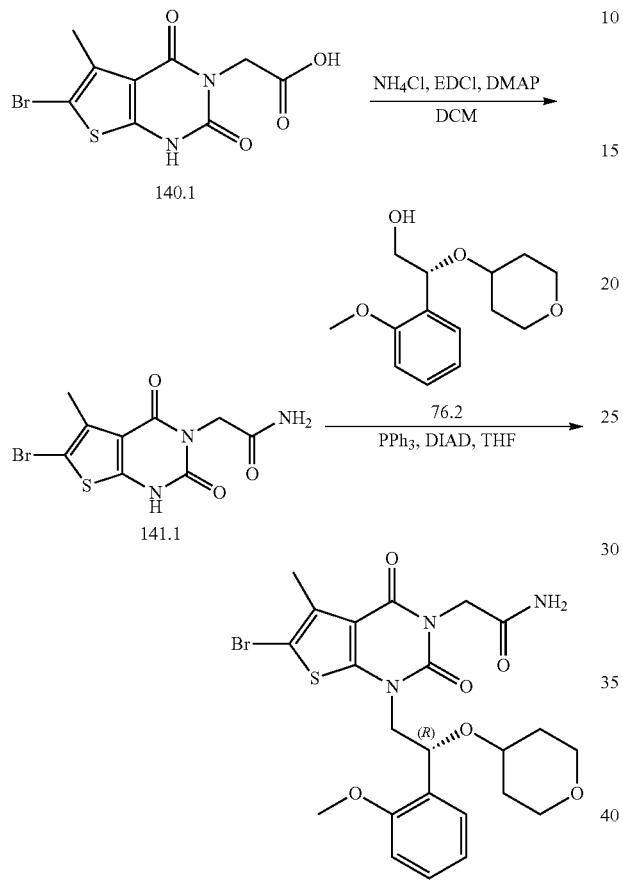

Synthesis of compound 141.1. Into a 100-mL round-bottom flask was placed 140.1 (1 g, 3.13 mmol, 1.00 equiv), NH$_4$Cl (500 mg, 9.35 mmol, 2.98 equiv), 4-dimethylaminopyridine (575 mg, 4.71 mmol, 1.50 equiv), EDCI (900 mg, 4.69 mmol, 1.50 equiv) and dichloromethane (25 mL). The resulting solution was stirred overnight at room temperature. The reaction was then quenched by the addition of 10 mL of water. The resulting solution was extracted with 2×100 mL of ethyl acetate and the organic layers were combined, dried over anhydrous sodium sulfate and concentrated under vacuum. The residue was applied onto a silica gel column with dichloromethane/methanol (20/1/0.1). Purification afforded 320 mg (32%) of 141.1 as a white solid.

Synthesis of Compound I-285. Into a 50-mL round-bottom flask, purged and maintained with an inert atmosphere of nitrogen, was placed 141.1 (300 mg, 0.94 mmol, 1.00 equiv), 76.2 (303 mg, 1.20 mmol, 1.27 equiv), tetrahydrofuran (15 mL), DIAD (379 mg, 1.87 mmol, 1.99 equiv) and PPh$_3$ (490 mg, 1.87 mmol, 1.98 equiv). The resulting solution was stirred for 8 h at room temperature and then concentrated under vacuum. The residue was applied onto a silica gel column with ethyl acetate/petroleum ether (1:1). Purification afforded 106 mg (20%) of Compound I-285 as a white solid. MS (ES): m/z 554, 552 (M+H$^+$). $^1$H NMR (DMSO-d$_6$, 300 MHz): δ 7.69 (1H, s), 7.46-7.44 (1H, d, J=6.9 Hz), 7.32-7.23 (2H, m) 7.04-7.00 (2H, m), 5.18-5.13 (1H, m), 4.61-4.46 (2H, m), 4.42-4.38 (1H, m), 4.27-4.25 (1H, m), 3.81 (3H, s), 3.80-3.78 (1H, m), 3.48-3.41 (1H, m), 3.27-3.22 (1H, m), 2.38 (3H, s), 1.89-1.85 (1H, m), 1.70-1.64 (1H, m), 1.49-1.35 (2H, m).

Example 142

Synthesis of 2-[1-[(2R)-2-(2-methoxyphenyl)-2-(oxan-4-yloxy)ethyl]-5-methyl-6-(1,3-oxazol-2-yl)-2,4-dioxo-1H,2H,3H,4H-thieno[2,3-d]pyrimidin-3-yl]acetic acid (I-286)

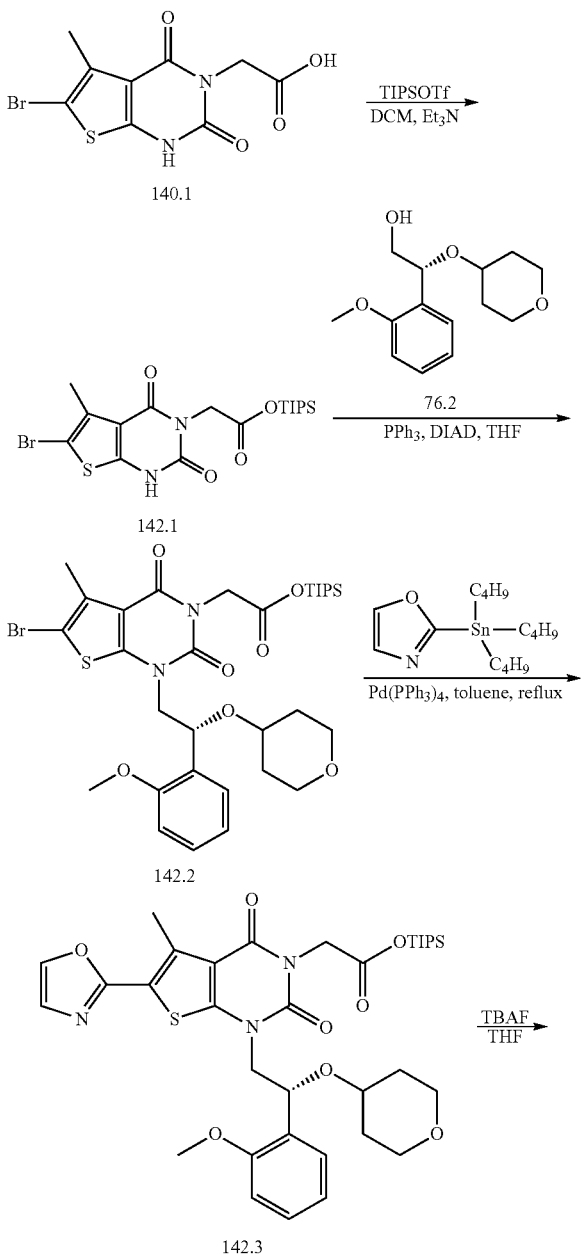

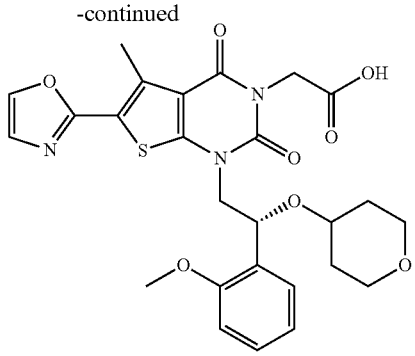

I-286

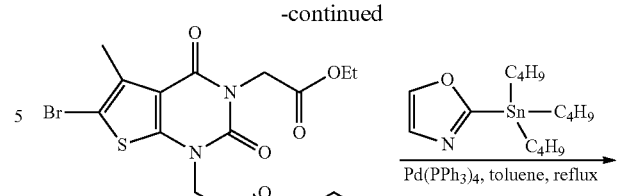

143.2

Synthesis of 142.1. Into a 100-mL 3-necked round-bottom flask was placed 140.1 (450 mg, 1.41 mmol, 1.00 equiv) and dichloromethane (10 mL). This was followed by the addition of TIPSOTf (475 mg, 1.55 mmol, 1.10 equiv) dropwise with stirring over 2 min. To this was added TEA (171 mg, 1.69 mmol, 1.20 equiv) dropwise with stirring over 2 min. The resulting solution was stirred for 2 h at room temperature. The resulting mixture was concentrated under vacuum. The residue was applied onto a silica gel column with ethyl acetate/petroleum ether (1:5). Purification afforded 235 mg (35%) of 142.1 as a white solid.

Synthesis of Compound I-286. Compound I-286 was prepared from 142.1 and 76.2 in a manner analogous to Example 57. Isolated 3.6 mg (1.4% from 142.1) of I-286 as a white solid. MS (ES): m/z 542 (M+H)$^+$. $^1$H NMR (300 MHz, CD$_3$OD): δ 1.18-1.42 (m, 2H), 1.59-1.62 (m, 2H), 2.741 (s, 3H), 3.16-3.63 (m, 4H), 3.75 (s, 3H), 3.92-4.13 (m, 2H), 4.45-4.76 (m, 1H), 5.32-5.35 (m, 1H), 6.85-6.95 (m, 2H), 7.17-7.23 (m, 2H), 7.44-7.47 (m, 1H), 7.85 (s, 1H).

Example 143

Synthesis of 3-(2-hydroxy-2-methylpropyl)-1-[(2R)-2-(2-methoxyphenyl)-2-(oxan-4-yloxy)ethyl]-5-methyl-6-(1,3-oxazol-2-yl)-1H,2H,3H,4H-thieno[2,3-d]pyrimidine-2,4-dione (I-287)

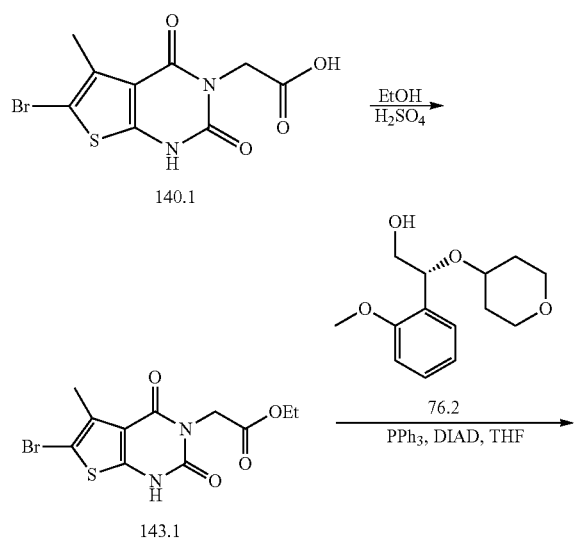

I-287

Synthesis of compound 143.1. Into a 100-mL round-bottom flask was placed 140.1 (420 mg, 1.32 mmol, 1.00 equiv), ethanol (30 mL) and sulfuric acid (conc.) (100 mg). The resulting solution was stirred overnight at 80° C. in an oil bath. The reaction was then quenched by the addition of 5 mL of sodium bicarbonate (sat.). The resulting solution was extracted with 2×150 mL of ethyl acetate and the organic layers were combined, dried over anhydrous sodium sulfate and concentrated under vacuum. The residue was applied onto a silica gel column with ethyl acetate/petroleum ether (1:5). Purification afforded 230 mg (50%) of 143.1 as a white solid.

Synthesis of compound 143.3. Compound 143.3 was prepared from 143.1 in a manner analogous to compound 13.5. Isolated a white solid in 8% yield.

Synthesis of Compound I-287. Into a 10-mL sealed tube purged and maintained with an inert atmosphere of nitrogen was placed a solution of 143.3 (57 mg, 0.10 mmol, 1.00 equiv) in toluene (1 mL). This was followed by the addition of bromo(methyl)magnesium (1 M in THF, 3 mL) dropwise with stirring at room temperature. The resulting solution was heated to reflux overnight. The reaction was then quenched by the addition of 1 mL of NH$_4$Cl (sat., aq.). The resulting solution was extracted with 3×2 mL of ethyl acetate and the organic layers combined and concentrated under vacuum. The residue was applied onto a silica gel column with methanol/DCM/HOAc (7:200:1). Purification afforded 2.2 mg (4%) of I-287 as a white solid. MS (ES): m/z 556 (M+H)+. 1H NMR (CD3OD, 300 MHz): δ 7.92 (1H, s), 7.54-7.50 (1H, d), 7.30-7.24 (2H, m), 7.02-6.92 (2H, m), 5.45-5.40 (1H, m), 4.20-4.10 (4H, m), 3.80 (3H, s), 3.70-3.51 (2H, m), 3.43-3.33 (1H, m), 2.83 (3H, s), 1.73-1.67 (2H, m), 1.48-1.33 (2H, m), 1.21-1.20 (6H, d).

Example 144

Synthesis of 2-[5-methyl-1-[(2R)-2-(oxan-4-yloxy)-2-phenylethyl]-6-(1,3-oxazol-2-yl)-2,4-dioxo-1H,2H,3H,4H-thieno[2,3-d]pyrimidin-3-yl]acetamide (I-288)

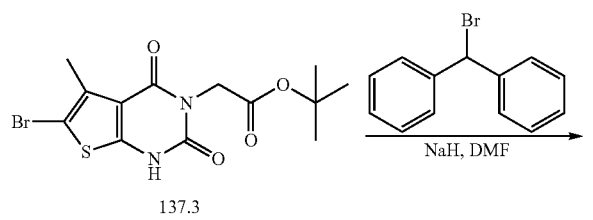

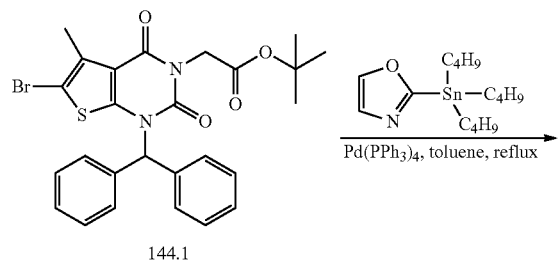

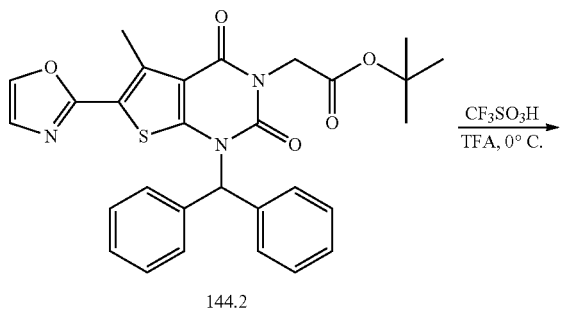

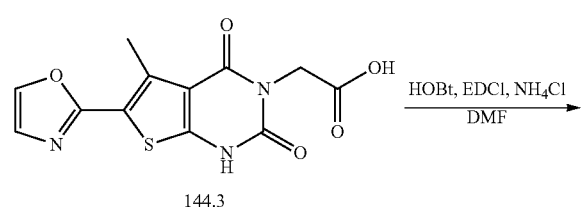

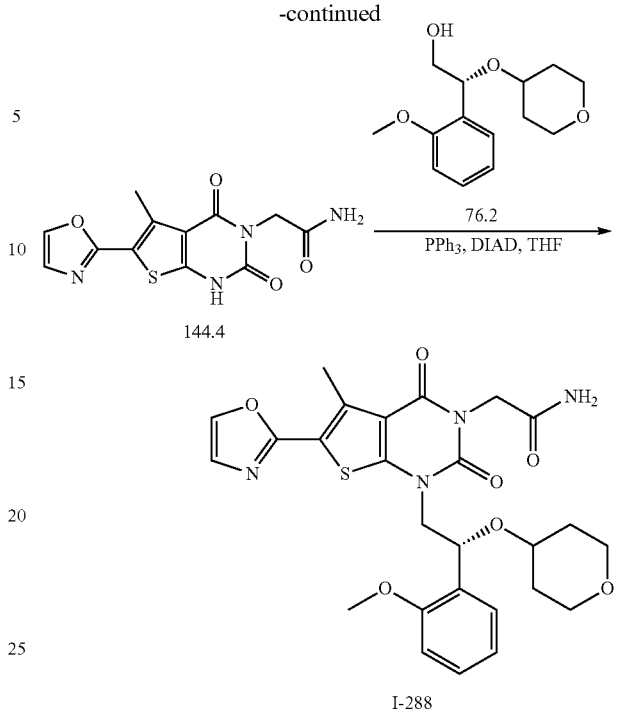

Synthesis of compound 144.1. Into a 100-mL 3-necked round-bottom flask, purged and maintained under an inert atmosphere of nitrogen, was placed 137.3 (2.651 g, 7.06 mmol, 1.00 equiv) and N,N-dimethylformamide (50 mL). This was followed by the addition of sodium hydride (368 mg, 9.20 mmol, 1.30 equiv, 60%) in portions at 0° C. over 10 min. The resulting solution was stirred for 30 min at room temperature. To this was added [bromo(phenyl)methyl]benzene (2.3 g, 9.31 mmol, 1.32 equiv) in portions at 0° C. in 10 min. The resulting solution was stirred overnight at room temperature. The reaction was then quenched by the addition of 50 mL of NH4Cl (aq.). The resulting solution was extracted with 3×100 mL of ethyl acetate and the organic layers were combined and concentrated under vacuum. The residue was applied onto a silica gel column with ethyl acetate/petroleum ether (1:5). Purification afforded 2.26 g (59%) of 144.1 as a white solid.

Synthesis of compound 144.2. To a 100-mL 3-necked round-bottom flask, purged and maintained under an inert atmosphere of nitrogen, was added 144.1 (2.26 g, 4.17 mmol, 1.00 equiv), toluene (50 mL), 2-(tributylstannyl)-1,3-oxazole (3 g, 8.38 mmol, 2.01 equiv) and Pd(PPh3)4 (728 mg, 0.63 mmol, 0.15 equiv). The resulting solution was stirred overnight at 110° C. and then concentrated under vacuum. The residue was applied onto a silica gel column with ethyl acetate/petroleum ether (1:2). Purification afforded 1.9 g (crude) of 144.2 as a yellow solid.

Synthesis of compound 144.3. Into a 50-mL round-bottom flask was placed 144.2 (950 mg, 1.79 mmol, 1.00 equiv) and CF3COOH (10 mL). This was followed by the addition of CF3SO3H (540 mg) dropwise with stirring at 0° C. over 2 min. The resulting solution was stirred for 20 min at room temperature. The reaction was then quenched by the addition of 50 mL of water. The solids were washed with EA (100 mL) and then collected by filtration to afford 490 mg (89%) of 144.3 as a white solid.

Synthesis of compound 144.4. Into a 50-mL 3-necked round-bottom flask, purged and maintained with an inert atmosphere of nitrogen, was placed 144.3 (490 mg, 1.59 mmol, 1.00 equiv), HOBt (432 mg, 3.20 mmol, 2.00 equiv), N,N-dimethylformamide (10 mL), 4-dimethylaminopyridine (390 mg, 3.19 mmol, 2.00 equiv) and EDCI (614 mg, 3.20 mmol, 2.01 equiv). The resulting solution was stirred for 2 hours at room temperature. Then NH₄Cl (346 mg, 6.47 mmol, 4.06 equiv) was added. The resulting solution was stirred overnight at room temperature. The reaction was then quenched by the addition of 50 mL of water. The solids were collected by filtration and washed with EA. Purification afforded 90 mg (18%) of 144.4 as a white solid.

Synthesis of Compound I-288. Into a 50-mL 3-necked round-bottom flask, purged and maintained with an inert atmosphere of nitrogen, was placed 144.4 (90 mg, 0.29 mmol, 1.00 equiv), 76.2 (89 mg, 0.35 mmol, 1.20 equiv), DIAD (119 mg, 0.59 mmol, 2.00 equiv), tetrahydrofuran (5 mL) and PPh₃ (154 mg, 0.59 mmol, 2.00 equiv). The resulting solution was stirred overnight at room temperature. The resulting mixture was concentrated under vacuum. The residue was applied onto a silica gel column with dichloromethane/methanol (20:1). Purification afforded 11.1 mg (7%) of Compound I-288 as a pink solid. MS (ES): m/z 541 (M+H)⁺. ¹H NMR (300 MHz, CDCl₃): δ 7.70 (d, J=8.7 Hz, 1H), 7.58 (d, J=7.5 Hz, 1H), 7.36-7.26 (m, 1H), 7.23 (s, 1H), 7.06-7.01 (m, 1H), 6.88 (d, J=8.1 Hz, 1H), 5.81-5.47 (m, 2H), 5.41 (d, J=8.7 Hz, 1H), 4.80-4.69 (m, 2H), 4.27 (d, J=14.7 Hz, 1H), 4.01-3.93 (m, 2H), 3.88 (s, 2H), 3.75-3.63 (m, 2H), 3.42-3.28 (m, 3H), 2.90 (s, 3H), 1.68-1.37 (m, 4 H).

Example 145

1-[(2R)-2-(2-methoxyphenyl)-2-(oxan-4-yloxy) ethyl]-5-methyl-6-(1,3-oxazol-2-yl)-3-(4H-1,2,4-triazol-3-ylmethyl)-1H,2H,3H,4H-thieno[2,3-d]pyrimidine-2,4-dione (I-289)

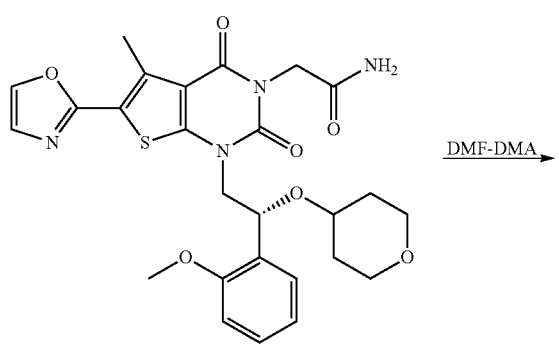

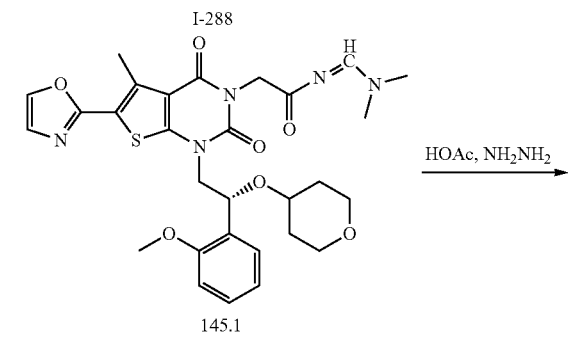

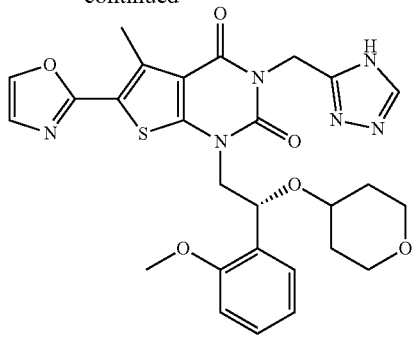

I-289

Synthesis of compound 145.1. Into a 25-mL round-bottom flask, purged and maintained with an inert atmosphere of nitrogen, was placed Compound I-288 (Example 144) (20 mg, 0.03 mmol, 1.00 equiv, 90%) and (dimethoxymethyl) dimethylamine (0.5 mL). The resulting solution was stirred for 2 h at 120° C. The resulting mixture was concentrated under vacuum to afford 20 mg (crude) of 145.1 as a yellow liquid.

Synthesis of Compound I-289. Into a 25-mL round-bottom flask, purged and maintained with an inert atmosphere of nitrogen, was placed 145.1 (20 mg, 0.03 mmol, 1.00 equiv), AcOH (1 mL) and NH₂NH₂ (4 mg, 0.06 mmol, 1.91 equiv, 98%). The resulting solution was stirred for 2 h at 90° C. The resulting mixture was concentrated under vacuum. The crude product (500 mg) was purified by preparative HPLC under the following conditions (Waters): Column: SunFire Prep C18, 19*150 mm 5 μm; mobile phase: water (0.05% NH₄HCO₃) and CH₃CN (10.0% CH₃CN up to 42.0% over 11 min, up to 100.0% over 2 min, down to 10.0% over 1 min); detector: UV 220, 254 nm. Purification afforded 4.5 mg (24%) of Compound I-289 as a white solid. MS (ES): m/z 565 (M+H)⁺. ¹H NMR (300 MHz, CDCl₃): δ 8.14 (s, 1H), 7.72 (s, 1H), 7.56 (d, J=7.2 Hz, 1H), 7.33-7.22 (m, 2H), 7.03 (t, J=6.0 Hz, 1H), 6.87 (d, J=8.1 Hz, 1H), 5.43 (s, 3 H), 4.29-4.09 (m, 2H), 3.85 (s, 3H), 3.75-3.62 (m, 2H), 3.40-3.21 (m, 3H), 2.91 (s, 3H), 1.77-1.25 (m, 4H).

Example 146

Synthesis of 3-(1-hydroxy-2-methylpropan-2-yl)-1-[(2R)-2-(2-methoxyphenyl)-2-(oxan-4-yloxy)ethyl]-5-methyl-6-(1,3-oxazol-2-yl)-1H,2H,3H,4H-thieno[2,3-d]pyrimidine-2,4-dione (I-290)

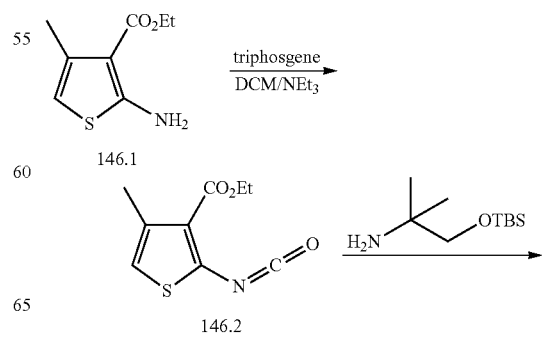

-continued

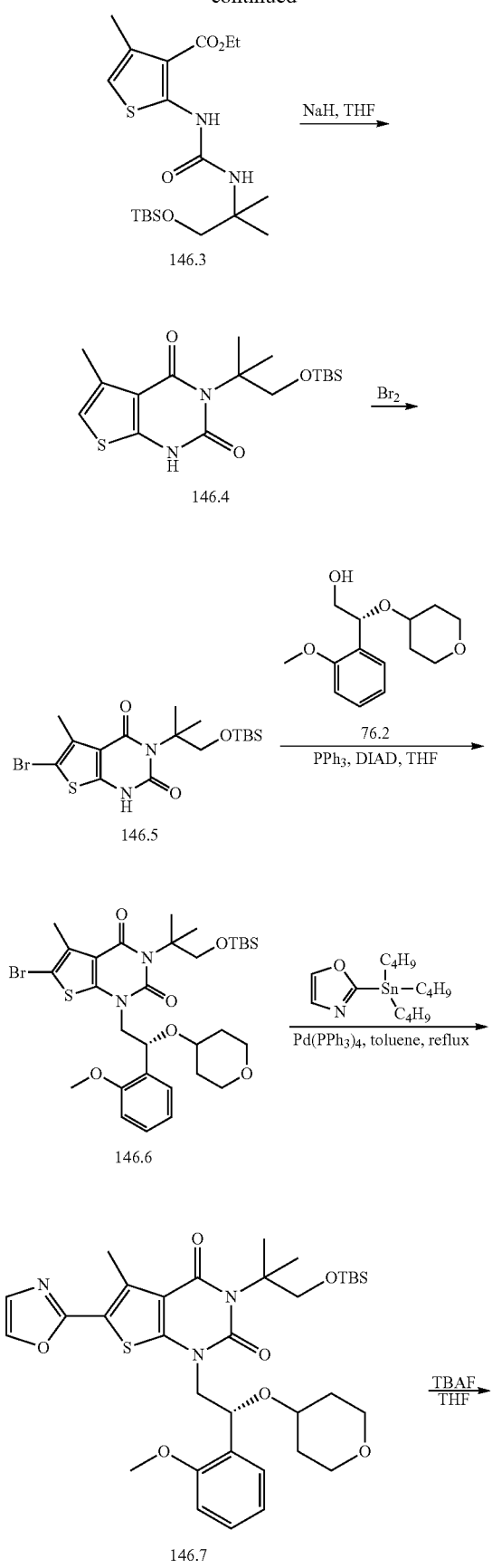

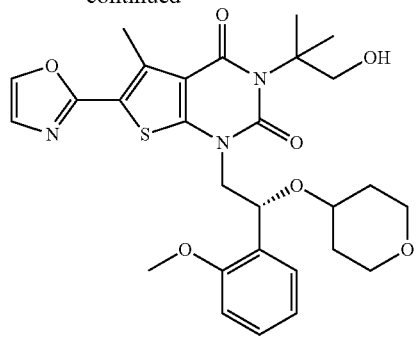

I-290

Synthesis of compound 146.2. Into a 250-mL 3-necked round-bottom flask, purged and maintained under an inert atmosphere of nitrogen, was placed ethyl 2-amino-4-methylthiophene-3-carboxylate (146.1, 7.4 g, 39.95 mmol, 1.00 equiv) and dichloromethane (150 mL). This was followed by the addition of ditrichloromethyl carbonate (4 g, 13.48 mmol, 0.34 equiv), in portions, at 0° C. The mixture was stirred for 0.5 h at 0° C. To this was added Et$_3$N (16.2 g) dropwise with stirring at 0° C. The resulting solution was stirred for 5 h at room temperature. The mixture was used in the next step directly.

Synthesis of compound 146.3. Into a 250-mL 3-necked round-bottom flask, purged and maintained with an inert atmosphere of nitrogen, was placed the crude solution of 146.2 (150 mL, from the previous step). This was followed by the addition of (2-amino-2-methylpropoxy)(tert-butyl)dimethylsilane (9.2 g, 45.23 mmol, 1.00 equiv), in portions at 10° C. over 20 min. The resulting solution was stirred overnight at room temperature. The reaction was then quenched by the addition of 200 mL of water. The resulting solution was extracted with 2×300 mL of ethyl acetate and the organic layers combined, dried over sodium sulfate and concentrated under vacuum. The residue was applied onto a silica gel column with ethyl acetate/petroleum ether (1:20). Purification afforded 11 g (61%) of 146.3 as a yellow solid.

Synthesis of compound 146.4. Into a 250-mL 3-necked round-bottom flask, purged and maintained with an inert atmosphere of nitrogen, was placed a solution of 146.3 (2.07 g, 4.99 mmol, 1.00 equiv) in tetrahydrofuran (100 mL). This was followed by the addition of sodium hydride (600 mg, 15.00 mmol, 3.00 equiv) in portions at 0-10° C. The resulting solution was stirred for 1 h at 0-10° C. and warmed to 60° C. overnight. The reaction was then quenched by the addition of 100 mL of NH$_4$Cl (sat., aq.). The resulting solution was extracted with 3×100 mL of ethyl acetate and the organic layers combined and concentrated under vacuum. The residue was applied onto a silica gel column with ethyl acetate/petroleum ether (1:20). Purification afforded 510 mg (28%) of 146.4 as a white solid.

Synthesis of compound 146.5. Into a 50-mL round-bottom flask was placed 146.4 (510 mg, 1.38 mmol, 1.00 equiv), acetic acid (10 mL) and NaOAc (227 mg). The resulting solution was stirred for 30 min at room temperature. This was followed by the addition of Br$_2$ (222 mg, 1.39 mmol, 1.00 equiv) dropwise with stirring at room temperature. The resulting solution was stirred for 30 min at room temperature. The reaction was then quenched by the addition of 10 mL of Na$_2$SO$_3$ (aq.). The resulting solution was diluted with 50 mL of H$_2$O. The resulting solution was extracted with 2×50 mL of ethyl acetate, the organic layers were combined and concentrated under vacuum. The residue was purified by preparative TLC (ethyl acetate/petroleum ether=1:5). Purification afforded 334 mg (54%) of 146.5 as a white solid.

Synthesis of Compound I-290. Compound I-290 was prepared from 146.5 and 76.2 in a manner analogous to Example 57. Isolated 57.8 mg of a white solid in 14% yield from 146.5. MS (ES): m/z 556 (M+H)+. $^1$H NMR (300 MHz, DMSO-d$_6$): δ 1.23-1.35 (m, 2H), 1.57-1.65 (m, 8H), 2.74 (s, 3H), 3.20-3.27 (m, 2H), 3.39-3.59 (m, 2H), 3.79-3.96 (m, 7H), 4.72-4.76 (m, 1H), 5.25-5.29 (m, 1H), 7.00-7.05 (m, 2H), 7.27-7.37 (m, 2H), 7.46-7.49 (d, 1H), 8.20 (s, 1H).

Example 147

Synthesis of 2-methyl-2-[5-methyl-1-[(2R)-2-(oxan-4-yloxy)-2-[2-(propan-2-yloxy)phenyl]ethyl]-6-(1,3-oxazol-2-yl)-2,4-dioxo-1H,2H,3H,4H-thieno[2,3-d]pyrimidin-3-yl]propanoic acid (I-291)

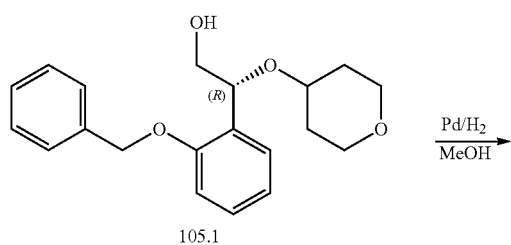

105.1

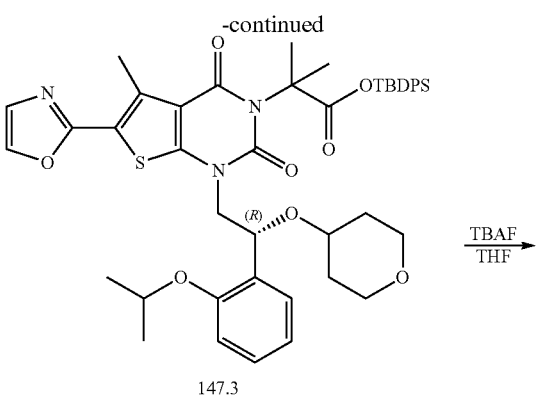

147.3

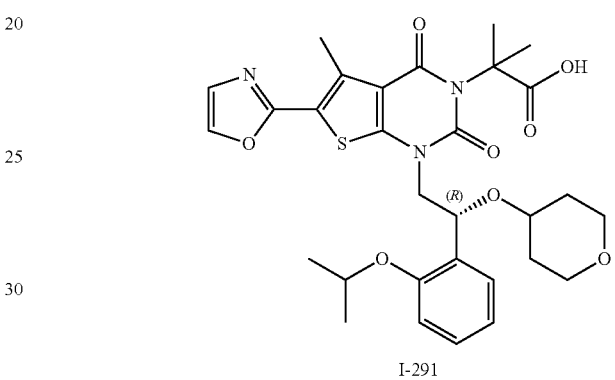

I-291

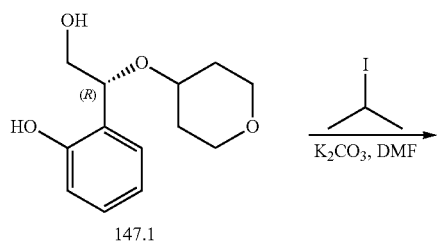

147.1

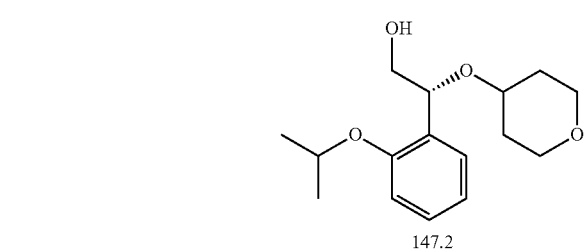

147.2

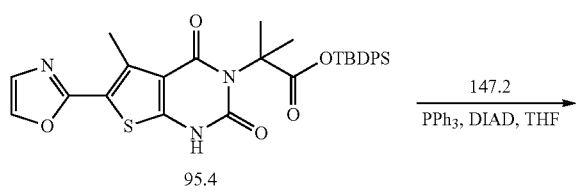

95.4

Synthesis of compound 147.1. Into a 100-mL round-bottom flask was placed 105.1 (500 mg, 1.52 mmol, 1.00 equiv) and methanol (10 mL). This was followed by the addition of palladium on carbon (50 mg). Hydrogen was added to the system. The resulting solution was stirred overnight at room temperature. The solids were filtered out. The resulting mixture was concentrated under vacuum to afford 320 mg (88%) of 147.1 as an oil.

Synthesis of compound 147.2. Into a 25-mL round-bottom flask was placed 147.1 (280 mg, 1.18 mmol, 1.00 equiv), potassium carbonate (487 mg, 3.52 mmol, 3.00 equiv), N,N-dimethylformamide (5 mL) and 2-iodopropane (400 mg, 2.35 mmol, 2.00 equiv). The resulting solution was stirred overnight at room temperature. The reaction was then quenched by the addition of 10 mL of water. The resulting solution was extracted with 10 mL of ethyl acetate and the organic layers combined and concentrated under vacuum. The residue was applied onto a silica gel column with ethyl acetate/petroleum ether (1:50). This resulted in 260 mg (79%) of 147.2 as a colorless oil.

Synthesis of Compound I-291. Compound I-291 was synthesized from 147.2 and intermediate 95.4 in a manner analogous to Example 96. Isolated a white solid in 15% yield from 95.1. MS (ES): m/z 598 (M+H)+, 620 (M+Na)+. $^1$H NMR (300 MHz, DMSO-d$_6$): δ 1.19-1.32 (m, 8H), 1.60-1.67 (m, 8H), 2.76 (s, 3H), 3.18-3.35 (m, 2H), 3.45-3.58 (m, 2H), 3.85-4.20 (m,2H), 4.67 (m, 1H), 5.27 (t, 1H), 7.03 (m, 2H), 7.33-7.50 (m, 3H), 8.23 (s, 1H).

Example 148

Synthesis of 2-methyl-2-[5-methyl-1-[(2R)-2-(oxan-4-yloxy)-2-[2-(propan-2-yloxy)phenyl]ethyl]-6-(1,3-oxazol-2-yl)-2,4-dioxo-1H,2H,3H,4H-thieno[2,3-d]pyrimidin-3-yl]propanamide (I-292)

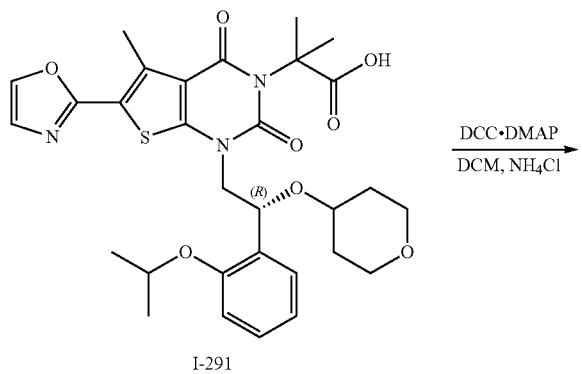

Synthesis of Compound I-292. Compound I-292 was synthesized from I-291 in a manner analogous to Example 4. Isolated 284.1 mg of a white solid in 81% yield. MS (ES): m/z 619 (M+Na)+. $^1$H NMR (300 MHz, DMSO-d$_6$): δ 1.18-1.32 (m, 8H), 1.60-1.66 (m, 8H), 2.75 (s, 3H), 3.18-3.33 (m, 2H), 3.47-3.58 (m, 2H), 3.85-4.20 (m, 2H), 4.66 (m, 1H), 5.27 (t, 1H), 6.80 (br s, 1H), 7.01 (m, 3H), 7.30 (m,1H), 7.39 (s,1H), 7.45 (d,1H), 8.22 (s, 1H).

Example 149

Synthesis of 2-[1-[(2R)-2-[2-(methoxymethyl)phenyl]-2-(oxan-4-yloxy)ethyl]-5-methyl-6-(1,3-oxazol-2-yl)-2,4-dioxo-1H,2H,3H,4H-thieno[2,3-d]pyrimidin-3-yl]-2-methylpropanoic acid (I-293)

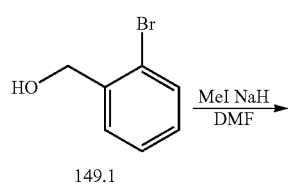

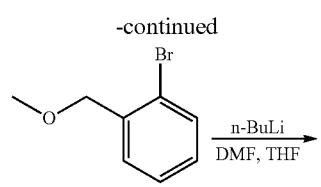

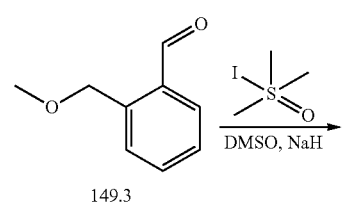

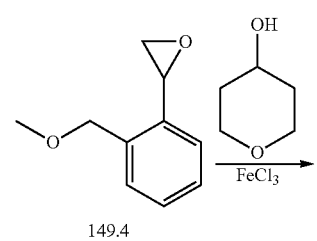

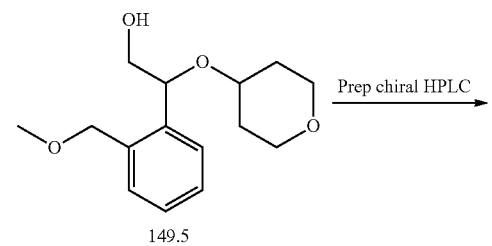

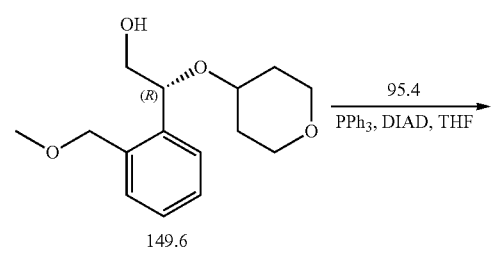

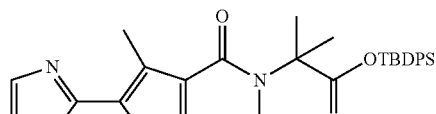

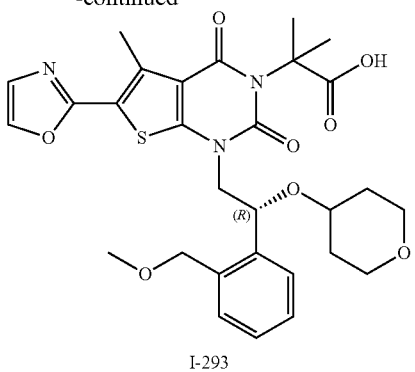

I-293

Synthesis of compound 149.2. Into a 250-mL 3-necked round-bottom flask was placed (2-bromophenyl)methanol (20 g, 106.93 mmol, 1.00 equiv), N,N-dimethylformamide (50 mL) and sodium hydride (5.136 g, 128.40 mmol, 1.20 equiv). The resulting solution was stirred for 0.5 h at room temperature. This was followed by the addition of MeI (45.582 g, 323.28 mmol, 3.02 equiv) dropwise with stirring at 0° C. The resulting solution was allowed to react, with stirring, overnight at room temperature. The reaction was then quenched by the addition of 100 mL of NH₄Cl (aq.). The resulting solution was extracted with 2×200 mL of ethyl acetate and the organic layers combined and concentrated under vacuum. The residue was applied onto a silica gel column with ethyl acetate/petroleum ether (1:200). Purification afforded 6 g (28%) of 149.2 as a brown oil.

Synthesis of compound 149.3. Into a 500-mL 3-necked round-bottom flask, purged and maintained with an inert atmosphere of nitrogen, was placed a solution of 149.2 (12 g, 59.68 mmol, 1.00 equiv) in tetrahydrofuran (200 mL). This was followed by the addition of n-butyllithium (26.3 mL, 2.5 M) dropwise with stirring at −78° C. The resulting solution was stirred for 1 h at −78° C. To this was added N,N-dimethylformamide (8.7 g, 119.03 mmol, 1.99 equiv) dropwise with stirring at −78° C. The resulting solution was allowed to react, with stirring, for an additional 1 h from −78° C. to room temperature. The reaction was then quenched by the addition of 100 mL of NH₄Cl (aq.). The resulting solution was extracted with 3×100 mL of ethyl acetate and the organic layers combined and concentrated under vacuum. The residue was applied onto a silica gel column with ethyl acetate/petroleum ether (1:50). This resulted in 7.7 g (86%) of 149.3 as a colorless oil.

Synthesis of compound 149.6. Compound 149.6 was prepared from 149.3 in a manner consistent with the synthesis of compound 57.5. Isolated 390 mg of a colorless oil in 3% overall yield.

Synthesis of Compound I-293. Compound I-293 was prepared from 149.6 and 95.4 in a manner analogous to Example 96. Isolated 68.3 mg (23%) of I-293 as a white solid. MS (ES): m/z 606 (M+Na)⁺. ¹H NMR (300 MHz, DMSO-d₆): δ 1.23 (m, 2H), 1.56-1.70 (m, 8H), 2.77 (s, 3H), 3.18-3.39 (m, 6H), 3.54 (m, 2H), 3.81(m, 1H), 4.22 (d, 1H), 4.44 (d, 1H), 4.70 (d, 1H), 5.22 (dd, 1H), 7.33-7.47 (m, 4H), 7.64 (m, 1H), 8.24 (s, 1H).

Example 150

Synthesis of 2-(1-((R)-2-(((1r,4R)-4-hydroxycyclohexyl)oxy)-2-(2-isopropoxyphenyl)ethyl)-5-methyl-6-(oxazol-2-yl)-2,4-dioxo-1,2-dihydrothieno[2,3-d]pyrimidin-3(4H)-yl)-2-methylpropanoic acid (I-294) and Example 151: Synthesis of 2-(1-((R)-2-(((1s,4S)-4-hydroxycyclohexyl)oxy)-2-(2-isopropoxyphenyl)ethyl)-5-methyl-6-(oxazol-2-yl)-2,4-dioxo-1,2-dihydrothieno[2,3-d]pyrimidin-3(4H)-yl)-2-methylpropanoic acid (I-295)

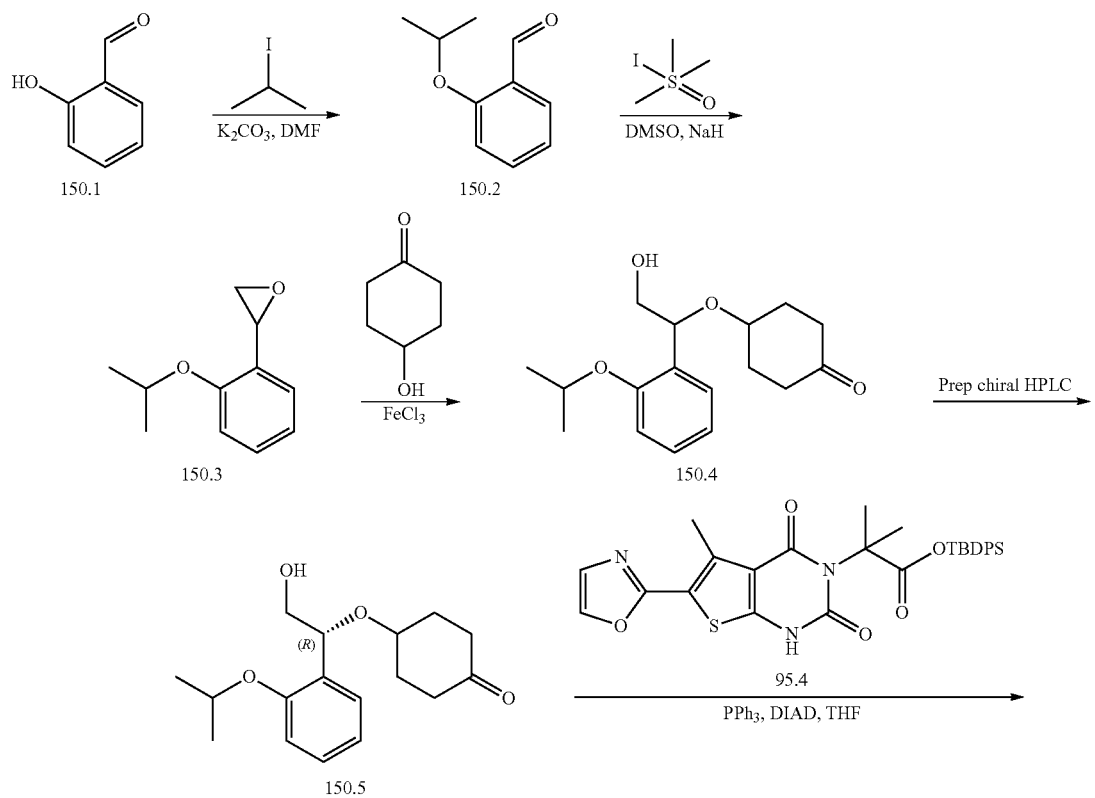

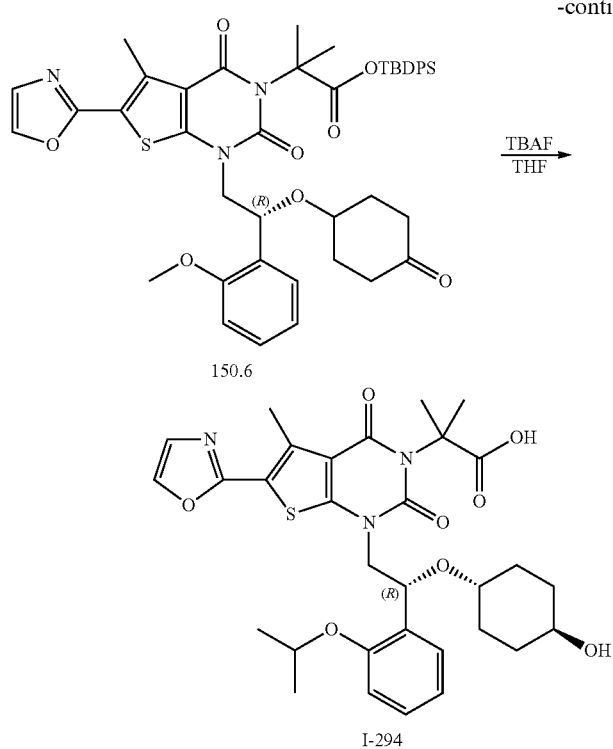

150.6

I-294

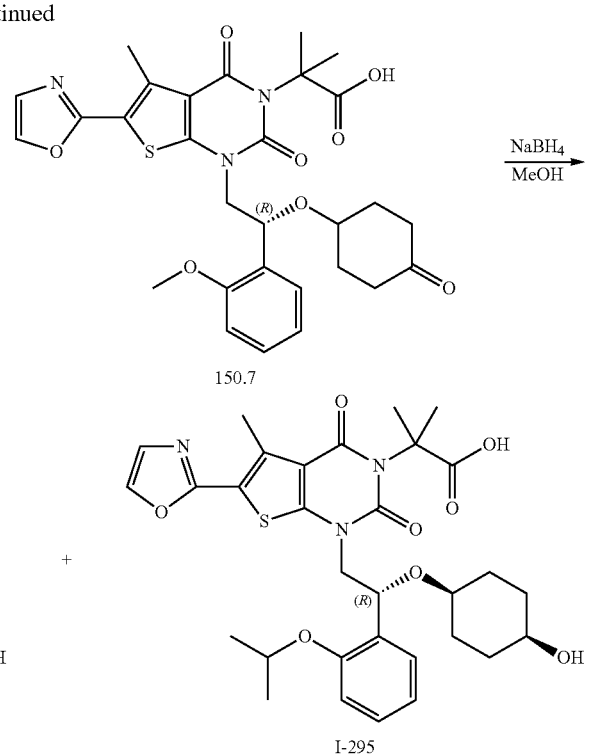

150.7

I-295

Synthesis of compound 150.2. Into a 1000-mL 3-necked round-bottom flask was placed 2-hydroxybenzaldehyde (36 g, 294.79 mmol, 1.00 equiv), 2-iodopropane (100 g, 588.26 mmol, 2.00 equiv), potassium carbonate (122 g, 882.71 mmol, 2.99 equiv) and N,N-dimethylformamide (500 g, 6.84 mol, 23.21 equiv). The resulting solution was stirred overnight at room temperature. The reaction was then quenched by the addition of 1000 mL of water. The resulting solution was extracted with 3×500 mL of ethyl acetate and the organic layers combined, dried over anhydrous sodium sulfate and concentrated under vacuum to afford 50 g (crude) of 2-(propan-2-yloxy)benzaldehyde as a yellow oil.

Synthesis of compound 150.5. Compound 150.5 was prepared from 150.2 in a manner analogous to compound 57.5. Isolated 4.7 g of a colorless oil in 3% overall yield.

Synthesis of compound 150.7. Compound 150.7 was prepared from 150.5 and 95.4 in a manner analogous to Example 96. Isolated 1.2 g of a white solid in 25% overall yield.

Synthesis of Compounds I-294 and I-295. Into a 50-mL 3-necked round-bottom flask was 150.7 (1.1 g, 1.89 mmol, 1.00 equiv), methanol (20 mL) and NaBH$_4$ (143 mg, 3.78 mmol, 2.00 equiv). The resulting solution was stirred overnight at room temperature and then concentrated under vacuum. The residue was purified by thin layer chromatography developed with dichloromethane/MeOH/HOAc (30:1: 0.15) to afford 122.4 mg (9%) of Compound I-294 and 256.3 mg (22%) of Compound I-295.

Analytical Data for Compound I-294: MS (ES): m/z 612 (M+H)$^+$, 634 (M+Na)$^+$. $^1$H NMR (300 MHz, DMSO-d$_6$): δ 0.96-1.32 (m, 10H), 1.50-1.65 (m, 10H), 2.74 (s, 3H), 3.17 (m, 1H), 3.89-4.03 (m,2H), 4.35 (m, 1H), 4.70 (m, 1H), 5.22 (t, 1H), 6.99 (m, 2H), 7.29 (m,1H), 7.38 (s, 1H), 7.45 (m,1H), 8.21 (s, 1H).

Analytical Data for Compound I-295: MS (ES): m/z 612 (M+H)$^+$, 634 (M+Na)$^+$. $^1$H NMR (300 MHz, DMSO-d$_6$): δ1.29-1.30 (m, 12H), 1.50-1.68 (m, 8H), 2.75 (s, 3H), 3.14 (m, 1H), 3.91-3.99 (m, 1H), 4.11 (m, 1H), 4.24 (m, 1H), 4.68 (m, 1H), 5.25 (t, 1H), 6.97 (m, 2H), 7.29 (m, 1H), 7.39 (s, 1H), 7.46 (m, 1H), 8.22 (s, 1H), 12.30 (br s, 1H).

Example 152

Synthesis of 2-[1-[(2R)-2-[2-(hydroxymethyl)phenyl]-2-(oxan-4-yloxy)ethyl]-5-methyl-6-(1,3-oxazol-2-yl)-2,4-dioxo-1H,2H,3H,4H-thieno[2,3-d]pyrimidin-3-yl]-2-methylpropanoic acid (I-296)

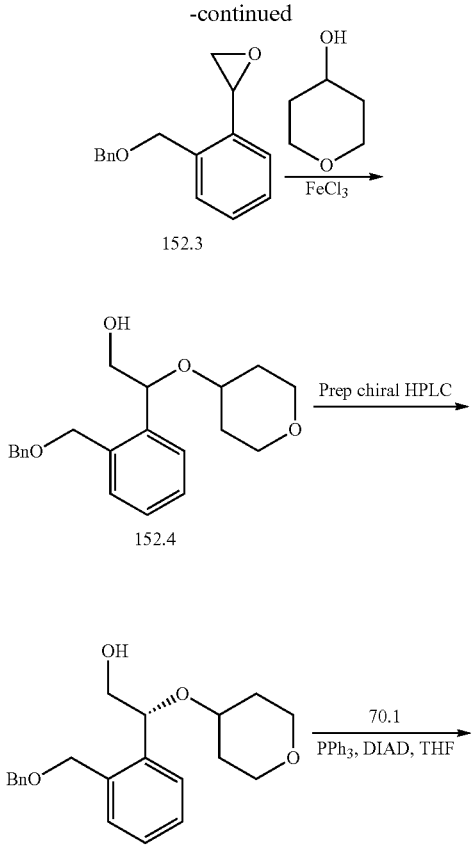

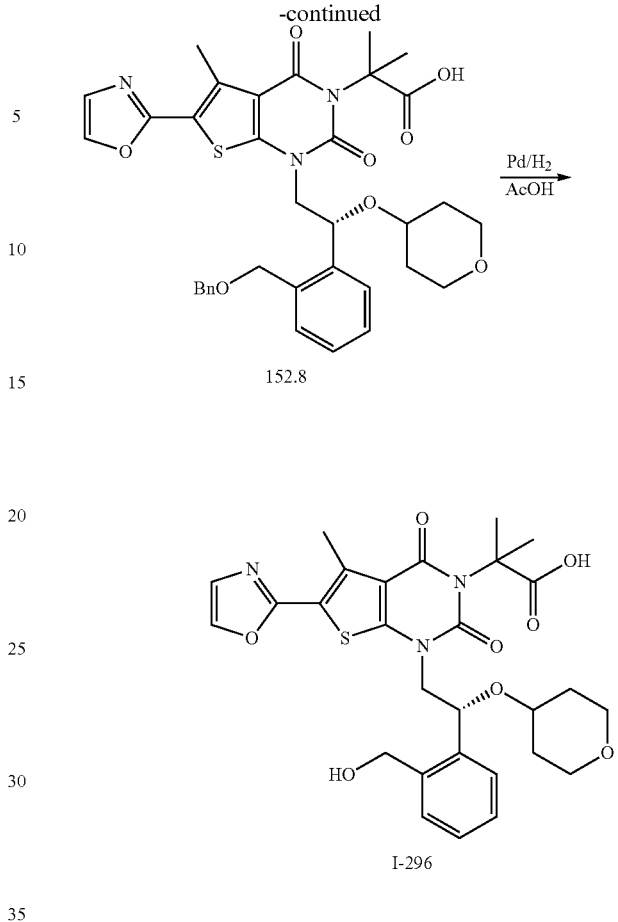

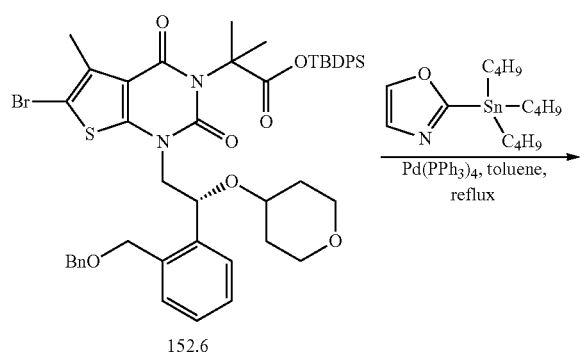

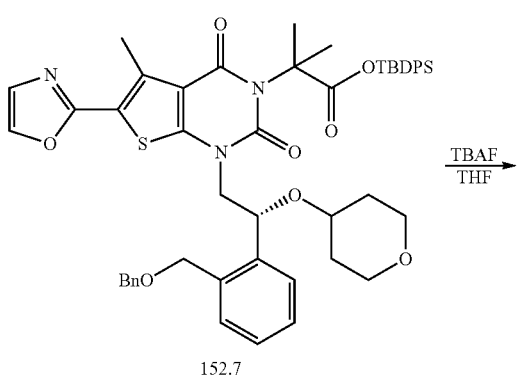

Synthesis of compound 152.5. Compound 152.5 was prepared from 149.1 in a manner analogous to the preparation of compound 149.6, substituting benzyl bromide for methyl iodide in the first step. Isolated 0.814 g of a colorless oil in 2% overall yield.

Synthesis of compound 152.8 (I-299). Compound 152.8 was prepared from 70.1 and 152.5 in a manner analogous to Example 57. Isolated 50 mg of a white solid in 32% overall yield from 70.1.

Synthesis of Compound I-296. Into a 50-mL round-bottom flask was placed 152.8 (100 mg, 0.15 mmol, 1.00 equiv), AcOH (5 mL) and 10% palladium on carbon (50 mg). The resulting solution was stirred overnight at room temperature under an atmosphere of hydrogen. The solids were filtered out. The resulting mixture was concentrated under vacuum. The residue was applied onto a silica gel column with dichloromethane/methanol (20:1). Purification afforded 9.9 mg (11%) of Compound I-296 as a white solid. MS (ES): 570 (M+H)$^+$, 592 (M+Na)$^+$. $^1$H NMR (400 MHz, DMSO-d$_6$): δ 8.25 (s, 1 H), 7.59 (d, 1H), 7.46 (d, 1H), 7.41-7.33 (m, 3H), 5.26-5.21 (m, 2H), 4.77 (d, 1H), 4.63 (d, 1H), 4.25-4.17 (m, 1H), 3.72 (s, 1H), 3.49 (m, 1 H), 3.21 (t, 3H), 2.78 (s, 3H), 1.71 (s, 3H), 1.70 (s, 3H), 1.62-1.58 (m, 2H), 1.28-1.24 (m, 2H).

Example 153

Synthesis of 2-methyl-2-[5-methyl-1-[(2R)-2-(oxan-4-yloxy)-2-[2-[(propan-2-yloxy)methyl]phenyl]ethyl]-6-(1,3-oxazol-2-yl)-2,4-dioxo-1H,2H,3H,4H-thieno[2,3-d]pyrimidin-3-yl]propanoic acid (I-297)

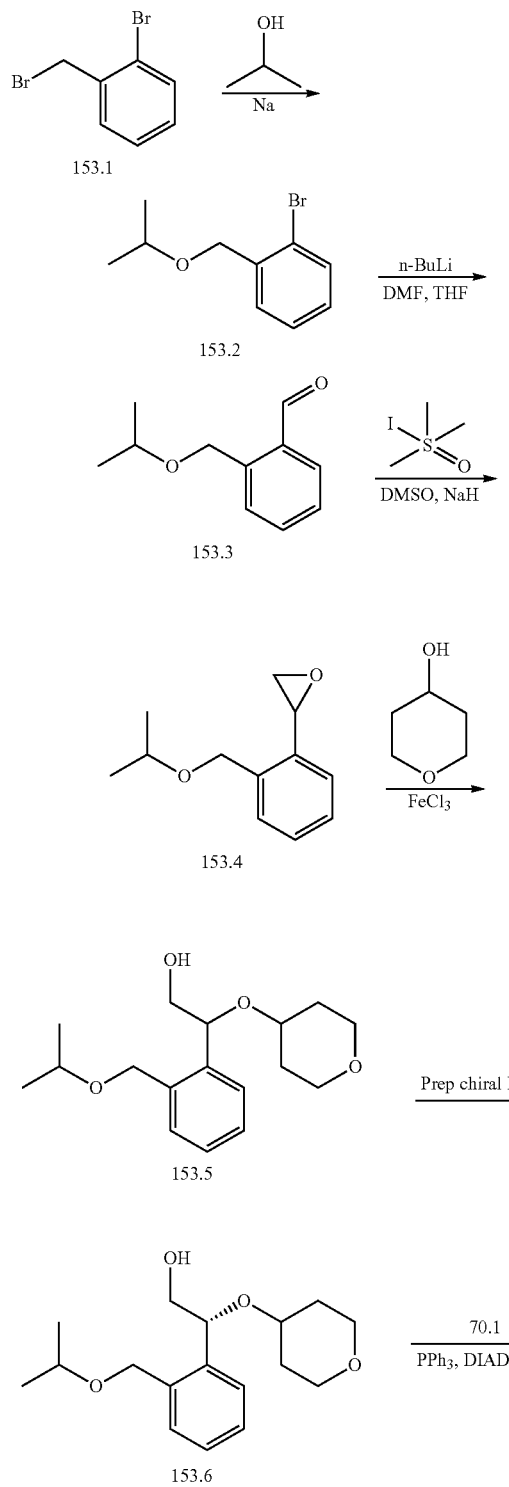

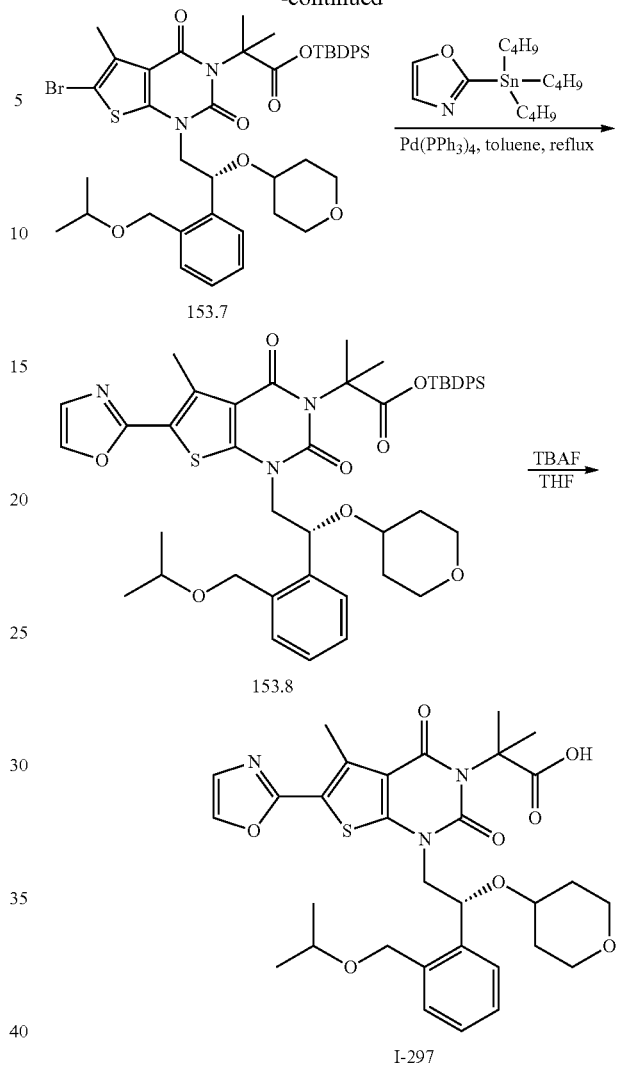

Synthesis of compound 153.2. Into a 250-mL 3-necked round-bottom flask was placed propan-2-ol (48 g, 798.74 mmol, 9.98 equiv). This was followed by the addition of Na (3.68 g) at 80° C. When the solids had disappeared 1-bromo-2-(bromomethyl)benzene (20 g, 80.02 mmol, 1.00 equiv) was added dropwise with stirring. The resulting solution was stirred overnight at 80° C. in an oil bath. The reaction was then quenched by the addition of 200 mL of water. The resulting solution was extracted with 200 mL of ethyl acetate and the organic layers combined and concentrated under vacuum. The residue was applied onto a silica gel column with ethyl acetate/petroleum ether (1:100). This resulted in 16 g (87%) of 153.2 as a light yellow oil.

Synthesis of compound 153.6. Compound 153.6 was prepared from 153.2 in a manner analogous to the synthesis of compound 149.6 from 149.2. Isolated 0.8 g of a colorless oil in 13% yield from 153.2

Synthesis of Compound I-297. Compound I-297 was prepared from 70.1 and 153.6 in a manner analogous to Example 57. Isolated 7.4 mg of a white solid in 2% overall yield. MS (ES): m/z 634 (M+Na)$^+$. $^1$H NMR (300 MHz, DMSO-d$_6$): δ 1.15-1.31 (m, 8H), 1.59-1.71 (m, 8H), 2.73 (s, 3H), 3.20-3.24 (m, 2H), 3.33-3.42 (m, 2H), 3.64-3.81 (m, 2H), 4.24-4.29 (d, 1H), 4.42-4.46 (d, 1H), 4.72-4.76 (d, 1H), 5.27-5.29 (d, 1H), 7.30-7.45 (m, 4H), 7.61-7.64 (d, 1H), 8.24 (s, 1H).

Example 154

Synthesis of 2-[1-[(2R)-2-[2-(cyanomethyl)phenyl]-2-(oxan-4-yloxy)ethyl]-5-methyl-6-(1,3-oxazol-2-yl)-2,4-dioxo-1H,2H,3H,4H-thieno[2,3-d]pyrimidin-3-yl]-2-methylpropanoic acid (I-298)

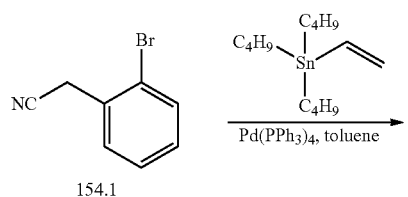

154.1

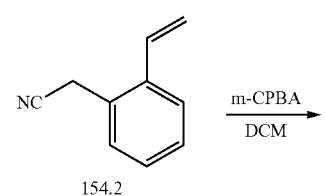

154.2

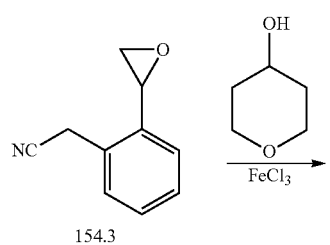

154.3

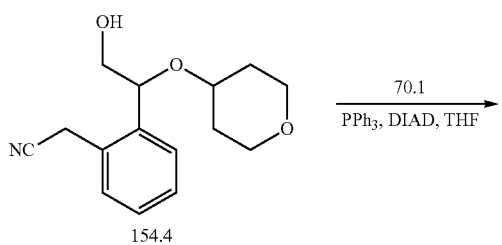

154.4

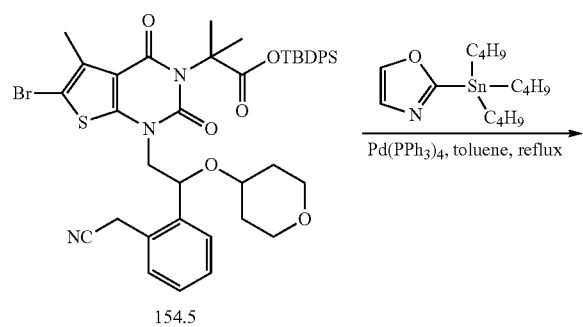

154.5

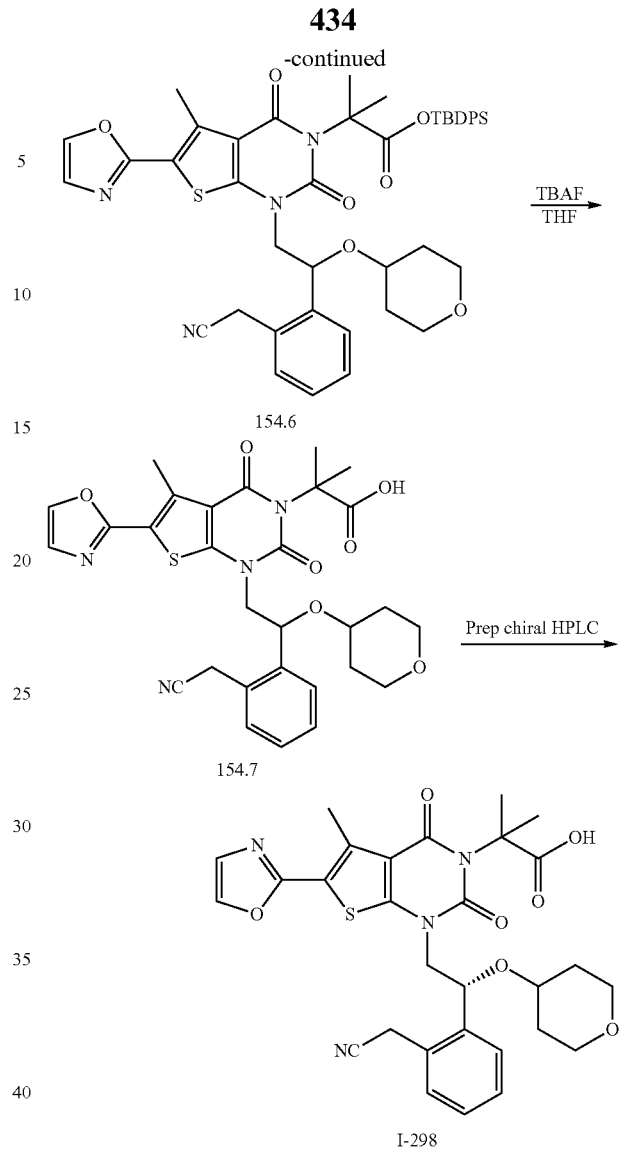

Synthesis of compound 154.2. Into a 500-mL 3-necked round-bottom flask, purged and maintained with an inert atmosphere of nitrogen, was placed 2-(2-bromophenyl)acetonitrile (10 g, 51.01 mmol, 1.00 equiv), toluene (200 mL), Pd(PPh$_3$)$_4$ (5.9 g, 5.11 mmol, 0.10 equiv) and tributyl(ethenyl)stannane (25.6 g, 80.73 mmol, 1.58 equiv). The resulting solution was stirred overnight at 110° C. The resulting mixture was concentrated under vacuum. The residue was applied onto a silica gel column with ethyl acetate/petroleum ether (1:100). This resulted in 5.5 g (75%) of 154.2 as a colorless oil.

Synthesis of compound 154.3. Into a 250-mL round-bottom flask was placed 154.2 (5.5 g, 38.41 mmol, 1.00 equiv), dichloromethane (100 mL) and m-CPBA (20.4 g, 82.75 mmol, 2.15 equiv, 70%). The resulting solution was stirred for 5 h at room temperature. The solids were filtered out. The resulting solution was extracted with 2×100 mL of Na$_2$SO$_3$ (aq.) and the organic layers combined. The resulting solution was extracted with 100 mL of sodium bicarbonate(aq.) and the organic layers combined and concentrated under vacuum. The residue was applied onto a silica gel column with ethyl acetate/petroleum ether (1:2). Purification afforded 5.4 g (88%) of 154.3 as a colorless oil.

Synthesis of compound 154.4. Compound 154.4 was prepared from 154.3 in a manner analogous to the synthesis of 57.3. Isolated 3.0 g (34%) of 154.4 as a colorless oil.

Synthesis of compound 154.7. Compound 154.7 was synthesized from 154.4 and 70.1 in a manner analogous to Example 57. Isolated 120 mg of 154.7 as a white solid in 6% overall yield from 70.1.

Purification of Compound I-298. The enantiomers of 154.7 (120 mg, 0.21 mmol, 1.00 equiv) were separated by chiral preparative HPLC under the following conditions (Gilson Gx 281): Column: Chiralpak IC, 2*25 cm, 5 um; mobile phase: hexanes (AcOH 0.1%) and IPA (hold at 30.0% IPA for 30 min); detector: UV 220/254 nm. This resulted in 11.4 mg of I-298 (tR=23.375 min; 10%) as a white solid.

Analytical Data for I-298: MS (ES): m/z 579 (M+H)$^+$, 601 (M+Na)$^+$. (400 MHz, DMSO-d$_6$): δ 12.41(br s, 1 H), 8.26 (s, 1 H), 7.63 (d, 1 H), 7.49-7.42 (m, 4H), 5.12 (d, 1H), 4.31-4.16 (m, 3H), 3.70 (s, 1H), 3.53 (d, 1H), 3.43-3.32 (m, 2H), 3.25-3.20 (m, 2H), 2.78 (s, 3H), 1.72-1.62 (m, 8H), 1.33-1.21 (m, 2H).

Example 155

Synthesis of ethyl 3-(2-methoxyethyl)-5-methyl-2,4-dioxo-1-(2-phenylethyl)-1H,2H,3H,4H-thieno[2,3-d]pyrimidine-6-carboxylate (I-6)

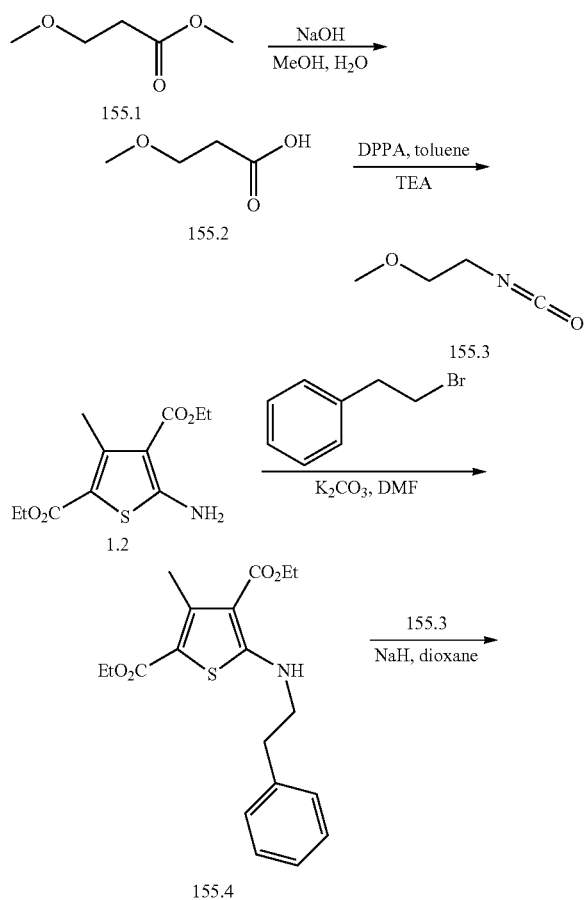

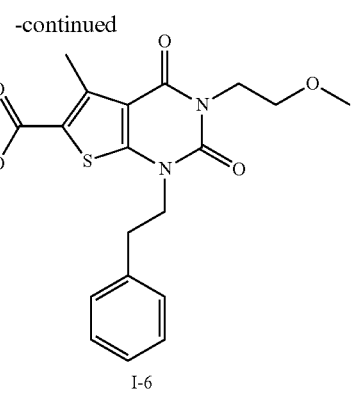

I-6

Synthesis of compound 155.2. A mixture of methyl 3-methoxypropanoate (3 g, 25.40 mmol, 1.00 equiv), methanol (60 mL), water (12 mL) and sodiumol (3.2 g, 80 mmol, 3.15 equiv) was stirred for 2 h at 50° C. in an oil bath. The pH value of the solution was adjusted to 2-3 with hydrochloric acid (2 mol/L). The resulting solution was extracted with 3×50 mL of dichloromethane and the organic layers combined. The resulting mixture was washed with 50 mL of brine. The resulting solution was dried over anhydrous sodium sulfate and concentrated under vacuum to give 2.0 g (76%) of 155.2 as a colorless oil.

Synthesis of compound 155.3. A mixture of 3-methoxypropanoic acid (3.0 g, 28.82 mmol, 1.00 equiv), DPPA (8.0 g, 29.07 mmol, 1.01 equiv) and triethylamine (2.92 g, 28.86 mmol, 1.00 equiv) in dry toluene (80 mL) was heated to reflux for 2 hr under nitrogen atmosphere. The reaction mixture was cooled to room temperature and then quenched by the addition of 50 mL of water/ice. The resulting solution was extracted with 100 mL of ethyl acetate and the organic layer dried over anhydrous sodium sulfate and concentrated under vacuum to yield 1.5 g (51%) of 155.3 as colorless oil.

Synthesis of compound 155.4. A mixture of 2,4-diethyl 5-amino-3-methylthiophene-2,4-dicarboxylate (5.0 g, 19.43 mmol, 1.00 equiv) and potassium carbonate (5.4 g, 39.07 mmol, 2.01 equiv) in N,N-dimethylformamide (70 mL) was stirred for 15 min at 25° C. To this was added (2-bromoethyl)benzene (7.2 g, 38.91 mmol, 2.00 equiv). The resulting solution was stirred overnight at 50° C. in an oil bath. The reaction was then quenched by the addition of 100 mL of water and ice mixture. The resulting solution was extracted with 2×100 mL of ethyl acetate and the organic layers combined. The resulting solution was dried over anhydrous sodium sulfate and concentrated under vacuum. The residue was applied onto a silica gel column with ethyl acetate:petroleum ether (1:10) to yield 4.0 g (57%) of 155.4 as a brown solid. The 500 mg crude was recrystallized with EtOH to obtain 208.9 mg of the pure compound.

Synthesis of Compound I-6. Sodium hydride (60%) (100 mg, 2.5 mmol, 1.81 equiv) was added to a solution of 155.4 (500 mg, 1.38 mmol, 1.00 equiv) in dioxane (15 mL) batchwise under a nitrogen atmosphere. 30 minutes later, was added 155.3 (300 mg, 2.97 mmol, 2.15 equiv). The resulting solution was heated to reflux for 8 h in an oil bath. The reaction mixture was cooled to room temperature and concentrated under vacuum. The residue was applied onto a silica gel column with ethyl acetate/petroleum ether (1/10) to give 0.25 g (43%) of I-6 as a white solid. MS (ES): m/z: (M+H)$^+$ calcd for $C_{21}H_{25}N_2O_5S$ 417. found 417. $^1$H NMR (400 MHz, CDCl$_3$) δ7.28-7.35 (5H, m), 4.36-4.41 (2H, q), 4.26-4.28 (2H, t), 4.14-4.18 (2H, t), 3.64-3.67 (2H, t), 3.39 (3H, s), 3.07-3.11 (2H, t), 2.90 (3H, s), 1.40-1.44 (3H, t).

Example 156

Synthesis of ethyl 3-ethyl-5-methyl-2,4-dioxo-1-(2-phenylethyl)-1H,2H,3H,4H-thieno[2,3-d]pyrimidine-6-carboxylate (I-7)

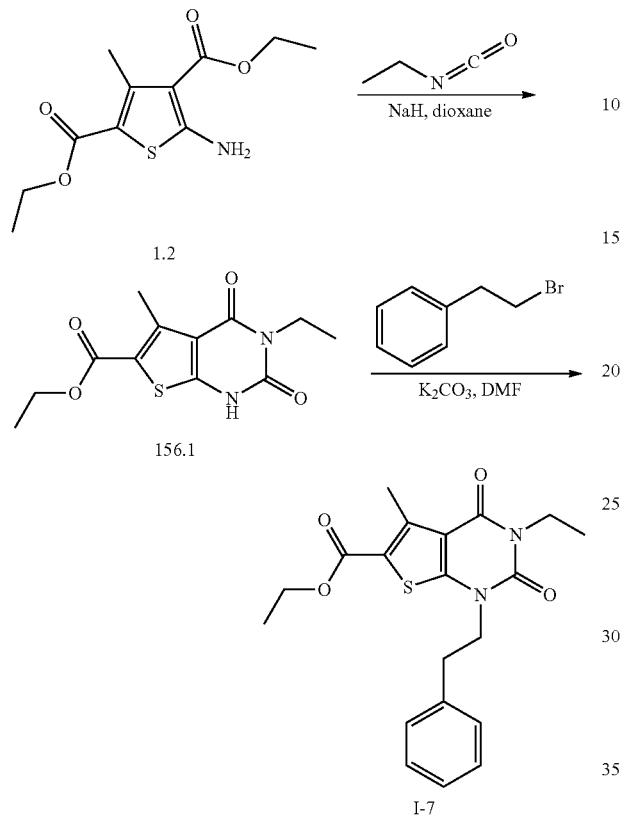

Synthesis of Compound I-7. Compound I-7 was prepared from isocyanatoethane and 1.2 in a manner analogous to the synthesis of compound 136.1. Isolated a white solid in 45% yield. MS (ES): m/z: (M+H)+ calcd for $C_{20}H_{23}N_2O_4S$ 387. found 387. $^1$H NMR (300 MHz, CDCl$_3$) δ7.29-7.39 (5H, m), 4.36-4.43 (2H, q), 4.115-4.20 (2H, t), 4.05-4.10 (2H, q), 3.08-3.13 (2H, t), 2.92 (3H, s), 1.41-1.45 (3H, t), 1.25-1.29 (3H, t).

Example 157

Synthesis of ethyl 3-[2-(benzyloxy)ethyl]-5-methyl-2,4-dioxo-1-(2-phenylethyl)-1H,2H,3H,4H-thieno[2,3-d]pyrimidine-6-carboxylate (I-10)

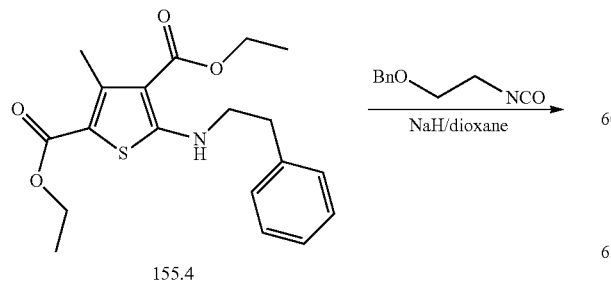

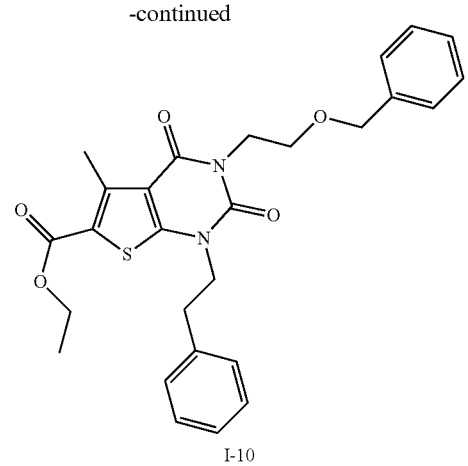

Compound I-10 was prepared from 155.4 and [(2-isocyanatoethoxy)methyl]benzene in a manner analogous to Compound I-6 (Example 155). Isolated a white solid in 51% yield. MS (ES): m/z: 493 (M+H)+. $^1$H NMR (300 MHz, CDCl$_3$): δ7.21-7.35 (10H, m), 4.55 (2H, s), 4.33-4.40 (2H, q), 4.27-4.31 (2H, t), 4.07-4.13 (2H, t), 3.73-3.77 (2H, t), 3.01-3.06 (2H, t), 2.87 (3H, s), 1.38-1.42 (3H, t).

Example 157

Synthesis of ethyl 5-methyl-2,4-dioxo-1-(2-phenylethyl)-3-propyl-1H,2H,3H,4H-thieno[2,3-d]pyrimidine-6-carboxylate (I-9)

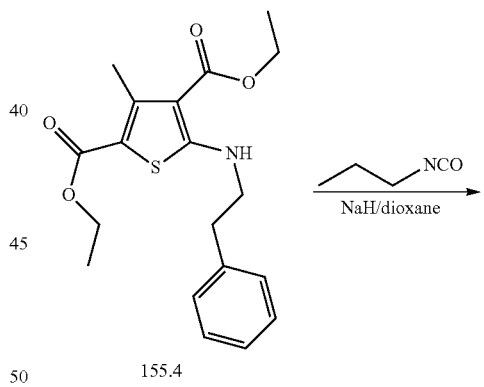

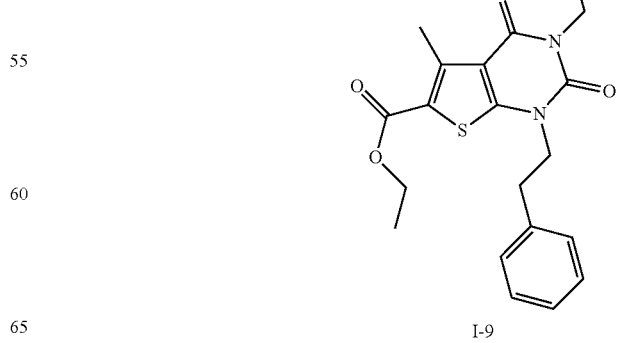

Compound I-9 was prepared from 155.4 and 1-isocyanatopropane in a manner analogous to Compound I-6 (Example 155). Isolated a white solid in 3% yield. MS (ES): m/z: 401 (M+H)+.
$^1$H NMR (400 MHz, CDCl$_3$): δ7.28-7.35 (5H, m), 4.35-4.42 (2H, q), 4.14-4.16 (2H, t), 3.95-4.00 (2H, t), 3.07-3.12 (2H, t), 2.90 (3H, s), 1.67-1.72 (2H, q), 1.40-1.45 (3H, t), 0.96-1.01 (3H, t).

Example 158

Synthesis of ethyl 1-ethyl-3-(2-hydroxyethyl)-5-methyl-2,4-dioxo-1H,2H,3H,4H-thieno[2,3-d]pyrimidine-6-carboxylate (I-11)

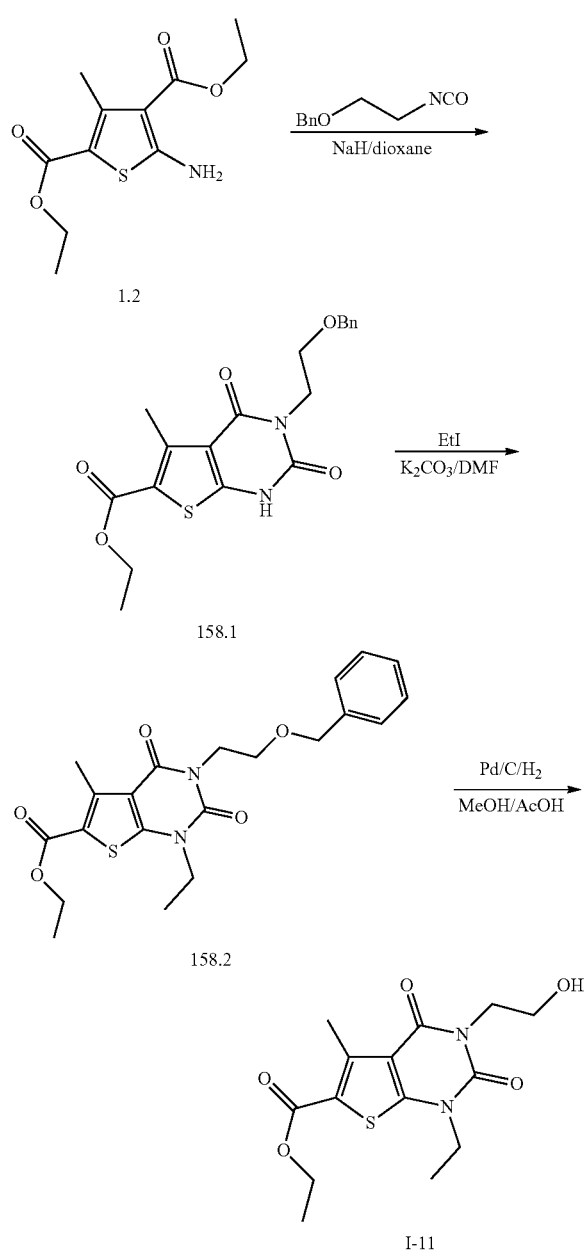

Synthesis of compound 158.1. Compound 158.1 was prepared from 1.2 and [(2-isocyanatoethoxy)methyl]benzene in a manner analogous to the synthesis of compound 135.3. Isolated 38.9 mg of a white solid in 10% yield. MS (ES): m/z: 389 (M+H)+.
$^1$H NMR (300 MHz, CDCl$_3$): δ9.68 (1H, s), 7.21-7.34 (5H, m), 4.60 (2H, s), 4.28-4.40 (4H, m), 3.81-3.85 (2H, t), 2.86 (3H, s), 1.38-1.42 (3H, t).

Synthesis of compound 158.2. A mixture of 158.1 (200 mg, 0.51 mmol, 1.00 equiv), potassium carbonate (140 mg, 1.01 mmol, 1.95 equiv) and iodoethane (321 mg, 2.06 mmol, 4.00 equiv) in N,N-dimethylformamide (10 mL) was stirred for 4 h at 35° C. The reaction was then quenched by the addition of 15 mL of water and ice mixture. The resulting solution was extracted with 2×15 mL of ethyl acetate and the organic layers combined. The resulting mixture was washed with 2×20 mL of brine. The mixture was dried over anhydrous sodium sulfate and concentrated under vacuum to give 120 mg (56%) of 158.2 as a yellow solid.

Synthesis of Compound I-11. Excess hydrogen gas was introduced into a mixture of 158.2 (120 mg, 0.29 mmol, 1.00 equiv), acetic acid (5 mL), 10% palladium on carbon (100 mg) in ethanol (20 mL) and the pressure maintained at 4 atm. The resulting solution was stirred for 12 h at room temperature. The solids were filtered out. The filtrate was concentrated under vacuum. The residue was purified by re-crystallization from ethanol to yield 12.4 mg (13%) of I-11 as a white solid. MS (ES): m/z: 327 (M+H)+. $^1$H NMR (300 MHz, CDCl$_3$): δ4.32-4.39 (2H, q), 4.27-4.30 (2H, t), 4.00-4.07 (2H, q), 3.89-3.92 (2H, t), 2.87 (3H, s), 1.36-1.42 (6H, dt).

Example 159

Synthesis of ethyl 3-(2-hydroxyethyl)-5-methyl-1-(naphthalen-2-ylmethyl)-2,4-dioxo-1H,2H,3H,4H-thieno[2,3-d]pyrimidine-6-carboxylate (I-16)

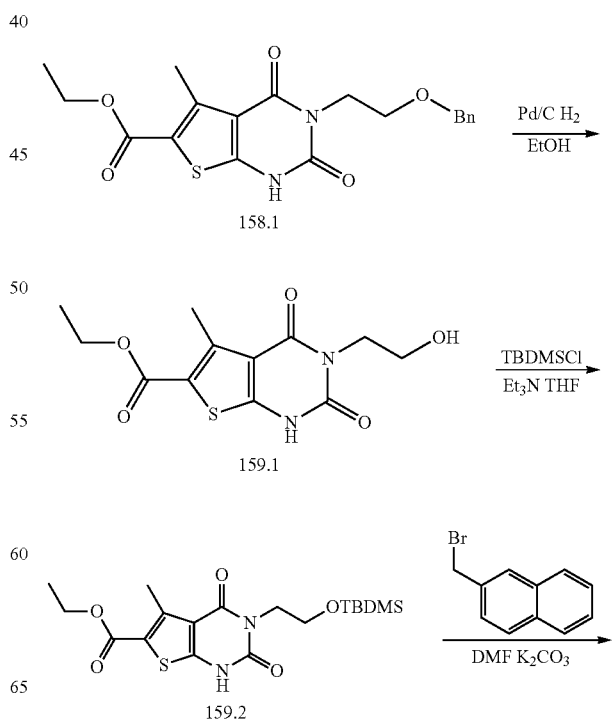

-continued

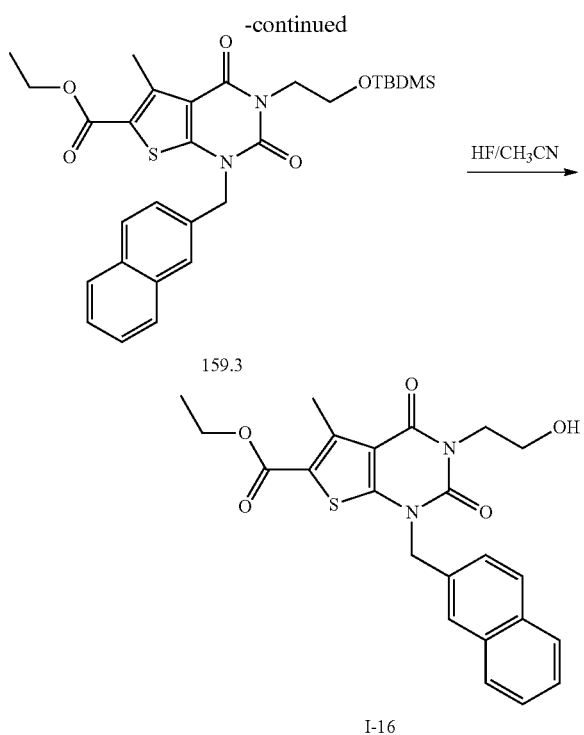

Synthesis of Compound 159.1. Into a 100-mL round-bottom flask was placed 158.1 (650 mg, 1.67 mmol, 1.00 equiv), ethanol (35 mL), acetic acid (7 mL) and 10% palladium on carbon (300 mg). Hydrogen was introduced (4 atm). The resulting solution was stirred for 24 h at room temperature. The solids were filtered out. The filtrate was concentrated under vacuum to yield 400 mg (80%) of 159.1 as a brown solid.

Synthesis of compound 159.2. A mixture of 159.1 (400 mg, 1.34 mmol, 1.00 equiv), tert-butyl(chloro)dimethylsilane (240 mg, 1.59 mmol, 1.19 equiv) and triethylamine (203 mg, 2.01 mmol, 1.50 equiv) in oxolane (20 mL) was stirred for 12 h at room temperature. The reaction was then quenched by the addition of 20 mL of water. The resulting solution was extracted with 2×40 mL of ethyl acetate and the organic layers combined and dried over anhydrous sodium sulfate and concentrated under vacuum to give 360 mg (65%) of 159.2 as a white oil.

Synthesis of compound 159.3. A mixture of 159.2 (120 mg, 0.29 mmol, 1.00 equiv), potassium carbonate (60 mg, 0.43 mmol, 1.48 equiv) and 2-(bromomethyl)naphthalene (77 mg, 0.35 mmol, 1.20 equiv) in N,N-dimethylformamide (10 mL) was stirred for 12 h at 35° C. The reaction was then quenched by the addition of 10 mL of water. The resulting solution was extracted with 2×15 mL of ethyl acetate and the organic layers combined. The resulting mixture was washed with 1×35 mL of brine. The mixture was dried over anhydrous sodium sulfate and concentrated under vacuum. The residue was applied onto a silica gel column with ethyl acetate/petroleum ether (1/15-1/10) to give 60 mg (37%) of 159.3 as a yellow solid.

Synthesis of Compound I-16. Into a 50-mL round-bottom flask was placed a solution of 159.3 (20 mg, 0.04 mmol, 1.00 equiv, 99%) in CH₃CN (5 mL). This was followed by the addition of HF (0.25 mL) dropwise with stirring. The resulting solution was stirred overnight at room temperature. The resulting solution was diluted with 30 mL of water. The solids were collected by filtration and dried under reduced pressure to yield 15 mg (93%) of I-16 as a white solid. MS (ES, m/z): 439 [M+H]⁺. ¹H NMR (300 MHz, CDCl₃): δ 7.84 (d, 4H), 7.52-7.45 (m, 3H), 5.35 (s, 2H), 4.37-4.27 (m, 4H), 3.96 (t, 2H), 2.85 (s, 3H), 2.31 (s, 1H), 1.35 (t, 3H).

Example 160

Synthesis of ethyl 1-[2-(2-chlorophenyl)ethyl]-3-(2-hydroxyethyl)-5-methyl-2,4-dioxo-1H,2H,3H,4H-thieno[2,3-d]pyrimidine-6-carboxylate (I-20)

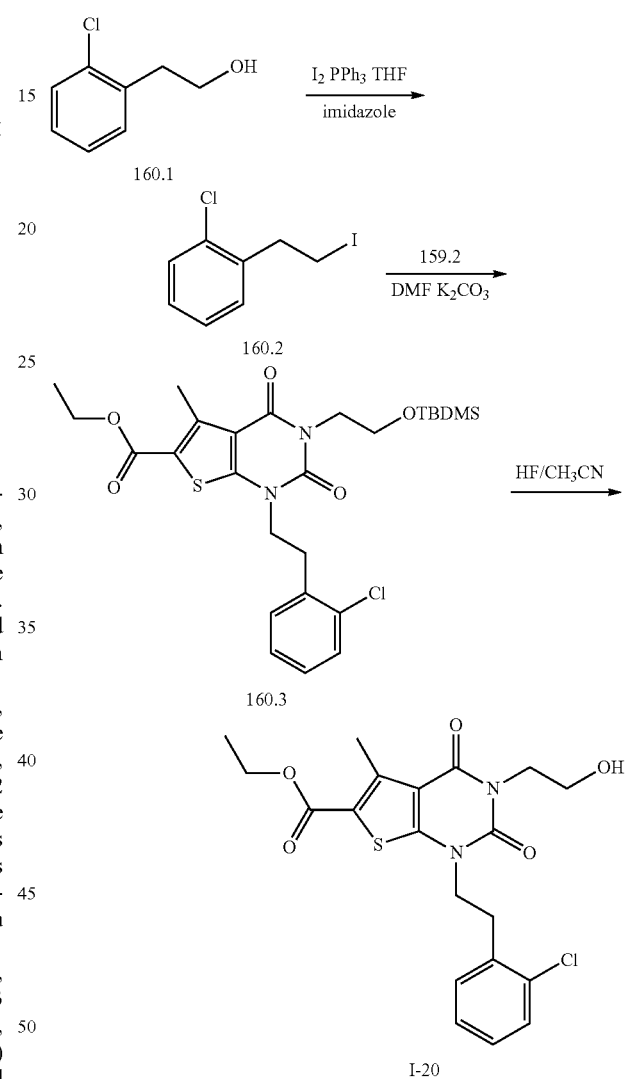

Synthesis of compound 160.2. Into a 50-mL 3-necked round-bottom flask was placed 2-(2-chlorophenyl)ethan-1-ol (1.5 g, 9.58 mmol, 1.00 equiv), PPh₃ (2.5 g, 9.53 mmol, 1.00 equiv), tetrahydrofuran (30 mL) and imidazole (0.9 g, 13.2 mmol, 1.4 equiv). This was followed by the addition of I₂ (3.4 g) in several batches. The resulting solution was stirred for 30 min at 0-5° C. and then quenched by the addition of 20 mL of water/ice. The resulting solution was extracted with 2×50 mL of ether and the organic layers combined. The resulting mixture was washed with 1×50 mL of sat. aqueous Na₂SO₃. The mixture was dried over anhydrous sodium sulfate and concentrated under vacuum. The residue was applied onto a silica gel column with ethyl acetate/petroleum ether (1/3). This resulted in 2.5 g (98%) of 160.2 as a colorless oil.

Synthesis of Compound I-20. Compound I-20 was prepared from 159.2 and 160.2 in a manner analogous to the synthesis of Compound I-16 (Example 159). Isolated a white solid in 54% yield. MS (ES): m/z: 437 (M+H)+ 1H NMR (300 MHz, CDCl3): δ 7.39-7.35 (m, 1H), 7.22-7.19 (m, 3H), 4.39-4.32 (m, 2H), 4.28-4.18 (m, 4H), 3.87 (t, 2H), 3.24 (t, 2H), 2.86 (s, 3H), 2.26 (s, 1H), 1.39 (t, 3H).

Example 161

Synthesis of ethyl 3-(2-hydroxyethyl)-5-methyl-1-[2-(naphthalen-2-yl)ethyl]-2,4-dioxo-1H,2H,3H,4H-thieno[2,3-d]pyrimidine-6-carboxylate (I-30)

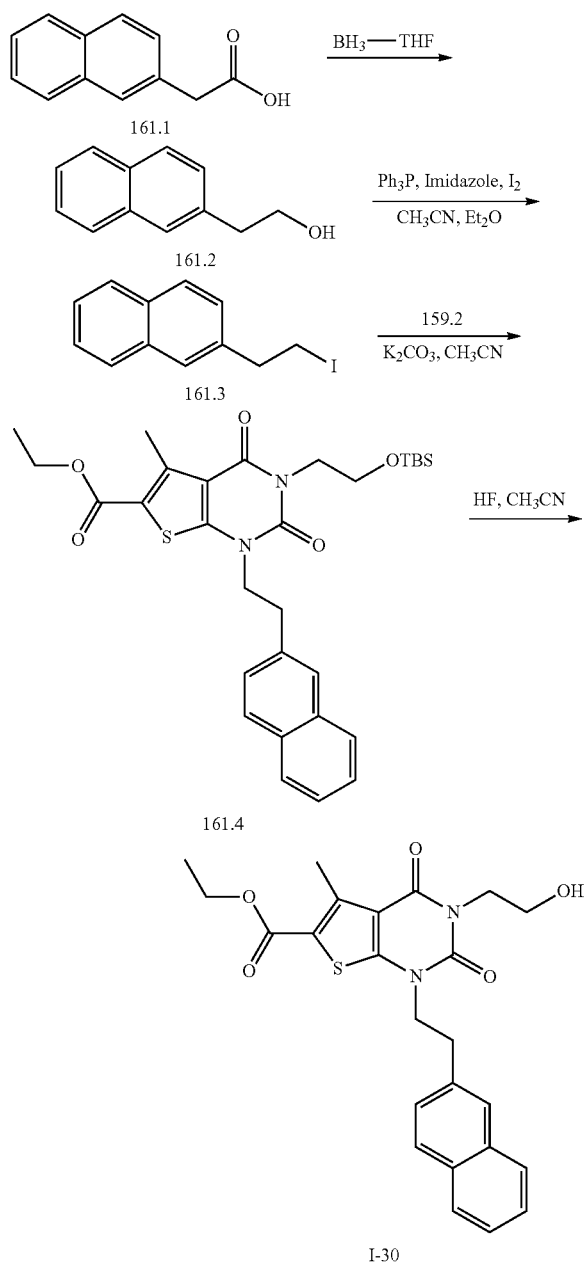

Synthesis of compound 161.2. Into a 250-mL round-bottom flask purged and maintained with an inert atmosphere of nitrogen was placed 161.1 (7.44 g, 39.96 mmol, 1.00 equiv) and tetrahydrofuran (80 mL). This was followed by the addition of BH3/THF (1 M) (80 mL) dropwise with stirring at 0° C. The resulting solution was stirred for 2 h at room temperature. The reaction was then quenched by the addition of 20 mL of water. The resulting solution was extracted with 2×150 mL of ethyl acetate and the organic layers combined and dried over anhydrous sodium sulfate and concentrated under vacuum. This resulted in 7.05 g (crude) of 161.2 as a colorless oil.

Synthesis of Compound I-30. Compound I-30 was prepared from 161.2 and 159.2 in a manner analogous to the synthesis of Compound I-20 (Example 160). Isolated a white solid in 31% yield from 159.2. MS (ES): m/z (M+H)+ 453, (M+Na)+ 475. 1H NMR (400 MHz, DMSO-d6): δ 1.28 (t, J=7.2, 3H), 2.76 (s, 3H), 3.18 (t, J=7.6, 2H), 3.49 (t, J=6.4, 2H), 3.95 (t, J=6.4, 2H), 4.20-4.30 (m, 4H), 7.42-7.51 (m, 3H), 7.78 (s, 3H), 7.85-7.90 (m, 3H).

Example 162

Synthesis of ethyl 3-(3-hydroxypropyl)-5-methyl-2,4-dioxo-1-(2-phenylethyl)-1H,2H,3H,4H-thieno[2,3-d]pyrimidine-6-carboxylate (I-19)

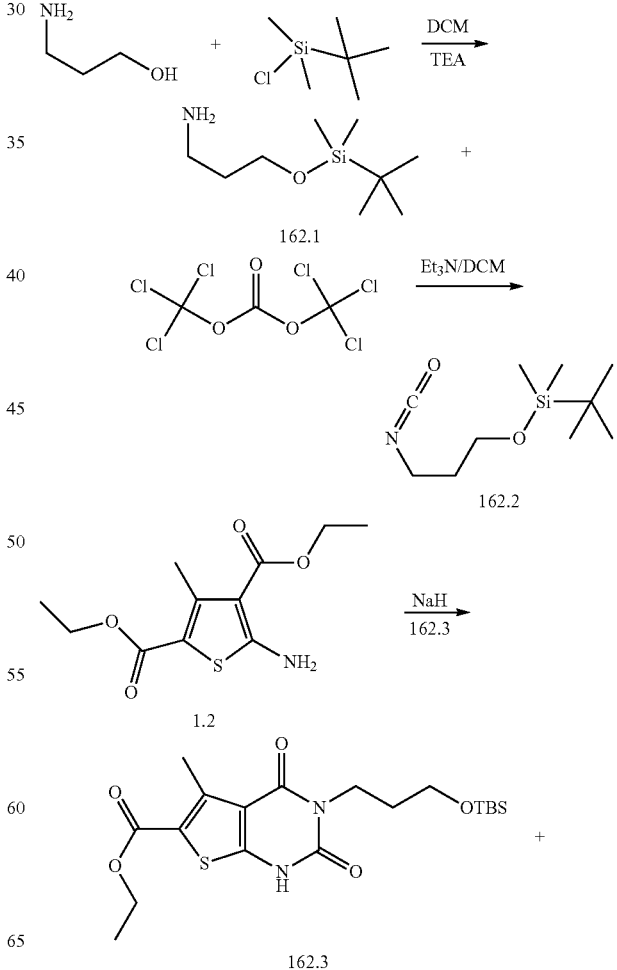

-continued

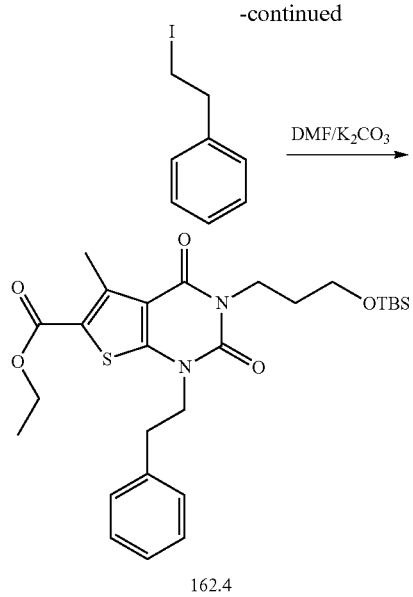

The solids were collected by filtration and dried under reduced pressure to give 60 mg (70%) of I-19 as a white solid. MS (ES): m/z 417 (M+H)+.

$^1$H NMR (300 MHz, CDCl$_3$): δ 7.327 (m, 4H), 7.261 (m, 1H), 4.385 (m, 2H), 4.137 (m, 4H), 3.513 (t, 2H), 3.084 (t, 2H), 2.873 (s, 3H), 1.429 (t, 2H), 0.962 (t, 3H).

Example 163

Synthesis of 2-[1-[2-(2-chlorophenyl)ethyl]-6-(ethoxycarbonyl)-5-methyl-2,4-dioxo-1H,2H,3H,4H-thieno[2,3-d]pyrimidin-3-yl]acetic acid (I-31)

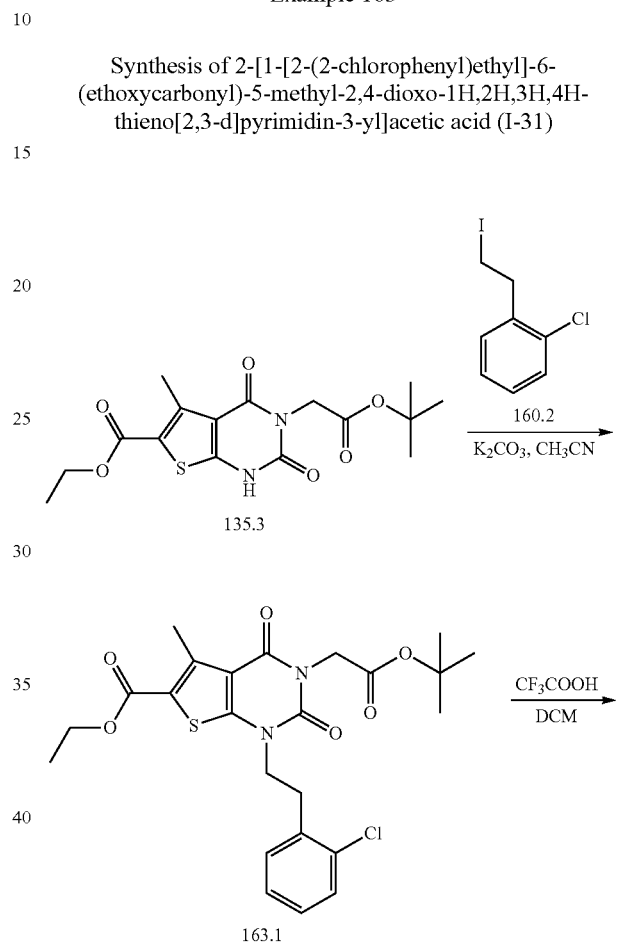

Synthesis of compound 162.1. Into a 500-mL 3-necked round-bottom flask was placed a solution of 3-aminopropan-1-ol (15 g, 195.71 mmol, 1.00 equiv, 98%) in dichloromethane (200 mL), tert-butyl(chloro)dimethylsilane (36 g, 234.07 mmol, 1.20 equiv), triethylamine (60.6 g, 588.00 mmol, 3.00 equiv, 98%). The resulting solution was stirred for 18 h at 20° C. The reaction was then quenched by the addition of 200 mL of water. The resulting solution was extracted with 1×200 mL of dichloromethane and the organic layers combined. The resulting mixture was washed with 1×200 mL of brine. The mixture was dried over anhydrous magnesium sulfate and concentrated under vacuum. This resulted in 20 g (51%) of 162.1 as a colorless oil.

Synthesis of compound 162.2. Compound 162.2 was prepared from 162.1 in a manner analogous to 135.2. Isolated 2 g of a yellow oil in 74% yield.

Synthesis of compound 162.4. Compound 162.4 was prepared from 162.2 and 1.2 in a manner analogous to the synthesis of compound 136.1 (Examples 135 and 136). Isolated 110 mg of a white solid in 15% yield from 1.2.

Synthesis of Compound I-19. Into a 50-mL round-bottom flask was placed a solution of 162.4 (110 mg, 0.20 mmol, 1.00 equiv, 98%) in CH$_3$CN (20 mL) and hydrogen fluoride (1 mL). The resulting solution was stirred for 3 h at 20° C. The reaction was then quenched by the addition of 10 mL of water.

Compound I-31 was prepared from 135.3 and 160.2 in a manner analogous to the synthesis of 136.2. Isolated 73.1 mg of a white solid in 11% overall yield. MS (ES): m/z (M+H)+ 451. $^1$H NMR (400 MHz, CD$_3$OD): δ 1.35-1.86 (t, 3H), 2.80

(s, 3H), 3.27-3.37 (m, 2H), 4.23-4.27 (t, 2H), 4.30-4.35 (q, 2H), 4.71 (s, 2H), 7.21-7.23 (t, 2H), 7.30-7.36 (m, 1H), 7.36-7.37 (m, 1H).

4.21-4.24 (t, 2H), 4.31-4.37 (q, 2H), 4.70 (s, 2H), 7.01-7.11 (m, 2H), 7.26-7.28 (q, 2H). $^{19}$F-NMR (300 MHz, CD$_3$OD): δ −120.64 (1).

Example 164

Synthesis of 2-[6-(ethoxycarbonyl)-1-[2-(2-fluorophenyl)ethyl]-5-methyl-2,4-dioxo-1H,2H,3H,4H-thieno[2,3-d]pyrimidin-3-yl]acetic acid (I-32)

Example 165

Synthesis of ethyl 1-[2-(2-fluorophenyl)ethyl]-3-(2-hydroxyethyl)-5-methyl-2,4-dioxo-1H,2H,3H,4H-thieno[2,3-d]pyrimidine-6-carboxylate (I-23)

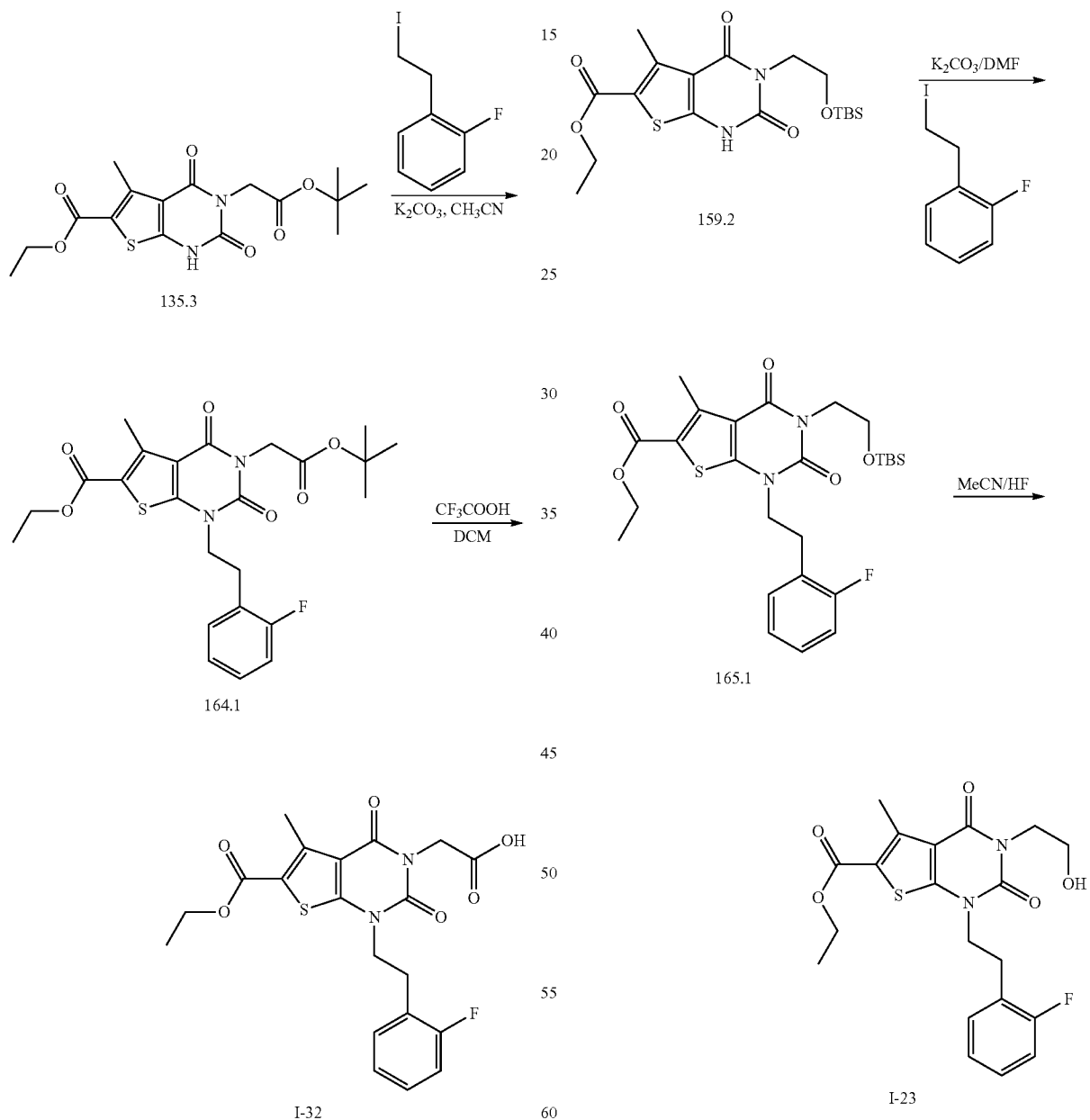

Compound I-32 was prepared from 135.3 and 1-fluoro-2-(2-iodoethyl)benzene in a manner analogous to the synthesis of 136.2. Isolated 42.9 mg of a white solid in 23% overall yield. MS (ES): m/z (M+H)$^+$ 435. $^1$H NMR (400 MHz, CD$_3$OD): δ 1.36-1.94 (t, 3H), 2.81 (s, 1H), 3.16-3.20 (t, 2H), Compound I-23 was prepared from 159.2 and 1-fluoro-2-(2-iodoethyl)benzene in a manner analogous to the synthesis of Compound I-16 (Example 159). Isolated 500 mg of a white solid in 59% overall yield. MS (ES): m/z 421 (M+H)$^+$. $^1$H NMR (300 MHz, CDCl₃): δ 7.279 (m, 2H), 7.053 (m, 2H), 4.370 (m, 2H), 4.162 (m, 4H), 3.870 (t, 2H), 3.144 (m, 2H), 2.861 (s, 3H), 1.396 (t, 3H).

Example 166

Synthesis of 3-[6-(ethoxycarbonyl)-5-methyl-2,4-dioxo-1-(2-phenylethyl)-1H,2H,3H,4H-thieno[2,3-d]pyrimidin-3-yl]propanoic acid (I-46)

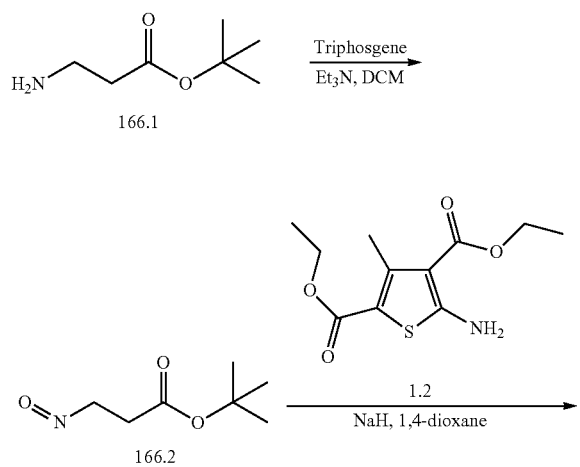

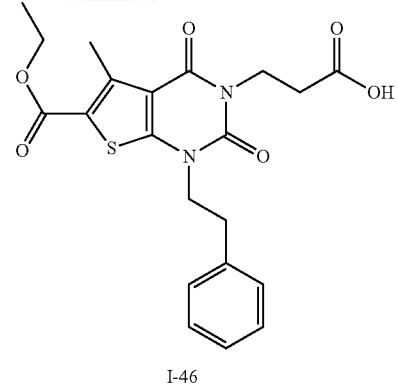

I-46

Compound I-46 was prepared from 166.1 and 1.2 in a manner analogous to the synthesis of compound 136.2 (Examples 135 and 136). Isolated 1.8 g of a white solid in 25% overall yield. MS (ES): m/z (M+H)⁺ 431, (M+Na)⁺ 453. ¹H NMR (300 MHz, DMSO-d₆): δ 1.29 (t, J=7.2, 3H), 2.75 (s, 3H), 3.09 (t, J=6.3, 2H), 4.04-4.13 (m, 4H), 4.28 (q, J=6.9, 2H), 7.20-7.32 (m, 5H), 12.37 (s, 1H).

Example 167

Synthesis of ethyl 3-(2-carbamoylethyl)-5-methyl-2,4-dioxo-1-(2-phenylethyl)-1H,2H,3H,4H-thieno[2,3-d]pyrimidine-6-carboxylate (I-55)

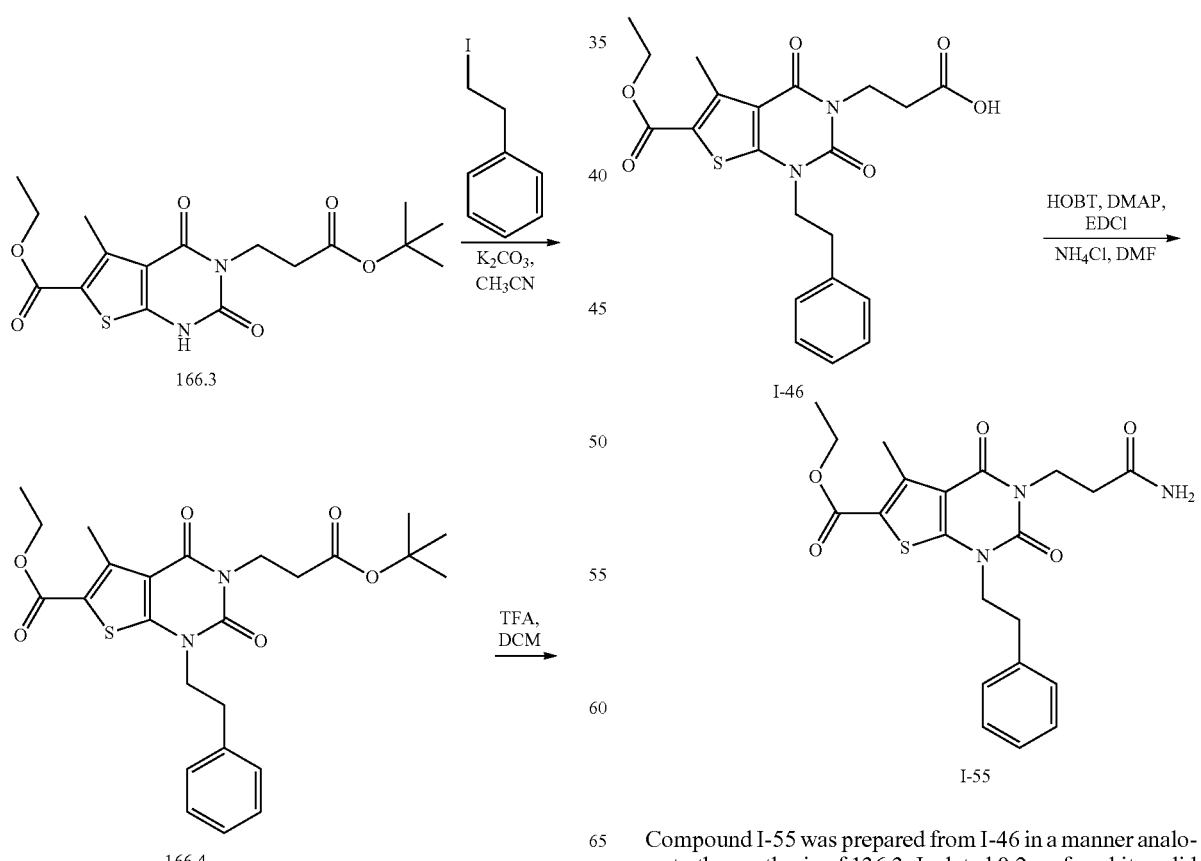

Compound I-55 was prepared from I-46 in a manner analogous to the synthesis of 136.3. Isolated 0.2 g of a white solid in 56% yield. MS (ES): m/z (M+H)⁺ 430. ¹H NMR (300

MHz, DMSO-$d_6$): δ 1.29 (t, J=7.2, 3H), 2.34 (t, J=7.5, 2H), 2.76 (s, 3H), 3.00 (t, J=7.5, 2H), 4.02-4.13 (m, 4H), 4.28 (q, J=7.2, 2H), 6.86 (s, 1H), 7.24-7.38 (m, 6H).

Example 168

Synthesis of ethyl 5-methyl-2,4-dioxo-1-(2-phenyl-ethyl)-3-[2-(1H-1,2,3,4-tetrazol-5-yl)ethyl]-1H,2H,3H,4H-thieno[2,3-d]pyrimidine-6-carboxylate (I-61)

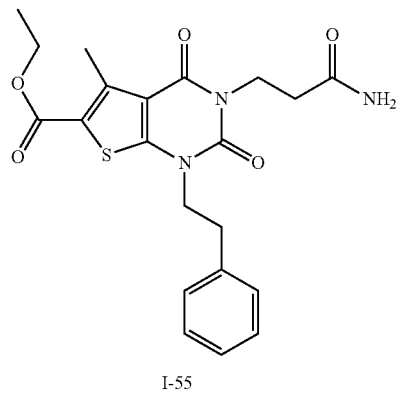

I-55

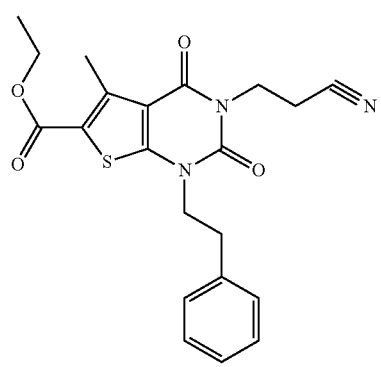

168.1

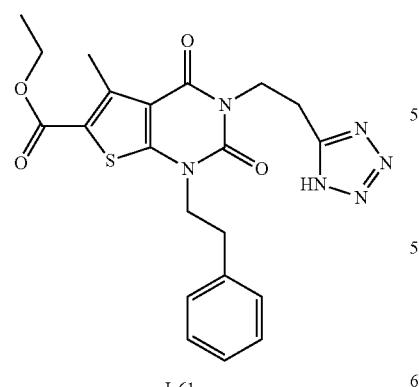

I-61

Compound I-61 was prepared from I-55 in a manner analogous to the synthesis of Compound 1-45 from 136.3 (Example 136). Isolated 16.7 mg of a white solid in 10% overall yield. MS (ES): m/z (M+H)$^+$ 455, (M+H+CH$_3$CN)$^+$ 496. $^1$H NMR (400 MHz, CD$_3$OD): δ 1.38 (t, J=7.2, 3H), 2.79 (s, 3H), 3.05 (t, J=7.2, 2H), 3.27 (t, J=7.2, 2H), 4.13 (t, J=7.2, 3H), 4.31-4.39 (m, 4H), 7.23-7.32 (m, 5H).

Example 169

Synthesis of ethyl 3-(4-hydroxybutyl)-5-methyl-2,4-dioxo-1-(2-phenylethyl)-1H,2H,3H,4H-thieno[2,3-d]pyrimidine-6-carboxylate (I-34)

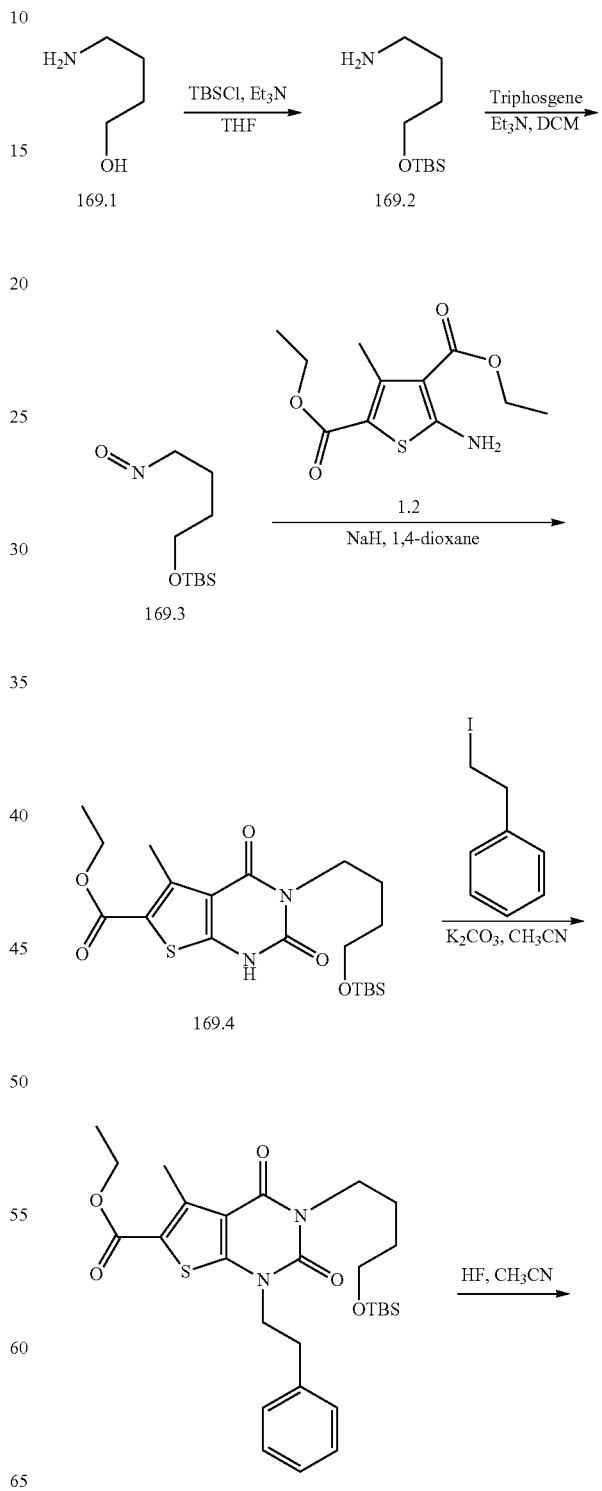

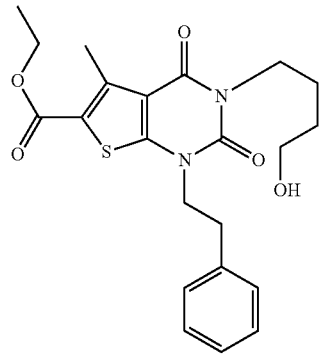

I-34

Compound I-34 was prepared from 169.1 and 1.2 in a manner analogous to Compound I-19 (Example 162). Isolated 26 mg of a colorless oil in 1.4% overall yield. MS (ES): m/z (M+H)$^+$ 431. $^1$H NMR (300 MHz, CD$_3$OD): δ 1.38 (t, J=7.5, 2H), 1.52-1.64 (m, 2H), 1.66-1.78 (m, 2H), 2.82 (s, 3H), 3.10 (t, J=7.2, 2H), 3.60 (t, J=6.3, 2H), 3.99 (t, J=7.2, 2H), 4.19 (t, J=7.5, 2H), 4.34 (q, J=7.2, 2H), 7.19-7.31 (m, 2H).

Example 170

Synthesis of ethyl 1-[2-(4-fluorophenyl)ethyl]-3-(2-hydroxyethyl)-5-methyl-2,4-dioxo-1H,2H,3H,4H-thieno[2,3-d]pyrimidine-6-carboxylate (I-26)

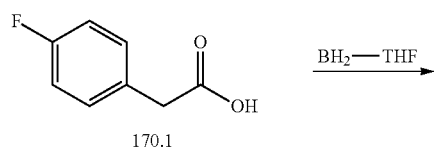

170.1

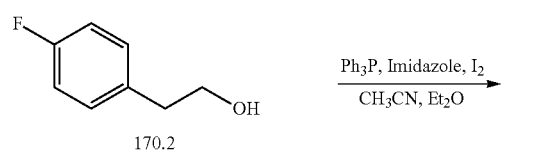

170.2

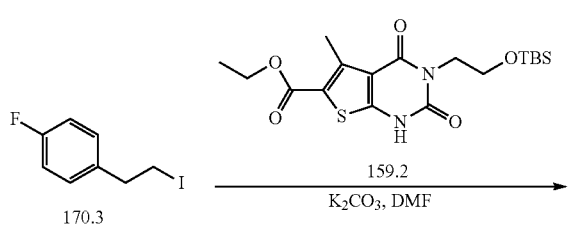

170.3

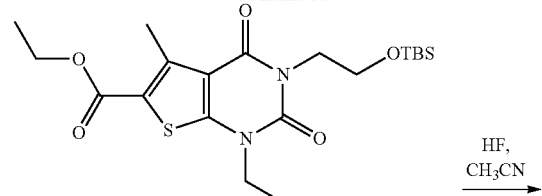

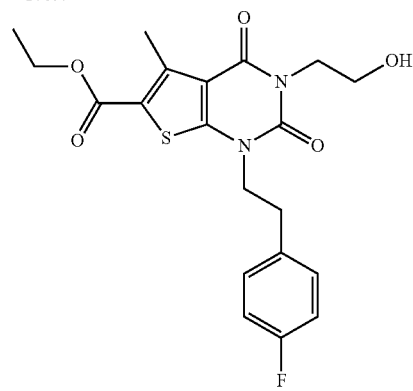

I-26

Compound I-26 was prepared from 170.1 and 159.2 in a manner analogous to the synthesis of Compound I-30 (Example 161). Isolated 80 mg of a white solid in 60% overall yield. MS (ES): m/z (M+H)$^+$ 421. $^1$H NMR (300 MHz, CDCl$_3$): δ 1.40 (t, J=7.2, 3H), 2.24 (s, 3H), 2.87 (s, 3H), 3.06 (t, J=7.5, 2H), 3.89 (s, 2H), 4.12 (t, J=7.8, 2H), 4.27 (t, J=5.1, 3H), 4.37 (q, J=7.2, 3H), 6.91-7.26 (m, 4H).

Example 171

Synthesis of ethyl 1-[2-(3,5-difluorophenyl)ethyl]-3-(2-hydroxyethyl)-5-methyl-2,4-dioxo-1H,2H,3H,4H-thieno[2,3-d]pyrimidine-6-carboxylate (I-29)

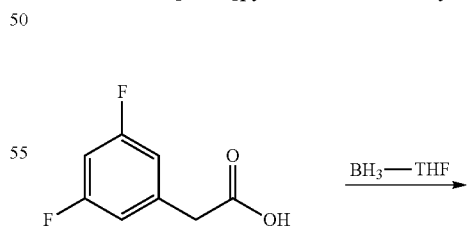

171.1

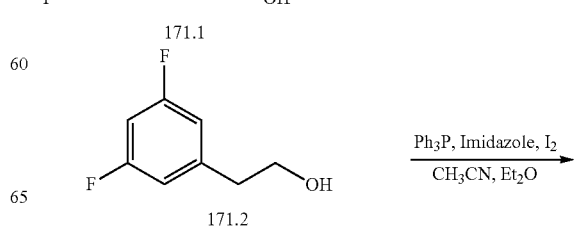

171.2

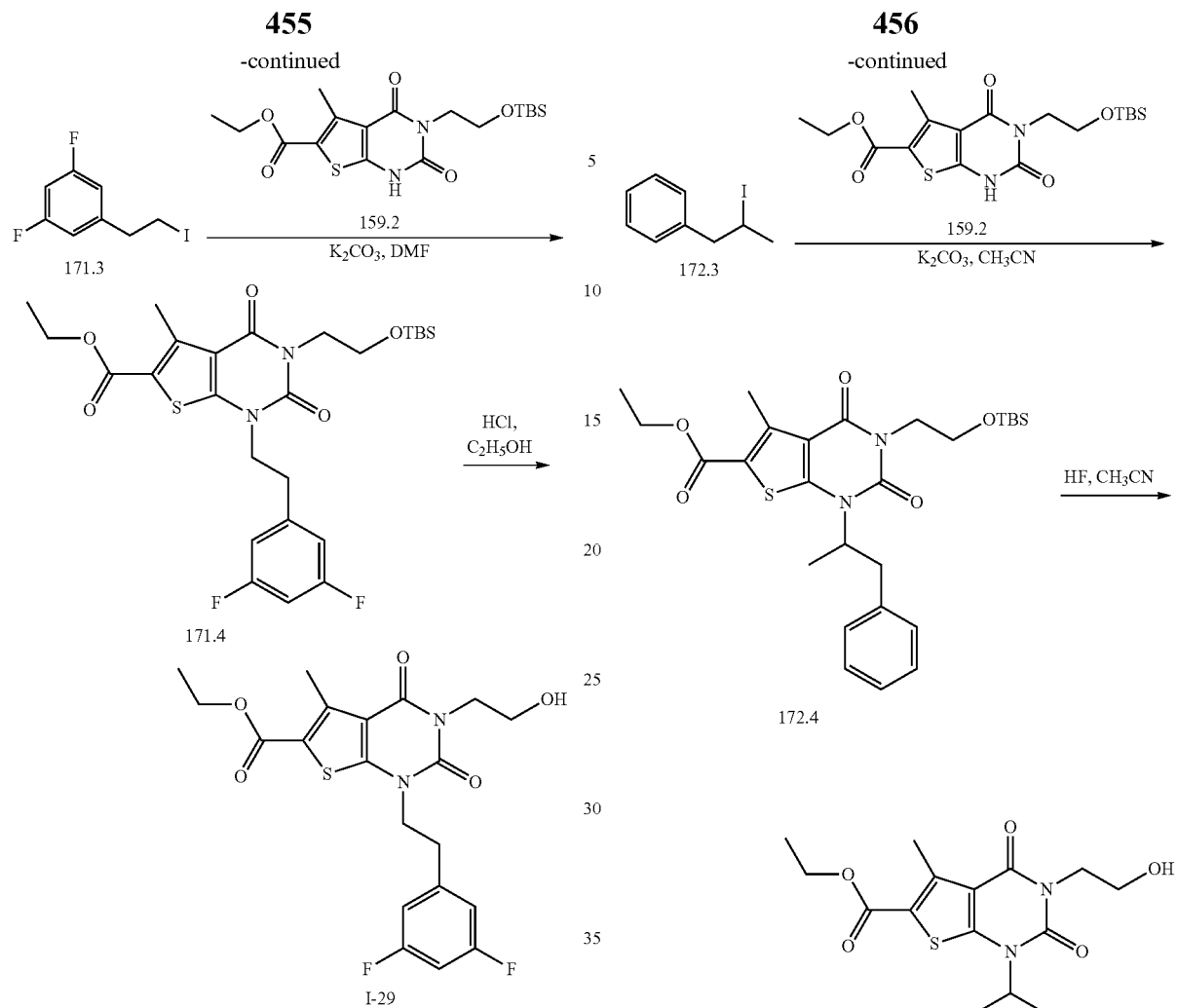

Compound I-29 was prepared from 171.1 and 159.2 in a manner analogous to Compound I-30 (Example 161), except that HCl/ethanol was used in the last step rather than HF/acetonitrile. Isolated 60 mg of an off-white solid in 39% overall yield. MS (ES, m/z): (M+H)+ 439. $^1$H NMR (300 MHz, CDCl$_3$): δ 1.41 (t, J=7.2, 3H), 2.87 (s, 3H), 3.06 (t, J=7.8, 2H), 3.90 (t, J=5.4, 2H), 4.14 (t, J=8.1, 2H), 4.28 (t, J=8.1, 2H), 4.38 (q, J=7.2, 2H), 6.69-6.84 (m, 3H).

Example 172

Synthesis of ethyl 3-(2-hydroxyethyl)-5-methyl-2,4-dioxo-1-(1-phenylpropan-2-yl)-1H-2H,3H,4H-thieno[2,3-d]pyrimidine-6-carboxylate (I-36)

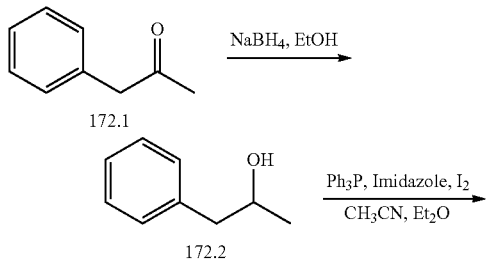

Synthesis of compound 172.2. Into a 100-mL 3-necked round-bottom flask, maintained with an inert atmosphere of nitrogen, was placed 1-phenylpropan-2-one (3 g, 22.36 mmol, 1.00 equiv) and ethanol (50 mL). This was followed by the addition of NaBH$_4$ (1.7 g, 44.94 mmol, 2.01 equiv) at 5° C. The resulting solution was stirred overnight at room temperature. The reaction was then quenched by the addition of 10 mL of ammonium chloride (sat.). The resulting solution was extracted with 2×50 mL of ethyl acetate and the organic layers combined and concentrated under vacuum. The residue was applied onto a silica gel column with ethyl acetate/petroleum ether (1:2). This resulted in 2.8 g (92%) of 1-phenylpropan-2-ol as a colorless oil.

Synthesis of Compound I-36. Compound I-36 was prepared from 172.2 and 159.2 in a manner analogous to the synthesis of I-30 (Example 161). Isolated 23.4 mg of a white solid in 45% overall yield. MS (ES): m/z 417 (M+H)+, 439 (M+Na)+, 480 (M+Na+CH$_3$CN)+. $^1$H NMR (300 MHz, CD$_3$OD): δ 1.36(t, J=7.2, 3H), 1.70 (t, J=6.6, 3H), 2.75 (s, 3H), 3.10-3.17 (m, 1H), 3.56-3.63 (m, 4H), 4.13 (s, 2H), 4.32 (q, J=6.6, 2H), 7.12-7.21 (m, 5H).

2H), 4.01 (t, J=6.6, 2H), 4.25 (q, J=7.2, 3H), 4.79 (t, J=6.0, 1H), 5.10 (s, 2H), 6.01 (s, 2H), 6.85-6.95 (m, 3H).

Example 173

Synthesis of ethyl 1-(2H-1,3-benzodioxol-4-ylm-ethyl)-3-(2-hydroxyethyl)-5-methyl-2,4-dioxo-1H,2H,3H,4H-thieno[2,3-d]pyrimidine-6-carboxylate (I-40)

Example 174

Synthesis of ethyl 3-(2-hydroxyethyl)-1-(1H-indol-5-ylmethyl)-5-methyl-2,4-dioxo-1H,2H,3H,4H-thieno[2,3-d]pyrimidine-6-carboxylate (I-51)

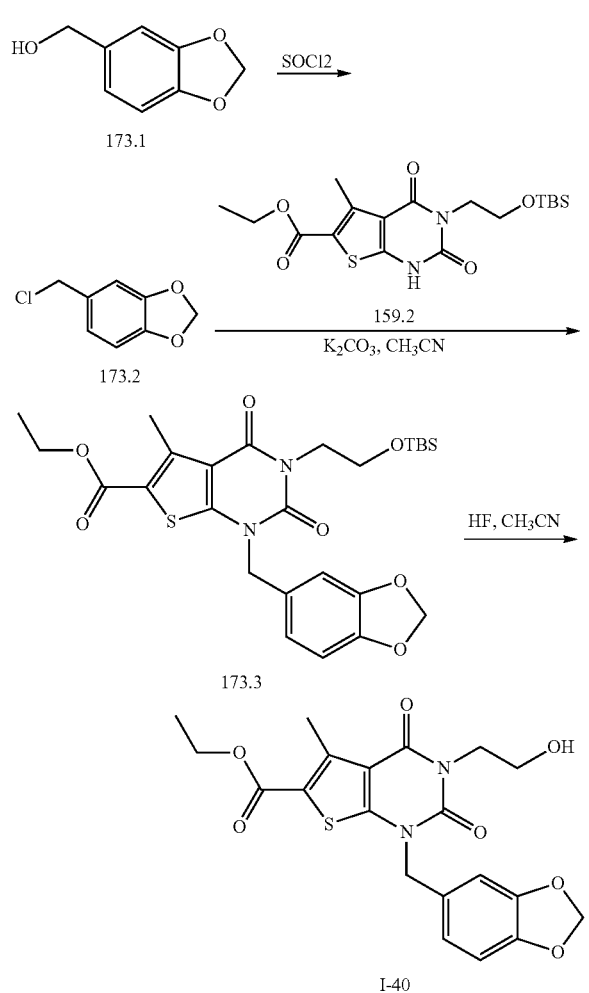

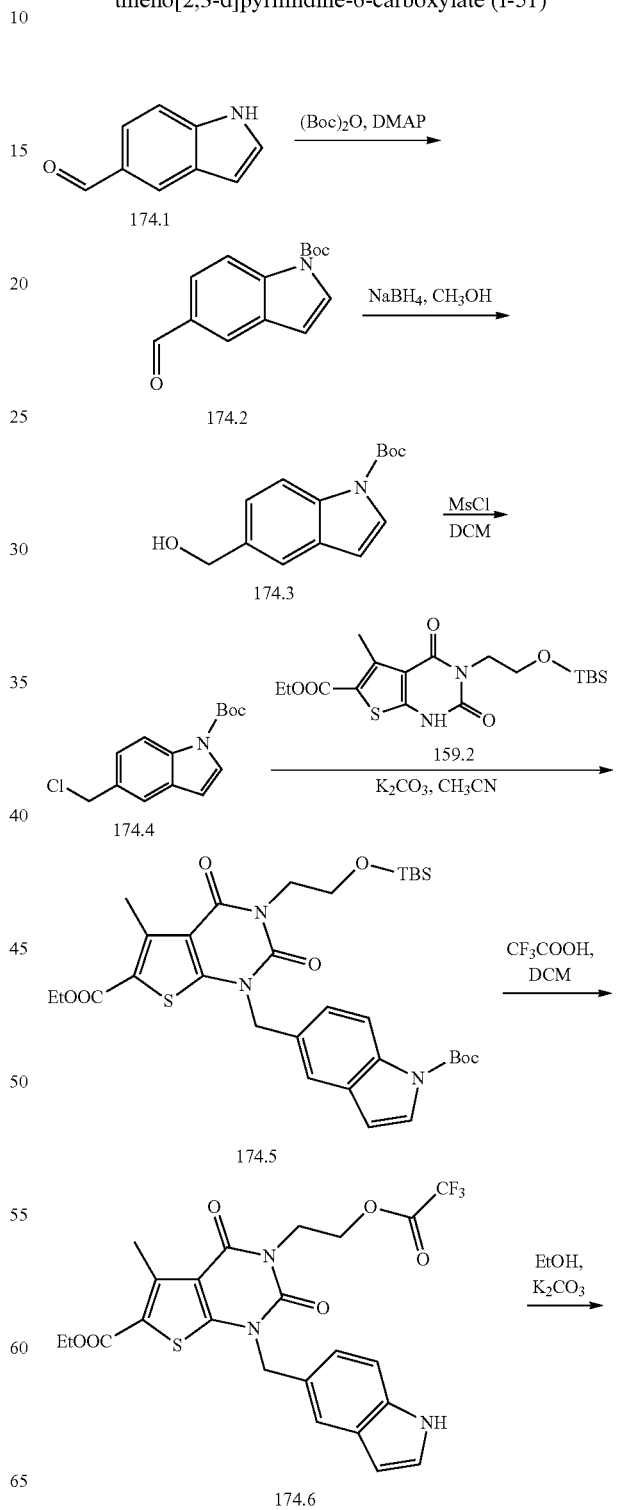

Synthesis of compound 173.2. Into a 50-mL round-bottom flask, purged and maintained with an inert atmosphere of nitrogen, was placed 173.1 (400 mg, 2.63 mmol, 1.00 equiv), thionyl chloride (626 mg, 5.26 mmol, 2.00 equiv) and dichloromethane (20 mL). The resulting solution was stirred for 1 h at room temperature. The resulting mixture was concentrated under vacuum. This resulted in 460 mg (97%) of 173.2 as a yellow oil.

Synthesis of Compound I-40. I-40 was synthesized from 173.2 and 159.2 in a manner consistent with the synthesis of Compound I-30 (Example 161). Isolated 27.5 mg of a white solid in 39% overall yield. MS (ES): m/z 433 (M+H)+, 455 (M+Na)+, 496 (M+Na+CH₃CN)+. ¹H NMR(300 MHz, DMSO-d₆): δ 1.26 (t, J=7.2, 3H), 2.77 (s, 3H), 3.59 (t, J=6.0,

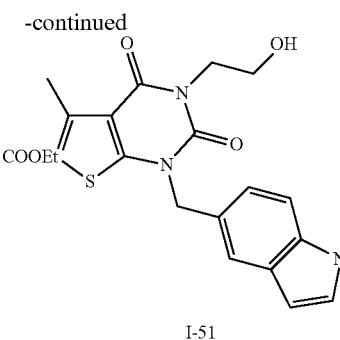

I-51

Synthesis of compound 174.2. Into a 50-mL round-bottom flask was placed tetrahydrofuran (20 mL), 4-dimethylaminopyridine (1.32 g, 10.80 mmol, 1.08 equiv), 1H-indole-5-carbaldehyde (1.45 g, 9.99 mmol, 1.00 equiv) and (Boc)$_2$O (2.18 g, 9.99 mmol, 1.00 equiv). The resulting solution was stirred for 12 h at room temperature. The reaction was then quenched by the addition of 10 mL of water. The resulting solution was extracted with 3×50 mL of ethyl acetate and the organic layers combined and dried over anhydrous sodium sulfate and concentrated under vacuum. This resulted in 2.1 g (86%) of 174.2 as a yellow solid.

Synthesis of compound 174.3. Into a 50-mL round-bottom flask was placed a solution of 174.2 (2.1 g, 8.56 mmol, 1.00 equiv) in methanol (20 mL). Then NaBH$_4$ (740 mg, 19.56 mmol, 2.28 equiv) was added at 0° C. The resulting solution was stirred for 4 h at 0° C. in a water/ice bath. The reaction was then quenched by the addition of 10 mL of water. The resulting solution was extracted with 3×50 mL of ethyl acetate and the organic layers combined and dried over anhydrous sodium sulfate and concentrated under vacuum. This resulted in 1.85 g (87%) of 174.3 as a yellow solid.

Synthesis of compound 174.4. Into a 50-mL round-bottom flask was placed a solution of 174.3 (320 mg, 1.29 mmol, 1.00 equiv) in dichloromethane (20 mL). Then Et$_3$N (0.223 g, 2.21 mmol, 1.70 equiv) and methanesulfonyl chloride (222 mg, 1.94 mmol, 1.50 equiv) were added to the above mixture at 0° C. The resulting solution was stirred for 5 h at 0° C. in a water/ice bath. The reaction was then quenched by the addition of 15 mL of water. The resulting solution was extracted with 3×40 mL of ethyl acetate and the organic layers combined and concentrated under vacuum. The residue was applied onto a silica gel column with ethyl acetate/petroleum ether (1:4). Purification afforded 0.112 g (33%) of 174.4 as a yellow oil.

Synthesis of compound 174.5. Into a 25-mL round-bottom flask was placed CH$_3$CN (5 mL), NaI (0.005 g), potassium carbonate (105 mg, 0.76 mmol, 2.02 equiv), 159.2 (155 mg, 0.38 mmol, 1.00 equiv) and 174.4 (100 mg, 0.38 mmol, 1.00 equiv). The resulting solution was stirred overnight at 50° C. in an oil bath. The reaction was then quenched by the addition of 40 mL of water. The resulting solution was extracted with 3×60 mL of ethyl acetate and the organic layers combined and dried over anhydrous sodium sulfate and concentrated under vacuum. The residue was applied onto a silica gel column with ethyl acetate/petroleum ether (1:5). Purification afforded 0.143 g (59%) of 174.5 as a white solid.

Synthesis of compound 174.6. Into a 25-mL round-bottom flask was placed dichloromethane (10 mL), 174.5 (143 mg, 0.22 mmol, 1.00 equiv) and CF$_3$COOH (2 mL). The resulting solution was stirred overnight at room temperature and then concentrated under vacuum. This resulted in 0.126 g (crude) of crude 174.6 as a yellow solid.

Synthesis of Compound I-51. Into a 25-mL round-bottom flask was placed ethanol (5 mL), potassium carbonate (276 mg, 2.00 mmol, 8.30 equiv) and I-51 (126 mg, 0.24 mmol, 1.00 equiv). The resulting solution was stirred overnight at room temperature, concentrated under vacuum and diluted with 50 mL of H$_2$O. The resulting solution was extracted with 3×50 mL of ethyl acetate and the organic layers combined, dried over anhydrous sodium sulfate and concentrated under vacuum. The crude product was purified by re-crystallization from ethyl acetate:hexane(1/10). This resulted in 0.043 g (42%) of I-51 as a white solid. MS (ES): m/z 428 (M+H)$^+$. $^1$H NMR (CDCl$_3$, 300 MHz): δ 1.27 (t, 3H), 2.85 (s, 3H), 3.96 (m, 2H), 4.34 (m, 4H), 5.29 (s, 2H), 6.56 (s, 1H), 7.25 (m, 2H), 7.38 (m, 1H), 7.70 (s, 1H), 8.23 (s,1H).

Example 175

Synthesis of 3-[2-[(tert-butyldimethylsilyl)oxy]ethyl]-5-methyl-2,4-dioxo-1-(2-phenylethyl)-1H,2H,3H,4H-thieno[2,3-d]pyrimidine-6-carboxylic acid (I-5)

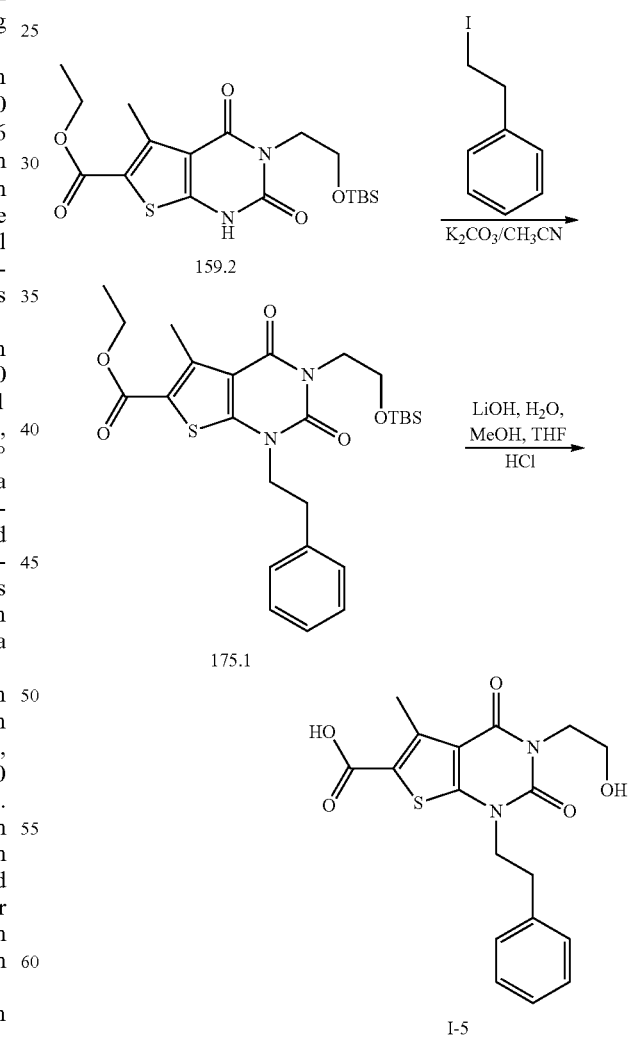

Synthesis of compound 175.1. Into a 100-mL round-bottom flask was placed a solution of 159.2 (1.2 g, 2.91 mmol, 1.00 equiv) in CH$_3$CN (50 mL), (2-iodoethyl)benzene (1.35 g, 5.82 mmol, 2.00 equiv) and potassium carbonate (1.2 g). The resulting solution was heated to reflux overnight. The resulting mixture was concentrated under vacuum. The residue was applied onto a silica gel column with ethyl acetate/petroleum ether (1:20). Purification afforded 1.5 g (95%) of 175.1 as a white solid.

Synthesis of Compound I-5. Into a 100-mL round-bottom flask was placed 175.1 (500 mg, 0.9676 mmol, 1.00 equiv), tetrahydrofuran (5 mL), methanol (5 mL), water (5 mL) and LiOH (0.07 g). The resulting solution was stirred overnight at room temperature. The resulting mixture was concentrated under vacuum. The pH value of the solution was adjusted to 1 with hydrogen chloride. The mixture was stirred for 1 h at room temperature. The solids were collected by filtration. The filter cake was washed with ethanol. 300 mg (63%) of I-5 were obtained as a white solid. MS (ES): m/z 375 (M+1)$^+$. $^1$H NMR (300 MHz, DMSO-d$_6$): δ 2.74 (s, 3H), 3.00 (t, J=7.2, 2H), 3.51 (t, J=6.3, 2H), 3.96 (t, J=6.6, 2H), 4.09 (t, J=7.2, 2H), 4.78 (s, 1H), 7.20-7.33 (m, 5H).

Example 176

Synthesis of methyl 3-(2-hydroxyethyl)-5-methyl-2,4-dioxo-1-(2-phenylethyl)-1H,2H,3H,4H-thieno[2,3-d]pyrimidine-6-carboxylate (I-37)

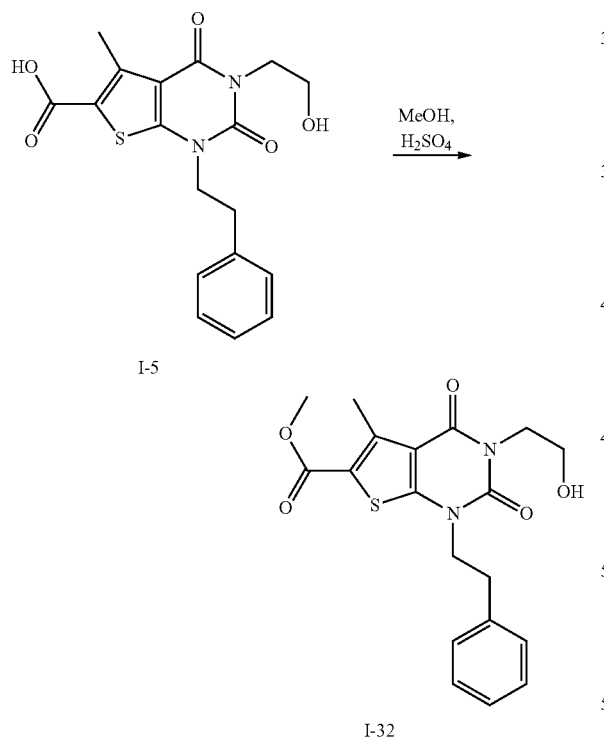

Into a 100-mL round-bottom flask was placed I-5 (200 mg, 0.53 mmol, 1.00 equiv), methanol (20 mL) and sulfuric acid (0.1 mL). The resulting solution was stirred for 4 days at 50° C. The reaction was then quenched by the addition of 5 mL of water. The pH value of the solution was adjusted to >7 with sodium carbonate (aq.). The resulting solution was extracted with 3×20 mL of ethyl acetate and the organic layers combined and concentrated under vacuum. The crude product (200 mg) was purified by preparative HPLC under the following conditions (SHIMADZU): column: SunFire Prep C18, 19*150 mm 5 um; mobile phase: water with 0.05% NH$_4$HCO$_3$ and CH$_3$CN (8.0% CH$_3$CN up to 55.0% in 20 min); detector: 254/220 nm. 20.2 mg (10%) of I-32 were obtained as a white solid. MS (ES): m/z 389 (M+H)$^+$. $^1$H NMR (300 MHz, CD$_3$OD): δ 2.83(s, 3H), 3.10 (t, J=7.5, 2H), 3.74 (t, J=6.3, 2H), 3.87 (s, 3H), 4.14-4.20 (m, 4H), 7.22-7.30 (m, 5H).

Example 177

Synthesis of propyl 3-(2-hydroxyethyl)-5-methyl-2,4-dioxo-1-(2-phenylethyl)-1H,2H,3H,4H-thieno[2,3-d]pyrimidine-6-carboxylate (I-41)

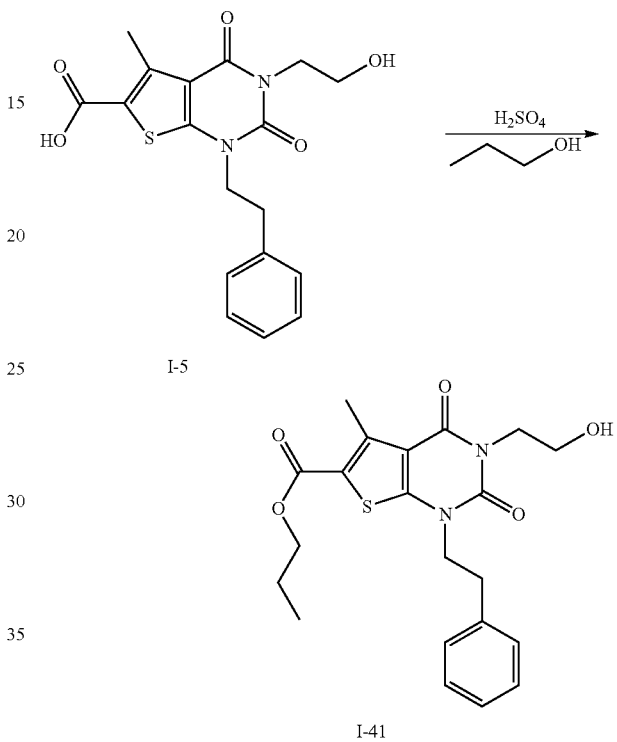

Compound I-41 was prepared from I-5 and 1-propanol in a manner analogous to the synthesis of Compound I-32 (Example 176). This resulted in 4.7 mg (2%) of I-41 as a white solid. MS (ES): m/z 417 (M+H)$^+$. $^1$H NMR (400 MHz, CD$_3$OD): δ 1.05 (t, J=7.6, 3H), 1.78 (m, J=7.2, 2H), 2.83 (s, 3H), 3.11 (t, J=7.6, 2H), 3.75 (t, J=6.8, 2H), 4.15-4.21 (m, 4H), 4.25 (t, J=6.4, 2H), 7.23-7.32 (m, 5H).

Example 178

Synthesis of 2-hydroxyethyl 3-(2-hydroxyethyl)-5-methyl-2,4-dioxo-1-(2-phenylethyl)-1H,2H,3H,4H-thieno[2,3-d]pyrimidine-6-carboxylate (I-42)

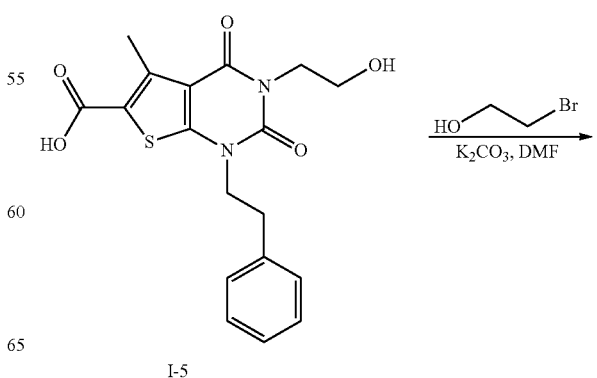

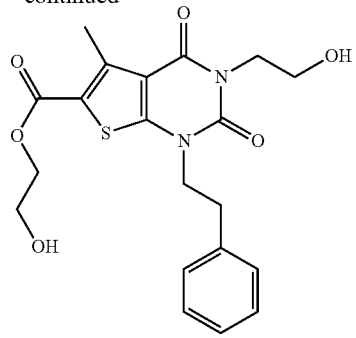

I-42

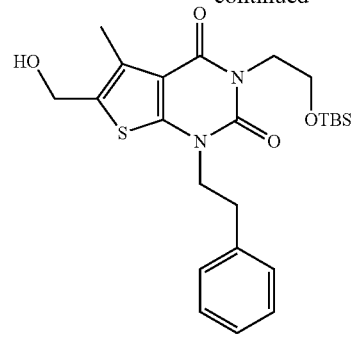

179.1

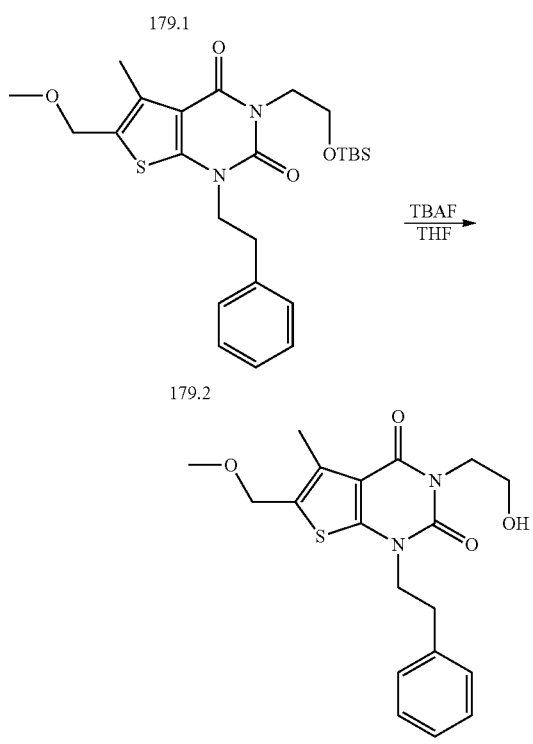

Into a 100-mL 3-necked round-bottom flask was placed I-5 (200 mg, 0.53 mmol, 1.00 equiv), potassium carbonate (221 mg, 1.60 mmol, 2.99 equiv), 2-bromoethan-1-ol (100 mg, 0.80 mmol, 1.50 equiv) and N,N-dimethylformamide (10 mL). The resulting solution was stirred overnight at 80° C. The reaction mixture was cooled. The resulting mixture was concentrated under vacuum. The crude product (200 mg) was purified by preparative HPLC under the following conditions (SHIMADZU): column: SunFire Prep C18, 19*150 mm 5 μm; mobile phase: water with 0.05% NH$_4$HCO$_3$ and CH$_3$CN (6.0% CH$_3$CN up to 60.0% in 14 min); detector: 254/220 nm. This resulted in 30.7 mg (14%) of I-42 as a white solid. MS (ES): m/z 419 (M+H)$^+$, 441 (M+Na)$^+$, 482 (M+Na+ CH$_3$CN)$^+$. $^1$H NMR (400 MHz, DMSO-d$_6$): δ 2.77 (s, 3H), 3.01 (t, J=7.6, 2H), 3.52 (t, J=6.0, 2H), 3.68 (t, J=4.8, 2H), 4.11 (t, J=7.6, 2H), 3.02 (t, J=7.6, 2H), 4.26 (t, J=4.8, 2H), 3.02 (t, J=7.6, 2H), 4.78 (t, 1H), 4.92 (t, 1H), 7.24-7.33 (m, 5H).

Example 179

Synthesis of 3-(2-hydroxyethyl)-6-(methoxymethyl)-5-methyl-1-(2-phenylethyl)-1H,2H,3H,4H-thieno[2,3-d]pyrimidine-2,4-dione (I-39)

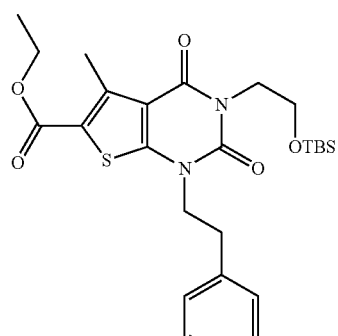

175.1

Synthesis of compound 179.1. Into a 100-mL 3-necked round-bottom flask, purged and maintained with an inert atmosphere of nitrogen, was placed a solution 175.1 (1 g, 1.94 mmol, 1.00 equiv) in tetrahydrofuran (20 mL). This was followed by the addition of LiAlH$_4$ (100 mg, 2.63 mmol, 1.36 equiv) at −78° C. The resulting solution was stirred for 2 h at room temperature. The reaction was then quenched by the addition of 50 mL of NH$_4$Cl (aq.). The resulting solution was extracted with 3×50 mL of ethyl acetate and the organic layers combined and concentrated under vacuum. The residue was applied onto a silica gel column with ethyl acetate/petroleum ether (1:2). This resulted in 0.5 g (54%) of 179.1 as a light yellow solid.

Synthesis of compound 179.2. Into a 10-mL sealed tube was placed a solution of 179.1 (150 mg, 0.31 mmol, 1.00 equiv), N,N-dimethylformamide (5 mL), and sodium hydride (19 mg, 0.55 mmol, 1.76 equiv, 70%). The resulting solution was stirred for 10 min at room temperature. This was followed by the addition of iodomethane (67 mg, 0.47 mmol, 1.50 equiv) dropwise with stirring. The resulting solution was allowed to react, with stirring, for an additional 2 h at room temperature. The reaction was then quenched by the addition of 5 mL of NH₄Cl(aq.). The resulting solution was extracted with 3×10 mL of ethyl acetate and the organic layers combined and concentrated under vacuum. The residue was applied onto a silica gel column with ethyl acetate/petroleum ether (1:10). Purification afforded 90 mg (59%) of 179.2 as a white solid.

Synthesis of Compound I-39. Into a 10-mL sealed tube was placed a solution of 179.2 (90 mg, 0.18 mmol, 1.00 equiv) in tetrahydrofuran (2.5 mL) and TBAF (200 mg). The resulting solution was stirred overnight at room temperature. The resulting mixture was concentrated under vacuum. The residue was applied onto a silica gel column with ethyl acetate/petroleum ether (1:2). Purification afforded 34.7 mg (50%) of I-39 as a white solid. MS (ES): m/z 375 (M+H)⁺, 397 (M+Na)⁺.

¹H NMR (300 MHz, DMSO-d₆): δ 2.37 (s, 3H), 2.98 (t, J=7.5, 2H), 3.26 (s, 3H), 3.50 (q, J=6.6, 2H), 3.96 (t, J=6.6, 2H), 4.06 (t, J=7.5, 2H), 4.51 (s, 2H), 4.76 (t, J=6.0, 1H), 7.20-7.33 (m, 5H).

Example 180

Synthesis of 6-(ethoxymethyl)-3-(2-hydroxyethyl)-5-methyl-1-(2-phenylethyl)-1H,2H,3H,4H-thieno[2,3-d]pyrimidine-2,4-dione (I-38)

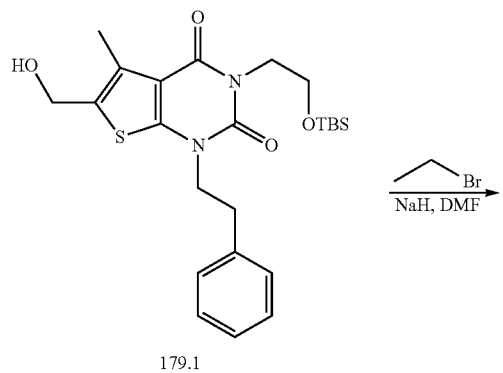

179.1

NaH, DMF

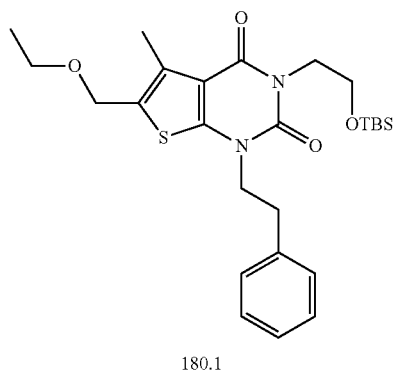

180.1

TBAF
THF

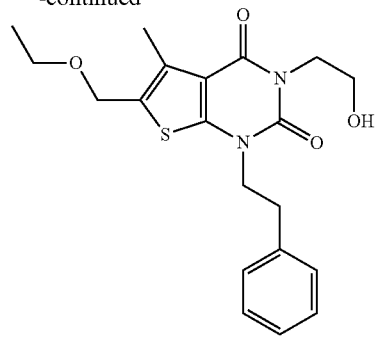

I-38

Compound I-38 was prepared from 179.1 and ethyl bromide in a manner analogous to the synthesis of Compound I-39 (Example 179). Isolated 50.5 mg of a white solid in 42% overall yield. MS (ES): m/z 389 (M+H)⁺, 411 (M+Na)⁺, 452 (M+Na+CH₃CN)⁺. ¹H NMR (300 MHz, DMSO-d₆): δ 1.13 (t, J=7.2, 3H), 2.35 (s, 3H), 2.98 (t, J=7.5, 2H), 3.42-3.51 (m, 4H), 4.14-4.20 (m, 4H), 4.54 (s, 2H), 4.74 (s, 1H), 7.20-7.32 (m, 5H).

Example 181

Synthesis of 2-[1-[2-(2,6-difluorophenyl)ethyl]-6-(ethoxycarbonyl)-5-methyl-2,4-dioxo-1H,2H,3H,4H-thieno[2,3-d]pyrimidin-3-yl]acetic acid (I-33)

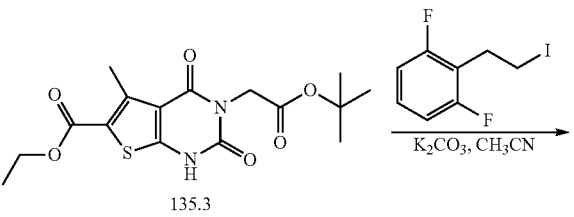

135.3

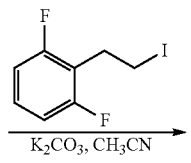
K₂CO₃, CH₃CN

CF₃COOH
DCM 181.1

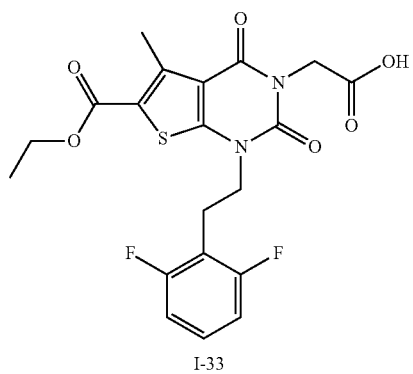

I-33

Compound I-33 was prepared from 135.3 and 1,3-difluoro-2-(2-iodoethyl)benzene in a manner analogous to the synthesis of 136.2. Isolated 36 mg of a white solid in 30% overall yield. MS (ES): m/z 453 (M+H)+. $^1$H NMR (300 MHz, CD$_3$OD): δ 1.32-1.40 (t, 3H), 2.82 (s, 3H), 3.21-3.26 (t,2H), 4.22-4.27 (t, 2H), 4.31-4.38 (q, 2H), 4.67 (s, 2H), 6.91-6.96 (t, 2H), 7.26-7.31 (m, 1H). $^{19}$F-NMR (300 MHz, CD$_3$OD): δ 117.76.

Example 182

Synthesis of 2-[6-(ethoxycarbonyl)-5-methyl-2,4-dioxo-1-(2-phenylethyl)-1H,2H,3H,4H-thieno[2,3-d]pyrimidin-3-yl]propanoic acid (I-56)

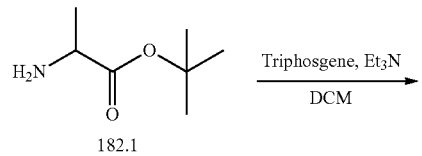

182.1

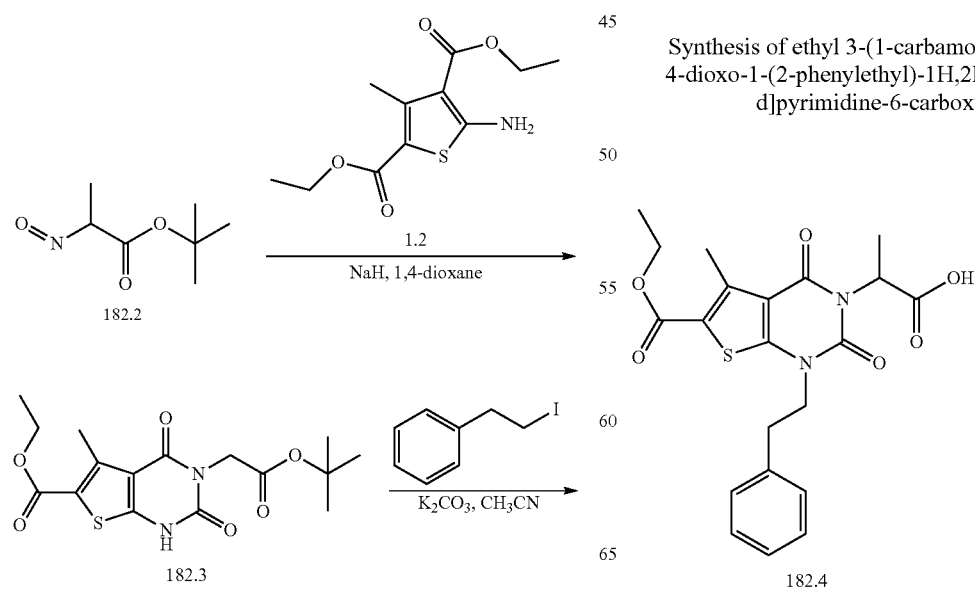

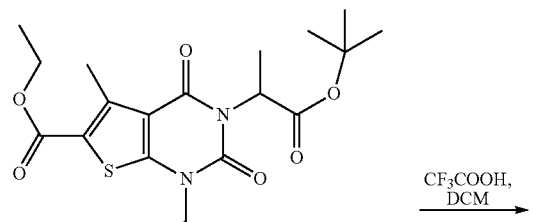

182.4

I-56

Compound I-56 was prepared from 182.1 and 1.2 in a manner analogous to compound 136.2 (Examples 135 and 136). Isolated 1.4 g of a white solid in 42% overall yield. MS (ES): m/z 431 (M+H)+. $^1$H NMR (400 MHz, DMSO-d$_6$): δ 1.30 (t, J=7.2, 3H), 1.41 (d, J=6.8, 3H), 2.75 (s, 3H), 3.01 (t, J=7.2, 2H), 4.13 (t, J=7.2, 2H), 4.29 (q, J=7.2, 2H), 5.39 (q, J=6.8, 1H), 7.20-7.30 (m, 5H), 12.70 (s, 1H).

Example 183

Synthesis of ethyl 3-(1-carbamoylethyl)-5-methyl-2,4-dioxo-1-(2-phenylethyl)-1H,2H,3H,4H-thieno[2,3-d]pyrimidine-6-carboxylate (I-69)

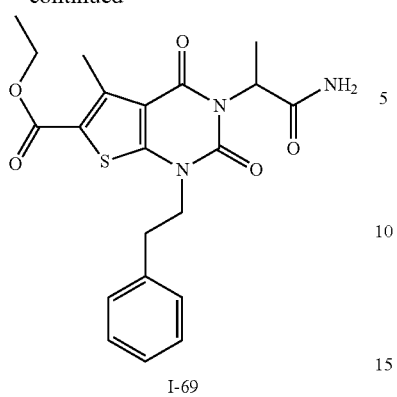

I-69

Into a 100-mL round-bottom flask was placed 4-dimethylaminopyridine (82 mg, 0.67 mmol, 1.44 equiv), 182.4 (200 mg, 0.46 mmol, 1.00 equiv), NH$_4$Cl (1 g, 18.70 mmol, 40.24 equiv), EDCI (130 mg, 0.68 mmol, 1.46 equiv), CH$_3$CN (10 mL), ethyl acetate (10 mL) and HOBT (100 mg, 0.74 mmol, 1.59 equiv). The resulting solution was stirred for 5 h at room temperature. The reaction was then quenched by the addition of 20 mL of water. The resulting solution was extracted with 3×50 mL of ethyl acetate and the organic layers combined and dried over anhydrous magnesium sulfate and concentrated under vacuum. The residue was applied onto a silica gel column with dichloromethane/methanol (20:1). This resulted in 0.12 g (60%) of I-69 as a white solid. MS (ES): m/z 430 (M+H)$^+$. $^1$H NMR (400 MHz, DMSO-d$_6$): δ 1.25 (t, J=7.2 Hz, 3H), 1.36 (d, J=6.8 Hz, 3H), 2.68 (s, 3H), 2.97 (t, J=7.2 Hz, 2H), 4.07 (t, J=7.2 Hz, 2H), 4.23 (q, J=7.2 Hz, 2H), 5.30 (q, J=7.2 Hz, 1H), 7.15-7.24 (m, 5H).

Example 184

Synthesis of ethyl 3-(1-carbamoyl-1-methylethyl)-5-methyl-2,4-dioxo-1-(2-phenylethyl)-1H,2H,3H,4H-thieno[2,3-d]pyrimidine-6-carboxylate (I-107)

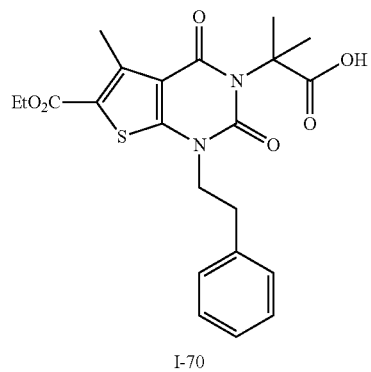

I-70

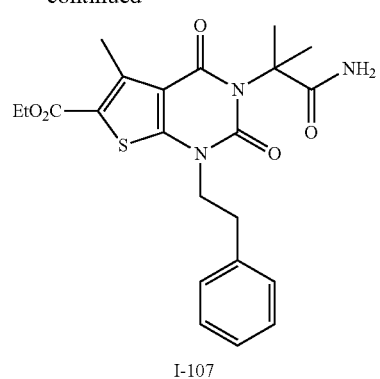

I-107

Compound I-107 was prepared from I-70 (Example 120) and ammonium chloride in a manner analogous to the synthesis of Compound I-121 (Example 4). Isolated 70 mg of a white solid in 70% yield. MS (ES): m/z 466 (M+Na)$^+$. $^1$H NMR (300 MHz, CD$_3$OD): δ 1.37 (t, J=7.2, 3H), 1.80 (s, 6H), 2.76 (s, 3H), 3.07 (t, J=7.2, 2H), 4.12 (t, J=7.2, 2H), 4.33 (q, J=7.2, 2H), 7.22-7.34 (m, 5H).

Example 185

Synthesis of ethyl 3-(2-hydroxypropyl)-5-methyl-2,4-dioxo-1-(2-phenylethyl)-1H,2H,3H,4H-thieno[2,3-d]pyrimidine-6-carboxylate (I-62)

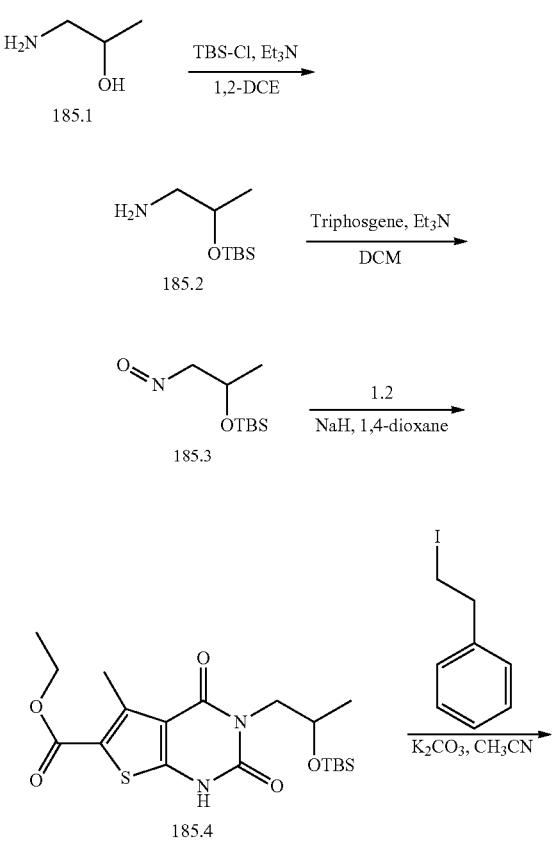

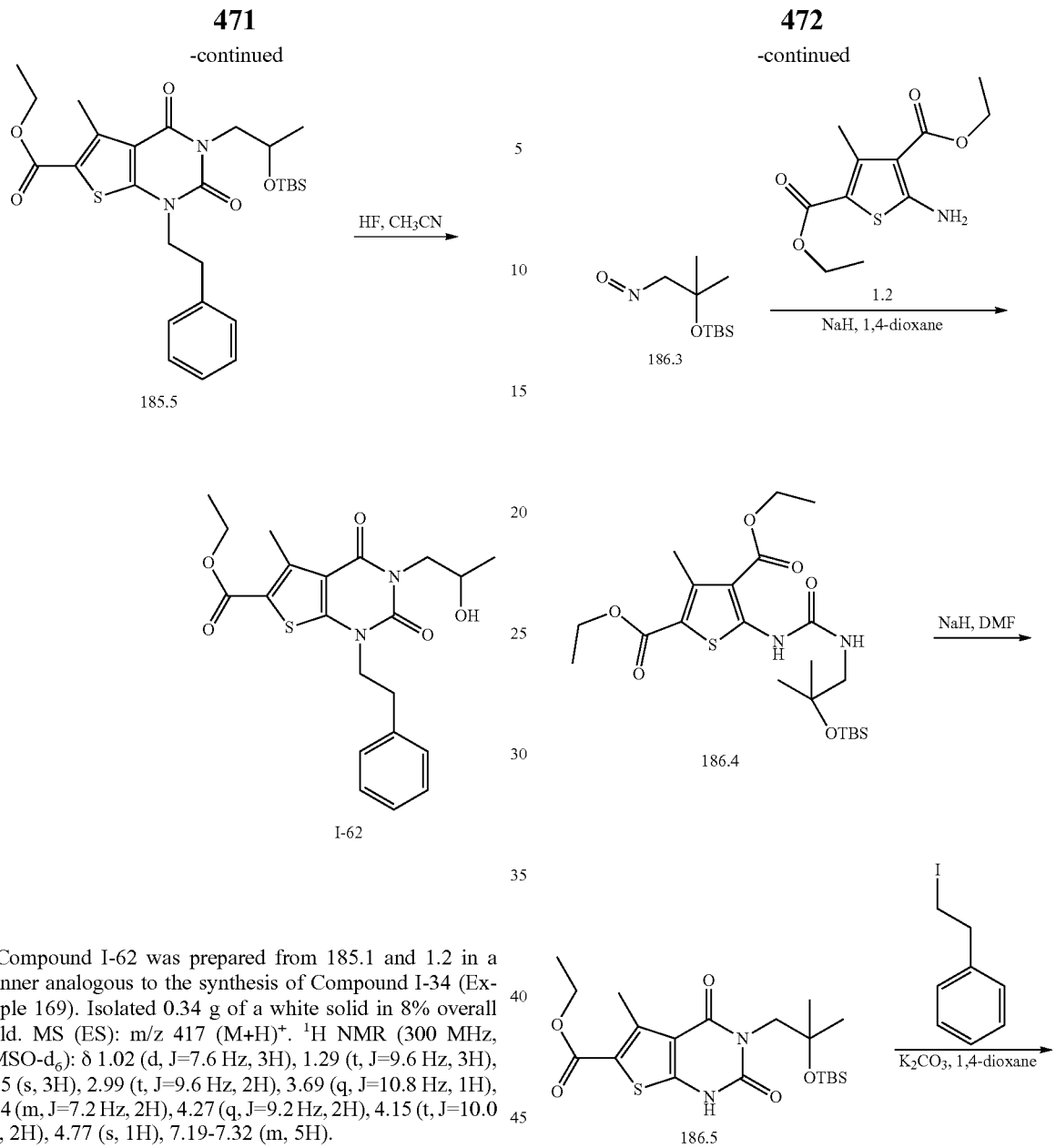
Compound I-62 was prepared from 185.1 and 1.2 in a manner analogous to the synthesis of Compound I-34 (Example 169). Isolated 0.34 g of a white solid in 8% overall yield. MS (ES): m/z 417 (M+H)+. $^1$H NMR (300 MHz, DMSO-$d_6$): δ 1.02 (d, J=7.6 Hz, 3H), 1.29 (t, J=9.6 Hz, 3H), 2.75 (s, 3H), 2.99 (t, J=9.6 Hz, 2H), 3.69 (q, J=10.8 Hz, 1H), 3.94 (m, J=7.2 Hz, 2H), 4.27 (q, J=9.2 Hz, 2H), 4.15 (t, J=10.0 Hz, 2H), 4.77 (s, 1H), 7.19-7.32 (m, 5H).
Example 186
Synthesis of ethyl 3-(2-hydroxy-2-methylpropyl)-5-methyl-2,4-dioxo-1-(2-phenylethyl)-1H,2H,3H,4H-thieno[2,3-d]pyrimidine-6-carboxylate (I-79)
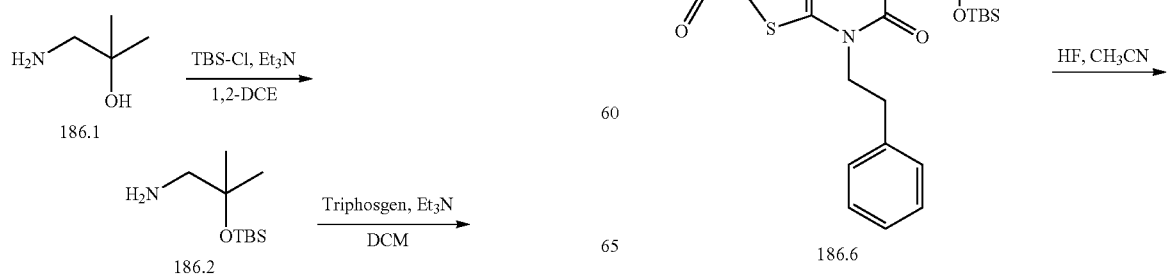

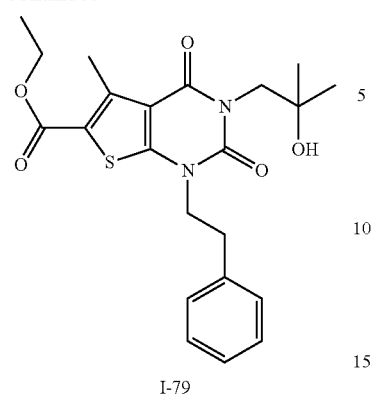

I-79

Compound I-79 was prepared from 186.1 and 1.2 in a manner analogous to the synthesis of Compound I-34 (Example 169). Isolated 80 mg of a white solid in 10% overall yield. MS (ES): m/z 431 (M+H)+. $^1$H NMR (400 MHz, DMSO-$d_6$): δ 1.07 (s, 6H), 1.30 (t, J=7.2 Hz, 3H), 2.76 (s, 3H), 3.01 (t, J=7.2 Hz, 2H), 3.96 (s, 2H), 4.13 (t, J=7.2 Hz, 2H), 4.29 (q, 2H), 4.41 (s, 1H), 7.20-7.32 (m, 5H).

Example 187

Synthesis of 2-[6-(ethoxycarbonyl)-1-[2-(4-iodophenyl)ethyl]-5-methyl-2,4-dioxo-1H,2H,3H,4H-thieno[2,3-d]pyrimidin-3-yl]acetic acid (I-53)

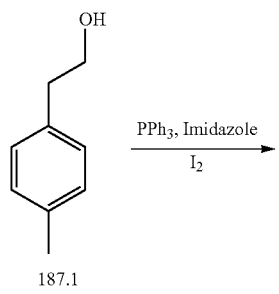

187.1

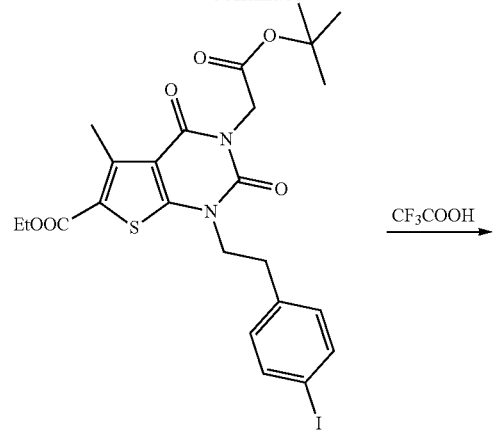

187.3

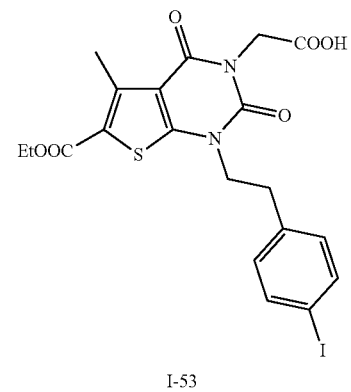

I-53

Synthesis of compound 187.2. 187.2 was prepared from 187.1 in a manner analogous to the synthesis of 160.2. Isolated 2.23 g of a white solid in 78% yield.

Synthesis of Compound I-53. I-53 was prepared from 187.2 and 135.3 in a manner analogous to the synthesis of 136.2. Isolated 0.134 g of an off-white solid in 57% overall yield from 135.3. MS (ES): m/z 543 (M+H)+. $^1$H NMR (CDCl$_3$, 400 MHz): δ 1.43 (t, 3H), 2.88 (s, 3H), 3.04 (m, 2H), 4.14 (m, 2H), 4.38 (m, 2H), 4.85 (s, 2H), 7.03 (d, J=8.4 Hz, 2H), 7.66 (d, J=8.4 Hz, 2H).

Example 188

Synthesis of 2-(1-(4-deuterophenethyl)-6-(ethoxycarbonyl)-5-methyl-2,4-dioxo-1,2-dihydrothieno[2,3-d]pyrimidin-3(4H)-yl)acetic acid (I-66)

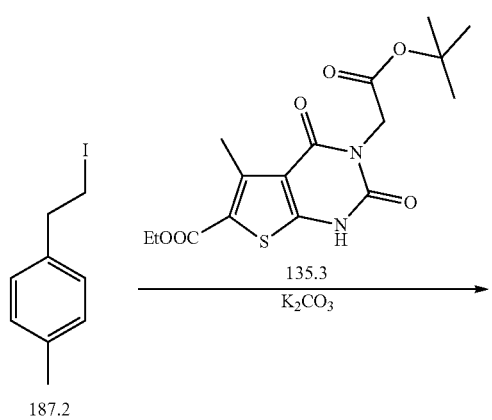

187.2

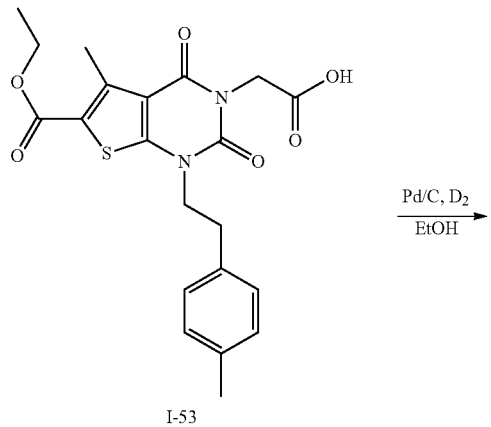

I-53

475

-continued

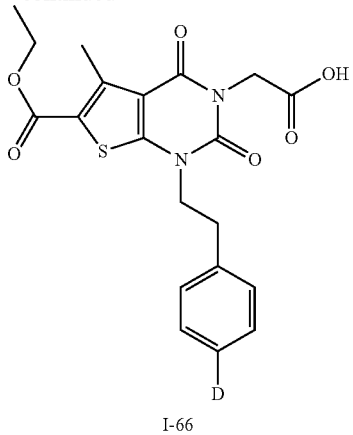

I-66

Into a 50-mL round-bottom flask was placed ethanol (20 mL), I-53 (Example 187; 73 mg, 0.13 mmol, 1.00 equiv). This was followed by the addition of 10% palladium on carbon (100 mg) under nitrogen. The flask was evacuated and flushed three times with nitrogen, followed by flushing with deuterium gas. The mixture was stirred overnight at room temperature under an atmosphere of deuterium gas. The solids were filtered out. The resulting mixture was concentrated under vacuum. The crude product (80 mg) was purified by preparative HPLC under the following conditions (SHIMADZU): column: SunFire Prep C18, 19*150 mm 5 μm; mobile phase: water with 0.05% $NH_4HCO_3$ and $CH_3CN$ (5.0% $CH_3CN$ up to 53.0% in 16 min); detector: 254/220 nm. This resulted in 0.04 g (71%) of I-66 as a white solid. MS (ES): m/z (M+H)$^+$ 418.

$^1$H NMR (300 MHz, CDCl$_3$): δ 1.41 (t, J=7.2, 3H), 2.87 (s, 3H), 3.09 (t, J=8.1, 2H), 4.16 (t, 2H), 4.38 (q, J=7.2, 2H), 4.82 (s, 2H), 7.26-7.35 (m, 4H).

Example 189

Synthesis of 2-[1-[2-(2-bromophenyl)ethyl]-6-(ethoxycarbonyl)-5-methyl-2,4-dioxo-1H,2H,3H,4H-thieno[2,3-d]pyrimidin-3-yl]acetic acid (I-54)

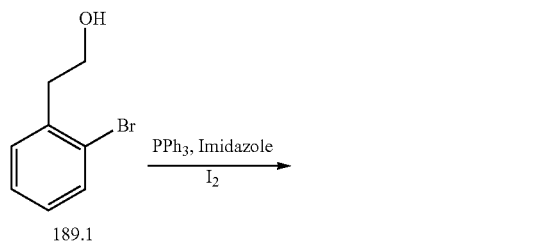

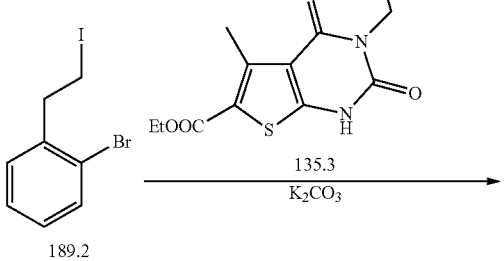

476

-continued

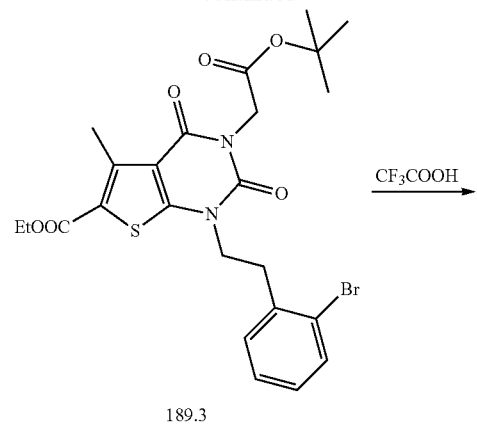

189.3

$\xrightarrow{CF_3COOH}$

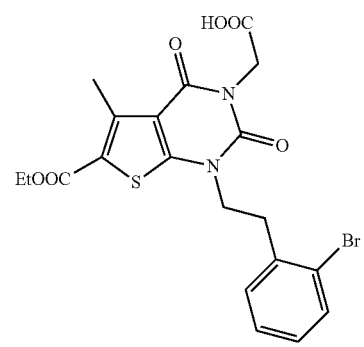

I-54

Compound I-54 was prepared from 189.1 and 135.3 in a manner analogous to the synthesis of I-53 (Example 187). Isolated 0.2 g of a white solid in 38% overall yield from 135.3. MS (ES): m/z 495 (M+H)$^+$. $^1$H NMR (CDCl$_3$, 300 MHz): δ 1.38 (t, 3H), 2.85 (s, 3H), 3.24 (t, 2H), 4.24 (t, 2H), 4.37 (t, 2H), 4.81 (s, 2H), 7.11 (m, 1H), 7.20 (m, 2H), 7.54 (m, 1H).

Example 190

Synthesis of 2-[1-[2-(1,3-benzothiazol-2-yl)ethyl]-6-(ethoxycarbonyl)-5-methyl-2,4-dioxo-1H,2H,3H,4H-thieno[2,3-d]pyrimidin-3-yl]acetic acid (I-84)

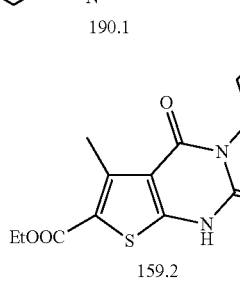

190.1

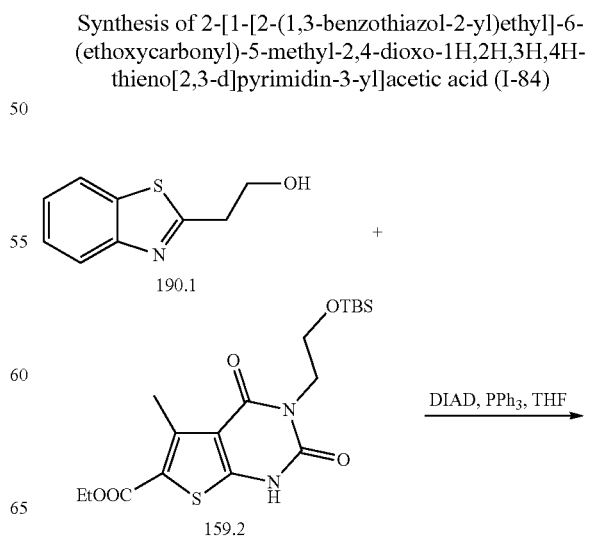

159.2

$\xrightarrow{DIAD, PPh_3, THF}$

-continued

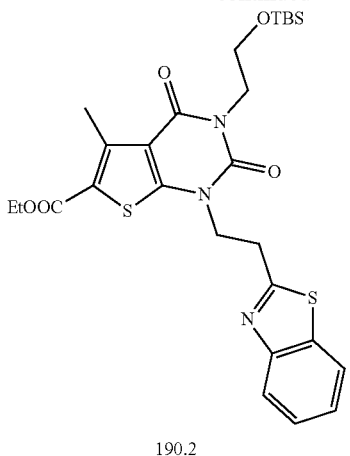

190.2

HF, CH₃CH →

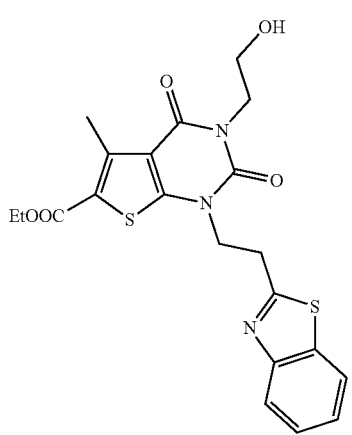

190.3

Dess-Martin Reagent
DCM →

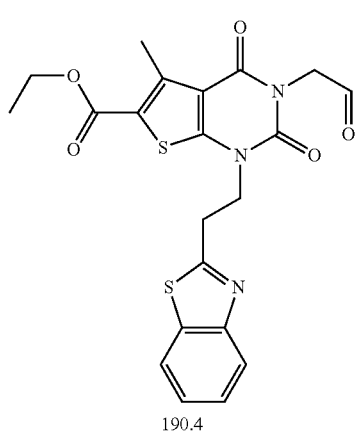

190.4

KMnO₄
Acetone, H₂O →

-continued

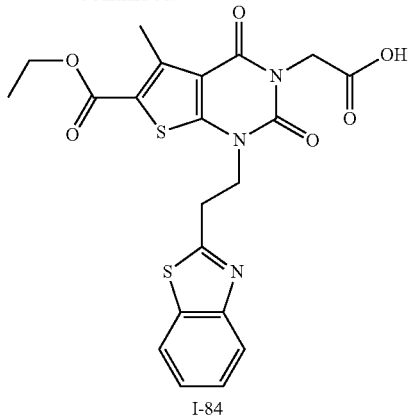

I-84

Synthesis of compound 190.2. Into a 25-mL round-bottom flask flushed with N₂ was placed tetrahydrofuran (5 mL), 2-(1,3-benzothiazol-2-yl)ethan-1-ol (358 mg, 2.00 mmol, 2.00 equiv), PPh₃ (524 mg, 2.00 mmol, 2.00 equiv), DIAD (292 mg, 1.44 mmol, 1.45 equiv) and 159.2 (412 mg, 1.00 mmol, 1.00 equiv). The resulting solution was stirred overnight at room temperature. The reaction was then quenched by the addition of 50 mL of water. The resulting solution was extracted with 3×50 mL of ethyl acetate and the organic layers combined, dried over anhydrous sodium sulfate and concentrated under vacuum. The residue was applied onto a silica gel column with ethyl acetate/petroleum ether (1:10). This resulted in 0.350 g (61%) of 190.2 as a white solid.

Synthesis of compound 190.3. Into a 50-mL round-bottom flask was placed CH₃CN (15 mL), 190.2 (352 mg, 0.61 mmol, 1.00 equiv) and HF (5 mL). The resulting solution was stirred for 2 h at room temperature. The reaction was then quenched by the addition of 20 mL of sodium bicarbonate (sat.). The resulting solution was extracted with 3×50 mL of ethyl acetate and the organic layers combined and dried over anhydrous sodium sulfate and concentrated under vacuum. The crude product (50 mg) was purified by preparative HPLC under the following conditions (SHIMADZU): column: SunFire Prep C18, 19*150 mm 5 μm; mobile phase: water with 0.05% TFA and CH₃CN (12.0% CH₃CN up to 58.0% in 10 min); detector: 254/220 nm. 142 mg product was obtained. This resulted in 14.7 mg (5%) of 190.3 as a white solid. MS (ES): m/z 460 (M+H)⁺. ¹H NMR (CDCl₃, 400 MHz): δ 1.39 (m, 3H), 2.89 (s, 3H), 3.62 (m, 2H), 3.90 (m, 2H), 4.28 (m, 2H), 4.36 (m, 2H), 4.53 (m, 2H), 7.42 (m, 1H), 7.49 (m, 1H), 7.88 (d, J=8.0 Hz, 1H), 8.01 (d, J=8.0 Hz, 1H).

Synthesis of compound 190.4. Into a 50-mL round-bottom flask was placed 190.3 (74 mg, 0.16 mmol, 1.00 equiv), dichloromethane (10 mL) and Dess-Martin reagent (740 mg, 1.75 mmol, 10.84 equiv). The resulting solution was stirred overnight at 40° C. in an oil bath. The solids were filtered out. The filtrate was concentrated under vacuum. The residue was applied onto a silica gel column with ethyl acetate/petroleum ether (1:2). This resulted in 87 mg (crude) of 190.4 as a white solid.

Synthesis of Compound I-84. Into a 10-mL round-bottom flask was placed 190.4 (87 mg, 0.19 mmol, 1.00 equiv), acetone (3 mL), H₂O (2 mL) and tetraoxo(potassio)manganese (25.4 mg, 0.16 mmol, 0.85 equiv). The resulting solution was stirred for 4 h at room temperature. The resulting mixture was concentrated under vacuum. The residue was applied onto a silica gel column with ethyl acetate/petroleum ether (1:2). This resulted in 16 mg (18%) of I-84 as a white solid.

MS (ES): m/z 474 (M+H)+. 1H NMR (400 MHz, DMSO-d6): δ 1.27 (t, J=7.2, 3H), 2.76 (s, 3H), 3.57 (t, J=7.2, 2H), 4.27 (q, J=7.2, 2H), 4.44 (t, J=7.2, 2H), 4.53 (s, 3H), 7.43 (t, J=7.6, 1H), 7.51 (t, J=7.2, 1H), 7.95 (d, J=8.0, 1H), 8.08 (d, J=7.6, 1H).

Example 191

Synthesis of 2-[6-(ethoxycarbonyl)-1-(1H-indol-5-ylmethyl)-5-methyl-2,4-dioxo-1H,2H,3H,4H-thieno[2,3-d]pyrimidin-3-yl]acetic acid (I-90)

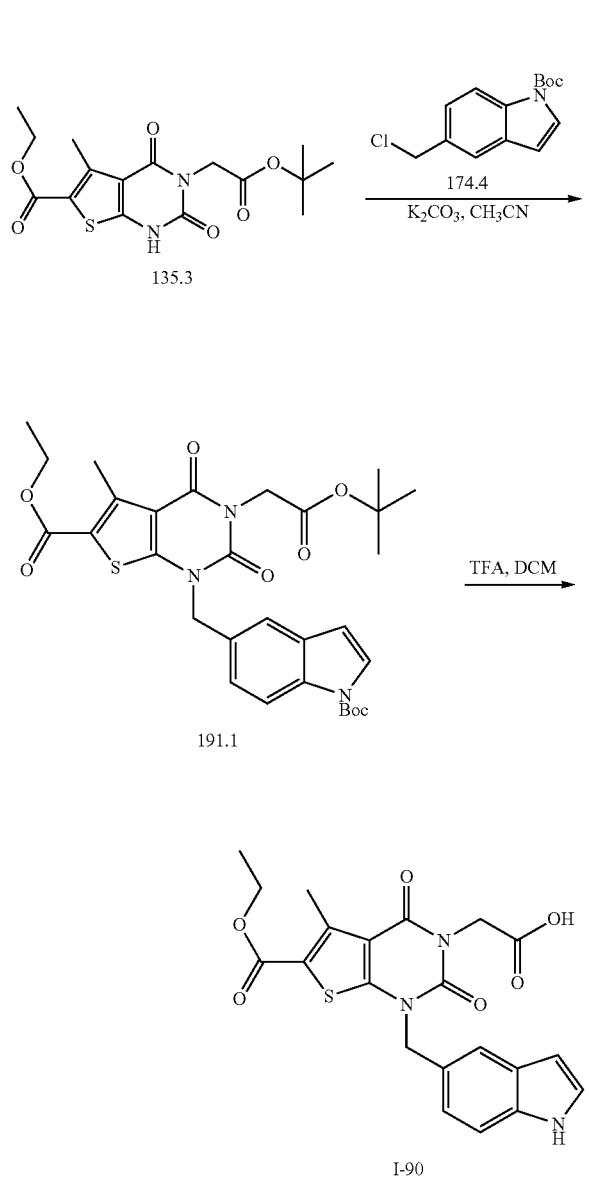

Compound I-90 was prepared from 135.3 and 174.4 in a manner analogous to the synthesis of 136.2. Isolated 11 mg of an off-white solid in 12% yield from 135.3. MS (ES): m/z 442 (M+H)+. 1H NMR (300 MHz, DMSO-d6): δ 1.25 (t, J=7.2, 3H), 2.75 (s, 3H), 4.23 (q, J=7.2, 2H), 4.46 (s, 2H), 5.28 (s, 2H), 6.40 (s, 1H), 7.08 (d, J=6.6, 1H), 7.34-7.39 (m, 2H), 7.52 (s, 1H), 11.14 (s, 3H).

Example 192

Synthesis of 2-[6-(ethoxycarbonyl)-5-methyl-1-[(1-methyl-1H-indol-6-yl)methyl]-2,4-dioxo-1H,2H,3H,4H-thieno[2,3-d]-pyrimidin-3-yl]acetic acid (I-74)

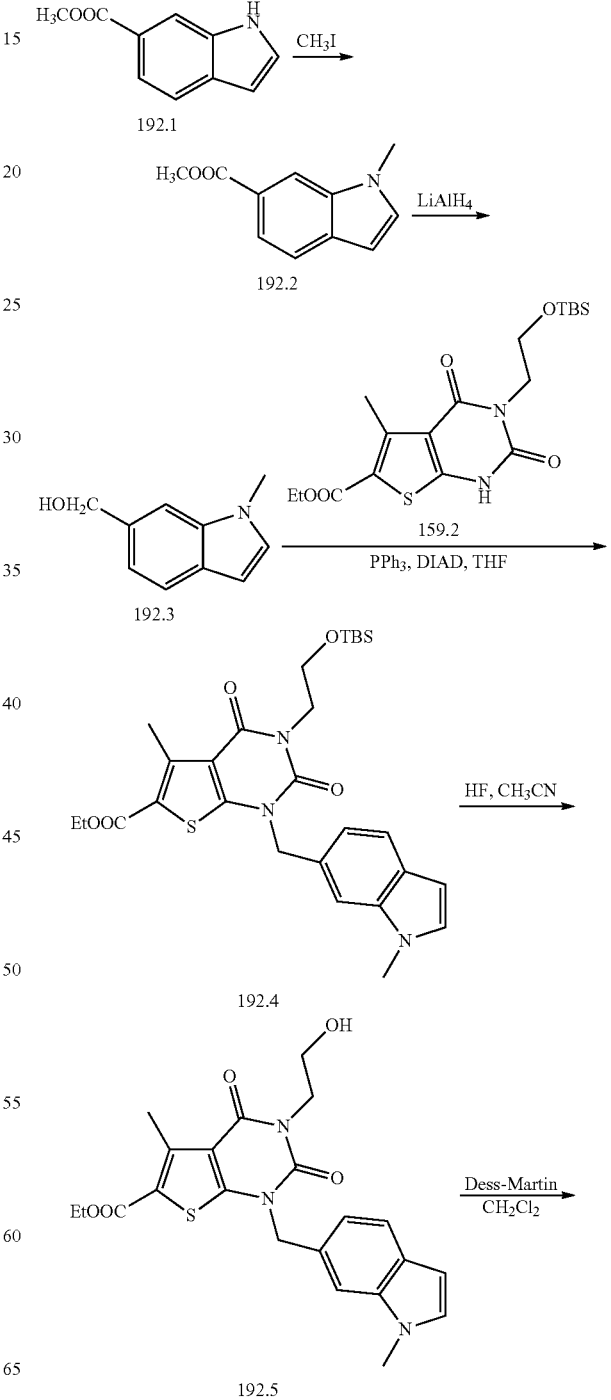

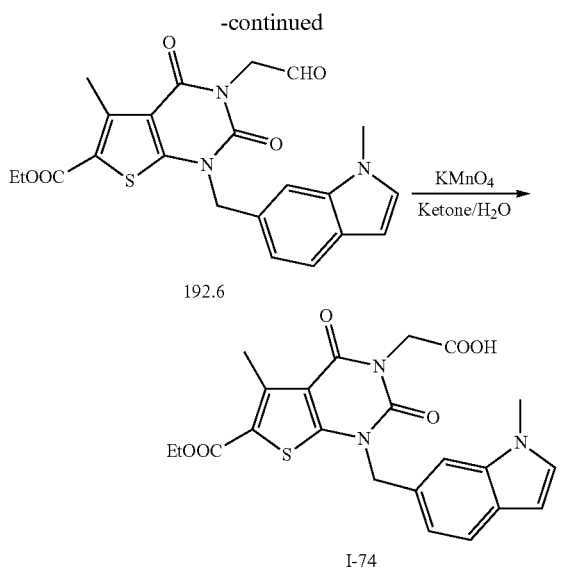

Synthesis of compound 192.2. Into a 500-mL round-bottom flask was placed N,N-dimethylformamide (200 mL) and methyl 1H-indole-6-carboxylate (7 g, 39.96 mmol, 1.00 equiv). Sodium hydride (1.9 g, 47.50 mmol, 1.19 equiv, 60%) was added at 0° C. and stirring continued for 30 min at this temperature, whereupon CH$_3$I (6.8 g, 47.91 mmol, 1.20 equiv) was added. The resulting solution was stirred for 2 h at 0° C. in a water/ice bath. The reaction was then quenched by the addition of 120 mL of water. The resulting solution was extracted with 3×150 mL of ethyl acetate and the organic layers combined and dried over anhydrous sodium sulfate and concentrated under vacuum. The residue was applied onto a silica gel column with ethyl acetate/petroleum ether (1:5). Purification afforded 7.2 g (95%) of 192.2 as a yellow solid.

Synthesis of compound 192.3. Into a 500-mL round-bottom flask was placed tetrahydrofuran (300 mL) and 192.2 (5.67 g, 29.97 mmol, 1.00 equiv). To this solution LiAlH$_4$ (2.28 g, 60.08 mmol, 2.00 equiv) was added at −5° C. The resulting solution was stirred for 2 h at −5° C. in an ice/salt bath. The reaction was then quenched by the addition of 10 mL of ethyl acetate and 150 mL of NH$_4$Cl (aq). The resulting solution was extracted with 3×150 mL of ethyl acetate and the organic layers combined and dried over anhydrous sodium sulfate and concentrated under vacuum. The residue was applied onto a silica gel column with ethyl acetate/petroleum ether (1:2). Purification afforded 5.0 g (98%) of 192.3 as a light yellow oil.

Synthesis of compound 192.4. Into a 25-mL round-bottom flask was placed a solution of 192.3 (322 mg, 2.00 mmol, 2.00 equiv) in tetrahydrofuran (5 mL), PPh$_3$ (524 mg, 2.00 mmol, 2.00 equiv), DIAD (292 mg, 1.44 mmol, 1.45 equiv) and 159.2 (412 mg, 1.00 mmol, 1.00 equiv). The resulting solution was stirred overnight at room temperature. The reaction was then quenched by the addition of 50 mL of water. The resulting solution was extracted with 3×50 mL of ethyl acetate and the organic layers combined and dried over anhydrous sodium sulfate and concentrated under vacuum. The residue was applied onto a silica gel column with ethyl acetate/petroleum ether (1:10). This resulted in 0.12 g (22%) of 192.4 as a white solid.

Synthesis of compound 192.5. Into a 50-mL round-bottom flask was placed CH$_3$CN (15 mL), 192.4 (120 mg, 0.22 mmol, 1.00 equiv) and HF (3 mL). The resulting solution was stirred for 4 h at room temperature. The reaction was then quenched by the addition of 10 mL of NaHCO$_3$ (sat.). The resulting solution was extracted with 3×50 mL of ethyl acetate and the organic layers combined, washed with sodium carbonate (aq.) and brine, dried and concentrated under vacuum. The crude product (80 mg) was purified by preparative HPLC under the following conditions (SHIMADZU): column: SunFire Prep C18, 19*150 mm 5 μm; mobile phase: water with 0.05% NH$_4$HCO$_3$ and CH$_3$CN (7.0% CH$_3$CN up to 63.0% in 18 min); detector: 254/220 nm. This resulted in 0.075 g (79%) of 192.5 as a white solid. MS (ES): m/z 442 (M+H)$^+$.

$^1$H NMR (CDCl$_3$, 400 MHz) δ 1.38 (t, 3H), 2.86 (s, 3H), 3.81 (s, 3H), 3.97 (m, 2H), 4.36 (m, 4H), 5.34 (s, 2H), 6.48 (d, J=2.8 Hz, 1H), 7.09 (d, J=3.2 Hz, 1H), 7.16 (m,1H), 7.39 (s,1H), 7.61 (d, J=8.0 Hz, 1H).

Synthesis of compound 192.6. Into a 50-mL round-bottom flask was placed dichloromethane (20 mL), 192.5 (61 mg, 0.14 mmol, 1.00 equiv) and Dess-Martin reagent (157 mg, 0.37 mmol, 2.68 equiv). The resulting solution was heated to reflux overnight in an oil bath. The resulting mixture was concentrated under vacuum. The residue was applied onto a silica gel column with ethyl acetate/petroleum ether (1:2). This resulted in 0.035 g (58%) of 192.6 as a white solid.

Synthesis of Compound I-74. Into a 50-mL round-bottom flask was placed water (4 mL), acetone (20 mL) and 192.6 (35 mg, 0.08 mmol, 1.00 equiv). This was followed by the addition of KMnO$_4$ (13 mg, 0.08 mmol, 1.03 equiv). The resulting solution was stirred for 1 h at room temperature. The reaction was then quenched by the addition of 2 mL of ethyl acetate. The resulting mixture was concentrated under vacuum. The crude product (50 mg) was purified by preparative HPLC under the following conditions (SHIMADZU): column: SunFire Prep C18, 19*150 mm 5 μm; mobile phase: water with 0.05% TFA and CH$_3$CN (8.0% CH$_3$CN up to 57.0% in 16 min); detector: 254/220 nm. This resulted in 0.011 g (30%) of I-74 as a white solid. MS (ES): m/z 456 (M+H)$^+$. $^1$H NMR (DMSO-d$_6$, 400 MHz): δ 1.25 (t, 3H), 2.76 (s, 3H), 3.76 (s, 3H), 4.23 (m, 2H), 4.65 (s, 2H), 5.36 (s, 2H), 6.41 (d, J=2.8 Hz, 1H), 7.00 (d, J=7.2 Hz, 1H), 7.34 (d, J=3.2 Hz, 1H), 7.42 (s, 1H), 7.52 (d, J=8.0 Hz, 1H).

Example 193

Synthesis of 2-[1-(2H-1,3-benzodioxol-5-ylmethyl)-6-(ethoxycarbonyl)-5-methyl-2,4-dioxo-1H,2H,3H,4H-thieno[2,3-d]pyrimidin-3-yl]acetic acid (I-50)

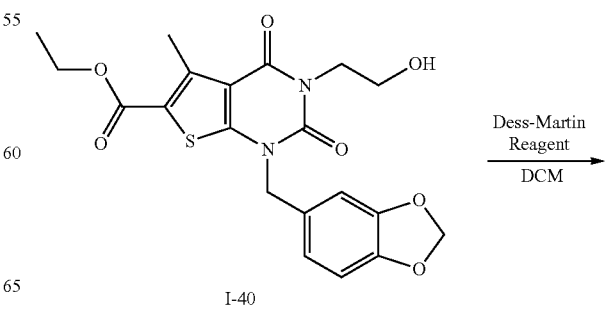

483

-continued

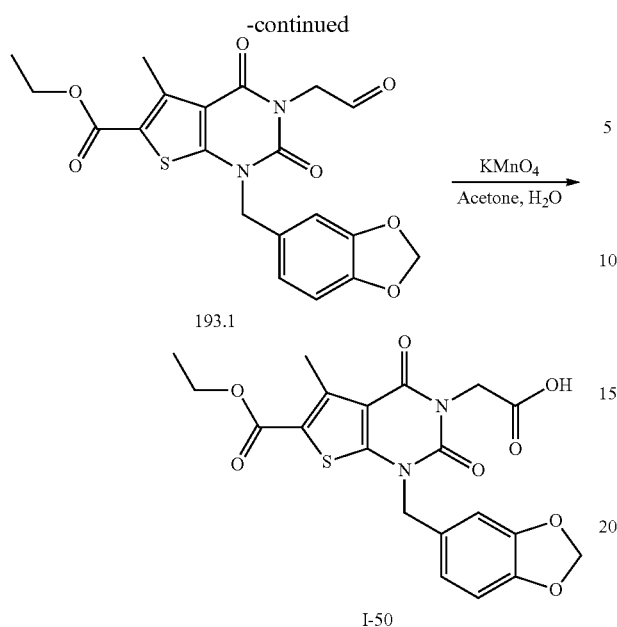

193.1

I-50

Compound I-50 was prepared from Compound I-40 (Example 173) in a manner analogous to the synthesis of Compound I-74 (Example 192). Isolated 7.6 mg of a white solid in 6% yield from I-40. MS (ES): m/z 447 (M+H)+. ¹H NMR (300 MHz, CD₃OD): δ 1.35 (t, J=7.2, 3H), 2.81 (s, 3H), 4.32 (q, J=7.2, 3H), 4.76 (s, 2H), 5.15 (s, 2H), 5.94 (s, 3H), 6.79-6.91 (m, 3H).

Example 194

Synthesis of 2-[6-(ethoxycarbonyl)-1-(1H-indol-2-ylmethyl)-5-methyl-2,4-dioxo-1H,2H,3H,4H-thieno[2,3-d]pyrimidin-3-yl]acetic acid (I-88)

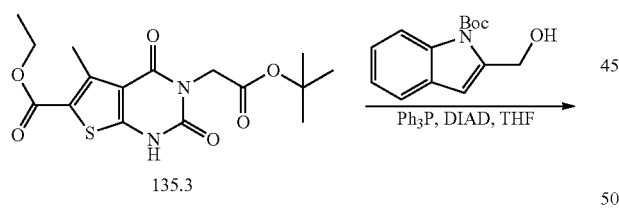

135.1

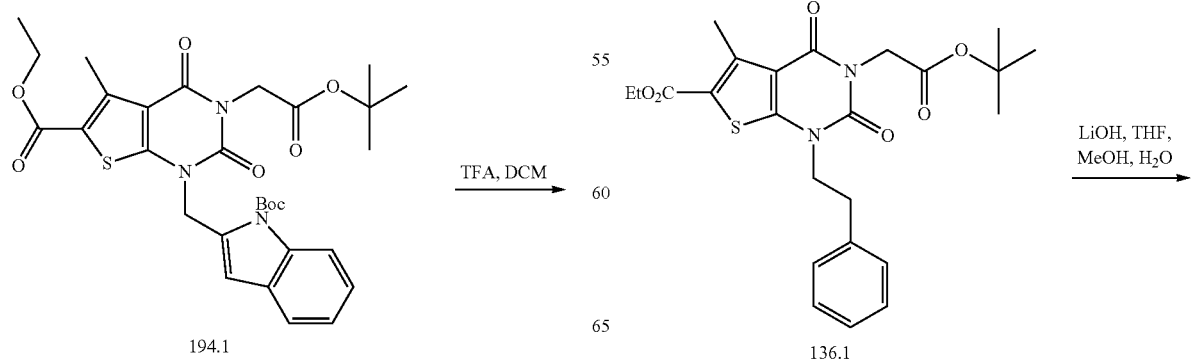

194.1

484

-continued

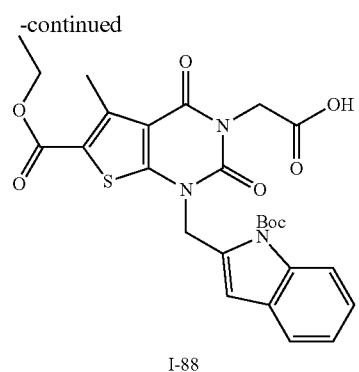

I-88

Synthesis of compound 194.1. Into a 25-mL round-bottom flask was placed a solution of 174.4 (322 mg, 1.30 mmol, 1.30 equiv) in tetrahydrofuran (5 mL), PPh₃ (524 mg, 2.00 mmol, 2.00 equiv), DIAD (292 mg, 1.44 mmol, 1.45 equiv) and 135.3 (368 mg, 1.00 mmol, 1.00 equiv). The resulting solution was stirred for 48 h at room temperature. The resulting mixture was concentrated under vacuum. The residue was applied onto a silica gel column with ethyl acetate/petroleum ether (1:15). Purification afforded 0.244 g (41%) of 194.1 as a white solid.

Synthesis of Compound I-88. Into a 25-mL round-bottom flask was placed dichloromethane (10 mL), 194.1 (20 mg, 0.03 mmol, 1.00 equiv) and CF₃COOH (4 mL). The resulting solution was stirred overnight at room temperature. The resulting mixture was concentrated under vacuum. The crude product (30 mg) was purified by preparative HPLC under the following conditions (SHIMADZU): column: SunFire Prep C18, 19*150 mm 5 μm; mobile phase: water with 0.05% NH₄HCO₃ and CH₃CN (6.0% CH₃CN up to 55.0% in 13 min); detector: 254/220 nm. This resulted in 0.0065 g (44%) of I-88 as a white solid. MS (ES): m/z 442 (M+H)+. ¹H NMR (400 MHz, CDCl₃): δ 1.44 (t, J=7.2, 3H), 2.85 (s, 3H), 4.40 (q, J=7.2, 2H), 4.89 (s, 2H), 5.25 (s, 2H), 6.71 (s, 1H), 7.11 (t, J=7.2, 1H), 7.20 (t, J=7.6, 1H), 7.36 (d, J=8.4, 1H), 7.60 (d, J=8.0, 1H), 8.79 (s, 1H).

Example 195

Synthesis of 2-[5-methyl-2,4-dioxo-1-(2-phenylethyl)-6-(propoxycarbonyl)-1H,2H,3H,4H-thieno[2,3-d]pyrimidin-3-yl]acetic acid (I-68)

136.1

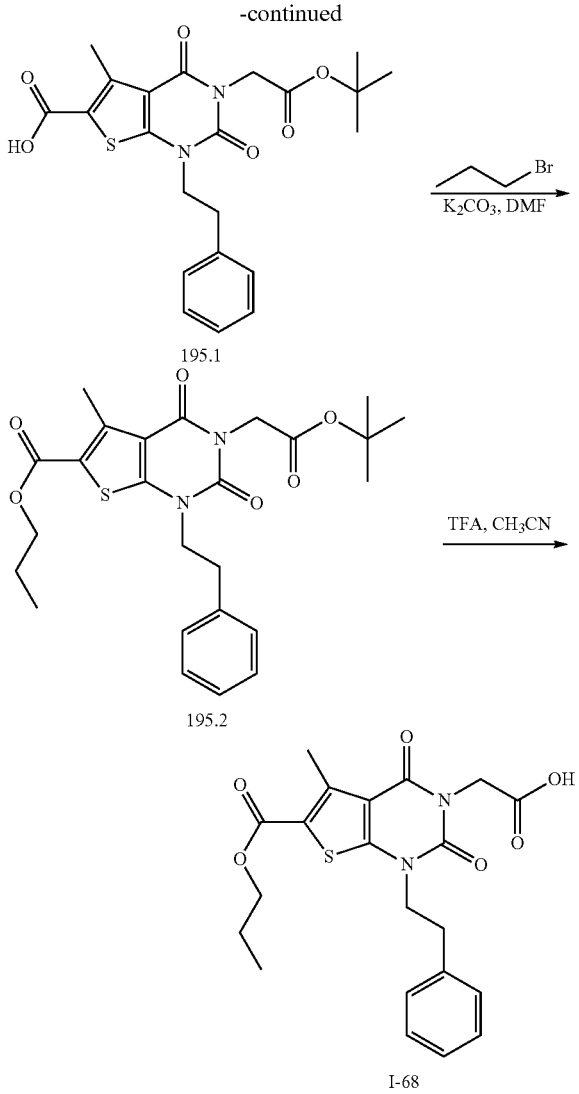

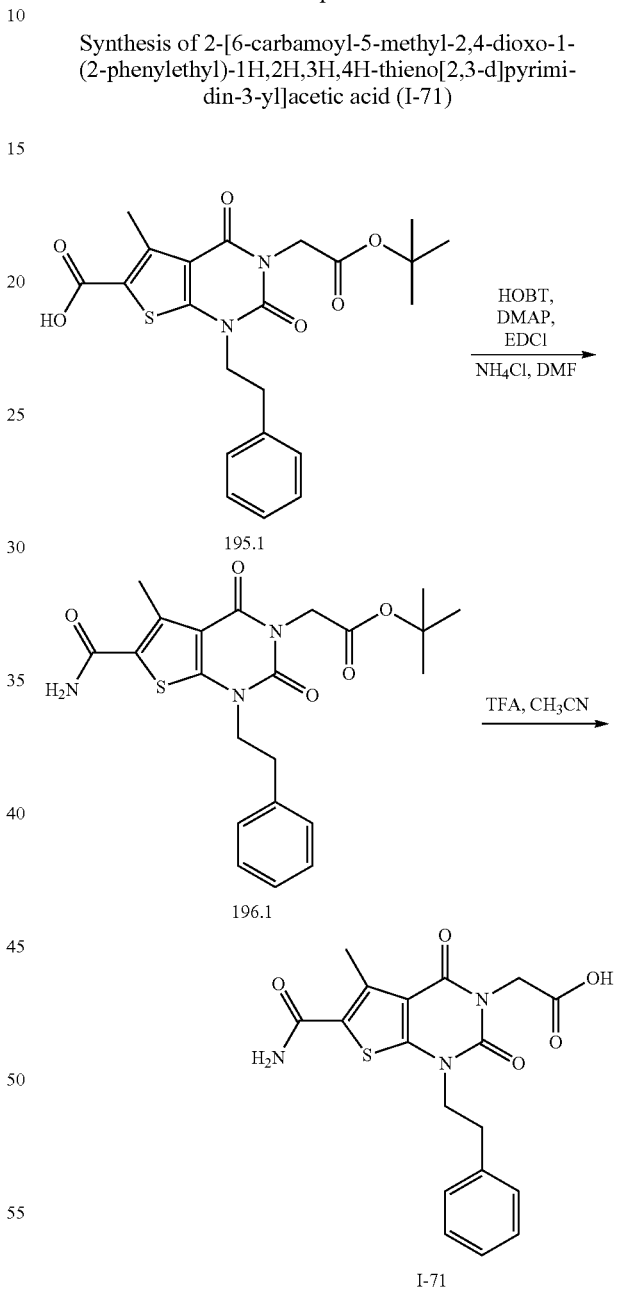

Synthesis of compound 195.1. Into a 100-mL round-bottom flask was placed 136.1 (5.1 g, 10.79 mmol, 1.00 equiv), tetrahydrofuran (5 mL), methanol (10 mL), water (10 mL) and LiOH (770 mg, 32.15 mmol, 2.98 equiv). The resulting solution was stirred overnight at room temperature. The resulting mixture was diluted with 100 mL of $H_2O$. The pH value of the solution was adjusted to 3 with hydrogen chloride (10%). The resulting solution was extracted with 3×100 mL of ethyl acetate and the organic layers combined and concentrated under vacuum. The residue was applied onto a silica gel column with dichloromethane/methanol (100:1). This resulted in 2.3 g (48%) of 195.1 as a white solid.

Synthesis of compound 195.2. Into a 50-mL round-bottom flask was placed 195.1 (150 mg, 0.34 mmol, 1.00 equiv), N,N-dimethylformamide (10 mL), potassium carbonate (140 mg, 1.01 mmol, 3.00 equiv) and 1-bromopropane (83 mg, 0.67 mmol, 2.00 equiv). The resulting solution was stirred overnight at 50° C. The resulting mixture was concentrated under vacuum. The residue was applied onto a silica gel column with ethyl acetate/petroleum ether (1:50). This resulted in 130 mg (79%) of 195.2 as a white solid.

Synthesis of Compound I-68. Into a 25-mL round-bottom flask was placed 195.2 (130 mg, 0.27 mmol, 1.00 equiv), $CF_3COOH$ (2 mL) and $CH_3CN$ (5 mL). The resulting solution was stirred for 5 h at room temperature and then concentrated under vacuum. The crude product was re-crystallized from EA: n-hexane in the ratio of 1:5. This resulted in 40.9 mg (36%) of I-68 as a white solid. MS (ES): m/z 431 (M+H)$^+$. $^1$H NMR (400 MHz, DMSO-$d_6$): δ 0.87 (t, J=6.4, 3H), 1.65-1.74 (m, 2H), 2.75 (s, 3H), 3.01 (t, J=7.2, 2H), 4.14 (t, J=7.2, 2H), 4.21 (t, J=6.8, 3H), 2.75 (s, 2H), 7.20-7.31 (m, 5H).

Example 196

Synthesis of 2-[6-carbamoyl-5-methyl-2,4-dioxo-1-(2-phenylethyl)-1H,2H,3H,4H-thieno[2,3-d]pyrimidin-3-yl]acetic acid (I-71)

Synthesis of compound 196.1. Into a 50-mL round-bottom flask was placed HOBT (50 mg, 0.37 mmol, 1.10 equiv), 195.1 (150 mg, 0.34 mmol, 1.00 equiv), 4-dimethylaminopyridine (45 mg, 0.37 mmol, 1.09 equiv), $NH_4Cl$ (72 mg, 1.35 mmol, 3.99 equiv), N,N-dimethylformamide (10 mL) and EDC (71 mg, 0.46 mmol, 1.36 equiv). The resulting solution was stirred overnight at room temperature. The reaction was then quenched by the addition of 20 mL of water. The resulting solution was extracted with 3×20 mL of ethyl acetate and the organic layers combined, dried and concentrated under vacuum. The residue was applied onto a silica gel column with ethyl acetate/petroleum ether (1:5). This resulted in 500 mg (crude) of 196.1 as a white solid.

Synthesis of Compound I-71. Compound I-71 was prepared from 196.1 in a manner analogous to the synthesis of Compound I-68 (Example 195). Isolated 27 mg of a white solid in 6% yield. MS (ES): m/z 388 (M+H)$^+$, 410 (M+Na)$^+$, 429 (M+H+CH$_3$CN)$^+$. $^1$H NMR (400 MHz, DMSO-d$_6$): δ 2.66 (s, 3H), 2.99 (t, J=8.0, 2H), 4.07 (t, J=7.6, 2H), 4.37 (s, 2H), 7.22-7.34 (m, 5H), 7.55 (s, 2H).

Example 197

Synthesis of 2-[6-[(2-hydroxyethoxy)carbonyl]-5-methyl-2,4-dioxo-1-(2-phenylethyl)-1H,2H,3H,4H-thieno[2,3-d]pyrimidin-3-yl]acetic acid (I-83)

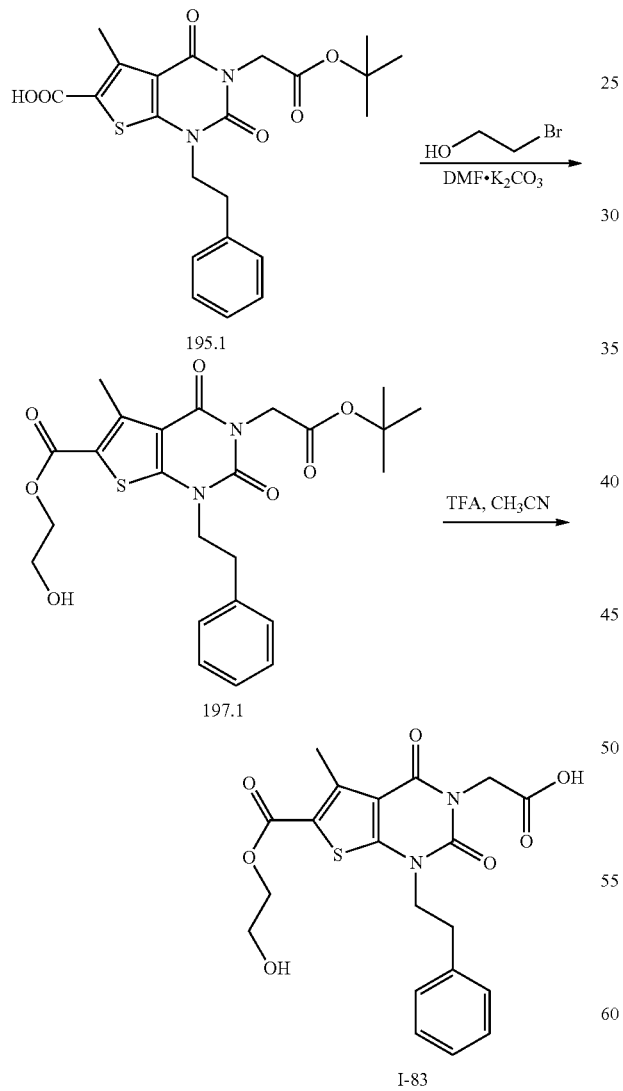

Synthesis of compound 197.1. 197.1 was prepared from 195.1 in a manner analogous to the synthesis of I-42 (Example 178). Isolated 140 mg (85%) of a white solid.

Synthesis of Compound I-83. Compound I-83 was prepared from 197.1 in a manner analogous to Compound I-68 (Example 195). Isolated 35.2 mg of a white solid in 28% yield. MS (ES): m/z 433 (M+H)$^+$, 455 (M+Na)$^+$, 496 (M+H+CH$_3$CN)$^+$. $^1$H NMR (400 MHz, DMSO-d$_6$): δ 2.76 (s, 3H), 3.02 (t, J=7.6, 2H), 3.68 (t, J=4.8, 2H), 4.14 (t, J=7.6, 2H), 4.27 (t, J=4.8, 2H), 4.56 (s, 2H), 7.21-7.32 (m, 5H).

Example 198

Synthesis of 2-[6-(methoxymethyl)-5-methyl-2,4-dioxo-1-(2-phenylethyl)-1H,2H,3H,4H-thieno[2,3-d]pyrimidin-3-yl]acetic acid (I-75)

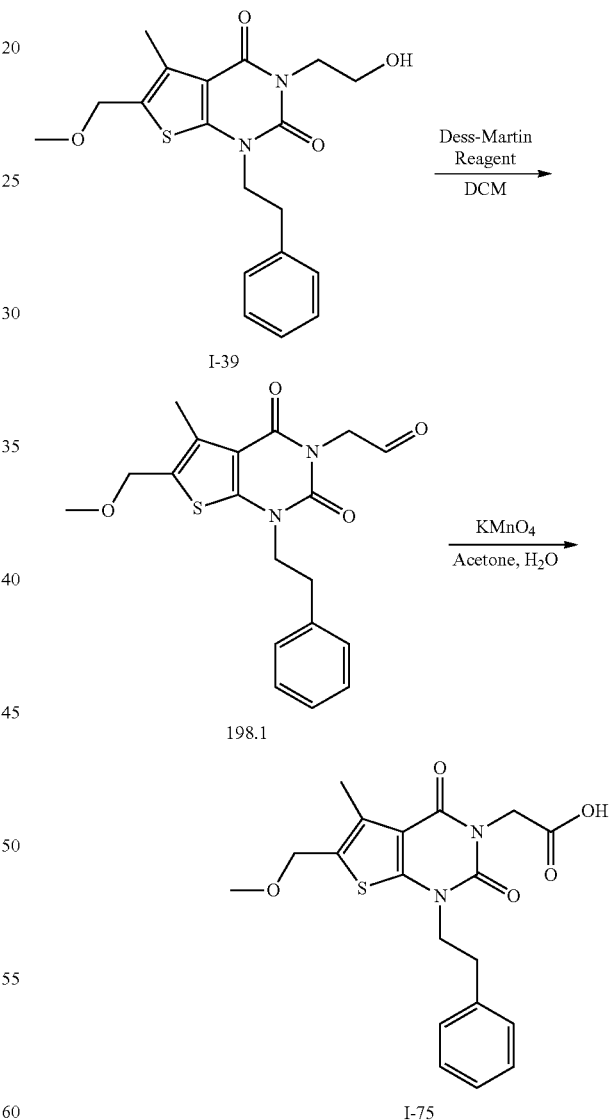

Compound I-75 was prepared from I-39 (Example 179) in a manner analogous to the synthesis of Compound I-84 (Example 190). Isolated a 49.5 mg of a white solid in 40% yield from I-39. MS (ES): m/z 389 (M+H)$^+$, 411 (M+Na)$^+$, 452 (M+Na+CH$_3$CN)$^+$. $^1$H NMR (300 MHz, DMSO-d$_6$): δ 2.35

(s, 3H), 2.99 (t, J=7.5, 2H), 3.32 (s, 3H), 4.08 (t, J=7.2, 2H), 4.51 (s, 2H), 7.19-7.32 (m, 5H), 12.94 (s, 1H).

Example 199

Synthesis of 2-[5-methyl-6-(1,3-oxazol-2-yl)-2,4-dioxo-1-(2-phenylethyl)-1H,2H,3H,4H-thieno[2,3-d]pyrimidin-3-yl]acetic acid (I-92)

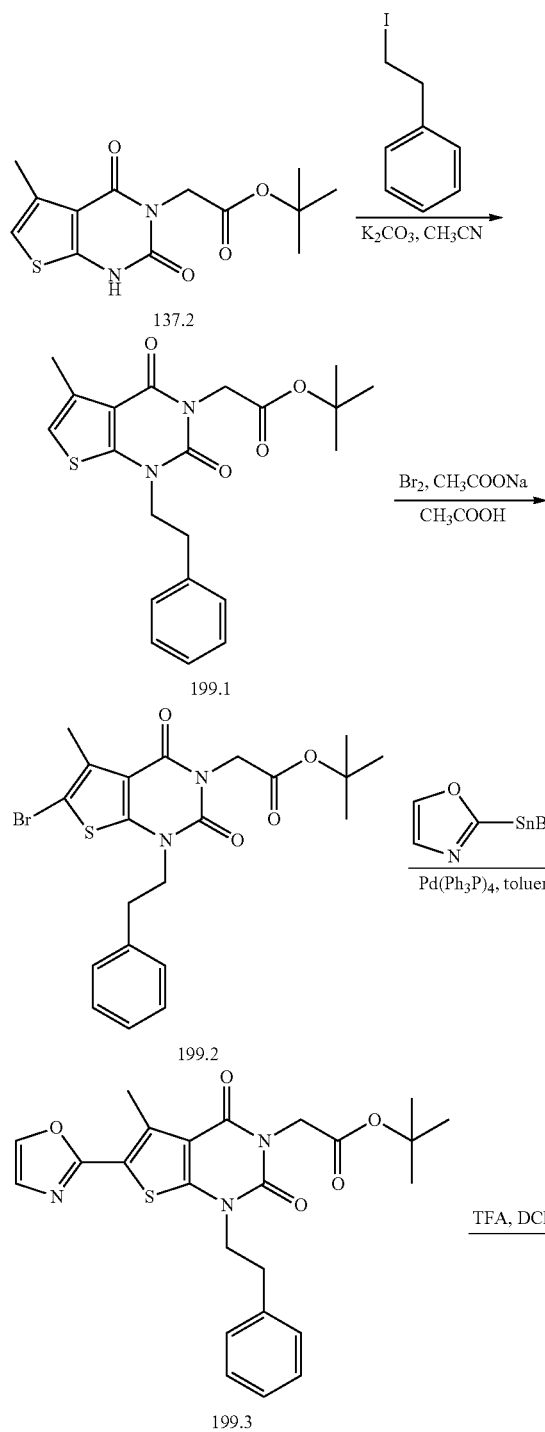

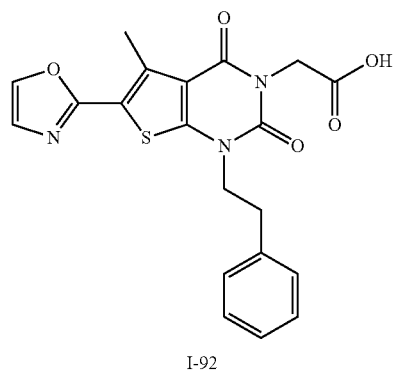

I-92

Synthesis of compound 199.1. Compound 199.1 was prepared from 137.2 in a manner analogous to the synthesis of 136.1. Isolated 0.87 g of a yellow solid in 64% yield.

Synthesis of compound 199.2. Compound 199.2 was prepared from 199.1 in a manner analogous to the synthesis of compound 137.3. Isolated 0.56 g of a white solid in 94% yield.

Synthesis of Compound I-92. Compound I-92 was prepared from 199.2 in a manner analogous to Compound I-141 (Example 7). Isolated 24 mg (52%) of a white solid.

Example 200

Synthesis of 2-[6-(ethoxycarbonyl)-2,4-dioxo-1-(2-phenylethyl)-1H,2H,3H,4H-thieno[2,3-d]pyrimidin-3-yl]acetic acid (I-91)

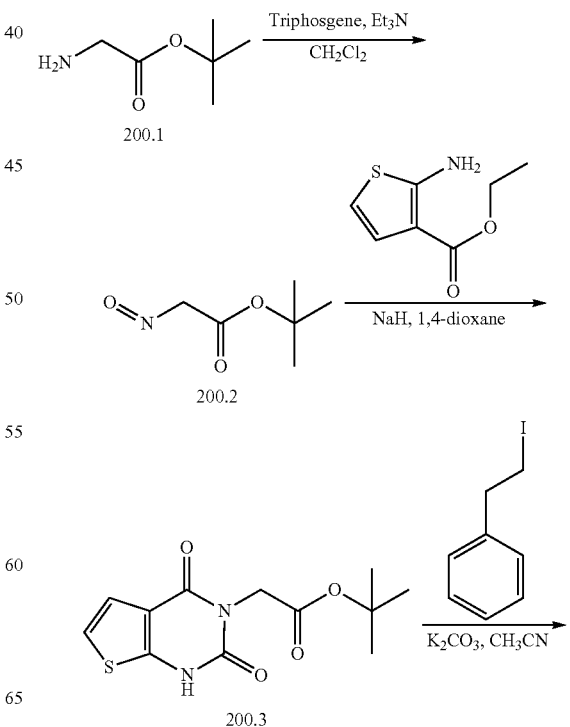

-continued

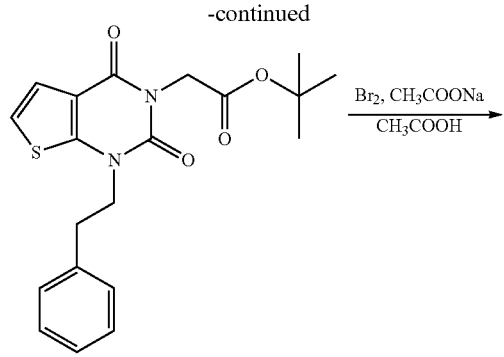
200.4

Br₂, CH₃COONa / CH₃COOH →

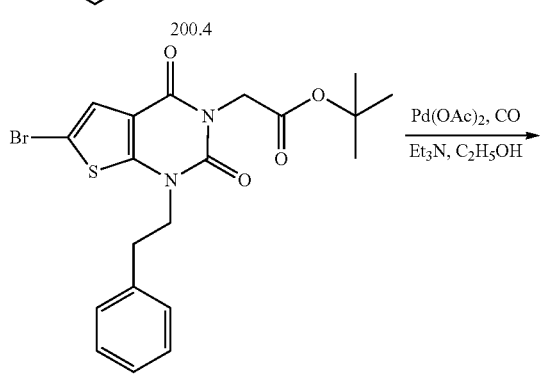
200.5

Pd(OAc)₂, CO / Et₃N, C₂H₅OH →

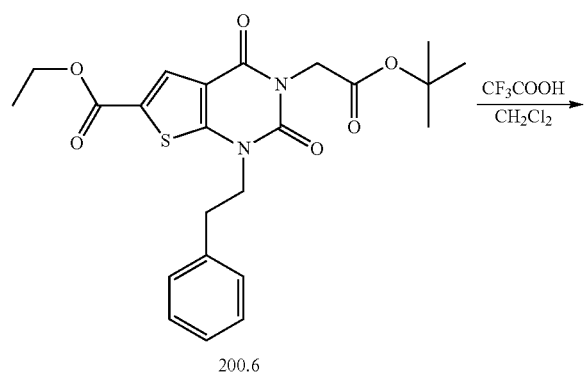
200.6

CF₃COOH / CH₂Cl₂ →

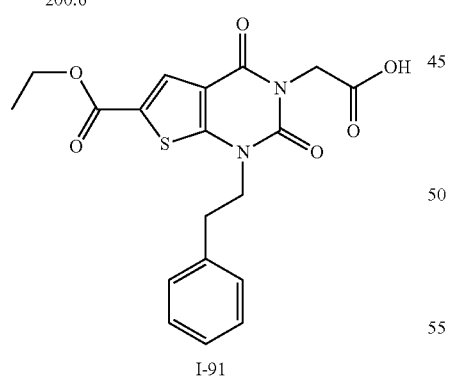
I-91

Synthesis of compound 200.4. Compound 200.4 was prepared from 200.1 and ethyl 2-aminothiophene-3-carboxylate in a manner analogous to the synthesis of 136.1 (Examples 135 and 136). Isolated 1.1 g of a yellow solid in 12% overall yield.

Synthesis of compound 200.5. Compound 200.5 was prepared from 200.4 in a manner consistent with the synthesis of 137.3. Isolated 1.1 g of a white solid in 83% yield.

Synthesis of compound 200.6. Into a 100-mL pressure tank reactor (7 atm) was placed Pd(OAc)₂ (100 mg, 0.45 mmol, 0.41 equiv), 200.5 (500 mg, 1.07 mmol, 1.00 equiv), ethanol (50 mL) and triethylamine (220 mg, 2.17 mmol, 2.02 equiv). Then CO (gas) was introduced to keep the pressure at 7 atm. The resulting solution was stirred overnight at 100° C. After cooling, the resulting mixture was concentrated under vacuum. The residue was applied onto a silica gel column with ethyl acetate/petroleum ether (1:20). Purification afforded 130 mg (26%) of 200.6 as a white solid.

Synthesis of Compound I-91. Compound I-91 was prepared from 200.6 in a manner analogous to the synthesis of compound 2.5. MS (ES): m/z 403 (M+H)⁺, 425 (M+Na)⁺, 444 (M+H+CH₃CN)⁺. ¹H NMR (300 MHz, DMSO-d₆): δ 1.29 (t, J=6.9, 3H), 3.02 (t, J=7.2, 2H), 4.15 (t, J=7.2, 2H), 4.30 (q, J=6.9, 2H), 4.56 (s, 2H), 7.18-7.30 (m, 5H), 7.81 (s, 1H), 13.09 (s, 1H).

Example 201

Synthesis of 2-[2,4-dioxo-1-(2-phenylethyl)-1H,2H,3H,4H-thieno[2,3-d]pyrimidin-3-yl]acetic acid (I-65)

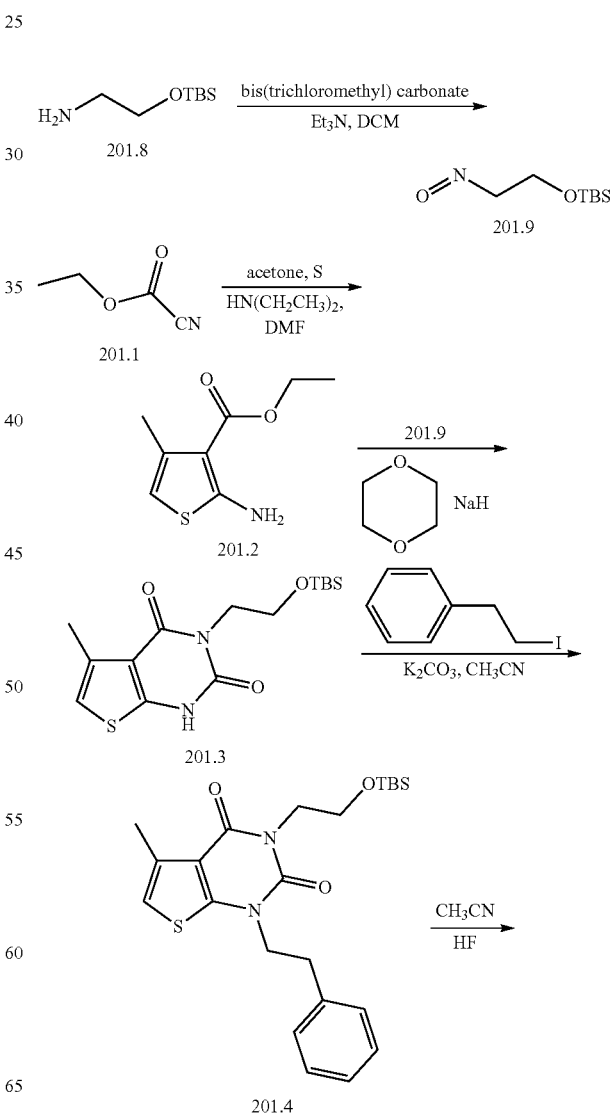

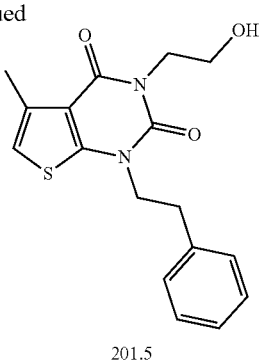
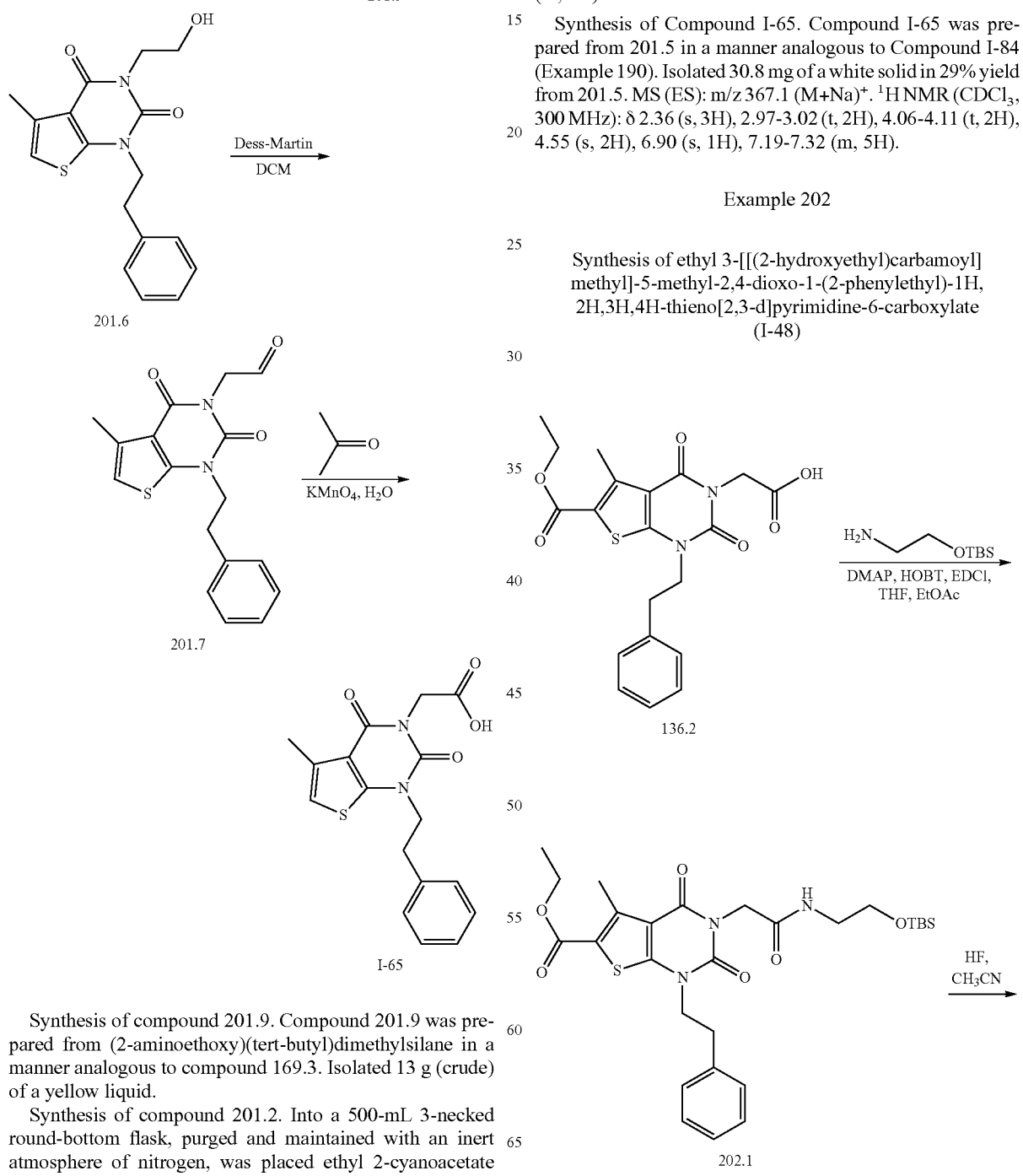

2-one (11.6 g, 199.73 mmol, 1.00 equiv), diethylamine (14.6 g) and S (6.4 g). The resulting solution was stirred overnight at 50° C. The solids were filtered out. The filtrate was concentrated under vacuum. The residue was applied onto a silica gel column with ethyl acetate/PE (1:100-1:20). This resulted in 6.47 g (17%) of 201.2 as a white solid.

Synthesis of compound 201.5. Compound 201.5 was prepared from 201.2 in a manner analogous to Compound I-34 (Example 169). Isolated 12.6 mg of a white solid in 0.003% overall yield. MS (ES): m/z 331.1 (M+H)+. $^1$H NMR (CDCl$_3$, 400 MHz): δ 2.37 (s,3H), 2.96-3.01 (t, 2H), 3.58-3.62 (t, 2H), 3.92-3.96 (t, 2H), 4.04-4.09 (t, 2H), 6.81 (s, 1H), 7.21-7.32 (m, 5H).

Synthesis of Compound I-65. Compound I-65 was prepared from 201.5 in a manner analogous to Compound I-84 (Example 190). Isolated 30.8 mg of a white solid in 29% yield from 201.5. MS (ES): m/z 367.1 (M+Na)+. $^1$H NMR (CDCl$_3$, 300 MHz): δ 2.36 (s, 3H), 2.97-3.02 (t, 2H), 4.06-4.11 (t, 2H), 4.55 (s, 2H), 6.90 (s, 1H), 7.19-7.32 (m, 5H).

Example 202

Synthesis of ethyl 3-[[(2-hydroxyethyl)carbamoyl]methyl]-5-methyl-2,4-dioxo-1-(2-phenylethyl)-1H,2H,3H,4H-thieno[2,3-d]pyrimidine-6-carboxylate (I-48)

Synthesis of compound 201.9. Compound 201.9 was prepared from (2-aminoethoxy)(tert-butyl)dimethylsilane in a manner analogous to compound 169.3. Isolated 13 g (crude) of a yellow liquid.

Synthesis of compound 201.2. Into a 500-mL 3-necked round-bottom flask, purged and maintained with an inert atmosphere of nitrogen, was placed ethyl 2-cyanoacetate (22.6 g, 199.80 mmol, 1.00 equiv), ethanol (200 mL), propan-

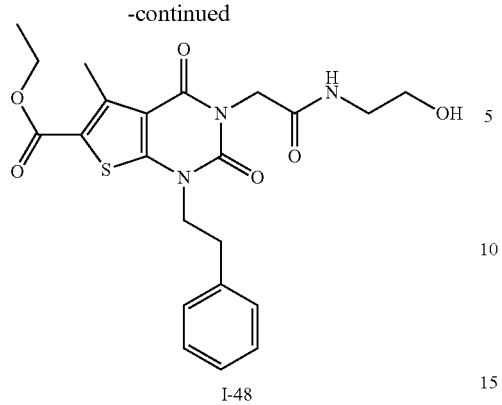

I-48

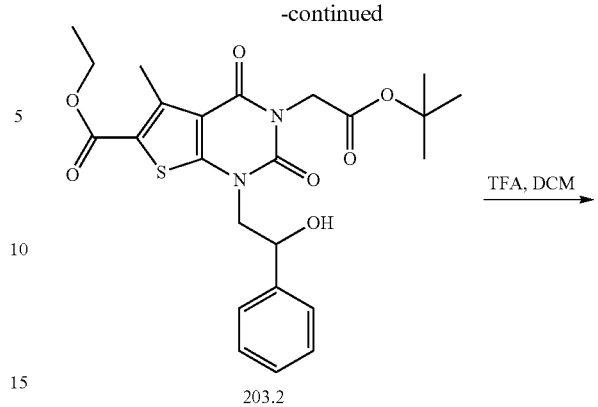

203.2

Synthesis of compound 202.1. Compound 202.1 was prepared from 136.2 and (2-aminoethoxy)(tert-butyl)dimethylsilane in a manner analogous to 136.3. Isolated 0.7 g of a white solid in 98% yield.

Synthesis of Compound I-48. Compound I-48 was prepared from 202.1 in a manner analogous to Compound I-20 (Example 160). Isolated 0.46 g of a white solid in 80% yield. MS (ES): m/z 460 (M+H)$^+$.

$^1$H NMR (CD$_3$OD, 400 MHz): δ 1.38 (t, J=7.2 Hz, 3H), 2.82 (s, 3H), 3.10 (t, J=7.2 Hz, 2H), 3.37 (t, J=5.6 Hz, 2H), 3.64 (t, J=5.6 Hz, 2H), 4.18 (t, J=7.2 Hz, 2H), 4.34 (q, 2H), 4.69 (s, 2H), 7.23-7.33 (m, 5H).

Example 203

Synthesis of 2-[6-(ethoxycarbonyl)-1-(2-hydroxy-2-phenylethyl)-5-methyl-2,4-dioxo-1H,2H,3H,4H-thieno[2,3-d]pyrimidin-3-yl]acetic acid (I-60)

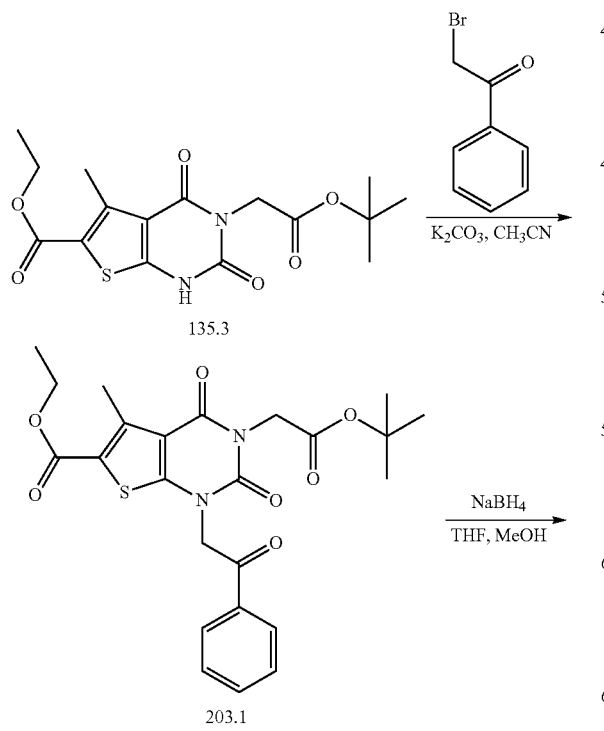

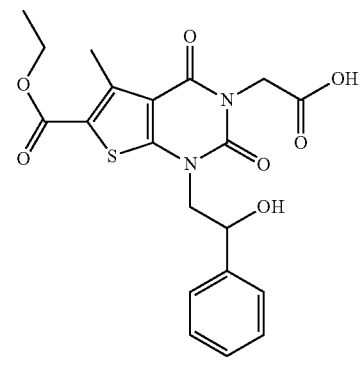

I-60

Synthesis of 203.1. Compound 203.1 was prepared from 135.3 and 2-bromo-1-phenylethan-1-one in a manner analogous to 136.1. Isolated 0.34 g of a light yellow solid in 51% yield.

Synthesis of 203.2. Into a 50-mL round-bottom flask was placed 203.1 (300 mg, 0.62 mmol, 1.00 equiv), methanol (5 mL), tetrahydrofuran (5 mL) and NaBH$_4$ (25 mg, 0.66 mmol, 1.07 equiv). The resulting solution was stirred for 2 h at room temperature. The reaction was then quenched by the addition of 5 mL of NH$_4$Cl (aq.). The resulting solution was extracted with 2×5 mL of ethyl acetate and the organic layers combined, dried over anhydrous sodium sulfate and concentrated under vacuum. The residue was applied onto a silica gel column with ethyl acetate/petroleum ether (1:5). This resulted in 160 mg (53%) of 203.2 as a white solid.

Synthesis of Compound I-60. Compound I-60 was prepared from 203.2 in a manner consistent with the synthesis of compound 2.5. Isolated 20.4 mg of a white solid in 38% yield. MS (ES): m/z 433 (M+H)$^+$, 455 (M+Na)$^+$, 496 (M+Na+CH$_3$CN)$^+$.

$^1$H NMR (300 MHz, DMSO-d$_6$): δ 1.31 (t, J=7.2, 3H), 2.76 (s, 3H), 3.77-3.85 (m, 1H), 4.12-4.15 (m, 1H), 4.29 (q, J=6.9, 2H), 4.44 (s, 2H), 4.99 (d, J=7.2, 1H), 5.89(s, 1H), 7.30-7.43 (m, 5H).

Example 204

Synthesis of 2-[6-(ethoxycarbonyl)-1-(2-methoxy-2-phenylethyl)-5-methyl-2,4-dioxo-1H,2H,3H,4H-thieno[2,3-d]pyrimidin-3-yl]acetic acid (I-67)

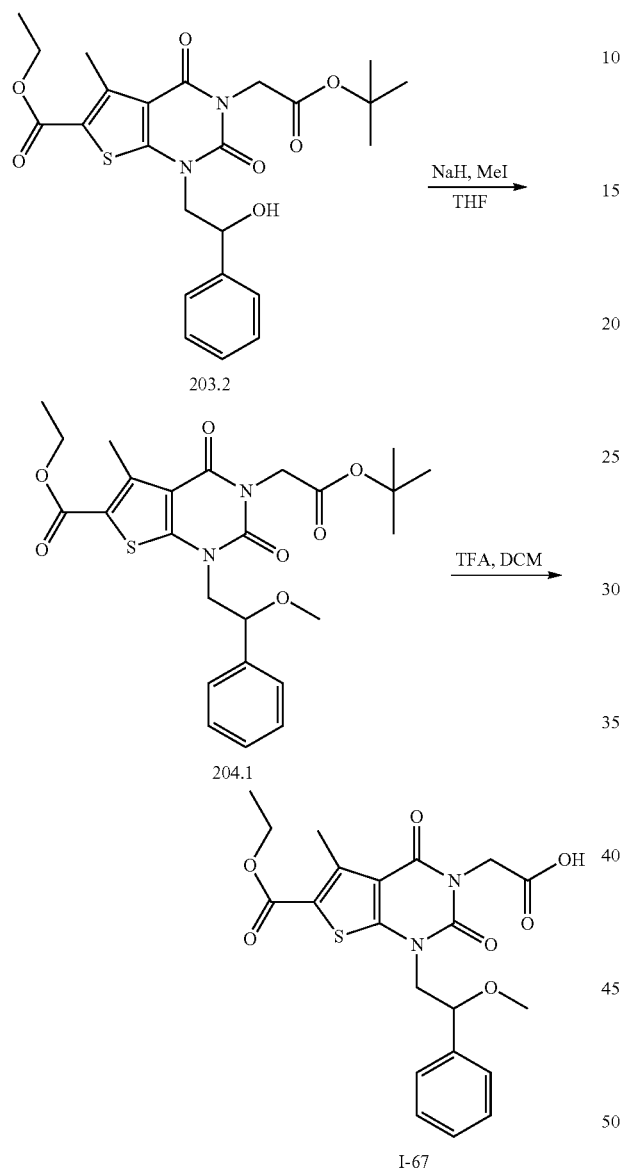

Synthesis of compound 204.1. Into a 50-mL round-bottom flask, purged and maintained with an inert atmosphere of nitrogen, was placed 203.2 (100 mg, 0.20 mmol, 1.00 equiv), tetrahydrofuran (10 mL). This was followed by the addition of sodium hydride (8.2 mg, 0.20 mmol, 1.00 equiv). The mixture was stirred for 15 min at 0° C. To this was added CH$_3$I (43.6 mg, 0.31 mmol, 1.50 equiv). The resulting solution was stirred overnight at room temperature. The reaction was then quenched by the addition of 5 ml of NH$_4$Cl (aq.). The resulting solution was extracted with 2×5 mL of ethyl acetate. The organic layers were combined, dried over sodium sulfate and concentrated under vacuum. The residue was applied onto a silica gel column with ethyl acetate/PE (1:10). This resulted in 70 mg (68%) of 204.1 as a white solid.

Synthesis of Compound I-67. Compound I-67 was prepared from 204.1 in a manner consistent with the synthesis of compound 2.5. Isolated 30.5 mg of a white solid in 49% yield. MS (ES): m/z 447 (M+H)$^+$, 469 (M+Na)$^+$, 469 (M+Na+CH$_3$CN)$^+$. $^1$H NMR (300 MHz, DMSO-d$_6$): δ 1.31 (t, J=7.2, 3H), 2.76 (s, 3H), 3.09 (s, 3H), 3.94-4.15 (m, 2H), 4.30 (q, J=6.6, 2H), 4.56-4.65 (m, 3H), 7.34-7.46 (m, 5H), 12.98 (s, 1H).

Example 205

Synthesis of 2-[6-(ethoxycarbonyl)-5-methyl-2,4-dioxo-1-[2-phenyl-2-(propan-2-yloxy)ethyl]-1H,2H,3H,4H-thieno[2,3-d]pyrimidin-3-yl]acetic acid (I-89)

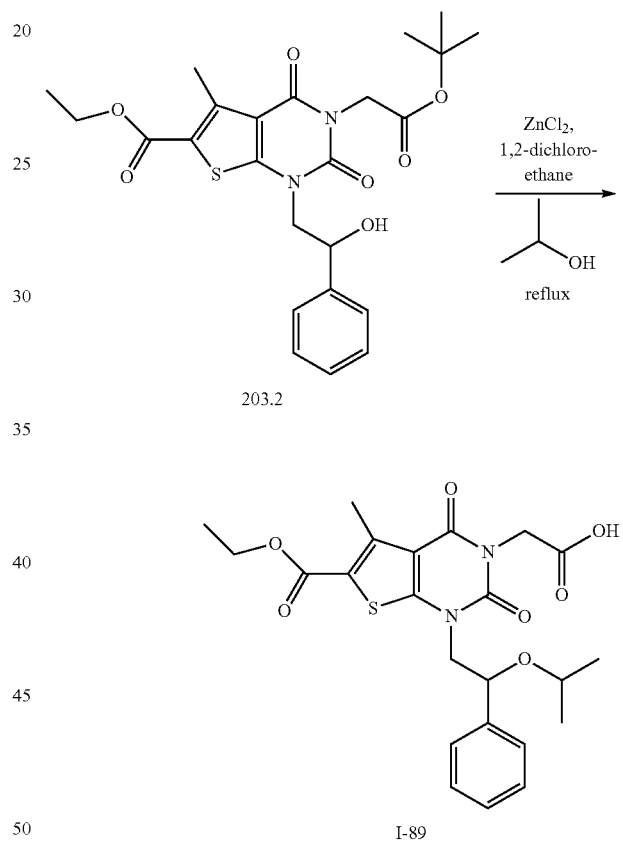

Into a 50-mL round-bottom flask was placed 203.2 (100 mg, 0.20 mmol, 1.00 equiv), 1,2-dichloroethane (20 mL), ZnCl$_2$ (33 mg, 0.24 mmol, 1.18 equiv) and propan-2-ol (25 mg, 0.42 mmol, 2.03 equiv). The resulting solution was stirred overnight at 50° C. The resulting mixture was concentrated under vacuum. The residue was applied onto a silica gel column with ethyl acetate/petroleum ether (1:10). The crude product (110 mg) was purified by preparative HPLC under the following conditions (SHIMADZU): column: SunFire Prep C18, 19*150 mm 5 μm; mobile phase: water with 0.05% NH$_4$HCO$_3$ and CH$_3$CN (6.0% CH$_3$CN up to 49.0% in 19 min); detector: 254/220 nm. Purification afforded 23.8 mg (25%) of I-89 as a white solid. MS (ES): m/z 475 (M+H)$^+$, 497 (M+Na)$^+$, 538 (M+Na+CH$_3$CN)$^+$. $^1$H NMR (400 MHz, DMSO-d$_6$): δ 0.85 (d, 3H), 0.95 (d, 3H), 1.33 (t, 3H), 2.77 (s, 3H), 3.46 (m, 1H), 3.78 (m, 1H), 3.91 (m, 1H), 4.14 (m, 1H), 4.34 (m, 2H), 4.61 (m, 2H), 4.81 (m, 1H), 7.34-7.42 (m, 5H).

Example 206

Synthesis of 2-[1-[2-(acetyloxy)-2-phenylethyl]-6-(ethoxycarbonyl)-5-methyl-2,4-dioxo-1H,2H,3H,4H-thieno[2,3-d]pyrimidin-3-yl]acetic acid (I-85)

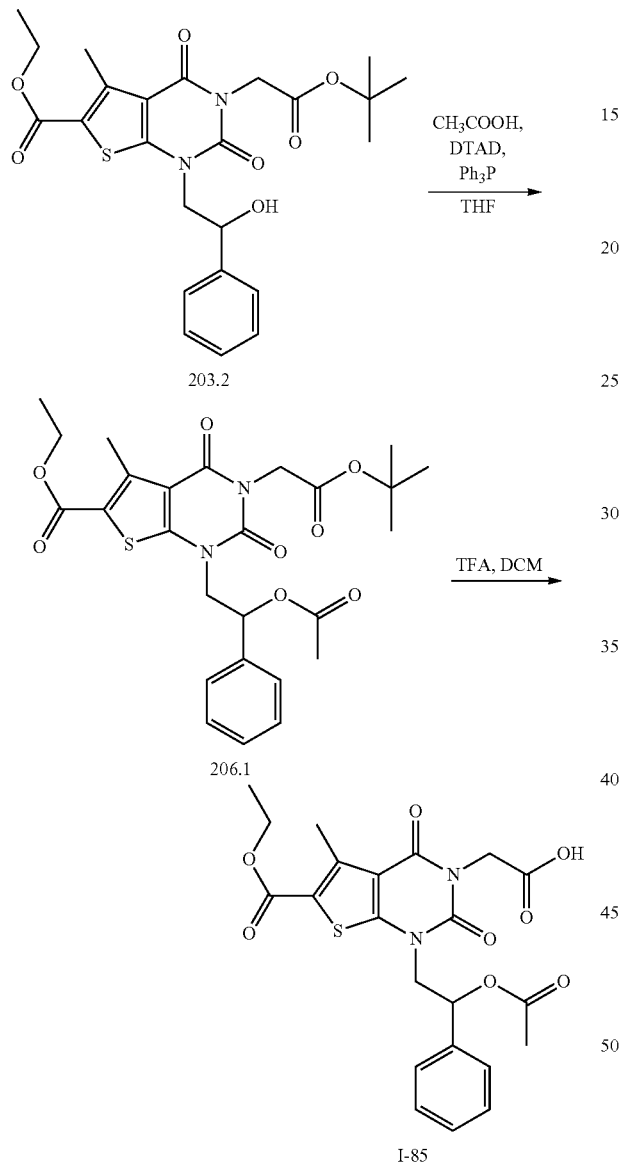

Synthesis of compound 206.1. Into a 10-mL seal-tube, purged and maintained with an inert atmosphere of nitrogen, was placed 203.2 (200 mg, 0.41 mmol, 1.00 equiv), DTAD (188 mg, 0.82 mmol, 2.00 equiv), tetrahydrofuran (5 mL), PPh$_3$ (214 mg, 0.82 mmol, 2.00 equiv) and acetic acid (49 mg, 0.82 mmol, 2.00 equiv). The resulting solution was stirred overnight at room temperature and then concentrated under vacuum. The residue was applied onto a silica gel column with ethyl acetate/PE (1:15). This resulted in 76 mg (35%) of 206.1 as a white solid.

Synthesis of Compound I-85. Compound I-85 was prepared from 206.1 in a manner analogous to 2.5. Isolated 23.1 mg (34%) of a white solid. MS (ES): m/z 475 (M+H)$^+$, 415 (M+H–CH$_3$COOH)$^+$. $^1$H NMR (300 MHz, CD$_3$OD): δ 1.40 (t, J=7.2, 3H), 2.00 (s, 3H), 2.84 (s, 3H), 4.33-4.40 (m, 4H), 4.72 (t, J=5.1, 2H), 6.25 (t, J=7.2, 1H), 7.37-7.50 (m, 5H).

Example 207

Synthesis of 2-[6-(ethoxycarbonyl)-1-[(2S)-2-hydroxy-2-phenylethyl]-5-methyl-2,4-dioxo-1H,2H,3H,4H-thieno[2,3-d]pyrimidin-3-yl]acetic acid (I-77) and Example 208: 2-[6-(ethoxycarbonyl)-1-[(2R)-2-hydroxy-2-phenylethyl]-5-methyl-2,4-dioxo-1H,2H,3H,4H-thieno[2,3-d]pyrimidin-3-yl]acetic acid (I-78)

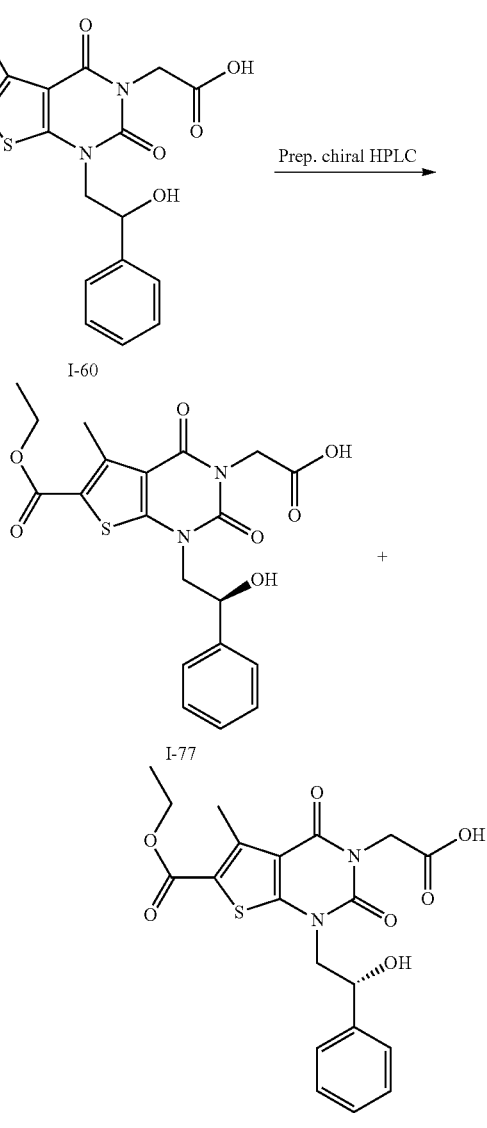

I-60 (120 mg, 0.28 mmol, 1.00 equiv) was purified by chiral preparative HPLC under the following conditions (Gilson Gx 281): column: Chiralpak IC(SFC), 2*25 cm, 5 μm; mobile phase: hexanes and ethanol (0.1% TFA) (hold at 20.0% ethanol (0.1% TFA) in 18 min); detector: UV 220/254 nm. This resulted in 24.6 mg (tR=10.1 min, 21%) of I-77 as a white solid and 15.2 mg (12.5 min, 13%) of I-78 as a white solid.

Analytical Data for I-77: MS (ES): m/z 433 (M+H)+, 496 (M+Na+CH3CN)+. $^1$H NMR (400 MHz, DMSO-$d_6$): δ 1.32 (t, J=7.2, 3H), 2.77 (s, 3H), 3.80-3.86 (m, 1H), 4.13-4.18 (m, 1H), 4.29 (q, J=6.9, 2H), 4.57 (d, J=6.0, 2H), 4.99 (t, J=4.8, 1H), 5.90 (d, J=4.4, 1H), 7.29-7.44 (m, 5H).

Analytical Data for I-78: MS (ES): m/z 433 (M+H)+, 496 (M+Na+CH$_3$CN)+. $^1$H NMR (400 MHz, DMSO-$d_6$): δ 1.32 (t, J=7.2, 3H), 2.77 (s, 3H), 3.80-3.86 (m, 1H), 4.13-4.18 (m, 1H), 4.29 (q, J=6.9, 2H), 4.57 (d, J=6.0, 2H), 4.99 (t, J=4.8, 1H), 5.90 (d, J=4.4, 1H), 7.29-7.44 (m, 5H).

Example 209

Synthesis of (2R)-2-[6-(ethoxycarbonyl)-5-methyl-2,4-dioxo-1-(2-phenylethyl)-1H,2H,3H,4H-thieno[2,3-d]pyrimidin-3-yl]propanoic acid (I-76) and Example 210: Synthesis of (2S)-2-[6-(ethoxycarbonyl)-5-methyl-2,4-dioxo-1-(2-phenylethyl)-1H,2H,3H,4H-thieno[2,3-d]pyrimidin-3-yl]propanoic acid (I-80)

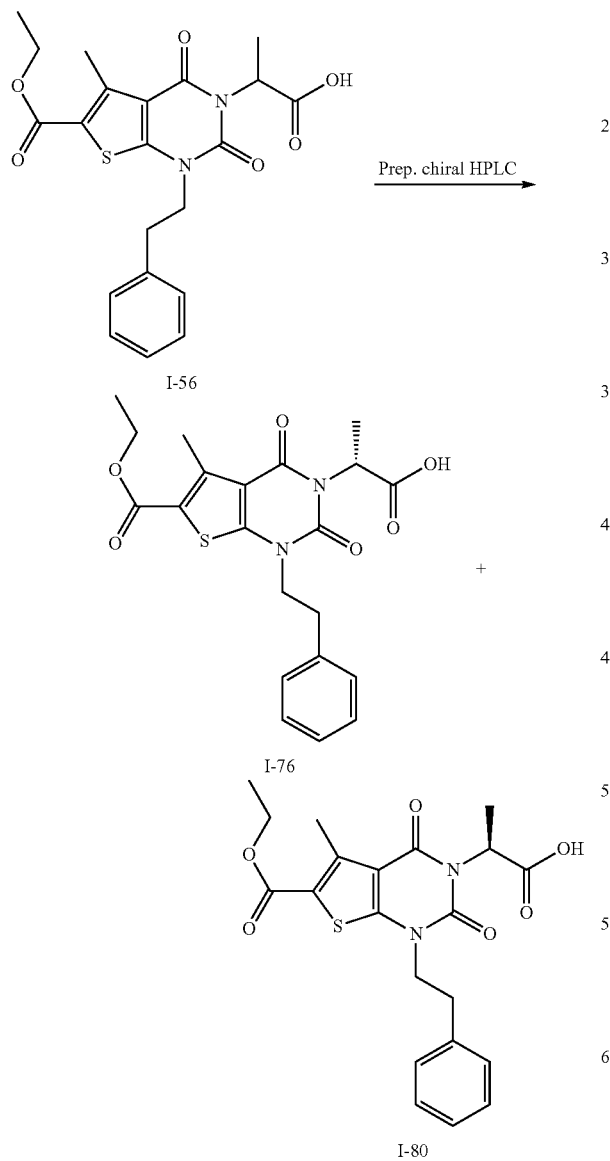

The enantiomers of I-56 were separated by chiral HPLC under the following conditions (Gilson Gx 281): column: Chiralpak IA, 2*25 cm, 5 μm; mobile phase: hexanes and ethanol (0.1% DEA) (hold at 40.0% ethanol (0.1% DEA) in 20 min); detector: UV 220/254 nm. This resulted in 20 mg (tR=5.27 min, 31%) of I-76 as a white solid and 20 mg (tR=10.4 min, 27%) of I-80 as a white solid.

Analytical Data for I-76: MS (ES): m/z 431 (M+H)+. $^1$H NMR (CDCl$_3$, 300 MHz): δ 1.29 (t, J=9.6 Hz, 3H), 1.48 (d, J=10.0 Hz, 3H), 2.74 (s, 3H), 3.00 (t, J=9.6 Hz, 2H), 4.12 (t, J=10.0 Hz, 2H), 4.28 (q, J=9.6 Hz, 2H), 5.37(q, 1H), 7.18-7.30 (m, 5H), 12.72 (s, 1H).

Analytical Data for I-80: MS (ES): m/z 431 (M+H)+. $^1$H NMR (CDCl$_3$, 300 MHz): δ 1.29 (t, J=9.6 Hz, 3H), 1.42 (d, J=9.6 Hz, 3H), 2.73 (s, 3H), 2.98 (t, J=9.6 Hz, 2H), 4.12 (t, J=6.8 Hz, 2H), 4.27 (q, 2H), 4.96 (q, 1H), 7.19-7.32 (m, 5H).

Example 211

Synthesis of 2-[6-(cyclobutoxycarbonyl)-5-methyl-2,4-dioxo-1-(2-phenylethyl)-1H,2H,3H,4H-thieno[2,3-d]pyrimidin-3-yl]acetic acid (I-86)

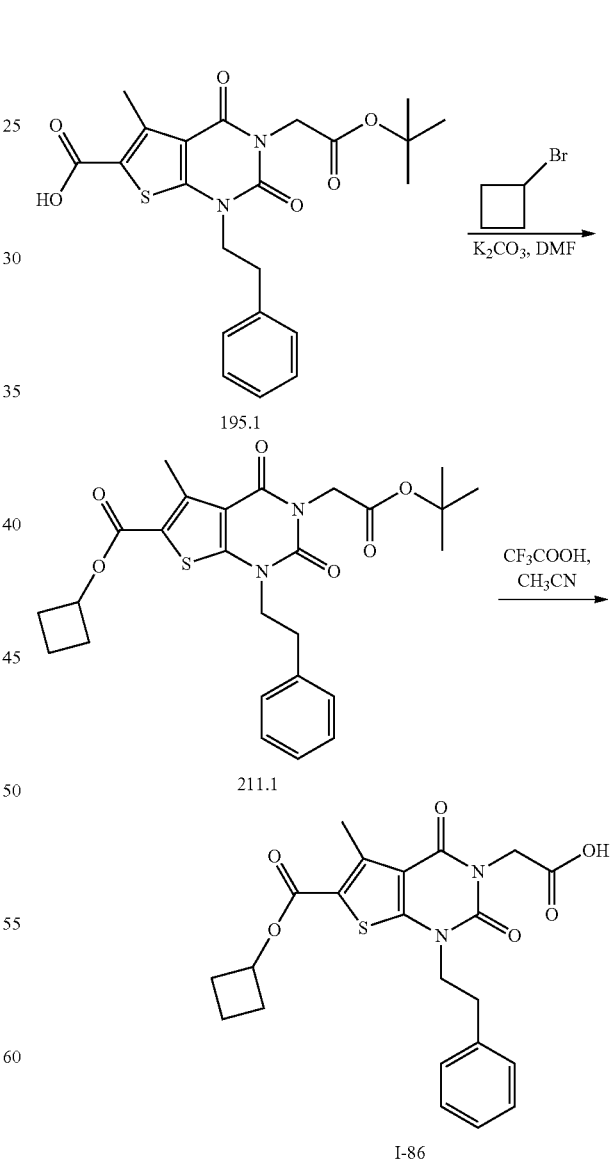

Compound I-86 was prepared from 195.1 and bromocyclobutane in a manner analogous to the synthesis of Compound I-68 (Example 195). Isolated 93 mg (55%) of a dark yellow solid. MS (ES): m/z 443 (M+H)⁺. ¹H NMR (CD₃OD, 300 MHz): δ 1.69-1.95 (m, 2H), 2.14-2.28 (m, 2H), 2.39-2.48 (m, 2H), 2.80 (s, 3H), 3.08-3.13 (t, 2H), 4.17-4.22 (t, 2H), 4.71 (s, 2H), 5.12-5.22 (m, 1H), 7.22-7.32 (m, 5H).

Example 212

Synthesis of ethyl 3-[(2R)-2-hydroxypropyl]-5-methyl-2,4-dioxo-1-(2-phenylethyl)-1H,2H,3H,4H-thieno[2,3-d]pyrimidine-6-carboxylate (I-81) and Example 213: Synthesis of ethyl 3-[(2S)-2-hydroxypropyl]-5-methyl-2,4-dioxo-1-(2-phenylethyl)-1H,2H,3H,4H-thieno[2,3-d]pyrimidine-6-carboxylate (I-82)

UV 220/254 nm. This resulted in 100 mg (tR=15.2 min, 80%) of I-81 as a white solid and 100 mg (tR=17.6 min, 80%) of I-82 as a white solid.

Analytical Data for I-81: MS (ES): m/z 417 (M+H)⁺. ¹H NMR (400 MHz, DMSO-d₆): δ 1.03 (d, J=5.2 Hz, 3H), 1.30 (t, J=6.8 Hz, 3H), 2.76 (s, 3H), 3.00 (m, J=7.2 Hz, 2H), 3.70 (q, 1H), 3.95 (t, J=8.0 Hz, 2H), 4.12 (t, J=8.0 Hz, 2H), 4.28 (m, J=7.2 Hz, 2H), 4.77 (s, 1H), 7.19-7.32 (m, 5H).

Analytical Data for I-82: MS (ES): m/z 417 (M+H)⁺. ¹H NMR (DMSO-d₆, 400 MHz): δ 1.03 (d, J=5.2 Hz, 3H), 1.30 (t, J=6.8 Hz, 3H), 2.76 (s, 3H), 3.00 (t, J=7.2 Hz, 2H), 3.70 (q, 1H), 3.95 (t, J=8.0 Hz, 2H), 4.12 (t, J=8.0 Hz, 2H), 4.28 (q, J=7.2 Hz, 2H), 4.77 (s, 1H), 7.19-7.32 (m, 5H).

Example 214

Synthesis of 2-[6-(ethoxycarbonyl)-5-methyl-2,4-dioxo-1-(2-oxo-2-phenylethyl)-1H,2H,3H,4H-thieno[2,3-d]pyrimidin-3-yl]acetic acid (I-73)

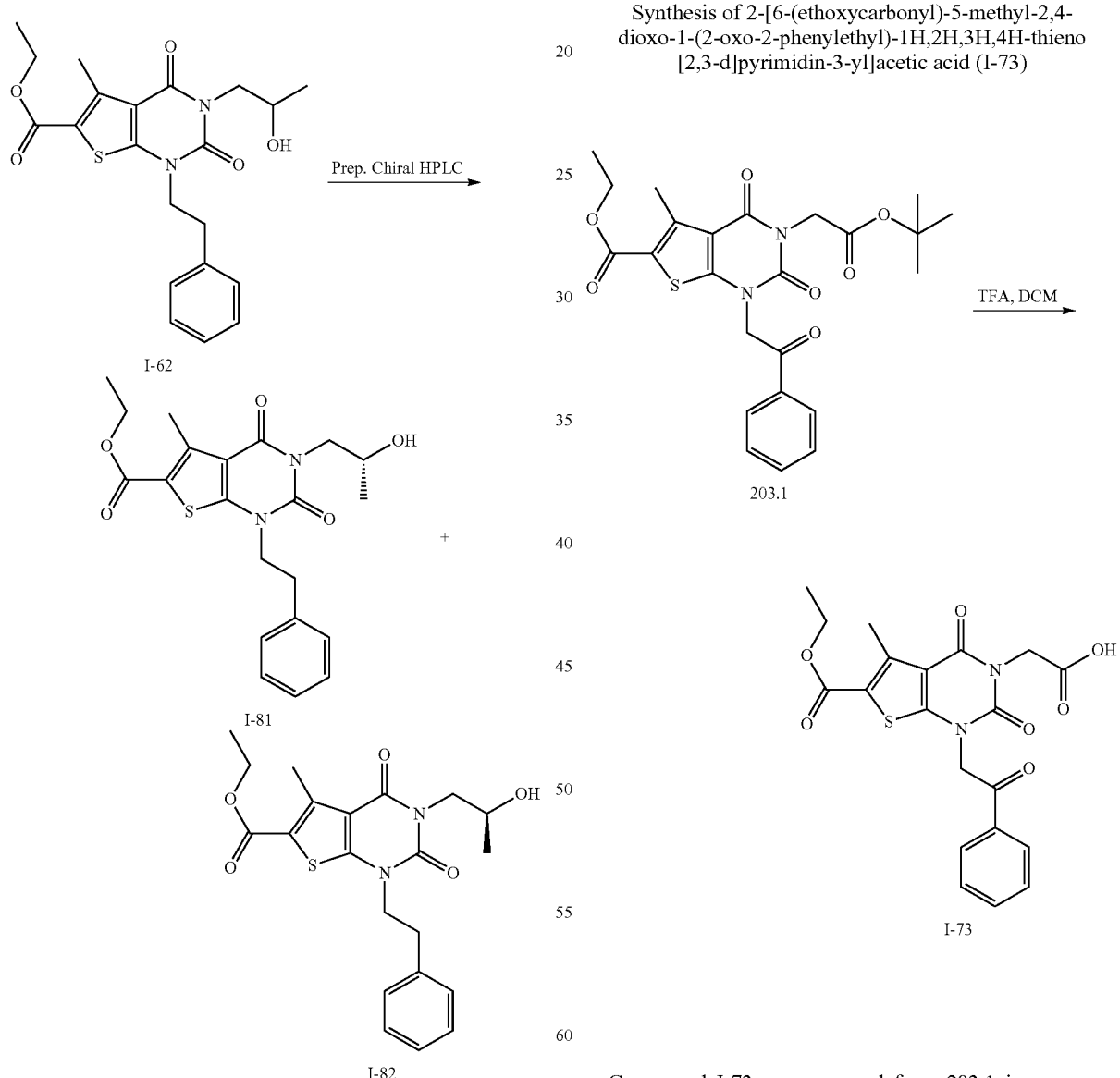

The enantiomers of I-62 (250 mg) were separated by chiral preparative HPLC under the following conditions (Gilson Gx 281): column: Chiralpak IB, 2*25 cm, 5 μm; mobile phase: hexanes and ethanol (hold 5.0% ethanol in 12 min); detector:

Compound I-73 was prepared from 203.1 in a manner analogous to the synthesis of 2.5. Isolated 69.2 mg (78%) of a white solid. MS (ES): m/z 431 (M+H)⁺. ¹H NMR (400 MHz, DMSO-d₆): δ 1.26 (t, J=7.2, 3H), 2.80 (s, 3H), 4.26 (q, J=7.2, 2H), 4.57 (s, 2H), 5.73 (s, 2H), 7.63 (t, J=7.6, 2H), 7.78 (t, J=7.6, 1H), 8.12 (d, J=7.6, 2H).

Example 215

Synthesis of 2-[6-(ethoxycarbonyl)-2,4-dioxo-1-(2-phenylethyl)-5-(trifluoromethyl)-1H,2H,3H,4H-thieno[2,3-d]pyrimidin-3-yl]acetic acid (I-94)

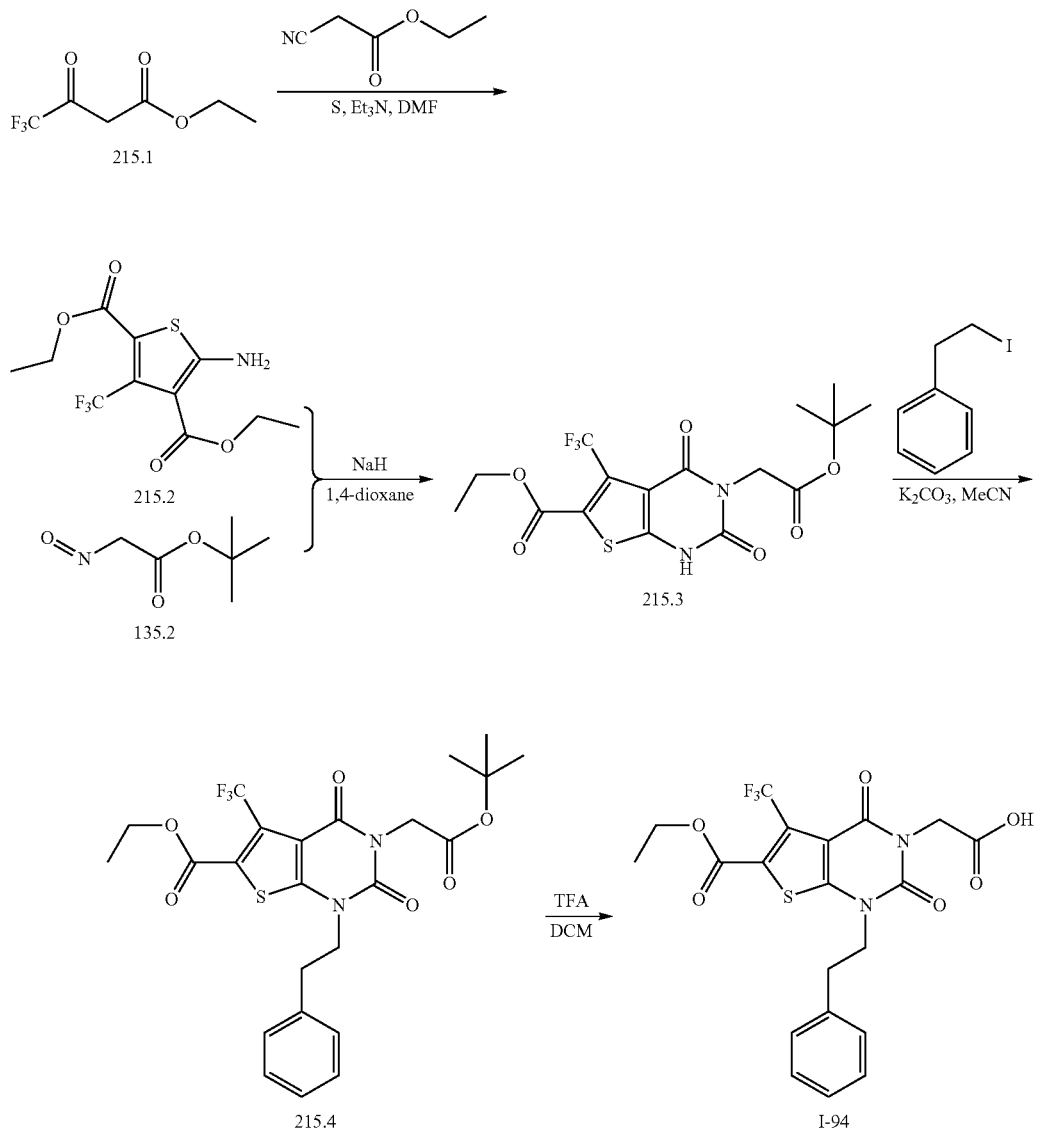

Synthesis of compound 215.2. Into a 1-L 3-necked round-bottom flask was placed S (8.84 g, 276.25 mmol, 1.00 equiv), ethyl 4,4,4-trifluoro-3-oxobutanoate (50.8 g, 275.92 mmol, 1.00 equiv), N,N-dimethylformamide (300 mL) and ethyl 2-cyanoacetate (31.2 g, 275.83 mmol, 1.00 equiv). This was followed by the addition of triethylamine (28 g, 276.71 mmol, 1.00 equiv) dropwise with stirring at 0° C. The resulting solution was stirred overnight at room temperature. The resulting solution was allowed to react, with stirring, for an additional 1 day while the temperature was maintained at 40° C. in an oil bath. The reaction was then quenched by the addition of 500 mL of water. The resulting solution was extracted with 3×500 mL of ether and the organic layers combined and concentrated under vacuum. The residue was applied onto a silica gel column with ethyl acetate/petroleum ether (1:12). This resulted in 5.8 g (7%) of 215.2 as a yellow solid.

Synthesis of Compound I-94. Compound I-94 was prepared from 215.2 and 135.2 in a manner analogous to the synthesis of compound 136.2. Isolated 0.4 g of a white solid in 53% yield. MS (ES): m/z 471 (M+H)$^+$. $^1$H NMR (400 MHz, DMSO-d$_6$): δ 1.30 (t, J=6.8, 3H), 3.02 (t, J=7.2, 2H), 4.17 (t, J=7.2, 2H), 4.34 (t, J=7.2, 2H), 4.58 (s, 2H), 7.21-7.32 (m, 5H), 13.11 (s, 1H).

Example 216

Synthesis of 2-[6-(4,5-dihydro-1,3-oxazol-2-yl)-5-methyl-2,4-dioxo-1-(2-phenylethyl)-1H,2H,3H,4H-thieno[2,3-d]pyrimidin-3-yl]acetic acid (I-87)

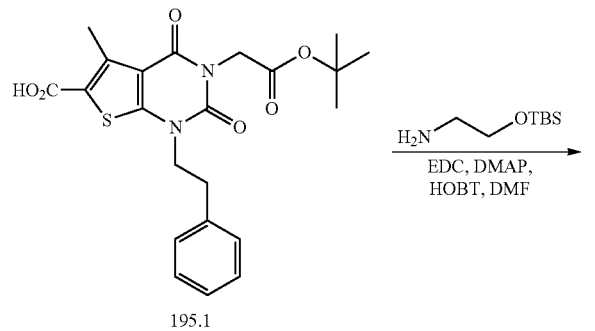

195.1

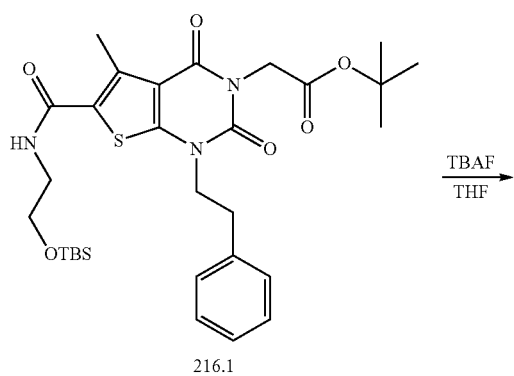

216.1

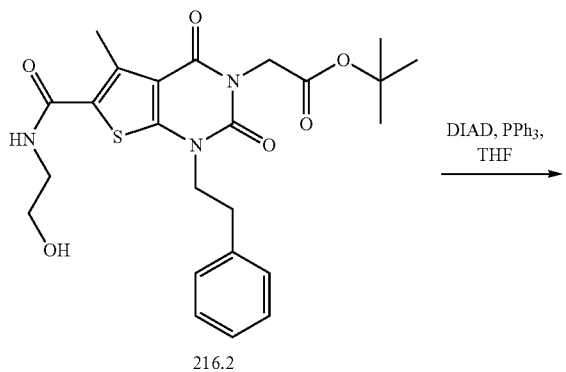

216.2

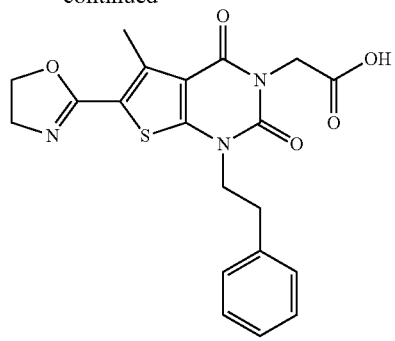

216.3

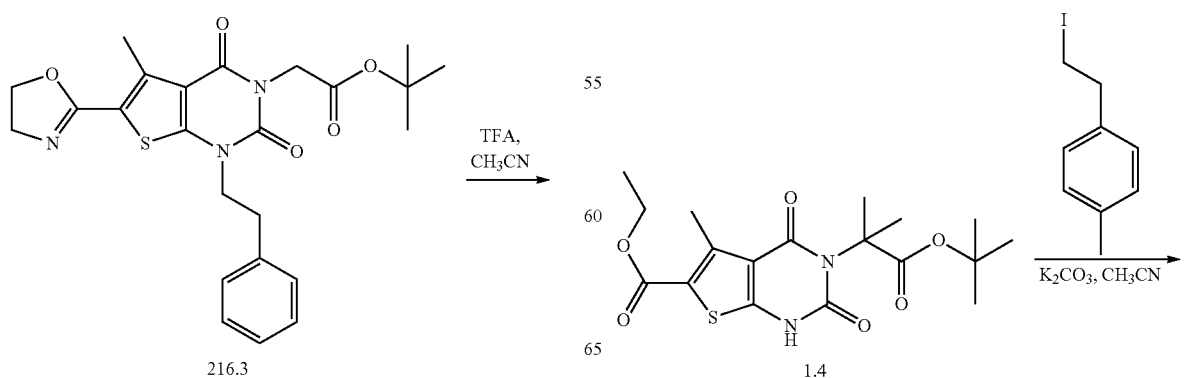

I-87

Synthesis of compound 216.1. Compound 216.1 was prepared from 195.1 in a manner analogous to compound 136.3. Isolated 600 mg (89%) of a white solid.

Synthesis of compound 216.2. Into a 50-mL round-bottom flask was placed 216.1 (600 mg, 1.00 mmol, 1.00 equiv), oxolane (10 mL) and TBAF (300 mg, 1.15 mmol, 1.15 equiv). The resulting solution was stirred overnight at room temperature. The resulting mixture was concentrated under vacuum. The residue was applied onto a silica gel column with ethyl acetate/PE (1:5). Purification afforded 205 mg (42%) of 216.2 as a white solid.

Synthesis of compound 216.3. Into a 10-mL round-bottom flask was placed 216.2 (100 mg, 0.21 mmol, 1.00 equiv), DIAD (94 mg, 0.46 mmol, 1.99 equiv), PPh₃ (107 mg, 0.41 mmol, 2.00 equiv) and tetrahydrofuran (5 mL). The resulting solution was stirred overnight at room temperature. The resulting mixture was concentrated under vacuum. The residue was applied onto a silica gel column with ethyl acetate/petroleum ether (1:20). Purification afforded 70 mg (73%) of 216.3 as a white solid.

Synthesis of Compound I-87. Compound I-87 was prepared from 216.3 in a manner analogous to the synthesis of 2.5. Isolated 2.8 mg (9%) of I-87 as a white solid. MS (ES): m/z 414 (M+H)⁺. ¹H NMR (400 MHz, CD₃OD): δ 2.76 (s, 1H), 3.11 (t, J=8.0, 2H), 3.99 (t, J=9.6, 2H), 4.17 (t, J=7.6, 2H), 4.49 (t, J=9.6, 2H), 4.62 (s, 2H), 7.22-7.30 (m, 5H).

Example 217

Synthesis of 2-[6-(ethoxycarbonyl)-1-[2-(4-iodophenyl)ethyl]-5-methyl-2,4-dioxo-1H,2H,3H,4H-thieno[2,3-d]pyrimidin-3-yl]-2-methylpropanoic acid (I-95)

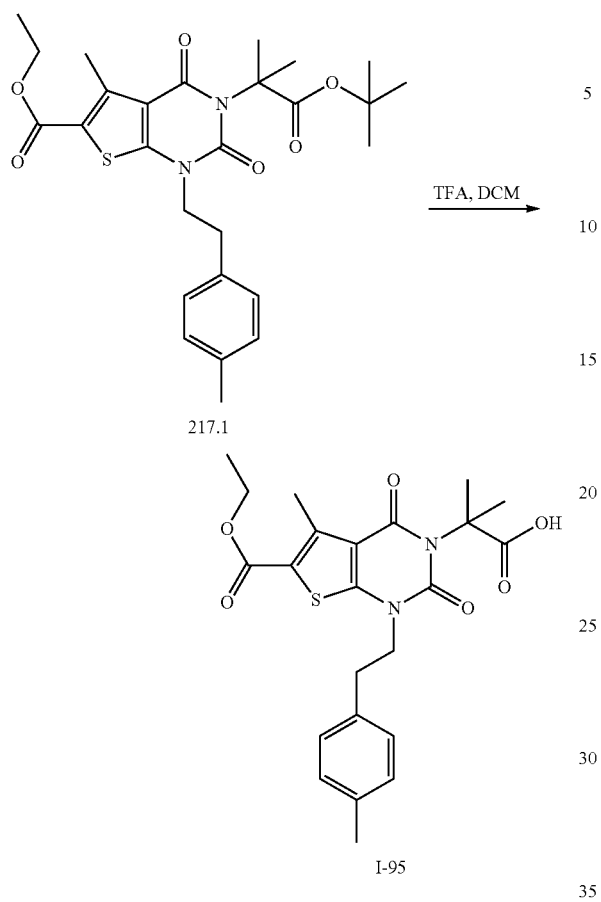

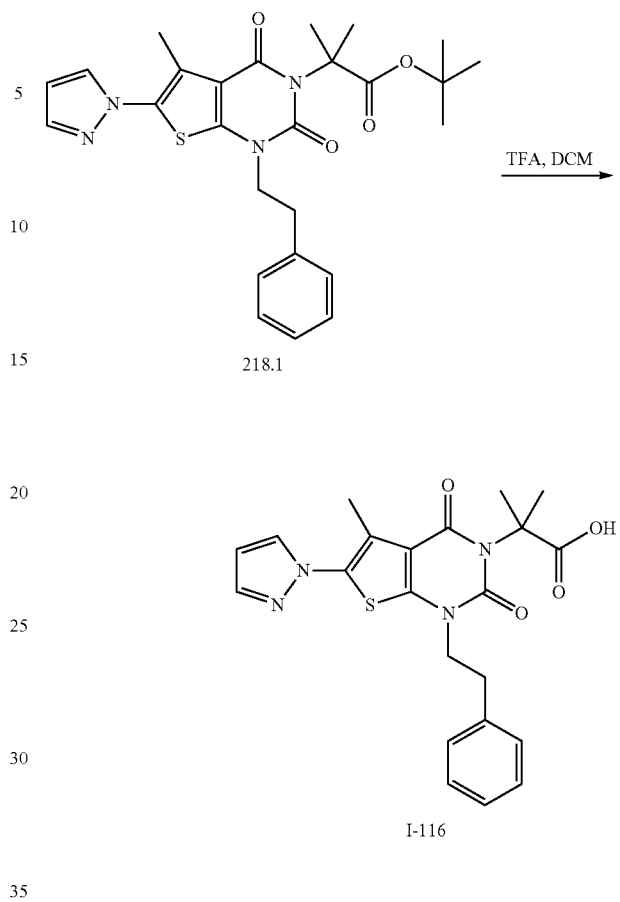

Synthesis of Compound I-95. Compound I-95 was prepared from 1.4 and 1-iodo-4-(2-iodoethyl)benzene in a manner analogous to the synthesis of 136.2. MS (ES): m/z 571 (M+H)$^+$, 612 (M+H+CH$_3$CN)$^+$. $^1$H NMR (400 MHz, CD$_3$CN): δ 1.32 (t, J=7.2, 3H), 1.67 (s, 6H), 2.71 (s, 3H), 2.98 (t, J=7.2, 2H), 4.05 (t, J=7.2, 2H), 4.28 (q, J=7.2, 2H), 7.01 (d, J=8.4, 2H), 7.62 (d, J=8.0, 2H).

Example 218

Synthesis of 2-methyl-2-[5-methyl-2,4-dioxo-1-(2-phenylethyl)-6-(1H-pyrazol-1-yl)-1H,2H,3H,4H-thieno[2,3-d]pyrimidin-3-yl]propanoic acid (I-116)

Compound I-116 was prepared from 121.3 and pyrazole in a manner analogous to Compound I-157. Isolated 150 mg of a white solid in 30% overall yield. MS (ES): m/z 439 (M+H)$^+$, 480 (M+H+CH$_3$CN)$^+$. $^1$H NMR (300 MHz, DMSO-d$_6$): δ 1.62 (s, 6H), 2.27 (s, 3H), 2.95 (t, J=7.2, 2H), 4.00 (t, J=7.2, 2H), 6.52 (t, J=2.1, 1H), 7.15-7.28 (m, 5H), 7.73 (d, J=2.1, 1H), 8.10 (d, J=2.4, 1H), 12.40 (s, 1H).

Example 219

Synthesis of 2-[6-(ethoxycarbonyl)-1-[2-(2-ethylphenyl)ethyl]-5-methyl-2,4-dioxo-1H,2H,3H,4H-thieno[2,3-d]pyrimidin-3-yl]-2-methylpropanoic acid (I-100)

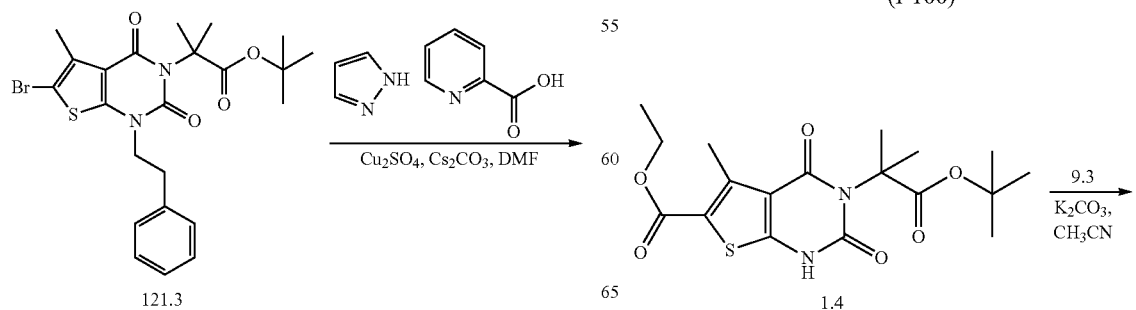

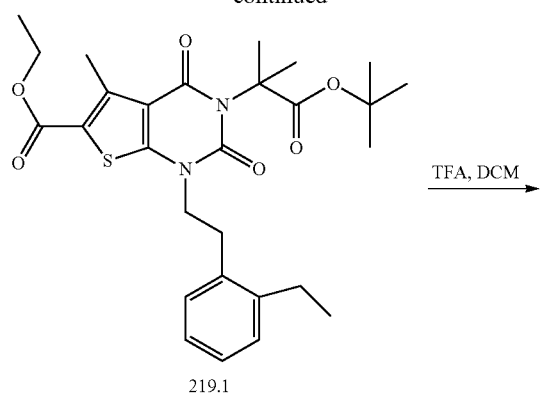

219.1

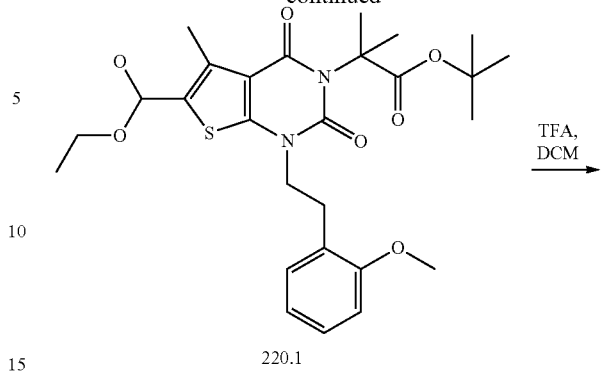

220.1

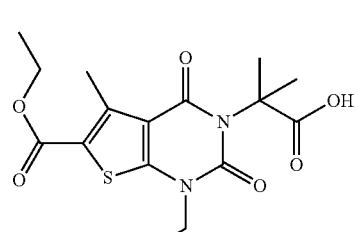

I-100

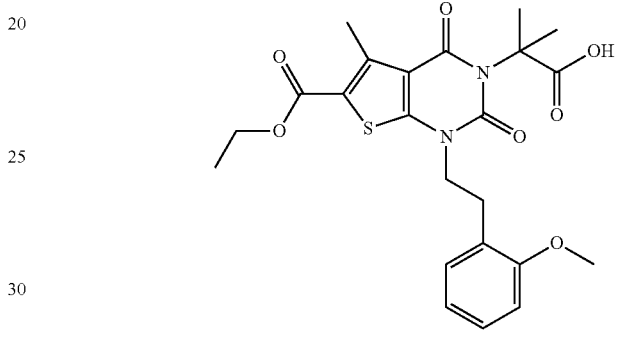

I-93

Compound I-100 was prepared from 1.4 and 9.3 in a manner analogous to the synthesis of 136.2. Isolated 0.041 g of a white solid in 59% overall yield from 1.4. MS (ES): m/z 473 (M+H)$^+$. $^1$H NMR (300 MHz, CD$_3$OD): δ 1.25 (t, J=7.5, 3H), 1.36 (t, J=7.5, 3H), 1.25 (s, 6H), 2.76 (q, J=7.5, 5H), 3.12 (t, J=7.5, 2H), 4.10 (t, J=7.5, 2H), 4.32 (q, J=7.2, 3H), 7.08-7.20 (m, 4H).

Example 220

Synthesis of 2-[6-(ethoxycarbonyl)-1-[2-(2-methoxyphenyl)ethyl]-5-methyl-2,4-dioxo-1H,2H,3H,4H-thieno[2,3-d]pyrimidin-3-yl]-2-methylpropanoic acid (I-93)

Compound I-93 was prepared from 1.4 and commercially available 1-(2-bromoethyl)-2-methoxybenzene in a manner analogous to the synthesis of 136.2. MS (ES): m/z 475 (M+H)$^+$.

$^1$H NMR (DMSO-d$_6$, 400 MHz): δ 1.29~1.32 (t, 3H), 1.64 (s, 6H), 2.70 (s, 3H), 2.96~2.95 (t, 2H), 3.76 (s, 3H), 4.03~4.07 (t, 2H), 4.25~4.30 (q, 2H), 6.84~6.87 (t, 1H), 6.91~6.93 (d, 1H), 7.12~7.14 (d, 1H), 7.19~7.23 (t, 1H).

Example 221

Synthesis of 2-[6-(ethoxycarbonyl)-5-methyl-2,4-dioxo-1-[2-[2-(trifluoromethoxy)phenyl]ethyl]-1H,2H,3H,4H-thieno[2,3-d]pyrimidin-3-yl]-2-methylpropanoic acid (I-106)

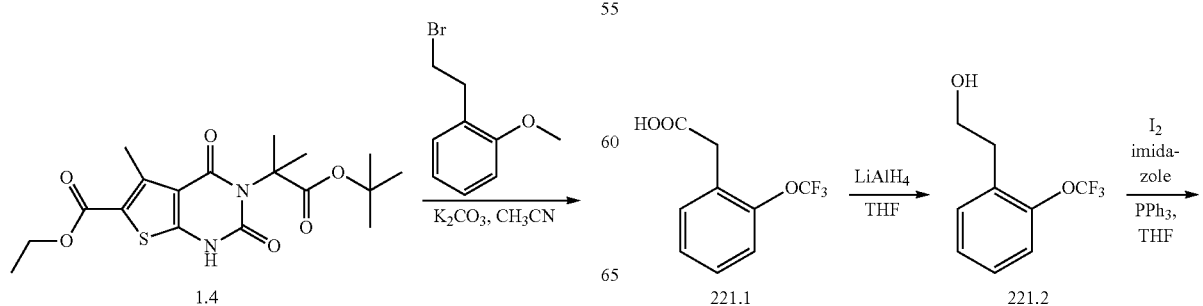

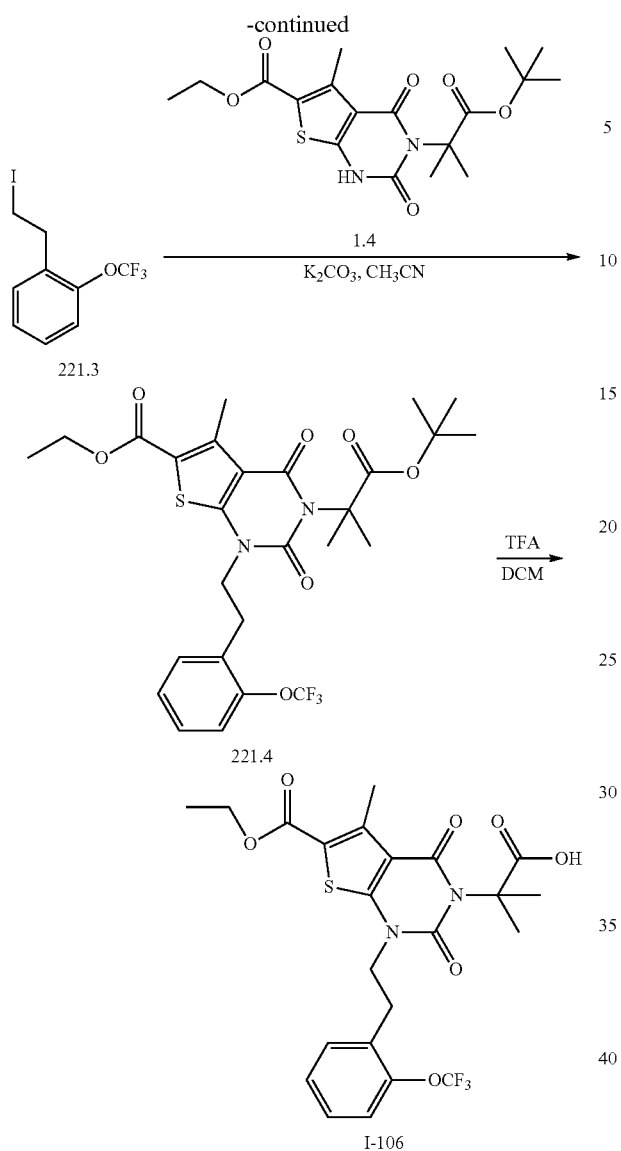

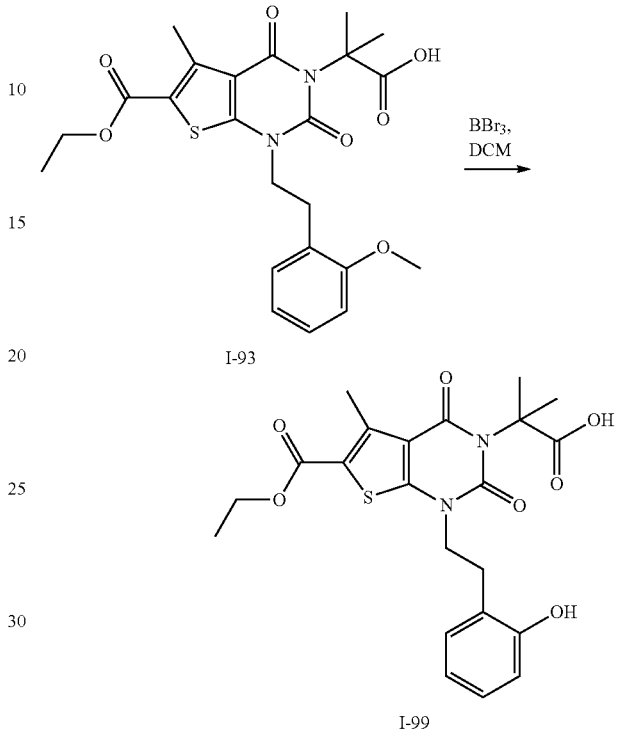

Example 222

Synthesis of 2-[6-(ethoxycarbonyl)-1-[2-(2-hydroxyphenyl)ethyl]-5-methyl-2,4-dioxo-1H,2H,3H,4H-thieno[2,3-d]pyrimidin-3-yl]-2-methylpropanoic acid (I-99)

Synthesis of compound 221.2. Into a 100-mL round-bottom flask was placed 2-[2-(trifluoromethoxy)phenyl]acetic acid (1 g, 4.54 mmol, 1.00 equiv), THF (30 mL) and alumane lithium (173 mg, 4.55 mmol, 1.00 equiv). The resulting solution was stirred for 2 h at room temperature. The reaction was then quenched by the addition of 40 mL of $NH_4Cl$ (aq). The resulting solution was extracted with 3×50 mL of ethyl acetate and the organic layers combined and dried over anhydrous sodium sulfate and concentrated under vacuum. The residue was applied onto a silica gel column with ethyl acetate/petroleum ether (1:20). This resulted in 300 mg (32%) of 221.2 as a colorless oil.

Synthesis of compound 221.3. 221.3 was prepared from 221.2 in a manner analogous to the synthesis of compound 9.3. Isolated 300 mg of a colorless oil in 65% yield.

Synthesis of Compound I-106. Compound I-106 was prepared from 221.3 and 1.4 in a manner analogous to the synthesis of 136.2. Isolated 80 mg (60% overall yield) as a white solid. MS (ES): m/z 528.8 (M+H)+, 591.8 (M+Na+$CH_3CN$)+. $^1$H NMR (300 MHz, DMSO-$d_6$): δ1.26 (t, 3H), 1.56 (s, 6H), 2.67 (s, 3H), 3.05 (t, 2H), 4.04 (t, 2H), 4.26 (q, 2H), 7.24-7.40 (m, 4H).

Into a 10-mL round-bottom flask was placed I-93 (50 mg, 0.11 mmol, 1.00 equiv), $BBr_3$ (105 mg) and dichloromethane (5 mL). The resulting solution was stirred overnight at room temperature. The reaction was then quenched by the addition of 2 mL of water. The resulting solution was extracted with 3×5 mL of ethyl acetate and the organic layers combined and concentrated under vacuum. The residue was applied onto a silica gel column with ethyl acetate/hexane (1:2). This resulted in 4.6 mg (9%) of I-99 as a colorless oil. MS (ES): m/z 461 (M+H)+. $^1$H NMR ($CD_3OD$, 300 Mz): δ 1.29~1.37 (t, 3H), 1.77 (s, 6H), 2.73 (s, 3H), 3.04~3.09 (t, 2H), 4.13~4.17 (t, 2H), 4.26~4.33 (q, 2H), 6.68~6.72 (m, 2H), 6.98~7.03 (m, 2H).

Example 223

Synthesis of 2-[6-(ethoxycarbonyl)-1-[(2S)-2-hydroxy-2-phenylethyl]-5-methyl-2,4-dioxo-1H,2H,3H,4H-thieno[2,3-d]pyrimidin-3-yl]-2-methylpropanoic acid (I-102) and Example 224: Synthesis of 2-[6-(ethoxycarbonyl)-1-[(2S)-2-hydroxy-2-phenylethyl]-5-methyl-2,4-dioxo-1H,2H,3H,4H-thieno[2,3-d]pyrimidin-3-yl]-2-methylpropanoic acid (I-103)

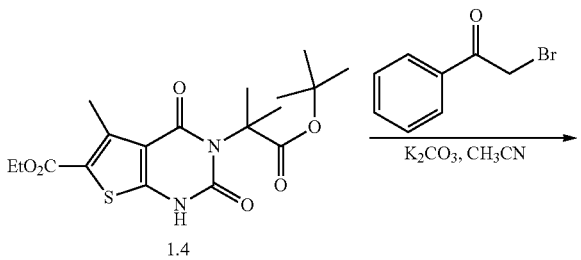

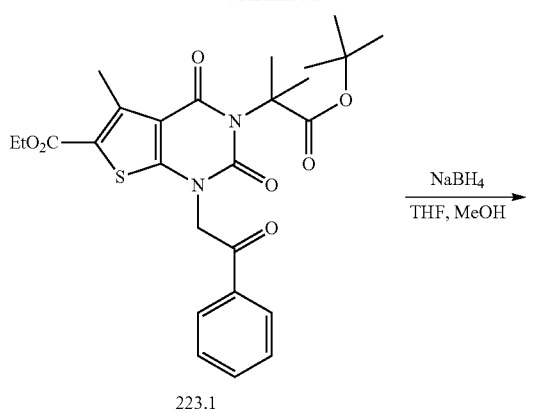

223.1

NaBH₄, THF, MeOH →

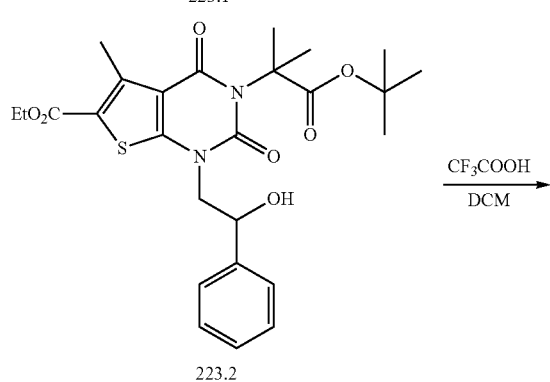

223.2

CF₃COOH / DCM →

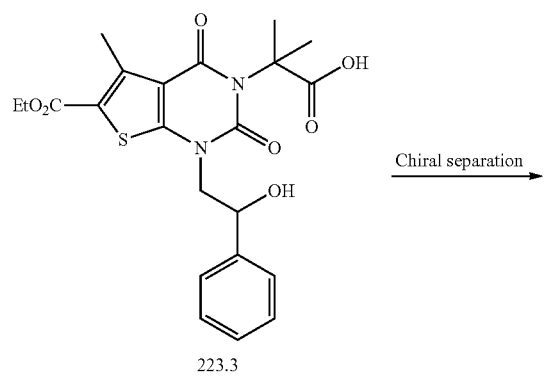

223.3

Chiral separation →

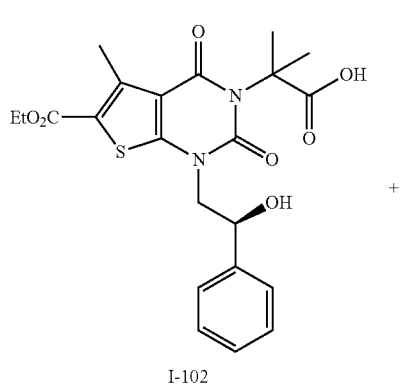

I-102

+

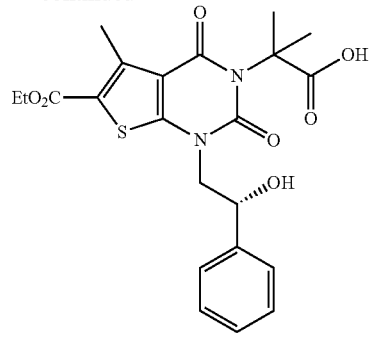

I-103

Synthesis of compound 223.3. Compound 223.3 was prepared from 1.4 and 2-bromo-1-phenylethan-1-one in a manner analogous to the synthesis of I-60 (Example 203). Isolated 140 mg of a white solid in 60% overall yield from 1.4.

Synthesis of Compound I-102 and I-103. The enantiomers of 223.3 (140 mg) were isolated by chiral preparative HPLC under the following conditions (Gilson Gx 281): column: Chiralpak IC(SFC), 2*25 cm, 5 μm; mobile phase: hexanes (0.1% TFA) and ethanol (hold at 10.0% ethanol in 16 min); detector: UV 220/254 nm. This resulted in 15.9 mg (11%) of I-102 as a white solid and 15.2 mg (11%) of I-103 as a white solid.

Analytical Data for I-102: MS (ES): m/z 461 (M+H)⁺. ¹H NMR (300 MHz, DMSO-d₆): δ 1.30 (t, 3H), 1.66 (s, 6H), 2.71 (s, 3H), 3.73 (m, 1H), 4.14 (m, 1H), 4.27 (m, 2H), 4.98 (q, 1H), 5.88 (d, 1H), 7.28-7.41 (m, 5H), 12.3 (s,1H).

Analytical Data for I-103: MS (ES): m/z 461 (M+H)⁺. ¹H NMR (300 MHz, DMSO-d₆): δ 1.30 (t, 3H), 1.66 (s, 6H), 2.71 (s, 3H), 3.73 (m, 1H), 4.14 (m, 1H), 4.27 (q, 2H), 4.98 (d, 1H), 5.88 (m, 1H), 7.28-7.41 (m, 5H), 12.3 (br s, 1H).

Example 225

Synthesis of 2-[6-(ethoxycarbonyl)-1-[(2R)-2-methoxy-2-phenylethyl]-5-methyl-2,4-dioxo-1H,2H,3H,4H-thieno[2,3-d]pyrimidin-3-yl]-2-methylpropanoic acid (I-110)

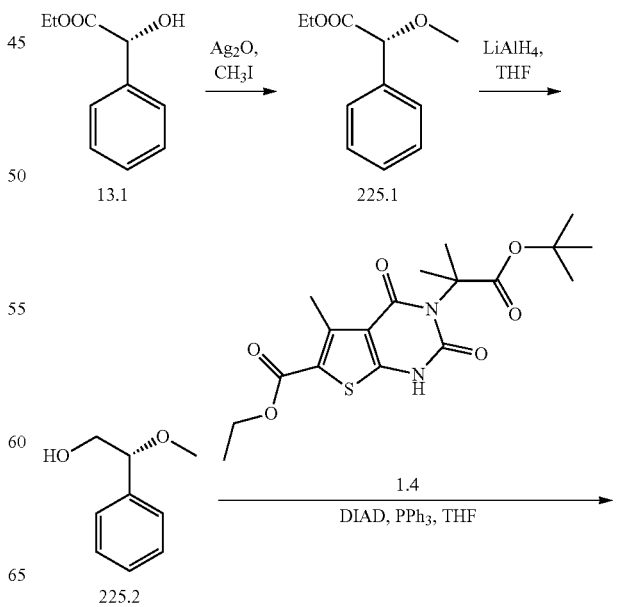

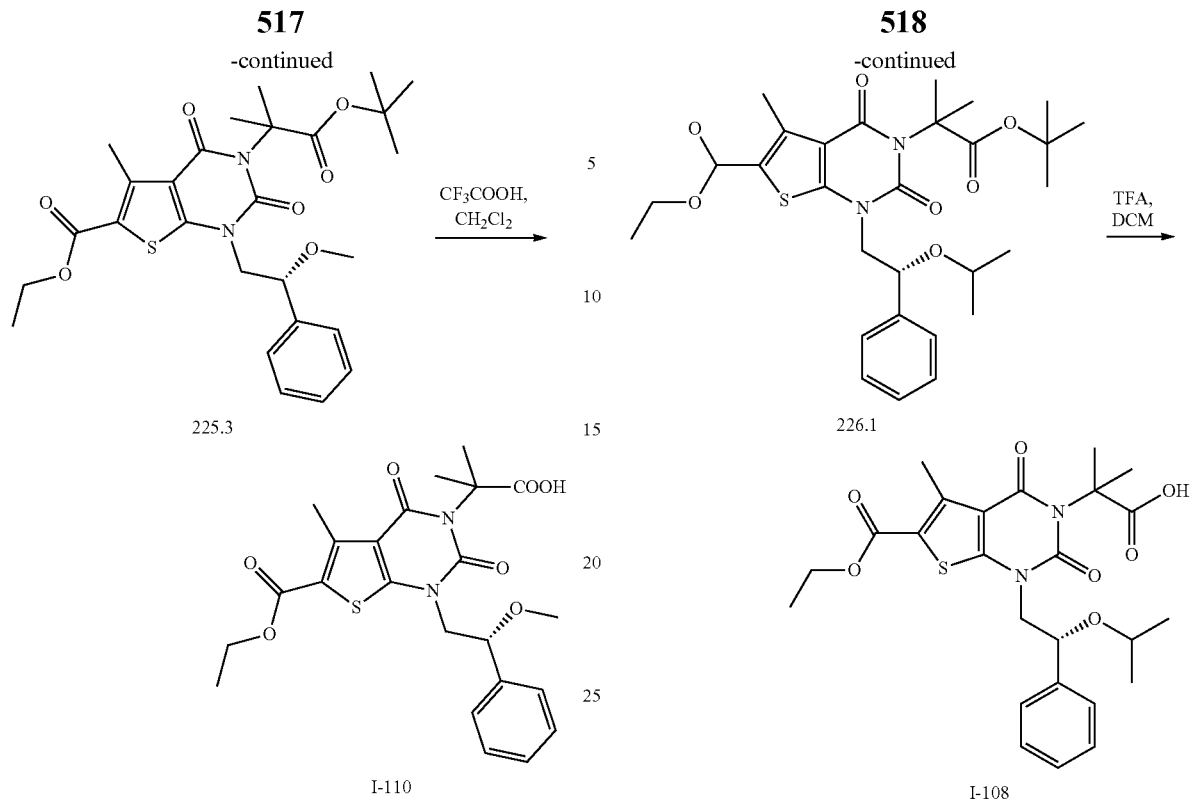

Synthesis of compound 225.1. 225.1 was prepared from 13.1 in a manner analogous to the synthesis of 13.2. Isolated 1.26 g (22%) of a colorless oil.

Synthesis of compound 225.2. Into a 100-mL 3-necked round-bottom flask was placed tetrahydrofuran (50 mL) and 225.1 (1.26 g, 6.49 mmol, 1.00 equiv). This was followed by the addition of LiAlH$_4$ (247 mg, 6.51 mmol, 1.00 equiv) in portions at 0° C. The resulting solution was stirred for 2 h at 0° C. The reaction was then quenched by the addition of 20 mL of NH$_4$Cl (aq.). The resulting mixture was concentrated under vacuum. The residue was applied onto a silica gel column with ethyl acetate/hexane (1:5). This resulted in 610 mg (62%) of 225.2 as a colorless oil.

Synthesis of Compound I-110. Compound I-110 was prepared from 225.2 in a manner analogous to the synthesis of 2.5. Isolated 70 mg (78%) of a white solid. MS (ES): m/z 475 (M+H)$^+$. $^1$H NMR (CD$_3$OD, 300 MHz): δ 1.34 (m, 3H), 1.75 (s, 6H), 2.74 (s, 3H), 3.27 (s, 3H), 3.92 (m, 1H), 4.10 (m, 1H), 4.28 (m, 2H), 4.66 (m, 1H), 7.37 (m, 5H).

Example 226

Synthesis of 2-[6-(ethoxycarbonyl)-5-methyl-2,4-dioxo-1-[(2R)-2-phenyl-2-(propan-2-yloxy)ethyl]-1H,2H,3H,4H-thieno[2,3-d]pyrimidin-3-yl]-2-methylpropanoic acid (I-108)

Compound I-108 was prepared from 1.4 and 3.3 in a manner analogous to the synthesis of 2.5. Isolated 51.6 mg (22% overall) of a white solid. MS (ES): m/z 503 (M+H)$^+$. $^1$H NMR (CDCl$_3$, 400 MHz): δ 0.85 (d, 3H), 0.89 (d, 3H), 1.25~1.33 (t, 3H), 1.67~1.71 (d, 6H), 2.73 (s, 3H), 3.41~3.47 (m, 1H), 3.81~3.85 (m, 1H), 4.02~4.11 (m, 1H), 4.27~4.34 (m, 2H), 4.80~4.82 (m, 1H), 7.32~7.37 (m, 1H), 7.41~7.42 (d, 4H), 12.45 (s, 1H).

Example 227

Synthesis of 2-[6-(ethoxycarbonyl)-1-[(2S)-2-methoxy-2-phenylethyl]-5-methyl-2,4-dioxo-1H,2H,3H,4H-thieno[2,3-d]pyrimidin-3-yl]acetic acid (I-104) and Example 228: Synthesis of 2-[6-(ethoxycarbonyl)-1-[(2S)-2-methoxy-2-phenylethyl]-5-methyl-2,4-dioxo-1H,2H,3H,4H-thieno[2,3-d]pyrimidin-3-yl]acetic acid (I-105)

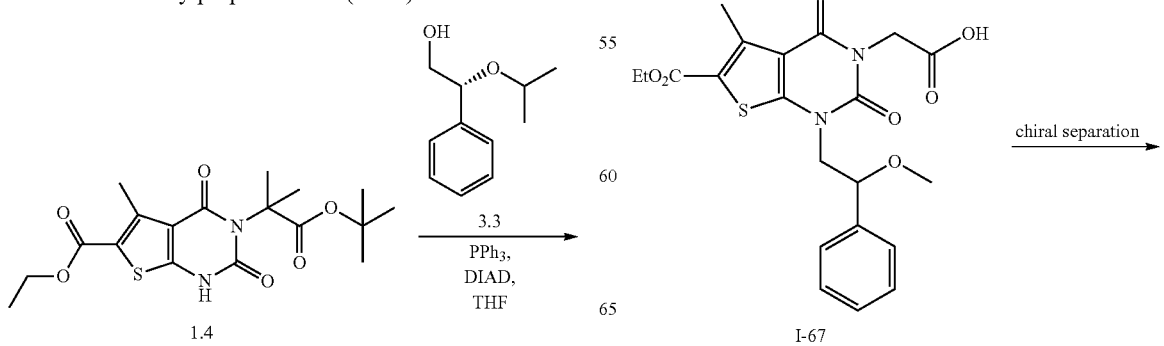

-continued

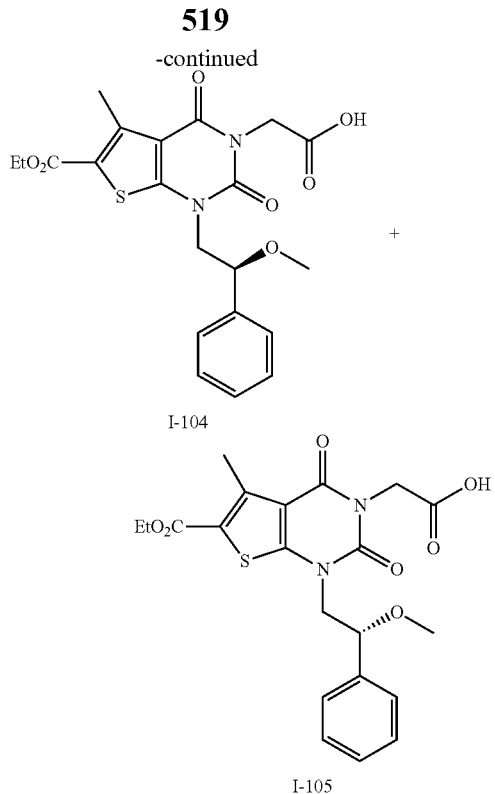

I-104

+

I-105

Synthesis of Compounds I-104 and I-105. The enantiomers of I-67 were isolated by chiral preparative HPLC under the following conditions (Gilson Gx 281): column: Chiralpak IC(SFC), 2*25 cm, 5 μm; mobile phase: hexanes (0.1% TFA) and ethanol (hold at 30.0% ethanol over 15 min); detector: UV 220/254 nm. This resulted in 4.4 mg of I-104 as a white solid (tR=11.52 min) and 3.7 mg of I-105 as a white solid (tR=14.07 min).

Analytical Data for I-104: MS (ES): m/z 446.9 (M+H)+, 509.8 (M+Na+CH₃CN)+. ¹H NMR (300 MHz, CD₃OD): δ 1.39 (t, 3H), 2.83 (s, 3H), 3.20 (s, 3H), 4.02 (m, 2H), 4.16 (q, 2H), 4.70 (m, 3H), 7.33-7.46 (m, 5H).

Analytical Data for I-105: MS (ES): m/z 446.9 (M+H)+, 509.8 (M+Na+CH₃CN)+. ¹H NMR (300 MHz, CD₃OD): δ 1.39 (t, 3H), 2.83 (s, 3H), 3.21 (s, 3H), 4.02 (m, 2H), 4.16 (q, 2H), 4.70 (m, 3H), 7.33-7.46 (m, 5H).

Example 229

Synthesis of (S)-2-(6-(ethoxycarbonyl)-1-(2-isopropoxy-2-phenylethyl)-5-methyl-2,4-dioxo-1,2-dihydrothieno[2,3-d]pyrimidin-3(4H)-yl)acetic acid (I-96)

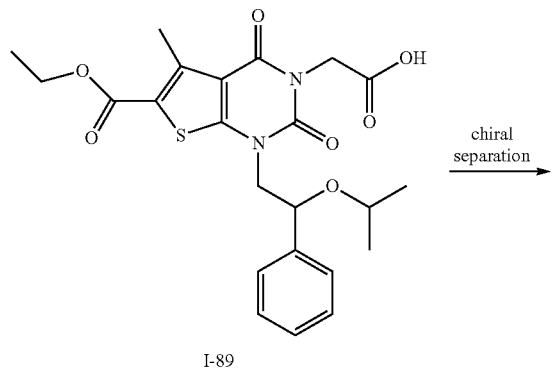

I-89 chiral separation

-continued

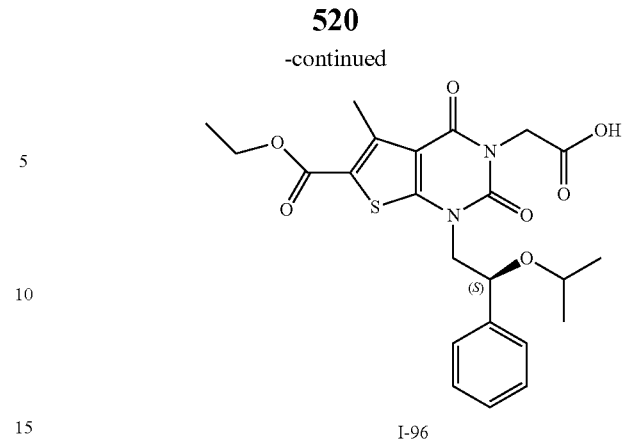

I-96

The (S) enantiomer of I-89 was isolated by chiral preparative HPLC under the following conditions (Gilson Gx 281): column: Chiralpak IC(SFC), 2*25 cm, 5 μm; mobile phase: hexanes and ethanol (0.1% DEA) (hold at 10.0% ethanol (0.1% DEA) in 25 min); detector: UV 220/254 nm. 1.7 mg (tR=14.9 min, 9%) of product were obtained as a white solid. MS (ES): m/z 475 (M+H)+, 497 (M+Na)+, 538 (M+Na+CH₃CN)+. ¹H NMR (300 MHz, DMSO-d₆): δ 0.98 (d, 3H), 1.03 (d, 3H), 1.42 (t, 3H), 2.84 (s, 3H), 3.51 (m, 1H), 3.98 (m, 1H), 4.22 (m, 1H), 4.40 (m, 2H), 4.75 (m, 2H), 4.92 (m, 1H), 7.33-7.49 (m, 5H).

Example 230

Synthesis of (R)-2-(6-(ethoxycarbonyl)-1-(2-isopropoxy-2-phenylethyl)-5-methyl-2,4-dioxo-1,2-dihydrothieno[2,3-d]pyrimidin-3(4H)-yl)acetic acid (I-97)

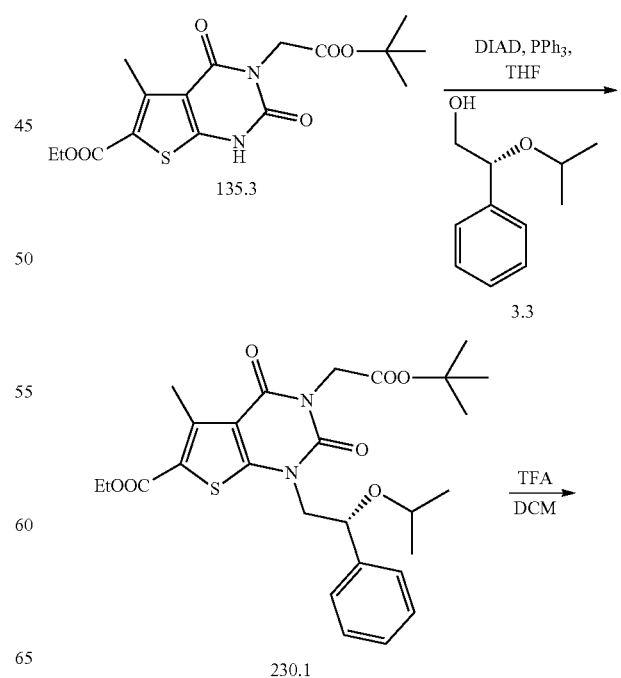

135.3

DIAD, PPh₃, THF 3.3

230.1

TFA / DCM

-continued

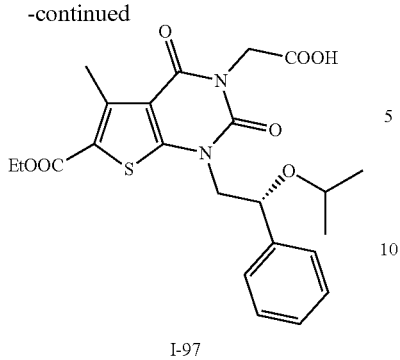

I-97

Compound I-97 was prepared from 135.3 and 3.3 in a manner analogous to the synthesis of compound 2.5. Isolated 180 mg of a white solid (tR=17.8 min) in 21% overall yield. MS (ES): m/z (M+H)$^+$ 475. $^1$H NMR (CD$_3$OD, 300 MHz): δ 0.90 (d, J=6.0 Hz, 3H), 0.97 (d, J=6.3 Hz, 3H), 1.35 (t, 3H), 2.80 (s, 3H), 3.48 (m, 1H), 3.88 (m, 1H), 4.16 (m,1H), 4.32 (m, 2H), 4.68 (m, 2H), 4.89 (m, 1H), 7.25-7.44 (m, 5H).

Example 231

2-[6-(ethoxycarbonyl)-1-[(2S)-2-methoxy-2-phenyl-ethyl]-5-methyl-2,4-dioxo-1H,2H,3H,4H-thieno[2,3-d]pyrimidin-3-yl]-2-methylpropanoic acid (I-111)

-continued

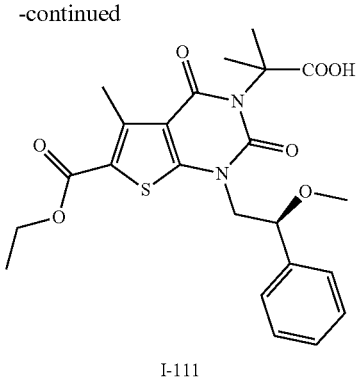

I-111

Compound I-111 was prepared from 2.1 and 1.4 in a manner analogous to the synthesis of Compound I-110 (Example 225). Isolated 65 mg of a white solid in 11% yield from 2.1. MS (ES): m/z 475 (M+H)$^+$. $^1$H NMR (CD$_3$OD, 300 MHz): δ 1.34 (t, 3H), 2.00 (s, 6H), 2.74 (s, 3H), 3.18 (s, 3H), 3.93 (m, 1H), 4.10 (m, 1H), 4.28 (q, 2H), 4.65 (m, 1H), 7.34 (m, 5H).

Example 232

Synthesis of 2-[6-(ethoxycarbonyl)-5-methyl-2,4-dioxo-1-[(2S)-2-phenyl-2-(propan-2-yloxy)ethyl]-1H,2H,3H,4H-thieno[2,3-d]pyrimidin-3-yl]-2-methylpropanoic acid (I-109)

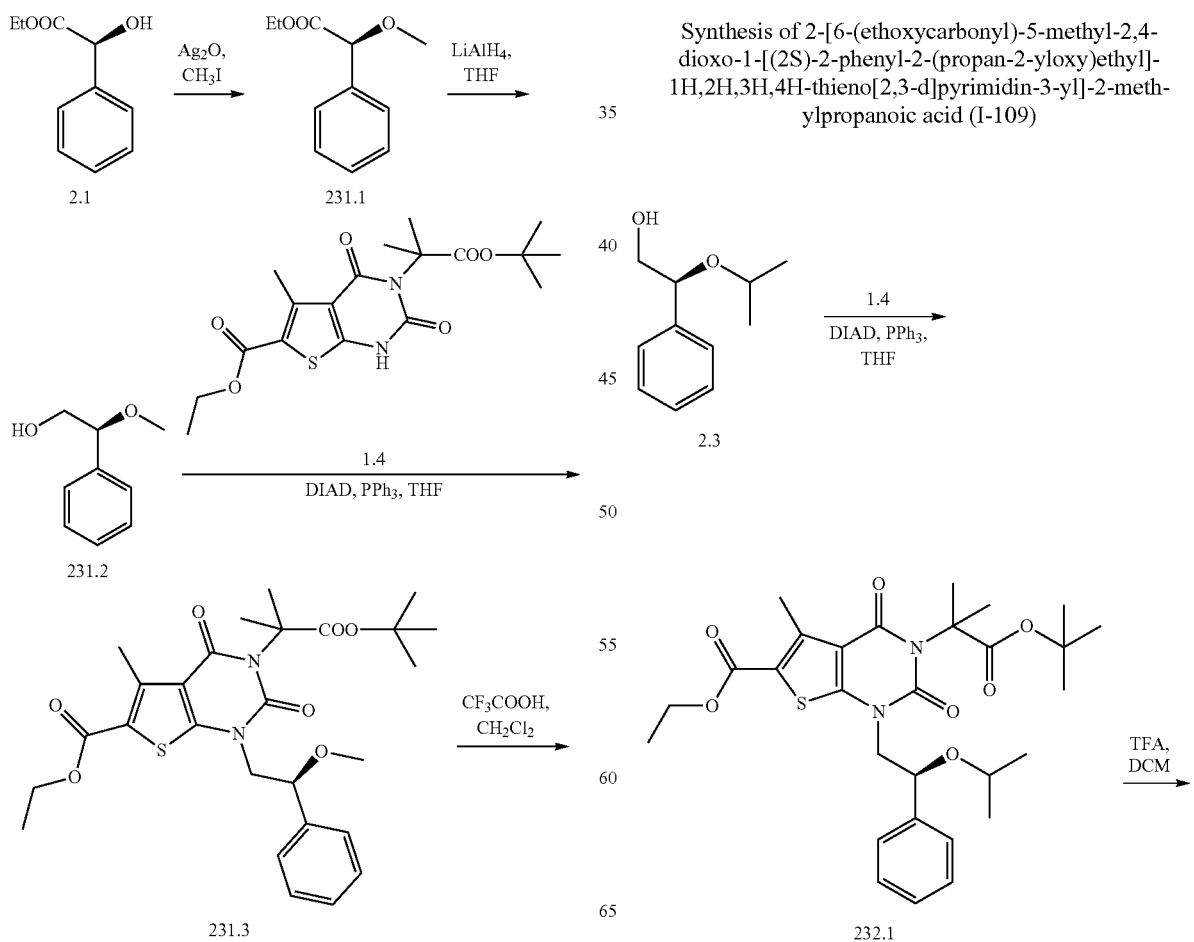

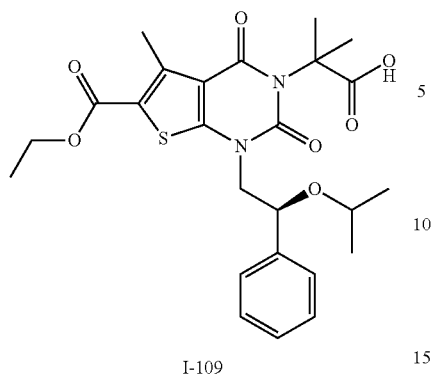

I-109

Compound I-109 was prepared from 2.3 and 1.4 in a manner analogous to the synthesis of 2.5. Isolated 11.3 mg of a white solid in 10% overall yield from 1.4. MS (ES): m/z 503 (M+H)$^+$. $^1$H NMR (CD$_3$OD, 400 MHz): δ 0.97~1.04 (m, 6H), 1.37~1.41 (t, 3H), 1.79~1.81 (d, 6H), 2.79 (s, 3H), 3.48~3.51 (m, 1H), 3.82~3.87 (m, 1H), 4.14~4.17 (m, 1H), 4.32~4.38 (m, 2H), 4.87~4.92 (m, 1H), 7.31~7.34 (m, 1H), 7.38~7.42 (t, 2H), 7.45~7.47 (d, 2H).

Example 233

Synthesis of 2-[6-(ethoxycarbonyl)-1-[2-[(2-methoxyacetyl)oxy]-2-phenylethyl]-5-methyl-2,4-dioxo-1H,2H,3H,4H-thieno[2,3-d]pyrimidin-3-yl]acetic acid (I-101)

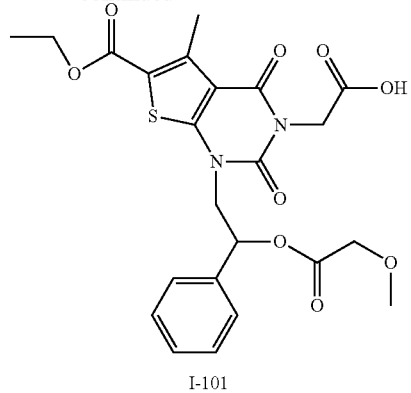

I-101

Synthesis of compound 233.1 Into a 50-mL round-bottom flask was placed 203.2 (200 mg, 0.41 mmol, 1.00 equiv), DCC (101 mg, 0.49 mmol, 1.20 equiv), 4-dimethylaminopyridine (90 mg, 0.74 mmol, 1.80 equiv), dichloromethane (10 mL) and 2-methoxyacetic acid (73 mg, 0.81 mmol, 1.98 equiv). The resulting solution was stirred overnight at room temperature. The resulting mixture was concentrated under vacuum. The residue was applied onto a silica gel column with ethyl acetate/petroleum ether (1:10). This resulted in 190 mg (85%) of 233.1.

Synthesis of Compound I-101. Compound I-101 was prepared from 233.1 in a manner analogous to the synthesis of compound 2.5. Isolated 60.4 mg (67%) of a white solid. MS (ES): m/z 527 (M+H)$^+$. $^1$H NMR (300 MHz, DMSO-d$_6$): δ 1.33 (t, 3H), 2.74 (s, 3H), 3.16 (s, 3H), 3.91 (d, 1H), 4.09 (d, 1H), 4.34 (m, 4H), 4.53 (s, 2H), 6.18 (m, 1H), 7.35-7.44 (m, 5H) 13.05 (br s, 1H).

Example 234

Synthesis of ethyl 3-(1-carbamoyl-1-methylethyl)-5-methyl-2,4-dioxo-1-[(2R)-2-phenyl-2-(propan-2-yloxy)ethyl]-1H,2H,3H,4H-thieno[2,3-d]pyrimidine-6-carboxylate (I-115)

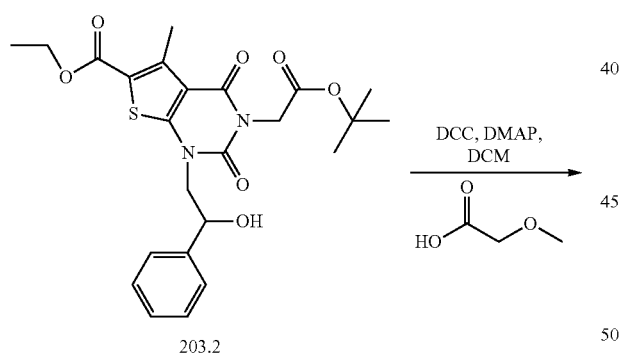

203.2

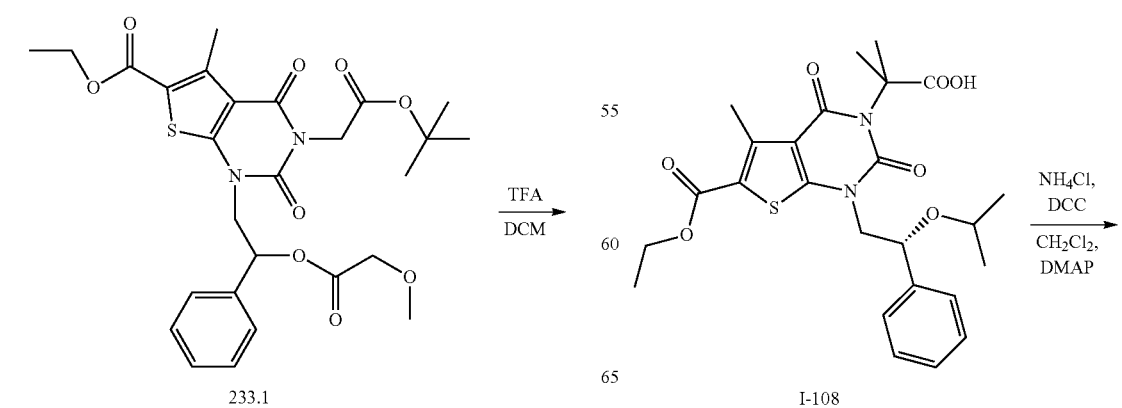

-continued

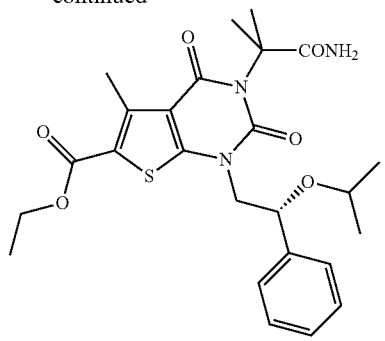

I-115

Compound I-115 was prepared from I-108 (Example 226) and ammonium chloride in a manner analogous to the synthesis of I-121 (Example 4). Isolated 0.059 g (42%) of a white solid. MS (ES): m/z 524 (M+Na)$^+$. $^1$H NMR (DMSO-d$_6$, 300 MHz): δ 0.90 (m, 6H), 1.26 (t, 3H), 1.63 (d, J=8.1 Hz, 6H), 3.29 (s, 3H), 3.40 (m, 1H), 3.73 (m, 1H), 4.03 (m, 1H), 4.26 (m, 2H), 4.74 (m, 1H), 7.23 (m, 5H).

Example 235

Synthesis of ethyl 3-(carbamoylmethyl)-5-methyl-2,4-dioxo-1-[(2R)-2-phenyl-2-(propan-2-yloxy)ethyl]-1H,2H,3H,4H-thieno[2,3-d]pyrimidine-6-carboxylate (I-112)

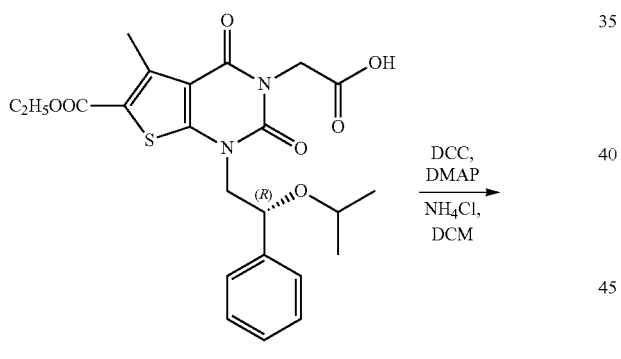

I-97

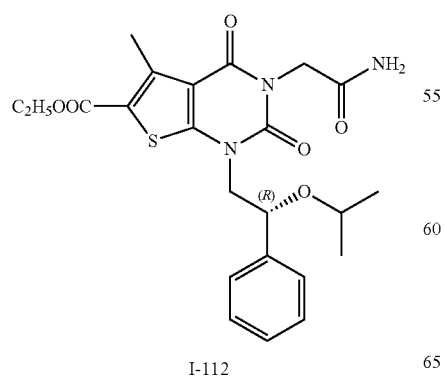

I-112

Compound I-112 was prepared from I-97 (Example 230) and ammonium chloride in a manner analogous to the synthesis of I-121 (Example 4). Isolated 53.7 mg (41%) of a white solid. MS (ES): m/z 474 (M+H)$^+$. $^1$H NMR (300 MHz, CD$_3$OD): δ 0.97 (d, 3H), 0.99 (d, 3H), 1.37 (t, 3H), 2.78 (s, 3H), 3.49 (m, 1H), 3.88 (m, 1H), 4.15 (dd, 1H), 4.32 (q, 2H), 4.65 (s, 2H), 4.87 (m, 1H), 7.25-7.44 (m, 5H).

Example 236

Synthesis of ethyl 3-(carbamoylmethyl)-5-methyl-2,4-dioxo-1-[(2S)-2-phenyl-2-(propan-2-yloxy)ethyl]-1H,2H,3H,4H-thieno[2,3-d]pyrimidine-6-carboxylate (I-113)

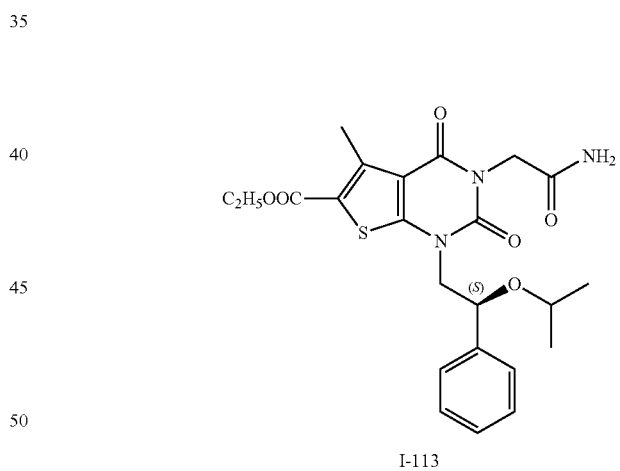

I-96

I-113

Compound I-113 was prepared from I-96 (Example 229) and ammonium chloride in a manner analogous to the synthesis of I-121 (Example 4). MS (ES): m/z 474 (M+H)$^+$. $^1$H NMR (300 MHz, CD$_3$OD): δ 0.97 (d, 3H), 0.99 (d, 3H), 1.37 (t, 3H), 2.78 (s, 3H), 3.49 (m, 1H), 3.88 (m, 1H), 4.15 (dd, 1H), 4.32 (q, 2H), 4.65 (s, 2H), 4.87 (m,1H), 7.25-7.44 (m, 5H).

Example 237

Synthesis of ethyl 3-(1-carbamoyl-1-methylethyl)-5-methyl-2,4-dioxo-1-[(2S)-2-phenyl-2-(propan-2-yloxy)ethyl]-1H,2H,3H,4H-thieno[2,3-d]pyrimidine-6-carboxylate (I-114)

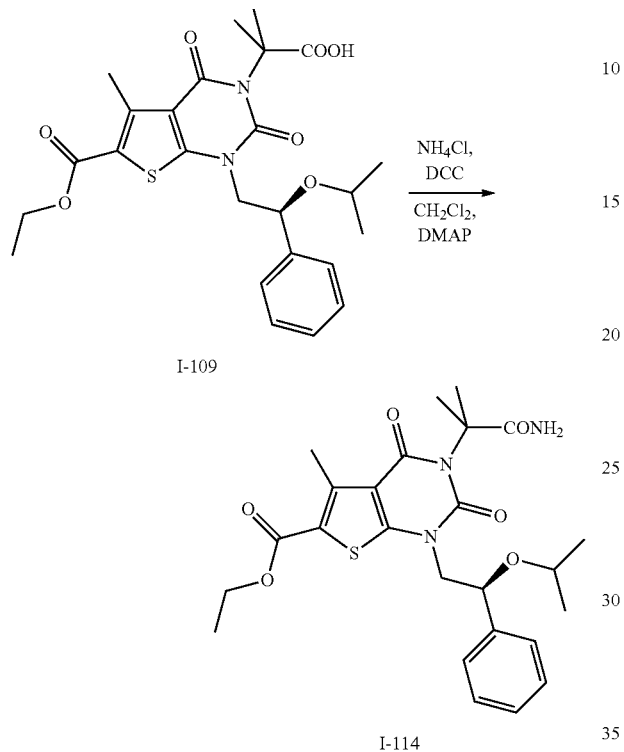

Compound I-114 was prepared from I-109 (Example 232) and ammonium chloride in a manner analogous to the synthesis of I-121 (Example 4). Isolated 0.064 g (64%) of a white solid. MS (ES): m/z 524 (M+H)$^+$. $^1$H NMR (DMSO-d$_6$, 300 MHz): δ 0.89 (m, 6H), 1.26 (q, 3H), 1.62 (d, J=8.7 Hz, 6H), 2.67 (s, 3H), 3.38 (m, 1H), 3.76 (m, 1H), 4.03 (m, 1H), 4.26 (m, 2H), 4.75 (m, 1H), 7.35 (m, 5H).

Example 238

Synthesis of 2-[1-[(2R)-2-[(4-hydroxycyclohexyl)oxy]-2-phenylethyl]-5-methyl-6-(1,3-oxazol-2-yl)-2,4-dioxo-1H,2H,3H,4H-thieno[2,3-d]pyrimidin-3-yl]-2-methylpropanoic acid (I-165)

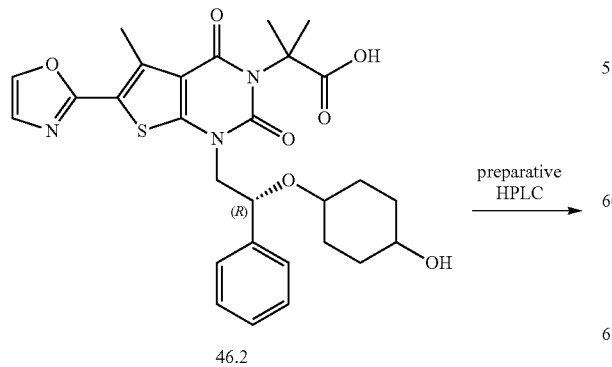

The (R)-enantiomer of compound 46.2 (30 mg) was isolated by preparative HPLC under the following conditions (Waters): Column: XBridge Shield RP18 OBD 5 μm, 19*150 mm; mobile phase: water (50 mM NH$_4$HCO$_3$) and CH$_3$CN (6.0% CH$_3$CN up to 50.0% in 14 min); detector: UV 254/220 nm. 11.1 mg of I-165 (tR=8.82) were obtained as a white solid. MS (ES): m/z 554 (M+H)$^+$, 576 (M+Na)$^+$, 617 (M+Na+CH$_3$CN)$^+$. $^1$H NMR (300 MHz, CD$_3$OD): δ 1.29-1.38 (m, 6H), 1.44-1.64 (m, 2H), 1.75 (s, 6H), 2.77 (s, 3H), 3.50 (m, 1H), 3.81 (m, 1H), 4.19 (m, 1H), 4.95 (m, 1H), 7.24-7.45 (m, 6H), 7.94 (s, 1H).

Example 239

Synthesis of 2-[1-[(2R)-2-(2-chlorophenyl)-2-(oxan-4-yloxy)ethyl]-5-methyl-6-(1,3-oxazol-2-yl)-2,4-dioxo-1H,2H,3H,4H-thieno[2,3-d]pyrimidin-3-yl]-2-methylpropanoic acid (I-300)

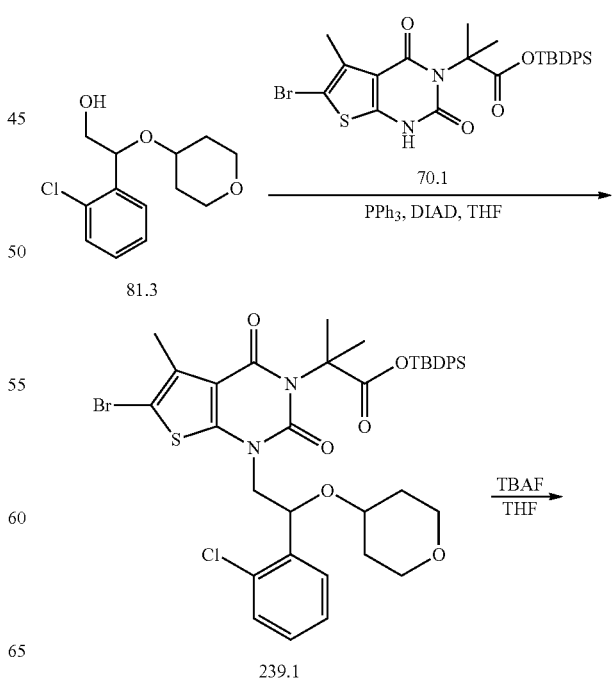

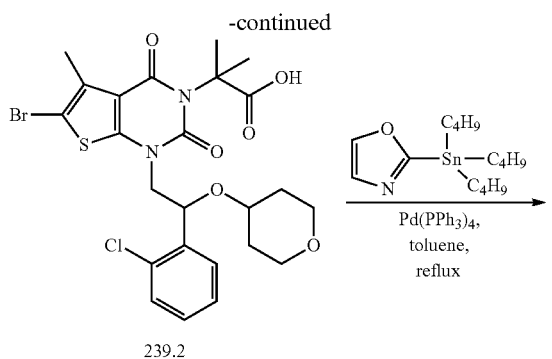

1H), 3.70 (m, 2 H), 3.50 (m, 1H), 3.40 (m, 2H), 2.83 (s, 3H), 1.82 (s, 3H), 1.80 (s, 3H), 1.75 (m, 2H), 1.52 (m, 2H).

Example 240

Synthesis of 6-bromo-1-[(2R)-2-(2-methoxyphenyl)-2-(oxan-4-yloxy)ethyl]-5-methyl-3-(4H-1,2,4-triazol-3-ylmethyl)-1H,2H,3H,4H-thieno[2,3-d]pyrimidine-2,4-dione (I-301)

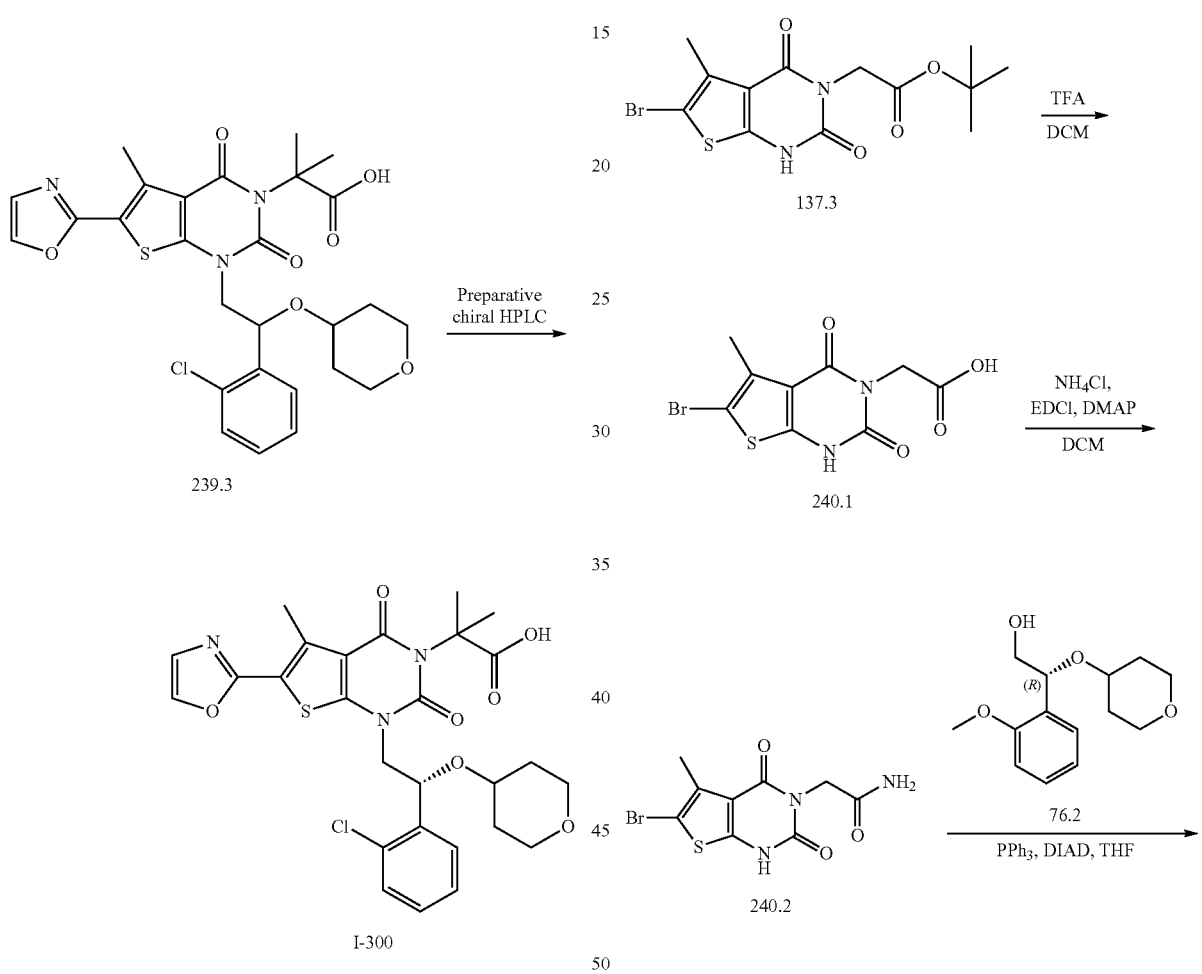

Synthesis of compound 239.2. Compound 239.2 was prepared from 70.1 and 81.3 in a manner analogous to I-264 (Example 96). Isolated 180 mg of a colorless oil in 36% yield from 70.1.

Synthesis of compound 239.3. Compound 239.3 was prepared from 239.2 in a manner analogous to the synthesis of I-120 (Example 2). Isolated a 40 mg (23%) of a colorless oil.

Synthesis of Compound I-300. The crude product (41 mg) was purified by chiral preparative HPLC under the following conditions (Gilson Gx 281): Column: Chiralpak IA, 2*25 cm, 5 μm; mobile phase: hexanes and IPA (hold at 20% IPA over 22 min); detector: UV 220/254 nm. Purification afforded 2.8 mg (7%) of Compound I-300 as a white solid. MS (ES): m/z 574 (M+H)$^+$. $^1$H NMR (300 MHz, CD$_3$OD): δ 8.00 (s, 1H), 7.75 (d, 1H, J=6.0 Hz), 7.45 (m, 2H), 7.35 (d, 1H, J=5.1 Hz), 7.29 (s, 1H), 5.49 (q, 1H, J=5.1 Hz), 4.32 (m, 1 H), 3.99 (m,

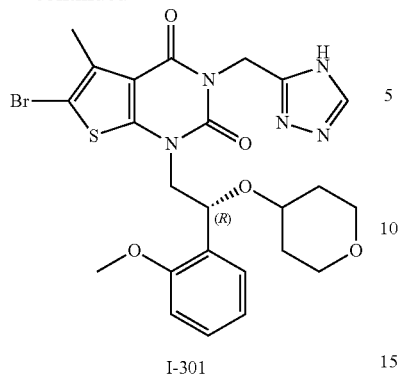

I-301

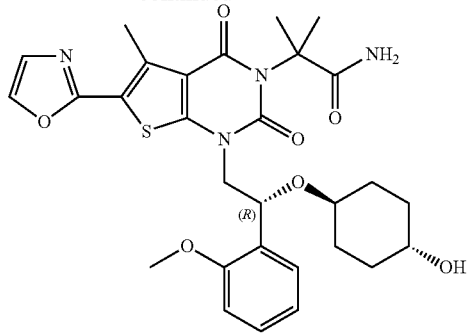

I-302

Synthesis of compound 240.1. Compound 240.1 was prepared from 137.3 in a manner analogous to the synthesis of 136.2 from 136.1. Isolated 1.9 g of a white solid in 97% yield.

Synthesis of compound 240.3. Compound 240.3 was prepared from 240.1 and 76.2 in a manner analogous to the synthesis of I-285 from 141.1 (Example 141). Isolated 106 mg of a white solid in 6% overall yield.

Synthesis of Compound I-301. Compound I-301 was prepared from 240.3 in a manner analogous to the synthesis of I-289 from I-285 (Example 145). Isolated 40 mg of a white solid in 43% yield. MS (ES): m/z 576 (M+H)$^+$. $^1$H NMR (300 MHz, d$_6$-DMSO): δ 13.81 (1H, br s), 8.42 (1H, s), 7.49-7.46 (1H, dd, J$_1$=7.2 Hz, J$_2$=1.5 Hz), 7.31 (1H, m), 7.05-6.98 (2H, m), 5.23-5.16 (3H, m), 4.15-4.09 (1H, m), 3.77-3.75 (4H, m), 3.53-3.48 (2H, m), 3.29-3.24 (2H, m), 2.36 (3H, s), 1.59 (2H, m), 1.28-1.15 (2H, m).

Example 241

Synthesis of 2-[1-[(2R)-2-[(4-hydroxycyclohexyl)oxy]-2-(2-methoxyphenyl)ethyl]-5-methyl-6-(1,3-oxazol-2-yl)-2,4-dioxo-1H,2H,3H,4H-thieno[2,3-d]pyrimidin-3-yl]-2-methylpropanamide (I-302)

Compound I-302 was prepared from 129.1 in a manner analogous to the synthesis of I-279 from 129.1. The desired enantiomer was isolated by preparative HPLC under the following conditions (Waters): Column: HPrepC-012 (T) Xbridge Prep Phenyl 5 µm, 19*150 mm; mobile phase: water (50 mM NH$_4$HCO$_3$) and CH$_3$CN (30.0% CH$_3$CN up to 70.0% in 15 min); detector: 254/220 nm. This resulted in 17.4 mg (3%) of I-302 (9.34 min) as a white solid. MS (ES): m/z 605 (M+Na)$^+$. $^1$H NMR (300 MHz, DMSO-d$_6$): δ 1.02-1.08 (m, 4H), 1.21 (m, 1H), 1.59 (m, 4H), 1.66 (d, 6H), 2.74 (s, 3H), 3.17 (m,1H), 3.78 (s, 3H), 3.99 (m, 2H), 4.29 (s, 1H), 5.28 (t, 1H), 6.79-7.28 (m, 4H), 7.30 (m,1H), 7.37 (s,1H), 7.47 (m, 1H), 8.21 (s, 1H).

Example 242

Synthesis of (S)-2-(1-(2-(2-(cyanomethyl)phenyl)-2-((tetrahydro-2H-pyran-4-yl)oxy)ethyl)-5-methyl-6-(oxazol-2-yl)-2,4-dioxo-1,2-dihydrothieno[2,3-d]pyrimidin-3(4H)-yl)-2-methylpropanoic acid (I-303)

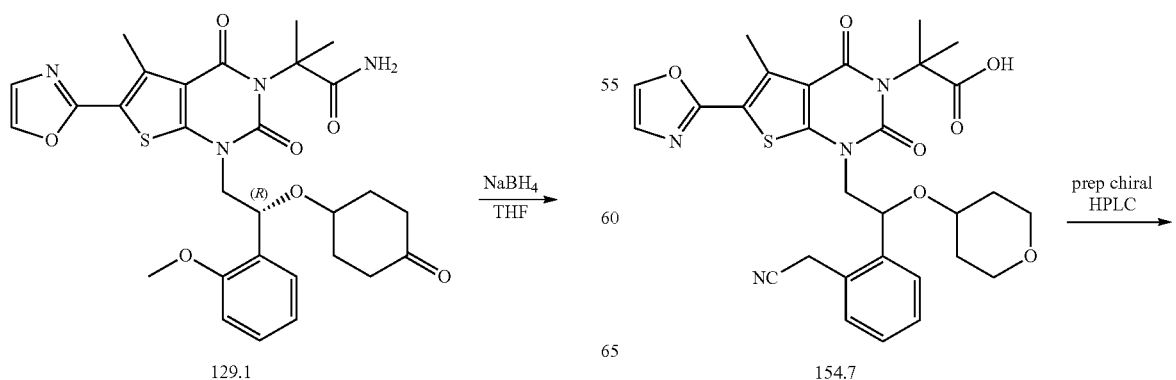

129.1      154.7

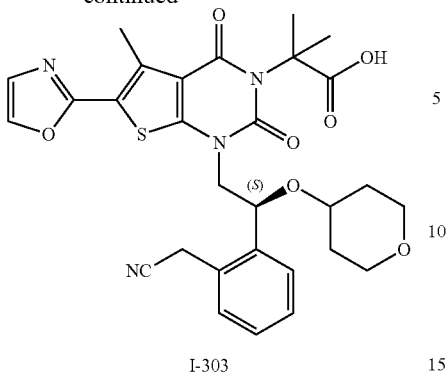

I-303

The S enantiomer of 154.7 was isolated by chiral preparative HPLC under the following conditions: column: CHIRALPK IC-3; mobile phase: hexanes (0.1% AcOH):IPA=70:30; detector: UV 254 nm; retention time: 23.375 min. 11.4 mg (white solid) of the desired product were obtained. MS (ES): m/z 579 (M+H)$^+$, 601 (M+Na)$^+$. $^1$H NMR (400 MHz, DMSO-$d_6$): δ 12.41 (br s, 1 H), 8.26 (s, 1H), 7.63 (d, 1H), 7.49-7.42 (m, 4H), 5.12 (d, 1H), 4.31-4.16 (m, 3H), 3.70 (s, 1H), 3.53 (d, 1H), 3.43-3.32 (m, 2H), 3.25-3.20 (m, 2H), 2.78 (s, 3H), 1.72-1.62 (m, 8H), 1.33-1.21 (m, 2H).

Example 243

Synthesis of 2-(1-((R)-2-(((1r,4R)-4-hydroxycyclohexyl)oxy)-2-(2-isopropoxyphenyl)ethyl)-5-methyl-6-(oxazol-2-yl)-2,4-dioxo-1,2-dihydrothieno[2,3-d]pyrimidin-3(4H)-yl)-2-methylpropanamide (I-304) and Example 244: Synthesis of 2-(1-((R)-2-(((1s,4S)-4-hydroxycyclohexyl)oxy)-2-(2-isopropoxyphenyl)ethyl)-5-methyl-6-(oxazol-2-yl)-2,4-dioxo-1,2-dihydrothieno[2,3-d]pyrimidin-3(4H)-yl)-2-methylpropanamide (I-305)

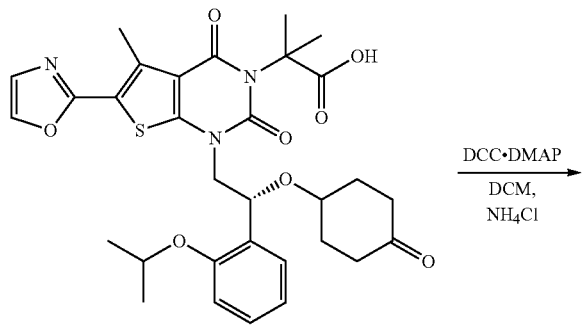

150.7

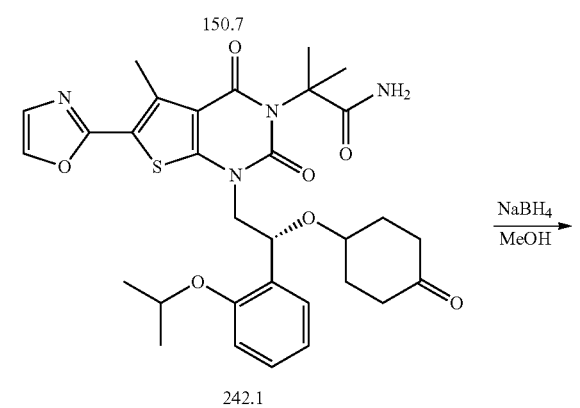

242.1

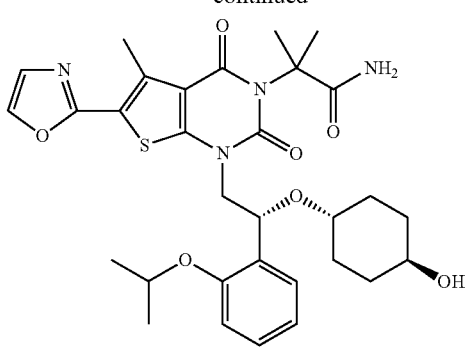

I-304

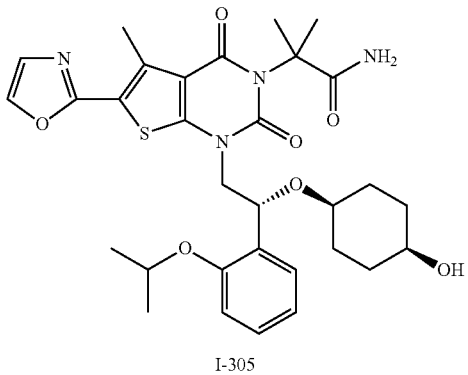

I-305

Synthesis of compound 242.1. Compound 242.1 was prepared from 150.7 in a manner analogous to I-121 (Example 4). Isolated 1.6 g (84%) of a white solid.

Synthesis of Compounds I-304 and I-305. Into a 50-mL round-bottom flask was placed 242.1 (1.6 g, 2.63 mmol, 1.00 equiv) and methanol (20 mL). This was followed by the addition of NaBH$_4$ (208 mg, 5.50 mmol, 2.09 equiv) at 0° C. The resulting solution was stirred overnight at room temperature. The resulting mixture was concentrated under vacuum. The residue was purified by thin layer chromatography developed with dichloromethane/MeOH/HOAc (30:1:0.15). This resulted in 86.4 mg (5%) of I-304 as a white solid and 270 mg (17%) of I-305 as a white solid.

Analytical Data for I-304: MS (ES): m/z 633 (M+Na)$^+$. $^1$H NMR (400 MHz, CD$_3$OD): δ 1.15-1.39 (m, 10H), 1.69-1.80 (m, 10H), 2.82 (s, 3H), 3.17 (m, 1H), 3.52 (m, 1H), 3.95 (m, 1H), 4.18 (m, 1H), 4.69 (m, 1H), 5.42 (t, 1H), 6.99 (m, 2H), 7.28 (m, 2H), 7.52 (m, 1H), 8.01 (s, 1H).

Analytical Data for I-305: MS (ES): m/z 633 (M+Na)$^+$. $^1$H NMR (400 MHz, CD$_3$OD): δ 1.31-1.49 (m, 12H), 1.70-1.83 (m, 8H), 2.82 (s, 3H), 3.50 (m, 1H), 4.02-4.22 (m, 2H), 4.69 (m, 1H), 5.43 (t, 1H), 6.99 (m, 2H), 7.28 (m, 2H), 7.55 (m, 1H), 7.98 (s, 1H).

Example 244

Synthesis of 2-[1-[(2R)-2-[(4-hydroxycyclohexyl)oxy]-2-[2-(propan-2-yloxy)phenyl]ethyl]-5-methyl-6-(1,3-oxazol-2-yl)-2,4-dioxo-1H,2H,3H,4H-thieno[2,3-d]pyrimidin-3-yl]-2-methylpropanamide (I-306)

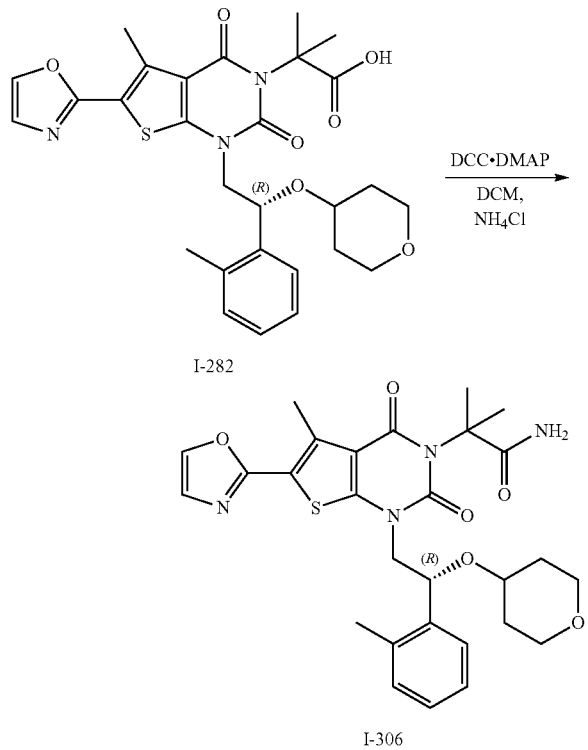

Compound I-306 was prepared from I-282 in a manner analogous to the synthesis of I-121 (Example 4). MS (ES): m/z 575 (M+Na)⁺. $^1$H NMR (400 MHz, DMSO-$d_6$): δ 1.12-1.30 (m, 2H), 1.58-1.71 (m, 8H), 2.43-2.51 (s, 3H), 2.75 (s, 3H), 3.19-3.24 (m, 2H), 3.33-3.49 (m, 2H), 3.51-353 (m, 1H), 4.17-4.20 (m, 1H), 5.10-5.13 (m, 1H), 6.80 (br s, 1H), 7.20 (br s, 1H), 7.21-7.31 (m, 3H), 7.40 (s, 1H), 7.54 (m, 1H), 8.24 (s, 1H).

Example 245

Synthesis of 2-[1-[(2R)-2-(3-methoxypyridin-2-yl)-2-(oxan-4-yloxy)ethyl]-5-methyl-6-(1,3-oxazol-2-yl)-2,4-dioxo-1H,2H,3H,4H-thieno[2,3-d]pyrimidin-3-yl]-2-methylpropanoic acid (I-307)

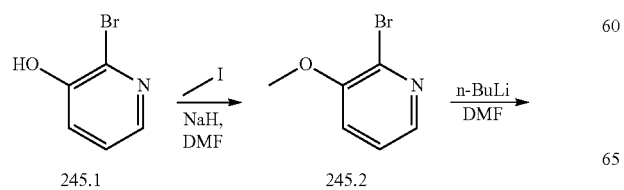

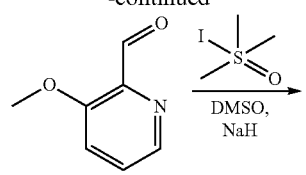

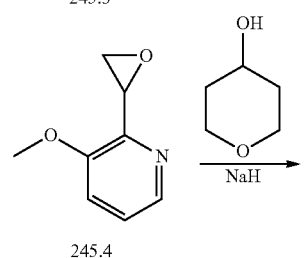

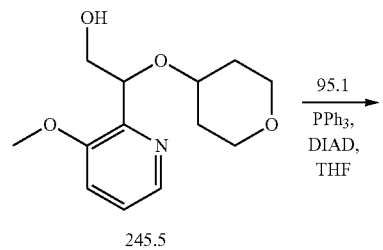

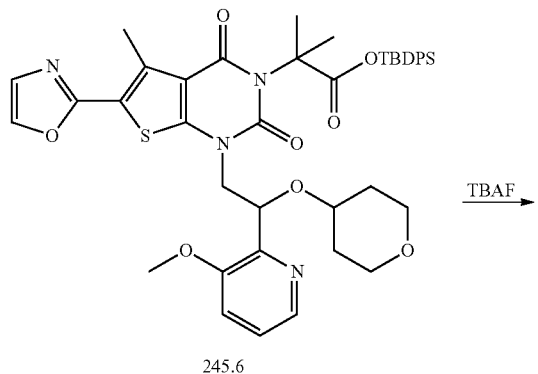

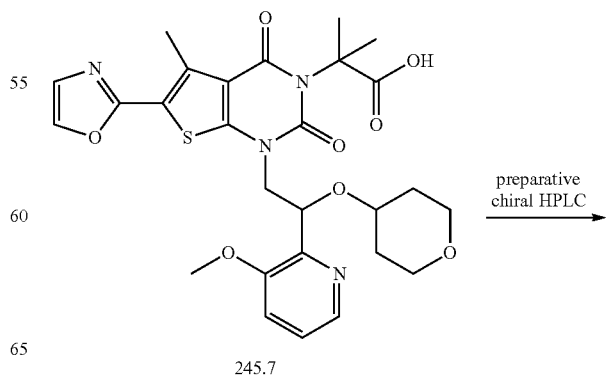

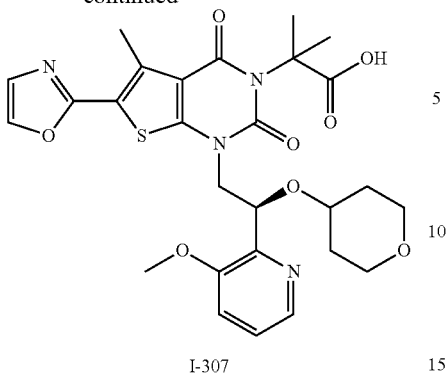

I-307

Synthesis of compound 245.4. Compound 245.4 was prepared from 245.1 in a manner analogous to the synthesis of 149.4 from 149.1. Isolated 500 mg of a yellow oil in 5% overall yield.

Synthesis of compound 245.5. Compound 245.5 was prepared from 245.4 in a manner analogous to the synthesis of 73.2 from 73.1. Isolated 200 mg (24%) of a colorless oil.

Synthesis of Compound I-307. Compound I-307 was prepared from 245.4 in a manner analogous to the synthesis of Compound I-265 (Example 97). Purification: I-307 (20 mg) was isolated by chiral preparative HPLC under the following conditions (Gilson Gx 281): Column: Chiralpak IC, 2*25 cm, 5 μm; mobile phase: hexanes and EtOH (0.1% HAC) (hold at 30.0% EtOH (0.1% HAC) for 13 min); detector: UV 254/220 nm. Isolated 2.4 mg of I-307 (retention time 10.9 min) as a white solid. MS (ES): m/z 571 (M+H)$^+$, 593 (M+Na)$^+$. $^1$H NMR (300 MHz, CD$_3$OD): δ 1.33-1.48 (m, 2H), 1.67-1.75 (m, 8H), 2.67 (s, 3H), 3.21 (m, 2H), 3.63-3.70 (m, 6H), 4.32 (m, 1H), 4.57 (m, 1H), 6.20 (m, 1H), 7.11 (m, 1H), 7.29 (d, 2H), 7.82 (s, 1H), 8.09 (m, 1H).

Example 246

Synthesis of 2-[1-[2-(5-chloro-1,3-thiazol-4-yl)ethyl]-5-methyl-6-(1,3-oxazol-2-yl)-2,4-dioxo-1H,2H,3H,4H-thieno[2,3-d]pyrimidin-3-yl]-2-methyl-propanoic acid (I-308)

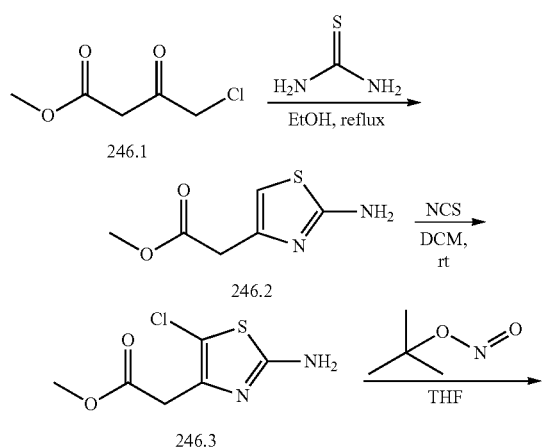

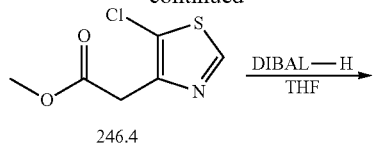

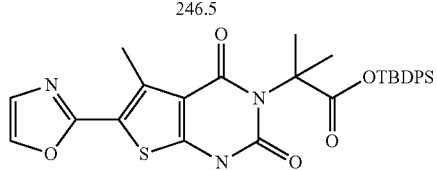

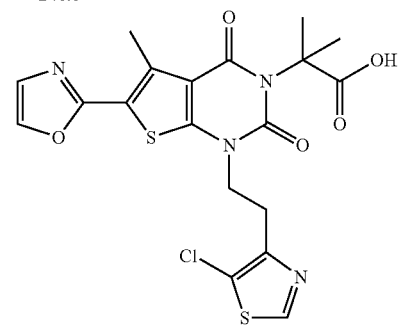

I-308

Synthesis of 246.2. Into a 1000-mL 3-necked round-bottom flask was placed methyl 4-chloro-3-oxobutanoate (28 g, 185.97 mmol, 1.00 equiv), thiourea (15.2 g, 199.68 mmol, 1.07 equiv) and ethanol (400 ml, 46.69 equiv). The resulting solution was heated to reflux for 4 hr. The solids were collected by filtration. 20 g (62%) of 246.2 were obtained as a light yellow solid.

Synthesis of 246.3. Into a 50-mL 3-necked round-bottom flask was placed 246.2 (10 g, 58.07 mmol, 1.00 equiv) and dichloromethane (40 mL). This was followed by the addition of NCS (7.76 g, 58.11 mmol, 1.00 equiv) dropwise with stirring at 0° C. The resulting solution was stirred overnight at room temperature. The resulting mixture was concentrated under vacuum. The residue was applied onto a silica gel column with ethyl acetate/petroleum ether (1:5). Purification afforded 1 g (crude) of 246.3 as a yellow solid.

Synthesis of 246.4. Into a 100-mL 3-necked round-bottom flask was placed 246.3 (1 g, 4.84 mmol, 1.00 equiv), tetrahydrofuran (40 mL) and tert-butyl nitrite (8.98 g, 87.08 mmol, 18.00 equiv). The resulting solution was stirred for 0.5 h at room temperature. The resulting mixture was concentrated under vacuum. The residue was applied onto a silica gel column with ethyl acetate/petroleum ether (1:10). Purification afforded 200 mg (22%) of 246.4 as a yellow oil.

Synthesis of 246.5. Into a 100-mL 3-necked round-bottom flask, purged and maintained with an inert atmosphere of nitrogen, was placed 246.4 (200 mg, 1.04 mmol, 1.00 equiv) and tetrahydrofuran (50 mL). This was followed by the addition of DIBAL-H (5 mL, 25% in toluene) dropwise with stirring at −78° C. The resulting solution was stirred for 0.5 h at −78° C. The reaction was then quenched by the addition of 50 mL of NH$_4$Cl (aq). The resulting solution was extracted with 3×100 mL of ethyl acetate and the organic layers combined. The residue was applied onto a silica gel column with ethyl acetate/petroleum ether (1:5). Purification afforded 40 mg (23%) of 246.5 as a yellow oil.

Synthesis of Compound I-308. Compound I-308 was prepared from 246.5 and 95.1 in a manner analogous to the synthesis of Compound I-264 (Example 96). 11.2 mg (14% from 95.1) of I-308 were isolated as a white solid. MS (ES): m/z 481 (M+H)$^+$. $^1$H NMR (400 MHz, DMSO): δ 1.67 (s, 6H), 2.75 (s, 3H), 3.09-3.13 (t, 2H), 4.14-4.18 (t, 2H), 7.40 (s, 1H), 7.48 (s, 1H), 8.24 (s, 1H).

Additional compounds of formula I were prepared in a manner substantially similar to that described above. Mass spectroscopy data are provided in Table 1, supra.

In certain embodiments, compounds of the present invention are assayed as inhibitors of ACC using methods known in the art including those contained in Harwood et al. Isozyme-nonselective N-Substituted Bipiperidylcarboxamide Acetyl-CoA Carboxylase Inhibitors Reduce Tissue Malonyl-CoA Concentrations, Inhibit Fatty Acid Synthesis, and Increase Fatty Acid Oxidation in Cultured Cells and in Experimental Animals, J. Biol. Chem., 2003, vol. 278, 37099-37111. In some embodiments the assays used are selected from an in vitro ACC enzyme inhibition assays, in vitro cell culture assays, and in vivo efficacy assays in animals. In some embodiments, assay results for compounds of the present invention are compared to results obtained for known inhibitors of ACC or related enzymes. In some embodiments, the ACC inhibitor used for comparison is CP-640186 or soraphen A.

Compounds of the present invention were evaluated in an in vitro ACC inhibition assay as described by Harwood, et al, 2003, the entirety of which is incorporated herein by reference.

Example 247

In Vitro Acetyl-CoA Carboxylase (ACC) Inhibition Assay

An exemplary procedure for the in vitro ACC inhibition assay, which can be used to determine the inhibitory action of compounds of the invention toward either ACC1 or ACC2, follows. The ADP-Glo™ Kinase Assay kit from Promega was used. The ADP-Glo™ Kinase Assay is a luminescent ADP detection assay to measure enzymatic activity by quantifying the amount of ADP produced during an enzyme reaction. The assay is performed in two steps; first, after the enzyme reaction, an equal volume of ADP-Glo™ Reagent is added to terminate the reaction and deplete the remaining ATP. Second, the Kinase Detection Reagent is added to simultaneously convert ADP to ATP and allow the newly synthesized ATP to be measured using a luciferase/luciferin reaction. Luminescence can be correlated to ADP concentrations by using an ATP-to-ADP conversion curve. The detailed procedure is as follows. 50 μL of the compound being tested (600 uM in DMSO) was added to a 384-well dilution plate. The compound was diluted 1:3 in succession in DMSO for each row for 11 wells. 0.5 μL ACC2 working solution was added to 384-well white Optiplate assay plate. 0.5 μL diluted compound solution in each column from step 2 to assay plate, each row containing 2 replicates. For the last 2 rows, add 0.5 μL negative control (DMSO) in one row and 0.5 μL positive control (compound I-97) in the other. The plates were incubated at room temperature for 15 minutes. 5 μL substrate working solution was added to each well to initiate reaction. Final ACC2 reaction concentrations consist of: 5 nM ACC2, 20 μM ATP, 20 μM acetyl-CoA, 12 mM NaHCO3, 0.01% Brij35, 2 mM DTT, 5% DMSO, test compound concentrations: 30 μM, 10 μM, 3.33 μM, 1.11 μM, 0.37 μM, 0.123 μM, 0.0411 μM, 0.0137 μM, 0.00457 μM, 0.00152 μM, and 0.00051 μM. Plates were incubated at room temperature for 60 minutes. 10 μL ADP glo reagent was added. Plates were incubated at room temperature for 40 minutes. 20 μL kinase detection reagent was added. Plates were incubated at room temperature for 40 minutes, then read on a Perkin Elmer EnVision 2104 plate reader for luminescence as Relative Light Units (RLU).

Data for each concentration, as well as the positive and negative controls were averaged, and the standard deviation calculated. Percent inhibition was calculated by the formula: 100×(average negative control−compound)/(average negative control−average positive control). The IC50 for each compound was calculated by fitting the data with a non-linear regression equation: Y=Bottom+(Top−Bottom)/(1+10^((LogIC50−X*HillSlope)), where X is the log of compound concentration and Y is percent inhibition.

The results of the in vitro ACC1 and ACC2 inhibition assays are set forth in Table 2. The compound numbers correspond to the compound numbers in Table 1. Compounds having an activity designated as "AAA" provided an IC$_{50}$≤0.1 μM; compounds having an activity designated as "AA" provided an IC$_{50}$≤1 μM; compounds having an activity designated as "A" provided an IC$_{50}$≤5 μM; compounds having an activity designated as "B" provided an IC$_{50}$ of 5-20 μM; compounds having an activity designated as "C" provided an IC$_{50}$ of 20-50 μM; and compounds having an activity designated as "D" provided an IC$_{50}$≥50 μM. "NA" stands for "not assayed." Enzyme inhibition curves for compound I-158 against ACC1 and ACC2 are shown in FIG. 1. Enzyme inhibition curves for compound I-181 against ACC1 and ACC2 are shown in FIG. 6.

TABLE 2

Results of in vitro ACC1 and ACC2 inhibition assays.

| Compound ID | ACC1 | ACC2 |
|---|---|---|
| I-1 | A | B |
| I-2 | NA | D |
| I-3 | NA | C |
| I-4 | NA | C |
| I-5 | NA | D |
| I-6 | NA | C |
| I-7 | NA | D |
| I-8 | NA | B |
| I-9 | NA | D |
| I-10 | NA | D |
| I-11 | NA | D |
| I-12 | NA | D |
| I-13 | A | A |
| I-14 | A | A |
| I-15 | NA | D |
| I-16 | NA | D |
| I-17 | NA | D |
| I-18 | NA | D |
| I-19 | A | B |
| I-20 | B | A |
| I-21 | NA | D |
| I-22 | NA | D |
| I-23 | NA | C |

TABLE 2-continued

Results of in vitro ACC1 and ACC2 inhibition assays.

| Compound ID | ACC1 | ACC2 |
| --- | --- | --- |
| I-24 | NA | D |
| I-25 | NA | D |
| I-26 | NA | B |
| I-27 | NA | D |
| I-28 | NA | D |
| I-29 | NA | D |
| I-30 | NA | D |
| I-31 | A | A |
| I-32 | A | A |
| I-33 | B | B |
| I-34 | NA | B |
| I-35 | NA | D |
| I-36 | NA | C |
| I-37 | NA | B |
| I-38 | NA | D |
| I-39 | NA | C |
| I-40 | NA | D |
| I-41 | NA | D |
| I-42 | NA | C |
| I-43 | NA | B |
| I-44 | NA | D |
| I-45 | A | A |
| I-46 | A | A |
| I-47 | NA | D |
| I-48 | NA | B |
| I-49 | NA | D |
| I-50 | NA | D |
| I-51 | NA | D |
| I-52 | D | D |
| I-53 | NA | B |
| I-54 | NA | B |
| I-55 | A | A |
| I-56 | NA | A |
| I-57 | NA | D |
| I-58 | NA | D |
| I-59 | NA | D |
| I-60 | A | A |
| I-61 | A | A |
| I-62 | NA | B |
| I-63 | NA | C |
| I-64 | NA | D |
| I-65 | NA | D |
| I-66 | NA | A |
| I-67 | NA | A |
| I-68 | NA | B |
| I-69 | NA | A |
| I-70 | AA | AA |
| I-71 | NA | D |
| I-72 | NA | D |
| I-73 | NA | C |
| I-74 | NA | B |
| I-75 | NA | B |
| I-76 | NA | A |
| I-77 | NA | B |
| I-78 | NA | A |
| I-79 | NA | B |
| I-80 | NA | A |
| I-81 | NA | B |
| I-82 | NA | B |
| I-83 | NA | A |
| I-84 | NA | D |
| I-85 | NA | A |
| I-86 | NA | B |
| I-87 | NA | A |
| I-88 | NA | D |
| I-89 | AA | AA |
| I-90 | NA | C |
| I-91 | NA | B |
| I-92 | NA | A |
| I-93 | AA | AA |
| I-94 | NA | A |
| I-95 | NA | C |
| I-96 | AAA | B |
| I-97 | AAA | AA |
| I-98 | NA | C |
| I-99 | NA | A |
| I-100 | AAA | AA |
| I-101 | NA | B |
| I-102 | NA | B |
| I-103 | NA | AA |
| I-104 | NA | C |
| I-105 | NA | AA |
| I-106 | NA | A |
| I-107 | NA | A |
| I-108 | AAA | AA |
| I-109 | NA | B |
| I-110 | AA | AA |
| I-111 | NA | B |
| I-112 | AAA | AA |
| I-113 | NA | C |
| I-114 | NA | C |
| I-115 | AA | AA |
| I-116 | NA | A |
| I-117 | NA | A |
| I-118 | NA | C |
| I-119 | AAA | AA |
| I-120 | NA | B |
| I-121 | AA | AA |
| I-122 | NA | AA |
| I-123 | AAA | AA |
| I-124 | NA | B |
| I-125 | NA | B |
| I-126 | NA | C |
| I-127 | NA | C |
| I-128 | NA | C |
| I-129 | NA | B |
| I-130 | AAA | AA |
| I-131 | AA | AA |
| I-132 | NA | C |
| I-133 | AAA | AA |
| I-134 | AA | AA |
| I-135 | AAA | AA |
| I-136 | NA | A |
| I-137 | NA | AA |
| I-138 | NA | B |
| I-139 | AA | AA |
| I-140 | AAA | AA |
| I-141 | NA | A |
| I-142 | NA | AA |
| I-143 | AA | AA |
| I-144 | NA | B |
| I-145 | AAA | AA |
| I-146 | NA | AA |
| I-147 | AA | AA |
| I-148 | NA | A |
| I-149 | NA | AA |
| I-150 | NA | B |
| I-151 | NA | AA |
| I-152 | NA | AA |
| I-153 | NA | AA |
| I-154 | NA | AA |
| I-155 | NA | AA |
| I-156 | NA | A |
| I-157 | NA | C |
| I-158 | AAA | AAA |
| I-159 | NA | AA |
| I-160 | AAA | AAA |
| I-161 | NA | A |
| I-162 | AAA | AA |
| I-163 | AA | AA |
| I-164 | AAA | AAA |
| I-165 | AAA | AAA |
| I-166 | NA | AA |
| I-167 | NA | A |
| I-168 | NA | AA |
| I-169 | NA | AAA |
| I-170 | NA | AA |
| I-171 | NA | AA |
| I-172 | NA | AA |
| I-173 | NA | AA |
| I-174 | AAA | AAA |
| I-175 | NA | AA |

TABLE 2-continued

Results of in vitro ACC1 and ACC2 inhibition assays.

| Compound ID | ACC1 | ACC2 |
|---|---|---|
| I-176 | NA | A |
| I-177 | AAA | AAA |
| I-178 | NA | A |
| I-179 | AAA | AAA |
| I-180 | AAA | AAA |
| I-181 | AAA | AAA |
| I-182 | NA | C |
| I-183 | NA | AAA |
| I-184 | NA | AA |
| I-185 | NA | AA |
| I-186 | NA | AA |
| I-227 | NA | |
| I-229 | NA | |
| I-228 | NA | |
| I-249 | AAA | AAA |
| I-230 | NA | A |
| I-235 | AAA | AAA |
| I-236 | AAA | AAA |
| I-231 | NA | A |
| I-234 | NA | A |
| I-246 | AAA | AAA |
| I-243 | AAA | AAA |
| I-233 | NA | A |
| I-257 | NA | A |
| I-277 | AAA | AAA |
| I-278 | AAA | AAA |
| I-254 | AAA | AAA |
| I-258 | AAA | AAA |
| I-244 | AAA | AAA |
| I-245 | AAA | AAA |
| I-256 | AAA | AAA |
| I-237 | AAA | AAA |
| I-238 | AAA | AAA |
| I-239 | AAA | AAA |
| I-242 | AAA | AAA |
| I-255 | AAA | AAA |
| I-263 | NA | AA |
| I-240 | NA | AAA |
| I-241 | AAA | AAA |
| I-286 | AAA | AAA |
| I-251 | NA | A |
| I-261 | NA | A |
| I-262 | NA | A |
| I-285 | NA | A |
| I-259 | AAA | AAA |
| I-290 | AAA | AAA |
| I-287 | AAA | AAA |
| I-247 | AAA | AAA |
| I-270 | A | NA |
| I-267 | AAA | AAA |
| I-260 | AAA | AAA |
| I-275 | AAA | NA |
| I-266 | AA | NA |
| I-265 | AA | NA |
| I-271 | AAA | AAA |
| I-253 | AA | NA |
| I-272 | AAA | AAA |
| I-268 | AAA | AAA |
| I-252 | AA | NA |
| I-248 | AA | NA |
| I-264 | AAA | AAA |
| I-276 | AAA | NA |
| I-274 | AAA | AAA |
| I-269 | A | NA |
| I-273 | AAA | NA |
| I-283 | AAA | NA |
| I-284 | AAA | NA |
| I-288 | AAA | AAA |
| I-289 | AAA | AAA |
| I-291 | AAA | AAA |
| I-279 | AAA | AAA |
| I-282 | AAA | AAA |
| I-296 | NA | AAA |
| I-293 | NA | AAA |
| I-297 | AAA | AAA |
| I-303 | AAA | AAA |
| I-292 | AAA | AAA |
| I-294 | AAA | AAA |
| I-295 | AAA | AAA |

Example 248

Thermal Shift Assay

Compounds of the present invention were evaluated in a thermal shift assay using methods substantially similar to those described by Vedadi et al. "Chemical screening methods to identify ligands that promote protein stability, protein crystallization, and structure determination." PNAS (2006) vol. 103, 43, 15835-15840, the entirety of which is incorporated herein by reference.

The results of the thermal shift assay showing the ability of compound I-97 to bind effectively to and elicit a conformational change on the protein resulting in its allosteric inhibition mechanism is highlighted by the data in FIG. 2. FIG. 2 shows the results from a Thermal Shift Assay (TSA) comparing I-97 and Soraphen A (IC50=4 nM), and illustrating the ability of compound I-97 to change the tertiary structure of the target protein, resulting in a thermal melting point change of more than 14° C.

The results of the thermal shift assay showing the ability of compound I-97 to bind effectively to and elicit a conformational change on the protein resulting in its allosteric inhibition mechanism is highlighted by the data in FIG. 3. FIG. 3 shows the results from a Thermal Shift Assay (TSA) comparing compounds I-1, I-158, I-174, and Soraphen A (IC50=4 nM), and illustrating the ability of compounds I-158 and I-174 to change the tertiary structure of the target protein, resulting in a thermal melting point change equivalent to that of Soraphen A.

Example 249

[$^{14}$C] Acetate Incorporation Assay

Compounds of the present invention were evaluated in a [$^{14}$C] Acetate Incorporation Assay. An exemplary procedure for the assay, which measures the incorporation of isotopically labeled acetate into fatty acids, follows. HepG2 cells were maintained in T-75 flasks containing DMEM supplemented with 2 mM 1-glutamine, penicillin G (100 units/ml), streptomycin 100 μg/ml with 10% FBS and incubated in a humidified incubator with 5% CO2 at 37° C. Cells were fed every 2-3 days. On Day 1. cells were seeded in 24 well plates at a density of 1.2×105 cells/ml/well with the growth medium. On Day 3 the medium was replaced with fresh medium containing 10% FBS. On Day 4 the medium was replaced with 0.5 ml of fresh medium containing test compound (in DMSO; final [DMSO] is 0.5%) and the cells were incubated at 37° C. for 1 hour. To one copy of plate, 4 ul of [2-$^{14}$C] acetate (56 mCi/mmol; 1 mCi/ml; PerkinElmer) was added and the cells were incubated at 37° C., 5% CO2 for 5 hrs. To a second copy of plate, 4 ul of cold acetate were added and the cells were incubated at 37° C., 5% CO2 for 5 hrs. This plate was used for protein concentration measurement. Medium was removed and placed in a 15 ml centrifuge tube (BD, Falcon/352096). Cells were rinsed with 1 ml PBS, then aspirated, and the rinse and aspiration steps were repeated. 0.5 ml of 0.1N NaOH were added to each well and let sit at RT to dissolve cell monolayer. The remaining cell suspension was pooled with medium. For the protein determination plate, an aliquot was removed for protein determination (25 ul). 1.0 ml of EtOH and 0.17 ml 50% KOH were added to tubes containing medium and cell suspensions. Cells were incubated at 90° C. for 1 hr, then cooled to room temperature. 5 ml petroleum ether was added per tube, shaken vigorously, centrifuged at 1000 rpm for 5 min, and 500 uL of the petroleum ether layer was transferred to tubes for Microbeta reading, then 2 ml Aquasol-2 were added to each tube, the tubes were shaken and counted with a Microbeta Liquid Scintillation Counter (Perkin Elmer).

The remaining petroleum ether layer was discarded and the aqueous phase reserved for fatty acid extractions. The aqueous phase was acidified with 1 ml of concentrated HCl, checking pH of one or two extracts to make sure pH was below 1. 5 ml of petroleum ether was added per tube, shaken vigorously, centrifuged at 1000 rpm for 5 min, and 4 ml of the petroleum ether layer was transferred to a new glass tube (10*18 mm). 5 ml of petroleum ether was added per tube, shaken vigorously, centrifuged at 1000 rpm for 5 min, and 5 ml of the petroleum ether layer was transferred to the glass tube, and the extraction repeated again. The petroleum ether extracts were pooled and evaporated to dryness overnight. On Day 5 the residue from the petroleum ether fractions was resuspended in 120 uL of chloroform-hexane (1:1) containing 200 ug of linoleic acid as a carrier. 5 uL of this was spotted onto silica gel sheets, and the plates developed using heptane-diethyl ether-acetic acid (90:30:1) as eluent. The fatty acid band was visualized with iodine vapor and the corresponding bands were cut out into scintillation vials. 2 ml of Aquasol-2 was added to each vial, and the vials were shaken and counted on a scintillation counter.

The results of the [$^{14}$C] Acetate Incorporation Assay are shown in FIG. 4 and FIG. 7. FIG. 4 illustrates the ability of compounds I-158 and I-174 to inhibit incorporation of isotopically labeled acetate into fatty acids with an IC$_{50}$ of less than 100 nM. Another inhibitor, CP-640186 (at a single concentration of 3 uM) is shown for comparison. FIG. 7 illustrates the ability of compound I-181 to inhibit incorporation of isotopically labeled acetate into fatty acids in Hep-G2 cells.

Example 250

Compounds of the present invention were evaluated in an Anti-Fungal Activity Assay. An exemplary procedure for the assay, which measures the susceptibility of various *Candida* species to anti-fungal compounds, follows. Compounds to be tested (including fluconazole and amphotericin B) were dissolved in DMSO to obtain a solution having a concentration of 1 mg/mL. These stock solutions were sterile filtered using a 0.22 um nylon syringe filter, then diluted in sterile water to achieve a final concentration of 128 ug/mL.

All species were grown from frozen stock by directly plating on to freshly prepared Sabouraud Dextrose agar (BD, Difco) and incubated overnight in ambient air at 35° C. for 24 h. A direct suspension was prepared in RPMI 1640+MOPS (Lonza, Biowhittaker) by taking individual colonies from the overnight cultures using sterile swabs soaked in sterile saline. The concentration of the suspension was determined using pre-determined standard curves. These suspensions were then diluted down to 5×10$^3$ CFU/mL to achieve a final concentration of 2.5×10$^3$ CFU/mL once added to the microtiter plate as per CLSI guidelines (M27-A3, Vol. 28 No. 14).

Broth microtiter MIC challenge plates were prepared following CLSI guidelines (M27-A3, Vol. 28 No. 14). The original CLSI guidelines focused on reading *Candida* MICs after 48 h of incubation. As reading after only 24 h offers a clear advantage of patient care, QC limits are being established for all drugs at 24 h. That being said there are no known interpretive breakpoints for amphotericin B at 24 h and the current fluconazole interpretive breakpoints are based on a 48 h reading. The MIC breakpoints for the Pharmaron test compounds were recorded at 48 h, and for the soraphen the 24 h time-point was added. All MIC determinations were achieved by visually comparing the growth found in the antibiotic challenged wells to that of the growth control. The first well found in the dilution scheme that showed no growth (or complete inhibition) was recorded as the MIC.

The results of the Anti-Fungal Activity Assay are shown in Table 3. Table 3 illustrates that compound I-158, I-159, I-174, I-235, I-236, and I-246 have anti-fungal activity MICs in the low ug/mL range.

TABLE 3

Anti-Fungal Activity Assay Results

| Candida species | MIC (μg/mL; 3 replicates) | | | | | | | | | | | |
|---|---|---|---|---|---|---|---|---|---|---|---|---|
| | Amph. B | Fluc. | I-158 | I-174 | I-181 | I-235 | I-236 | I-246 | I-159 | I-160 | I-162 | I-165 |
| C. albicans | 0.5 | 1 | 2 | 2 | >64 | 8 | 8 | 4 | 8 | >64 | >64 | >64 |
| ATCC 90028 | 0.5 | 1 | 2 | 2 | >64 | 8 | 8 | 4 | 8 | >64 | >64 | >64 |
| | 1 | 2 | 2 | 2 | >64 | 8 | 8 | 4 | 8 | >64 | >64 | >64 |
| C. parapsilosis | 1 | 2 | 8 | 8 | >64 | 8 | 2 | 4 | >64 | >64 | >64 | >64 |
| ATCC 22019 | 1 | 2 | 8 | 8 | >64 | 8 | 2 | 4 | >64 | >64 | >64 | >64 |
| | 1 | 4 | 8 | 8 | >64 | 8 | 2 | 4 | >64 | >64 | >64 | >64 |
| C. krusei | 1 | 32 | 2 | 2 | >64 | 8 | 8 | 16 | 16 | >64 | >64 | >64 |
| ATCC 6258 | 1 | 32 | 2 | 2 | >64 | 8 | 4 | 16 | 16 | >64 | >64 | >64 |
| | 1 | 2 | 2 | 2 | >64 | 8 | 4 | 16 | 32 | >64 | >64 | >64 |

Example 251

Compounds of the invention were also assayed in a Cancer Cell Viability Assay as described by Beckers et al. "Chemical Inhibition of Acetyl-CoA Carboxylase Induces Growth Arrest and Cytotoxicity Selectively in Cancer Cells" Cancer Res. (2007) 67, 8180-8187. An exemplary procedure for the assay, which measures the percentage of cancer cells surviving following administration of inhibitor compounds, follows.

LNCaP (prostate cancer cell line) cells plated at 4×10$^5$ per 6 cm dish were incubated at 37° C., and the following day they were treated with increasing concentrations of inhibitor compounds and incubated. Viable cells and the percentage of dead cells was counted and calculated every day for 5 days from day 0, using trypan blue staining The results of the Cancer Cell Viability Assay are shown in FIG. 5, which shows the ability of compound I-158 to completely inhibit cell population growth at a concentration of 5 uM.

Example 252

Compounds of the present invention were also assayed in an In Vivo Fatty Acid Synthesis Study as described by Harwood et al. "Isozyme-nonselective N-Substituted Bipiperidylcarboxamide Acetyl-CoA Carboxylase Inhibitors Reduce Tissue Malonyl-CoA Concentrations, Inhibit Fatty Acid Synthesis, and Increase Fatty Acid Oxidation in Cultured Cells and in Experimental Animals" Journal of Biological Chemistry (2008) 278, 37099-37111. An exemplary procedure for the assay, which measures the amount of radioactive $[C^{14}]$-acetate incorporated into rat liver tissue, follows.

Animals given food ad water ad libitum were treated orally at a volume of 1.0 mL/200 g body weight (rat) with either an aqueous solution containing 0.5% methylcellulose (vehicle), or an aqueous solution containing 0.5% methylcellulose plus test compound. One to four hours after compound administration, animals received an intraperitoneal injection of 0.5 mL of $[C^{14}]$-acetate (64 uCi/mL; 56 uCi/mL). One hour after radiolabeled acetate administration, animals were sacrificed by $CO_2$ asphyxiation and two 0.75 g liver pieces were removed and saponified at 70 degrees C. for 120 minutes in 1.5 mL of 2.5M NaOH. After saponification, 2.5 mL of absolute ethanol were added to each sample and the solutions were mixed and allowed to stand overnight. Petroleum ether (4.8 mL) was then added to each sample, and the mixtures were first shaken vigorously for 2 minutes and then centrifuged at 1000×g in a benchtop Sorvall for 5 minutes. The resultant petroleum ether layers, which contain non-saponifiable lipids, were removed and discarded. The remaining aqueous layer was acidified to pH<2 by the addition of 12M HCl and extracted two times with 4.8 mL of petroleum ether. The pooled organic fractions were transferred to liquid scintillation vials, dried under nitrogen, dissolved in 7 mL of Aquasol liquid scintillation fluid, and assessed for radioactivity using a Beckman 6500 liquid scintillation counter. Results were recorded as disintigrations per minute (DPM) per milligram of tissue.

Results of the In Vivo Fatty Acid Synthesis Study are shown in FIG. 8 and FIG. 16, which show that the $ED_{50}$ of each of compounds I-181 and I-278 is less than 0.3 mg/Kg body weight.

Example 253

Compounds of the present invention were also assayed in a Respiratory Quotient Measurement Assay, as described by Harwood et al. "Isozyme-nonselective N-Substituted Bipiperidylcarboxamide Acetyl-CoA Carboxylase Inhibitors Reduce Tissue Malonyl-CoA Concentrations, Inhibit Fatty Acid Synthesis, and Increase Fatty Acid Oxidation in Cultured Cells and in Experimental Animals" Journal of Biological Chemistry (2008) 278, 37099-37111. An exemplary procedure for the assay, which measures the ratio of carbon dioxide production to oxygen consumption in rats, follows.

Male Sprague-Dawley rats (350-400 g) housed under standard laboratory conditions, either fed chow, fasted, or fasted and refed a diet high in sucrose for 2 days prior to experimentation were removed from their home cages, weighed, and placed into sealed chambers (43"43"10 cm) of the calorimeter (one rat per chamber). The chambers were placed in activity monitors. The calorimeter was calibrated before each use, air flow rate was adjusted to 1.6 liters/min, and the system settling and sampling times were set to 60 and 15 s, respectively. Base-line oxygen consumption, $CO_2$ production, and ambulatory activity were measured every 10 min for up to 3 h before treatment. After collecting base-line data, the chambers were opened and rats were given a 1.0-ml oral bolus of either an aqueous 0.5% methylcellulose solution (vehicle control) or an aqueous 0.5% methylcellulose solution containing test compound and then returned to the Oxymax chambers. Measurements were made every 30 min for an additional 3-6 h after dose. Fed vehicle controls were used to assess effects produced by vehicle administration and by drift in the RQ measurement during the course of the experimentation (if any). Overnight-fasted, vehicle-treated controls were used to determine maximal potential RQ reduction. Results were plotted as their absolute RQ value (±SEM) over time.

Results of the In Vivo Fatty Acid Synthesis Study are shown in FIG. 9 and FIG. 10, which shows that the compound I-181 decreases RQ to approximately 80-90% of its baseline value and shows dose-dependent decreases in RQ upon treatment with I-181.

Example 254

Compounds of the present invention were also assayed in a propidium iodide (PI) cell death assay, based on the procedure described by van Engeland et al. "A novel assay to measure loss of plasma membrane asymmetry during apoptosis of adherent cells in culture" Cytometry (1996) 24 (2), 131-139. An exemplary procedure for the assay, which measures the number of intact mitotic cells following drug application follows.

Hepatocellular carcinoma cells (such as HepG2 or Hep3B) were seeded in a 24-well plate at a density of 1.106/ml in 0.5 ml of culture medium, and incubated for 3 hours to allow time for cells to adhere. Cells were treated with experimental compounds, 1 uM doxorubicin (1,2) or vehicle (DMSO) control for 120 hours after treatment: a. First removed culture supernatant into 2 mL polypropylene tube and place on ice; b. Washed wells with 0.5 mL PBS, transferring the wash volume to the 2 mL tube containing culture supernatant (floating cells). Kept cells on ice. Harvested by adding into the wells 200 uL of accutase for 5 min. Inactivated with 300 uL media. Pipetted up and down and transferred trypsinized cells from the well into the 2 mL tube with the floating cells (total volume: 1.5 mL). Kept cells on ice. Spun cells 0.6 rcf for 10 min at 4 degrees. Aspirated medium. Resuspended in 500 uL of Media by vortexing in pulses for about 15 s. Kept cells on ice.

For cell counting: added 20 uL of cells to a plate after vortexing in pulses for 15 s. Kept the plate on ice. Then added 20 uL trypan blue right before counting. Counted cells with TC10 biorad cell counter. Spun cells 0.6 rcf for 10 min at 4 degrees. Aspirated the medium carefully. Resuspended in 500 uL of annexin binding buffer 1× by vortexing. Transferred the cell suspension in a 5 ml FACS tube then added 5 ul of Propidium Iodide. Gently mixed the cells and incubated for 15 min at RT in the dark.

For the flow cytometric analysis, unstained/untreated samples were used at each time point as negative control, and doxorubicin treated samples were used at each time point as a positive control. A FACScan flow cytometer was used, and FL2-A histograms were analyzed with FlowJo software. The results of a PI cell death assay are depicted in FIG. 14.

Example 255

Compounds of the present invention were also assayed in high fat diet induced obesity (DIO) studies. A representative protocol for the assay follows.

The compounds of the present invention are readily adapted to clinical use as anti-obesity agents, insulin sensitizing agents, hyperinsulinemia-reversing agents, and hepatic steatosis-reversing agents. Such activity was determined by assessing the amount of test compound that reduces body weight and percentage body fat, reduces plasma insulin levels, blunts the rise and/or accelerates the reduction in plasma insulin and glucose levels in response to an oral glucose challenge, and reduces hepatic lipid content relative to a control vehicle without test compound in mammals. Sprague Dawley rats were fed either chow, a diet high in sucrose (for example AIN76A rodent diet; Research diets Inc. Cat #10001) or a diet high in fat (for example Research diets Inc. Cat #12451), for from 3-8 weeks prior to and during test compound administration.

The anti-obesity, insulin sensitizing, hyperinsulinemia-reversing, and hepatic steatosis-reversing potential of compounds of the present invention were demonstrated by evaluating modifications to a variety of parameters of lipid and carbohydrate metabolism using methods based on standard procedures known to those skilled in the art. For example, after a 3-8 week period of ad libitum feeding of either a chow, high-fat, or high-sucrose diet, animals that continued to receive the diet were treated for 1-8 weeks with test compound administered either by oral gavage in water or saline or water or saline containing 0.5% methylcelulose using a Q.D., B.I.D, or T.I.D. dosing regimen. At various times during study and at sacrifice (by $CO_2$ asphyxiation), blood was collected either from the tail vein of an unanesthesized rat or from the vena cava of animals at sacrifice into heparin or EDTA containing tubes for centrifugal separation to prepare plasma. Plasma levels of parameters of lipid and carbohydrate metabolism known by those skilled in the art to be altered coincident with anti-obesity, insulin sensitizing, hyperinsulinemia-reversing, and hepatic steatosis-reversing actions, including but not limited to cholesterol and triglycerides, glucose, insulin, leptin, adiponectin, ketone bodies, free fatty acids, and glycerol, are measured using methods known to those skilled in the art.

The anti-obesity potential of compounds of the present invention can also be demonstrated by evaluating their potential to produce a reduction in body weight, a reduction in percentage body fat (measured by for example dual-energy x-ray absorptiometry (DEXA) analysis), and a reduction in plasma leptin levels. The anti-obesity and hepatic steatosis-reversing potential of compounds of the present invention can also be demonstrated by evaluating their potential to reduce the concentration of triglycerides in the liver, using extraction and quantitation procedures known to those skilled in the art.

The insulin sensitizing and hyperinsulinemia-reversing potential of compounds of the present invention can also be demonstrated by evaluating their potential to blunt the rise and/or accelerate the reduction in plasma insulin and glucose levels in response to an oral glucose challenge, using procedures known to those skilled in the art.

The anti-obesity, insulin sensitizing, hyperinsulinemia-reversing, and hepatic steatosis-reversing potential of compounds of the present invention are exemplified through the actions of example compound I-181. When compound I-181 was administered once daily by oral gavage in 0.5% methylcellulose in saline at doses of 0, 3, 10, and 30 mg/kg to Sprague Dawley rats that had been consuming a high-fat diet for 4 weeks prior to initiation of dosing and continued to consume the same high-fat diet throughout the 2-weeks of test compound administration, compound I-181 produced a dose-dependent reduction in total body weight relative to vehicle-treated control animals with no concomitant reduction in food consumption. Results of the reduction in total body weight measurements after treatment of high fat diet-fed DIO rats with compound I-181 are shown in FIG. 11. The degree of body weight reduction paralleled plasma drug levels measured at the end of the study. Plasma leptin levels, which are known to be an indicator of whole-body fat mass and which were increased by administration of the high-fat diet, were reduced by all compound I-181 doses evaluated, indicating that the body weight reduction was the result of a reduction in body fat. The plasma leptin levels for animals receiving the standard chow diet (lean controls) were also evaluated to determine the extent of parameter normalization produced by compound I-181. Plasma insulin levels, which were increased by the high-fat diet, were reduced to near lean control levels by all three compound I-181 doses with no concomitant reduction in plasma glucose levels, indicating an improvement in insulin sensitivity after treatment with compound I-181. Results of the reduction in plasma insulin measurements after treatment of high fat diet-fed DIO rats with compound I-181 are shown in FIG. 12. Hepatic triglycerides, which were elevated by the high-fat diet, were reduced in a dose-dependent manner after compound I-181 treatment and were normalized to lean control levels by the highest dose evaluated. Results of the reduction in hepatic triglyceride and cholesterol measurements after treatment of high fat diet-fed DIO rats with compound I-181 are shown in FIG. 13. Treatment with compound I-181 did not increase either liver weight or the markers of liver function, ALT and AST. In studies where compound I-181 was administered once daily by oral gavage in 0.5% methylcellulose in salin at doses of 0, 3, 10, and 30 mg/kg to Sprague Dawley rats that had been consuming a high sucrose diet for 4 weeks prior to initiation of dosing and continued to consume the same high sucrose diet throughout the two weeks of test compound administration, compound I-181 produced a dose-dependent reduction in plasma cholesterol and triglyceride levels. Results of diet-induced obesity studies measuring the effect of compound I-181 on plasma cholesterol and plasma triglycerides are shown in Table 4 below. Data shown are mean values for n=14 animals per group±SEM.

TABLE 4

Plasma cholesterol and triglyceride lowering in high sucrose-fed DIO rats after treatment with I-181.

| Dose I-181 | Plasma Cholesterol* (mg/dL) | | | Plasma Triglycerides* (mg/dL) | | |
| --- | --- | --- | --- | --- | --- | --- |
| | Prebleed | Day 7 | Day 14 | Prebleed | Day 7 | Day 14 |
| 0 mg/kg | 100 ± 3 | 106 ± 3 | 110 ± 6 | 170 ± 11 | 226 ± 16 | 195 ± 15 |
| 3 mg/kg | 96 ± 2 | 94 ± 3 | 96 ± 3 | 144 ± 12 | 154 ± 15 | 171 ± 16 |

TABLE 4-continued

Plasma cholesterol and triglyceride lowering in high sucrose-fed DIO rats after treatment with I-181.

| Dose I-181 | Plasma Cholesterol* (mg/dL) | | | Plasma Triglycerides* (mg/dL) | | |
|---|---|---|---|---|---|---|
| | Prebleed | Day 7 | Day 14 | Prebleed | Day 7 | Day 14 |
| 10 mg/kg | 96 ± 3 | 82 ± 3 | 87 ± 3 | 183 ± 18 | 139 ± 10 | 165 ± 15 |
| 30 mg/kg | 99 ± 3 | 78 ± 3 | 78 ± 2 | 166 ± 13 | 116 ± 9 | 118 ± 14 |
| Chow-fed controls | 109 ± 2 | 107 ± 3 | 107 ± 3 | 61 ± 5 | 69 ± 5 | 67 ± 5 |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of formula II:

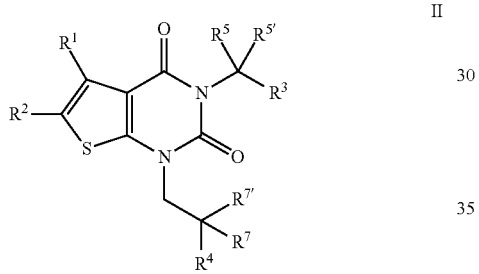

or a pharmaceutically acceptable salt thereof, wherein:

$R^1$ is hydrogen or $C_{1-4}$ aliphatic, optionally substituted with one or more halogen, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, or —SO$_2$R;

$R^2$ is Hy, where Hy is selected from 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

$R^3$ is hydrogen, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, —SO$_2$R, —B(OH)$_2$, or an optionally substituted ring selected from phenyl or 5-6 membered heteroaryl having 1-4 heteroatoms independently selected from nitrogen, oxygen, or sulfur;

$R^4$ is an optionally substituted phenyl or naphthyl ring;

each of $R^5$ and $R^{5'}$ is independently —R, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, or —SO$_2$R; or $R^5$ and $R^{5'}$ are taken together to form a cyclopropylenyl, cyclobutylenyl, or oxetanyl group;

each of $R^7$ and $R^{7'}$ is independently hydrogen, —R, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, or —SO$_2$R; or $R^7$ and $R^{7'}$ are taken together to form a 3-8 membered saturated or partially unsaturated monocyclic carbocyclic ring, or a 4-8 membered saturated or partially unsaturated monocyclic heterocyclic ring having 1-2 heteroatoms independently selected from nitrogen, oxygen, or sulfur; and each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring; a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur.

2. The compound according to claim 1, wherein $R^1$ is methyl or trifluoromethyl, or a pharmaceutically acceptable salt thereof.

3. The compound according to claim 2, wherein $R^2$ is oxazolyl, or a pharmaceutically acceptable salt thereof.

4. The compound according to claim 2, wherein $R^3$ is tetrazolyl, —C(O)OR, —C(O)N(R)$_2$, or —OR, or a pharmaceutically acceptable salt thereof.

5. The compound of claim 1 wherein $R^5$ and $R^{5'}$ are each methyl, or a pharmaceutically acceptable salt thereof.

6. The compound of claim 1 wherein $R^3$ is —C(O)OR or —C(O)NR$_2$, or a pharmaceutically acceptable salt thereof.

7. The compound of claim 6 wherein $R^3$ is —C(O)OH, or a pharmaceutically acceptable salt thereof.

8. A composition comprising a compound according to claim 1 or a pharmaceutically acceptable salt thereof and a pharmaceutically acceptable carrier, adjuvant, or vehicle.

9. A compound of formula III:

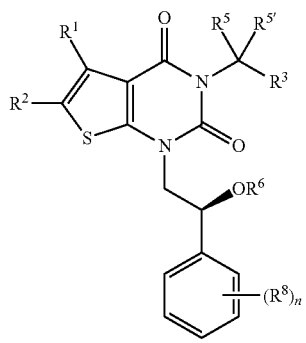

or a pharmaceutically acceptable salt thereof, wherein:
- $R^1$ is hydrogen or $C_{1-4}$ aliphatic, optionally substituted with one or more halogen, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, or —SO$_2$R;
- $R^2$ is Hy, where Hy is selected from 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;
- $R^3$ is hydrogen, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, —SO$_2$R, —B(OH)$_2$, or an optionally substituted ring selected from phenyl or 5-6 membered heteroaryl having 1-4 heteroatoms independently selected from nitrogen, oxygen, or sulfur;
- each of $R^5$ and $R^{5'}$ is independently —R, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, or —SO$_2$R; or $R^5$ and $R^{5'}$ are taken together to form a cyclopropylenyl, cyclobutylenyl, or oxetanyl group;
- $R^6$ is —R, —C(O)N(R)$_2$, or —C(O)R;
- each $R^8$ is independently selected from halogen, —R, —OR, —SR, —N(R)$_2$ or deuterium;
- each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring; a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; and
- n is 0-5.

10. A compound of formula IV:

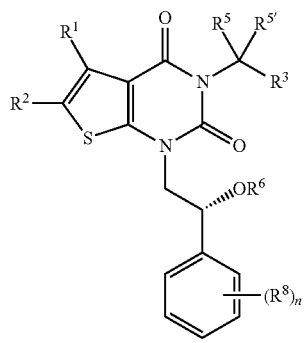

or a pharmaceutically acceptable salt thereof, wherein:
- $R^1$ is hydrogen or $C_{1-4}$ aliphatic, optionally substituted with one or more halogen, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, or —SO$_2$R;
- $R^2$ is Hy, where Hy is selected from 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;
- $R^3$ is hydrogen, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, —SO$_2$R, —B(OH)$_2$, or an optionally substituted ring selected from phenyl or 5-6 membered heteroaryl having 1-4 heteroatoms independently selected from nitrogen, oxygen, or sulfur;
- each of $R^5$ and $R^{5'}$ is independently —R, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, or —SO$_2$R; or $R^5$ and $R^{5'}$ are taken together to form a cyclopropylenyl, cyclobutylenyl, or oxetanyl group;
- $R^6$ is —R, —C(O)N(R)$_2$, or —C(O)R;
- each $R^8$ is independently selected from halogen, —R, —OR, —SR, —N(R)$_2$ or deuterium;
- each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring; a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; and
- n is 0-5.

* * * * *